US008569016B2

(12) United States Patent
Obayashi et al.

(10) Patent No.: US 8,569,016 B2
(45) Date of Patent: Oct. 29, 2013

(54) CONSTRUCTION AND CRYSTALLIZATION OF EXPRESSION SYSTEM FOR RNA POLYMERASE PB1-PB2 PROTEIN DERIVED FROM INFLUENZA VIRUS

(75) Inventors: Eiji Obayashi, Kanagawa (JP); Sam-Yong Park, Kanagawa (JP); Kyosuke Nagata, Ibaraki (JP); Atsushi Kawaguchi, Ibaraki (JP)

(73) Assignees: Public University Corporation Yokohama City University, Yokohama-Shi (JP); University of Tsukuba, Tsukuba-Shi (JP)

( * ) Notice: Subject to any disclaimer, the term of this patent is extended or adjusted under 35 U.S.C. 154(b) by 0 days.

(21) Appl. No.: 13/124,581

(22) PCT Filed: Oct. 16, 2009

(86) PCT No.: PCT/JP2009/067926
§ 371 (c)(1),
(2), (4) Date: Jul. 5, 2011

(87) PCT Pub. No.: WO2010/044468
PCT Pub. Date: Apr. 22, 2010

(65) Prior Publication Data
US 2011/0262944 A1 Oct. 27, 2011

(30) Foreign Application Priority Data

Oct. 17, 2008 (JP) ................................ 2008-268052
May 19, 2009 (JP) ................................ 2009-121376

(51) Int. Cl.
*C12P 21/06* (2006.01)
*G01N 33/48* (2006.01)
*C12N 1/20* (2006.01)
*C07K 14/00* (2006.01)

(52) U.S. Cl.
USPC ..................... 435/69.1; 435/252.33; 530/300; 530/344; 436/86; 702/19

(58) Field of Classification Search
None
See application file for complete search history.

(56) References Cited

FOREIGN PATENT DOCUMENTS

EP 2 277 891 A1 1/2011

OTHER PUBLICATIONS

Wiencek, J. M. Ann. Rev. Biomed. Eng. 1999, 1, 505-534.*

(Continued)

*Primary Examiner* — Nashaat Nashed
(74) *Attorney, Agent, or Firm* — Birch, Stewart, Kolasch & Birch, LLP

(57) ABSTRACT

The present invention aims to express influenza virus RNA polymerase on a large scale, to crystallize the influenza virus RNA polymerase, and to provide a method for screening a substance capable of serving as an active ingredient in anti-influenza drugs.

The present invention provides a complex comprising a polypeptide consisting of an amino acid sequence at positions 678-757 of the RNA polymerase PB1 subunit in influenza A/Puerto Rico/8/34 H1N1 (SEQ ID NO: 2) and a polypeptide consisting of an amino acid sequence at positions 1-37 of RNA polymerase PB2 subunit in influenza A/Puerto Rico/8/34 H1N1 (SEQ ID NO: 4). This complex can be crystallized in the presence of a precipitant such as potassium phosphate and PEG4000. Moreover, with the use of information on the crystal structure of this complex, it is possible to provide a method for screening a substance capable of serving as an active ingredient in anti-influenza drugs.

20 Claims, 8 Drawing Sheets
(7 of 8 Drawing Sheet(s) Filed in Color)

(56) References Cited

OTHER PUBLICATIONS

Deng et al., "In Vitro Assembly of PB2 with a PB1-PA Dimer Supports a New Model of Assembly of Influenza A Virus Polymerase . . . ," Journal of Virology (Jul. 2005), vol. 79, No. 13, pp. 8669-8674.
Extended European Search Report issued Oct. 14, 2011, in European Patent Application No. 09773545.0.
Ghanem et al., "Peptide-Mediated Interference with Influenza A Virus Polymerase," Journal of Virology (Jul. 2007), vol. 81, No. 14, pp. 7801-7804.
He et al., "Crystal Structure of the polymerase PAc-PB1N complex from an avian influenza H5N1 virus," Nature (Aug. 2008), vol. 454, pp. 1123-1127.
Perez et al., "Functional Analysis of PA Binding by Influenza A Virus PB1: Effects on Polymerase Activity and Viral Infectivity," Journal of Virology (Sep. 2001), vol. 75, No. 17, pp. 8127-8136.
Toyoda et al., "Molecular assembly of the influenza virus RNA polymerase: determination of the subunit-subunit contact sites," Journal of General Virology (1996), vol. 77, pp. 2149-2157.
Zurcher et al., "Mutational analysis of the influenza virus A/Victoria/3/75 PA protein: studies of interaction with PB1 protein and identification of a dominant negative mutant," Journal of General Virology (1996), vol. 77, pp. 1745-1749.
"International Search Report, dated Nov. 10, 2009, issued in PCT/JP2009/067926".
Area et al., "3D structure of the influenza virus polymerase complex: Localization of subunit domains", Proc. Natl. Acad. Sci. USA, Jan. 6, 2004, vol. 101, No. 1, pp. 308-313.
Guilligay et al., "The structural basis for cap binding by influenza virus polymerase subunit PB2", Nature Structural & Molecular Biology, May 2008, vol. 15, No. 5, pp. 500-506.
Obayashi et al., "The structural basis for an essential subunit interaction in influenza virus RNA polymerase", Nature, Aug. 28, 2008, vol. 454, pp. 1127-1131.
Poole et al., "Evidence that the C-terminal PB2-binding region of the influenza A virus PB1 protein is a discrete •-helical domain", FEBS Letters, 2007, vol. 581, pp. 5300-5306.
Sugiyama et al., "Structural insight into the essential PB1-PB2 subunit contact of the influenza virus RNA polymerase", The EMBO Journal, May 21, 2009, vol. 28, No. 12, pp. 1803-1811.
Torreira et al., "Three-dimensional model for the isolated recombinant influenza virus polymerase heterotrimer", Nucleic Acids Research, May 21, 2007, vol. 35, No. 11, pp. 3774-3783.
Bárcena et al., "Monoclonal Antibodies against Influenza Virus PB2 and NP Polypeptides Interfere with the Initiation Step of Viral mRNA Synthesis In Vitro", Journal of Virology, vol. 68, No. 11, pp. 6900-6909, Nov. 1994.
Cianci et al., "Differential Activation of the Influenza Virus Polymerase via Template RNA Binding", Journal of Virology, vol .69, No. 7, pp. 3995-3999, Jul. 1995.
Elton et al., "Structure and function of the influenza virus RNP", Influenza Virology: Current Topics (edited by Yoshihiro Kawaoka), Chapter 1, pp. 1-36, 2006.
Fodor et al., "A Single Amino Acid Mutation in the PA Subunit of the Influenza Virus RNA Polymerase Promotes the Generation of Defective Interfering RNAs", Journal of Virology, vol. 77, No. 8, pp. 5017-5020, Apr. 2003.
Gastaminza et al., "Mutations in the N-Terminal Region of Influenza Virus PB2 Protein Affect Virus RNA Replication but Not Transcription", Journal of Virology, vol. 77, No. 9, pp. 5098-5108, May 2003.
González et al., "Identification of two separate domains in the influenza virus PB1 protein involved in the interaction witth the PB2 and PA subunits: a model for the viral RNA polymerase structure", Nucleic Acids Research, vol. 24, No. 22, pp. 4456-4463, 1996.
Hara et al., "Amino Acid Residue in the N-Terminal Region of the PA Subunit of Influenza A Virus RNA Polymerase Play a Critical Role in Protein Stability, Endonuclease Activity, Cap Binding, and Virion RNA Promoter Binding", Journal of Virology, vol. 80, No. 16, pp. 7789-7798, Aug. 2006.
He et al., "Crystal structure of the polymerase PAc-PB1n complex from an avian influenza H5N1 virus", Nature, vol. 454, pp. 1123-1126 (5 pages total), Aug. 28, 2008 (Published online Jul. 9, 2008).
Kawaguchi et al., "De novo replication of the influenza virus RNA genome is regulated by DNA replicative helicase, MCM", The EMBO Journal, vol. 26, No. 21, pp. 4566-4575, 2007 (Published online Oct. 11, 2007).
Kim et al., "Influenza Neuraminidase Inhibitors Possessing a Novel Hydrophobic Interaction in the Enzyme Active Site: Design, Synthesis, and Structural Analysis of Carbocyclic Sialic Acid Analogues with Potent Anti-Influenza Activity", J. Am. Chem. Soc., vol. 119, pp. 681-690, 1997.
Li et al., "RNA-dependent activation of primer RNA production by influenza virus polymerase: different regions of the same protein subunit constitute the two required RNA-binding sites", The EMBO Journal, vol. 17, No. 19, pp. 5844-5852, 1998.
Liu et al., "Recent Progress in Rational Drug Design of Neuraminidase Inhibitors", Current Medicinal Chemistry, vol. 14, No. 27, pp. 2872-2891, 2007.
Nagata et al., "Host factors for replication and transcription of the influenza virus genome", Rev. Med. Virol., 14 pages, 2008.
Ochoa et al., "Epitope mapping of cross-reactive monoclonal antibodies specific for the influenza A virus PA and PB2 polypeptides", Virus Research, vol. 37, pp. 305-315, 1995.
Ohtsu et al., "Fine Mapping of the Subunit Binding Sites of Influenza Virus RNA Polymerase", Microbiol. Immunol., vol. 46, No. 3, pp. 167-175, 2002.
Perales et al., "Mutational Analysis Indentifies Functional Domains in the Influenza A Virus PB2 Polymerase Subunit", Journal of Virology, vol. 70, No. 3, pp. 1678-1686, Mar. 1996.
Poole et al., "Functional domains of the influenza A virus PB2 protein: identification of NP- and PB1-binding sites", Virology, vol. 321, pp. 120-133, 2004.
Russell et al., "The structure of H5N1 avian influenza neuraminidase suggests new opportunities for drug design", Nature, vol. 443, pp. 45-49, Sep. 7, 2006 (Published online Aug. 16, 2006).
Schnell et al., "Structure and mechanism of the M2 proton channel of influenza A virus", Nature, vol. 451, pp. 591-595 (6 total pages), Jan. 31, 2008.
Tarendeau et al., "Host Determinant Residue Lysine 627 Lies on the Surface of a Discrete, Folded Domain of Influenza Virus Polymerase PB2 Subunit", PLoS Pathogens, vol. 4, Issue 8, e1000136, pp. 1-8, Aug. 29, 2008.
Tarendeau et al., "Structure and nuclear import function of the C-terminal domain of influenza virus polymerase PB2 subunit", Nature Structural & Molecular Biology, vol. 14, No. 3, pp. 229-233, Mar. 2007 (Published online Feb. 25, 2007).
von Itzstein et al., "Rational design of potent sialidase-based inhibitors of influenza virus replication", Nature, vol. 363, pp. 418-423, Jun. 3, 1993.
Wit, E. et al., "Efficient generation and growth of influenza virus A/PR/8/34 from eight cDNA fragments", Virus Research, vol. 103, pp. 155-161, (2004).

\* cited by examiner a b d

Figure 1C

```
PB1-subunit
                        α1
H1N1    --------  ▬▬▬▬▬▬▬▬▬▬▬▬▬                              ▬▬
          680       690        700         710
H1N1    SQRGVLEDEQMYQRCCN FEK FPSSSYRRPVGISSM EA
H5N1    SQRGILEDEQMYQKCCN FEK FPSSSYRRPVGISSM EA
H7N7    SQRGVLEDEQMYQRCCN FEK FPSSSYRRPVGISSM EA α2                      α3
H1N1    ▬▬▬▬▬▬▬▬▬▬▬       ▬▬▬▬▬▬▬▬▬▬▬▬▬▬▬▬▬ ---
          720       730        740         750
H1N1    M SR RIDARIDFESGRIKKEEF EIMK CST EELRRQK
H5N1    M SR RIDARIDFESGRIKKEEF AEIMK CST E......
H7N7    M SR RIDARIDFESGRIKKEEF EIMK CST EELRRQK PB2-subunit
         α1          α2           α3
H1N1    ▬▬▬▬▬▬▬   ▬▬▬▬▬▬▬    ▬▬▬▬▬▬▬▬▬  ---
          1         10          20          30
H1N1    MER KE R MSQSRTREILTKTTVDHMAIIKKYTSG
H5N1    MER KE R MSQSRTREILTKTTVDHMAIIKKYTSG
H7N7    MER KE R MSQSRTREILTKTTVDHMAIIKKYTSG
```

CONSTRUCTION AND CRYSTALLIZATION OF EXPRESSION SYSTEM FOR RNA POLYMERASE PB1-PB2 PROTEIN DERIVED FROM INFLUENZA VIRUS

REFERENCE TO SEQUENCE LISTING SUBMITTED VIA EFS-WEB

This application is being filed electronically via EFS-Web and includes an electronically submitted sequence listing in .txt format. The .txt file contains a sequence listing entitled "2013-05-08 4456-0156PUS1_ST25.txt" created on May 8, 2013 and is 48,837 bytes in size. The sequence listing contained in this .txt file is part of the specification and is hereby incorporated by reference herein in its entirety.

TECHNICAL FIELD

The present invention relates to the construction of an expression system for RNA polymerase PB1-PB2 protein derived from influenza virus and the crystallization of the same.

The present invention also relates to a method for screening a substance capable of serving as an active ingredient in anti-influenza drugs.

BACKGROUND ART

Influenza is a respiratory infection caused by influenza virus. Influenza-infected patients complain of not only respiratory symptoms such as rhinorrhea and coughing, but also strong systemic symptoms including hyperthermia, arthralgia and/or chilliness, which may lead to death especially among the elderly and young children. Influenza virus is an RNA virus having negative-strand RNA as its genome. Frequent mutations occur in the phenotype or genomic nucleotide sequences of influenza virus, and hence the influenza virus occasionally gives rise to inter-species infection. In recent years, avian and swine influenza viruses have been confirmed to infect humans, and there is a concern that infection of these viruses will spread widely.

Influenza virus has hemagglutinin (HA) and neuraminidase (NA) on its surface. Currently, it is known that there are 16 subtypes for HA and 9 subtypes for NA. Depending on the combination of these subtypes, the type of influenza virus (e.g., H1N1, H3N2, H5N1, H7N7) is identified.

In recent years, various studies have been conducted for the development of anti-influenza virus drugs. At present, Tamiflu is commonly used as an anti-influenza virus drug. However, this drug is intended to suppress virus multiplication by prevention of virus spreading, but not intended to kill the virus. Thus, this drug has a problem in that it must be taken during the early stage of infection.

Conventionally used anti-influenza drugs are designed to target a protein on the virus surface, including NA as mentioned above or M2. For example, Tamiflu (oseltamivir) and Relenza (zanamivir) are NA inhibitors and inhibit the release of virus particles from infected cells (Non-patent Documents 2-5). Likewise, amantadine targets the viral proton channel (M2 protein) and inhibits virus uncoating (Non-patent Document 1).

However, due to its high ability to mutate, as described above, influenza virus will cause a mutation in the protein targeted by the drugs and will thereby acquire drug resistance. In fact, influenza virus strains resistant to amantadine and oseltamivir have already appeared and become a problem on a global scale.

Since influenza virus RNA polymerase plays an important role in virus multiplication after infection in humans, it can be a target for anti-influenza virus drugs. However, its expression has not yet been succeeded on a large scale. Furthermore, the three-dimensional structure of a target protein is essential information for the development of anti-influenza virus drugs, but such information has not yet been provided so far.

PRIOR ART DOCUMENTS

Non-Patent Documents

[Non-patent Document 1] Nature 2008, 451, 591-595
[Non-patent Document 2] Kim, C. U. et al. J. Am. Chem. Soc. 119, 681-690 (1997)
[Non-patent Document 3] von Itzstein, M. et al. Nature 363, 418-423 (1993)
[Non-patent Document 4] Russell, R. J. et al. Nature 443, 45-49 (2006)
[Non-patent Document 5] Liu, Y., Zhang, J. & Xu, W. Curr. Med. Chem. 14, 2872-2891 (2007)

DISCLOSURE OF THE INVENTION

Problem to be Solved by the Invention

The present invention aims to express RNA polymerase PB1-PB2 subunits derived from influenza virus on a large scale.

The present invention also aims to crystallize RNA polymerase PB1-PB2 subunits derived from influenza virus.

The present invention further aims to provide a method for screening anti-influenza drugs, which is based on information about the crystal structure of RNA polymerase PB1-PB2 subunits derived from influenza virus.

Means to Solve the Problem

Influenza RNA polymerase plays a key role in virus multiplication and has various functions not only to replicate viral RNA, but also to recognize host RNA to use it as a primer. The inventors of the present invention have used a gene derived from influenza virus to construct an expression system (in *E. coli*) for a complex of RNA polymerase PB1-PB2 subunits and to establish a method for its crystallization. This method is essential for the development of anti-influenza virus drugs that target the RNA polymerase.

Moreover, as a result of structural analysis on the RNA polymerase complex, the inventors of the present invention have succeeded in determining the structure of an interaction site between PB1 and PB2 subunits, each constituting the RNA polymerase. Then, the inventors have found that an amino acid sequence related to this site is highly conserved among virus species, and that the above interaction site is useful as a target site for anti-influenza drugs. These findings led to the completion of the present invention.

The present invention is summarized as follows.
(1) A complex comprising a polypeptide shown in (a1), (a2) or (a3) below and a polypeptide shown in (b1), (b2) or (b3) below:

(a1) a polypeptide which consists of the amino acid sequence shown in SEQ ID NO: 2;
(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1); and (b1) a polypeptide which consists of the amino acid sequence shown in SEQ ID NO: 4;

(b2) a polypeptide which consists of an amino acid sequence with deletion, substitution or addition of one or several amino acids in the amino acid sequence shown in SEQ ID NO: 4 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 3 and which has the same biological activity as the polypeptide shown in (b1).

(2) A complex comprising a polypeptide shown in (a1), (a2) or (a3) below and a polypeptide shown in (b4), (b5) or (b6) below:

(a1) a polypeptide which consists of the amino acid sequence shown in SEQ ID NO: 2;

(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1); and (b4) a polypeptide which consists of the amino acid sequence shown in SEQ ID NO: 20;

(b5) a polypeptide which consists of an amino acid sequence with deletion, substitution or addition of one or several amino acids in the amino acid sequence shown in SEQ ID NO: 20 and which has the same biological activity as the polypeptide shown in (b4); or (b6) a polypeptide which is encoded by DNA hybridizable under stringent conditions with DNA complementary to DNA consisting of the nucleotide sequence shown in SEQ ID NO: 19 and which has the same biological activity as the polypeptide shown in (b4).

(3) A recombinant vector comprising DNA encoding the polypeptide shown in (a1), (a2) or (a3) and DNA encoding the polypeptide shown in (b1), (b2) or (b3).

(4) A recombinant vector comprising DNA encoding the polypeptide shown in (a1), (a2) or (a3) and DNA encoding the polypeptide shown in (b4), (b5) or (b6).

(5) A transformed cell carrying DNA encoding the polypeptide shown in (a1), (a2) or (a3) and DNA encoding the polypeptide shown in (b1), (b2) or (b3).

(6) A transformed cell carrying DNA encoding the polypeptide shown in (a1), (a2) or (a3) and DNA encoding the polypeptide shown in (b4), (b5) or (b6).

(7) A method for producing the complex according to (1) above, which comprises culturing a transformed cell carrying DNA encoding the polypeptide shown in (a1), (a2) or (a3) and DNA encoding the polypeptide shown in (b1), (b2) or (b3), and collecting the complex according to (1) above from the cultured product.

(8) A method for producing the complex according to (2) above, which comprises culturing a transformed cell carrying DNA encoding the polypeptide shown in (a1), (a2) or (a3) and DNA encoding the polypeptide shown in (b4), (b5) or (b6), and collecting the complex according to (2) above from the cultured product.

(9) A crystal of the complex according to (1) above.

(10) A crystal of the complex according to (2) above.

(11) The crystal according to (9) above, having a space group of $P2_1$.

(12) The crystal according to (11) above, having a unit lattice of a=41.12±50 Å, b=61.37±50 Å and c=45.36±50 Å with an angle of $\beta$=103.5±30°.

(13) A method for producing a crystal of the complex according to (1) or (2) above, which comprises crystallizing the complex according to (1) or (2) above in the presence of a precipitant.

(14) The method according to (13) above, wherein the precipitant comprises potassium phosphate and PEG 4000.

(15) A polypeptide shown in (a1), (a2) or (a3) below:

(a1) a polypeptide which consists of the amino acid sequence shown in SEQ ID NO: 2;

(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1).

(16) DNA encoding the polypeptide according to (15) above.

(17) A recombinant vector comprising the DNA according to (16) above.

(18) A transformed cell carrying DNA encoding the polypeptide according to (15) above.

(19) A method for producing the polypeptide according to (15) above, which comprises culturing a transformed cell carrying DNA encoding the polypeptide according to (15) above, and collecting the polypeptide according to (15) above from the cultured product.

(20) A polypeptide shown in (b1), (b2) or (b3) below:

(b1) a polypeptide which consists of the amino acid sequence shown in SEQ ID NO: 4;

(b2) a polypeptide which consists of an amino acid sequence with deletion, substitution or addition of one or several amino acids in the amino acid sequence shown in SEQ ID NO: 4 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 3 and which has the same biological activity as the polypeptide shown in (b1).

(21) A polypeptide shown in (b4), (b5) or (b6) below:

(b4) a polypeptide which consists of the amino acid sequence shown in SEQ ID NO: 20;

(b5) a polypeptide which consists of an amino acid sequence with deletion, substitution or addition of one or several amino acids in the amino acid sequence shown in SEQ ID NO: 20 and which has the same biological activity as the polypeptide shown in (b4); or (b6) a polypeptide which is encoded by DNA hybridizable under stringent conditions with DNA complementary to DNA consisting of the nucleotide sequence shown in SEQ ID NO: 19 and which has the same biological activity as the polypeptide shown in (b4). (22) DNA encoding the polypeptide according to (20) or (21) above.

(23) A recombinant vector comprising the DNA according to (22) above.
(24) A transformed cell carrying DNA encoding the polypeptide according to (20) or (21) above.
(25) A method for producing the polypeptide according to (20) or (21) above, which comprises culturing a transformed cell carrying DNA encoding the polypeptide according to (20) or (21) above, and collecting the polypeptide according to (20) or (21) above from the cultured product.
(26) A method for screening a substance capable of serving as an active ingredient in anti-influenza drugs, which comprises the steps of: allowing PB1 subunit or a partial fragment thereof and PB2 subunit or a partial fragment thereof, each of which constitutes influenza virus RNA polymerase, to contact with each other in the presence of a candidate substance; and selecting a substance which inhibits the interaction between the PB1 subunit or partial fragment thereof and the PB2 subunit or partial fragment thereof
(27) The method according to (26) above, wherein the PB1 subunit consists of a polypeptide shown in (a4) or (a5) below:
  (a4) a polypeptide which consists of the amino acid sequence shown in SEQ ID NO: 16; or
  (a5) a polypeptide which consists of an amino acid sequence with deletion, substitution or addition of one or several amino acids in the amino acid sequence shown in SEQ ID NO: 16 and which has the activity of influenza virus RNA polymerase PB1 subunit.
(28) The method according to (26) above, wherein the partial fragment of PB1 subunit consists of the polypeptide according to (15) above.
(29) The method according to (26) above, wherein the PB2 subunit consists of a polypeptide shown in (b7) or (b8) below:
  (b7) a polypeptide which consists of the amino acid sequence shown in SEQ ID NO: 18; or
  (b8) a polypeptide which consists of an amino acid sequence with deletion, substitution or addition of one or several amino acids in the amino acid sequence shown in SEQ ID NO: 18 and which has the activity of influenza virus RNA polymerase PB2 subunit.
(30) The method according to (26) above, wherein the partial fragment of PB2 subunit consists of the polypeptide according to (20) or (21) above.
(31) The method according to any one of (26) to (30) above, wherein amino acid residues in the interaction site of PB1 subunit comprise at least one amino acid residue selected from the group consisting of amino acid residues Leu 695, Lys 698, Phe 699, Val 715, Asp 725, Ile746 and Ile 750 in the amino acid sequence shown in SEQ ID NO: 16, as well as corresponding residues in the amino acid sequence shown in SEQ ID NO: 2.
(32) The method according to any one of (26) to (30) above, wherein amino acid residues in the interaction site of PB2 subunit comprise at least one amino acid residue selected from the group consisting of Glu 2, Arg 3, Ile 4, Lys 5, Glu 6, Leu 7, Arg 8, Asn 9 and Leu 10 in the amino acid sequence shown in SEQ ID NO: 4, 18 or 20.
(33) The method according to any one of (26) to (30) above, wherein amino acid residues in the interaction site of PB1 subunit comprise at least one amino acid residue selected from the group consisting of amino acid residues Leu 695, Phe 699, Val 715, Ile746 and Ile 750 in the amino acid sequence shown in SEQ ID NO: 16, as well as corresponding residues in the amino acid sequence shown in SEQ ID NO: 2.
(34) The method according to any one of (26) to (30) above, wherein amino acid residues in the interaction site of PB2 subunit comprise at least one amino acid residue selected from the group consisting of Glu 2, Ile 4, Leu 7 and Leu 10 in the amino acid sequence shown in SEQ ID NO: 4, 18 or 20.
(35) The method according to any one of (26) to (34) above, wherein the candidate substance is at least one selected from the group consisting of a compound and a salt thereof, a peptide, an antibody, and a nucleic acid.

Effect of the Invention

The present invention enables the large-scale expression of an RNA polymerase PB1-PB2 complex derived from influenza virus. The present invention also enables to obtain a crystal of the RNA polymerase PB1-PB2 complex derived from influenza virus for use in three-dimensional structure analysis of the protein.

The present invention further enables to provide a method for screening a substance capable of serving as an active ingredient in anti-influenza drugs. Since the interaction site between PB1 and PB2 is located in a region where amino acid sequence is highly conserved, this site can be a target for development of anti-influenza drugs, regardless of the phenotypes of influenza viruses or mutations in their genome.

BRIEF DESCRIPTION OF THE DRAWINGS

The application file contains at least one drawing executed in color. Copies of this patent application publication with color drawings will be provided by the Office upon request and payment of the necessary fee.

BEST MODES FOR CARRYING OUT THE INVENTION

Figure 1:
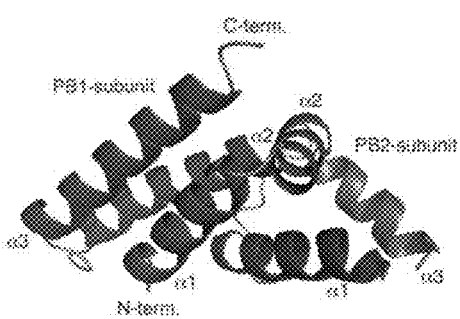
FIG. 1 shows the crystal structure of the C-terminal end of PB-1 bound to the N-terminal domain of PB2. (A) Overall ribbon diagram showing the structure of the complex, with helixes from PB1 (red), helixes from PB2 (blue), and coil regions (green). (B) The same model as shown in (A), but rotated 90° around the horizontal axis to show separation between the three helixes of the N-terminal peptide of PB2. (C) Sequences of the complexed fragments, along with sequence alignment of human (H1N1) (SEQ ID NO: 2 and 4) influenza virus, avian influenza virus (A/Duck/Hong Kong/2000) (SEQ ID NO: 6 and 8) and H7N7 influenza virus (A/Equine/London/1416/1973) (SEQ ID NO: 10 and 12). Secondary structure is indicated with red or blue bars showing helixes in PB1 and PB2, respectively, and broken lines indicate disordered regions. Amino acid residues shown in white on blue form hydrophobic contacts across the PB1-PB2 interface. Residues shown in red are not conserved among different viral strains, and hence are not likely to have an essential function. Overall, the interface region between PB1 and PB2 is very highly conserved. (D) Pull-down experiment using Ni-NTA and a fragment of PB1-C (residues 678-757 of SEQ ID NO: 16). The PB1-C fragment was co-expressed with different fragments of PB2 carrying a hexa-histidine tag at the N-terminal end. The red arrow indicates the presence of the PB1 fragment.
Figure 1:
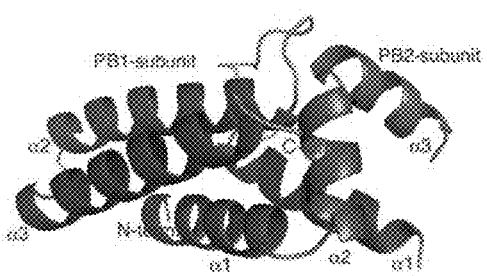
Figure 1:
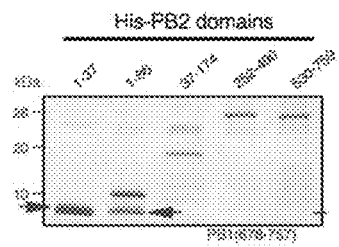

Embodiments of the present invention will be described in more detail below. The following embodiments are illustrated to describe the present invention, and it is not intended to limit the present invention only to these embodiments. The present invention can be implemented in various modes, without departing from the spirit of the present invention.

It should be noted that all documents cited herein, including prior art documents, patent gazettes and other patent documents, are incorporated herein by reference. Moreover, this specification incorporates the contents disclosed in the specification and drawings of the Japanese patent applications filed on Oct. 17, 2008 and May 19, 2009 (Japanese Patent Application Nos. 2008-268052 and 2009-121376, respectively), based on which the present application claims priority.

A. Construction of Expression System for RNA Polymerase PB1-PB2 Protein Derived from Influenza Virus and Crystallization of the Same The present invention provides a complex comprising a polypeptide shown in (a1), (a2) or (a3) below and a polypeptide shown in (b1), (b2) or (b3) below:

(a1) a polypeptide which consists of the amino acid sequence shown in SEQ ID NO: 2;

(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1); and (b1) a polypeptide which consists of the amino acid sequence shown in SEQ ID NO: 4;

(b2) a polypeptide which consists of an amino acid sequence with deletion, substitution or addition of one or several amino acids in the amino acid sequence shown in SEQ ID NO: 4 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 3 and which has the same biological activity as the polypeptide shown in (b1).

The polypeptide shown in (a1) consists of the amino acid sequence shown in SEQ ID NO: 2. The amino acid sequence shown in SEQ ID NO: 2 is an amino acid sequence at positions 678-757 of the RNA polymerase PB1 subunit in influenza A/Puerto Rico/8/34 H1N1.

The polypeptide shown in (a2) consists of an amino acid sequence with deletion, substitution or addition of one or several amino acids in the amino acid sequence shown in SEQ ID NO: 2 and has the same biological activity as the polypeptide shown in (a1).

There is no particular limitation on the total number and position of amino acids to be deleted, substituted or added. The total number of amino acids to be deleted, substituted or added is one or more, preferably one or several. More specifically, it generally ranges from 1 to 10, preferably from 1 to 5, and more preferably from 1 to 2 for deletion, generally from 1 to 20, preferably from 1 to 10, and more preferably from 1 to 3 for substitution, or generally from 1 to 10, preferably from 1 to 5, and more preferably from 1 to 2 for addition. The polypeptide shown in (a2) may be exemplified by a polypeptide which consists of the amino acid sequence shown in SEQ ID NO: 6 or 10. The amino acid sequence shown in SEQ ID NO: 6 is SQR GILEDEQMYQ KCCN-LFEKFF PSSSYRRPVG ISSMVEAMVS RARIDARIDF ESGRIKKEEF AEIMKICSTI E (678-751) found in the RNA polymerase PB1 subunit of influenza A virus (A/Duck/Hong Kong/2986.1/2000 (H5N1)). The amino acid sequence shown in SEQ ID NO: 10 is SQR GVLEDEQMYQ KCCN-LFEKFF PSSSYRRPVG ISSMVEAMVS RARIDARIDF ESGRIKKEEF AEIMKICSTI EELRRQK (678-757) found in the RNA polymerase PB1 subunit of influenza A virus (A/Equine/London/1416/1973 (H7N7)).

In the context of the present invention, "the same biological activity as the polypeptide shown in (a1)" is intended to encompass the ability to interact with the influenza virus RNA polymerase PB2 subunit or a fragment thereof (e.g., a polypeptide which consists of the amino acid sequence shown in SEQ ID NO: 4), as well as activity as an antigen, activity as an immunogen and so on. Moreover, "the same biological activity as the polypeptide shown in (a1)" is also used to mean the "activity of RNA polymerase PB1 subunit" described later.

The polypeptide shown in (a3) is encoded by DNA hybridizable under stringent conditions with DNA complementary to DNA consisting of the nucleotide sequence shown in SEQ ID NO: 1 and has the same biological activity as the polypeptide shown in (a1).

"Stringent conditions" may be selected as appropriate by those skilled in the art. Hybridization conditions may be low stringent conditions, by way of example. Low stringent conditions include, for example, 42° C., 2×SSC and 0.1% SDS, preferably 50° C., 2×SSC and 0.1% SDS. More preferred may be high stringent conditions. High stringent conditions include, for example, 65° C., 2×SSC and 0.1% SDS. Under these conditions, when the temperature is lowered, not only DNAs with high homology, but also DNAs with only low homology can be obtained comprehensively. Conversely, it can be expected that only DNAs with high homology are obtained at an elevated temperature. However, not only the temperature but also a plurality of factors (e.g., salt concentration) will affect the stringency of hybridization, and those skilled in the art would achieve the desired stringency by selecting these factors as appropriate. DNA hybridizable under stringent conditions with DNA complementary to DNA consisting of the nucleotide sequence shown in SEQ ID NO: 1 may be exemplified by DNA sharing a homology of at least 86% or more, preferably 88% or more, more preferably 90% or more, even more preferably 95% or more with the DNA consisting of the nucleotide sequence shown in SEQ ID NO: 1. Such DNA hybridizable under stringent conditions with DNA complementary to DNA consisting of the nucleotide sequence shown in SEQ ID NO: 1 may also be exemplified by DNA consisting of the nucleotide sequence shown in SEQ ID NO: 5 or 9. The nucleotide sequence shown in SEQ ID NO: 5 is the nucleotide sequence of DNA encoding an amino acid sequence at positions 678-751 of the RNA polymerase PB1 subunit in influenza A virus (A/Duck/Hong Kong/2986.1/2000 (H5N1)). The nucleotide sequence shown in SEQ ID NO: 9 is the nucleotide sequence of DNA encoding an amino acid sequence at positions 678-757 of the RNA polymerase PB1 subunit in influenza A virus (A/Equine/London/1416/1973 (H7N7)).

Polypeptides encoded by such DNAs isolated through hybridization techniques usually share high homology in amino acid sequence with the polypeptide shown in (a1). High homology generally refers to a homology of 97% or more, preferably 98% or more, more preferably 99% or more. The homology of each polypeptide can be determined in accordance with the algorithm described in Wilbur, W. J. and Lipman, D. J. Proc. Natl. Acad. Sci. USA (1983) 80, 726-730.

The same biological activity as the polypeptide shown in (a1) is as defined above.

The polypeptide shown in (b1) consists of the amino acid sequence shown in SEQ ID NO: 4. The amino acid sequence shown in SEQ ID NO: 4 is an amino acid sequence at positions 1-37 of the RNA polymerase PB2 subunit in influenza A/Puerto Rico/8/34 H1N1.

The polypeptide shown in (b2) consists of an amino acid sequence with deletion, substitution or addition of one or several amino acids in the amino acid sequence shown in SEQ ID NO: 4 and has the same biological activity as the polypeptide shown in (b1).

There is no particular limitation on the total number and position of amino acids to be deleted, substituted or added. The total number of amino acids to be deleted, substituted or added is one or more, preferably one or several. More specifically, it generally ranges from 1 to 10, preferably from 1 to 5, and more preferably from 1 to 2 for deletion, generally from 1 to 20, preferably from 1 to 10, and more preferably from 1 to 3 for substitution, or generally from 1 to 10, preferably from 1 to 5, and more preferably from 1 to 2 for addition.

The polypeptide shown in (b2) may be exemplified by a polypeptide which consists of the amino acid sequence shown in SEQ ID NO: 8 or 12. The amino acid sequence shown in SEQ ID NO: 8 is MERIKELRDL MSQSRTREIL TKT-TVDHMAI IKKYTSG (1-37) found in the RNA polymerase PB2 subunit of influenza A virus (A/Duck/Hong Kong/2986.1/2000 (H5N1)). The amino acid sequence shown in SEQ ID NO: 12 is MERIKELRDL MSQSRTREIL TKT-TVDHMAI IKKYTSG (1-37) found in the RNA polymerase PB2 subunit of influenza A virus (A/Equine/London/1416/1973 (H7N7)).

In the context of the present invention, "the same biological activity as the polypeptide shown in (b1)" is intended to encompass the ability to interact with the influenza virus RNA polymerase PB1 subunit or a fragment thereof (e.g., a polypeptide which consists of the amino acid sequence shown in SEQ ID NO: 2), as well as activity as an antigen, activity as an immunogen and so on. Moreover, "the same biological activity as the polypeptide shown in (b1)" is also used to mean the "activity of RNA polymerase PB2 subunit" described later.

The polypeptide shown in (b3) is encoded by DNA hybridizable under stringent conditions with DNA complementary to DNA consisting of the nucleotide sequence shown in SEQ ID NO: 3 and has the same biological activity as the polypeptide shown in (b1).

"Stringent conditions" may be selected as appropriate by those skilled in the art. Hybridization conditions may be low stringent conditions, by way of example. Low stringent conditions include, for example, 42° C., 2×SSC and 0.1% SDS, preferably 50° C., 2×SSC and 0.1% SDS. More preferred may be high stringent conditions. High stringent conditions include, for example, 65° C., 2×SSC and 0.1% SDS. Under these conditions, when the temperature is lowered, not only DNAs with high homology, but also DNAs with only low homology can be obtained comprehensively. Conversely, it can be expected that only DNAs with high homology are obtained at an elevated temperature. However, not only the temperature but also a plurality of factors (e.g., salt concentration) will affect the stringency of hybridization, and those skilled in the art would achieve the desired stringency by selecting these factors as appropriate. DNA hybridizable under stringent conditions with DNA complementary to DNA consisting of the nucleotide sequence shown in SEQ ID NO: 3 may be exemplified by DNA sharing a homology of at least 86% or more, preferably 88% or more, more preferably 90% or more, even more preferably 95% or more with the DNA consisting of the nucleotide sequence shown in SEQ ID NO: 3. Such DNA hybridizable under stringent conditions with DNA complementary to DNA consisting of the nucleotide sequence shown in SEQ ID NO: 3 may also be exemplified by DNA consisting of the nucleotide sequence shown in SEQ ID NO: 7 or 11. The nucleotide sequence shown in SEQ ID NO: 7 is the nucleotide sequence of DNA encoding an amino acid sequence at positions 1-37 of the RNA polymerase PB2 subunit in influenza A virus (A/Duck/Hong Kong/2986.1/2000 (H5N1)). The nucleotide sequence shown in SEQ ID NO: 11 is the nucleotide sequence of DNA encoding an amino acid sequence at positions 1-37 of the RNA polymerase PB2 subunit in influenza A virus (A/Equine/London/1416/1973 (H7N7)).

Polypeptides encoded by such DNAs isolated through hybridization techniques usually share high homology in amino acid sequence with the polypeptide shown in (b1). High homology generally refers to a homology of 97% or more, preferably 98% or more, more preferably 99% or more. The homology of each polypeptide can be determined in accordance with the algorithm described in Wilbur, W. J. and Lipman, D. J. Proc. Natl. Acad. Sci. USA (1983) 80, 726-730.

The same biological activity as the polypeptide shown in (b1) is as defined above.

The polypeptide shown in (a1), (a2) or (a3) is able to bind to and form a complex with the polypeptide shown in (b1), (b2) or (b3).

In another embodiment, the present invention provides a complex comprising a polypeptide shown in (a1), (a2) or (a3) below and a polypeptide shown in (b4), (b5) or (b6) below:

(a1) a polypeptide which consists of the amino acid sequence shown in SEQ ID NO: 2;

(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1); and (b4) a polypeptide which consists of the amino acid sequence shown in SEQ ID NO: 20;

(b5) a polypeptide which consists of an amino acid sequence with deletion, substitution or addition of one or several amino acids in the amino acid sequence shown in SEQ ID NO: 20 and which has the same biological activity as the polypeptide shown in (b4); or (b6) a polypeptide which is encoded by DNA hybridizable under stringent conditions with DNA complementary to DNA consisting of the nucleotide sequence shown in SEQ ID NO: 19 and which has the same biological activity as the polypeptide shown in (b4).

The polypeptides shown in (a1) to (a3) are as explained above.

The polypeptide shown in (b4) consists of the amino acid sequence shown in SEQ ID NO: 20. The amino acid sequence shown in SEQ ID NO: 20 is an amino acid sequence at positions 1-86 of the RNA polymerase PB2 subunit in influenza A/Puerto Rico/8/34 H1N1.

The polypeptide shown in (b5) consists of an amino acid sequence with deletion, substitution or addition of one or several amino acids in the amino acid sequence shown in SEQ ID NO: 20 and has the same biological activity as the polypeptide shown in (b4).

There is no particular limitation on the total number and position of amino acids to be deleted, substituted or added. The total number of amino acids to be deleted, substituted or added is one or more, preferably one or several. More specifically, it generally ranges from 1 to 10, preferably from 1 to 5, and more preferably from 1 to 2 for deletion, generally from 1 to 20, preferably from 1 to 10, and more preferably from 1 to 3 for substitution, or generally from 1 to 10, preferably from 1 to 5, and more preferably from 1 to 2 for addition.

In the context of the present invention, "the same biological activity as the polypeptide shown in (b4)" is intended to encompass the ability to interact with the influenza virus RNA polymerase PB1 subunit or a fragment thereof (e.g., a polypeptide which consists of the amino acid sequence shown in SEQ ID NO: 2), as well as activity as an antigen, activity as an immunogen and so on. Moreover, "the same biological activity as the polypeptide shown in (b4)" is also used to mean the "activity of RNA polymerase PB2 subunit" described later.

The polypeptide shown in (b6) is encoded by DNA hybridizable under stringent conditions with DNA complementary to DNA consisting of the nucleotide sequence shown in SEQ ID NO: 19 and has the same biological activity as the polypeptide shown in (b4).

"Stringent conditions" may be selected as appropriate by those skilled in the art. Hybridization conditions may be low stringent conditions, by way of example. Low stringent conditions include, for example, 42° C., 2×SSC and 0.1% SDS, preferably 50° C., 2×SSC and 0.1% SDS. More preferred may be high stringent conditions. High stringent conditions include, for example, 65° C., 2×SSC and 0.1% SDS.

Under these conditions, when the temperature is lowered, not only DNAs with high homology, but also DNAs with only low homology can be obtained comprehensively. Conversely, it can be expected that only DNAs with high homology are obtained at an elevated temperature. However, not only the temperature but also a plurality of factors (e.g., salt concentration) will affect the stringency of hybridization, and those skilled in the art would achieve the desired stringency by selecting these factors as appropriate. DNA hybridizable under stringent conditions with DNA complementary to DNA consisting of the nucleotide sequence shown in SEQ ID NO: 19 may be exemplified by DNA sharing a homology of at least 86% or more, preferably 88% or more, more preferably 90% or more, even more preferably 95% or more with the DNA consisting of the nucleotide sequence shown in SEQ ID NO: 19.

Polypeptides encoded by such DNAs isolated through hybridization techniques usually share high homology in amino acid sequence with the polypeptide shown in (b4). High homology generally refers to a homology of 97% or more, preferably 98% or more, more preferably 99% or more. The homology of each polypeptide can be determined in accordance with the algorithm described in Wilbur, W. J. and Lipman, D. J. Proc. Natl. Acad. Sci. USA (1983) 80, 726-730.

The same biological activity as the polypeptide shown in (b4) is as defined above.

The polypeptide shown in (a1), (a2) or (a3) is able to bind to and form a complex with the polypeptide shown in (b4), (b5) or (b6).

The complex of the present invention can be produced by culturing a transformed cell carrying DNA encoding the polypeptide shown in (a1), (a2) or (a3) and DNA encoding the polypeptide shown in (b1), (b2) or (b3), and collecting the desired complex from the cultured product.

In another embodiment, the complex of the present invention can be produced by culturing a transformed cell carrying DNA encoding the polypeptide shown in (a1), (a2) or (a3) and DNA encoding the polypeptide shown in (b4), (b5) or (b6), and collecting the desired complex from the cultured product.

Such a transformed cell carrying DNA encoding the polypeptide shown in (a1), (a2) or (a3) and DNA encoding the polypeptide shown in (b1), (b2) or (b3) may be obtained by transfecting an appropriate host cell with a recombinant vector comprising DNA encoding the polypeptide shown in (a1), (a2) or (a3) and DNA encoding the polypeptide shown in (b1), (b2) or (b3). The present invention also provides such a transformed cell carrying DNA encoding the polypeptide shown in (a1), (a2) or (a3) and DNA encoding the polypeptide shown in (b1), (b2) or (b3).

In another embodiment of the present invention, a transformed cell carrying DNA encoding the polypeptide shown in (a1), (a2) or (a3) and DNA encoding the polypeptide shown in (b4), (b5) or (b6) may be obtained by transfecting an appropriate host cell with a recombinant vector comprising DNA encoding the polypeptide shown in (a1), (a2) or (a3) and DNA encoding the polypeptide shown in (b4), (b5) or (b6). The present invention also provides such a transformed cell carrying DNA encoding the polypeptide shown in (a1), (a2) or (a3) and DNA encoding the polypeptide shown in (b4), (b5) or (b6).

To construct a recombinant vector, a DNA fragment covering the coding region of a desired polypeptide may be first prepared in an appropriate length. In the nucleotide sequence of the coding region of the desired polypeptide, one or more nucleotides may be substituted to give a codon(s) optimal for expression in host cells.

Then, this DNA fragment may be inserted downstream of a promoter in an appropriate expression vector to construct a recombinant vector (see, e.g., Molecular Cloning 2nd Edition, J. Sambrook et al., Cold Spring Harbor Lab. Press, 1989). The DNA fragment should be integrated into an expression vector such that the fragment exerts its functions. The present invention provides a recombinant vector comprising DNA encoding the polypeptide shown in (a1), (a2) or (a3) and DNA encoding the polypeptide shown in (b1), (b2) or (b3). The present invention also provides a recombinant vector comprising DNA encoding the polypeptide shown in (a1), (a2) or (a3) and DNA encoding the polypeptide shown in (b4), (b5) or (b6).

DNA encoding the polypeptide shown in (a1), (a2) or (a3), DNA encoding the polypeptide shown in (b1), (b2) or (b3), and DNA encoding the polypeptide shown in (b4), (b5) or (b6) can be prepared by PCR amplification using influenza virus cDNA.

Such DNA encoding the polypeptide shown in (a1), (a2) or (a3) may be exemplified by DNA consisting of the nucleotide sequence shown in SEQ ID NO: 1, and DNA hybridizable under stringent conditions with DNA complementary to DNA consisting of the nucleotide sequence shown in SEQ ID NO: 1, etc. Such DNA hybridizable under stringent conditions with DNA complementary to DNA consisting of the nucleotide sequence shown in SEQ ID NO: 1 may be exemplified by DNA sharing a homology of at least 86% or more, preferably 88% or more, more preferably 90% or more, even more preferably 95% or more with the DNA consisting of the nucleotide sequence shown in SEQ ID NO: 1. Such DNA hybridizable under stringent conditions with DNA complementary to DNA consisting of the nucleotide sequence shown in SEQ ID NO: 1 may also be exemplified by DNA consisting of the nucleotide sequence shown in SEQ ID NO: 5 or 9. The nucleotide sequence shown in SEQ ID NO: 5 is the nucleotide sequence of DNA encoding an amino acid sequence at positions 678-751 of the RNA polymerase PB1 subunit in influenza A virus (A/Duck/Hong Kong/2986.1/2000 (H5N1)). The nucleotide sequence shown in SEQ ID NO: 9 is the nucleotide sequence of DNA encoding an amino acid sequence at positions 678-757 of the RNA polymerase PB1 subunit in influenza A virus (A/Equine/London/1416/1973 (H7N7)).

DNA encoding the polypeptide shown in (b1), (b2) or (b3) may be exemplified by DNA consisting of the nucleotide sequence shown in SEQ ID NO: 3, and DNA hybridizable under stringent conditions with DNA complementary to DNA consisting of the nucleotide sequence shown in SEQ ID NO: 3, etc. Such DNA hybridizable under stringent conditions with DNA complementary to DNA consisting of the nucleotide sequence shown in SEQ ID NO: 3 may be exemplified by DNA sharing a homology of at least 86% or more, preferably 88% or more, more preferably 90% or more, even more preferably 95% or more with the DNA consisting of the nucleotide sequence shown in SEQ ID NO: 3. Such DNA hybridizable under stringent conditions with DNA complementary to DNA consisting of the nucleotide sequence shown in SEQ ID NO: 3 may also be exemplified by DNA consisting of the nucleotide sequence shown in SEQ ID NO: 7 or 11. The nucleotide sequence shown in SEQ ID NO: 7 is the nucleotide sequence of DNA encoding an amino acid sequence at positions 1-37 of the RNA polymerase PB2 subunit in influenza A virus (A/Duck/Hong Kong/2986.1/2000 (H5N1)) (SEQ ID NO: 8). The nucleotide sequence shown in SEQ ID NO: 11 is the nucleotide sequence of DNA encoding an amino acid sequence at positions 1-37 of the RNA polymerase PB2 subunit in influenza A virus (A/Equine/London/1416/1973 (H7N7)) (SEQ ID NO: 12).

DNA encoding the polypeptide shown in (b4), (b5) or (b6) may be exemplified by DNA consisting of the nucleotide sequence shown in SEQ ID NO: 19, and DNA hybridizable under stringent conditions with DNA complementary to DNA consisting of the nucleotide sequence shown in SEQ ID NO: 19, etc.

Examples of an expression vector available for use include E. coli plasmids (e.g., pBR322, pBR325, pUC12, pUC13), Bacillus subtilis plasmids (e.g., pUB110, pTP5, pC194), yeast plasmids (e.g., pSH19, pSH15), bacteriophages (e.g., λ phage), animal viruses (e.g., retrovirus, vaccinia virus), insect pathogenic viruses (e.g., baculovirus) and so on.

Such an expression vector may have a promoter, an enhancer, a ribosomal binding site, various signal sequences (e.g., splicing signal, poly(A) addition signal), a cloning site, a translation and/or transcription terminator, a selective marker, an SV40 replication origin, etc.

Such an expression vector may also be a fusion protein expression vector. Various fusion protein expression vectors are commercially available, including pGEX series (Amersham Pharmacia Biotech), pET Expression System (Novagen) and so on.

Examples of host cells include bacterial cells (e.g., Escherichia spp., Bacillus spp., Bacillus subtilis), fungal cells (e.g., yeast, Aspergillus), insect cells (e.g., S2 cells, Sf cells), animal cells (e.g., CHO cells, COS cells, HeLa cells, C127 cells, 3T3 cells, BHK cells, HEK293 cells), plant cells and so on.

Transfection of a recombinant vector into host cells may be accomplished by any method as described in Molecular Cloning 2nd Edition, J. Sambrook et al., Cold Spring Harbor Lab. Press, 1989 (e.g., calcium phosphate method, DEAE-dextran method, transvection, microinjection, lipofection, electroporation, transduction, scrape-loading method, shotgun method) or by infection.

Transformed cells carrying DNA encoding the polypeptide shown in (a1), (a2) or (a3) and DNA encoding the polypeptide shown in (b1), (b2) or (b3) can be cultured in a medium to thereby collect a complex between the polypeptide shown in (a1), (a2) or (a3) and the polypeptide shown in (b1), (b2) or (b3) from the cultured product. Likewise, transformed cells carrying DNA encoding the polypeptide shown in (a1), (a2) or (a3) and DNA encoding the polypeptide shown in (b4), (b5) or (b6) can be cultured in a medium to thereby collect a complex between the polypeptide shown in (a1), (a2) or (a3) and the polypeptide shown in (b4), (b5) or (b6) from the cultured product.

In a case where the complex is secreted into the medium, the medium may be collected and the complex may be separated and purified therefrom. In a case where the complex is produced within the transformed cells, the cells may be lysed and the complex may be separated and purified from the resulting lysate.

In a case where the complex is expressed in the form of a fusion protein with another protein (serving as a tag), the fusion protein may be separated and purified, followed by treatment with Factor Xa or an enzyme (e.g., enterokinase) to cleave another protein, thereby obtaining the desired complex.

Separation and purification of the complex may be accomplished in a known manner. Examples of known techniques used for separation and purification include those based on solubility (e.g., salting-out, solvent precipitation), those based on differences in molecular weight (e.g., dialysis, ultrafiltration, gel filtration, SDS-polyacrylamide gel electrophoresis), those based on differences in charge (e.g., ion exchange chromatography), those based on specific affinity (e.g., affinity chromatography), those based on differences in hydrophobicity (e.g., reversed-phase high performance liquid chromatography), those based on differences in isoelectric point (e.g., isoelectric focusing) and so on.

After being purified to have a purity sufficient for crystallization and then concentrated as needed, the complex can be crystallized in the presence of a precipitant. The present invention also provides a crystal of the complex. Examples of a precipitant include sodium formate. Techniques which can be used for crystallization include the batch method, the dialysis method, the vapor diffusion method and so on. In the case of using the batch method, crystallization is preferably accomplished by the hanging drop method. As an example, a crystal of the complex may have a space group of $P2_1$ and a unit lattice of a=41.12±50 Å, b=61.37±50 Å and c=45.36±50 Å with an angle of β=103.5±30°.

The present invention also provides the polypeptide shown in (a1), (a2) or (a3), DNA encoding this polypeptide, a recombinant vector comprising this DNA, and a transformed cell carrying this DNA. Moreover, the present invention also provides a method for producing the polypeptide shown in (a1), (a2) or (a3), which comprises culturing a transformed cell carrying DNA encoding the polypeptide shown in (a1), (a2) or (a3), and collecting the polypeptide shown in (a1), (a2) or (a3) from the cultured product. Such a polypeptide, DNA, recombinant vector and transformed cell, and a production method thereof are defined in the same way as described above for the complex. The polypeptide shown in (a1), (a2) or (a3) may also be produced according to known peptide synthesis techniques.

In addition, the present invention provides the polypeptide shown in (b1), (b2) or (b3), DNA encoding this polypeptide, a recombinant vector comprising this DNA, and a transformed cell carrying this DNA. Moreover, the present invention also provides a method for producing the polypeptide shown in (b1), (b2) or (b3), which comprises culturing a transformed cell carrying DNA encoding the polypeptide shown in (b1), (b2) or (b3), and collecting the polypeptide shown in (b1), (b2) or (b3) from the cultured product. Such a polypeptide, DNA, recombinant vector and transformed cell, and a production method thereof are defined in the same way as described above for the complex.

Further, the present invention provides the polypeptide shown in (b4), (b5) or (b6), DNA encoding this polypeptide, a recombinant vector comprising this DNA, and a transformed cell carrying this DNA. Moreover, the present invention also provides a method for producing the polypeptide shown in (b4), (b5) or (b6), which comprises culturing a transformed cell carrying DNA encoding the polypeptide shown in (b4), (b5) or (b6), and Collecting the polypeptide shown in (b4), (b5) or (b6) from the cultured product. Such a polypeptide, DNA, recombinant vector and transformed cell, and a production method thereof are defined in the same way as described above for the complex.

Alternatively, the polypeptide shown in (a1), (a2) or (a3), the polypeptide shown in (b1), (b2) or (b3) and the polypeptide shown in (b4), (b5) or (b6) may also be produced by protein synthesis in a cell-free system. Protein synthesis in a cell-free system can be accomplished by using a commercially available kit, and examples of such a kit include reagent kits PROTEIOS™ (Toyobo Co., Ltd., Japan) and TNT™ System (Promega), as well as synthesizers PG-Mate™ (Toyobo Co., Ltd., Japan) and RTS (Roche Diagnostics), etc.

The polypeptide shown in (b1), (b2) or (b3) and the polypeptide shown in (b4), (b5) or (b6) may also be produced according to known peptide synthesis techniques.

The polypeptide shown in (a1), (a2) or (a3) and the polypeptide shown in (b1), (b2) or (b3), or alternatively, the polypeptide shown in (a1), (a2) or (a3) and the polypeptide shown in (b4), (b5) or (b6) can be used in binding assay to screen anti-influenza virus drugs.

B. Screening Method for Anti-Influenza Drugs

1. Overview

The present invention relates to a method for screening a substance which inhibits the interaction between PB1 and PB2 subunits, each of which constitutes influenza virus RNA polymerase. The present invention is characterized in that such a substance is selected as a candidate capable of serving as an active ingredient in anti-influenza drugs.

Influenza virus RNA polymerase is composed of three subunits, i.e., PA, PB1 and PB2 subunits. PB1 binds to PA and PB2 further binds to PB1 to thereby form a trimeric complex, which is an active form exerting the activity of RNA polymerase.

The RNA polymerase plays a necessary and crucial role, e.g., in replication of influenza virus genome. Moreover, an amino acid sequence related to the interaction site between PB1 and PB2 subunits is highly conserved among influenza virus species. Thus, anti-influenza drugs targeting this interaction site can be expected to exert their effect, regardless of virus type (e.g., H1N1, H3N2, H5N1, H7N7), differences in host type (e.g., human, avian, swine), as well as mutations in proteins. For this reason, the inventors of the present invention conducted structural analysis with a focus on the subunits PB1 and PB2 of influenza virus RNA polymerase. As a result, the inventors succeeded in structural analysis of the interaction site between PB1 and PB2. The results of this analysis suggested that a substance capable of inhibiting the interaction between PB1 and PB2 would inhibit multiplication of influenza virus and would serve as an active ingredient in anti-influenza drugs. The present invention was completed based on these findings.

Namely, the present invention is directed to a method for screening a substance capable of serving as an active ingredient in anti-influenza drugs. More specifically, the method comprises the steps of: allowing PB1 subunit or a partial fragment thereof and PB2 subunit or a partial fragment thereof, each of which constitutes influenza virus RNA polymerase, to contact with each other in the presence of a candidate substance; and selecting a substance which inhibits the interaction between the PB1 subunit or partial fragment thereof and the PB2 subunit or partial fragment thereof.

2. RNA Polymerase (1) RNA-Dependent RNA Polymerase Complex

The RNA-dependent RNA polymerase complex of influenza virus is a protein complex associating with eight segments in influenza virus genome, and is essential for viral transcription and replication.

This complex also plays an essential role in developing viral pathogenicity. For example, by cap snatching, the complex recognizes the cap structure of host mRNA and cleaves the host mRNA including the cap structure.

In view of the fact that the RNA polymerase complex plays an essential role in viral transcription, replication and pathogenicity, its amino acid sequence is highly conserved across virus species. On the other hand, the amino acid sequence shares no homology with human proteins, and hence drugs targeting this complex are advantageous in that their side effects can be reduced.

The RNA polymerase complex is composed of three subunits, i.e., PA, PB1 and PB2. All of these three subunits are required for viral transcription and replication.

Although some reports have been issued for the structure of these subunits, their structural information is very limited (Area, E. et al., Proc. Natl. Acad. Sci. USA 101, 308-313 (2004); Torreira, E. et al. Nucleic Acids Res. 35, 3774-3783 (2007); Tarendeau, F. et al. Nature Struct. Mol. Biol. 14, 229-233 (2007); Guilligay, D. et al. Nature Struct. Mol. Biol. 15, 500-506 (2008)). This means that the X-ray crystal structure analysis of the influenza virus RNA polymerase complex as such was very difficult for those skilled in the art.

(2) PB1 Subunit

In the context of the present invention, PB1 subunit (also referred to as "PB1") may be exemplified by a polypeptide which consists of the amino acid sequence shown in SEQ ID NO: 16.

In addition to such a polypeptide which consists of the amino acid sequence shown in SEQ ID NO: 16, some mutants of this polypeptide may also have interactions with PB2. Thus, in the method of the present invention, it is also possible to use a polypeptide which consists of an amino acid sequence with deletion, substitution or addition of one or several amino acids in the amino acid sequence shown in SEQ ID NO: 16 and which has the activity of influenza virus RNA polymerase PB1 subunit.

Moreover, a partial fragment of PB1 subunit may also be used for this purpose.

Examples of a partial fragment of PB1 subunit used in the present invention include a polypeptide shown in (a1), (a2) or (a3) below:

(a1) a polypeptide which consists of the amino acid sequence shown in SEQ ID NO: 2;

(a2) a polypeptide which consists of an amino acid sequence with deletion, substitution or addition of one or several amino acids in the amino acid sequence shown in SEQ ID NO: 2 and which has the same biological activity as the polypeptide shown in (a1); or (a3) a polypeptide which is encoded by DNA hybridizable under stringent conditions with DNA complementary to DNA consisting of the nucleotide sequence shown in SEQ ID NO: 1 and which has the same biological activity as the polypeptide shown in (a1).

The individual polypeptides shown in (a1) to (a3) are as explained above in the section "A. Construction of expression system for RNA polymerase PB1-PB2 protein derived from influenza virus and crystallization of the same." It should be noted that "the same biological activity as the polypeptide shown in (a1)" is also used to mean the "activity of RNA polymerase PB1 subunit" described below.

In the context of the present invention, the "activity of RNA polymerase PB1 subunit" is intended to mean binding activity to PB2 subunit. RNA polymerase activity acquired by binding of PB1 to both PB2 and PA to form a complex, and complex formation activity acquired by binding of PB1 to PB2 are both encompassed by the "activity of RNA polymerase PB1 subunit" defined above. Moreover, the "activity of RNA polymerase PB1 subunit" in mutants is intended to mean having at least 30% or more, preferably 50% or more, more preferably 90% or more activity, as compared to the activity of PB1 consisting of the amino acid sequence shown in SEQ ID NO: 16.

If it is possible to confirm the presence or absence of binding activity between PB1 and PB2, a substance which inhibits the interaction between the subunits can be selected by the screening method of the present invention. Thus, as long as at least the PB2-binding site in PB1 is maintained, the amino acid sequence of PB1 may be mutated by deletion, substitution, addition or any combination thereof. It should be noted that the PB1 subunit activity in this case does not always need to have polymerase activity upon binding between PB1 and PB2.

The presence or absence of binding activity between PB1 and PB2 can be detected in a known manner, for example, by immunoprecipitation, pull-down assay, etc.

The term "PB1 subunit" or "PB1" is used herein to encompass either or both the full-length polypeptide of influenza virus RNA polymerase PB1 subunit and a partial fragment thereof.

In the context of the present invention, as described above, PB1 also encompasses a protein which consists of an amino acid sequence mutated by deletion, substitution, addition or any combination thereof of one or several amino acids in the amino acid sequence shown in SEQ ID NO: 16 or a partial sequence thereof (e.g., the amino acid sequence shown in SEQ ID NO: 2) and which has the activity of RNA polymerase PB1 subunit.

Examples of such an amino acid sequence mutated by deletion, substitution, addition or any combination thereof of one or several amino acids in the amino acid sequence shown in SEQ ID NO: 16 or a partial sequence thereof include:

(i) an amino acid sequence with deletion of 1 to 9 (e.g., 1 to 5, preferably 1 to 3, more preferably 1 to 2, even more preferably 1) amino acids from the amino acid sequence shown in SEQ ID NO: 16;

(ii) an amino acid sequence with 1 to 9 (e.g., 1 to 5, preferably 1 to 3, more preferably 1 to 2, even more preferably 1) amino acids in the amino acid sequence shown in SEQ ID NO: 16 being substituted with other amino acids;

(iii) an amino acid sequence with addition of other 1 to 9 (e.g., 1 to 5, preferably 1 to 3, more preferably 1 to 2, even more preferably 1) amino acids to the amino acid sequence shown in SEQ ID NO: 16; and (iv) an amino acid sequence mutated by any combination of (i) to (iii) above.

Moreover, examples of PB1 mutants include amino acid sequences which share a homology of about 80% or more, preferably 90% or more, more preferably about 95% or more, even more preferably about 98% or more with the amino acid sequence shown in SEQ ID NO: 16 or with the amino acid sequence of a partial sequence of SEQ ID NO: 16, and which have the activity of RNA polymerase PB1 subunit.

Homology may be determined by using a homology search site on the Internet, for example, by homology search such as FASTA, BLAST, PSI-BLAST or the like in the DNA Data Bank of Japan (DDBJ).

It should be noted that Leu 695, Lys 698, Phe 699, Val 715, Asp 725, Ile746 and Ile 750, preferably Leu 695, Phe 699, Val 715, Ile746 and Ile 750 in the amino acid sequence shown in SEQ ID NO: 2 or SEQ ID NO: 16 are amino acids required to interact with PB2 and to maintain binding with PB2. It is therefore desired that any of the mutations described above does not occur in at least one amino acid residue selected from the group consisting of the amino acid residues listed above.

It should be noted that protein amino acid residues are represented herein either by their number alone, counting from the N-terminal end of the full-length amino acid sequence of each subunit, or by their number and their three letter code. For example, the valine residue at position 715 counted from the N-terminal end of the amino acid sequence shown in SEQ ID NO: 16, which is the full-length amino acid sequence of PB1, is indicated as "Val 715" (the same applies to other amino acid residues).

In addition, the amino acid sequence shown in SEQ ID NO: 2 is identical to amino acid residues at positions 678 to 757 counted from the N-terminal end of the amino acid sequence shown in SEQ ID NO: 16. Thus, the amino acid sequence shown in SEQ ID NO: 2 contains residues corresponding to amino acid residues in the amino acid sequence shown in SEQ ID NO: 16. For this reason, amino acid residues in the amino acid sequence shown in SEQ ID NO: 2 are represented by amino acid number counted from the N-terminal end of the amino acid sequence shown in SEQ ID NO: 16. Amino acid residues thus represented are referred to as "corresponding residues." For example, the valine residue at position 38 counted from the N-terminal end of the amino acid sequence shown in SEQ ID NO: 2 corresponds to Val 715 in the amino acid sequence shown in SEQ ID NO: 16, and this valine residue at position 38 is therefore referred to as a "residue corresponding to Val 715" (the same applies to other amino acid residues in the amino acid sequence shown in SEQ ID NO: 2).

A polynucleotide encoding a mutated amino acid sequence with deletion, substitution or addition of one or several amino acids in the amino acid sequence shown in SEQ ID NO: 2 or 16 can be prepared according to site-directed mutagenesis or other techniques, as described in "Molecular Cloning, A Laboratory Manual 2nd ed." (Cold Spring Harbor Press (1989)), "Current Protocols in Molecular Biology" (John Wiley & Sons (1987-1997)), Kunkel (1985) Proc. Natl. Acad. Sci. USA 82: 488-92, Kramer and Fritz (1987) Method. Enzymol. 154: 350-67, Kunkel (1988) Method. Enzymol. 85: 2763-6, etc.

To introduce mutations into a polynucleotide for preparation of the above PB1 mutants, it is also possible to use a mutation introduction kit based on site-directed mutagenesis (e.g., Kunkel method, Gapped duplex method), such as a QuikChange™ Site-Directed Mutagenesis Kit (Stratagene), a GeneTailor™ Site-Directed Mutagenesis System (Invitrogen), a TaKaRa Site-Directed Mutagenesis System (e.g., Mutan-K, Mutan-Super Express Km; Takara Bio Inc., Japan).

In the context of the present invention, PB1 further encompasses a fusion protein having another peptide sequence added thereto. As a peptide sequence added to PB1, a tag sequence that facilitates protein detection may be selected, including influenza agglutinin (HA), glutathione S transferase (GST), multi-histidine tag (e.g., 6×His, 10×His), maltose-binding protein (MBP), etc. Such a tag sequence may be easily linked to PB1 through standard genetic engineering procedures.

PB1 also encompasses a protein which is encoded by the nucleotide sequence shown in SEQ ID NO: 15 or a partial sequence thereof (e.g., the nucleotide sequence shown in SEQ ID NO: 1), as well as a protein which is encoded by a polynucleotide hybridizable under stringent conditions with a polynucleotide consisting of a nucleotide sequence complementary to the nucleotide sequence shown in SEQ ID NO: 15 or a partial sequence thereof and which has the activity of RNA polymerase PB1 subunit.

In the present invention, such a polynucleotide encoding PB1 is used for preparation of PB1 or mutants thereof.

In the context of the present invention, "stringent conditions" may be selected as appropriate by those skilled in the art. Hybridization conditions may be low stringent conditions, by way of example. Low stringent conditions include, for example, 42° C., 2×SSC and 0.1% SDS, preferably 50° C., 2×SSC and 0.1% SDS. More preferred may be high stringent conditions. High stringent conditions include, for example, 65° C., 2×SSC and 0.1% SDS. Under these conditions, when the temperature is lowered, not only DNAs with high homology, but also DNAs with only low homology can be obtained comprehensively. Conversely, it can be expected that only DNAs with high homology are obtained at an elevated temperature. However, not only the temperature but also a plurality of factors (e.g., salt concentration) will affect the stringency of hybridization, and those skilled in the art would achieve the desired stringency by selecting these factors as appropriate.

Hybridization may be accomplished in a known manner. For detailed procedures of hybridization, reference may be made to, for example, "Molecular Cloning, A Laboratory Manual 2nd ed." (Cold Spring Harbor Laboratory Press (1989)), "Current Protocols in Molecular Biology" (John Wiley & Sons (1987-1997)), etc.

A polynucleotide hybridizable under stringent conditions is intended herein to encompass, for example, polynucleotides which comprise a nucleotide sequence sharing an identity (homology) of at least 80% or more, preferably 90% or more, more preferably 95% or more, even more preferably 97% or more with the nucleotide sequence shown in SEQ ID NO: 15 or a partial sequence thereof. A value representing identity can be calculated using a known program such as BLAST.

Examples of a polynucleotide hybridizable under stringent conditions with a polynucleotide consisting of a nucleotide sequence complementary to the nucleotide sequence shown in SEQ ID NO: 15 or a partial sequence thereof include a polynucleotide which comprises a nucleotide sequence mutated, e.g., by deletion, substitution or addition of one or several nucleic acids in the nucleotide sequence shown in SEQ ID NO: 15 or a partial sequence thereof.

In this case, examples of such a polynucleotide which comprises a nucleotide sequence mutated, e.g., by deletion, substitution or addition of one or several nucleic acids in the nucleotide sequence shown in SEQ ID NO: 15 or a partial sequence thereof include:

(i) a nucleotide sequence with deletion of 1 to 10 (e.g., 1 to 5, preferably 1 to 3, more preferably 1 to 2, even more preferably 1) nucleic acids from the nucleotide sequence shown in SEQ ID NO: 15 or a partial sequence thereof;

(ii) a nucleotide sequence with 1 to 10 (e.g., 1 to 5, preferably 1 to 3, more preferably 1 to 2, even more preferably 1) nucleic acids in the nucleotide sequence shown in SEQ ID NO: 15 or a partial sequence thereof being substituted with other nucleic acids;

(iii) a nucleotide sequence with addition of other 1 to 10 (e.g., 1 to 5, preferably 1 to 3, more preferably 1 to 2, even more preferably 1) nucleic acids to the nucleotide sequence shown in SEQ ID NO: 15 or a partial sequence thereof; and (iv) a nucleotide sequence mutated by any combination of (i) to (iii) above.

In the present invention, a polynucleotide encoding PB1 can be obtained, for example, by gene amplification (PCR) from influenza virus genomic cDNA using primers which are designed based on the nucleotide sequence shown in SEQ ID NO: 15 or a partial sequence thereof (Current Protocols in Molecular Biology, John Wiley & Sons (1987) Section 6.1-6.4).

In the present invention, nucleotide sequences can be confirmed by sequencing in a conventional manner. For example, dideoxynucleotide chain termination (Sanger et al. (1977) Proc. Natl. Acad. Sci. USA 74: 5463) or other techniques can be used for this purpose. Moreover, an appropriate DNA sequencer can also be used to analyze the sequences.

A polynucleotide encoding PB1 can be obtained by reverse transcription reaction and PCR from the viral genome purified from influenza virus particles using primers which are designed to give a desired sequence, based on sequence information of the full-length nucleotide sequence or amino acid sequence shown in SEQ ID NO: 15 or 16 or a partial sequence thereof. For reverse transcription reaction, reference may be made to "Molecular Cloning, A Laboratory Manual 2nd ed." (Cold Spring Harbor Press (1989)). Moreover, these primers can be used to obtain a desired fragment by PCR amplification from a polynucleotide containing a PB1-encoding gene. In this case, the primers may be modified to have an appropriate restriction enzyme sequence(s) or the like.

(3) PB2 Subunit

In the context of the present invention, PB2 subunit (also referred to as "PB2") may be exemplified by a polypeptide which consists of the amino acid sequence shown in SEQ ID NO: 18.

In addition to such a polypeptide which consists of the amino acid sequence shown in SEQ ID NO: 18, some mutants of this polypeptide may also have interactions with PB1. Thus, in the method of the present invention, it is also possible to use a polypeptide which consists of an amino acid sequence with deletion, substitution or addition of one or several amino acids in the amino acid sequence shown in SEQ ID NO: 18 and which has the activity of influenza virus RNA polymerase PB2 subunit.

A partial fragment of PB2 may also be used for this purpose.

Examples of a partial fragment of PB2 subunit used in the present invention include a polypeptide shown in (b1), (b2) or (b3) below:

(b1) a polypeptide which consists of the amino acid sequence shown in SEQ ID NO: 4;

(b2) a polypeptide which consists of an amino acid sequence with deletion, substitution or addition of one or several amino acids in the amino acid sequence shown in SEQ ID NO: 4 and which has the same biological activity as the polypeptide shown in (b1); or (b3) a polypeptide which is encoded by DNA hybridizable under stringent conditions with DNA complementary to DNA consisting of the nucleotide sequence shown in SEQ ID NO: 3 and which has the same biological activity as the polypeptide shown in (b1).

In another embodiment, examples of a partial fragment of PB2 subunit used in the present invention include a polypeptide shown in (b4), (b5) or (b6) below:

(b4) a polypeptide which consists of the amino acid sequence shown in SEQ ID NO: 20;

(b5) a polypeptide which consists of an amino acid sequence with deletion, substitution or addition of one or several amino acids in the amino acid sequence shown in SEQ ID NO: 20 and which has the same biological activity as the polypeptide shown in (b4); or (b6) a polypeptide which is encoded by DNA hybridizable under stringent conditions with DNA complementary to DNA consisting of the nucleotide sequence shown in SEQ ID NO: 19 and which has the same biological activity as the polypeptide shown in (b4).

The individual polypeptides shown in (b1) to (b3) and (b4) to (b6) are as explained above in "A. Construction of expression system for RNA polymerase PB1-PB2 protein derived from influenza virus and crystallization of the same." It should be noted that "the same biological activity as the polypeptide shown in (b1)" and "the same biological activity as the polypeptide shown in (b4)" are also used to mean the "activity of RNA polymerase PB2 subunit" described below.

In the context of the present invention, the "activity of RNA polymerase PB2 subunit" is intended to mean binding activity to PB1 subunit. RNA polymerase activity acquired by binding of PB2 to PB1 to form a complex, and complex formation activity acquired by binding of PB2 to PB1 are both encompassed by the "activity of RNA polymerase PB2 subunit" defined above. Moreover, the "activity of RNA polymerase PB2 subunit" in mutants is intended to mean having at least 30% or more, preferably 50% or more, more preferably 90% or more activity, as compared to the activity of PB2 consisting of the amino acid sequence shown in SEQ ID NO: 18.

If it is possible to confirm the presence or absence of binding activity between PB2 and PB1, a substance which inhibits the interaction between the subunits can be selected by the screening method of the present invention. Thus, as long as at least the PB1-binding site in PB2 is maintained, the amino acid sequence of PB2 may be mutated by deletion, substitution, addition or any combination thereof. It should be noted that the PB2 subunit activity in this case does not always need to have polymerase activity upon binding between PB2 and PB1.

The presence or absence of binding activity between PB2 and PB1 subunits can be determined in the same known manner as described above.

In the context of the present invention, as described above, PB2 also encompasses a protein which consists of an amino acid sequence mutated by deletion, substitution, addition or any combination thereof of one or several amino acids in the amino acid sequence shown in SEQ ID NO: 18 or a partial sequence thereof (e.g., the amino acid sequence shown in SEQ ID NO: 4 or 20) and which has the activity of RNA polymerase PB2 subunit.

Examples of such an amino acid sequence mutated by deletion, substitution, addition or any combination thereof of one or several amino acids in the amino acid sequence shown in SEQ ID NO: 18 or a partial sequence thereof include:

(i) an amino acid sequence with deletion of 1 to 9 (e.g., 1 to 5, preferably 1 to 3, more preferably 1 to 2, even more preferably 1) amino acids from the amino acid sequence shown in SEQ ID NO: 18;

(ii) an amino acid sequence with 1 to 9 (e.g., 1 to 5, preferably 1 to 3, more preferably 1 to 2, even more preferably 1) amino acids in the amino acid sequence shown in SEQ ID NO: 18 being substituted with other amino acids;

(iii) an amino acid sequence with addition of other 1 to 9 (e.g., 1 to 5, preferably 1 to 3, more preferably 1 to 2, even more preferably 1) amino acids to the amino acid sequence shown in SEQ ID NO: 18; and (iv) an amino acid sequence mutated by any combination of (i) to (iii) above.

In the context of the present invention, as described above, PB2 also encompasses a protein which consists of an amino acid sequence mutated by deletion, substitution, addition or any combination thereof of one or several amino acids in the amino acid sequence shown in SEQ ID NO: 4 or 20 and which has the activity of RNA polymerase PB2 subunit.

Examples of such an amino acid sequence mutated by deletion, substitution, addition or any combination thereof of one or several amino acids in the amino acid sequence shown in SEQ ID NO: 4 or 20 include:

(i) an amino acid sequence with deletion of 1 to 9 (e.g., 1 to 5, preferably 1 to 3, more preferably 1 to 2, even more preferably 1) amino acids from the amino acid sequence shown in SEQ ID NO: 4 or 20;

(ii) an amino acid sequence with 1 to 9 (e.g., 1 to 5, preferably 1 to 3, more preferably 1 to 2, even more preferably 1) amino acids in the amino acid sequence shown in SEQ ID NO: 4 or 20 being substituted with other amino acids;

(iii) an amino acid sequence with addition of other 1 to 9 (e.g., 1 to 5, preferably 1 to 3, more preferably 1 to 2, even more preferably 1) amino acids to the amino acid sequence shown in SEQ ID NO: 4 or 20; and (iv) an amino acid sequence mutated by any combination of (i) to (iii) above.

Moreover, examples of PB2 mutants include amino acid sequences which share a homology of about 80% or more, preferably 90% or more, more preferably about 95% or more, even more preferably about 98% or more with the amino acid sequence shown in SEQ ID NO: 18 or with the amino acid sequence of a partial sequence of SEQ ID NO: 18 (e.g., the amino acid sequence shown in SEQ ID NO: 4 or 20), and which have the activity of RNA polymerase PB2 subunit.

Glu 2, Arg 3, Ile 4, Lys 5, Glu 6, Leu 7, Arg 8, Asn 9 and Leu 10, preferably Glu 2, Ile 4, Leu 7 and Leu 10 in the amino acid sequence shown in SEQ ID NO: 4, 18 or 20 are amino acids required to interact with PB1 and to maintain binding with PB1. It is therefore desired that any of the mutations described above does not occur in at least one amino acid residue selected from the group consisting of the amino acid residues listed above.

Homology may be determined by using a homology search site on the Internet, for example, by homology search such as FASTA, BLAST, PSI-BLAST or the like in the DNA Data Bank of Japan (DDBJ).

PB2 also encompasses a protein which is encoded by the nucleotide sequence shown in SEQ ID NO: 17 or a partial sequence thereof, as well as a protein which is encoded by a polynucleotide hybridizable under stringent conditions with a polynucleotide consisting of a nucleotide sequence complementary to the nucleotide sequence shown in SEQ ID NO: 17 or a partial sequence thereof and which has the activity of RNA polymerase PB2 subunit. In the present invention, such a polynucleotide encoding PB2 is used for preparation of PB2 or mutants thereof.

With respect to other information about PB2, including procedures for site-directed mutagenesis, addition of a tag sequence, definition of stringent conditions, procedures for hybridization, embodiments of mutations, and procedures for PCR, they are the same as those described above, except that the intended nucleotide sequence and amino acid sequence are SEQ ID NO: 17 and SEQ ID NO: 18, respectively.

The term "PB2 subunit" or "PB2" is used herein to encompass either or both the full-length polypeptide of influenza virus RNA polymerase PB2 subunit and a partial fragment thereof.

(4) Interaction Between PB1 and PB2

In the context of the present invention, "interaction" between PB1 and PB2 is intended to mean that the constituent factors PB1 and PB2, which form a complex in the influenza virus RNA polymerase, are associated and bound to each other. The type of interaction includes, but is not limited to, hydrogen bonding, hydrophobic association, hydrophobic binding and so on.

Moreover, "interaction" between PB1 and PB2 is also intended to encompass signaling between PB1 and PB2. For example, signaling between PB1 and PB2 is mediated by at least one amino acid residue in the interaction site between PB1 and PB2 subunits.

The manner in which a candidate substance inhibits the interaction between PB1 and PB2 is not limited, and may include, for example, that the candidate substance may bind to the interaction site of PB1 or PB2 or that the candidate substance may bind to any site in PB1 or PB2 to thereby inhibit the interaction between these subunits.

The phrase "in the presence of a candidate substance" is intended to mean conditions that allow a test substance to contact with PB1 or PB2 or a complex thereof, which may be achieved by addition of a candidate substance to a reaction system containing PB1 or PB2 or a complex thereof, or by culturing cells containing PB1 or PB2 or a complex thereof (including cells into which genes for these elements are integrated in expressible form) in the presence of a candidate substance.

Candidate substances to be screened are not limited, however preferred are compounds having affinity to PB1 or PB2.

In the context of the present invention, the term "interaction site" is intended to mean an amino acid sequence consisting of at least one amino acid residue among those exposed on the interface between PB1 and PB2.

Amino acid residues in the interaction site of PB1 subunit are not limited as long as they are amino acid residues included in the amino acid sequence shown in SEQ ID NO: 2 or 16. However, preferred is at least one amino acid residue selected from the group consisting of Leu 695, Lys 698, Phe 699, Val 715, Asp 725, Ile 746 and Ile 750 listed above. More preferred is at least one amino acid residue selected from the group consisting of Leu 695, Phe 699, Val 715, Ile 746 and Ile 750.

Even more preferred is Val 715.

Amino acid residues in the interaction site of PB2 subunit comprise at least one amino acid residue selected from the group consisting of Glu 2, Arg 3, Ile 4, Lys 5, Glu 6, Leu 7, Arg 8, Asn 9 and Leu 10 in the amino acid sequence shown in SEQ ID NO: 4, 18 or 20. Preferred is at least one amino acid residue selected from the group consisting of Glu 2, Ile 4, Leu 7 and Leu 10 in the amino acid sequence shown in SEQ ID NO: 4, 18 or 20.

In the context of the present invention, the term "contact" is intended to mean that cells modified to have genes encoding the above subunits and a candidate substance (test substance) are allowed to exist in the same reaction system or culture system, for example, by adding the candidate substance to a cell culture vessel, by mixing the cells with the candidate substance, or by culturing the cells in the presence of the candidate substance.

3. Candidate Substance

As used herein, the term "candidate substance" refers to any molecule capable of altering the RNA polymerase activity of influenza virus. Examples include naturally-occurring or synthetic compounds from a low-molecular-weight compound library, expression products (e.g., peptides, proteins) of a gene library, naturally-occurring or synthetic oligonucleic acids, naturally-occurring or synthetic peptides from a peptide library, antibodies, bacterial substances (e.g., substances released from bacteria by metabolism), microorganisms, plant cell extracts, animal cell extracts, compounds from cultured solutions (cultured products of microorganisms, plant cells, animal cells, etc.), compounds in soil, compounds contained in a phage display library, etc. Such compounds may be modified by conventional chemical, physical and/or biochemical means. For example, they can be converted into structural analogs by being subjected to direct chemical modification (e.g., alkylation, esterification, amidation) or random chemical modification.

Further, candidate compounds may also be those identified by pharmacophore search or with a computational structure comparison program. In the case of using such compounds identified by pharmacophore search or with a computational structure comparison program in the present invention, candidates for compounds that inhibit the interaction between PB1 and PB2 can be screened in silico, based on the results of structural analysis on the binding site between these subunits. As an in silico search for compounds, multiple target screening (MTS) whose hit rate is significantly higher than that of standard screening methods can be used for screening.

These compounds may be either novel or known, and may also be in salt form. The term "salt" refers to a pharmaceutically acceptable salt, and is not limited as long as pharmaceutically acceptable salts are formed with the above compounds. More specifically, preferred examples include halogenated hydroacid salts (e.g., hydrofluoride salt, hydrochloride salt, hydrobromide salt, hydroiodide salt), inorganic acid salts (e.g., sulfate salt, nitrate salt, perchlorate salt, phosphate salt, carbonate salt, bicarbonate salt), organic carboxylic acid salts (e.g., acetate salt, oxalate salt, maleate salt, tartrate salt, fumarate salt, citrate salt), organic sulfonic acid salts (e.g., methanesulfonate salt, trifluoromethanesulfonate salt, ethanesulfonate salt, benzenesulfonate salt, toluenesulfonate salt, camphorsulfonate salt), amino acid salts (e.g., aspartate salt, glutamate salt), quaternary amine salts, alkali metal salts (e.g., lithium salt, sodium salt, potassium salt), alkaline earth metal salts (e.g., magnesium salt, calcium salt) and so on.

4. Screening

The screening method of the present invention can be accomplished, for example, by biochemical procedures using PB1- or PB2-producing cells or cell preparations thereof. Alternatively, at least one of PB1 and PB2 may be used in a purified form. Examples of "cell preparations" include cultured cells, homogenates of cultured cells, organella (e.g., cytoplasm, nuclei) fractionated from cultured cells, etc. Examples of PB1- or PB2-producing cells include those used in standard genetic engineering procedures. For use in this purpose, these cells may be modified by gene transfer to express at least one of the PB1 and PB2 genes. Procedures for gene transfer are well known in the art and can be easily accomplished (see, e.g., Sambrook et al., Molecular Cloning, A Laboratory Manual 2nd ed., (Cold Spring Harbor Laboratory Press (1989)).

To prepare PB1 and PB2, as described above, a gene encoding PB1 or PB2 (e.g., a gene having the nucleotide sequence shown in SEQ ID NO: 15 or 17 or a partial sequence thereof) may be adequately integrated into an expression vector to give a vector carrying the gene in a form suitable for expression of the encoded protein, and the resulting vector may be introduced into any of animal cells, plant cells, insect cells or microorganisms (e.g., yeast, E. coli) to give a transformant, followed by culturing the transformant thus obtained. Alternatively, their preparation may also be accomplished by using protein synthesis in a cell-free system. Protein synthesis in a cell-free system can be carried out using a commercially available kit, and examples of such a kit include reagent kits PROTEIOS™ (Toyobo Co., Ltd., Japan) and TNT™ System (Promega), as well as synthesizers PG-Mate™ (Toyobo Co., Ltd., Japan) and RTS (Roche Diagnostics), etc.

If desired, PB1 or PB2 produced in such a transformant or through protein synthesis in such a cell-free system may be separated and purified by various separation operations based on its physical properties, chemical properties, etc. Techniques used for purification may be exemplified by, for example, standard salting-out, centrifugation, ultrasonication, ultrafiltration, gel filtration, various liquid chromatographic techniques (e.g., ion exchange chromatography, affinity chromatography, high performance liquid chromatography (HPLC)), dialysis, or combinations thereof.

In another method for preparing PB1 or PB2, PB1 or PB2 may be produced in a form fused with an affinity tag in a transformant or through cell-free protein synthesis, followed by separation and purification.

The screening method of the present invention can be used to select a substance serving as an active ingredient in anti-influenza drugs by evaluating replication of influenza virus or transcription activity of its genome. Examples of assays using mammalian cells include those in a model viral replicon system which introduces a model viral genome and viral proteins related to transcription and replication (Turan, K. et al., Nucleic Acids Res. 29, 643-652 (2004)), as well as those in a virus infection system. Likewise, a model viral replicon system in yeast, for which genetic engineering procedures can be used, can also be adopted for the purpose of measuring transcription activity (International Publication No. WO2008/139627 A1). Further, it is also possible to use an in vitro viral genomic RNA synthesis system (Kawaguchi, A. and Nagata, K., EMBO J. 26, 4566-4575 (2007)). Those skilled in the art would be able to select an appropriate assay from those listed above to thereby construct a screening system that uses transcription activity as an index.

For use in the present invention, PB1 and PB2 can also be expressed as fusion proteins with a tag such as FLAG, HA, His, immunoglobulin Fc, GST or GFP or with a labeled peptide. In this case, screening can be accomplished by immunoprecipitation or immunological procedures. The antibody used in these procedures may be an antibody recognizing such a tag. Instead of antibody immunoprecipitation, a Ni- or glutathione-immobilized solid layer (e.g., beads) may be used to capture a complex between PB1 and PB2. Further, the complex can also be detected using properties of the fused tag or peptide, i.e., enzyme activity or fluorescence activity. Furthermore, when the complex between PB1 and PB2 or a constituent factor thereof is detected, the constituent factor can be separated and detected by Western blotting.

When one of PB1 or PB2 is expressed as a fusion protein with a fluorescent protein such as GFP, a PB1/PB2 complex may be captured on a solid layer with an antibody or the like that recognizes the molecule of the other subunit, and then directly measured for fluorescence activity to evaluate the interaction (binding state) between PB1 and PB2.

In these assays, the determination of whether a candidate substance inhibits binding between PB1 and PB2 may be accomplished, for example, by evaluation based on the absolute amount of inhibitory effect, evaluation based on comparison with a control, etc.

For example, in the evaluation based on comparison with a control, (i) PB1 and PB2 are brought into contact with each other in the presence and absence of a candidate compound, (ii) interaction between PB1 and PB2 is measured in both the presence and absence of the candidate compound, and (iii) a candidate compound affecting the interaction between PB1 and PB2 is selected based on the results measured in (ii) above.

The candidate compound selected in (iii) above is identified as a substance affecting the interaction between PB1 and PB2 or as an active ingredient in anti-influenza drugs.

According to the screening method of the present invention, any system which allows measurement of interaction (binding) between proteins can be used to search a substance inhibiting the desired interaction between PB1 and PB2. Such a system may be either a cell-based or cell-free system, such as ELISA, RIA and other immunological procedures, as well as a two-hybrid system.

As a system for quantitative analysis of complex formation between PB1 and PB2, a technique such as pull-down assay or immunoprecipitation may be used, by way of example.

As a system for kinetic analysis of binding between PB1 and PB2, a technique based on surface plasmon resonance may also be used, by way of example. In this case, for example, a BIACORE® protein interaction analysis system or the like may be used.

In a system for quantitative analysis of the interaction between PB1 and PB2, cells producing all of PB1 and PB2 or cell preparations thereof may be used for analysis.

5. Screening Kit

PB1 and PB2 in the present invention can be provided in the form of a kit for use in screening a substance inhibiting their interaction or a substance capable of serving as an active ingredient in anti-influenza drugs. In addition to PB1 and PB2, the kit of the present invention may comprise other components such as a vector necessary for gene expression, a primer, a restriction enzyme, a labeling substance, a detection reagent and so on. The term "labeling substance" refers to an enzyme, a radioisotope, a fluorescent compound, a chemiluminescent compound or the like. In addition to the above components, the kit of the present invention may further comprise other reagents required to accomplish the method of the present invention, for example, an enzyme substrate (e.g., a chromogenic substrate), an enzyme substrate diluent, an enzyme reaction stop solution and so on in a case where the labeled product is an enzymatically labeled product. Furthermore, the kit of the present invention may also comprise a diluent for candidate compounds, various buffers, sterilized water, various cell culture vessels, various reaction vessels (e.g., Eppendorf tubes), a detergent, an instruction manual for experimental operations (manufacturer's instructions) and so on.

EXAMPLES

The present invention will be described in more detail below based on the following illustrative examples, which are not intended to limit the scope of the invention.

Example 1

Influenza virus RNA-dependent RNA polymerase is a multi-functional heterotrimer, which uses a "cap-snatching" mechanism to produce viral mRNA. Host cell mRNA is cleaved to yield a cap-bearing oligonucleotide, which can be extended using viral genomic RNA as a template. The cap-binding and endonuclease activities are activated upon binding of viral genomic RNA. This requires signaling from the RNA-binding PB1 subunit to the cap-binding PB2 subunit, and the interface between these two subunits essential for the polymerase activity. The inventors of the present invention have defined this interaction surface by protein crystallography and tested the effect of mutated contact residues on holoenzyme functions. This novel interface is surprisingly small although it plays a crucial role in regulating the 250 kDa polymerase, and it is completely conserved among avian and human influenza viruses.

Influenza kills over 50,000 people in the United States each year on an average, and it is estimated that the death toll in the 1918 pandemic ranges up to 50 million people in the world. Recent outbreaks of highly pathogenic avian influenza in Asia have rapidly spread across continents, and currently used vaccines and medications are unlikely to greatly alleviate any epidemic or pandemic because these viral strains adapt to human hosts. The viral RNA polymerase is not yet a target of any approved medicaments, but has recently become a focus for the development of new anti-influenza drugs. This is because the viral RNA polymerase is highly conserved among influenza strains which infect both birds and humans. The viral RNA polymerase is responsible for a number of essential processes in the viral life cycle, but many of these and their regulation remain poorly understood (1). The three subunits, i.e., PB1, PB2 and PA play different roles within the polymerase and are all essential for viral replication; but relatively little is known about their structure despite considerable functional analyses (2-6). The inventors of the present invention have analyzed the crystal structure of a complex formed between fragments of PB1 and PB2. This subunit interface is a major interface between these two proteins and is essential for transcription initiation. Similar to the PA-PB1 interface, this interaction depends on a short N-terminal fragment of one protein, which raises the possibility that a suitable small molecule may be able to disrupt the interaction in vivo and significantly restrict viral replication.

The RNA polymerase of influenza A virus forms an RNP complex with each of eight negative-strand RNA genome segments and nucleoprotein packaged within the mature virion (7). When released into the host cell cytoplasm, the RNP complex uses nuclear import machinery to move into the nucleus (8), where it initiates viral mRNA transcription by the process of "cap snatching" (9). This process involves cleavage of an mRNA cap-containing oligonucleotide from host cell pre-mRNA to extend into viral mRNA, and the subsequent polyadenylation at the 3'-terminal end (10, 11). The polymerase synthesizes viral genomic RNA (vRNA) and complementary RNA (cRNA) in appropriate proportions, each having the correct ends and no cap. The regulation of these processes is not well understood although there are some reports. For example, cap binding to PB2 requires vRNA binding (12, 13). This may reflect interactions between the three subunits, all of which are essential for both RNA transcription and replication (14-16). The nature of PA-PB1 contact has been determined by functional studies and characterized crystallographically (4, 5). PB2 can also interact with PB1, whereas there is no direct interaction between PA and PB2 (17, 18). Although additional regions of contact are reported between these subunits (19), mutational analyses first suggest that the C-terminal end of PB1 (residues 712-746) will form the core interaction with the N-terminal end of PB2 (20, 21). Toyoda et al. used an immunoprecipitation assay and deletion mutants to show that the N-terminal 249 amino acid residues of PB2 can bind to PB1 (22). However, the subsequent studies from the same laboratory detected PB1 by co-precipitation with N-terminally truncated PB2, suggesting the possibility of another region of interaction with PB1 (23). This was supported by Poole et al., who identified a second PB1-binding site within the C-terminal end of PB2 (24).

1. PB1-PB2 Interaction Domain

To characterize the interaction between PB1 and PB2 in more detail, the inventors of the present invention used a co-precipitation assay to observe binding between C-terminal fragment of PB1 and N-terminal fragment of PB2. It was already known that only a short region, residues 678-757, of PB1 (SEQ ID NO: 16) was required for tight binding (21). This fragment (referred to as PB1-C) was tested together with residues 1-37, 1-86, 37-174, 252-490 or 530-759 of PB2 (SEQ ID NO: 18), indicating that only the 1-37 and 1-86 fragments of PB2 showed binding (FIG. 1D). Residues 37-177 of PB2 (SEQ ID NO: 18) did not bind to the C-terminal end of PB1, in agreement with Perales et al., who demonstrated that deletion of N-terminal 27 amino acids in PB2 dramatically eliminated viral RNA polymerase activity (25). They further demonstrated that the N-terminal 124 residues of PB2 (SEQ ID NO: 18) would behave as a dominant-negative inhibitor of viral transcription. Furthermore, a PB2-specific monoclonal antibody against the N-terminal end of this protein is able to inhibit the initiation step of transcription in vitro, probably by interfering with binding to PB1 (26, 27).

According to the experiments by the inventors of the present invention, PB2 residues 530-759 of SEQ ID NO: 18, including the proposed second PB1-binding site, were not found to interact with the C-terminal end of PB1. These results clearly indicate that the C-terminal end of PB1 and the N-terminal end of PB2 form a tight and essential subunit interface. The interacting fragments are especially short sequences from each subunit, only 80 and 37 residues of PB1 (SEQ ID NO: 2) and PB2 (SEQ ID NO: 4), respectively. These fragments together constitute only about 6% of the total molecular weight of the complex although they are responsible for crucial communication between subunits.

Figure 2:
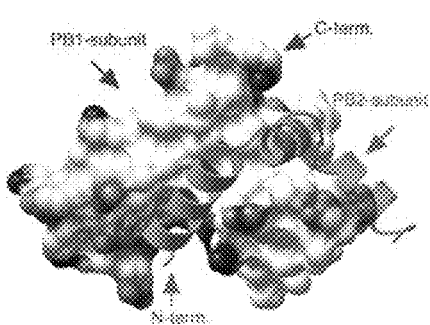
FIG. 2 shows the molecular surface of the C-terminal domain of PB1. (a) Schematic diagram showing the molecular surface of PB1 colored by charge (blue: positive, red: negative). The potential scale ranges from −1 kT/e (blue) to 1 kT/e (red). PB2 is shown as a green ribbon to reveal the PB1-binding surface beneath it is largely nonpolar. This diagram was prepared using CCP 4 mg (29). (b) The same diagram as shown in (a), in which the molecular surface of PB1 is colored yellow, except that hydrophobic residues Leu 695, Phe 699, Val 715 and Ile 750, which were mutated for testing, are colored red. Residues Ile 4, Leu 7 and Leu 10 in PB2 helix 1 (shown in green) form strong hydrophobic contacts with these four PB1 residues.
Figure 2:
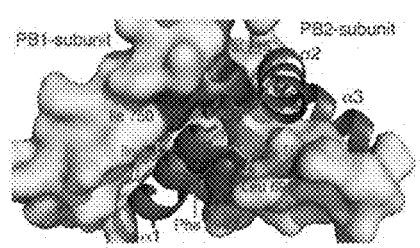
Figure 3:
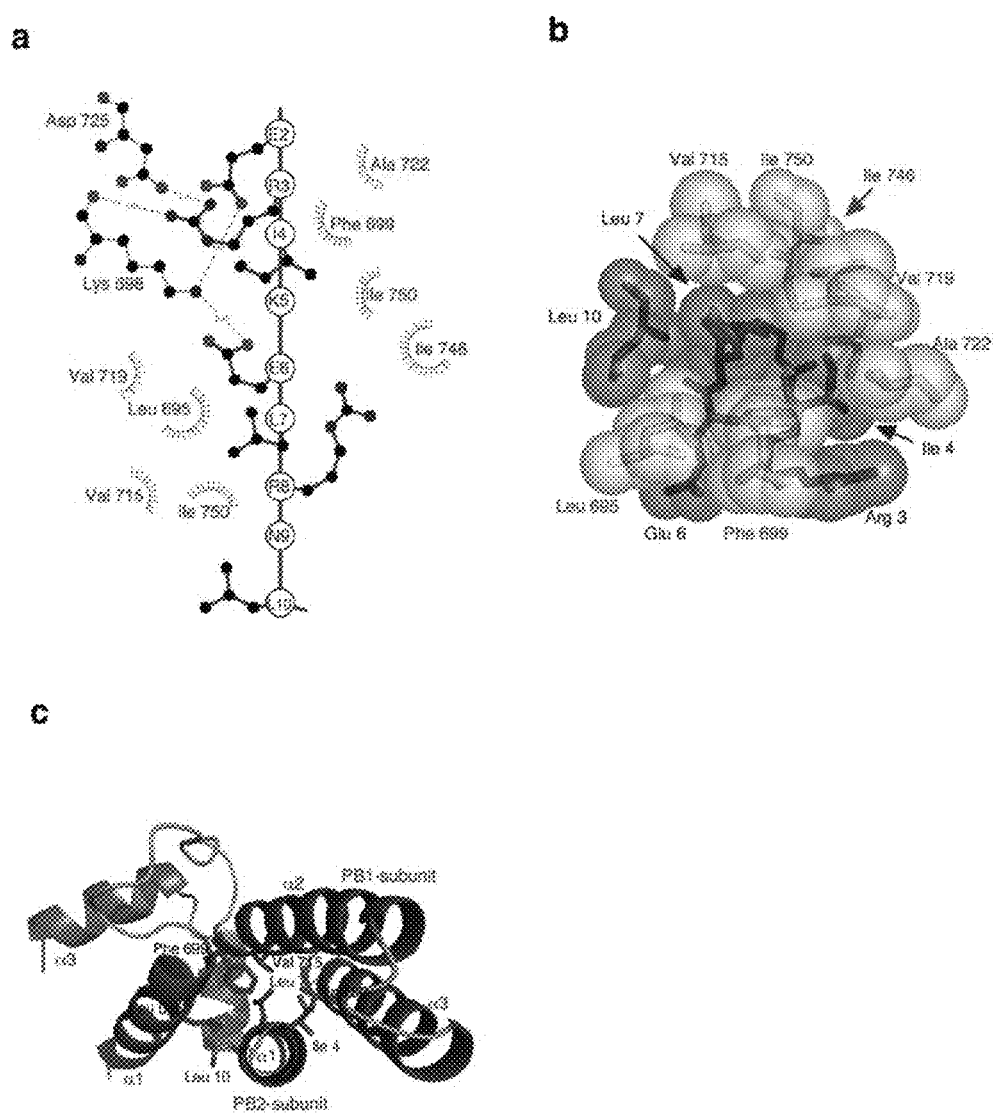
FIG. 3 shows the contact between PB1 and PB2. (a) Schematic diagram showing the interaction formed between PB2-N and PB1. Helix 1 of PB2-N is drawn as a linear model, and the side chain touching PB1 is shown in two-dimensional ball and stick form. Lys 698 and Asp 725 in PB1 form only salt bridges across the interface. Green broken lines indicate salt bridge bonds of 2.4-3.1 Å in length. Nonpolar residues in PB1 are shown in red, and simple dashed arcs indicate hydrophobic contacts of 3.4-3.9 Å in length. This diagram was prepared using LIGPLOT (30). (b) Space-filling representation of the same interaction interface as shown in (a). PB1 residues are shown in yellow and labeled in red. PB2 residues are shown and labeled in blue. The van der Waals surface of each atom is shown in semi-transparent. (c) Ribbon diagram showing Cα trace of PB1-C and PB2-N in red and blue, respectively, together with residues selected for mutagenesis.
Figure 4:
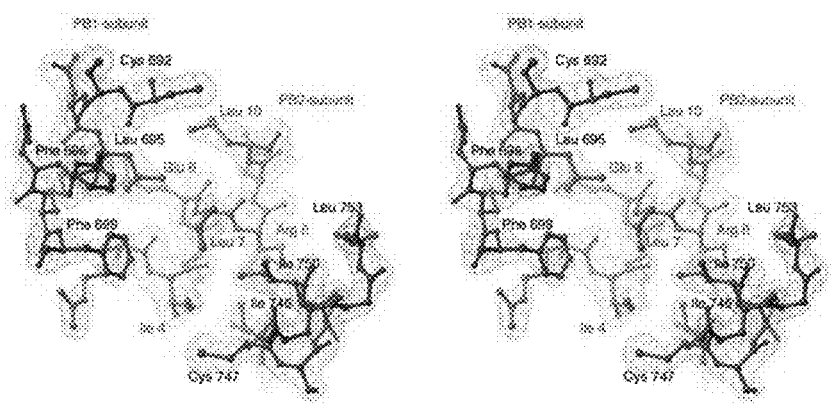
FIG. 4 shows electron density maps. Stereo view of the final electron density map (2mFo-DFc) covering key residues of the complex. PB1 is shown in red, and PB2 is shown in blue. The maps were contoured at 1.3 σ.
Figure 5:
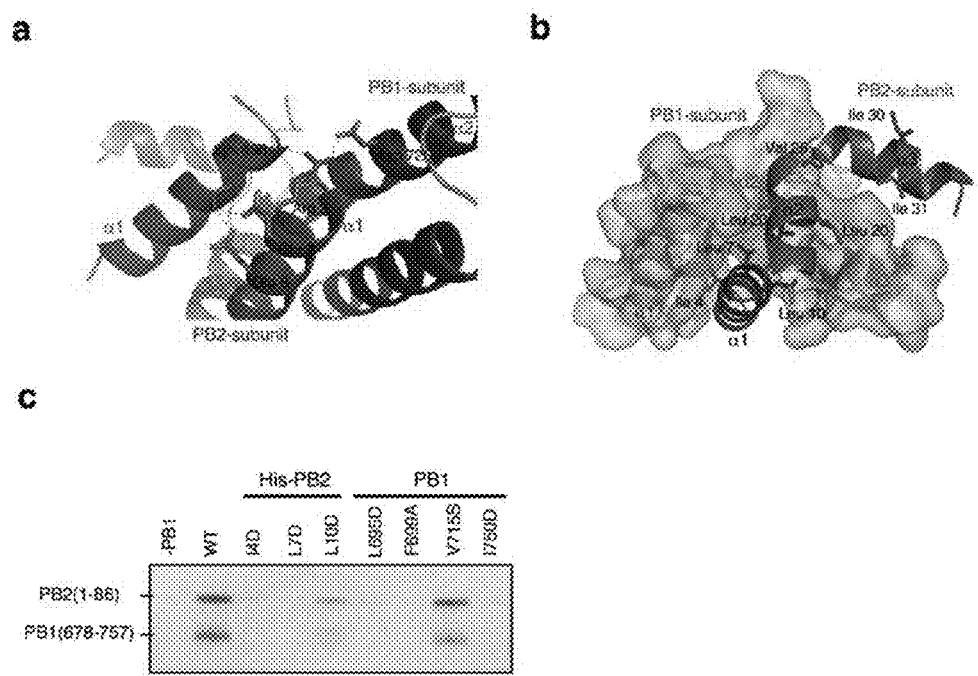
FIG. 5 shows interface contact and binding assay. (A) Ribbon diagram showing helixes from PB1 and PB2 in red and blue, respectively, and coil regions in green. Salt bridges formed between two proteins are indicated with blue dotted lines. The side chains of residues Glu 2 and Lys 698, Arg 3 and Asp 725, as well as Glu 6 and Lys 698 are shown in stick form, while oxygen and nitrogen atoms are colored red and blue, respectively. (B) Ribbon diagram of PB2 subunit (blue) together with PB1 having a semi-transparent molecular surface shown in yellow. Hydrophobic residues in PB2 are shown in blue, and their side chains are shown as blue bars. Helix 1 forms a major contact with PB1, whereas helix 3 forms little contact with PB1. (C) Pull-down experiment using Ni-NTA and wild-type and mutant fragments of PB1-C (residues 678-757) co-expressed with PB2-N (residues 1-86) carrying a hexa-histidine tag at the N-terminal end. Free PB2-N is unstable and cannot be detected when PB1-C is removed from the complex during the washing step. The results of Coomassie blue staining on a SDS PAGE gel indicated that the PB2 fragment would be degraded when not bound to PB1 (Lane "PB1"). Only the wild-type PB1 and V715S mutant were found to bind strongly to PB2-N.

Co-expression of PB1-C(C-terminal residues 678-757 of PB1, (SEQ ID NO: 16) with PB2-N(N-terminal residues 1-37 of PB2, (SEQ ID NO: 18) in *E. coli* yielded a stable complex that was able to be purified and crystallized. Its X-ray crystal structure was determined at 2.1 Å resolution, indicating that there were two copies of the complex in the asymmetric unit, which form a single compact domain (FIGS. 1A and 1B). This domain was found to be very highly conserved among all influenza virus strains (FIG. 1C) and to be stable in vitro (FIG. 1D). Almost all the residues of the two polypeptide chains were visible in the electron density, with only a few residues at the chain ends being disordered. The final electron density map covering key interface residues is shown in FIG. 4. PB1-C and PB2-N are each composed of three α-helices, but neither polypeptide alone takes a stable tertiary structure. Helix 1 of PB2-N is located against helices 2 and 3 of PB1-C, and helix 1 of PB1-C is held between all the three helixes of PB2-N. PB2-N has an extended shape with almost no intermolecular contact between its three helixes. N-terminal fragments of PB2 could be easily expressed and purified with an N-terminal GST tag, but these fusion proteins show no binding to PB1 in vitro, suggesting that they are not properly folded. Only the complex was produced by co-expression of the PB1 and PB2 domains. The interface is buried over a surface area of 1400 Å$^2$, is consistent with tight binding, and includes four salt bridges between Glu 2 and Lys 698, between Arg 3 and Asp 725, between Arg 3 and Lys 698, and between Glu 6 and Lys 698 (FIG. 3a). All the other eight hydrogen bonds between the polypeptides involve main-chain atoms. Analysis of the model by PISA (28) suggests that a similar interface is present in the KIX domain of mouse CREB-binding protein (PDB 1kdx), but direct superposition of the model shows a rather different interaction between polypeptide chains. No subunit interface in PDB was found to have the same "3 plus 3" helix structure, and the most similar ones, including 1 kdx, each have a buried surface area less than half that of the model. Unlike the interaction between the C-terminal end of PA and the N-terminal end of PB1, which has a predominantly hydrophobic character, the PB1-PB2 interface shows more polar interactions and is more extensive in sequence length and buried surface area (FIG. 2a, FIG. 3b and FIG. 5B). However, the majority of the interaction energy appears to be contributed by helix 1 of PB2-N, which involves not only the four salt bridges to PB1-C, but also the key nonpolar contacts, such as Ile 4 and Leu 7 (FIG. 3b, FIG. 3c and FIG. 6A). These two residues are completely buried in the protein interface.

2. Transcription Activity Assay in Double Mutations

To test this model for its functions, various PB2 mutants were prepared and examined for their effects on the level of viral RNA synthesis and on complex stability in vitro (FIGS. 6B to 6D). In this functional assay, no RNA product was detectable in the absence of PB2. Moreover, deletion of helix 1 in PB2 eliminated the RNA polymerase activity.

Further experiments were conducted with a PB2-N mutant ("14S/L7S") in which Ile 4 and Leu 7 of SEQ ID NO: 20 were replaced with serine residues, indicating that the yield of RNA products was greatly reduced (FIGS. 6B to 6D). Another mutant ("L7S/L105") in which Leu 7 and Leu 10 of SEQ ID NO: 20 were simultaneously replaced with serine also showed a great reduction in the yield of RNA products, as in the case of the 14S/L7S mutant (FIGS. 6B to 6D).

Furthermore, two double mutants were prepared from PB1 by replacement of Val 715 and Ile 750 with serine ("V7155/17505") or by replacement of Ile 746 and Ile 750 with serine ("1746S/1750S"). Both of these PB1 mutants showed a remarkable reduction in the yield of vRNA (FIG. 6B). These mutants also showed significant but smaller reductions in the yields of cRNA and mRNA (FIGS. 6C and 6D). These results can also be understood from the structural model, in which Leu 7 is buried within the hydrophobic core.

The side chain of nonpolar residue Val 715 is buried near the side chain of polar residue Leu 7. However, the side chain of Val 715 is located near polar residues on the protein surface (including Ser 713 and Arg 754, etc.), and hence its replacement with a serine side chain would not provide any great impact. Moreover, Ile 750 is located near the protein surface in this structural model, which presumably allows a serine residue, which is a polar residue, to occupy this position without inhibiting PB1-PB2 binding.

3. Transcription Activity Assay in Single Mutantion

Figure 7:
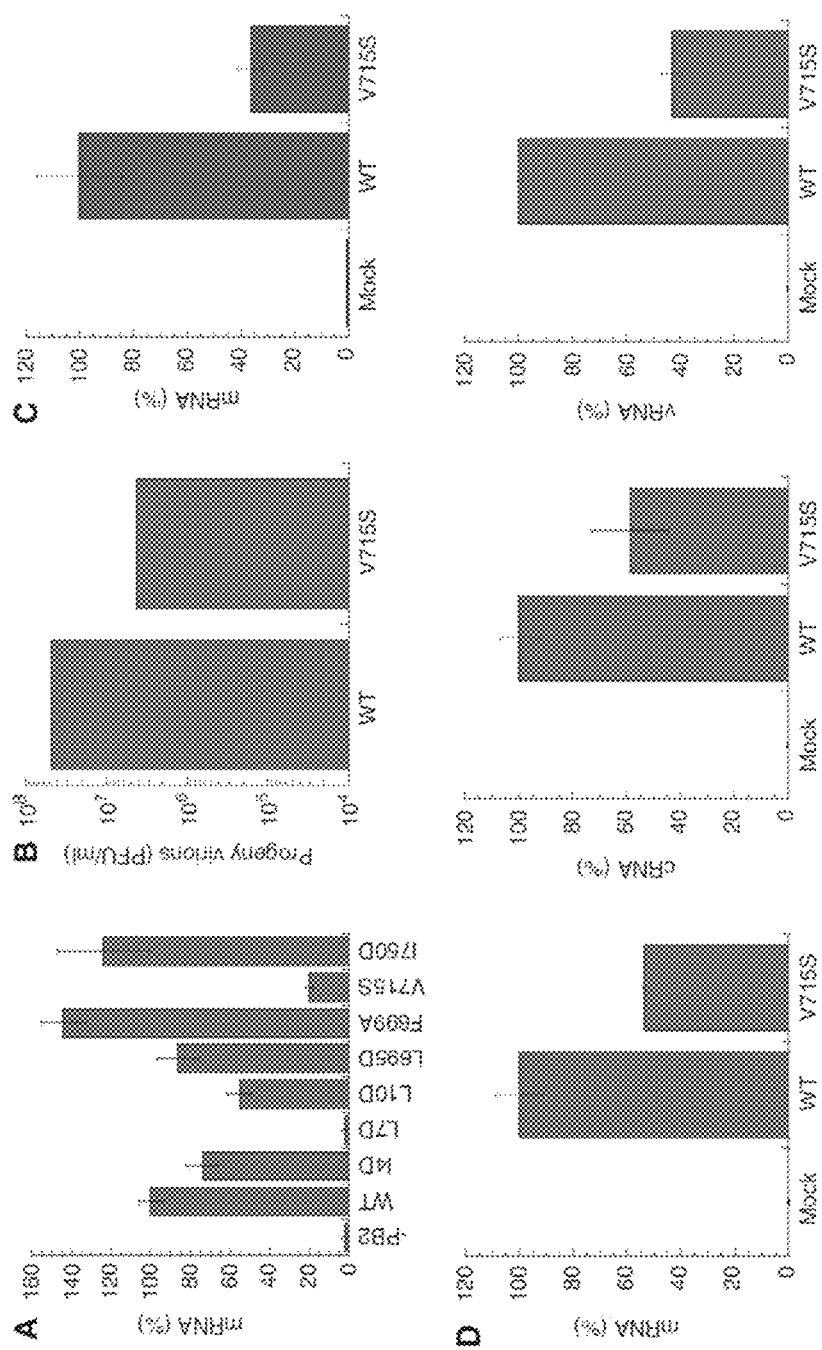
FIG. 7 shows RNA synthesis activity in PB1 single mutants or PB2 single mutants. (A) Bar chart showing the level of mRNA synthesis in various RNA polymerase single mutants, in comparison with the wild-type polymerase (WT). (B) Yield of progeny virus. (C) Level of mRNA produced in MDCK cells infected with the wild-type virus or PB1-V715S virus in the presence of cycloheximide. (D) Level of mRNA produced in MDCK cells infected with the wild-type virus or PB1-V715S virus in the absence of cycloheximide. The panels show the yields of mRNA (left panel), cRNA (middle panel) and segment 5 vRNA (right panel), respectively.

Further experiments were conducted with PB2-N mutants, in which a single residue was replaced. The yield of viral mRNA was evaluated in HeLa cells. The RNA synthesis activity was significantly reduced in the case of 14D mutant (in which the amino acid residue at position 4 was changed from isoleucine to aspartic acid; the same applies hereinafter). However, a more remarkable reduction in the yield of mRNA was found in another mutant (L7D) in which Leu 7 was replaced with aspartic acid (FIG. 7A). Similar experiments were also performed on PB1 mutants, i.e., L695D in which Leu 695 was replaced with aspartic acid, I750D in which Ile 750 was replaced with aspartic acid, F699A in which Phe 699 was replaced with alanine, and V715S in which Val715 was replaced with serine. None of these mutants showed a significant reduction in the yield of mRNA, except for V715S showing an 80% reduction (FIG. 7A).

Leu 695 and Ile 750 are both accessible to solvent water, which presumably allows an aspartic acid residue to replace either Leu 695 or Ile 750 without preventing PB1-PB2 binding. The nearby Arg 8 on PB2 may form a novel interaction with the carboxylate group of Asp 750 in the mutant. The side chains of both Val 715 and Phe 699 are buried near the side chain of Leu 7. When Phe 699 of PB2 is replaced with alanine ("F699A"), it is expected to introduce a substantial cavity within the interface. The significant increase in the yield of mRNA in the F699A mutant during functional assay may be caused by extra flexibility resulting from this cavity. As described above, the very strong decrease in the enzyme activity of the V715S mutant cannot be predicted from the structural model, which suggests that polar residues on the protein surface, including Ser 713 and Arg 754, will be able to hold a serine side chain. The structural model gives no reason that the valine to serine mutation inhibit or greatly reduce the PB1-PB2 interaction. Thus, the inventors of the present invention attempted to perform further experiments on this V715S mutation.

4. Analysis with Val715 mutant of PB1

According to procedures based on reverse genetics, a recombinant virus was constructed to have a PB1 genome segment carrying the V715S mutation (hereinafter referred to as "V715S virus"). In this V715S virus, all the seven segments other than the segment carrying the V715S mutation are of wild-type origin. With the use of the V715S virus in experiments, it was possible to analyze the effect of single-site mutation on the level of primary transcription from infected vRNP.

MDCK cells were infected with either wild-type or PB1-V715S virus at MOI=1. After 24 hours post infection, the cell supernatants were collected and the plaque titer was determined using the MDCK cells.

The inventors of the present invention succeeded in recovery of the V715S virus although the virus titer was slightly less than that of the wild-type virus (FIG. 7B). RNA polymerase is a part of the vRNP structure. Thus, the result that the V715S virus was able to be isolated indicates that the PB1-PB2 interaction is not inhibited by the Val715 mutation.

To test the level of viral primary transcription from infected vRNP, the inventors of the present invention infected MDCK cells with wild-type or PB1-V715S virus in the presence of 100 µg/ml cycloheximide (CHX). CHX is a potent protein synthesis inhibitor. It is known that inhibition of viral protein synthesis suppresses new vRNP formation, thereby resulting in a decrease in the level of replicated viral genomic RNA, but not of viral mRNA (S10).

With the use of CHX in the above test, the inventors of the present invention could evaluate the viral transcription activity independently of viral genome replication or the efficiency of trimeric polymerase complex formation.

Then, real-time quantitative PCR assay was performed with a primer set specific for NP mRNA.

As a result, the level of primary transcription from infected V715S vRNP was found to be remarkably reduced when compared to that from the wild-type vRNP (FIG. 7C).

In addition, RNA synthesis activity was measured for the wild-type or PB1-V715S virus in the absence of cycloheximide. In the measurement, the yields of mRNA, cRNA and segment 5 vRNA were evaluated separately. In the PB1-V715S virus, the yield of each RNA was significantly reduced. β-Actin mRNA was used as an internal control for the whole procedure.

As expected from the lower level of primary transcription, the synthesis of vRNA, cRNA and viral mRNA in the cells infected with the V715S virus was also reduced in the absence of CHX (FIG. 7D).

5. Pull-Down Assay

The results of the in vitro and in vivo functional assays strongly suggested that the Val 715 residue in PB1 would be involved in two or more steps in RNA synthesis reaction. To exclude the possibility that the V715S mutation simply blocks PB1-PB2 binding, pull-down assay was performed as follows: PB2-N fused with a histidine tag and PB1 were co-expressed and the resulting complex was bound to a Ni-NTA column.

The results of this pull-down assay were contrary to those of the functional assays described above. In this example, the complex was washed before being eluted with imidazole, and the loss or retention of PB1 was determined by gel electrophoresis. Free PB2-N was unstable and not detected in this assay. None of the L695D, F699A and I750D mutants showed binding to PB2-N, whereas the V715S mutant showed binding to PB2-N, as expected from the structural model (FIG. 5C). The reason why there is no correlation between the results of polymerase assay and pull-down assay is probably in part because of the fact that the latter is not a test of equilibrium binding and depends on the dissociation rate of the partner protein. The results of pull-down assay clearly indicate that the V715S mutation does not block PB1-PB2 binding. A weakened interaction between PB1 and PB2 is not apparently incompatible with the enzyme activity under the assay conditions used. In the polymerase activity assay, full-length PB1 and PB2 were used. The V715S mutant shows both considerable PB2 binding and greatly reduced enzyme activity, which suggests that a slightly altered mode of interaction may have an effect on the polymerase efficiency. The enzyme activity is not lost in this case because PB1 and PB2 do not bind to each other. The F699A and I750D mutants show weak PB2 binding, but their enzyme activity is enhanced. These contrary results indicate that the PB1-PB2 interface is not only a passive attachment surface by which the partner proteins come together, but it also plays an important role in regulating the overall enzyme activity.

Although the precise nature of signals induced by vRNA bound to PB1 is not elucidated, the structure of the cap-binding region in PB2 has been crystallized and structurally analyzed to show that it is an independently folded domain (3). Since loose PB1-PB2 binding is correlated at least somewhat with high polymerase activity, the wild-type model appears to be in a "tense" state, while the F699A and I750D mutants appear to be in a more relaxed state. Inhibition of the PB1-PB2 interaction would lead to the development of anti-influenza drugs against all strains of influenza A virus.

6. Discussion

Earlier reports have shown that a mutation in one of the polymerase subunits affects the functions of other subunits and is suppressed by a compensating mutation in another subunit (S11, S12).

These reports suggest that there are regulatory mechanisms for different polymerase functions through communication between subunits. Moreover, in view of the above reports, Val 715 in PB1 would assist the transcription of virus genes through signaling between PB1 and PB2. In this scenario, it can be understood that the V715S mutation allows binding between PB1 and PB2, but it inhibits proper communication between PB1 and PB2.

In T7 RNA polymerase, a major reorganization occurs during RNA synthesis (S13). If a major reorganization also occurs during RNA synthesis in the influenza RNA polymerase, as in the case of T7 RNA polymerase, it can be explained that the reduced polymerase activity of the V715S mutant is due to a conformational change in the polymerase protein, inhibition of the switch, and destabilization of the structure, etc.

In the V715S mutant, the polymerase activity is reduced although PB1 and PB2 bind to each other. This would be because, although valine and serine are of almost the same size, the replaced serine forms hydrogen bonding with surrounding water to cause a conformational change between PB1 and PB2, which in turn affects the polymerase activity.

Thus, the effects of the V715S mutation appear to occur through structural or dynamic changes in the complex during the RNA synthesis process. Moreover, the high sequence conservation in the PB1-PB2 interface also suggests that this interface not only simply serves to fold the two subunits together, but it also plays an important role in communication between the subunits.

Figure 6:
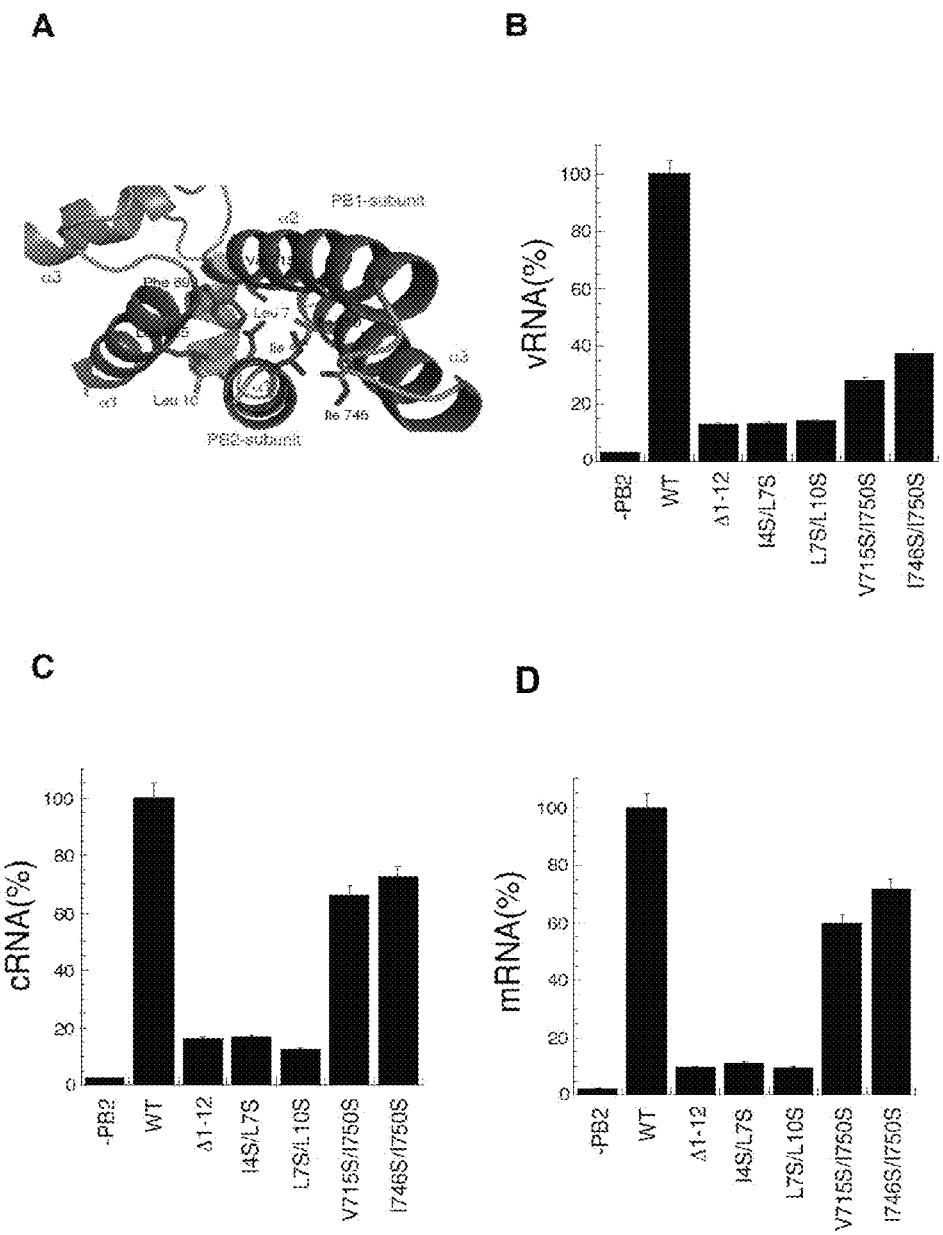
FIG. 6 shows viral RNA synthesis in double mutants. (A) Ribbon diagram showing Cα trace of PB1-C and PB2-N in red and blue, respectively, together with residues selected for mutagenesis. (B) Bar chart showing the level of viral genome (vRNA) synthesis in various RNA polymerase double mutants, in comparison with the wild-type complex. In the absence of PB2 subunit, enzyme activity is negligible. (C) Bar chart showing the level of viral genome replication intermediates (cRNA) produced by the mutants. (D) Bar chart showing the level of viral mRNA produced by the mutants.

Based on the above functional studies including transcription activity assay, the inventors of the present invention confirmed that helix 1 of PB2-N played an important role in viral mRNA synthesis. As shown in FIG. 6, deletion of this helix (residues 1-12) eliminated the RNA polymerase activity.

The inventors of the present invention also conducted additional experiments with the PB2 mutants. As a result, the various interface mutants showed a remarkable reduction in mRNA levels. This result is in agreement with the results of the above pull-down assay using the PB1-PB2 complex and Ni-NTA.

In contrast, some of the PB1 mutants carrying site-directed mutations showed greatly different results between enzyme activity assay and pull-down assay. For example, the F699A and I750D mutants show weak PB2 binding, but their enzyme activity is enhanced. In contrast, the V715S mutant bound significantly to PB2, but its enzyme activity was remarkably reduced.

This result suggests that a slightly altered mode of interaction will produce a remarkable effect on the polymerase efficiency.

The foregoing results prove that the PB1-PB2 interface is not only an interface for contact by which the partner proteins come together, but it also plays an important role in regulating the overall enzyme activity. The PB1-PB2 interface occupies a considerably low proportion of the entire 250 kDa polymerase complex, but it plays an important role in regulating the complex. Although the PB1-PB2 interface is completely conserved among avian and human influenza viruses (especially including species associated with high mortality), it has a different structure from any other proteins registered in the Protein Data Bank. Given its importance to viral replication and strict conservation, the PB1-PB2 interface can be expected as a target for novel anti-influenza drugs used against all types of influenza A virus. The structure presented herein will assist search for such compounds.

[Materials and Methods]

1. Cloning, Expression and Purification of PB1-PB2 Complex

The PA-PB1 complex was cloned and purified as reported earlier (S1). The sequence used was derived from influenza A/Puerto Rico/8/34 (S2). A PB2 gene fragment encoding residues 1-37, 1-86, 37-174, 252-490 or 530-759 of SEQ ID NO: 17 was cloned into pET28b together with a hexa-histidine tag and a TEV cleavage site at the N-terminal end. The PB1-C coding region (SEQ ID NO: 1) was cloned downstream of the PB2 gene with a Shine-Dalgarno sequence. The resulting co-expression plasmid was transformed into $E.\ coli$ BL21(DE3)RILP codon-plus strain, and the cells were cultured overnight at 15° C. after induction with 0.5 mM IPTG. The PB1-PB2 complex was purified by chromatography with a Ni-NTA agarose (Qiagen), followed by SP and Q (GE Healthcare) sepharose. After Ni-NTA chromatography, the histidine tag was removed by TEV protease digestion, and the purified complex was then concentrated to 5 mg/ml by centricon YM-3 (Millipore) for crystallization.

2. Pull-Down Assay

Pull-down assay was performed in the same manner as reported earlier (S1). The complex was bound to a nickel affinity column and then eluted with 500 mM imidazole. The eluted proteins were analyzed by SDS-acrylamide gel electrophoresis (15%) and Coomassie blue staining.

3. Reorganization of Model Viral RNP in Transformed Cells

Model viral RNP assay was prepared as reported earlier (S1, S14). HeLa cells were transfected with a viral protein expression plasmid encoding PA, PB1 (either wild-type or mutant), PB2 (either wild-type or mutant), NP and pHH21-vNS-Luc reporter plasmid. This reporter plasmid carries the luciferase gene in reverse orientation sandwiched between the 5'-terminal promoter sequence of 23 nucleotides and the 3'-terminal promoter sequence of 26 nucleotides from influenza virus segment 8. The luciferase gene is under the control of the human Pol I promoter. After incubation for 16 hours, luciferase assay (Promega) and real-time RT-PCR were performed. RNA purified from the cells was reverse transcribed with oligo $(dT)_{20}$ to determine the level of viral mRNA. The synthesized single-stranded cDNA was subjected to real-time quantitative PCR with two specific primers, i.e., 5'-TATGAA-CATTTCGCAGCCTACCGTAGTGTT-3' (SEQ ID NO: 13) corresponding to the luciferase coding region at nucleotide sequence positions 351-380 and 5'-CCGGAATGATTTGAT-TGCCA-3' (SEQ ID NO: 14) complementary to the luciferase coding region at nucleotide sequence positions 681-700. NP mRNA transcribed from the expression plasmid was used as an internal control.

4. Construction of Recombinant Virus

A recombinant virus carrying viral genome encoding a segment related to PB1-V715S was constructed by the plasmid-based transfection method reported by Neumann et al. (S15). The PB1-V715S genome segment and seven other wild-type genome segments were prepared by cellular RNA polymerase I. Wild-type PB1, PB2, PA and NP were prepared from plasmids encoding these proteins by cellular RNA polymerase II. After transfection, the cells were incubated for 48 hours and an aliquot of the cell culture supernatant was used for virus amplification in MDCK cells. At 48 hours after transfection, the culture solution was collected and stored at −80° C. until use.

5. Crystallization and Data Collection

Crystals of the PB1-PB2 complex were grown by the hanging drop vapor diffusion method against a crystallization buffer containing 0.1 M potassium phosphate (pH 5.8) and 15% PEG 4,000 at 20° C. Diffraction data were collected from the crystals cooled to −180° C. A crystallization buffer containing 25% glycerol was used to prevent freezing. X-ray diffraction data were collected on beam-line 17A at the Photon Factory in Japan. Selenomethionyl-substituted crystals were used to collect data sets at three different levels of X-ray energy around the Se—K absorption edge. An ADSC Quantum 270 CCD detector was used for data measurement. The crystals were formed in space group P2$_1$ with a=44.27 Å, b=61.48 Å, c=45.47 Å and β=103.4°, and contained two copies of the complex in the asymmetric unit. Diffraction data integration, scaling and merging were performed using HKL2000 and SCALEPACK (S3).

6. Structure Determination and Refinement

Using SHELXC and SHELXD (S4, S16), 12 positions of selenium were found among 14 possible Se-Met sites. Phase determination was performed with SOLVE (S5). After solvent flattening, high quality electron density maps at 2.1 Å resolution were obtained with RESOLVE (S6). The electron density was analyzed and traced with COOT (S7), followed by refinement of the model with REFMAC (S8). Solvent molecules were placed at positions where spherical electron density peaks were found above 1.3 σ in the |2Fo-Fc| map and above 3.0 σ in the |Fo-Fc| map, and where stereochemically reasonable hydrogen bonds were allowed. Structural evaluation was performed on the final model of the PB1-PB2 complex using PROCHECK (S9), indicating that 94% of the residues were in the most favorable regions of the Ramachandran plot, and no residues were in "disallowed" regions. The final model contained 109 of the 117 residues in the sequence, while residues 678-684 of PB1 (SEQ ID NO: 16) and residues 36-37 of PB2 (SEQ ID NO: 18) were not observed. The data collection and refinement statistics are summarized in Table 1 below. Atomic coordinates and structure factors of the complex have been registered in the Protein Data Bank under accession code 2ZTT. The data of the atomic coordinates for accession code 2ZTT follows.

TABLE 1

Data collection and refinement statistics.

| | | | |
|---|---|---|---|
| Space group/unit cell (Å) | P2$_1$/a = 44.27, b = 61.48, c = 45.47, β = 103.4 | | |
| Data sets | remote | inflection | peak |
| Resolution range (Å) | 20.0-2.1 | 20.0-2.1 | 20.0-2.1 |
| Reflections (Measured/Unique) | 72,079/13,052 | 72,082/12,849 | 73,974/12,930 |
| Completeness (Overall/Outer Shell, %)$^a$ | 92.9/85.6 | 93.0/81.5 | 94.3/83.7 |
| Rmerge$^b$ (Overall/Outer Shell, %) | 4.9/13.1 | 8.4/15.8 | 9.5/16.1 |
| Redundancy (Overall) | 5.6 | 5.7 | 5.8 |
| Mean <I/σ (I)> (Overall) | 20.5 | 21.1 | 22.1 |
| Phasing (20.0-2.1 Å) | | | |
| Riso$^c$ | 4.4 | 11.1 | 13.5 |
| Mean FOM$^d$ after RESOLVE phasing | 0.70 | | |
| Refinement statistics | | | |
| R-factor/free R-factor (%)$^e$ | 23.0/26.0 | | |
| R.m.s.d. bond lengths (Å)/bond angles (°) | 0.022/2.0 | | |
| Number of water molecules | 33 | | |
| Average B-factor (PB1/PB2/water, Å$^2$) | 52/47/45 | | |
| Ramachandran plot | | | |
| residues in most favorable regions (%) | 93.6 | | |
| residues in additiional allowed regions (%) | 6.4 | | |

$^a$Completeness and Rmerge, are given for overall data and for the highest resolution shell. The highest resolution shells for the MAD datasets are 2.18-2.10 Å, respectively.
$^b$Rmerge = Σ|I$_j$ − <I>|/Σ|I$_j$|; where I$_j$ is intensity of an observation and <I> in the mean value for that reflection and the summations are over all equivalents.
$^c$Riso = Σ|FPH − FP|/Σ|FPH|; where FPH and FP are the derivative and the native structure factor amplitudes respectively.
$^d$Figure of merit (FOM) = |Fbest| − |F|.
$^e$R factor = Σh|Fo(h) − Fc(h)|/Σ|hFo(h)|; where Fo and Fc are the observed and calculated structure factor amplitudes, respectively.
The free R-factor was calculated with 5% of the data excluded from the refinement.
$^c$Figure of merit (FOM) = |Fbest| − |F|.

TABLE 2a

Data of atomic coordinates for accession code 2ZTT

```
HEADER            TRANSFERASE 08-OCT-08 2ZTT
TITLE             CRYSTAL STRUCTURE OF RNA POLYMERASE PB1-PB2 SUBUNITS FROM
TITLE          2  INFLUENZA A VIRUS
COMPND    MOL_ID: 1;
COMPND         2  MOLECULE: RNA-DIRECTED RNA POLYMERASE CATALYTIC SUBUNIT;
COMPND         3  CHAIN: A, C;
COMPND         4  FRAGMENT: PB1 C-TERMINAL FRAGMENT, UNP RESIDUES 679-757;
COMPND         5  SYNONYM: RNA POLYMERASE PB1 SUBUNIT, POLYMERASE BASIC
COMPND         6  PROTEIN 1, PB1, RNA-DIRECTED RNA POLYMERASE SUBUNIT P1;
COMPND         7  EC: 2.7.7.48;
COMPND         8  ENGINEERED: YES;
COMPND         9  MOL_ID: 2;
COMPND        10  MOLECULE: POLYMERASE BASIC PROTEIN 2;
COMPND        11  CHAIN: B, D;
COMPND        12  FRAGMENT: PB2 N-TERMINAL FRAGMENT, UNP RESIDUES 1-37;
COMPND        13  SYNONYM: RNA POLYMERASE PB2 SUBUNIT, RNA-DIRECTED RNA
COMPND        14  POLYMERASE SUBUNIT P3;
COMPND        15  ENGINEERED: YES
SOURCE    MOL_ID: 1;
SOURCE         2  ORGANISM_SCIENTIFIC: INFLUENZA A VIRUS (A/PUERTO
SOURCE         3  RICO/8/34(H1N1));
SOURCE         4  ORGANISM TAXID: 211044;
SOURCE         5  GENE: PB1;
SOURCE         6  EXPRESSION_SYSTEM: ESCHERICHIA COLI;
```

TABLE 2a-continued

Data of atomic coordinates for accession code 2ZTT

| | | | |
|---|---|---|---|
| SOURCE | 7 | EXPRESSION_SYSTEM TAXID: 562; | |
| SOURCE | 8 | EXPRESSION_SYSTEM STRAIN: B824(DE3)CODONPLUS; | |
| SOURCE | 9 | EXPRESSION_SYSTEM VECTOR TYPE: PLASMID; | |
| SOURCE | 10 | EXPRESSION_SYSTEM PLASMID: MODIFIED PET28B; | |
| SOURCE | 11 | MOL_ID: 2; | |
| SOURCE | 12 | ORGANISM_SCIENTIFIC: INFLUENZA A VIRUS (A/PUERTO | |
| SOURCE | 13 | RICO/8/34(H1N1)); | |
| SOURCE | 14 | ORGANISM_TAXID: 211044; | |
| SOURCE | 15 | GENE: PB2; | |
| SOURCE | 16 | EXPRESSION_SYSTEM: *ESCHERICHIA COLI*; | |
| SOURCE | 17 | EXPRESSION_SYSTEM TAXID: 562; | |
| SOURCE | 18 | EXPRESSION_SYSTEM STRAIN: B834(DE3)CODONPLUS; | |
| SOURCE | 19 | EXPRESSION_SYSTEM VECTOR TYPE: PLASMID; | |
| SOURCE | 20 | EXPRESSION_SYSTEM PLASMID: MODIFIED PET28B | |
| KEYWDS | | INFLUENZA VIRUS,RNA POLYMERASE, PB1-PB2 COMPLEX FORM, | |
| KEYWDS | 2 | NUCLEOTIDE-BINDING, NUCLEOTIDYLTRANSFERASE, NUCLEUS, RNA | |
| KEYWDS | 3 | REPLICATION, RNA-DIRECTED RNA POLYMERASE, TRANSFERASE, | |
| KEYWDS | 4 | MITOCHONDRION, MRNA CAPPING, MRNA PROCESSING, VIRION | |
| EXPDTA | | X-RAY DIFFRACTION | |
| AUTHOR | | K.SUGIYAMA,E.OBAYASHI,S.-Y.PARK | |
| REVDAT | 2 | 07-JUL-09 2ZTT 1 JRNL | |
| REVDAT | 1 | 09-JUN-09 2ZTT 0 | |
| JRNL | AUTH | K.SUGIYAMA,E.OBAYASHI,A.KAWAGUCHI,Y.SUZUKI, | |
| JRNL | AUTH 2 | J.R.H.TAME,K.NAGATA,S.-Y.PARK | |
| JRNL | TITL | STRUCTURAL INSIGHT INTO THE ESSENTIAL PB1-PB2 | |
| JRNL | TITL 2 | SUBUNIT CONTACT OF THE INFLUENZA VIRUS RNA | |
| JRNL | TITL 3 | POLYMERASE | |
| JRNL | REF | EMBO J. V. 28 1803 2009 | |
| JRNL | REFN | ISSN 0261-4189 | |
| JRNL | PMID | 19461581 | |
| JRNL | DOI | 10.1038/EMBOJ.2009.138 | |
| REMARK | 1 | | |
| REMARK | 2 | | |
| REMARK | 2 | RESOLUTION. 2.10 ANGSTROMS. | |
| REMARK | 3 | | |
| REMARK | 3 | REFINEMENT. | |
| REMARK | 3 | PROGRAM: REFMAC 5.2.0019 | |
| REMARK | 3 | AUTHORS: MURSHUDOV,VAGIN,DODSON | |
| REMARK | 3 | | |
| REMARK | 3 | REFINEMENT TARGET: MAXIMUM LIKELIHOOD | |
| REMARK | 3 | | |
| REMARK | 3 | DATA USED IN REFINEMENT. | |
| REMARK | 3 | RESOLUTION RANGE HIGH (ANGSTROMS): | 2.10 |
| REMARK | 3 | RESOLUTION RANGE LOW (ANGSTROMS): | 20.0 |
| REMARK | 3 | DATA CUTOFF (SIGMA(F)): | NULL |
| REMARK | 3 | COMPLETENESS FOR RANGE (%): | 100.0 |
| REMARK | 3 | NUMBER OF REFLECTIONS: | 12352 |
| REMARK | 3 | | |
| REMARK | 3 | FIT TO DATA USED IN REFINEMENT. | |
| REMARK | 3 | CROSS-VALIDATION METHOD: | THROUGHOUT |
| REMARK | 3 | FREE R VALUE TEST SET SELECTION: | RANDOM |
| REMARK | 3 | R VALUE (WORKING +TEST SET): | 0.235 |
| REMARK | 3 | R VALUE (WORKING SET): | 0.232 |
| REMARK | 3 | FREE R VALUE: | 0.272 |
| REMARK | 3 | FREE R VALUE TEST SET SIZE (%): | 4.90 |
| REMARK | 3 | FREE R VALUE TEST SET COUNT: | 633 |
| REMARK | 3 | | |
| REMARK | 3 | FIT IN THE HIGHEST RESOLUTION BIN. | |
| REMARK | 3 | TOTAL NUMBER OF BINS USED: | 20 |
| REMARK | 3 | BIN RESOLUTION RANGE HIGH (A): | 2.10 |
| REMARK | 3 | BIN RESOLUTION RANGE LOW (A): | 2.15 |
| REMARK | 3 | REFLECTION IN BIN (WORKING SET): | 841 |
| REMARK | 3 | BIN COMPLETENESS (WORKING+TEST) (%): | 100.0 |
| REMARK | 3 | BIN R VALUE (WORKING SET): | 0.3060 |
| REMARK | 3 | BIN FREE R VALUE SET COUNT: | 43 |
| REMARK | 3 | BIN FREE R VALUE: | 0.2970 |
| REMARK | 3 | | |
| REMARK | 3 | NUMBER OF NON-HYDROGEN ATOM S USED IN REFINEMENT. | |
| REMARK | 3 | PROTEIN ATOMS: | 1797 |
| REMARK | 3 | NUCLEIC ACID ATOMS: | 0 |
| REMARK | 3 | HETEROGEN ATOMS: | 0 |
| REMARK | 3 | SOLVENT ATOMS: | 33 |
| REMARK | 3 | | |
| REMARK | 3 | B VALUES. | |
| REMARK | 3 | FROM WILSON PLOT (A**2): | NULL |
| REMARK | 3 | MEAN B VALUE (OVERALL, A**2): | 49.20 |
| REMARK | 3 | OVERALL ANISOTROPIC B VALUE. | |
| REMARK | 3 | B11 (A**2): 5.7000 | |

TABLE 2a-continued

Data of atomic coordinates for accession code 2ZTT

| REMARK | 3 | B22 (A**2): | −3.9700 | | |
|---|---|---|---|---|---|
| REMARK | 3 | B33 (A**2): | 1.5500 | | |
| REMARK | 3 | B12 (A**2): | 0.0000 | | |
| REMARK | 3 | B13 (A**2): | 7.1000 | | |
| REMARK | 3 | B23 (A**2): | 0.0000 | | |
| REMARK | 3 | | | | |
| REMARK | 3 | ESTIMATED OVERALL COORDINATE ERROR. | | | |
| REMARK | 3 | ESU BASED ON R VALUE (A): | 0.299 | | |
| REMARK | 3 | ESU BASED ON FREE R VALUE (A): | 0.223 | | |
| REMARK | 3 | ESU BASED ON MAXIMUM LIKELIHOOD (A): | 0.219 | | |
| REMARK | 3 | ESU FOR B VALUES BASED ON MAXIMUM LIKELIHOOD (A**2): | 8.532 | | |
| REMARK | 3 | | | | |
| REMARK | 3 | CORRELATION COEFFICIENTS. | | | |
| REMARK | 3 | CORRELATION COEFFICIENT FO-FC: | 0.939 | | |
| REMARK | 3 | | | | |
| REMARK | 3 | RMS DEVIATIONS FROM IDEAL VALUES | COUNT | RMS | WEIGHT |
| REMARK | 3 | BOND LENGTHS REFINED ATOMS (A): | 1815 | ; 0.022 ; | 0.022 |
| REMARK | 3 | BOND LENGTHS OTHERS (A): | NULL | ; NULL ; | NULL |
| REMARK | 3 | BOND ANGLES REFINED ATOMS (DEGREES): | 2411 | ; 2.066 ; | 1.975 |
| REMARK | 3 | BOND ANGLES OTHERS (DEGREES): | NULL | ; NULL ; | NULL |
| REMARK | 3 | TORSION ANGLES, PERIOD 1 (DEGREES): | 214 | ; 7.115 ; | 5.00 |
| REMARK | 3 | TORSION ANGLES, PERIOD 2 (DEGREES): | 87 | ; 35.731 ; | 22.184 |
| REMARK | 3 | TORSION ANGLES, PERIOD 3 (DEGREES): | 393 | ; 21.270 ; | 15.00 |
| REMARK | 3 | TORSION ANGLES, PERIOD 4 (DEGREES): | 25 | ; 22.698 ; | 15.00 |
| REMARK | 3 | CHIRAL-CENTER RESTRAINTS (A**3): | 266 | ; 0.138 ; | 0.20 |
| REMARK | 3 | GENERAL PLANES REFINED ATOMS (A): | 1307 | ; 0.007 ; | 0.020 |
| REMARK | 3 | GENERAL PLANES OTHERS (A): | NULL | ; NULL ; | NULL |
| REMARK | 3 | NON-BONDED CONTACTS REFINED ATOMS (A): | 880 | ; 0.271 ; | 0.20 |
| REMARK | 3 | NON-BONDED CONTACTS OTHERS (A): | NULL | ; NULL ; | NULL |
| REMARK | 3 | NON-BONDED TORSION REFINED ATOMS (A): | 1274 | ; 0.314 ; | 0.20 |
| REMARK | 3 | NON-BONDED TORSION OTHERS (A): | NULL | ; NULL ; | NULL |
| REMARK | 3 | H-BOND (X...Y) REFINED ATOMS (A): | 62 | ; 0.213 ; | 0.20 |
| REMARK | 3 | H-BOND (X...Y) OTHERS (A): | NULL | ; NULL ; | NULL |
| REMARK | 3 | POTENTIAL METAL-ION REFINED ATOMS (A): | NULL | ; NULL ; | NULL |
| REMARK | 3 | POTENTIAL METAL-ION OTHERS (A): | NULL | ; NULL ; | NULL |
| REMARK | 3 | SYMMETRY VDW REFINED ATOMS (A): | 36 | ; 0.224 ; | 0.20 |
| REMARK | 3 | SYMMETRY VDW OTHERS (A): | NULL | ; NULL ; | NULL |
| REMARK | 3 | SYMMETRY H-BOND REFINED ATOMS (A): | 2 | ; 0.174 ; | 0.20 |
| REMARK | 3 | SYMMETRY H-BOND OTHERS (A): | NULL | ; NULL ; | NULL |
| REMARK | 3 | SYMMETRY METAL-ION REFINED ATOMS (A): | NULL | ; NULL ; | NULL |
| REMARK | 3 | SYMMETRY METAL-ION OTHERS (A): | NULL | ; NULL ; | NULL |
| REMARK | 3 | | | | |
| REMARK | 3 | ISOTROPIC THERMAL FACTOR RESTRAINTS. | COUNT | RMS | WEIGHT |
| REMARK | 3 | MAIN-CHAIN BOND REFINED ATOMS (A**2): | 1135 | ; 1.593 ; | 1.50 |
| REMARK | 3 | MAIN-CHAIN BOND OTHER ATOMS (A**2): | NULL | ; NULL ; | NULL |
| REMARK | 3 | MAIN-CHAIN ANGLE REFINED ATOMS (A**2): | 1764 | ; 2.259 ; | 2.00 |
| REMARK | 3 | SIDE-CHAIN BOND REFINED ATOMS (A**2): | 766 | ; 3.984 ; | 3.00 |
| REMARK | 3 | SIDE-CHAIN ANGLE REFINED ATOMS (A**2): | 647 | ; 5.516 ; | 4.50 |
| REMARK | 3 | | | | |
| REMARK | 3 | ANISOTROPIC THERMAL FACTOR RESTRAINTS. | COUNT | RMS | WEIGHT |
| REMARK | 3 | RIGID-BOND RESTRAINTS (A**2): | NULL | ; NULL ; | NULL |
| REMARK | 3 | SPHERICITY; FREE ATOM (A**2): | NULL | ; NULL ; | NULL |
| REMARK | 3 | SPHERICITY; BONDED ATOMS (A**2): | NULL | ; NULL ; | NULL |
| REMARK | 3 | | | | |
| REMARK | 3 | NCS RESTRAINTS STATISTICS | | | |
| REMARK | 3 | NUMBER OF DIFFERENT NCS GROUPS: | NULL | | |
| REMARK | 3 | | | | |
| REMARK | 3 | TLS DETAILS | | | |
| REMARK | 3 | NUMBER OF TLS GROUPS: | NULL | | |
| REMARK | 3 | | | | |
| REMARK | 3 | BULK SOLVENT MODELLING. | | | |
| REMARK | 3 | METHOD USED: BABINET MODEL WITH MASK | | | |
| REMARK | 3 | PARAMETERS FOR MASK CALCULATION | | | |
| REMARK | 3 | VDW PROBE RADIUS: | 1.20 | | |
| REMARK | 3 | ION PROBE RADIUS: | 0.80 | | |
| REMARK | 3 | SHRINKAGE RADIUS: | 0.80 | | |
| REMARK | 3 | | | | |
| REMARK | 3 | OTHER REFINEMENT REMARKS: NULL | | | |
| REMARK | 4 | | | | |
| REMARK | 4 | 2ZTT COMPLIES WITH FORMAT V. 3.20, 01-DEC-08 | | | |
| REMARK | 10 | | | | |
| REMARK | 100 | THIS ENTRY HAS BEEN PROCESSED BY PDBJ ON 14-OCT-08. | | | |
| REMARK | 100 | THE RCSB ID CODE IS RCSB028416. | | | |
| REMARK | 200 | | | | |
| REMARK | 200 | EXPERIMENTAL DETAILS | | | |
| REMARK | 200 | EXPERIMENT TYPE: | X-RAY DIFFRACTION | | |
| REMARK | 200 | DATE OF DATA COLLECTION: | 18-JUN-08 | | |
| REMARK | 200 | TEMPERATURE (KELVIN): | 273 | | |

TABLE 2a-continued

Data of atomic coordinates for accession code 2ZTT

| REMARK | 200 | PH: | 5.8 | |
|---|---|---|---|---|
| REMARK | 200 | NUMBER OF CRYSTALS USED: | 1 | |
| REMARK | 200 | | | |
| REMARK | 200 | SYNCHROTRON (Y/N): | Y | |
| REMARK | 200 | RADIATION SOURCE: | PHOTON FACTORY | |
| REMARK | 200 | BEAMLINE: | BL-17A | |
| REMARK | 200 | X-RAY GENERATOR MODEL: | NULL | |
| REMARK | 200 | MONOCHROMATIC OR LAUE (M/L): | M | |
| REMARK | 200 | WAVELENGTH OR RANGE (A): | 0.97898,0.97931,0.9832 | |
| REMARK | 200 | MONOCHROMATOR: | NULL | |
| REMARK | 200 | OPTICS: | MIRRORS | |
| REMARK | 200 | | | |
| REMARK | 200 | DETECTOR TYPE: | CCD | |
| REMARK | 200 | DETECTOR MANUFACTURER: | ADSC QUANTUM 270 | |
| REMARK | 200 | INTENSITY-INTEGRATION SOFTWARE: | HKL-200 | |
| REMARK | 200 | DATA SCALING SOFTWARE: | SCALEPACK | |
| REMARK | 200 | | | |
| REMARK | 200 | NUMBER OF UNIQUE REFLECTIONS: | 13052 | |
| REMARK | 200 | RESOLUTION RANGE HIGH (A): | 2.10 | |
| REMARK | 200 | RESOLUTION RANGE LOW (A): | 50.00 | |
| REMARK | 200 | REJECTION CRITERIA (SIGMA(I)): | 0.00 | |
| REMARK | 200 | | | |
| REMARK | 200 | OVERALL. | | |
| REMARK | 200 | COMPLETENESS FOR RANGE (%): | 92.9 | |
| REMARK | 200 | DATA REDUNDANCY: | 5.60 | |
| REMARK | 200 | R MERGE (I): | 0.0490 | |
| REMARK | 200 | R SYM (I): | NULL | |
| REMARK | 200 | <I/SIGMA(I)>FOR THE DATA SET: | 20.500 | |
| REMARK | 200 | | | |
| REMARK | 200 | IN THE HIGHEST RESOLUTION SHELL. | | |
| REMARK | 200 | HIGHEST RESOLUTION SHELL, RANGE HIGH (A): | | 2.10 |
| REMARK | 200 | HIGHEST RESOLUTION SHELL, RANGE LOW (A): | | 2.18 |
| REMARK | 200 | COMPLETENESS FOR SHELL (%): | 85.6 | |
| REMARK | 200 | DATA REDUNDANCY IN SHELL: | NULL | |
| REMARK | 200 | R MERGE FOR SHELL (I): | 0.1310 | |
| REMARK | 200 | R SYM FOR SHELL (I): | NULL | |
| REMARK | 200 | <I/SIGMA(I)>FOR SHELL: | NULL | |
| REMARK | 200 | | | |
| REMARK | 200 | DIFFRACTION PROTOCOL: MAD | | |
| REMARK | 200 | METHOD USED TO DETERMINE THE STRUCTURE: MAD | | |
| REMARK | 200 | SOFTWARE USED: SOLVE | | |
| REMARK | 200 | STARTING MODEL: NULL | | |
| REMARK | 200 | | | |
| REMARK | 200 | REMARK: NULL | | |
| REMARK | 280 | | | |
| REMARK | 280 | CRYSTAL | | |
| REMARK | 280 | SOLVENT CONTENT, VS (%): 41.50 | | |
| REMARK | 280 | MATTHEWS COEFFICIENT, VM (ANGSTROMS**3/DA): 2.10 | | |
| REMARK | 280 | | | |
| REMARK | 280 | CRYSTALLIZATION CONDITIONS: 0.1M POTASSIUM PHOSPHATE, 15% PEG | | |
| REMARK | 280 | 4000, PH 5.8, VAPOR DIFFUSION, HANGING DROP, TEMPERATURE 298K | | |
| REMARK | 290 | | | |
| REMARK | 290 | CRYSTALLOGRAPHIC SYMMETRY | | |
| REMARK | 290 | SYMMETRY OPERATORS FOR SPACE GROUP: P 1 21 1 | | |
| REMARK | 290 | | | |
| REMARK | 290 | SYMOP SYMMETRY | | |
| REMARK | 290 | NNNMMH OPERATOR | | |
| REMARK | 290 | 1555 X,Y,Z | | |
| REMARK | 290 | 2555 −X,Y+1/2,−Z | | |
| REMARK | 290 | | | |
| REMARK | 290 | WHERE NNN ->OPERATOR NUMBER | | |
| REMARK | 290 | MMM ->TRANSLATION VECTOR | | |
| REMARK | 290 | | | |
| REMARK | 290 | CRYSTALLOGRAPHIC SYMMETRY TRANSFORMATIONS | | |
| REMARK | 290 | THE FOLLOWING TRANSFORMATIONS OPERATE ON THE ATOM/HETATM | | |
| REMARK | 290 | RECORDS IN THIS ENTRY TO PRODUCE CRYSTALLOGRAPHICALLY | | |
| REMARK | 290 | RELATED MOLECULES. | | |
| REMARK | 290 | SMTRY1 1 1.00000 0.00000 0.00000 0.0000 | | |
| REMARK | 290 | SMTRY2 1 0.00000 1.00000 0.00000 0.0000 | | |
| REMARK | 290 | SMTRY3 1 0.00000 0.00000 1.00000 0.0000 | | |
| REMARK | 290 | SMTRY1 2 −1.00000 0.00000 0.0000 0.00000 | | |
| REMARK | 290 | SMTRY2 2 0.00000 1.00000 0.00000 30.73850 | | |
| REMARK | 290 | SMTRY3 2 0.00000 0.000000 −1.00000 0.0000 | | |
| REMARK | 290 | | | |
| REMARK | 290 | REMARK: NULL | | |
| REMARK | 300 | | | |
| REMARK | 300 | BIOMOLECULE: 1, 2 | | |
| REMARK | 300 | SEE REMARK 350 FOR THE AUTHOR PROVIDED AND/OR PROGRAM | | |

TABLE 2a-continued

Data of atomic coordinates for accession code 2ZTT

| | | |
|---|---|---|
| REMARK | 300 | GENERATED ASSEMBLY INFORMATION FOR THE STRUCTURE IN |
| REMARK | 300 | THIS ENTRY. THE REMARK MAY ALSO PROVIDE INFORMATION ON |
| REMARK | 300 | BURIED SURFACE AREA. |
| REMARK | 350 | |
| REMARK | 350 | COORDINATES FOR A COMPLETE MULTIMER REPRESENTING THE KNOWN |
| REMARK | 350 | BIOLOGICALLY SIGNIFICA NT OLIGOMERIZATION STATE OF THE |
| REMARK | 350 | MOLECULE CAN BE GENERATED BY APPLYING BIOMT TRANSFORMATIONS |
| REMARK | 350 | GIVEN BELOW. BOTH NON-CRYSTALLOGRAPHIC AND |
| REMARK | 350 | CRYSTALLOGRAPHIC OPERATIONS ARE GIVEN. |
| REMARK | 350 | |
| REMARK | 350 | BIOMOLECULE: 1 |
| REMARK | 350 | AUTHOR DETERMINED BIOLOGICAL UNIT: DIMERIC |
| REMARK | 350 | SOFTWARE DETERMINED QUATERNARY STRUCTURE: DIMERIC |
| REMARK | 350 | SOFTWARE USED: PISA |
| REMARK | 350 | TOTAL BURIED SURFACE AREA: 2800 ANGSTROM**2 |
| REMARK | 350 | SURFACE AREA OF THE COMPLEX: 7250 ANGSTROM**2 |
| REMARK | 350 | CHANGE IN SOLVENT FREE ENERGY: −24.0 KCAL/MOL |
| REMARK | 350 | APPLY THE FOLLOWING TO CHAINS: A, B |
| REMARK | 350 |    BIOMT1  1  1.00000  0.00000  0.00000  0.0000 |
| REMARK | 350 |    BIOMT2  1  0.00000  1.00000  0.00000  0.0000 |
| REMARK | 350 |    BIOMT3  1  0.00000  0.00000  1.00000  0.0000 |
| REMARK | 350 | |
| REMARK | 350 | BIOMOLECULE: 2 |
| REMARK | 350 | AUTHOR DETERMINED BIOLOGICAL UNIT: DIMERIC |
| REMARK | 350 | SOFTWARE DETERMINED QUATERNARY STRUCTURE: DIMERIC |
| REMARK | 350 | SOFTWARE USED: PISA |
| REMARK | 350 | TOTAL BURIED SURFACE AREA: 3100 ANGSTROM**2 |
| REMARK | 350 | SURFACE AREA OF THE COMPLEX: 6820 ANGSTROM**2 |
| REMARK | 350 | CHANGE IN SOLVENT FREE ENERGY: −27.0 KCAL/MOL |
| REMARK | 350 | APPLY THE FOLLOWING TO CHAINS: C, D |
| REMARK | 350 |    BIOMT1  1  1.00000  0.00000  0.00000  0.0000 |
| REMARK | 350 |    BIOMT2  1  0.00000  1.00000  0.00000  0.0000 |
| REMARK | 350 |    BIOMT3  1  0.00000  0.00000  1.00000  0.0000 |
| REMARK | 465 | |
| REMARK | 465 | MISSING RESIDUES |
| REMARK | 465 | THE FOLLOWING RESIDUES WERE NOT LOCATED IN THE |
| REMARK | 465 | EXPERIMENT. (M=MODEL NUMBER; RES=RESIDUE NAME; C=CHAIN |
| REMARK | 465 | IDENTIFIER; SSSEQ=SEQUENCE NUMBER; I=INSERTION CODE.) |
| REMARK | 465 | |
| REMARK | 465 |   M   RES   C   SSSEQI |
| REMARK | 465 |       GLN  A  679 |
| REMARK | 465 |       ARG  A  680 |
| REMARK | 465 |       GLY  A  681 |
| REMARK | 465 |       VAL  A  682 |
| REMARK | 465 |       LEU  A  683 |
| REMARK | 465 |       GLU  A  684 |
| REMARK | 465 |       GLY  B  −2 |
| REMARK | 465 |       SER  B  36 |
| REMARK | 465 |       GLY  B  37 |
| REMARK | 465 |       GLN  C  679 |
| REMARK | 465 |       ARG  C  680 |
| REMARK | 465 |       GLY  C  681 |
| REMARK | 465 |       VAL  C  682 |
| REMARK | 465 |       LEU  C  683 |
| REMARK | 465 |       ARG  C  755 |
| REMARK | 465 |       GLN  C  756 |
| REMARK | 465 |       LYS  C  757 |
| REMARK | 465 |       GLY  D  −2 |
| REMARK | 465 |       SER  D  36 |
| REMARK | 465 |       GLY  D  37 |
| REMARK | 500 | |
| REMARK | 500 | GEOMETRY AND STEREOCHEMISTRY |
| REMARK | 500 | SUBTOPIC: TORSION ANGLES |
| REMARK | 500 | |
| REMARK | 500 | TORSION ANGLES OUTSIDE THE EXPECTED RAMACHANDRAN REGIONS: |
| REMARK | 500 | (M=MODEL NUMBER; RES=RESIDUE NAME; C=CHAIN IDENTIFIER; |
| REMARK | 500 | SSEQ=SEQUENCE NUMBER; I=INSERTION CODE). |
| REMARK | 500 | |
| REMARK | 500 | STANDARD TABLE: |
| REMARK | 500 | FORMAT:(10X,I3,1X,A3,1X,A1,14,A1,4X,F7.2,3X,F7.2) |
| REMARK | 500 | |
| REMARK | 500 | EXPECTED VALUES: GJ KLEYWEGT AND TA JONES (1996). PHI/PSI- |
| REMARK | 500 | CHOLOGY: RAMACHANDRAN REVISITED. STRUCTURE 4, 1395 - 140 |
| REMARK | 500 | |
| REMARK | 500 |      M     RES    CSSEQI    PSI     PHI |
| REMARK | 500 |           GLU    A 686    33.24   −86.47 |
| REMARK | 500 |           GLN    A 756   153.21   178.74 |
| REMARK | 500 |           LYS    B  33    2.48   −64.66 |

TABLE 2a-continued

Data of atomic coordinates for accession code 2ZTT

| | | | | | | | |
|---|---|---|---|---|---|---|---|
| REMARK | 500 | | TYR | B 34 | 24.65 | -140.87 | |
| REMARK | 500 | | ARG | C 706 | 107.01 | -50.87 | |
| REMARK | 500 | | | | | | |
| REMARK | 500 | REMARK: NULL | | | | | |
| REMARK | 500 | | | | | | |
| REMARK | 500 | GEOMETRY AND STEREOCHEMISTRY | | | | | |
| REMARK | 500 | SUBTOPIC: CHIRAL CENTERS | | | | | |
| REMARK | 500 | | | | | | |
| REMARK | 500 | UNEXPECTED CONFIGURATION OF THE FOLLOWING CHIRAL | | | | | |
| REMARK | 500 | CENTER(S) USING IMPROPER CA--C--CB--N CHIRALITY | | | | | |
| REMARK | 500 | M=MODEL NUMBER; RES=RESIDUE NAME; C=CHAIN | | | | | |
| REMARK | 500 | IDENTIFIER; SSEQ=SEQUENCE NUMBER; I=INSERTION CODE | | | | | |
| REMARK | 500 | | | | | | |
| REMARK | 500 | STANDARD TABLE: | | | | | |
| REMARK | 500 | FORMAT: (11X,I3,1X,A3,1X,A1,I4,A1,6X,F5.1,6X,A1,10X,A1,3X,A16) | | | | | |
| REMARK | 500 | | | | | | |
| REMARK | 500 | M RES CSSEQI IMPROPER EXPECTED FOUND DETAILS | | | | | |
| REMARK | 500 | VAL A 715 22.8 L L OUTSIDE RANGE | | | | | |
| REMARK | 500 | | | | | | |
| REMARK | 500 | REMARK: NULL | | | | | |
| DBREF | 2ZTT | A 679 757 UNP P03431 RDRP_I34A1 679 757 | | | | | |
| DBREF | 2ZTT | B 1 37 UNP P03428 PB2_134A1 1 37 | | | | | |
| DBREF | 2ZTT | C 679 757 UNP P03431 RDRP_I34A1 679 757 | | | | | |
| DBREF | 2ZTT | D 1 37 UNP P03428 PB2_34A1 1 37 | | | | | |
| SEQADV | 2ZTT | GLY B -2 UNP P03428 EXPRESSION TAG | | | | | |
| SEQADV | 2ZTT | GLY B -1 UNP P03428 EXPRESSION TAG | | | | | |
| SEQADV | 2ZTT | SER B 0 UNP P03428 EXPRESSION TAG | | | | | |
| SEQADV | 2ZTT | GLY D -2 UNP P03428 EXPRESSION TAG | | | | | |
| SEQADV | 2ZTT | GLY D -1 UNP P03428 EXPRESSION TAG | | | | | |
| SEQADV | 2ZTT | SER D 0 UNP P03428 EXPRESSION TAG | | | | | |

Residues 2-80 of SEQ ID NO: 2, with selenomethionine residues instead of methionine

| | | | | | | | | | | | | | | | |
|---|---|---|---|---|---|---|---|---|---|---|---|---|---|---|---|
| SEQRES | 1 | A | 79 | GLN | ARG | GLY | VAL | LEU | GLU | ASP | GLU | GLN | MSE | TYR | GLN | ARG |
| SEQRES | 2 | A | 79 | CYS | CYS | ASN | LEU | PHE | GLU | LYS | PHE | PHE | PRO | SER | SER | SER |
| SEQRES | 3 | A | 79 | TYR | ARG | ARG | PRO | VAL | GLY | ILE | SER | SER | MSE | VAL | GLU | ALA |
| SEQRES | 4 | A | 79 | MSE | VAL | SER | ARG | ALA | ARG | ILE | ASP | ALA | ARG | ILE | ASP | PHE |
| SEQRES | 5 | A | 79 | GLU | SER | GLY | ARG | ILE | LYS | LYS | GLU | GLU | PHE | THR | GLU | ILE |
| SEQRES | 6 | A | 79 | MSE | LYS | ILE | CYS | SER | THR | ILE | GLU | GLU | LEU | ARG | ARG | GLN |
| SEQRES | 7 | A | 79 | LYS | | | | | | | | | | | | |

SEQ ID NO: 21

| | | | | | | | | | | | | | | | |
|---|---|---|---|---|---|---|---|---|---|---|---|---|---|---|---|
| SEQRES | 1 | B | 40 | GLY | GLY | SER | MSE | GLU | ARG | ILE | LYS | GLU | LEU | ARG | ASN | LEU |
| SEQRES | 2 | B | 40 | MSE | SER | GLN | SER | ARG | THR | ARG | GLU | ILE | LEU | THR | LYS | THR |
| SEQRES | 3 | B | 40 | THR | VAL | ASP | HIS | MSE | ALA | ILE | ILE | LYS | LYS | TYR | THR | SER |
| SEQRES | 4 | B | 40 | GLY | | | | | | | | | | | | |

Residues 679-757 of SEQ ID NO: 16, with selenomethione residues instead of methionine

| | | | | | | | | | | | | | | | |
|---|---|---|---|---|---|---|---|---|---|---|---|---|---|---|---|
| SEQRES | 1 | C | 79 | GLN | ARG | GLY | VAL | LEU | GLU | ASP | GLU | GLN | MSE | TYR | GLN | ARG |
| SEQRES | 2 | C | 79 | CYS | CYS | ASN | LEU | PHE | GLU | LYS | PHE | PHE | PRO | SER | SER | SER |
| SEQRES | 3 | C | 79 | TYR | ARG | ARG | PRO | VAL | GLY | ILE | SER | SER | MSE | VAL | GLU | ALA |
| SEQRES | 4 | C | 79 | MSE | VAL | SER | ARG | ALA | ARG | ILE | ASP | ALA | ARG | ILE | ASP | PHE |
| SEQRES | 5 | C | 79 | GLU | SER | GLY | ARG | ILE | LYS | LYS | GLU | GLU | PHE | THR | GLU | ILE |
| SEQRES | 6 | C | 79 | MSE | LYS | ILE | CYS | SER | THR | ILE | GLU | GLU | LEU | ARG | ARG | GLN |
| SEQRES | 7 | C | 79 | LYS | | | | | | | | | | | | |

SEQ ID NO: 21

| | | | | | | | | | | | | | | | |
|---|---|---|---|---|---|---|---|---|---|---|---|---|---|---|---|
| SEQRES | 1 | D | 40 | GLY | GLY | SER | MSE | GLU | ARG | ILE | LYS | GLU | LEU | ARG | ASN | LEU |
| SEQRES | 2 | D | 40 | MSE | SER | GLN | SER | ARG | THR | ARG | GLU | ILE | LEU | THR | LYS | THR |
| SEQRES | 3 | D | 40 | THR | VAL | ASP | HIS | MSE | ALA | ILE | ILE | LYS | LYS | TYR | THR | SER |
| SEQRES | 4 | D | 40 | GLY | | | | | | | | | | | | |
| MODRES | 2ZTT | MSE A 688 MET SELENOMETHIONINE | | | | | | | | | | | | | |
| MODRES | 2ZTT | MSE A 714 MET SELENOMETHIONINE | | | | | | | | | | | | | |
| MODRES | 2ZTT | MSE A 718 MET SELENOMETHIONINE | | | | | | | | | | | | | |
| MODRES | 2ZTT | MSE A 744 MET SELENOMETHIONINE | | | | | | | | | | | | | |
| MODRES | 2ZTT | MSE B 1 MET SELENOMETHIONINE | | | | | | | | | | | | | |
| MODRES | 2ZTT | MSE B 11 MET SELENOMETHIONINE | | | | | | | | | | | | | |
| MODRES | 2ZTT | MSE B 28 MET SELENOMETHIONINE | | | | | | | | | | | | | |
| MODRES | 2ZTT | MSE C 688 MET SELENOMETHIONINE | | | | | | | | | | | | | |
| MODRES | 2ZTT | MSE C 714 MET SELENOMETHIONINE | | | | | | | | | | | | | |
| MODRES | 2ZTT | MSE C 718 MET SELENOMETHIONINE | | | | | | | | | | | | | |
| MODRES | 2ZTT | MSE C 744 MET SELENOMETHIONINE | | | | | | | | | | | | | |
| MODRES | 2ZTT | MSE D 1 MET SELENOMETHIONINE | | | | | | | | | | | | | |
| MODRES | 2ZTT | MSE D 11 MET SELENOMETHIONINE | | | | | | | | | | | | | |
| MODRES | 2ZTT | MSE D 28 MET SELENOMETHIONINE | | | | | | | | | | | | | |
| HET | MSE A 688 8 | | | | | | | | | | | | | | |
| HET | MSE A 714 8 | | | | | | | | | | | | | | |
| HET | MSE A 718 8 | | | | | | | | | | | | | | |
| HET | MSE A 744 8 | | | | | | | | | | | | | | |
| HET | MSE B 1 8 | | | | | | | | | | | | | | |
| HET | MSE B 11 8 | | | | | | | | | | | | | | |
| HET | MSE B 28 8 | | | | | | | | | | | | | | |
| HET | MSE C 688 8 | | | | | | | | | | | | | | |

TABLE 2a-continued

Data of atomic coordinates for accession code 2ZTT

| HET | MSE | C | 714 | 8 | | | | | | | | | | |
|---|---|---|---|---|---|---|---|---|---|---|---|---|---|---|
| HET | MSE | C | 718 | 8 | | | | | | | | | | |
| HET | MSE | C | 744 | 8 | | | | | | | | | | |
| HET | MSE | D | 1 | 8 | | | | | | | | | | |
| HET | MSE | D | 11 | 8 | | | | | | | | | | |
| HET | MSE | D | 28 | 8 | | | | | | | | | | |
| HETNAM | | MSE | SELENOMETHIONINE | | | | | | | | | | | |
| FORMUL | 1 | MSE | 14(C5 H11 N O2 SE) | | | | | | | | | | | |
| FORMUL | 5 | HOH | *33(H2O) | | | | | | | | | | | |
| HELIX | 1 | 1 | GLU | A | 686 | PHE | A | 700 | 1 | | | | | 15 |
| HELIX | 2 | 2 | SER | A | 713 | SER | A | 732 | 1 | | | | | 20 |
| HELIX | 3 | 3 | LYS | A | 736 | ARG | A | 755 | 1 | | | | | 20 |
| HELIX | 4 | 4 | GLY | B | -1 | MSE | B | 11 | 1 | | | | | 13 |
| HELIX | 5 | 5 | GLN | B | 13 | THR | B | 23 | 1 | | | | | 11 |
| HELIX | 6 | 6 | THR | B | 24 | LYS | B | 33 | 1 | | | | | 10 |
| HELIX | 7 | 7 | ASP | C | 685 | PHE | C | 70 | 1 | | | | | 16 |
| HELIX | 8 | 8 | SER | C | 713 | SER | C | 732 | 1 | | | | | 20 |
| HELIX | 9 | 9 | LYS | C | 736 | LEU | C | 753 | 1 | | | | | 18 |
| HELIX | 10 | 10 | GLY | D | -1 | SER | D | 12 | 1 | | | | | 14 |
| HELIX | 11 | 11 | GLN | D | 13 | THR | D | 23 | 1 | | | | | 11 |
| HELIX | 12 | 12 | THR | D | 24 | LYS | D | 32 | 1 | | | | | 9 |
| LINK | | C | GLN | A | 687 | | N | MSE | A | 688 | 1555 | 1555 | 1.34 | |
| LINK | | C | MSE | A | 688 | | N | TYR | A | 689 | 1555 | 1555 | 1.34 | |
| LINK | | C | SER | A | 713 | | N | MSE | A | 714 | 1555 | 1555 | 1.32 | |
| LINK | | C | MSE | A | 714 | | N | VAL | A | 715 | 1555 | 1555 | 1.34 | |
| LINK | | C | ALA | A | 717 | | N | MSE | A | 718 | 1555 | 1555 | 1.32 | |
| LINK | | C | MSE | A | 718 | | N | VAL | A | 719 | 1555 | 1555 | 1.32 | |
| LINK | | C | ILE | A | 743 | | N | MSE | A | 744 | 1555 | 1555 | 1.30 | |
| LINK | | C | MSE | A | 744 | | N | LYS | A | 745 | 1555 | 1555 | 1.32 | |
| LINK | | C | SER | B | 0 | | N | MSE | B | 1 | 1555 | 1555 | 1.33 | |
| LINK | | C | MSE | B | 1 | | N | GLU | B | 2 | 1555 | 1555 | 1.34 | |
| LINK | | C | LEU | B | 10 | | N | MSE | B | 11 | 1555 | 1555 | 1.34 | |
| LINK | | C | MSE | B | 11 | | N | SER | B | 12 | 1555 | 1555 | 1.34 | |
| LINK | | C | HIS | B | 27 | | N | MSE | B | 28 | 1555 | 1555 | 1.32 | |
| LINK | | C | MSE | B | 28 | | N | ALA | B | 29 | 1555 | 1555 | 1.32 | |
| LINK | | C | GLN | C | 687 | | N | MSE | C | 688 | 1555 | 1555 | 1.34 | |
| LINK | | C | MSE | C | 688 | | N | TYR | C | 689 | 1555 | 1555 | 1.34 | |
| LINK | | C | SER | C | 713 | | N | MSE | C | 714 | 1555 | 1555 | 1.32 | |
| LINK | | C | MSE | C | 714 | | N | VAL | C | 715 | 1555 | 1555 | 1.33 | |
| LINK | | C | ALA | C | 717 | | N | MSE | C | 718 | 1555 | 1555 | 1.33 | |
| LINK | | C | MSE | C | 718 | | N | VAL | C | 719 | 1555 | 1555 | 1.34 | |
| LINK | | C | ILE | C | 743 | | N | MSE | C | 744 | 1555 | 1555 | 1.33 | |
| LINK | | C | MSE | C | 744 | | N | LYS | C | 745 | 1555 | 1555 | 1.36 | |
| LINK | | C | SER | D | 0 | | N | MSE | D | 1 | 1555 | 1555 | 1.33 | |
| LINK | | C | MSE | D | 1 | | N | GLU | D | 2 | 1555 | 1555 | 1.34 | |
| LINK | | C | LEU | D | 10 | | N | MSE | D | 11 | 1555 | 1555 | 1.33 | |
| LINK | | C | MSE | D | 11 | | N | SER | D | 12 | 1555 | 1555 | 1.36 | |
| LINK | | C | HIS | D | 27 | | N | MSE | D | 28 | 1555 | 1555 | 1.32 | |
| LINK | | C | MSE | D | 28 | | N | ALA | D | 29 | 1555 | 1555 | 1.33 | |
| CRYST1 | 44.273 | 61.477 | 45.473 | 90.00 | 103.35 | 90.00 P 1 21 1 | | 4 | | | | | | |
| ORIGX1 | | 1.00000 | 0.00000 | 0.00000 | | 0.0000 | | | | | | | | |
| ORIGX2 | | 0.000000 | 1.000000 | 0.000000 | | 0.0000 | | | | | | | | |
| ORIGX3 | | 0.000000 | 0.000000 | 1.000000 | | 0.0000 | | | | | | | | |
| SCALE1 | | 0.022587 | 0.000000 | 0.005362 | | 0.0000 | | | | | | | | |
| SCALE2 | | 0.000000 | 0.016266 | 0.000000 | | 0.0000 | | | | | | | | |
| SCALE3 | | 0.000000 | 0.000000 | 0.022602 | | 0.0000 | | | | | | | | |
| ATOM | 1 | N | ASP | A | 685 | -13.412 | 4.512 | 17.116 | 1.00 | 71.28 | N | | | |
| ATOM | 2 | CA | ASP | A | 685 | -12.001 | 5.062 | 17.086 | 1.00 | 70.83 | C | | | |
| ATOM | 3 | C | ASP | A | 685 | -10.979 | 3.959 | 17.432 | 1.00 | 70.56 | C | | | |
| ATOM | 5 | CB | ASP | A | 685 | -11.883 | 6.347 | 17.924 | 1.00 | 70.39 | C | | | |
| ATOM | 6 | CG | ASP | A | 685 | -10.476 | 6.961 | 17.897 | 1.00 | 71.26 | C | | | |
| ATOM | 7 | OD1 | ASP | A | 685 | -9.628 | 6.505 | 18.688 | 1.00 | 67.79 | O | | | |
| ATOM | 8 | OD2 | ASP | A | 685 | -10.226 | 7.907 | 17.108 | 1.00 | 70.60 | O | | | |
| ATOM | 9 | N | GLU | A | 686 | -11.344 | 2.737 | 17.048 | 1.00 | 69.99 | N | | | |
| ATOM | 10 | CA | GLU | A | 686 | -10.404 | 1.636 | 16.890 | 1.00 | 69.30 | C | | | |
| ATOM | 11 | C | GLU | A | 686 | -9.887 | 1.791 | 15.464 | 1.00 | 68.44 | C | | | |
| ATOM | 12 | O | GLU | A | 686 | -9.579 | 0.831 | 14.749 | 1.00 | 68.10 | O | | | |
| ATOM | 13 | CB | GLU | A | 686 | -11.135 | 0.301 | 17.131 | 1.00 | 69.98 | C | | | |
| ATOM | 14 | CG | GLU | A | 686 | -11.210 | -0.165 | 18.629 | 1.00 | 71.63 | C | | | |
| ATOM | 15 | CD | GLU | A | 686 | -10.710 | 0.891 | 19.634 | 1.00 | 74.05 | C | | | |
| ATOM | 16 | OE1 | GLU | A | 686 | -11.330 | 1.982 | 19.719 | 1.00 | 75.12 | O | | | |
| ATOM | 17 | OE2 | GLU | A | 686 | -9.689 | 0.638 | 20.326 | 1.00 | 72.20 | O | | | |
| ATOM | 18 | N | GLN | A | 687 | -9.810 | 3.060 | 15.080 | 1.00 | 67.43 | N | | | |
| ATOM | 19 | CA | GLN | A | 687 | -9.501 | 3.499 | 13.734 | 1.00 | 66.20 | C | | | |
| ATOM | 20 | C | GLN | A | 687 | -8.088 | 3.999 | 13.701 | 1.00 | 64.17 | C | | | |
| ATOM | 21 | O | GLN | A | 687 | -7.480 | 4.029 | 12.635 | 1.00 | 64.85 | O | | | |
| ATOM | 22 | CB | GLN | A | 687 | -10.457 | 4.610 | 13.323 | 1.00 | 66.50 | C | | | |
| ATOM | 23 | CG | GLN | A | 687 | -11.912 | 4.303 | 13.707 | 1.00 | 69.66 | C | | | |

TABLE 2a-continued

Data of atomic coordinates for accession code 2ZTT

| ATOM | 24 | CD | GLN | A | 687 | −12.908 | 4.819 | 12.683 | 1.00 | 71.66 | C |
|---|---|---|---|---|---|---|---|---|---|---|---|
| ATOM | 25 | OE1 | GLN | A | 687 | −13.062 | 4.234 | 11.596 | 1.00 | 71.76 | O |
| ATOM | 26 | NE2 | GLN | A | 687 | −13.591 | 5.915 | 13.021 | 1.00 | 70.83 | N |
| HETATM | 27 | N | MSE | A | 688 | −7.573 | 4.388 | 14.874 | 1.00 | 61.98 | N |
| HETATM | 28 | CA | MSE | A | 688 | −6.136 | 4.538 | 15.075 | 1.00 | 59.57 | C |
| HETATM | 29 | C | MSE | A | 688 | −5.483 | 3.278 | 14.546 | 1.00 | 55.11 | C |
| HETATM | 30 | O | MSE | A | 688 | −4.570 | 3.377 | 13.726 | 1.00 | 53.87 | O |
| HETATM | 31 | CB | MSE | A | 688 | −5.741 | 4.764 | 16.557 | 1.00 | 63.09 | C |
| HETATM | 32 | CG | MSE | A | 688 | −6.023 | 6.148 | 17.105 | 1.00 | 67.68 | C |
| HETATM | 33 | SE | MSE | A | 688 | −5.773 | 7.373 | 15.612 | 1.00 | 88.38 | SE |
| HETATM | 34 | CE | MSE | A | 688 | −6.715 | 8.990 | 16.288 | 1.00 | 76.34 | C |
| ATOM | 35 | N | TYR | A | 689 | −5.985 | 2.116 | 14.986 | 1.00 | 49.41 | N |
| ATOM | 36 | CA | TYR | A | 689 | −5.423 | 0.832 | 14.576 | 1.00 | 45.22 | C |
| ATOM | 37 | C | TYR | A | 689 | −5.846 | 0.368 | 13.137 | 1.00 | 43.12 | C |
| ATOM | 38 | O | TYR | A | 689 | −5.036 | −0.077 | 12.356 | 1.00 | 39.88 | O |
| ATOM | 39 | CB | TYR | A | 689 | −5.598 | −0.254 | 15.660 | 1.00 | 43.59 | C |
| ATOM | 40 | CG | TYR | A | 689 | −4.863 | −1.551 | 15.308 | 1.00 | 42.73 | C |
| ATOM | 41 | CD1 | TYR | A | 689 | −3.474 | −1.737 | 15.594 | 1.00 | 38.90 | C |
| ATOM | 42 | CD2 | TYR | A | 689 | −5.535 | −2.581 | 14.674 | 1.00 | 40.75 | C |
| ATOM | 43 | CE2 | TYR | A | 689 | −2.822 | −2.921 | 15.230 | 1.00 | 36.08 | C |
| ATOM | 44 | CE2 | TYR | A | 689 | −4.894 | −3.762 | 14.310 | 1.00 | 42.76 | C |
| ATOM | 45 | CZ | TYR | A | 689 | −3.536 | −3.927 | 14.577 | 1.00 | 42.46 | C |
| ATOM | 46 | OH | TYR | A | 689 | −2.961 | −5.129 | 14.178 | 1.00 | 43.77 | O |
| ATOM | 47 | N | GLN | A | 690 | −7.095 | 0.498 | 12.760 | 1.00 | 44.82 | N |
| ATOM | 48 | CA | GLN | A | 690 | −7.424 | 0.225 | 11.356 | 1.00 | 44.90 | C |
| ATOM | 49 | C | GLN | A | 690 | −6.566 | 1.009 | 10.324 | 1.00 | 43.56 | C |
| ATOM | 50 | O | GLN | A | 690 | −6.134 | 0.439 | 9.345 | 1.00 | 43.69 | O |
| ATOM | 51 | CB | GLN | A | 690 | −8.935 | 0.279 | 11.117 | 1.00 | 47.34 | C |
| ATOM | 52 | CG | GLN | A | 690 | −9.401 | −0.555 | 9.898 | 1.00 | 50.14 | C |
| ATOM | 53 | CD | GLN | A | 690 | −8.825 | −1.981 | 9.836 | 1.00 | 55.10 | C |
| ATOM | 54 | OE1 | GLN | A | 690 | −8.144 | −2.343 | 8.865 | 1.00 | 57.64 | O |
| ATOM | 55 | NE2 | GLN | A | 690 | −9.084 | −2.790 | 10.878 | 1.00 | 57.01 | N |
| ATOM | 56 | N | ARG | A | 691 | −6.198 | 2.251 | 10.622 | 1.00 | 44.37 | N |
| ATOM | 57 | CA | ARG | A | 691 | −5.344 | 3.114 | 9.743 | 1.00 | 44.95 | C |
| ATOM | 58 | C | ARG | A | 691 | −3.886 | 2.644 | 9.590 | 1.00 | 44.38 | C |
| ATOM | 59 | O | ARG | A | 691 | −3.327 | 2.635 | 8.483 | 1.00 | 44.01 | O |
| ATOM | 60 | CB | ARG | A | 691 | −5.404 | 4.535 | 10.268 | 1.00 | 44.64 | C |
| ATOM | 61 | CG | ARG | A | 691 | −4.938 | 5.629 | 9.316 | 1.00 | 48.37 | C |
| ATOM | 62 | CD | ARG | A | 691 | −5.144 | 7.006 | 9.975 | 1.00 | 48.80 | C |
| ATOM | 63 | NE | ARG | A | 691 | −4.211 | 8.070 | 9.552 | 1.00 | 54.83 | N |
| ATOM | 64 | CZ | ARG | A | 691 | −4.167 | 9.291 | 10.114 | 1.00 | 56.57 | C |
| ATOM | 65 | NH1 | ARG | A | 691 | −5.004 | 9.610 | 11.102 | 1.00 | 51.75 | N |
| ATOM | 66 | NH2 | ARG | A | 691 | −3.292 | 10.205 | 9.683 | 1.00 | 60.0 | N |
| ATOM | 67 | N | CYS | A | 692 | −3.271 | 2.241 | 10.711 | 1.00 | 43.64 | N |
| ATOM | 68 | CA | CYS | A | 692 | −1.977 | 1.557 | 10.689 | 1.00 | 41.98 | C |
| ATOM | 69 | C | CYS | A | 692 | −2.012 | 0.231 | 9.939 | 1.00 | 40.93 | C |
| ATOM | 70 | O | CYS | A | 692 | −1.068 | −0.116 | 9.268 | 1.00 | 40.08 | O |
| ATOM | 71 | CB | CYS | A | 692 | −1.464 | 1.336 | 12.121 | 1.00 | 42.06 | C |
| ATOM | 72 | SG | CYS | A | 692 | −1.361 | 2.826 | 13.176 | 1.00 | 43.81 | S |
| ATOM | 73 | N | CYS | A | 693 | −3.093 | −0.528 | 10.087 | 1.00 | 41.28 | N |
| ATOM | 74 | CA | CYS | A | 693 | −3.262 | −1.807 | 9.386 | 1.00 | 41.85 | C |
| ATOM | 75 | C | CYS | A | 693 | −3.334 | −1.583 | 7.938 | 1.00 | 40.38 | C |
| ATOM | 76 | O | CYS | A | 693 | −2.574 | −2.162 | 7.226 | 1.00 | 38.15 | O |
| ATOM | 77 | CB | CYS | A | 693 | −4.544 | −2.523 | 9.80 | 1.00 | 42.70 | C |
| ATOM | 78 | SG | CYS | A | 693 | −4.181 | −3.401 | 11.336 | 1.00 | 50.85 | S |
| ATOM | 79 | N | ASN | A | 694 | −4.259 | −0.701 | 7.523 | 1.00 | 41.19 | N |
| ATOM | 80 | CA | ASN | A | 694 | −4.352 | −0.283 | 6.137 | 1.00 | 40.95 | C |
| ATOM | 81 | C | ASN | A | 694 | −3.018 | 0.108 | 5.539 | 1.00 | 40.25 | C |
| ATOM | 82 | O | ASN | A | 694 | −2.621 | −0.419 | 4.479 | 1.00 | 39.21 | O |
| ATOM | 83 | CB | ASN | A | 694 | −5.403 | 0.830 | 5.968 | 1.00 | 42.35 | C |
| ATOM | 84 | CG | ASN | A | 694 | −6.856 | 0.353 | 6.277 | 1.00 | 45.30 | C |
| ATOM | 85 | OD1 | ASN | A | 694 | −7.161 | −0.846 | 6.326 | 1.00 | 50.66 | O |
| ATOM | 86 | ND2 | ASN | A | 694 | −7.747 | 1.311 | 6.473 | 1.00 | 49.09 | N |
| ATOM | 87 | N | LEU | A | 695 | −2.276 | 0.982 | 6.227 | 1.00 | 39.28 | N |
| ATOM | 88 | CA | LEU | A | 695 | −0.974 | 1.375 | 5.716 | 1.00 | 38.19 | C |
| ATOM | 89 | C | LEU | A | 695 | 0.023 | 0.220 | 5.654 | 1.00 | 37.45 | C |
| ATOM | 90 | O | LEU | A | 695 | 0.856 | 0.103 | 4.730 | 1.00 | 37.15 | O |
| ATOM | 91 | CB | LEU | A | 695 | −0.419 | 2.588 | 6.483 | 1.00 | 38.54 | C |
| ATOM | 92 | CG | LEU | A | 695 | 0.978 | 3.064 | 6.074 | 1.00 | 35.29 | C |
| ATOM | 93 | CD1 | LEU | A | 695 | 1.121 | 3.556 | 4.701 | 1.00 | 32.07 | C |
| ATOM | 94 | CD2 | LEU | A | 695 | 1.425 | 4.154 | 6.989 | 1.00 | 35.02 | C |
| ATOM | 95 | N | PHE | A | 696 | −0.076 | −0.672 | 6.615 | 1.00 | 38.79 | N |
| ATOM | 96 | CA | PHE | A | 696 | 0.859 | −1.772 | 6.696 | 1.00 | 38.71 | C |
| ATOM | 97 | C | PHE | A | 696 | 0.793 | −2.668 | 5.483 | 1.00 | 40.15 | C |
| ATOM | 98 | O | PHE | A | 696 | 1.794 | −3.227 | 5.048 | 1.00 | 38.99 | O |
| ATOM | 99 | CB | PHE | A | 696 | 0.488 | −2.646 | 7.884 | 1.00 | 37.28 | C |
| ATOM | 10 | CG | PHE | A | 696 | 1.494 | −3.726 | 8.157 | 1.00 | 38.0 | C |
| ATOM | 101 | CD1 | PHE | A | 696 | 2.678 | −3.407 | 8.793 | 1.00 | 39.53 | C |

TABLE 2a-continued

Data of atomic coordinates for accession code 2ZTT

| ATOM | 102 | CD2 | PHE | A | 696 | 1.270 | −5.059 | 7.780 | 1.00 | 38.72 | C |
|---|---|---|---|---|---|---|---|---|---|---|---|
| ATOM | 103 | CE1 | PHE | A | 696 | 3.655 | −4.416 | 9.066 | 1.00 | 34.29 | C |
| ATOM | 104 | CE2 | PHE | A | 696 | 2.220 | −6.071 | 8.044 | 1.00 | 40.31 | C |
| ATOM | 105 | CZ | PHE | A | 696 | 3.415 | −5.744 | 8.701 | 1.00 | 37.31 | C |
| ATOM | 106 | N | GLU | A | 697 | −0.439 | −2.885 | 5.032 | 1.00 | 41.77 | N |
| ATOM | 107 | CA | GLU | A | 697 | −0.708 | −3.731 | 3.877 | 1.00 | 44.87 | C |
| ATOM | 108 | C | GLU | A | 697 | −0.034 | −3.187 | 2.652 | 1.00 | 44.57 | C |
| ATOM | 109 | O | GLU | A | 697 | 0.323 | −3.952 | 1.775 | 1.00 | 46.98 | O |
| ATOM | 110 | CB | GLU | A | 697 | −2.213 | −3.821 | 3.537 | 1.00 | 44.96 | C |
| ATOM | 111 | CG | GLU | A | 697 | −3.190 | −3.997 | 4.701 | 1.00 | 50.50 | C |
| ATOM | 112 | CD | GLU | A | 697 | −3.132 | −5.361 | 5.348 | 1.00 | 59.01 | C |
| ATOM | 113 | OE1 | GLU | A | 697 | −4.170 | −5.792 | 5.939 | 1.00 | 60.85 | O |
| ATOM | 114 | OE2 | GLU | A | 697 | −2.041 | −5.989 | 5.286 | 1.00 | 64.15 | O |
| ATOM | 115 | N | LYS | A | 698 | 0.139 | −1.875 | 2.570 | 1.00 | 44.58 | N |
| ATOM | 116 | CA | LYS | A | 698 | 0.785 | −1.269 | 1.399 | 1.00 | 43.44 | C |
| ATOM | 117 | C | LYS | A | 698 | 2.267 | −1.634 | 1.297 | 1.00 | 44.37 | C |
| ATOM | 118 | O | LYS | A | 698 | 2.880 | −1.557 | 0.212 | 1.00 | 44.63 | O |
| ATOM | 119 | CB | LYS | A | 698 | 0.569 | 0.243 | 1.423 | 1.00 | 44.26 | C |
| ATOM | 120 | CG | LYS | A | 698 | −0.936 | 0.657 | 1.171 | 1.00 | 41.22 | C |
| ATOM | 121 | CD | LYS | A | 698 | −0.982 | 2.154 | 0.818 | 1.00 | 40.44 | C |
| ATOM | 122 | CE | LYS | A | 698 | −2.304 | 2.790 | 1.297 | 1.00 | 44.14 | C |
| ATOM | 123 | NZ | LYS | A | 698 | −2.206 | 4.269 | 1.429 | 1.00 | 48.24 | N |
| ATOM | 124 | N | PHE | A | 699 | 2.858 | −1.972 | 2.449 | 1.00 | 41.80 | N |
| ATOM | 125 | CA | PHE | A | 699 | 4.156 | −2.569 | 2.464 | 1.00 | 41.82 | C |
| ATOM | 126 | C | PHE | A | 699 | 4.025 | −4.074 | 2.309 | 1.00 | 41.91 | C |
| ATOM | 127 | O | PHE | A | 699 | 4.768 | −4.641 | 1.570 | 1.00 | 42.12 | O |
| ATOM | 128 | CB | PHE | A | 699 | 4.90 | −2.133 | 3.734 | 1.00 | 40.05 | C |
| ATOM | 129 | CG | PHE | A | 699 | 5.124 | −0.653 | 3.786 | 1.00 | 37.75 | C |
| ATOM | 130 | CD1 | PHE | A | 699 | 6.163 | −0.087 | 3.098 | 1.00 | 33.84 | C |
| ATOM | 131 | CD2 | PHE | A | 699 | 4.245 | 0.182 | 4.433 | 1.00 | 34.78 | C |
| ATOM | 132 | CE2 | PHE | A | 699 | 6.366 | 1.242 | 3.105 | 1.00 | 34.19 | C |
| ATOM | 133 | CE2 | PHE | A | 699 | 4.472 | 1.547 | 4.443 | 1.00 | 34.10 | C |
| ATOM | 134 | CZ | PHE | A | 699 | 5.526 | 2.064 | 3.764 | 1.00 | 32.15 | C |
| ATOM | 135 | N | PHE | A | 700 | 3.057 | −4.713 | 2.966 | 1.00 | 43.74 | N |
| ATOM | 136 | CA | PHE | A | 70 | 2.868 | −6.212 | 2.850 | 1.00 | 45.76 | C |
| ATOM | 137 | C | PHE | A | 700 | 1.489 | −6.675 | 2.421 | 1.00 | 47.14 | C |
| ATOM | 138 | O | PHE | A | 700 | 0.642 | −7.073 | 3.233 | 1.00 | 46.46 | O |
| ATOM | 139 | CB | PHE | A | 700 | 3.290 | −6.915 | 4.129 | 1.00 | 45.21 | C |
| ATOM | 140 | CG | PHE | A | 700 | 4.613 | −6.503 | 4.568 | 1.00 | 40.86 | C |
| ATOM | 141 | CD1 | PHE | A | 700 | 5.752 | −7.103 | 4.040 | 1.00 | 42.42 | C |
| ATOM | 142 | CD2 | PHE | A | 700 | 4.749 | −5.478 | 5.487 | 1.00 | 44.41 | C |
| ATOM | 143 | CE2 | PHE | A | 700 | 7.032 | −6.687 | 4.451 | 1.00 | 39.05 | C |
| ATOM | 144 | CE2 | PHE | A | 700 | 6.036 | −5.058 | 5.906 | 1.00 | 38.61 | C |
| ATOM | 145 | CZ | PHE | A | 700 | 7.146 | −5.677 | 5.395 | 1.00 | 40.28 | C |
| ATOM | 146 | N | PRO | A | 701 | 1.250 | −6.622 | 1.119 | 1.00 | 49.44 | N |
| ATOM | 147 | CA | PRO | A | 701 | −0.104 | −7.018 | 0.759 | 1.00 | 51.91 | C |
| ATOM | 148 | C | PRO | A | 701 | −0.244 | −8.502 | 0.952 | 1.00 | 54.41 | C |
| ATOM | 149 | O | PRO | A | 701 | 0.754 | −9.214 | 0.898 | 1.00 | 54.14 | O |
| ATOM | 150 | CB | PRO | A | 701 | −0.214 | −6.631 | −0.723 | 1.00 | 51.16 | C |
| ATOM | 151 | CG | PRO | A | 701 | 1.154 | −6.661 | −1.240 | 1.00 | 50.26 | C |
| ATOM | 152 | CD | PRO | A | 701 | 2.063 | −6.224 | −0.044 | 1.00 | 48.61 | C |
| ATOM | 153 | N | SER | A | 702 | −1.476 | −8.953 | 1.194 | 1.00 | 57.99 | N |
| ATOM | 154 | CA | SER | A | 702 | −1.788 | −10.392 | 1.357 | 1.00 | 61.25 | C |
| ATOM | 155 | C | SER | A | 702 | −1.037 | −11.268 | 0.353 | 1.00 | 62.95 | C |
| ATOM | 156 | O | SER | A | 702 | −0.669 | −12.418 | 0.658 | 1.00 | 63.98 | O |
| ATOM | 157 | CB | SER | A | 702 | −3.307 | −10.635 | 1.195 | 1.00 | 61.47 | C |
| ATOM | 158 | OG | SER | A | 702 | −4.085 | −9.562 | 1.748 | 1.00 | 61.19 | O |
| ATOM | 159 | N | SER | A | 703 | −0.805 | −10.702 | −0.834 | 1.00 | 64.46 | N |
| ATOM | 160 | CA | SER | A | 703 | −0.297 | −11.460 | −1.984 | 1.00 | 66.10 | C |
| ATOM | 161 | C | SER | A | 703 | 1.183 | −11.188 | −2.301 | 1.00 | 66.53 | C |
| ATOM | 162 | O | SER | A | 703 | 1.631 | −11.335 | −3.448 | 1.00 | 66.16 | O |
| ATOM | 163 | CB | SER | A | 703 | −1.199 | −11.234 | −3.216 | 1.00 | 65.61 | C |
| ATOM | 164 | OG | SER | A | 703 | −1.135 | −9.882 | −3.652 | 1.00 | 67.10 | O |
| ATOM | 165 | N | SER | A | 704 | 1.918 | −10.766 | −1.268 | 1.00 | 67.54 | N |
| ATOM | 166 | CA | SER | A | 704 | 3.381 | −10.798 | −1.240 | 1.00 | 68.53 | C |
| ATOM | 167 | C | SER | A | 704 | 3.751 | −12.189 | −0.704 | 1.00 | 69.33 | C |
| ATOM | 168 | O | SER | A | 704 | 2.901 | −12.909 | −0.133 | 1.00 | 69.20 | O |
| ATOM | 169 | CB | SER | A | 704 | 3.942 | −9.684 | −0.308 | 1.00 | 68.89 | C |
| ATOM | 170 | OG | SER | A | 704 | 5.306 | −9.378 | −0.546 | 1.00 | 67.54 | O |
| ATOM | 171 | N | TYR | A | 705 | 5.019 | −12.548 | −0.888 | 1.00 | 70.04 | N |
| ATOM | 172 | CA | TYR | A | 705 | 5.582 | −13.814 | −0.440 | 1.00 | 70.09 | C |
| ATOM | 173 | C | TYR | A | 705 | 6.823 | −13.422 | 0.370 | 1.00 | 69.97 | C |
| ATOM | 174 | O | TYR | A | 705 | 7.420 | −14.246 | 1.103 | 1.00 | 70.14 | O |
| ATOM | 175 | CB | TYR | A | 705 | 5.986 | −14.625 | −1.667 | 1.00 | 71.11 | C |
| ATOM | 176 | CG | TYR | A | 705 | 6.802 | −13.791 | −2.626 | 1.00 | 72.01 | C |
| ATOM | 177 | CD1 | TYR | A | 705 | 8.159 | −14.072 | −2.854 | 1.00 | 73.48 | C |
| ATOM | 178 | CD2 | TYR | A | 705 | 6.234 | −12.676 | −3.257 | 1.00 | 72.03 | C |
| ATOM | 179 | CE1 | TYR | A | 705 | 8.930 | −13.281 | −3.722 | 1.00 | 73.84 | C |

TABLE 2a-continued

Data of atomic coordinates for accession code 2ZTT

| ATOM | 180 | CE2 | TYR | A | 705 | 6.974 | −11.887 | −4.123 | 1.00 | 73.50 | C |
|---|---|---|---|---|---|---|---|---|---|---|---|
| ATOM | 181 | CZ | TYR | A | 705 | 8.318 | −12.190 | −4.361 | 1.00 | 74.26 | C |
| ATOM | 182 | OH | TYR | A | 705 | 9.041 | −11.390 | −5.229 | 1.00 | 73.76 | O |
| ATOM | 183 | N | ARG | A | 706 | 7.235 | −12.163 | 0.192 | 1.00 | 68.58 | N |
| ATOM | 184 | CA | ARG | A | 706 | 8.181 | −11.528 | 1.102 | 1.00 | 67.49 | C |
| ATOM | 185 | C | ARG | A | 706 | 7.303 | −11.054 | 2.261 | 1.00 | 65.88 | C |
| ATOM | 186 | O | ARG | A | 706 | 6.630 | −10.025 | 2.166 | 1.00 | 65.83 | O |
| ATOM | 187 | CB | ARG | A | 706 | 8.955 | −10.383 | 0.415 | 1.00 | 67.13 | C |
| ATOM | 188 | CG | ARG | A | 706 | 9.932 | −10.843 | −0.70 | 1.00 | 67.53 | C |
| ATOM | 189 | CD | ARG | A | 706 | 10.273 | −9.720 | −1.675 | 1.00 | 68.53 | C |
| ATOM | 190 | NE | ARG | A | 706 | 9.166 | −9.508 | −2.601 | 1.00 | 72.03 | N |
| ATOM | 191 | CZ | ARG | A | 706 | 8.764 | −8.329 | −3.073 | 1.00 | 74.08 | C |
| ATOM | 192 | NH1 | ARG | A | 706 | 9.379 | −7.199 | −2.722 | 1.00 | 74.20 | N |
| ATOM | 193 | NH2 | ARG | A | 706 | 7.731 | −8.289 | −3.911 | 1.00 | 74.72 | N |
| ATOM | 194 | N | ARG | A | 707 | 7.252 | −11.891 | 3.295 | 1.00 | 63.85 | N |
| ATOM | 195 | CA | ARG | A | 707 | 6.481 | −11.667 | 4.505 | 1.00 | 62.16 | C |
| ATOM | 196 | C | ARG | A | 707 | 7.375 | −11.007 | 5.560 | 1.00 | 59.61 | C |
| ATOM | 197 | O | ARG | A | 707 | 8.571 | −11.320 | 5.635 | 1.00 | 59.43 | O |
| ATOM | 198 | CB | ARG | A | 707 | 5.908 | −12.996 | 5.044 | 1.00 | 63.19 | C |
| ATOM | 199 | CG | ARG | A | 707 | 5.085 | −13.812 | 4.043 | 1.00 | 66.70 | C |
| ATOM | 20 | CD | ARG | A | 707 | 3.975 | −12.967 | 3.363 | 1.00 | 73.21 | C |
| ATOM | 201 | NE | ARG | A | 707 | 2.627 | −13.390 | 3.742 | 1.00 | 78.50 | N |
| ATOM | 202 | CZ | ARG | A | 707 | 1.795 | −14.106 | 2.965 | 1.00 | 81.59 | C |
| ATOM | 203 | NH1 | ARG | A | 707 | 2.155 | −14.493 | 1.726 | 1.00 | 82.71 | N |
| ATOM | 204 | NH2 | ARG | A | 707 | 0.585 | −14.432 | 3.425 | 1.00 | 79.03 | N |
| ATOM | 205 | N | PRO | A | 708 | 6.809 | −10.091 | 6.373 | 1.00 | 56.79 | N |
| ATOM | 206 | CA | PRO | A | 708 | 7.591 | −9.315 | 7.351 | 1.00 | 55.08 | C |
| ATOM | 207 | C | PRO | A | 708 | 8.043 | −10.210 | 8.480 | 1.00 | 54.47 | C |
| ATOM | 208 | O | PRO | A | 708 | 7.346 | −11.197 | 8.798 | 1.00 | 53.88 | O |
| ATOM | 209 | CB | PRO | A | 708 | 6.567 | −8.334 | 7.901 | 1.00 | 54.89 | C |
| ATOM | 210 | CG | PRO | A | 708 | 5.251 | −9.043 | 7.721 | 1.00 | 55.05 | C |
| ATOM | 211 | CD | PRO | A | 708 | 5.379 | −9.754 | 6.432 | 1.00 | 56.55 | C |
| ATOM | 212 | N | VAL | A | 709 | 9.176 | −9.885 | 9.102 | 1.00 | 52.94 | N |
| ATOM | 213 | CA | VAL | A | 709 | 9.585 | −10.646 | 10.312 | 1.00 | 51.14 | C |
| ATOM | 214 | C | VAL | A | 709 | 8.629 | −10.476 | 11.493 | 1.00 | 50.36 | C |
| ATOM | 215 | O | VAL | A | 709 | 8.277 | −9.353 | 11.882 | 1.00 | 48.58 | O |
| ATOM | 216 | CB | VAL | A | 709 | 11.101 | −10.481 | 10.687 | 1.00 | 51.01 | C |
| ATOM | 217 | CG1 | VAL | A | 709 | 11.630 | −9.143 | 10.271 | 1.00 | 51.37 | C |
| ATOM | 218 | CG2 | VAL | A | 709 | 11.368 | −10.738 | 12.162 | 1.00 | 50.58 | C |
| ATOM | 219 | N | GLY | A | 710 | 8.202 | −11.608 | 12.051 | 1.00 | 49.42 | N |
| ATOM | 220 | CA | GLY | A | 710 | 7.148 | −11.612 | 13.056 | 1.00 | 48.89 | C |
| ATOM | 221 | C | GLY | A | 710 | 7.513 | −10.850 | 14.327 | 1.00 | 48.37 | C |
| ATOM | 222 | O | GLY | A | 710 | 6.690 | −10.149 | 14.920 | 1.00 | 47.51 | O |
| ATOM | 223 | N | ILE | A | 711 | 8.748 | −10.976 | 14.759 | 1.00 | 47.53 | N |
| ATOM | 224 | CA | ILE | A | 711 | 9.121 | −10.365 | 16.025 | 1.00 | 47.47 | C |
| ATOM | 225 | C | ILE | A | 711 | 9.407 | −8.856 | 15.858 | 1.00 | 46.39 | C |
| ATOM | 226 | O | ILE | A | 711 | 9.704 | −8.153 | 16.827 | 1.00 | 47.56 | O |
| ATOM | 227 | CB | ILE | A | 711 | 10.291 | −11.142 | 16.702 | 1.00 | 48.48 | C |
| ATOM | 228 | CG1 | ILE | A | 711 | 11.658 | −10.649 | 16.228 | 1.00 | 51.45 | C |
| ATOM | 229 | CG2 | ILE | A | 711 | 10.183 | −12.659 | 16.420 | 1.00 | 49.31 | C |
| ATOM | 230 | CD1 | ILE | A | 711 | 12.749 | −10.898 | 17.274 | 1.00 | 52.65 | C |
| ATOM | 231 | N | SER | A | 712 | 9.309 | −8.365 | 14.628 | 1.00 | 44.61 | N |
| ATOM | 232 | CA | SER | A | 712 | 9.541 | −6.954 | 14.314 | 1.00 | 42.91 | C |
| ATOM | 233 | C | SER | A | 712 | 8.341 | −6.078 | 14.618 | 1.00 | 41.56 | C |
| ATOM | 234 | O | SER | A | 712 | 7.171 | −6.514 | 14.450 | 1.00 | 42.83 | O |
| ATOM | 235 | CB | SER | A | 712 | 9.954 | −6.807 | 12.851 | 1.00 | 42.71 | C |
| ATOM | 236 | OG | SER | A | 712 | 10.207 | −5.442 | 12.537 | 1.00 | 46.19 | O |
| ATOM | 237 | N | SER | A | 713 | 8.592 | −4.837 | 15.017 | 1.00 | 40.66 | N |
| ATOM | 238 | CA | SER | A | 713 | 7.522 | −3.857 | 15.154 | 1.00 | 40.68 | C |
| ATOM | 239 | C | SER | A | 713 | 6.969 | −3.515 | 13.763 | 1.00 | 39.89 | C |
| ATOM | 240 | O | SER | A | 713 | 7.634 | −3.720 | 12.765 | 1.00 | 38.35 | O |
| ATOM | 241 | CB | SER | A | 713 | 7.965 | −2.616 | 15.922 | 1.00 | 41.75 | C |
| ATOM | 242 | OG | SER | A | 713 | 8.866 | −1.830 | 15.165 | 1.00 | 42.22 | O |
| HETATM | 243 | N | MSE | A | 714 | 5.723 | −3.073 | 13.703 | 1.00 | 40.67 | N |
| HETATM | 244 | CA | MSE | A | 714 | 5.182 | −2.670 | 12.424 | 1.00 | 41.78 | C |
| HETATM | 245 | C | MSE | A | 714 | 6.120 | −1.665 | 11.803 | 1.00 | 39.81 | C |
| HETATM | 246 | O | MSE | A | 714 | 6.546 | −1.889 | 10.684 | 1.00 | 40.71 | O |
| HETATM | 247 | CB | MSE | A | 714 | 3.765 | −2.136 | 12.560 | 1.00 | 40.99 | C |
| HETATM | 248 | CG | MSE | A | 714 | 2.749 | −3.178 | 13.077 | 1.00 | 40.19 | C |
| HETATM | 249 | SE | MSE | A | 714 | 1.084 | −2.304 | 13.492 | 1.00 | 51.52 | SE |
| HETATM | 250 | CE | MSE | A | 714 | 0.616 | −1.814 | 11.626 | 1.00 | 48.26 | C |
| ATOM | 251 | N | VAL | A | 715 | 6.526 | −0.612 | 12.531 | 1.00 | 39.23 | N |
| ATOM | 252 | CA | VAL | A | 715 | 7.377 | 0.417 | 11.918 | 1.00 | 38.24 | C |
| ATOM | 253 | C | VAL | A | 715 | 8.680 | −0.042 | 11.322 | 1.00 | 38.98 | C |
| ATOM | 254 | O | VAL | A | 715 | 9.030 | 0.378 | 10.215 | 1.00 | 40.49 | O |
| ATOM | 255 | CB | VAL | A | 715 | 7.511 | 1.753 | 12.685 | 1.00 | 37.52 | C |
| ATOM | 256 | CG1 | VAL | A | 715 | 8.332 | 1.650 | 13.952 | 1.00 | 38.25 | C |
| ATOM | 257 | CG2 | VAL | A | 715 | 8.130 | 2.756 | 11.736 | 1.00 | 38.87 | C |

TABLE 2a-continued

Data of atomic coordinates for accession code 2ZTT

| ATOM | 258 | N | GLU | A | 716 | 9.430 | −0.889 | 12.011 | 1.00 | 39.62 | N |
|---|---|---|---|---|---|---|---|---|---|---|---|
| ATOM | 259 | CA | GLU | A | 716 | 10.721 | −1.285 | 11.401 | 1.00 | 40.50 | C |
| ATOM | 260 | C | GLU | A | 716 | 10.553 | −2.232 | 10.235 | 1.00 | 38.30 | C |
| ATOM | 261 | O | GLU | A | 716 | 11.327 | −2.243 | 9.331 | 1.00 | 37.69 | O |
| ATOM | 262 | CB | GLU | A | 716 | 11.707 | −1.873 | 12.403 | 1.00 | 39.47 | C |
| ATOM | 263 | CG | GLU | A | 716 | 11.078 | −2.650 | 13.477 | 1.00 | 44.64 | C |
| ATOM | 264 | CD | GLU | A | 716 | 11.989 | −3.765 | 14.078 | 1.00 | 50.43 | C |
| ATOM | 265 | OE1 | GLU | A | 716 | 11.678 | −4.246 | 15.212 | 1.00 | 49.31 | O |
| ATOM | 266 | OE2 | GLU | A | 716 | 12.975 | −4.168 | 13.406 | 1.00 | 52.56 | O |
| ATOM | 267 | N | ALA | A | 717 | 9.525 | −3.037 | 10.288 | 1.00 | 39.03 | N |
| ATOM | 268 | CA | ALA | A | 717 | 9.225 | −3.914 | 9.208 | 1.00 | 40.47 | C |
| ATOM | 269 | C | ALA | A | 717 | 8.933 | −3.067 | 7.988 | 1.00 | 40.87 | C |
| ATOM | 270 | O | ALA | A | 717 | 9.456 | −3.329 | 6.950 | 1.00 | 42.22 | O |
| ATOM | 271 | CB | ALA | A | 717 | 8.007 | −4.776 | 9.559 | 1.00 | 39.73 | C |
| HETATM | 272 | N | MSE | A | 718 | 8.147 | −2.016 | 8.124 | 1.00 | 42.35 | N |
| HETATM | 273 | CA | MSE | A | 718 | 7.762 | −1.206 | 6.939 | 1.00 | 45.26 | C |
| HETATM | 274 | C | MSE | A | 718 | 8.904 | −0.439 | 6.351 | 1.00 | 43.03 | C |
| HETATM | 275 | O | MSE | A | 718 | 9.143 | −0.455 | 5.140 | 1.00 | 43.18 | O |
| HETATM | 276 | CB | MSE | A | 718 | 6.615 | −0.236 | 7.250 | 1.00 | 44.54 | C |
| HETATM | 277 | CG | MSE | A | 718 | 5.252 | −0.918 | 7.587 | 1.00 | 47.33 | C |
| HETATM | 278 | SE | MSE | A | 718 | 4.003 | 0.274 | 8.572 | 1.00 | 57.06 | SE |
| HETATM | 279 | CE | MSE | A | 718 | 3.112 | 1.082 | 7.125 | 1.00 | 51.11 | C |
| ATOM | 280 | N | VAL | A | 719 | 9.624 | 0.271 | 7.195 | 1.00 | 42.97 | N |
| ATOM | 281 | CA | VAL | A | 719 | 10.796 | 0.971 | 6.740 | 1.00 | 42.01 | C |
| ATOM | 282 | C | VAL | A | 719 | 11.725 | 0.007 | 6.055 | 1.00 | 41.34 | C |
| ATOM | 283 | O | VAL | A | 719 | 12.319 | 0.298 | 5.031 | 1.00 | 39.94 | O |
| ATOM | 284 | CB | VAL | A | 719 | 11.579 | 1.531 | 7.927 | 1.00 | 41.38 | C |
| ATOM | 285 | CG1 | VAL | A | 719 | 12.867 | 1.994 | 7.438 | 1.00 | 41.68 | C |
| ATOM | 286 | CG2 | VAL | A | 719 | 10.832 | 2.666 | 8.503 | 1.00 | 43.25 | C |
| ATOM | 287 | N | SER | A | 720 | 11.866 | −1.159 | 6.642 | 1.00 | 41.45 | N |
| ATOM | 288 | CA | SER | A | 720 | 12.874 | −2.068 | 6.151 | 1.00 | 42.25 | C |
| ATOM | 289 | C | SER | A | 720 | 12.413 | −2.481 | 4.747 | 1.00 | 41.95 | C |
| ATOM | 290 | O | SER | A | 720 | 13.175 | −2.440 | 3.793 | 1.00 | 41.73 | O |
| ATOM | 291 | CB | SER | A | 720 | 13.012 | −3.259 | 7.123 | 1.00 | 41.55 | C |
| ATOM | 292 | OG | SER | A | 720 | 13.418 | −4.433 | 6.430 | 1.00 | 43.75 | O |
| ATOM | 293 | N | ARG | A | 721 | 11.146 | −2.868 | 4.592 | 1.00 | 43.24 | N |
| ATOM | 294 | CA | ARG | A | 721 | 10.637 | −3.079 | 3.229 | 1.00 | 42.05 | C |
| ATOM | 295 | C | ARG | A | 721 | 10.729 | −1.847 | 2.297 | 1.00 | 41.63 | C |
| ATOM | 296 | O | ARG | A | 721 | 10.959 | −1.993 | 1.082 | 1.00 | 41.87 | O |
| ATOM | 297 | CB | ARG | A | 721 | 9.224 | −3.684 | 3.230 | 1.00 | 43.04 | C |
| ATOM | 298 | CG | ARG | A | 721 | 8.648 | −3.884 | 1.848 | 1.00 | 43.21 | C |
| ATOM | 299 | CD | ARG | A | 721 | 9.298 | −5.063 | 1.068 | 1.00 | 46.36 | C |
| ATOM | 300 | NE | ARG | A | 721 | 8.302 | −5.614 | 0.131 | 1.00 | 54.84 | N |
| ATOM | 301 | CZ | ARG | A | 721 | 7.555 | −6.715 | 0.302 | 1.00 | 55.96 | C |
| ATOM | 302 | NH1 | ARG | A | 721 | 7.696 | −7.510 | 1.362 | 1.00 | 55.82 | N |
| ATOM | 303 | NH2 | ARG | A | 721 | 6.665 | −7.041 | −0.639 | 1.00 | 59.40 | N |
| ATOM | 304 | N | ALA | A | 722 | 10.542 | −0.645 | 2.825 | 1.00 | 40.57 | N |
| ATOM | 305 | CA | ALA | A | 722 | 10.647 | 0.547 | 1.994 | 1.00 | 40.68 | C |
| ATOM | 306 | C | ALA | A | 722 | 12.047 | 0.745 | 1.405 | 1.00 | 40.44 | C |
| ATOM | 307 | O | ALA | A | 722 | 12.204 | 1.211 | 0.262 | 1.00 | 40.71 | O |
| ATOM | 308 | CB | ALA | A | 722 | 10.247 | 1.808 | 2.784 | 1.00 | 39.70 | C |
| ATOM | 309 | N | ARG | A | 723 | 13.065 | 0.418 | 2.188 | 1.00 | 40.43 | N |
| ATOM | 310 | CA | ARG | A | 723 | 14.452 | 0.465 | 1.722 | 1.00 | 40.29 | C |
| ATOM | 311 | C | ARG | A | 723 | 14.738 | −0.547 | 0.629 | 1.00 | 40.11 | C |
| ATOM | 312 | O | ARG | A | 723 | 15.410 | −0.226 | −0.351 | 1.00 | 40.13 | O |
| ATOM | 313 | CB | ARG | A | 723 | 15.365 | 0.125 | 2.869 | 1.00 | 40.83 | C |
| ATOM | 314 | CG | ARG | A | 723 | 15.744 | 1.348 | 3.569 | 1.00 | 42.64 | C |
| ATOM | 315 | CD | ARG | A | 723 | 16.062 | 1.092 | 5.039 | 1.00 | 46.78 | C |
| ATOM | 316 | NE | ARG | A | 723 | 16.506 | 2.377 | 5.521 | 1.00 | 48.20 | N |
| ATOM | 317 | CZ | ARG | A | 723 | 16.562 | 2.758 | 6.784 | 1.00 | 49.90 | C |
| ATOM | 318 | NH1 | ARG | A | 723 | 16.226 | 1.913 | 7.749 | 1.00 | 52.89 | N |
| ATOM | 319 | NH2 | ARG | A | 723 | 16.970 | 3.993 | 7.051 | 1.00 | 44.07 | N |
| ATOM | 320 | N | ILE | A | 724 | 14.279 | −1.782 | 0.820 | 1.00 | 39.26 | N |
| ATOM | 321 | CA | ILE | A | 724 | 14.683 | −2.823 | −0.062 | 1.00 | 40.97 | C |
| ATOM | 322 | C | ILE | A | 724 | 13.958 | −2.502 | −1.359 | 1.00 | 42.20 | C |
| ATOM | 323 | O | ILE | A | 724 | 14.532 | −2.592 | −2.410 | 1.00 | 44.25 | O |
| ATOM | 324 | CB | ILE | A | 724 | 14.30 | −4.248 | 0.434 | 1.00 | 41.08 | C |
| ATOM | 325 | CG1 | ILE | A | 724 | 14.674 | −4.537 | 1.910 | 1.00 | 42.45 | C |
| ATOM | 326 | CG2 | ILE | A | 724 | 14.867 | −5.276 | −0.502 | 1.00 | 42.22 | C |
| ATOM | 327 | CD1 | ILE | A | 724 | 16.096 | −5.250 | 2.201 | 1.00 | 40.15 | C |
| ATOM | 328 | N | ASP | A | 725 | 12.708 | −2.073 | −1.269 | 1.00 | 41.71 | N |
| ATOM | 329 | CA | ASP | A | 725 | 11.996 | −1.590 | −2.418 | 1.00 | 41.73 | C |
| ATOM | 330 | C | ASP | A | 725 | 12.588 | −0.339 | −3.066 | 1.00 | 41.96 | C |
| ATOM | 331 | O | ASP | A | 725 | 12.451 | −0.191 | −4.271 | 1.00 | 40.46 | O |
| ATOM | 332 | CB | ASP | A | 725 | 10.560 | −1.296 | −2.038 | 1.00 | 41.48 | C |
| ATOM | 333 | CG | ASP | A | 725 | 9.756 | −2.517 | −1.838 | 1.00 | 43.21 | C |
| ATOM | 334 | OD1 | ASP | A | 725 | 10.308 | −3.60 | −2.104 | 1.00 | 47.11 | O |
| ATOM | 335 | OD2 | ASP | A | 725 | 8.559 | −2.404 | −1.419 | 1.00 | 47.08 | O |

TABLE 2a-continued

Data of atomic coordinates for accession code 2ZTT

| ATOM | 336 | N | ALA | A | 726 | 13.250 | 0.574 | −2.319 | 1.00 | 40.57 | N |
|---|---|---|---|---|---|---|---|---|---|---|---|
| ATOM | 337 | CA | ALA | A | 726 | 13.741 | 1.746 | −3.036 | 1.00 | 38.36 | C |
| ATOM | 338 | C | ALA | A | 726 | 14.944 | 1.357 | −3.859 | 1.00 | 39.67 | C |
| ATOM | 339 | O | ALA | A | 726 | 15.091 | 1.801 | −4.996 | 1.00 | 40.26 | O |
| ATOM | 340 | CB | ALA | A | 726 | 13.990 | 2.904 | −2.131 | 1.00 | 36.90 | C |
| ATOM | 341 | N | ARG | A | 727 | 15.796 | 0.489 | −3.316 | 1.00 | 41.34 | N |
| ATOM | 342 | CA | ARG | A | 727 | 16.909 | −0.072 | −4.093 | 1.00 | 43.46 | C |
| ATOM | 343 | C | ARG | A | 727 | 16.494 | −0.835 | −5.375 | 1.00 | 43.67 | C |
| ATOM | 344 | O | ARG | A | 727 | 17.038 | −0.630 | −6.461 | 1.00 | 42.57 | O |
| ATOM | 345 | CB | ARG | A | 727 | 17.749 | −0.973 | −3.198 | 1.00 | 44.11 | C |
| ATOM | 346 | CG | ARG | A | 727 | 18.761 | −0.189 | −2.351 | 1.00 | 48.91 | C |
| ATOM | 347 | CD | ARG | A | 727 | 18.280 | 0.106 | −0.934 | 1.00 | 54.42 | C |
| ATOM | 348 | NE | ARG | A | 727 | 18.350 | −1.098 | −0.101 | 1.00 | 61.08 | N |
| ATOM | 349 | CZ | ARG | A | 727 | 19.318 | −1.396 | 0.768 | 1.00 | 62.33 | C |
| ATOM | 350 | NH1 | ARG | A | 727 | 20.346 | −0.558 | 0.968 | 1.00 | 65.34 | N |
| ATOM | 351 | NH2 | ARG | A | 727 | 19.248 | −2.543 | 1.436 | 1.00 | 60.37 | N |
| ATOM | 352 | N | ILE | A | 728 | 15.563 | −1.755 | −5.234 | 1.00 | 43.92 | N |
| ATOM | 353 | CA | ILE | A | 728 | 15.071 | −2.471 | −6.386 | 1.00 | 44.14 | C |
| ATOM | 354 | C | ILE | A | 728 | 14.522 | −1.543 | −7.494 | 1.00 | 43.30 | C |
| ATOM | 355 | O | ILE | A | 728 | 14.954 | −1.620 | −8.625 | 1.00 | 42.94 | O |
| ATOM | 356 | CB | ILE | A | 728 | 14.073 | −3.509 | −5.934 | 1.00 | 44.58 | C |
| ATOM | 357 | CG1 | ILE | A | 728 | 14.815 | −4.411 | −4.940 | 1.00 | 44.18 | C |
| ATOM | 358 | CG2 | ILE | A | 728 | 13.547 | −4.339 | −7.143 | 1.00 | 43.74 | C |
| ATOM | 359 | CD1 | ILE | A | 728 | 14.090 | −5.604 | −4.443 | 1.00 | 46.02 | C |
| ATOM | 360 | N | ASP | A | 729 | 13.644 | −0.634 | −7.140 | 1.00 | 44.03 | N |
| ATOM | 361 | CA | ASP | A | 729 | 12.975 | 0.255 | −8.088 | 1.00 | 44.88 | C |
| ATOM | 362 | C | ASP | A | 729 | 13.929 | 1.202 | −8.822 | 1.00 | 45.82 | C |
| ATOM | 363 | O | ASP | A | 729 | 13.721 | 1.561 | −10.005 | 1.00 | 44.28 | O |
| ATOM | 364 | CB | ASP | A | 729 | 11.932 | 1.060 | −7.354 | 1.00 | 44.74 | C |
| ATOM | 365 | CG | ASP | A | 729 | 10.703 | 0.250 | −6.989 | 1.00 | 49.61 | C |
| ATOM | 366 | OD1 | ASP | A | 729 | 10.151 | −0.501 | −7.861 | 1.00 | 50.43 | O |
| ATOM | 367 | OD2 | ASP | A | 729 | 10.266 | 0.395 | −5.822 | 1.00 | 51.43 | O |
| ATOM | 368 | N | PHE | A | 730 | 14.964 | 1.603 | −8.089 | 1.00 | 45.05 | N |
| ATOM | 369 | CA | PHE | A | 730 | 16.013 | 2.481 | −8.578 | 1.00 | 46.67 | C |
| ATOM | 370 | C | PHE | A | 730 | 16.944 | 1.757 | −9.544 | 1.00 | 47.60 | C |
| ATOM | 371 | O | PHE | A | 730 | 17.415 | 2.343 | −10.493 | 1.00 | 48.08 | O |
| ATOM | 372 | CB | PHE | A | 730 | 16.833 | 3.053 | −7.384 | 1.00 | 45.02 | C |
| ATOM | 373 | CG | PHE | A | 730 | 17.722 | 4.201 | −7.754 | 1.00 | 42.18 | C |
| ATOM | 374 | CD1 | PHE | A | 730 | 17.295 | 5.166 | −8.632 | 1.00 | 43.23 | C |
| ATOM | 375 | CD2 | PHE | A | 730 | 18.957 | 4.350 | −7.173 | 1.00 | 38.58 | C |
| ATOM | 376 | CE2 | PHE | A | 730 | 18.123 | 6.221 | −8.958 | 1.00 | 43.17 | C |
| ATOM | 377 | CE2 | PHE | A | 730 | 19.777 | 5.375 | −7.508 | 1.00 | 37.24 | C |
| ATOM | 378 | CZ | PHE | A | 730 | 19.374 | 6.302 | −8.391 | 1.00 | 43.16 | C |
| ATOM | 379 | N | GLU | A | 731 | 17.242 | 0.488 | −9.289 | 1.00 | 49.67 | N |
| ATOM | 380 | CA | GLU | A | 731 | 17.888 | −0.332 | −10.299 | 1.00 | 50.99 | C |
| ATOM | 381 | C | GLU | A | 731 | 17.014 | −0.491 | −11.584 | 1.00 | 51.68 | C |
| ATOM | 382 | O | GLU | A | 731 | 17.433 | −0.175 | −12.705 | 1.00 | 51.92 | O |
| ATOM | 383 | CB | GLU | A | 731 | 18.149 | −1.685 | −9.704 | 1.00 | 51.33 | C |
| ATOM | 384 | CG | GLU | A | 731 | 19.308 | −1.778 | −8.763 | 1.00 | 54.79 | C |
| ATOM | 385 | CD | GLU | A | 731 | 19.351 | −3.170 | −8.138 | 1.00 | 58.09 | C |
| ATOM | 386 | OE1 | GLU | A | 731 | 19.143 | −4.168 | −8.872 | 1.00 | 60.49 | O |
| ATOM | 387 | OE2 | GLU | A | 731 | 19.528 | −3.268 | −6.916 | 1.00 | 57.81 | O |
| ATOM | 388 | N | SER | A | 732 | 15.780 | −0.952 | −11.404 | 1.00 | 51.87 | N |
| ATOM | 389 | CA | SER | A | 732 | 14.922 | −1.254 | −12.519 | 1.00 | 51.84 | C |
| ATOM | 390 | C | SER | A | 732 | 14.572 | 0.002 | −13.275 | 1.00 | 52.33 | C |
| ATOM | 391 | O | SER | A | 732 | 13.955 | −0.070 | −14.319 | 1.00 | 52.69 | O |
| ATOM | 392 | CB | SER | A | 732 | 13.659 | −1.923 | −12.029 | 1.00 | 51.96 | C |
| ATOM | 393 | OG | SER | A | 732 | 12.694 | −0.943 | −11.725 | 1.00 | 53.91 | O |
| ATOM | 394 | N | GLY | A | 733 | 14.974 | 1.161 | −12.759 | 1.00 | 53.02 | N |
| ATOM | 395 | CA | GLY | A | 733 | 14.580 | 2.421 | −13.365 | 1.00 | 53.65 | C |
| ATOM | 396 | C | GLY | A | 733 | 13.123 | 2.856 | −13.167 | 1.00 | 54.42 | C |
| ATOM | 397 | O | GLY | A | 733 | 12.694 | 3.796 | −13.808 | 1.00 | 55.40 | O |
| ATOM | 398 | N | ARG | A | 734 | 12.368 | 2.193 | −12.291 | 1.00 | 54.18 | N |
| ATOM | 399 | CA | ARG | A | 734 | 11.026 | 2.654 | −11.865 | 1.00 | 54.60 | C |
| ATOM | 400 | C | ARG | A | 734 | 11.004 | 4.032 | −11.199 | 1.00 | 54.17 | C |
| ATOM | 401 | O | ARG | A | 734 | 10.041 | 4.799 | −11.353 | 1.00 | 55.81 | O |
| ATOM | 402 | CB | ARG | A | 734 | 10.432 | 1.672 | −10.875 | 1.00 | 54.42 | C |
| ATOM | 403 | CG | ARG | A | 734 | 8.943 | 1.766 | −10.772 | 1.00 | 57.30 | C |
| ATOM | 404 | CD | ARG | A | 734 | 8.401 | 0.496 | −10.152 | 1.00 | 59.44 | C |
| ATOM | 405 | NE | ARG | A | 734 | 8.010 | −0.556 | −11.106 | 1.00 | 63.66 | N |
| ATOM | 406 | CZ | ARG | A | 734 | 7.390 | −0.359 | −12.282 | 1.00 | 61.60 | C |
| ATOM | 407 | NH1 | ARG | A | 734 | 7.124 | 0.861 | −12.726 | 1.00 | 59.82 | N |
| ATOM | 408 | NH2 | ARG | A | 734 | 7.076 | −1.395 | −13.026 | 1.00 | 59.87 | N |
| ATOM | 409 | N | ILE | A | 735 | 12.034 | 4.330 | −10.421 | 1.00 | 52.17 | N |
| ATOM | 410 | CA | ILE | A | 735 | 12.141 | 5.637 | −9.784 | 1.00 | 50.29 | C |
| ATOM | 411 | C | ILE | A | 735 | 13.505 | 6.251 | −10.161 | 1.00 | 49.54 | C |
| ATOM | 412 | O | ILE | A | 735 | 14.420 | 5.536 | −10.611 | 1.00 | 48.21 | O |
| ATOM | 413 | CB | ILE | A | 735 | 11.902 | 5.554 | −8.228 | 1.00 | 50.44 | C |

TABLE 2a-continued

Data of atomic coordinates for accession code 2ZTT

| ATOM | 414 | CG1 | ILE | A | 735 | 12.969 | 4.682 | −7.539 | 1.00 | 49.0 | C |
|---|---|---|---|---|---|---|---|---|---|---|---|
| ATOM | 415 | CG2 | ILE | A | 735 | 10.487 | 4.993 | −7.917 | 1.00 | 48.20 | C |
| ATOM | 416 | CD1 | ILE | A | 735 | 13.360 | 5.104 | −6.117 | 1.00 | 56.09 | C |
| ATOM | 417 | N | LYS | A | 736 | 13.604 | 7.572 | −10.016 | 1.00 | 49.66 | N |
| ATOM | 418 | CA | LYS | A | 736 | 14.798 | 8.353 | −10.389 | 1.00 | 50.35 | C |
| ATOM | 419 | C | LYS | A | 736 | 15.581 | 8.737 | −9.126 | 1.00 | 49.52 | C |
| ATOM | 420 | O | LYS | A | 736 | 15.106 | 8.418 | −8.038 | 1.00 | 49.84 | O |
| ATOM | 421 | CB | LYS | A | 736 | 14.371 | 9.588 | −11.203 | 1.00 | 50.85 | C |
| ATOM | 422 | CG | LYS | A | 736 | 14.547 | 9.486 | −12.737 | 1.00 | 53.92 | C |
| ATOM | 423 | CD | LYS | A | 736 | 14.087 | 8.151 | −13.303 | 1.00 | 59.62 | C |
| ATOM | 424 | CE | LYS | A | 736 | 15.094 | 7.601 | −14.329 | 1.00 | 61.59 | C |
| ATOM | 425 | NZ | LYS | A | 736 | 14.661 | 6.260 | −14.881 | 1.00 | 64.83 | N |
| ATOM | 426 | N | LYS | A | 737 | 16.750 | 9.40 | −9.246 | 1.00 | 48.16 | N |
| ATOM | 427 | CA | LYS | A | 737 | 17.559 | 9.750 | −8.049 | 1.00 | 48.81 | C |
| ATOM | 428 | C | LYS | A | 737 | 16.878 | 10.623 | −6.985 | 1.00 | 47.77 | C |
| ATOM | 429 | O | LYS | A | 737 | 17.027 | 10.391 | −5.792 | 1.00 | 46.36 | O |
| ATOM | 430 | CB | LYS | A | 737 | 18.979 | 10.284 | −8.382 | 1.00 | 48.75 | C |
| ATOM | 431 | CG | LYS | A | 737 | 19.073 | 11.721 | −8.819 | 1.00 | 51.78 | C |
| ATOM | 432 | CD | LYS | A | 737 | 20.312 | 12.402 | −8.215 | 1.00 | 56.26 | C |
| ATOM | 433 | CE | LYS | A | 737 | 21.482 | 12.441 | −9.215 | 1.00 | 57.73 | C |
| ATOM | 434 | NZ | LYS | A | 737 | 21.388 | 13.586 | −10.180 | 1.00 | 57.20 | N |
| ATOM | 435 | N | GLU | A | 738 | 16.141 | 11.631 | −7.438 | 1.00 | 48.0 | N |
| ATOM | 436 | CA | GLU | A | 738 | 15.485 | 12.565 | −6.545 | 1.00 | 48.06 | C |
| ATOM | 437 | C | GLU | A | 738 | 14.421 | 11.791 | −5.764 | 1.00 | 47.03 | C |
| ATOM | 438 | O | GLU | A | 738 | 14.371 | 11.832 | −4.538 | 1.00 | 47.14 | O |
| ATOM | 439 | CB | GLU | A | 738 | 14.888 | 13.756 | −7.323 | 1.00 | 48.76 | C |
| ATOM | 440 | CG | GLU | A | 738 | 15.896 | 14.704 | −8.038 | 1.00 | 50.76 | C |
| ATOM | 441 | CD | GLU | A | 738 | 16.455 | 14.142 | −9.355 | 1.00 | 56.88 | C |
| ATOM | 442 | OE1 | GLU | A | 738 | 15.999 | 13.060 | −9.823 | 1.00 | 58.84 | O |
| ATOM | 443 | OE2 | GLU | A | 738 | 17.361 | 14.789 | −9.932 | 1.00 | 57.37 | O |
| ATOM | 444 | N | GLU | A | 739 | 13.6031 | 1.035 | −6.480 | 1.00 | 46.59 | N |
| ATOM | 445 | CA | GLU | A | 739 | 12.640 | 10.179 | −5.842 | 1.00 | 44.38 | C |
| ATOM | 446 | C | GLU | A | 739 | 13.257 | 9.180 | −4.877 | 1.00 | 42.30 | C |
| ATOM | 447 | O | GLU | A | 739 | 12.678 | 8.919 | −3.864 | 1.00 | 41.78 | O |
| ATOM | 448 | CB | GLU | A | 739 | 11.793 | 9.443 | −6.868 | 1.00 | 43.95 | C |
| ATOM | 449 | CG | GLU | A | 739 | 10.835 | 8.448 | −6.160 | 1.00 | 44.71 | C |
| ATOM | 450 | CD | GLU | A | 739 | 9.426 | 8.419 | −6.747 | 1.00 | 52.94 | C |
| ATOM | 451 | OE1 | GLU | A | 739 | 9.183 | 9.076 | −7.802 | 1.00 | 53.45 | O |
| ATOM | 452 | OE2 | GLU | A | 739 | 8.567 | 7.737 | −6.134 | 1.00 | 54.25 | O |
| ATOM | 453 | N | PHE | A | 740 | 14.428 | 8.620 | −5.209 | 1.00 | 42.71 | N |
| ATOM | 454 | CA | PHE | A | 740 | 15.144 | 7.628 | −4.370 | 1.00 | 39.62 | C |
| ATOM | 455 | C | PHE | A | 740 | 15.696 | 8.242 | −3.068 | 1.00 | 40.09 | C |
| ATOM | 456 | O | PHE | A | 740 | 15.740 | 7.601 | −1.985 | 1.00 | 38.55 | O |
| ATOM | 457 | CB | PHE | A | 740 | 16.289 | 6.969 | −5.171 | 1.00 | 38.38 | C |
| ATOM | 458 | CG | PHE | A | 740 | 17.141 | 6.053 | −4.334 | 1.00 | 37.76 | C |
| ATOM | 459 | CD1 | PHE | A | 740 | 16.728 | 4.782 | −4.044 | 1.00 | 31.71 | C |
| ATOM | 460 | CD2 | PHE | A | 740 | 18.346 | 6.512 | −3.752 | 1.00 | 39.20 | C |
| ATOM | 461 | CE2 | PHE | A | 740 | 17.486 | 3.933 | −3.203 | 1.00 | 39.72 | C |
| ATOM | 462 | CE2 | PHE | A | 740 | 19.097 | 5.673 | −2.930 | 1.00 | 35.43 | C |
| ATOM | 463 | CZ | PHE | A | 740 | 18.669 | 4.377 | −2.669 | 1.00 | 35.91 | C |
| ATOM | 464 | N | THR | A | 741 | 16.145 | 9.478 | −3.223 | 1.00 | 39.59 | N |
| ATOM | 465 | CA | THR | A | 741 | 16.793 | 10.233 | −2.164 | 1.00 | 39.76 | C |
| ATOM | 466 | C | THR | A | 741 | 15.794 | 10.616 | −1.101 | 1.00 | 38.86 | C |
| ATOM | 467 | O | THR | A | 741 | 16.010 | 10.475 | 0.068 | 1.00 | 38.78 | O |
| ATOM | 468 | CB | THR | A | 741 | 17.5531 | 1.458 | −2.758 | 1.00 | 39.84 | C |
| ATOM | 469 | OG1 | THR | A | 741 | 18.728 | 10.993 | −3.427 | 1.00 | 41.32 | O |
| ATOM | 470 | CG2 | THR | A | 741 | 17.942 | 12.449 | −1.689 | 1.00 | 39.81 | C |
| ATOM | 471 | N | GLU | A | 742 | 14.649 | 11.050 | −1.534 | 1.00 | 38.78 | N |
| ATOM | 472 | CA | GLU | A | 742 | 13.654 | 11.465 | −0.634 | 1.00 | 38.47 | C |
| ATOM | 473 | C | GLU | A | 742 | 13.105 | 10.355 | 0.164 | 1.00 | 36.53 | C |
| ATOM | 474 | O | GLU | A | 742 | 12.617 | 10.562 | 1.287 | 1.00 | 38.58 | O |
| ATOM | 475 | CB | GLU | A | 742 | 12.512 | 12.046 | −1.432 | 1.00 | 38.92 | C |
| ATOM | 476 | CG | GLU | A | 742 | 11.506 | 12.671 | −0.561 | 1.00 | 43.82 | C |
| ATOM | 477 | CD | GLU | A | 742 | 10.492 | 13.452 | −1.363 | 1.00 | 47.86 | C |
| ATOM | 478 | OE1 | GLU | A | 742 | 10.467 | 13.293 | −2.624 | 1.00 | 50.37 | O |
| ATOM | 479 | OE2 | GLU | A | 742 | 9.747 | 14.233 | −0.717 | 1.00 | 52.36 | O |
| ATOM | 480 | N | ILE | A | 743 | 13.083 | 9.170 | −0.397 | 1.00 | 34.49 | N |
| ATOM | 481 | CA | ILE | A | 743 | 12.410 | 8.092 | 0.279 | 1.00 | 34.24 | C |
| ATOM | 482 | C | ILE | A | 743 | 13.377 | 7.635 | 1.388 | 1.00 | 34.79 | C |
| ATOM | 483 | O | ILE | A | 743 | 13.011 | 7.395 | 2.506 | 1.00 | 36.40 | O |
| ATOM | 484 | CB | ILE | A | 743 | 12.083 | 6.924 | −0.685 | 1.00 | 32.20 | C |
| ATOM | 485 | CG1 | ILE | A | 743 | 10.841 | 7.205 | −1.590 | 1.00 | 34.75 | C |
| ATOM | 486 | CG2 | ILE | A | 743 | 11.852 | 5.762 | 0.143 | 1.00 | 31.72 | C |
| ATOM | 487 | CD1 | ILE | A | 743 | 10.445 | 6.019 | −2.436 | 1.00 | 29.67 | C |
| HETATM | 488 | N | MSE | A | 744 | 14.617 | 7.550 | 1.012 | 1.00 | 36.38 | N |
| HETATM | 489 | CA | MSE | A | 744 | 15.725 | 7.239 | 1.910 | 1.00 | 38.16 | C |
| HETATM | 490 | C | MSE | A | 744 | 15.803 | 8.235 | 3.066 | 1.00 | 38.30 | C |
| HETATM | 491 | O | MSE | A | 744 | 15.798 | 7.826 | 4.181 | 1.00 | 37.94 | O |

TABLE 2a-continued

Data of atomic coordinates for accession code 2ZTT

| HETATM | 492 | CB  | MSE | A | 744 | 17.001 | 7.190  | 1.096  | 1.00 | 38.36 | C  |
| ------ | --- | --- | --- | - | --- | ------ | ------ | ------ | ---- | ----- | -- |
| HETATM | 493 | CG  | MSE | A | 744 | 16.983 | 5.992  | 0.169  | 1.00 | 43.64 | C  |
| HETATM | 494 | SE  | MSE | A | 744 | 16.663 | 4.223  | 1.039  | 1.00 | 63.43 | SE |
| HETATM | 495 | CE  | MSE | A | 744 | 18.206 | 4.178  | 2.262  | 1.00 | 50.81 | C  |
| ATOM   | 496 | N   | LYS | A | 745 | 15.771 | 9.530  | 2.80   | 1.00 | 39.39 | N  |
| ATOM   | 497 | CA  | LYS | A | 745 | 15.720 | 10.521 | 3.904  | 1.00 | 40.03 | C  |
| ATOM   | 498 | C   | LYS | A | 745 | 14.472 | 10.454 | 4.793  | 1.00 | 39.11 | C  |
| ATOM   | 499 | O   | LYS | A | 745 | 14.553 | 10.725 | 5.951  | 1.00 | 39.92 | O  |
| ATOM   | 500 | CB  | LYS | A | 745 | 15.899 | 11.931 | 3.373  | 1.00 | 38.96 | C  |
| ATOM   | 501 | CG  | LYS | A | 745 | 17.331 | 12.296 | 3.268  | 1.00 | 44.33 | C  |
| ATOM   | 502 | CD  | LYS | A | 745 | 17.535 | 13.531 | 2.441  | 1.00 | 46.25 | C  |
| ATOM   | 503 | CE  | LYS | A | 745 | 18.837 | 13.289 | 1.771  | 1.00 | 49.77 | C  |
| ATOM   | 504 | NZ  | LYS | A | 745 | 19.662 | 12.464 | 2.761  | 1.00 | 55.49 | N  |
| ATOM   | 505 | N   | ILE | A | 746 | 13.309 | 10.082 | 4.251  | 1.00 | 39.26 | N  |
| ATOM   | 506 | CA  | ILE | A | 746 | 12.097 | 9.949  | 5.088  | 1.00 | 37.66 | C  |
| ATOM   | 507 | C   | ILE | A | 746 | 12.284 | 8.747  | 6.006  | 1.00 | 37.60 | C  |
| ATOM   | 508 | O   | ILE | A | 746 | 11.846 | 8.783  | 7.154  | 1.00 | 37.33 | O  |
| ATOM   | 509 | CB  | ILE | A | 746 | 10.765 | 9.927  | 4.219  | 1.00 | 38.17 | C  |
| ATOM   | 510 | CG1 | ILE | A | 746 | 10.591 | 11.290 | 3.555  | 1.00 | 39.20 | C  |
| ATOM   | 511 | CG2 | ILE | A | 746 | 9.515  | 9.480  | 5.037  | 1.00 | 37.39 | C  |
| ATOM   | 512 | CD1 | ILE | A | 746 | 9.404  | 11.504 | 2.632  | 1.00 | 35.74 | C  |
| ATOM   | 513 | N   | CYS | A | 747 | 12.938 | 7.694  | 5.490  | 1.00 | 37.35 | N  |
| ATOM   | 514 | CA  | CYS | A | 747 | 13.216 | 6.497  | 6.258  | 1.00 | 38.01 | C  |
| ATOM   | 515 | C   | CYS | A | 747 | 14.163 | 6.774  | 7.471  | 1.00 | 38.37 | C  |
| ATOM   | 516 | O   | CYS | A | 747 | 13.960 | 6.241  | 8.550  | 1.00 | 37.59 | O  |
| ATOM   | 517 | CB  | CYS | A | 747 | 13.809 | 5.386  | 5.364  | 1.00 | 36.70 | C  |
| ATOM   | 518 | SG  | CYS | A | 747 | 12.664 | 4.466  | 4.210  | 1.00 | 40.72 | S  |
| ATOM   | 519 | N   | SER | A | 748 | 15.201 | 7.566  | 7.267  | 1.00 | 38.87 | N  |
| ATOM   | 520 | CA  | SER | A | 748 | 16.155 | 7.862  | 8.374  | 1.00 | 41.82 | C  |
| ATOM   | 521 | C   | SER | A | 748 | 15.455 | 8.752  | 9.414  | 1.00 | 41.06 | C  |
| ATOM   | 522 | O   | SER | A | 748 | 15.512 | 8.495  | 10.588 | 1.00 | 41.66 | O  |
| ATOM   | 523 | CB  | SER | A | 748 | 17.430 | 8.514  | 7.817  | 1.00 | 41.86 | C  |
| ATOM   | 524 | OG  | SER | A | 748 | 17.082 | 9.775  | 7.288  | 1.00 | 47.84 | O  |
| ATOM   | 525 | N   | THR | A | 749 | 14.664 | 9.716  | 8.954  | 1.00 | 41.82 | N  |
| ATOM   | 526 | CA  | THR | A | 749 | 13.729 | 10.430 | 9.827  | 1.00 | 40.42 | C  |
| ATOM   | 527 | C   | THR | A | 749 | 12.805 | 9.506  | 10.607 | 1.00 | 40.89 | C  |
| ATOM   | 528 | O   | THR | A | 749 | 12.672 | 9.664  | 11.795 | 1.00 | 38.72 | O  |
| ATOM   | 529 | CB  | THR | A | 749 | 12.967 | 11.482 | 9.035  | 1.00 | 40.50 | C  |
| ATOM   | 530 | CG1 | THR | A | 749 | 13.962 | 12.436 | 8.608  | 1.00 | 44.11 | O  |
| ATOM   | 531 | CG2 | THR | A | 749 | 11.875 | 12.183 | 9.890  | 1.00 | 36.30 | C  |
| ATOM   | 532 | N   | ILE | A | 750 | 12.167 | 8.530  | 9.956  | 1.00 | 41.94 | N  |
| ATOM   | 533 | CA  | ILE | A | 750 | 11.282 | 7.597  | 10.699 | 1.00 | 43.52 | C  |
| ATOM   | 534 | C   | ILE | A | 750 | 12.086 | 6.839  | 11.818 | 1.00 | 44.80 | C  |
| ATOM   | 535 | O   | ILE | A | 750 | 11.603 | 6.725  | 12.942 | 1.00 | 44.53 | O  |
| ATOM   | 536 | CB  | ILE | A | 750 | 10.492 | 6.650  | 9.736  | 1.00 | 43.26 | C  |
| ATOM   | 537 | CG1 | ILE | A | 750 | 9.486  | 7.458  | 8.924  | 1.00 | 40.85 | C  |
| ATOM   | 538 | CG2 | ILE | A | 750 | 9.723  | 5.611  | 10.485 | 1.00 | 43.46 | C  |
| ATOM   | 539 | CD1 | ILE | A | 750 | 9.046  | 6.813  | 7.647  | 1.00 | 39.38 | C  |
| ATOM   | 540 | N   | GLU | A | 751 | 13.284 | 6.339  | 11.474 | 1.00 | 45.35 | N  |
| ATOM   | 541 | CA  | GLU | A | 751 | 14.172 | 5.573  | 12.383 | 1.00 | 47.97 | C  |
| ATOM   | 542 | C   | GLU | A | 751 | 14.578 | 6.342  | 13.625 | 1.00 | 49.78 | C  |
| ATOM   | 543 | O   | GLU | A | 751 | 14.708 | 5.776  | 14.675 | 1.00 | 50.69 | O  |
| ATOM   | 544 | CB  | GLU | A | 751 | 15.453 | 5.147  | 11.666 | 1.00 | 48.65 | C  |
| ATOM   | 545 | CG  | GLU | A | 751 | 15.234 | 4.172  | 10.544 | 1.00 | 49.41 | C  |
| ATOM   | 546 | CD  | GLU | A | 751 | 14.970 | 2.778  | 11.040 | 1.00 | 55.12 | C  |
| ATOM   | 547 | OE1 | GLU | A | 751 | 15.862 | 1.919  | 10.862 | 1.00 | 56.40 | O  |
| ATOM   | 548 | OE2 | GLU | A | 751 | 13.879 | 2.526  | 11.603 | 1.00 | 58.64 | O  |
| ATOM   | 549 | N   | GLU | A | 752 | 14.759 | 7.641  | 13.477 | 1.00 | 52.58 | N  |
| ATOM   | 550 | CA  | GLU | A | 752 | 15.028 | 8.524  | 14.585 | 1.00 | 55.73 | C  |
| ATOM   | 551 | C   | GLU | A | 752 | 13.852 | 8.620  | 15.540 | 1.00 | 55.75 | C  |
| ATOM   | 552 | O   | GLU | A | 752 | 14.029 | 8.545  | 16.748 | 1.00 | 55.63 | O  |
| ATOM   | 553 | CB  | GLU | A | 752 | 15.370 | 9.899  | 14.052 | 1.00 | 56.31 | C  |
| ATOM   | 554 | CG  | GLU | A | 752 | 16.821 | 10.050 | 13.745 | 1.00 | 61.66 | C  |
| ATOM   | 555 | CD  | GLU | A | 752 | 17.203 | 11.510 | 13.738 | 1.00 | 69.32 | C  |
| ATOM   | 556 | OE1 | GLU | A | 752 | 16.890 | 12.183 | 12.711 | 1.00 | 71.91 | O  |
| ATOM   | 557 | OE2 | GLU | A | 752 | 17.781 | 11.981 | 14.770 | 1.00 | 71.81 | O  |
| ATOM   | 558 | N   | LEU | A | 753 | 12.661 | 8.805  | 14.984 | 1.00 | 56.56 | N  |
| ATOM   | 559 | CA  | LEU | A | 753 | 11.416 | 8.779  | 15.763 | 1.00 | 57.39 | C  |
| ATOM   | 560 | C   | LEU | A | 753 | 11.149 | 7.465  | 16.492 | 1.00 | 59.02 | C  |
| ATOM   | 561 | O   | LEU | A | 753 | 10.417 | 7.467  | 17.475 | 1.00 | 59.27 | O  |
| ATOM   | 562 | CB  | LEU | A | 753 | 10.217 | 9.147  | 14.895 | 1.00 | 56.32 | C  |
| ATOM   | 563 | CG  | LEU | A | 753 | 10.295 | 10.497 | 14.183 | 1.00 | 55.06 | C  |
| ATOM   | 564 | CD1 | LEU | A | 753 | 9.236  | 10.597 | 13.112 | 1.00 | 55.56 | C  |
| ATOM   | 565 | CD2 | LEU | A | 753 | 10.182 | 11.629 | 15.167 | 1.00 | 54.33 | C  |
| ATOM   | 566 | N   | ARG | A | 754 | 11.686 | 6.345  | 16.021 | 1.00 | 61.05 | N  |
| ATOM   | 567 | CA  | ARG | A | 754 | 11.595 | 5.115  | 16.820 | 1.00 | 64.13 | C  |
| ATOM   | 568 | C   | ARG | A | 754 | 12.669 | 5.142  | 17.905 | 1.00 | 66.60 | C  |
| ATOM   | 569 | O   | ARG | A | 754 | 12.396 | 4.840  | 19.059 | 1.00 | 67.38 | O  |

TABLE 2a-continued

Data of atomic coordinates for accession code 2ZTT

| ATOM | 570 | CB | ARG | A | 754 | 11.820 | 3.843 | 16.010 | 1.00 | 63.32 | C |
|---|---|---|---|---|---|---|---|---|---|---|---|
| ATOM | 571 | CG | ARG | A | 754 | 11.379 | 3.862 | 14.592 | 1.00 | 62.66 | C |
| ATOM | 572 | CD | ARG | A | 754 | 11.996 | 2.689 | 13.813 | 1.00 | 63.07 | C |
| ATOM | 573 | NE | ARG | A | 754 | 12.173 | 1.448 | 14.588 | 1.00 | 63.81 | N |
| ATOM | 574 | CZ | ARG | A | 754 | 13.354 | 0.953 | 14.985 | 1.00 | 64.77 | C |
| ATOM | 575 | NH1 | ARG | A | 754 | 14.488 | 1.595 | 14.706 | 1.00 | 63.70 | N |
| ATOM | 576 | NH2 | ARG | A | 754 | 13.402 | −0.189 | 15.667 | 1.00 | 62.76 | N |
| ATOM | 577 | N | ARG | A | 755 | 13.899 | 5.474 | 17.515 | 1.00 | 69.50 | N |
| ATOM | 578 | CA | ARG | A | 755 | 15.046 | 5.440 | 18.426 | 1.00 | 72.08 | C |
| ATOM | 579 | C | ARG | A | 755 | 15.134 | 6.733 | 19.212 | 1.00 | 73.45 | C |
| ATOM | 580 | O | ARG | A | 755 | 16.079 | 7.517 | 19.052 | 1.00 | 74.09 | O |
| ATOM | 581 | CB | ARG | A | 755 | 16.348 | 5.171 | 17.658 | 1.00 | 72.08 | C |
| ATOM | 582 | CG | ARG | A | 755 | 16.581 | 3.701 | 17.322 | 1.00 | 73.83 | C |
| ATOM | 583 | CD | ARG | A | 755 | 17.913 | 3.526 | 16.615 | 1.00 | 76.69 | C |
| ATOM | 584 | NE | ARG | A | 755 | 18.022 | 2.235 | 15.929 | 1.00 | 78.38 | N |
| ATOM | 585 | CZ | ARG | A | 755 | 18.645 | 2.045 | 14.762 | 1.00 | 78.49 | C |
| ATOM | 586 | NH1 | ARG | A | 755 | 19.209 | 3.071 | 14.118 | 1.00 | 78.24 | N |
| ATOM | 587 | NH2 | ARG | A | 755 | 18.692 | 0.825 | 14.226 | 1.00 | 77.75 | N |
| ATOM | 588 | N | GLN | A | 756 | 14.108 | 6.961 | 20.022 | 1.00 | 75.61 | N |
| ATOM | 589 | CA | GLN | A | 756 | 14.038 | 8.045 | 21.000 | 1.00 | 77.08 | C |
| ATOM | 590 | C | GLN | A | 756 | 12.682 | 7.846 | 21.592 | 1.00 | 77.74 | C |
| ATOM | 591 | O | GLN | A | 756 | 11.809 | 7.279 | 20.949 | 1.00 | 77.65 | O |
| ATOM | 592 | CB | GLN | A | 756 | 14.146 | 9.450 | 20.376 | 1.00 | 77.35 | C |
| ATOM | 593 | CG | GLN | A | 756 | 14.409 | 10.609 | 21.415 | 1.00 | 77.63 | C |
| ATOM | 594 | CD | GLN | A | 756 | 14.866 | 11.954 | 20.774 | 1.00 | 78.43 | C |
| ATOM | 595 | OE1 | GLN | A | 756 | 14.412 | 12.321 | 19.688 | 1.00 | 78.97 | O |
| ATOM | 596 | NE2 | GLN | A | 756 | 15.768 | 12.682 | 21.464 | 1.00 | 78.98 | N |
| ATOM | 597 | N | LYS | A | 757 | 12.525 | 8.283 | 22.831 | 1.00 | 79.03 | N |
| ATOM | 598 | CA | LYS | A | 757 | 11.241 | 8.247 | 23.528 | 1.00 | 80.26 | C |
| ATOM | 599 | C | LYS | A | 757 | 10.510 | 6.922 | 23.232 | 1.00 | 80.76 | C |
| ATOM | 600 | O | LYS | A | 757 | 11.029 | 5.819 | 23.460 | 1.00 | 81.26 | O |
| ATOM | 601 | CB | LYS | A | 757 | 10.400 | 9.480 | 23.141 | 1.00 | 80.28 | C |
| ATOM | 602 | CG | LYS | A | 757 | 9.667 | 10.183 | 24.293 | 1.00 | 80.53 | C |
| ATOM | 603 | CD | LYS | A | 757 | 8.452 | 9.404 | 24.803 | 1.00 | 80.58 | C |
| ATOM | 604 | CE | LYS | A | 757 | 7.399 | 9.118 | 23.70 4 | 1.00 | 81.60 | C |
| ATOM | 605 | NZ | LYS | A | 757 | 6.874 | 10.338 | 23.048 | 1.00 | 79.79 | N |
| ATOM | 606 | OXT | LYS | A | 757 | 9.387 | 6.896 | 22.742 | 1.00 | 81.71 | O |
| TER | 607 | | LYS | A | 757 | | | | | | |
| ATOM | 608 | N | GLY | B | −1 | 3.687 | 6.195 | −5.425 | 1.00 | 49.69 | N |
| ATOM | 609 | CA | GLY | B | −1 | 3.102 | 4.897 | −4.911 | 1.00 | 49.06 | C |
| ATOM | 610 | C | GLY | B | −1 | 3.90 | 4.449 | −3.699 | 1.00 | 49.01 | C |
| ATOM | 611 | O | GLY | B | −1 | 3.335 | 4.210 | −2.619 | 1.00 | 48.23 | O |
| ATOM | 612 | N | SER | B | 0 | 5.213 | 4.356 | −3.925 | 1.00 | 49.44 | N |
| ATOM | 613 | CA | SER | B | 0 | 6.274 | 4.184 | −2.903 | 1.00 | 50.23 | C |
| ATOM | 614 | C | SER | B | 0 | 6.430 | 5.443 | −2.082 | 1.00 | 51.05 | C |
| ATOM | 615 | O | SER | B | 0 | 6.848 | 5.397 | −0.887 | 1.00 | 51.04 | O |
| ATOM | 616 | CB | SER | B | 0 | 7.617 | 4.000 | −3.593 | 1.00 | 49.58 | C |
| ATOM | 617 | OG | SER | B | 0 | 7.689 | 2.747 | −4.191 | 1.00 | 50.44 | O |
| HETATM | 618 | N | MSE | B | 1 | 6.196 | 6.562 | −2.765 | 1.00 | 51.06 | N |
| HETATM | 619 | CA | MSE | B | 1 | 6.282 | 7.872 | −2.174 | 1.00 | 51.22 | C |
| HETATM | 620 | C | MSE | B | 1 | 5.054 | 8.145 | −1.287 | 1.00 | 50.75 | C |
| HETATM | 621 | O | MSE | B | 1 | 5.227 | 8.570 | −0.132 | 1.00 | 51.50 | O |
| HETATM | 622 | CB | MSE | B | 1 | 6.485 | 8.964 | −3.235 | 1.00 | 51.81 | C |
| HETATM | 623 | CG | MSE | B | 1 | 6.867 | 10.341 | −2.635 | 1.00 | 55.82 | C |
| HETATM | 624 | SE | MSE | B | 1 | 8.680 | 10.314 | −1.721 | 1.00 | 69.55 | SE |
| HETATM | 625 | CE | MSE | B | 1 | 9.695 | 10.439 | −3.369 | 1.00 | 65.74 | C |
| ATOM | 626 | N | GLU | B | 2 | 3.833 | 7.897 | −1.782 | 1.00 | 49.12 | N |
| ATOM | 627 | CA | GLU | B | 2 | 2.669 | 8.069 | −0.930 | 1.00 | 48.58 | C |
| ATOM | 628 | C | GLU | B | 2 | 2.743 | 7.284 | 0.388 | 1.00 | 46.95 | C |
| ATOM | 629 | O | GLU | B | 2 | 2.393 | 7.842 | 1.408 | 1.00 | 46.10 | O |
| ATOM | 630 | CB | GLU | B | 2 | 1.322 | 7.812 | −1.627 | 1.00 | 49.34 | C |
| ATOM | 631 | CG | GLU | B | 2 | 1.129 | 6.447 | −2.330 | 1.00 | 56.53 | C |
| ATOM | 632 | CD | GLU | B | 2 | 0.534 | 5.302 | −1.448 | 1.00 | 61.70 | C |
| ATOM | 633 | OE1 | GLU | B | 2 | 0.832 | 4.115 | −1.751 | 1.00 | 61.66 | O |
| ATOM | 634 | OE2 | GLU | B | 2 | −0.229 | 5.585 | −0.478 | 1.00 | 62.59 | O |
| ATOM | 635 | N | ARG | B | 3 | 3.193 | 6.019 | 0.33 | 51.00 | 44.52 | N |
| ATOM | 636 | CA | ARG | B | 3 | 3.214 | 5.106 | 1.489 | 1.00 | 42.20 | C |
| ATOM | 637 | C | ARG | B | 3 | 4.215 | 5.495 | 2.578 | 1.00 | 39.40 | C |
| ATOM | 638 | O | ARG | B | 3 | 3.887 | 5.457 | 3.728 | 1.00 | 37.88 | O |
| ATOM | 639 | CB | ARG | B | 3 | 3.381 | 3.631 | 1.074 | 1.00 | 41.28 | C |
| ATOM | 640 | CG | ARG | B | 3 | 4.806 | 3.161 | 0.665 | 1.00 | 42.42 | C |
| ATOM | 641 | CD | ARG | B | 3 | 4.861 | 1.676 | 0.120 | 1.00 | 42.52 | C |
| ATOM | 642 | NE | ARG | B | 3 | 6.213 | 1.301 | −0.370 | 1.00 | 42.55 | N |
| ATOM | 643 | CZ | ARG | B | 3 | 6.659 | 0.053 | −0.491 | 1.00 | 39.28 | C |
| ATOM | 644 | NH1 | ARG | B | 3 | 7.897 | −0.203 | −0.898 | 1.00 | 37.28 | N |
| ATOM | 645 | NH2 | ARG | B | 3 | 5.864 | −0.958 | −0.189 | 1.00 | 45.21 | N |
| ATOM | 646 | N | ILE | B | 4 | 5.428 | 5.854 | 2.193 | 1.00 | 39.66 | N |
| ATOM | 647 | CA | ILE | B | 4 | 6.418 | 6.353 | 3.161 | 1.00 | 39.53 | C |

TABLE 2a-continued

Data of atomic coordinates for accession code 2ZTT

| ATOM | 648 | C | ILE | B | 4 | 6.096 | 7.753 | 3.743 | 1.00 | 40.12 | C |
|---|---|---|---|---|---|---|---|---|---|---|---|
| ATOM | 649 | O | ILE | B | 4 | 6.519 | 8.084 | 4.875 | 1.00 | 41.05 | O |
| ATOM | 650 | CB | ILE | B | 4 | 7.890 | 6.207 | 2.630 | 1.00 | 39.49 | C |
| ATOM | 651 | CG1 | ILE | B | 4 | 8.911 | 6.140 | 3.804 | 1.00 | 39.21 | C |
| ATOM | 652 | CG2 | ILE | B | 4 | 8.245 | 7.301 | 1.621 | 1.00 | 37.03 | C |
| ATOM | 653 | CD1 | ILE | B | 4 | 9.067 | 4.767 | 4.491 | 1.00 | 35.08 | C |
| ATOM | 654 | N | LYS | B | 5 | 5.335 | 8.575 | 3.004 | 1.00 | 40.38 | N |
| ATOM | 655 | CA | LYS | B | 5 | 4.909 | 9.836 | 3.503 | 1.00 | 39.41 | C |
| ATOM | 656 | C | LYS | B | 5 | 3.758 | 9.609 | 4.424 | 1.00 | 39.66 | C |
| ATOM | 657 | O | LYS | B | 5 | 3.588 | 10.40 | 5.334 | 1.00 | 40.0 | O |
| ATOM | 658 | CB | LYS | B | 5 | 4.506 | 10.844 | 2.408 | 1.00 | 40.45 | C |
| ATOM | 659 | CG | LYS | B | 5 | 5.678 | 11.452 | 1.652 | 1.00 | 40.08 | C |
| ATOM | 660 | CD | LYS | B | 5 | 5.213 | 12.447 | 0.619 | 1.00 | 41.11 | C |
| ATOM | 661 | CE | LYS | B | 5 | 6.423 | 12.905 | −0.218 | 1.00 | 42.32 | C |
| ATOM | 662 | NZ | LYS | B | 5 | 6.068 | 14.065 | −1.043 | 1.00 | 47.84 | N |
| ATOM | 663 | N | GLU | B | 6 | 2.947 | 8.564 | 4.239 | 1.00 | 39.14 | N |
| ATOM | 664 | CA | GLU | B | 6 | 1.886 | 8.391 | 5.243 | 1.00 | 40.64 | C |
| ATOM | 665 | C | GLU | B | 6 | 2.453 | 7.770 | 6.528 | 1.00 | 38.58 | C |
| ATOM | 666 | O | GLU | B | 6 | 1.890 | 7.959 | 7.586 | 1.00 | 37.96 | O |
| ATOM | 667 | CB | GLU | B | 6 | 0.711 | 7.523 | 4.762 | 1.00 | 41.19 | C |
| ATOM | 668 | CG | GLU | B | 6 | 0.106 | 7.882 | 3.380 | 1.00 | 44.48 | C |
| ATOM | 669 | CD | GLU | B | 6 | −0.886 | 6.837 | 2.925 | 1.00 | 46.07 | C |
| ATOM | 670 | OE1 | GLU | B | 6 | −2.106 | 6.985 | 3.205 | 1.00 | 55.88 | O |
| ATOM | 671 | OE2 | GLU | B | 6 | −0.462 | 5.832 | 2.345 | 1.00 | 52.78 | O |
| ATOM | 672 | N | LEU | B | 7 | 3.524 | 6.997 | 6.414 | 1.00 | 37.08 | N |
| ATOM | 673 | CA | LEU | B | 7 | 4.202 | 6.440 | 7.592 | 1.00 | 37.41 | C |
| ATOM | 674 | C | LEU | B | 7 | 4.813 | 7.559 | 8.475 | 1.00 | 36.68 | C |
| ATOM | 675 | O | LEU | B | 7 | 4.573 | 7.566 | 9.683 | 1.00 | 38.86 | O |
| ATOM | 676 | CB | LEU | B | 7 | 5.286 | 5.414 | 7.183 | 1.00 | 35.50 | C |
| ATOM | 677 | CG | LEU | B | 7 | 5.643 | 4.232 | 8.10 | 1.00 | 39.30 | C |
| ATOM | 678 | CD1 | LEU | B | 7 | 7.115 | 3.759 | 8.004 | 1.00 | 39.35 | O |
| ATOM | 679 | CD2 | LEU | B | 7 | 5.148 | 4.236 | 9.544 | 1.00 | 34.85 | C |
| ATOM | 680 | N | ARG | B | 8 | 5.622 | 8.430 | 7.871 | 1.00 | 38.10 | N |
| ATOM | 681 | CA | ARG | B | 8 | 6.141 | 9.672 | 8.446 | 1.00 | 38.47 | C |
| ATOM | 682 | C | ARG | B | 8 | 5.006 | 10.434 | 9.139 | 1.00 | 39.44 | C |
| ATOM | 683 | O | ARG | B | 8 | 5.163 | 10.901 | 10.268 | 1.00 | 41.74 | O |
| ATOM | 684 | CB | ARG | B | 8 | 6.840 | 10.562 | 7.391 | 1.00 | 38.05 | C |
| ATOM | 685 | CG | ARG | B | 8 | 6.952 | 12.099 | 7.815 | 1.00 | 38.70 | C |
| ATOM | 686 | CD | ARG | B | 8 | 7.493 | 13.059 | 6.746 | 1.00 | 39.71 | C |
| ATOM | 687 | NE | ARG | B | 8 | 6.513 | 13.304 | 5.669 | 1.00 | 43.70 | N |
| ATOM | 688 | CZ | ARG | B | 8 | 6.816 | 13.878 | 4.509 | 1.00 | 47.41 | C |
| ATOM | 689 | NH1 | ARG | B | 8 | 8.053 | 14.332 | 4.256 | 1.00 | 51.26 | N |
| ATOM | 690 | NH2 | ARG | B | 8 | 5.876 | 14.013 | 3.572 | 1.00 | 53.45 | N |
| ATOM | 691 | N | ASN | B | 9 | 3.847 | 10.583 | 8.495 | 1.00 | 38.52 | N |
| ATOM | 692 | CA | ASN | B | 9 | 2.727 | 11.197 | 9.20 | 1.00 | 37.11 | C |
| ATOM | 693 | C | ASN | B | 9 | 2.223 | 10.470 | 10.436 | 1.00 | 34.82 | C |
| ATOM | 694 | O | ASN | B | 9 | 1.895 | 11.111 | 11.429 | 1.00 | 33.09 | O |
| ATOM | 695 | CB | ASN | B | 9 | 1.515 | 11.438 | 8.301 | 1.00 | 37.40 | C |
| ATOM | 696 | CG | ASN | B | 9 | 0.483 | 12.374 | 8.977 | 1.00 | 43.24 | C |
| ATOM | 697 | OD1 | ASN | B | 9 | 0.814 | 13.551 | 9.338 | 1.00 | 48.37 | O |
| ATOM | 698 | ND2 | ASN | B | 9 | −0.762 | 11.873 | 9.172 | 1.00 | 46.35 | N |
| ATOM | 699 | N | LEU | B | 10 | 2.108 | 9.150 | 10.353 | 1.00 | 34.28 | N |
| ATOM | 70 | CA | LEU | B | 10 | 1.478 | 8.391 | 11.411 | 1.00 | 36.19 | C |
| ATOM | 701 | C | LEU | B | 10 | 2.462 | 8.376 | 12.626 | 1.00 | 36.98 | C |
| ATOM | 702 | O | LEU | B | 10 | 2.052 | 8.282 | 13.817 | 1.00 | 35.07 | O |
| ATOM | 703 | CB | LEU | B | 10 | 1.136 | 6.984 | 10.907 | 1.00 | 35.82 | C |
| ATOM | 704 | CG | LEU | B | 10 | −0.325 | 6.543 | 10.723 | 1.00 | 38.75 | C |
| ATOM | 705 | CD1 | LEU | B | 10 | −1.245 | 7.611 | 10.049 | 1.00 | 37.11 | O |
| ATOM | 706 | CD2 | LEU | B | 10 | −0.445 | 5.174 | 10.036 | 1.00 | 36.19 | C |
| HETATM | 707 | N | MSE | B | 11 | 3.743 | 8.550 | 12.285 | 1.00 | 37.99 | N |
| HETATM | 708 | CA | MSE | B | 11 | 4.822 | 8.461 | 13.248 | 1.00 | 39.71 | C |
| HETATM | 709 | C | MSE | B | 11 | 4.961 | 9.838 | 13.898 | 1.00 | 41.25 | C |
| HETATM | 710 | O | MSE | B | 11 | 5.768 | 10.028 | 14.803 | 1.00 | 38.48 | O |
| HETATM | 711 | CB | MSE | B | 11 | 6.114 | 8.077 | 12.542 | 1.00 | 39.59 | C |
| HETATM | 712 | CG | MSE | B | 11 | 6.218 | 6.607 | 12.307 | 1.00 | 38.97 | C |
| HETATM | 713 | SE | MSE | B | 11 | 6.289 | 5.449 | 13.861 | 1.00 | 48.63 | SE |
| HETATM | 714 | CE | MSE | B | 11 | 8.104 | 5.923 | 14.497 | 1.00 | 44.09 | C |
| ATOM | 715 | N | SER | B | 12 | 4.126 | 10.778 | 13.424 | 1.00 | 41.15 | N |
| ATOM | 716 | CA | SER | B | 12 | 4.236 | 12.167 | 13.842 | 1.00 | 43.22 | C |
| ATOM | 717 | C | SER | B | 12 | 3.303 | 12.508 | 15.015 | 1.00 | 43.72 | C |
| ATOM | 718 | O | SER | B | 12 | 3.295 | 13.636 | 15.473 | 1.00 | 44.25 | O |
| ATOM | 719 | CB | SER | B | 12 | 3.966 | 13.108 | 12.653 | 1.00 | 42.96 | C |
| ATOM | 720 | OG | SER | B | 12 | 5.126 | 13.242 | 11.848 | 1.00 | 45.76 | O |
| ATOM | 721 | N | GLN | B | 13 | 2.566 | 11.512 | 15.502 | 1.00 | 44.10 | N |
| ATOM | 722 | CA | GLN | B | 13 | 1.421 | 11.717 | 16.373 | 1.00 | 45.95 | C |
| ATOM | 723 | C | GLN | B | 13 | 1.476 | 10.584 | 17.351 | 1.00 | 46.37 | C |
| ATOM | 724 | O | GLN | B | 13 | 1.653 | 9.427 | 16.969 | 1.00 | 46.54 | O |
| ATOM | 725 | CB | GLN | B | 13 | 0.073 | 11.629 | 15.593 | 1.00 | 45.31 | C |

TABLE 2a-continued

Data of atomic coordinates for accession code 2ZTT

| ATOM | 726 | CG | GLN | B | 13 | −0.065 | 12.459 | 14.349 | 1.00 | 46.47 | C |
|---|---|---|---|---|---|---|---|---|---|---|---|
| ATOM | 727 | CD | GLN | B | 13 | −1.347 | 12.086 | 13.543 | 1.00 | 48.92 | C |
| ATOM | 728 | OE1 | GLN | B | 13 | −1.287 | 11.482 | 12.436 | 1.00 | 53.09 | O |
| ATOM | 729 | NE2 | GLN | B | 13 | −2.502 | 12.429 | 14.112 | 1.00 | 50.0 | N |
| ATOM | 730 | N | SER | B | 14 | 1.322 | 10.910 | 18.623 | 1.00 | 47.92 | N |
| ATOM | 731 | CA | SER | B | 14 | 1.845 | 10.045 | 19.661 | 1.00 | 48.68 | C |
| ATOM | 732 | C | SER | B | 14 | 1.062 | 8.7791 | 9.752 | 1.00 | 48.93 | C |
| ATOM | 733 | O | SER | B | 14 | 1.603 | 7.768 | 20.123 | 1.00 | 50.59 | O |
| ATOM | 734 | CB | SER | B | 14 | 1.845 | 10.736 | 21.008 | 1.00 | 48.85 | C |
| ATOM | 735 | OG | SER | B | 14 | 0.510 | 11.063 | 21.326 | 1.00 | 49.15 | O |
| ATOM | 736 | N | ARG | B | 15 | −0.211 | 8.805 | 19.396 | 1.00 | 49.80 | N |
| ATOM | 737 | CA | ARG | B | 15 | −0.999 | 7.595 | 19.576 | 1.00 | 49.36 | C |
| ATOM | 738 | C | ARG | B | 15 | −0.621 | 6.519 | 18.575 | 1.00 | 48.10 | C |
| ATOM | 739 | O | ARG | B | 15 | −0.286 | 5.398 | 18.994 | 1.00 | 46.32 | O |
| ATOM | 740 | CB | ARG | B | 15 | −2.484 | 7.885 | 19.555 | 1.00 | 49.19 | C |
| ATOM | 741 | CG | ARG | B | 15 | −3.229 | 7.023 | 20.528 | 1.00 | 53.51 | C |
| ATOM | 742 | CD | ARG | B | 15 | −2.992 | 7.461 | 22.005 | 1.00 | 60.99 | C |
| ATOM | 743 | NE | ARG | B | 15 | −2.476 | 8.834 | 22.184 | 1.00 | 62.45 | N |
| ATOM | 744 | CZ | ARG | B | 15 | −2.825 | 9.641 | 23.196 | 1.00 | 67.15 | C |
| ATOM | 745 | NH1 | ARG | B | 15 | −3.723 | 9.239 | 24.101 | 1.00 | 66.93 | N |
| ATOM | 746 | NH2 | ARG | B | 15 | −2.296 | 10.862 | 23.304 | 1.00 | 67.57 | N |
| ATOM | 747 | N | THR | B | 16 | −0.660 | 6.882 | 17.278 | 1.00 | 46.22 | N |
| ATOM | 748 | CA | THR | B | 16 | −0.235 | 6.00 | 16.182 | 1.00 | 45.19 | C |
| ATOM | 749 | C | THR | B | 16 | 1.283 | 5.620 | 16.234 | 1.00 | 44.73 | C |
| ATOM | 750 | O | THR | B | 16 | 1.666 | 4.509 | 15.908 | 1.00 | 44.35 | O |
| ATOM | 751 | CB | THR | B | 16 | −0.671 | 6.576 | 14.813 | 1.00 | 44.69 | C |
| ATOM | 752 | OG1 | THR | B | 16 | −0.273 | 7.941 | 14.701 | 1.00 | 42.24 | O |
| ATOM | 753 | CG2 | THR | B | 16 | −2.207 | 6.573 | 14.694 | 1.00 | 47.78 | C |
| ATOM | 754 | N | ARG | B | 17 | 2.141 | 6.535 | 16.659 | 1.00 | 45.31 | N |
| ATOM | 755 | CA | ARG | B | 17 | 3.587 | 6.233 | 16.876 | 1.00 | 44.94 | C |
| ATOM | 756 | C | ARG | B | 17 | 3.799 | 5.041 | 17.839 | 1.00 | 44.50 | C |
| ATOM | 757 | O | ARG | B | 17 | 4.521 | 4.084 | 17.515 | 1.00 | 44.11 | O |
| ATOM | 758 | CB | ARG | B | 17 | 4.335 | 7.489 | 17.360 | 1.00 | 44.38 | C |
| ATOM | 759 | CG | ARG | B | 17 | 5.862 | 7.309 | 17.679 | 1.00 | 45.17 | C |
| ATOM | 760 | CD | ARG | B | 17 | 6.572 | 8.659 | 17.945 | 1.00 | 47.01 | C |
| ATOM | 761 | NE | ARG | B | 17 | 7.856 | 8.528 | 18.671 | 1.00 | 57.43 | N |
| ATOM | 762 | CZ | ARG | B | 17 | 8.596 | 9.544 | 19.168 | 1.00 | 60.21 | C |
| ATOM | 763 | NH1 | ARG | B | 17 | 8.193 | 10.803 | 19.039 | 1.00 | 62.97 | N |
| ATOM | 764 | NH2 | ARG | B | 17 | 9.753 | 9.319 | 19.801 | 1.00 | 59.15 | N |
| ATOM | 765 | N | GLU | B | 18 | 3.141 | 5.127 | 18.992 | 1.00 | 43.94 | N |
| ATOM | 766 | CA | GLU | B | 18 | 3.124 | 4.155 | 20.10 | 1.00 | 44.27 | C |
| ATOM | 767 | C | GLU | B | 18 | 2.710 | 2.756 | 19.604 | 1.00 | 42.45 | C |
| ATOM | 768 | O | GLU | B | 18 | 3.405 | 1.740 | 19.850 | 1.00 | 42.21 | O |
| ATOM | 769 | CB | GLU | B | 18 | 2.085 | 4.673 | 21.140 | 1.00 | 43.48 | C |
| ATOM | 770 | CG | GLU | B | 18 | 1.746 | 3.716 | 22.287 | 1.00 | 48.39 | C |
| ATOM | 771 | CD | GLU | B | 18 | 1.661 | 4.393 | 23.710 | 1.00 | 49.35 | C |
| ATOM | 772 | OE1 | GLU | B | 18 | 0.880 | 5.366 | 23.927 | 1.00 | 51.68 | O |
| ATOM | 773 | OE2 | GLU | B | 18 | 2.390 | 3.927 | 24.627 | 1.00 | 57.78 | O |
| ATOM | 774 | N | ILE | B | 19 | 1.583 | 2.712 | 18.890 | 1.00 | 37.60 | N |
| ATOM | 775 | CA | ILE | B | 19 | 1.10 | 1.490 | 18.232 | 1.00 | 35.35 | C |
| ATOM | 776 | C | ILE | B | 19 | 2.092 | 0.851 | 17.321 | 1.00 | 33.42 | C |
| ATOM | 777 | O | ILE | B | 19 | 2.387- | 0.359 | 17.432 | 1.00 | 35.52 | O |
| ATOM | 778 | CB | ILE | B | 19 | −0.163 | 1.826 | 17.278 | 1.00 | 35.33 | C |
| ATOM | 779 | CG1 | ILE | B | 19 | −1.402 | 2.065 | 18.128 | 1.00 | 35.78 | C |
| ATOM | 780 | CG2 | ILE | B | 19 | −0.321 | 0.677 | 16.231 | 1.00 | 36.19 | C |
| ATOM | 781 | CD1 | ILE | B | 19 | −2.670 | 2.743 | 17.431 | 1.00 | 36.19 | C |
| ATOM | 782 | N | LEU | B | 20 | 2.546 | 1.650 | 16.358 | 1.00 | 32.23 | N |
| ATOM | 783 | CA | LEU | B | 20 | 3.436 | 1.249 | 15.270 | 1.00 | 31.50 | C |
| ATOM | 784 | C | LEU | B | 20 | 4.817 | 0.828 | 15.816 | 1.00 | 32.21 | C |
| ATOM | 785 | O | LEU | B | 20 | 5.523 | 0.00 | 15.231 | 1.00 | 29.97 | O |
| ATOM | 786 | CB | LEU | B | 20 | 3.610 | 2.493 | 14.457 | 1.00 | 31.60 | C |
| ATOM | 787 | CG | LEU | B | 20 | 3.397 | 2.636 | 12.950 | 1.00 | 37.31 | C |
| ATOM | 788 | CD1 | LEU | B | 20 | 2.341 | 1.661 | 12.365 | 1.00 | 27.59 | O |
| ATOM | 789 | CD2 | LEU | B | 20 | 3.068 | 4.059 | 12.756 | 1.00 | 38.52 | C |
| ATOM | 790 | N | THR | B | 21 | 5.224 | 1.476 | 16.908 | 1.00 | 31.71 | N |
| ATOM | 791 | CA | THR | B | 21 | 6.473 | 1.0281 | 7.645 | 1.00 | 31.78 | C |
| ATOM | 792 | C | THR | B | 21 | 6.290 | −0.208 | 18.528 | 1.00 | 31.89 | C |
| ATOM | 793 | O | THR | B | 21 | 7.155 | −1.082 | 18.581 | 1.00 | 35.91 | O |
| ATOM | 794 | CB | THR | B | 21 | 7.086 | 2.233 | 18.472 | 1.00 | 29.59 | C |
| ATOM | 795 | OG1 | THR | B | 21 | 6.183 | 2.671 | 19.446 | 1.00 | 31.69 | O |
| ATOM | 796 | CG2 | THR | B | 21 | 7.306 | 3.4811 | 7.618 | 1.00 | 27.25 | C |
| ATOM | 797 | N | LYS | B | 22 | 5.192 | −0.328 | 19.232 | 1.00 | 34.07 | N |
| ATOM | 798 | CA | LYS | B | 22 | 5.063 | −1.382 | 20.256 | 1.00 | 34.77 | C |
| ATOM | 799 | C | LYS | B | 22 | 4.282 | −2.607 | 19.786 | 1.00 | 36.90 | C |
| ATOM | 800 | O | LYS | B | 22 | 4.344 | −3.662 | 20.449 | 1.00 | 37.85 | O |
| ATOM | 801 | CB | LYS | B | 22 | 4.392 | −0.814 | 21.505 | 1.00 | 34.14 | C |
| ATOM | 802 | CG | LYS | B | 22 | 5.120 | 0.379 | 22.129 | 1.00 | 36.95 | C |
| ATOM | 803 | CD | LYS | B | 22 | 6.460 | −0.117 | 22.818 | 1.00 | 41.36 | C |

TABLE 2a-continued

Data of atomic coordinates for accession code 2ZTT

| ATOM | 804 | CE | LYS | B | 22 | 7.365 | 1.090 | 23.116 | 1.00 | 44.46 | C |
|---|---|---|---|---|---|---|---|---|---|---|---|
| ATOM | 805 | NZ | LYS | B | 22 | 8.863 | 0.908 | 22.804 | 1.00 | 50.52 | N |
| ATOM | 806 | N | THR | B | 23 | 3.547 | −2.496 | 18.658 | 1.00 | 34.62 | N |
| ATOM | 807 | CA | THR | B | 23 | 2.943 | −3.713 | 18.065 | 1.00 | 34.38 | C |
| ATOM | 808 | C | THR | B | 23 | 3.876 | −4.428 | 17.099 | 1.00 | 34.70 | C |
| ATOM | 809 | O | THR | B | 23 | 4.281 | −3.873 | 16.074 | 1.00 | 35.89 | O |
| ATOM | 810 | CB | THR | B | 23 | 1.628 | −3.370 | 17.309 | 1.00 | 33.93 | C |
| ATOM | 811 | OG1 | THR | B | 23 | 0.814 | −2.715 | 18.237 | 1.00 | 32.62 | O |
| ATOM | 812 | CG2 | THR | B | 23 | 0.879 | −4.570 | 16.853 | 1.00 | 28.97 | C |
| ATOM | 813 | N | THR | B | 24 | 4.209 | −5.665 | 17.417 | 1.00 | 35.04 | N |
| ATOM | 814 | CA | THR | B | 24 | 5.008 | −6.442 | 16.532 | 1.00 | 35.72 | C |
| ATOM | 815 | C | THR | B | 24 | 4.085 | −7.110 | 15.460 | 1.00 | 36.93 | C |
| ATOM | 816 | O | THR | B | 24 | 2.914 | −7.282 | 15.667 | 1.00 | 35.02 | O |
| ATOM | 818 | OG1 | THR | B | 24 | 4.879 | −8.342 | 17.962 | 1.00 | 37.80 | O |
| ATOM | 817 | CB | THR | B | 24 | 5.791 | −7.446 | 17.326 | 1.00 | 36.66 | C |
| ATOM | 819 | CG2 | THR | B | 24 | 6.644 | −6.70 | 18.411 | 1.00 | 34.73 | C |
| ATOM | 820 | N | VAL | B | 25 | 4.655 | −7.469 | 14.336 | 1.00 | 38.62 | N |
| ATOM | 821 | CA | VAL | B | 25 | 3.993 | −8.205 | 13.322 | 1.00 | 39.71 | C |
| ATOM | 822 | C | VAL | B | 25 | 3.275 | −9.426 | 13.880 | 1.00 | 42.21 | C |
| ATOM | 823 | O | VAL | B | 25 | 2.152 | −9.705 | 13.457 | 1.00 | 43.20 | O |
| ATOM | 824 | CB | VAL | B | 25 | 5.017 | −8.626 | 12.268 | 1.00 | 39.51 | C |
| ATOM | 825 | CG1 | VAL | B | 25 | 4.384 | −9.578 | 11.226 | 1.00 | 41.02 | C |
| ATOM | 826 | CG2 | VAL | B | 25 | 5.590 | −7.405 | 11.605 | 1.00 | 37.62 | C |
| ATOM | 827 | N | ASP | B | 26 | 3.878 | −10.163 | 14.821 | 1.00 | 42.77 | N |
| ATOM | 828 | CA | ASP | B | 26 | 3.197 | −11.337 | 15.432 | 1.00 | 44.72 | C |
| ATOM | 829 | C | ASP | B | 26 | 1.882 | −10.991 | 16.139 | 1.00 | 43.99 | C |
| ATOM | 830 | O | ASP | B | 26 | 0.976 | −11.821 | 16.222 | 1.00 | 44.82 | O |
| ATOM | 831 | CB | ASP | B | 26 | 4.075 | −12.043 | 16.481 | 1.00 | 45.86 | C |
| ATOM | 832 | CG | ASP | B | 26 | 5.182 | −12.943 | 15.872 | 1.00 | 50.14 | C |
| ATOM | 833 | OD1 | ASP | B | 26 | 4.961 | −13.576 | 14.825 | 1.00 | 53.37 | O |
| ATOM | 834 | OD2 | ASP | B | 26 | 6.284 | −13.068 | 16.485 | 1.00 | 53.87 | O |
| ATOM | 835 | N | HIS | B | 27 | 1.814 | −9.790 | 16.710 | 1.00 | 43.30 | N |
| ATOM | 836 | CA | HIS | B | 27 | 0.674 | −9.345 | 17.510 | 1.00 | 42.54 | C |
| ATOM | 837 | C | HIS | B | 27 | −0.541 | −8.960 | 16.657 | 1.00 | 43.45 | C |
| ATOM | 838 | O | HIS | B | 27 | −1.677 | −9.109 | 17.078 | 1.00 | 42.39 | O |
| ATOM | 839 | CB | HIS | B | 27 | 1.126 | −8.210 | 18.454 | 1.00 | 42.85 | C |
| ATOM | 840 | CG | HIS | B | 27 | 2.002 | −8.715 | 19.556 | 1.00 | 44.43 | C |
| ATOM | 841 | ND1 | HIS | B | 27 | 2.584 | −7.894 | 20.504 | 1.00 | 47.17 | N |
| ATOM | 842 | CD2 | HIS | B | 27 | 2.411 | −9.979 | 19.842 | 1.00 | 44.40 | C |
| ATOM | 843 | CE2 | HIS | B | 27 | 3.289 | −8.641 | 21.347 | 1.00 | 46.22 | C |
| ATOM | 844 | NE2 | HIS | B | 27 | 3.206 | −9.906 | 20.966 | 1.00 | 46.89 | N |
| HETATM | 845 | N | MSE | B | 28 | −0.272 | −8.499 | 15.446 | 1.00 | 42.91 | N |
| HETATM | 846 | CA | MSE | B | 28 | −1.348 | −8.153 | 14.495 | 1.00 | 45.83 | C |
| HETATM | 847 | C | MSE | B | 28 | −2.331 | −9.306 | 14.312 | 1.00 | 43.46 | C |
| HETATM | 848 | O | MSE | B | 28 | −3.490 | −9.103 | 14.344 | 1.00 | 43.24 | O |
| HETATM | 849 | CB | MSE | B | 28 | −0.707 | −7.755 | 13.170 | 1.00 | 43.73 | C |
| HETATM | 850 | CG | MSE | B | 28 | 0.178 | −6.516 | 13.260 | 1.00 | 47.04 | C |
| HETATM | 851 | SE | MSE | B | 28 | 0.702 | −6.010 | 11.464 | 1.00 | 56.06 | SE |
| HETATM | 852 | CE | MSE | B | 28 | −1.036 | −5.246 | 10.922 | 1.00 | 41.57 | C |
| ATOM | 853 | N | ALA | B | 29 | −1.828 | −10.525 | 14.203 | 1.00 | 44.61 | N |
| ATOM | 854 | CA | ALA | B | 29 | −2.631 | −11.746 | 14.126 | 1.00 | 43.79 | C |
| ATOM | 855 | C | ALA | B | 29 | −3.424 | −12.060 | 15.395 | 1.00 | 44.02 | C |
| ATOM | 856 | O | ALA | B | 29 | −4.527 | −12.637 | 15.328 | 1.00 | 43.95 | O |
| ATOM | 857 | CB | ALA | B | 29 | −1.695 | −12.947 | 13.757 | 1.00 | 44.99 | C |
| ATOM | 858 | N | ILE | B | 30 | −2.869 | −11.691 | 16.563 | 1.00 | 43.49 | N |
| ATOM | 859 | CA | ILE | B | 30 | −3.546 | −11.90 | 17.834 | 1.00 | 41.56 | C |
| ATOM | 860 | C | ILE | B | 30 | −4.725 | −10.932 | 17.966 | 1.00 | 41.84 | C |
| ATOM | 861 | O | ILE | B | 30 | −5.716 | −11.261 | 18.570 | 1.00 | 42.57 | O |
| ATOM | 862 | CB | ILE | B | 30 | −2.562 | −11.745 | 19.044 | 1.00 | 42.14 | C |
| ATOM | 863 | CG1 | ILE | B | 30 | −1.374 | −12.698 | 18.851 | 1.00 | 41.56 | C |
| ATOM | 864 | CG2 | ILE | B | 30 | −3.315 | −11.937 | 20.320 | 1.00 | 39.34 | C |
| ATOM | 865 | CD1 | ILE | B | 30 | −0.776 | −13.288 | 20.090 | 1.00 | 45.11 | C |
| ATOM | 866 | N | ILE | B | 31 | −4.590 | −9.735 | 17.403 | 1.00 | 41.59 | N |
| ATOM | 867 | CA | ILE | B | 31 | −5.593 | −8.673 | 17.444 | 1.00 | 40.73 | C |
| ATOM | 868 | C | ILE | B | 31 | −6.734 | −8.969 | 16.429 | 1.00 | 43.53 | C |
| ATOM | 869 | O | ILE | B | 31 | −7.913 | −8.779 | 16.740 | 1.00 | 44.27 | O |
| ATOM | 870 | CB | ILE | B | 31 | −4.923 | −7.329 | 17.10 | 1.00 | 39.32 | C |
| ATOM | 871 | CG1 | ILE | B | 31 | −3.951 | −6.855 | 18.204 | 1.00 | 35.99 | C |
| ATOM | 872 | CG2 | ILE | B | 31 | −5.904 | −6.229 | 16.996 | 1.00 | 35.27 | C |
| ATOM | 873 | CD1 | ILE | B | 31 | −3.088 | −5.751 | 17.714 | 1.00 | 29.24 | C |
| ATOM | 874 | N | LYS | B | 32 | −6.345 | −9.384 | 15.224 | 1.00 | 44.27 | N |
| ATOM | 875 | CA | LYS | B | 32 | −7.239 | −9.762 | 14.162 | 1.00 | 47.56 | C |
| ATOM | 876 | C | LYS | B | 32 | −8.252 | −10.817 | 14.621 | 1.00 | 48.46 | C |
| ATOM | 877 | O | LYS | B | 32 | −9.455 | −10.673 | 14.365 | 1.00 | 50.03 | O |
| ATOM | 878 | CB | LYS | B | 32 | −6.394 | −10.270 | 12.994 | 1.00 | 48.57 | C |
| ATOM | 879 | CG | LYS | B | 32 | −7.165 | −10.542 | 11.711 | 1.00 | 46.81 | C |
| ATOM | 880 | CD | LYS | B | 32 | −6.191 | −11.101 | 10.696 | 1.00 | 51.68 | C |
| ATOM | 881 | CE | LYS | B | 32 | −5.614 | −12.463 | 11.212 | 1.00 | 52.54 | C |

TABLE 2a-continued

Data of atomic coordinates for accession code 2ZTT

| ATOM | 882 | NZ | LYS | B | 32 | −4.503 | −13.018 | 10.359 | 1.00 | 54.19 | N |
|---|---|---|---|---|---|---|---|---|---|---|---|
| ATOM | 883 | N | LYS | B | 33 | −7.775 | −11.826 | 15.348 | 1.00 | 49.39 | N |
| ATOM | 884 | CA | LYS | B | 33 | −8.639 | −12.858 | 15.912 | 1.00 | 50.41 | C |
| ATOM | 885 | C | LYS | B | 33 | −9.662 | −12.430 | 16.975 | 1.00 | 51.52 | C |
| ATOM | 886 | O | LYS | B | 33 | −10.412 | −13.268 | 17.474 | 1.00 | 52.67 | O |
| ATOM | 887 | CB | LYS | B | 33 | −7.815 | −14.046 | 16.373 | 1.00 | 50.13 | C |
| ATOM | 888 | CG | LYS | B | 33 | −8.596 | −15.070 | 17.192 | 1.00 | 51.35 | C |
| ATOM | 889 | CD | LYS | B | 33 | −7.694 | −16.251 | 17.549 | 1.00 | 56.77 | C |
| ATOM | 890 | CE | LYS | B | 33 | −8.225 | −17.088 | 18.761 | 1.00 | 59.64 | C |
| ATOM | 891 | NZ | LYS | B | 33 | −9.292 | −18.110 | 18.469 | 1.00 | 61.73 | N |
| ATOM | 892 | N | TYR | B | 34 | −9.738 | −11.133 | 17.286 | 1.00 | 52.33 | N |
| ATOM | 893 | CA | TYR | B | 34 | −10.627 | −10.618 | 18.331 | 1.00 | 53.26 | C |
| ATOM | 894 | C | TYR | B | 34 | −11.249 | −9.311 | 17.923 | 1.00 | 54.34 | C |
| ATOM | 895 | O | TYR | B | 34 | −11.640 | −8.503 | 18.767 | 1.00 | 54.29 | O |
| ATOM | 896 | CB | TYR | B | 34 | −9.873 | −10.403 | 19.662 | 1.00 | 52.85 | C |
| ATOM | 897 | CG | TYR | B | 34 | −9.411 | −11.696 | 20.289 | 1.00 | 52.69 | C |
| ATOM | 898 | CD1 | TYR | B | 34 | −10.332 | −12.549 | 20.902 | 1.00 | 52.99 | C |
| ATOM | 899 | CD2 | TYR | B | 34 | −8.079 | −12.080 | 20.247 | 1.00 | 52.02 | C |
| ATOM | 90 | CE2 | TYR | B | 34 | −9.942 | −13.751 | 21.467 | 1.00 | 52.08 | C |
| ATOM | 901 | CE2 | TYR | B | 34 | −7.658 | −13.281 | 20.814 | 1.00 | 53.34 | C |
| ATOM | 902 | CZ | TYR | B | 34 | −8.606 | −14.112 | 21.431 | 1.00 | 53.66 | C |
| ATOM | 903 | OH | TYR | B | 34 | −8.265 | −15.328 | 21.971 | 1.00 | 52.42 | O |
| ATOM | 904 | N | THR | B | 35 | −11.343 | −9.087 | 16.622 | 1.00 | 56.46 | N |
| ATOM | 905 | CA | THR | B | 35 | −11.788 | −7.794 | 16.094 | 1.00 | 57.69 | C |
| ATOM | 906 | C | THR | B | 35 | −13.204 | −7.410 | 16.508 | 1.00 | 58.11 | C |
| ATOM | 907 | O | THR | B | 35 | −14.027 | −8.281 | 16.817 | 1.00 | 59.23 | O |
| ATOM | 908 | CB | THR | B | 35 | −11.603 | −7.705 | 14.559 | 1.00 | 58.33 | C |
| ATOM | 909 | OG1 | THR | B | 35 | −11.899 | −8.975 | 13.945 | 1.00 | 58.98 | O |
| ATOM | 910 | CG2 | THR | B | 35 | −10.159 | −7.343 | 14.268 | 1.00 | 60.20 | C |
| TER | 911 | | THR | B | 35 | | | | | | |
| ATOM | 912 | N | GLU | C | 684 | 21.336 | 22.605 | 2.184 | 1.00 | 79.38 | N |
| ATOM | 913 | CA | GLU | C | 684 | 22.452 | 23.253 | 1.405 | 1.00 | 79.38 | C |
| ATOM | 914 | C | GLU | C | 684 | 22.093 | 24.283 | 0.252 | 1.00 | 79.32 | C |
| ATOM | 915 | O | GLU | C | 684 | 22.373 | 25.480 | 0.402 | 1.00 | 79.50 | O |
| ATOM | 916 | CB | GLU | C | 684 | 23.490 | 22.182 | 0.969 | 1.00 | 79.83 | C |
| ATOM | 917 | CG | GLU | C | 684 | 24.523 | 22.611 | −0.113 | 1.00 | 80.08 | C |
| ATOM | 918 | CD | GLU | C | 684 | 25.838 | 23.174 | 0.428 | 1.00 | 81.09 | C |
| ATOM | 919 | OE1 | GLU | C | 684 | 26.363 | 22.662 | 1.443 | 1.00 | 81.59 | O |
| ATOM | 920 | OE2 | GLU | C | 684 | 26.361 | 24.123 | −0.194 | 1.00 | 81.41 | O |
| ATOM | 921 | N | ASP | C | 685 | 21.483 | 23.839 | −0.857 | 1.00 | 78.80 | N |
| ATOM | 922 | CA | ASP | C | 685 | 21.398 | 24.656 | −2.104 | 1.00 | 78.32 | C |
| ATOM | 923 | C | ASP | C | 685 | 20.386 | 25.830 | −2.080 | 1.00 | 77.35 | C |
| ATOM | 924 | O | ASP | C | 685 | 19.641 | 25.979 | −1.112 | 1.00 | 77.27 | O |
| ATOM | 925 | CB | ASP | C | 685 | 21.315 | 23.732 | −3.357 | 1.00 | 78.76 | C |
| ATOM | 926 | CG | ASP | C | 685 | 20.186 | 24.099 | −4.337 | 1.00 | 79.36 | C |
| ATOM | 927 | OD1 | ASP | C | 685 | 20.467 | 24.663 | −5.425 | 1.00 | 80.45 | O |
| ATOM | 928 | OD2 | ASP | C | 685 | 19.015 | 23.788 | −4.034 | 1.00 | 79.55 | O |
| ATOM | 929 | N | GLU | C | 686 | 20.385 | 26.661 | −3.127 | 1.00 | 76.04 | N |
| ATOM | 930 | CA | GLU | C | 686 | 19.629 | 27.927 | −3.138 | 1.00 | 74.79 | C |
| ATOM | 931 | C | GLU | C | 686 | 18.121 | 27.822 | −3.248 | 1.00 | 73.91 | C |
| ATOM | 932 | O | GLU | C | 686 | 17.408 | 28.540 | −2.555 | 1.00 | 73.79 | O |
| ATOM | 933 | CB | GLU | C | 686 | 20.133 | 28.849 | −4.235 | 1.00 | 75.08 | C |
| ATOM | 934 | CG | GLU | C | 686 | 21.494 | 29.492 | −3.918 | 1.00 | 76.02 | C |
| ATOM | 935 | CD | GLU | C | 686 | 22.346 | 29.686 | −5.157 | 1.00 | 75.72 | C |
| ATOM | 936 | OE1 | GLU | C | 686 | 22.296 | 28.784 | −6.023 | 1.00 | 74.0 | O |
| ATOM | 937 | OE2 | GLU | C | 686 | 23.055 | 30.726 | −5.261 | 1.00 | 75.84 | O |
| ATOM | 938 | N | GLN | C | 687 | 17.630 | 26.947 | −4.120 | 1.00 | 72.71 | N |
| ATOM | 939 | CA | GLN | C | 687 | 16.182 | 26.766 | −4.311 | 1.00 | 72.03 | C |
| ATOM | 940 | C | GLN | C | 687 | 15.542 | 26.121 | −3.057 | 1.00 | 70.66 | C |
| ATOM | 941 | O | GLN | C | 687 | 14.308 | 26.112 | −2.895 | 1.00 | 70.10 | O |
| ATOM | 942 | CB | GLN | C | 687 | 15.920 | 25.997 | −5.629 | 1.00 | 72.04 | C |
| ATOM | 943 | CG | GLN | C | 687 | 14.567 | 25.243 | −5.780 | 1.00 | 73.43 | C |
| ATOM | 944 | CD | GLN | C | 687 | 14.554 | 24.222 | −6.951 | 1.00 | 73.37 | C |
| ATOM | 945 | OE1 | GLN | C | 687 | 13.518 | 23.605 | −7.258 | 1.00 | 75.11 | O |
| ATOM | 946 | NE2 | GLN | C | 687 | 15.703 | 24.046 | −7.596 | 1.00 | 72.48 | N |
| HETATM | 947 | N | MSE | C | 688 | 16.403 | 25.627 | −2.162 | 1.00 | 69.09 | N |
| HETATM | 948 | CA | MSE | C | 688 | 15.991 | 25.165 | −0.837 | 1.00 | 68.01 | C |
| HETATM | 949 | C | MSE | C | 688 | 15.688 | 26.326 | 0.086 | 1.00 | 65.76 | C |
| HETATM | 950 | O | MSE | C | 688 | 14.608 | 26.376 | 0.663 | 1.00 | 65.93 | O |
| HETATM | 951 | CB | MSE | C | 688 | 17.077 | 24.344 | −0.194 | 1.00 | 69.00 | C |
| HETATM | 952 | CG | MSE | C | 688 | 17.638 | 23.303 | −1.053 | 1.00 | 74.52 | C |
| HETATM | 953 | SE | MSE | C | 688 | 16.491 | 21.750 | −1.006 | 1.00 | 90.17 | SE |
| HETATM | 954 | CE | MSE | C | 688 | 15.009 | 22.277 | −2.217 | 1.00 | 82.47 | C |
| ATOM | 955 | N | TYR | C | 689 | 16.654 | 27.237 | 0.235 | 1.00 | 62.81 | N |
| ATOM | 956 | CA | TYR | C | 689 | 16.460 | 28.486 | 0.972 | 1.00 | 61.02 | C |
| ATOM | 957 | C | TYR | C | 689 | 15.128 | 29.134 | 0.687 | 1.00 | 58.88 | C |
| ATOM | 958 | O | TYR | C | 689 | 14.496 | 29.631 | 1.586 | 1.00 | 57.84 | O |
| ATOM | 959 | CB | TYR | C | 689 | 17.559 | 29.498 | 0.674 | 1.00 | 60.98 | C |

TABLE 2a-continued

Data of atomic coordinates for accession code 2ZTT

| ATOM | 960 | CG | TYR | C | 689 | 18.864 | 29.179 | 1.340 | 1.00 | 62.31 | C |
|---|---|---|---|---|---|---|---|---|---|---|---|
| ATOM | 961 | CD1 | TYR | C | 689 | 19.866 | 28.508 | 0.659 | 1.00 | 62.50 | C |
| ATOM | 962 | CD2 | TYR | C | 689 | 19.098 | 29.555 | 2.650 | 1.00 | 62.01 | C |
| ATOM | 963 | CE2 | TYR | C | 689 | 21.0712 | 8.229 | 1.258 | 1.00 | 62.62 | C |
| ATOM | 964 | CE2 | TYR | C | 689 | 20.290 | 29.274 | 3.262 | 1.00 | 63.30 | C |
| ATOM | 965 | CZ | TYR | C | 689 | 21.278 | 28.617 | 2.564 | 1.00 | 61.98 | C |
| ATOM | 966 | OH | TYR | C | 689 | 22.459 | 28.332 | 3.190 | 1.00 | 63.23 | O |
| ATOM | 967 | N | GLN | C | 690 | 14.730 | 29.095 | −0.574 | 1.00 | 57.93 | N |
| ATOM | 968 | CA | GLN | C | 690 | 13.457 | 29.654 | −1.052 | 1.00 | 57.31 | C |
| ATOM | 969 | C | GLN | C | 690 | 12.206 | 28.941 | −0.567 | 1.00 | 56.40 | C |
| ATOM | 970 | O | GLN | C | 690 | 11.1952 | 9.591 | −0.230 | 1.00 | 56.76 | O |
| ATOM | 971 | CB | GLN | C | 690 | 13.460 | 29.678 | −2.573 | 1.00 | 57.54 | C |
| ATOM | 972 | CG | GLN | C | 690 | 14.392 | 30.705 | −3.157 | 1.00 | 60.14 | C |
| ATOM | 973 | CD | GLN | C | 690 | 13.870 | 32.119 | −2.973 | 1.00 | 65.31 | C |
| ATOM | 974 | OE1 | GLN | C | 690 | 14.637 | 33.098 | −3.099 | 1.00 | 67.47 | O |
| ATOM | 975 | NE2 | GLN | C | 690 | 12.561 | 32.246 | −2.662 | 1.00 | 63.04 | N |
| ATOM | 976 | N | ARG | C | 691 | 12.259 | 27.612 | −0.556 | 1.00 | 55.52 | N |
| ATOM | 977 | CA | ARG | C | 691 | 11.173 | 26.797 | −0.038 | 1.00 | 54.90 | C |
| ATOM | 978 | C | ARG | C | 691 | 10.9322 | 7.120 | 1.435 | 1.00 | 54.16 | C |
| ATOM | 979 | O | ARG | C | 691 | 9.784 | 27.312 | 1.869 | 1.00 | 53.38 | O |
| ATOM | 980 | CB | ARG | C | 691 | 11.505 | 25.305 | −0.201 | 1.00 | 55.16 | C |
| ATOM | 981 | CG | ARG | C | 691 | 10.857 | 24.657 | −1.399 | 1.00 | 59.29 | C |
| ATOM | 982 | CD | ARG | C | 691 | 10.579 | 23.177 | −1.195 | 1.00 | 61.89 | C |
| ATOM | 983 | NE | ARG | C | 691 | 11.733 | 22.342 | −1.537 | 1.00 | 63.16 | N |
| ATOM | 984 | CZ | ARG | C | 691 | 11.708 | 21.005 | −1.570 | 1.00 | 65.05 | C |
| ATOM | 985 | NH1 | ARG | C | 691 | 10.579 | 20.338 | −1.283 | 1.00 | 63.03 | N |
| ATOM | 986 | NH2 | ARG | C | 691 | 12.812 | 20.322 | −1.887 | 1.00 | 64.95 | N |
| ATOM | 987 | N | CYS | C | 692 | 12.052 | 27.164 | 2.171 | 1.00 | 53.24 | N |
| ATOM | 988 | CA | CYS | C | 692 | 12.139 | 27.433 | 3.605 | 1.00 | 52.19 | C |
| ATOM | 989 | C | CYS | C | 692 | 11.6932 | 8.842 | 3.973 | 1.00 | 51.42 | C |
| ATOM | 990 | O | CYS | C | 692 | 11.1292 | 9.058 | 5.042 | 1.00 | 50.37 | O |
| ATOM | 991 | CB | CYS | C | 692 | 13.590 | 27.261 | 4.072 | 1.00 | 51.89 | C |
| ATOM | 992 | SG | CYS | C | 692 | 14.221 | 25.560 | 4.201 | 1.00 | 53.38 | S |
| ATOM | 993 | N | CYS | C | 693 | 11.968 | 29.803 | 3.091 | 1.00 | 51.04 | N |
| ATOM | 994 | CA | CYS | C | 693 | 11.562 | 31.173 | 3.311 | 1.00 | 50.93 | C |
| ATOM | 995 | C | CYS | C | 693 | 10.101 | 31.385 | 3.045 | 1.00 | 49.07 | C |
| ATOM | 996 | O | CYS | C | 693 | 9.465 | 32.142 | 3.772 | 1.00 | 48.40 | O |
| ATOM | 997 | CB | CYS | C | 693 | 12.319 | 32.101 | 2.393 | 1.00 | 51.09 | C |
| ATOM | 998 | SG | CYS | C | 693 | 13.706 | 32.794 | 3.228 | 1.00 | 60.13 | S |
| ATOM | 999 | N | ASN | C | 694 | 9.598 | 30.814 | 1.931 | 1.00 | 47.77 | N |
| ATOM | 1000 | CA | ASN | C | 694 | 8.141 | 30.847 | 1.642 | 1.00 | 45.97 | C |
| ATOM | 1001 | C | ASN | C | 694 | 7.331 | 30.352 | 2.829 | 1.00 | 44.31 | C |
| ATOM | 1002 | O | ASN | C | 694 | 6.498 | 31.049 | 3.345 | 1.00 | 46.63 | O |
| ATOM | 1003 | CB | ASN | C | 694 | 7.817 | 30.007 | 0.392 | 1.00 | 45.47 | C |
| ATOM | 1004 | CG | ASN | C | 694 | 8.475 | 30.521 | −0.863 | 1.00 | 46.69 | C |
| ATOM | 1005 | OD1 | ASN | C | 694 | 8.680 | 31.722 | −1.060 | 1.00 | 47.08 | O |
| ATOM | 1006 | ND2 | ASN | C | 694 | 8.834 | 29.596 | −1.727 | 1.00 | 51.83 | N |
| ATOM | 1007 | N | LEU | C | 695 | 7.608 | 29.154 | 3.309 | 1.00 | 44.77 | N |
| ATOM | 1008 | CA | LEU | C | 695 | 7.003 | 28.626 | 4.548 | 1.00 | 43.96 | C |
| ATOM | 1009 | C | LEU | C | 695 | 7.143 | 29.516 | 5.783 | 1.00 | 43.77 | C |
| ATOM | 1010 | O | LEU | C | 695 | 6.183 | 29.759 | 6.504 | 1.00 | 43.49 | O |
| ATOM | 1011 | CB | LEU | C | 695 | 7.556 | 27.223 | 4.837 | 1.00 | 42.87 | C |
| ATOM | 1012 | CG | LEU | C | 695 | 6.712 | 26.410 | 5.829 | 1.00 | 42.12 | C |
| ATOM | 1013 | CD1 | LEU | C | 695 | 5.269 | 26.169 | 5.346 | 1.00 | 39.42 | C |
| ATOM | 1014 | CD2 | LEU | C | 695 | 7.425 | 25.135 | 6.095 | 1.00 | 35.31 | C |
| ATOM | 1015 | N | PHE | C | 696 | 8.335 | 30.021 | 6.037 | 1.00 | 46.02 | N |
| ATOM | 1016 | CA | PHE | C | 696 | 8.520 | 30.974 | 7.158 | 1.00 | 47.09 | C |
| ATOM | 1017 | C | PHE | C | 696 | 7.480 | 32.095 | 7.174 | 1.00 | 48.37 | C |
| ATOM | 1018 | O | PHE | C | 696 | 7.016 | 32.517 | 8.225 | 1.00 | 48.35 | O |
| ATOM | 1019 | CB | PHE | C | 696 | 9.895 | 31.620 | 7.071 | 1.00 | 47.42 | C |
| ATOM | 1020 | CG | PHE | C | 696 | 10.288 | 32.373 | 8.346 | 1.00 | 48.52 | C |
| ATOM | 1021 | CD1 | PHE | C | 696 | 10.635 | 31.675 | 9.492 | 1.00 | 44.44 | C |
| ATOM | 1022 | CD2 | PHE | C | 696 | 10.270 | 33.775 | 8.380 | 1.00 | 50.67 | C |
| ATOM | 1023 | CE2 | PHE | C | 696 | 10.992 | 32.358 | 10.699 | 1.00 | 47.63 | C |
| ATOM | 1024 | CE2 | PHE | C | 696 | 10.643 | 34.469 | 9.550 | 1.00 | 51.34 | C |
| ATOM | 1025 | CZ | PHE | C | 696 | 11.026 | 33.739 | 10.720 | 1.00 | 45.83 | C |
| ATOM | 1026 | N | GLU | C | 697 | 7.129 | 32.566 | 5.980 | 1.00 | 49.36 | N |
| ATOM | 1027 | CA | GLU | C | 697 | 6.103 | 33.579 | 5.779 | 1.00 | 51.11 | C |
| ATOM | 1028 | C | GLU | C | 697 | 4.656 | 33.167 | 6.010 | 1.00 | 50.40 | C |
| ATOM | 1029 | O | GLU | C | 697 | 3.778 | 34.023 | 6.063 | 1.00 | 51.05 | O |
| ATOM | 1030 | CB | GLU | C | 697 | 6.202 | 34.116 | 4.372 | 1.00 | 51.31 | C |
| ATOM | 1031 | CG | GLU | C | 697 | 6.950 | 35.430 | 4.354 | 1.00 | 58.34 | C |
| ATOM | 1032 | CD | GLU | C | 697 | 6.735 | 36.162 | 3.058 | 1.00 | 63.87 | C |
| ATOM | 1033 | OE1 | GLU | C | 697 | 6.710 | 35.454 | 2.023 | 1.00 | 63.97 | O |
| ATOM | 1034 | OE2 | GLU | C | 697 | 6.587 | 37.419 | 3.091 | 1.00 | 66.24 | O |
| ATOM | 1035 | N | LYS | C | 698 | 4.402 | 31.869 | 6.121 | 1.00 | 49.48 | N |
| ATOM | 1036 | CA | LYS | C | 698 | 3.072 | 31.368 | 6.408 | 1.00 | 48.25 | C |
| ATOM | 1037 | C | LYS | C | 698 | 2.853 | 31.479 | 7.925 | 1.00 | 47.17 | C |

TABLE 2a-continued

Data of atomic coordinates for accession code 2ZTT

| ATOM | 1038 | O   | LYS | C | 698 | 1.703  | 31.413 | 8.425  | 1.00 | 46.20 | O |
|------|------|-----|-----|---|-----|--------|--------|--------|------|-------|---|
| ATOM | 1039 | CB  | LYS | C | 698 | 2.974  | 29.916 | 5.905  | 1.00 | 48.96 | C |
| ATOM | 1040 | CG  | LYS | C | 698 | 2.654  | 29.782 | 4.343  | 1.00 | 49.72 | C |
| ATOM | 1041 | CD  | LYS | C | 698 | 2.557  | 28.306 | 3.849  | 1.00 | 50.51 | C |
| ATOM | 1042 | CE  | LYS | C | 698 | 1.081  | 27.806 | 3.895  | 1.00 | 56.02 | C |
| ATOM | 1043 | NZ  | LYS | C | 698 | 0.839  | 26.491 | 4.566  | 1.00 | 56.19 | N |
| ATOM | 1044 | N   | PHE | C | 699 | 3.974  | 31.683 | 8.620  | 1.00 | 44.15 | N |
| ATOM | 1045 | CA  | PHE | C | 699 | 4.044  | 31.756 | 10.079 | 1.00 | 45.29 | C |
| ATOM | 1046 | C   | PHE | C | 699 | 4.161  | 33.196 | 10.512 | 1.00 | 45.48 | C |
| ATOM | 1047 | O   | PHE | C | 699 | 3.461  | 33.607 | 11.419 | 1.00 | 45.49 | O |
| ATOM | 1048 | CB  | PHE | C | 699 | 5.233  | 30.961 | 10.651 | 1.00 | 42.30 | C |
| ATOM | 1049 | CG  | PHE | C | 699 | 5.044  | 29.485 | 10.599 | 1.00 | 39.02 | C |
| ATOM | 1050 | CD1 | PHE | C | 699 | 4.343  | 28.817 | 11.600 | 1.00 | 38.91 | C |
| ATOM | 1051 | CD2 | PHE | C | 699 | 5.539  | 28.752 | 9.548  | 1.00 | 37.17 | C |
| ATOM | 1052 | CE1 | PHE | C | 699 | 4.154  | 27.448 | 11.552 | 1.00 | 31.76 | C |
| ATOM | 1053 | CE2 | PHE | C | 699 | 5.335  | 27.370 | 9.488  | 1.00 | 36.46 | C |
| ATOM | 1054 | CZ  | PHE | C | 699 | 4.668  | 26.733 | 10.500 | 1.00 | 36.50 | C |
| ATOM | 1055 | N   | PHE | C | 700 | 5.002  | 33.948 | 9.804  | 1.00 | 47.11 | N |
| ATOM | 1056 | CA  | PHE | C | 700 | 5.141  | 35.384 | 9.993  | 1.00 | 48.88 | C |
| ATOM | 1057 | C   | PHE | C | 700 | 4.782  | 36.239 | 8.753  | 1.00 | 51.83 | C |
| ATOM | 1058 | O   | PHE | C | 700 | 5.637  | 36.552 | 7.944  | 1.00 | 51.08 | O |
| ATOM | 1059 | CB  | PHE | C | 700 | 6.561  | 35.654 | 10.490 | 1.00 | 47.88 | C |
| ATOM | 1060 | CG  | PHE | C | 700 | 6.890  | 34.896 | 11.752 | 1.00 | 46.63 | C |
| ATOM | 1061 | CD1 | PHE | C | 700 | 6.585  | 35.434 | 12.992 | 1.00 | 46.86 | C |
| ATOM | 1062 | CD2 | PHE | C | 700 | 7.476  | 33.634 | 11.709 | 1.00 | 47.30 | C |
| ATOM | 1063 | CE2 | PHE | C | 700 | 6.890  | 34.751 | 14.176 | 1.00 | 44.69 | C |
| ATOM | 1064 | CE2 | PHE | C | 700 | 7.795  | 32.944 | 12.928 | 1.00 | 44.30 | C |
| ATOM | 1065 | CZ  | PHE | C | 700 | 7.470  | 33.498 | 14.127 | 1.00 | 43.32 | C |
| ATOM | 1066 | N   | PRO | C | 701 | 3.498  | 36.599 | 8.591  | 1.00 | 54.88 | N |
| ATOM | 1067 | CA  | PRO | C | 701 | 3.313  | 37.517 | 7.490  | 1.00 | 58.29 | C |
| ATOM | 1068 | C   | PRO | C | 701 | 4.072  | 38.835 | 7.759  | 1.00 | 61.74 | C |
| ATOM | 1069 | O   | PRO | C | 701 | 4.352  | 39.165 | 8.911  | 1.00 | 63.26 | O |
| ATOM | 1070 | CB  | PRO | C | 701 | 1.791  | 37.739 | 7.471  | 1.00 | 58.67 | C |
| ATOM | 1071 | CG  | PRO | C | 701 | 1.190  | 36.543 | 8.220  | 1.00 | 56.76 | C |
| ATOM | 1072 | CD  | PRO | C | 701 | 2.232  | 36.263 | 9.272  | 1.00 | 54.74 | C |
| ATOM | 1073 | N   | SER | C | 702 | 4.445  | 39.556 | 6.706  | 1.00 | 64.74 | N |
| ATOM | 1074 | CA  | SER | C | 702 | 4.821  | 40.980 | 6.816  | 1.00 | 67.38 | C |
| ATOM | 1075 | C   | SER | C | 702 | 3.692  | 41.826 | 7.440  | 1.00 | 69.05 | C |
| ATOM | 1076 | O   | SER | C | 702 | 3.956  | 42.850 | 8.090  | 1.00 | 69.76 | O |
| ATOM | 1077 | CB  | SER | C | 702 | 5.175  | 41.521 | 5.430  | 1.00 | 66.92 | C |
| ATOM | 1078 | OG  | SER | C | 702 | 5.731  | 40.482 | 4.630  | 1.00 | 68.66 | O |
| ATOM | 1079 | N   | SER | C | 703 | 2.443  | 41.384 | 7.219  | 1.00 | 71.40 | N |
| ATOM | 1080 | CA  | SER | C | 703 | 1.218  | 41.945 | 7.843  | 1.00 | 73.17 | C |
| ATOM | 1081 | C   | SER | C | 703 | 0.949  | 41.362 | 9.252  | 1.00 | 74.20 | C |
| ATOM | 1082 | O   | SER | C | 703 | -0.175 | 41.457 | 9.803  | 1.00 | 74.06 | O |
| ATOM | 1083 | CB  | SER | C | 703 | 0.007  | 41.735 | 6.924  | 1.00 | 72.90 | C |
| ATOM | 1084 | OG  | SER | C | 703 | -0.216 | 40.361 | 6.656  | 1.00 | 73.57 | O |
| ATOM | 1085 | N   | SER | C | 704 | 1.999  | 40.728 | 9.793  | 1.00 | 75.51 | N |
| ATOM | 1086 | CA  | SER | C | 704 | 2.136  | 40.429 | 11.207 | 1.00 | 76.10 | C |
| ATOM | 1087 | C   | SER | C | 704 | 2.788  | 41.665 | 11.827 | 1.00 | 76.89 | C |
| ATOM | 1088 | O   | SER | C | 704 | 3.785  | 42.186 | 11.309 | 1.00 | 77.27 | O |
| ATOM | 1089 | CB  | SER | C | 704 | 3.032  | 39.195 | 11.417 | 1.00 | 76.48 | C |
| ATOM | 1090 | OG  | SER | C | 704 | 2.481  | 38.245 | 12.332 | 1.00 | 76.04 | O |
| ATOM | 1091 | N   | TYR | C | 705 | 2.172  | 42.149 | 12.902 | 1.00 | 77.76 | N |
| ATOM | 1092 | CA  | TYR | C | 705 | 2.752  | 43.110 | 13.849 | 1.00 | 78.33 | C |
| ATOM | 1093 | C   | TYR | C | 705 | 3.883  | 42.339 | 14.534 | 1.00 | 78.0  | C |
| ATOM | 1094 | O   | TYR | C | 705 | 5.066  | 42.703 | 14.433 | 1.00 | 78.29 | O |
| ATOM | 1095 | CB  | TYR | C | 705 | 1.678  | 43.501 | 14.889 | 1.00 | 78.92 | C |
| ATOM | 1096 | CG  | TYR | C | 705 | 0.266  | 43.087 | 14.467 | 1.00 | 80.14 | C |
| ATOM | 1097 | CD1 | TYR | C | 705 | 0.007  | 41.783 | 13.981 | 1.00 | 80.51 | C |
| ATOM | 1098 | CD2 | TYR | C | 705 | -0.800 | 43.989 | 14.533 | 1.00 | 81.44 | C |
| ATOM | 1099 | CE2 | TYR | C | 705 | -1.265 | 41.397 | 13.571 | 1.00 | 81.56 | C |
| ATOM | 1100 | CE2 | TYR | C | 705 | -2.091 | 43.609 | 14.130 | 1.00 | 82.11 | C |
| ATOM | 1101 | CZ  | TYR | C | 705 | -2.319 | 42.311 | 13.645 | 1.00 | 81.53 | C |
| ATOM | 1102 | OH  | TYR | C | 705 | -3.591 | 41.934 | 13.243 | 1.00 | 79.66 | O |
| ATOM | 1103 | N   | ARG | C | 706 | 3.463  | 41.253 | 15.193 | 1.00 | 77.34 | N |
| ATOM | 1104 | CA  | ARG | C | 706 | 4.278  | 40.228 | 15.872 | 1.00 | 76.16 | C |
| ATOM | 1105 | C   | ARG | C | 706 | 5.411  | 39.632 | 15.024 | 1.00 | 74.92 | C |
| ATOM | 1106 | O   | ARG | C | 706 | 5.187  | 38.816 | 14.110 | 1.00 | 74.90 | O |
| ATOM | 1107 | CB  | ARG | C | 706 | 3.351  | 39.117 | 16.389 | 1.00 | 75.95 | C |
| ATOM | 1108 | CG  | ARG | C | 706 | 4.011  | 37.892 | 17.044 | 1.00 | 76.83 | C |
| ATOM | 1109 | CD  | ARG | C | 706 | 2.930  | 37.050 | 17.714 | 1.00 | 77.30 | C |
| ATOM | 1110 | NE  | ARG | C | 706 | 1.637  | 37.264 | 17.051 | 1.00 | 79.50 | N |
| ATOM | 1111 | CZ  | ARG | C | 706 | 0.523  | 36.572 | 17.283 | 1.00 | 79.81 | C |
| ATOM | 1112 | NH1 | ARG | C | 706 | -0.567 | 36.865 | 16.588 | 1.00 | 79.36 | N |
| ATOM | 1113 | NH2 | ARG | C | 706 | 0.493  | 35.587 | 18.184 | 1.00 | 79.10 | N |
| ATOM | 1114 | N   | ARG | C | 707 | 6.618  | 40.050 | 15.392 | 1.00 | 72.84 | N |
| ATOM | 1115 | CA  | ARG | C | 707 | 7.853  | 39.729 | 14.722 | 1.00 | 71.31 | C |

TABLE 2a-continued

Data of atomic coordinates for accession code 2ZTT

| ATOM | 1116 | C | ARG | C | 707 | 8.493 | 38.481 | 15.339 | 1.00 | 69.15 | C |
|---|---|---|---|---|---|---|---|---|---|---|---|
| ATOM | 1117 | O | ARG | C | 707 | 8.270 | 38.194 | 16.515 | 1.00 | 68.32 | O |
| ATOM | 1118 | CB | ARG | C | 707 | 8.801 | 40.950 | 14.790 | 1.00 | 71.73 | C |
| ATOM | 1119 | CG | ARG | C | 707 | 9.833 | 40.964 | 15.956 | 1.00 | 74.53 | C |
| ATOM | 1120 | CD | ARG | C | 707 | 9.226 | 41.294 | 17.331 | 1.00 | 78.44 | C |
| ATOM | 1121 | NE | ARG | C | 707 | 9.586 | 42.636 | 17.782 | 1.00 | 82.14 | N |
| ATOM | 1122 | CZ | ARG | C | 707 | 10.820 | 43.019 | 18.144 | 1.00 | 84.36 | C |
| ATOM | 1123 | NH1 | ARG | C | 707 | 11.849 | 42.163 | 18.105 | 1.00 | 83.89 | N |
| ATOM | 1124 | NH2 | ARG | C | 707 | 11.027 | 44.276 | 18.542 | 1.00 | 84.08 | N |
| ATOM | 1125 | N | PRO | C | 708 | 9.266 | 37.721 | 14.529 | 1.00 | 67.58 | N |
| ATOM | 1126 | CA | PRO | C | 708 | 10.066 | 36.601 | 15.037 | 1.00 | 66.26 | C |
| ATOM | 1127 | C | PRO | C | 708 | 11.239 | 37.076 | 15.895 | 1.00 | 64.75 | C |
| ATOM | 1128 | O | PRO | C | 708 | 11.726 | 38.197 | 15.727 | 1.00 | 65.41 | O |
| ATOM | 1129 | CB | PRO | C | 708 | 10.586 | 35.936 | 13.749 | 1.00 | 65.94 | C |
| ATOM | 1130 | CG | PRO | C | 708 | 10.647 | 37.035 | 12.773 | 1.00 | 66.14 | C |
| ATOM | 1131 | CD | PRO | C | 708 | 9.422 | 37.861 | 13.067 | 1.00 | 67.46 | C |
| ATOM | 1132 | N | VAL | C | 709 | 11.706 | 36.237 | 16.795 | 1.00 | 62.62 | N |
| ATOM | 1133 | CA | VAL | C | 709 | 12.892 | 36.590 | 17.531 | 1.00 | 60.73 | C |
| ATOM | 1134 | C | VAL | C | 709 | 14.099 | 36.395 | 16.606 | 1.00 | 59.75 | C |
| ATOM | 1135 | O | VAL | C | 709 | 14.524 | 35.268 | 16.331 | 1.00 | 59.32 | O |
| ATOM | 1136 | CB | VAL | C | 709 | 12.999 | 35.776 | 18.833 | 1.00 | 61.19 | C |
| ATOM | 1137 | CG1 | VAL | C | 709 | 12.808 | 34.263 | 18.550 | 1.00 | 61.92 | C |
| ATOM | 1138 | CG2 | VAL | C | 709 | 14.296 | 36.070 | 19.573 | 1.00 | 59.76 | C |
| ATOM | 1139 | N | GLY | C | 710 | 14.639 | 37.508 | 16.123 | 1.00 | 58.01 | N |
| ATOM | 1140 | CA | GLY | C | 710 | 15.781 | 37.495 | 15.234 | 1.00 | 55.74 | C |
| ATOM | 1141 | C | GLY | C | 710 | 16.894 | 36.493 | 15.527 | 1.00 | 54.51 | C |
| ATOM | 1142 | O | GLY | C | 710 | 17.541 | 36.000 | 14.590 | 1.00 | 53.26 | O |
| ATOM | 1143 | N | ILE | C | 711 | 17.138 | 36.161 | 16.793 | 1.00 | 54.58 | N |
| ATOM | 1144 | CA | ILE | C | 711 | 18.277 | 35.234 | 17.076 | 1.00 | 54.10 | C |
| ATOM | 1145 | C | ILE | C | 711 | 17.957 | 33.730 | 17.189 | 1.00 | 53.14 | C |
| ATOM | 1146 | O | ILE | C | 711 | 18.865 | 32.889 | 17.331 | 1.00 | 52.38 | O |
| ATOM | 1147 | CB | ILE | C | 711 | 19.158 | 35.681 | 18.284 | 1.00 | 55.28 | C |
| ATOM | 1148 | CG1 | ILE | C | 711 | 18.445 | 35.469 | 19.637 | 1.00 | 56.01 | C |
| ATOM | 1149 | CG2 | ILE | C | 711 | 19.644 | 37.119 | 18.112 | 1.00 | 55.19 | C |
| ATOM | 1150 | CD1 | ILE | C | 711 | 19.417 | 35.559 | 20.855 | 1.00 | 54.99 | C |
| ATOM | 1151 | N | SER | C | 712 | 16.676 | 33.405 | 17.203 | 1.00 | 51.92 | N |
| ATOM | 1152 | CA | SER | C | 712 | 16.225 | 32.004 | 17.215 | 1.00 | 51.25 | C |
| ATOM | 1153 | C | SER | C | 712 | 16.384 | 31.359 | 15.844 | 1.00 | 48.87 | C |
| ATOM | 1154 | O | SER | C | 712 | 16.310 | 32.028 | 14.823 | 1.00 | 48.48 | O |
| ATOM | 1155 | CB | SER | C | 712 | 14.773 | 31.928 | 17.628 | 1.00 | 51.17 | C |
| ATOM | 1156 | OG | SER | C | 712 | 14.674 | 32.154 | 19.034 | 1.00 | 54.09 | O |
| ATOM | 1157 | N | SER | C | 713 | 16.664 | 30.068 | 15.828 | 1.00 | 47.96 | N |
| ATOM | 1158 | CA | SER | C | 713 | 16.748 | 29.373 | 14.574 | 1.00 | 47.26 | C |
| ATOM | 1159 | C | SER | C | 713 | 15.384 | 29.465 | 13.865 | 1.00 | 46.33 | C |
| ATOM | 1160 | O | SER | C | 713 | 14.354 | 29.819 | 14.455 | 1.00 | 45.13 | O |
| ATOM | 1161 | CB | SER | C | 713 | 17.156 | 27.935 | 14.773 | 1.00 | 47.14 | C |
| ATOM | 1162 | OG | SER | C | 713 | 16.056 | 27.194 | 15.274 | 1.00 | 49.64 | O |
| HETATM | 1163 | N | MSE | C | 714 | 15.389 | 29.200 | 12.576 | 1.00 | 46.39 | N |
| HETATM | 1164 | CA | MSE | C | 714 | 14.150 | 29.330 | 11.804 | 1.00 | 46.66 | C |
| HETATM | 1165 | C | MSE | C | 714 | 13.100 | 28.382 | 12.323 | 1.00 | 44.04 | C |
| HETATM | 1166 | O | MSE | C | 714 | 11.988 | 28.799 | 12.549 | 1.00 | 46.70 | O |
| HETATM | 1167 | CB | MSE | C | 714 | 14.426 | 29.068 | 10.348 | 1.00 | 45.72 | C |
| HETATM | 1168 | CG | MSE | C | 714 | 15.075 | 30.242 | 9.642 | 1.00 | 49.05 | C |
| HETATM | 1169 | SE | MSE | C | 714 | 15.235 | 29.816 | 7.736 | 1.00 | 58.08 | SE |
| HETATM | 1170 | CE | MSE | C | 714 | 13.458 | 30.461 | 7.123 | 1.00 | 47.03 | C |
| ATOM | 1171 | N | VAL | C | 715 | 13.400 | 27.103 | 12.528 | 1.00 | 42.21 | N |
| ATOM | 1172 | CA | VAL | C | 715 | 12.354 | 26.167 | 12.999 | 1.00 | 39.06 | C |
| ATOM | 1173 | C | VAL | C | 715 | 11.776 | 26.527 | 14.401 | 1.00 | 39.39 | C |
| ATOM | 1174 | O | VAL | C | 715 | 10.545 | 26.516 | 14.639 | 1.00 | 36.18 | O |
| ATOM | 1175 | CB | VAL | C | 715 | 12.823 | 24.718 | 12.862 | 1.00 | 39.48 | C |
| ATOM | 1176 | CG1 | VAL | C | 715 | 14.112 | 24.408 | 13.802 | 1.00 | 35.84 | C |
| ATOM | 1177 | CG2 | VAL | C | 715 | 11.705 | 23.780 | 13.159 | 1.00 | 38.54 | C |
| ATOM | 1178 | N | GLU | C | 716 | 12.674 | 26.958 | 15.302 | 1.00 | 39.20 | N |
| ATOM | 1179 | CA | GLU | C | 716 | 12.334 | 27.413 | 16.635 | 1.00 | 39.99 | C |
| ATOM | 1180 | C | GLU | C | 716 | 11.380 | 28.546 | 16.563 | 1.00 | 38.65 | C |
| ATOM | 1181 | O | GLU | C | 716 | 10.323 | 28.543 | 17.205 | 1.00 | 41.69 | O |
| ATOM | 1182 | CB | GLU | C | 716 | 13.620 | 27.945 | 17.361 | 1.00 | 39.46 | C |
| ATOM | 1183 | CG | GLU | C | 716 | 13.586 | 27.706 | 18.916 | 1.00 | 44.55 | C |
| ATOM | 1184 | CD | GLU | C | 716 | 14.778 | 28.357 | 19.707 | 1.00 | 45.95 | C |
| ATOM | 1185 | OE1 | GLU | C | 716 | 15.457 | 27.618 | 20.486 | 1.00 | 51.82 | O |
| ATOM | 1186 | OE2 | GLU | C | 716 | 15.002 | 29.599 | 19.565 | 1.00 | 49.25 | O |
| ATOM | 1187 | N | ALA | C | 717 | 11.720 | 29.572 | 15.805 | 1.00 | 38.13 | N |
| ATOM | 1188 | CA | ALA | C | 717 | 10.801 | 30.663 | 15.711 | 1.00 | 38.05 | C |
| ATOM | 1189 | C | ALA | C | 717 | 9.476 | 30.037 | 15.269 | 1.00 | 37.80 | C |
| ATOM | 1190 | O | ALA | C | 717 | 8.450 | 30.446 | 15.772 | 1.00 | 39.39 | O |
| ATOM | 1191 | CB | ALA | C | 717 | 11.241 | 31.698 | 14.687 | 1.00 | 37.08 | C |
| HETATM | 1192 | N | MSE | C | 718 | 9.494 | 29.069 | 14.356 | 1.00 | 36.66 | N |
| HETATM | 1193 | CA | MSE | C | 718 | 8.206 | 28.533 | 13.714 | 1.00 | 39.98 | C |

TABLE 2a-continued

Data of atomic coordinates for accession code 2ZTT

| HETATM | 1194 | C   | MSE | C | 718 | 7.300  | 27.650 | 14.581 | 1.00 | 36.94 | C  |
|--------|------|-----|-----|---|-----|--------|--------|--------|------|-------|----|
| HETATM | 1195 | O   | MSE | C | 718 | 6.123  | 27.896 | 14.669 | 1.00 | 39.18 | O  |
| HETATM | 1196 | CB  | MSE | C | 718 | 8.537  | 27.759 | 12.420 | 1.00 | 36.23 | C  |
| HETATM | 1197 | CG  | MSE | C | 718 | 8.825  | 28.683 | 11.236 | 1.00 | 43.94 | C  |
| HETATM | 1198 | SE  | MSE | C | 718 | 9.752  | 27.861 | 9.661  | 1.00 | 53.70 | SE |
| HETATM | 1199 | CE  | MSE | C | 718 | 11.387 | 27.296 | 10.456 | 1.00 | 47.15 | C  |
| ATOM   | 1200 | N   | VAL | C | 719 | 7.857  | 26.594 | 15.197 | 1.00 | 38.61 | N  |
| ATOM   | 1201 | CA  | VAL | C | 719 | 7.170  | 25.727 | 16.157 | 1.00 | 36.34 | C  |
| ATOM   | 1202 | C   | VAL | C | 719 | 6.545  | 26.530 | 17.287 | 1.00 | 37.38 | C  |
| ATOM   | 1203 | O   | VAL | C | 719 | 5.474  | 26.227 | 17.802 | 1.00 | 39.86 | O  |
| ATOM   | 1204 | CB  | VAL | C | 719 | 8.142  | 24.700 | 16.755 | 1.00 | 37.24 | C  |
| ATOM   | 1205 | CG1 | VAL | C | 719 | 7.488  | 23.940 | 17.863 | 1.00 | 32.64 | C  |
| ATOM   | 1206 | CG2 | VAL | C | 719 | 8.574  | 23.730 | 15.739 | 1.00 | 32.86 | C  |
| ATOM   | 1207 | N   | SER | C | 720 | 7.198  | 27.592 | 17.652 | 1.00 | 36.88 | N  |
| ATOM   | 1208 | CA  | SER | C | 720 | 6.818  | 28.337 | 18.801 | 1.00 | 35.56 | C  |
| ATOM   | 1209 | C   | SER | C | 720 | 5.686  | 29.312 | 18.413 | 1.00 | 34.96 | C  |
| ATOM   | 1210 | O   | SER | C | 720 | 4.700  | 29.379 | 19.088 | 1.00 | 35.50 | O  |
| ATOM   | 1211 | CB  | SER | C | 720 | 7.994  | 29.144 | 19.196 | 1.00 | 33.10 | C  |
| ATOM   | 1212 | OG  | SER | C | 720 | 7.494  | 30.174 | 19.977 | 1.00 | 37.30 | O  |
| ATOM   | 1213 | N   | ARG | C | 721 | 5.862  | 30.124 | 17.390 | 1.00 | 36.01 | N  |
| ATOM   | 1214 | CA  | ARG | C | 721 | 4.643  | 30.666 | 16.717 | 1.00 | 37.74 | C  |
| ATOM   | 1215 | C   | ARG | C | 721 | 3.552  | 29.630 | 16.735 | 1.00 | 37.06 | C  |
| ATOM   | 1216 | O   | ARG | C | 721 | 2.5582 | 9.847  | 17.386 | 1.00 | 40.25 | O  |
| ATOM   | 1217 | CB  | ARG | C | 721 | 4.896  | 31.079 | 15.273 | 1.00 | 38.50 | C  |
| ATOM   | 1218 | CG  | ARG | C | 721 | 3.741  | 31.929 | 14.566 | 1.00 | 36.97 | C  |
| ATOM   | 1219 | CD  | ARG | C | 721 | 3.236  | 33.111 | 15.461 | 1.00 | 42.68 | C  |
| ATOM   | 1220 | NE  | ARG | C | 721 | 2.086  | 33.839 | 14.890 | 1.00 | 47.41 | N  |
| ATOM   | 1221 | CZ  | ARG | C | 721 | 2.162  | 35.049 | 14.284 | 1.00 | 49.60 | C  |
| ATOM   | 1222 | NH1 | ARG | C | 721 | 3.332  | 35.681 | 14.187 | 1.00 | 44.65 | N  |
| ATOM   | 1223 | NH2 | ARG | C | 721 | 1.065  | 35.639 | 13.756 | 1.00 | 50.03 | N  |
| ATOM   | 1224 | N   | ALA | C | 722 | 3.708  | 28.496 | 16.056 | 1.00 | 38.37 | N  |
| ATOM   | 1225 | CA  | ALA | C | 722 | 2.527  | 27.557 | 15.835 | 1.00 | 37.24 | C  |
| ATOM   | 1226 | C   | ALA | C | 722 | 1.862  | 27.018 | 17.111 | 1.00 | 37.62 | C  |
| ATOM   | 1227 | O   | ALA | C | 722 | 0.633  | 26.882 | 17.191 | 1.00 | 36.55 | O  |
| ATOM   | 1228 | CB  | ALA | C | 722 | 2.897  | 26.385 | 14.934 | 1.00 | 35.63 | C  |
| ATOM   | 1229 | N   | ARG | C | 723 | 2.673  | 26.680 | 18.120 | 1.00 | 38.45 | N  |
| ATOM   | 1230 | CA  | ARG | C | 723 | 2.183  | 26.344 | 19.434 | 1.00 | 37.75 | C  |
| ATOM   | 1231 | C   | ARG | C | 723 | 1.295  | 27.435 | 20.000 | 1.00 | 39.67 | C  |
| ATOM   | 1232 | O   | ARG | C | 723 | 0.171  | 27.167 | 20.454 | 1.00 | 40.09 | O  |
| ATOM   | 1233 | CB  | ARG | C | 723 | 3.393  | 26.094 | 20.354 | 1.00 | 38.21 | C  |
| ATOM   | 1234 | CG  | ARG | C | 723 | 3.937  | 24.714 | 20.088 | 1.00 | 37.82 | C  |
| ATOM   | 1235 | CD  | ARG | C | 723 | 5.172  | 24.390 | 20.837 | 1.00 | 41.50 | C  |
| ATOM   | 1236 | NE  | ARG | C | 723 | 5.343  | 22.948 | 20.936 | 1.00 | 40.51 | N  |
| ATOM   | 1237 | CZ  | ARG | C | 723 | 6.497  | 22.368 | 21.261 | 1.00 | 42.07 | C  |
| ATOM   | 1238 | NH1 | ARG | C | 723 | 7.575  | 23.126 | 21.466 | 1.00 | 40.67 | N  |
| ATOM   | 1239 | NH2 | ARG | C | 723 | 6.579  | 21.045 | 21.347 | 1.00 | 36.02 | N  |
| ATOM   | 1240 | N   | ILE | C | 724 | 1.764  | 28.685 | 19.911 | 1.00 | 41.71 | N  |
| ATOM   | 1241 | CA  | ILE | C | 724 | 0.990  | 29.872 | 20.385 | 1.00 | 42.84 | C  |
| ATOM   | 1242 | C   | ILE | C | 724 | -0.325 | 30.125 | 19.637 | 1.00 | 43.13 | C  |
| ATOM   | 1243 | O   | ILE | C | 724 | -1.369 | 30.419 | 20.252 | 1.00 | 44.14 | O  |
| ATOM   | 1244 | CB  | ILE | C | 724 | 1.851  | 31.119 | 20.354 | 1.00 | 43.64 | C  |
| ATOM   | 1245 | CG1 | ILE | C | 724 | 2.967  | 31.011 | 21.418 | 1.00 | 45.88 | C  |
| ATOM   | 1246 | CG2 | ILE | C | 724 | 1.020  | 32.302 | 20.641 | 1.00 | 44.74 | C  |
| ATOM   | 1247 | CD1 | ILE | C | 724 | 4.180  | 31.914 | 21.162 | 1.00 | 48.84 | C  |
| ATOM   | 1248 | N   | ASP | C | 725 | -0.322 | 29.969 | 18.323 | 1.00 | 42.60 | N  |
| ATOM   | 1249 | CA  | ASP | C | 725 | -1.561 | 30.211 | 17.585 | 1.00 | 41.80 | C  |
| ATOM   | 1250 | C   | ASP | C | 725 | -2.626 | 29.162 | 17.800 | 1.00 | 41.88 | C  |
| ATOM   | 1251 | O   | ASP | C | 725 | -3.840 | 29.477 | 17.732 | 1.00 | 43.26 | O  |
| ATOM   | 1252 | CB  | ASP | C | 725 | -1.330 | 30.377 | 16.086 | 1.00 | 40.55 | C  |
| ATOM   | 1253 | CG  | ASP | C | 725 | -0.772 | 31.710 | 15.729 | 1.00 | 40.37 | C  |
| ATOM   | 1254 | OD1 | ASP | C | 725 | -0.735 | 32.648 | 16.576 | 1.00 | 45.46 | O  |
| ATOM   | 1255 | OD2 | ASP | C | 725 | -0.308 | 31.836 | 14.583 | 1.00 | 38.49 | O  |
| ATOM   | 1256 | N   | ALA | C | 726 | -2.196 | 27.930 | 18.025 | 1.00 | 40.54 | N  |
| ATOM   | 1257 | CA  | ALA | C | 726 | -3.090 | 26.803 | 18.153 | 1.00 | 40.46 | C  |
| ATOM   | 1258 | C   | ALA | C | 726 | -3.862 | 26.864 | 19.441 | 1.00 | 40.56 | C  |
| ATOM   | 1259 | O   | ALA | C | 726 | -5.121 | 26.798 | 19.423 | 1.00 | 41.14 | O  |
| ATOM   | 1260 | CB  | ALA | C | 726 | -2.341 | 25.454 | 17.989 | 1.00 | 39.51 | C  |
| ATOM   | 1261 | N   | ARG | C | 727 | -3.123 | 26.977 | 20.540 | 1.00 | 39.40 | N  |
| ATOM   | 1262 | CA  | ARG | C | 727 | -3.631 | 27.346 | 21.866 | 1.00 | 39.59 | C  |
| ATOM   | 1263 | C   | ARG | C | 727 | -4.627 | 28.485 | 21.889 | 1.00 | 40.34 | C  |
| ATOM   | 1264 | O   | ARG | C | 727 | -5.801 | 28.267 | 22.249 | 1.00 | 41.46 | O  |
| ATOM   | 1265 | CB  | ARG | C | 727 | -2.463 | 27.629 | 22.821 | 1.00 | 40.84 | C  |
| ATOM   | 1266 | CG  | ARG | C | 727 | -1.743 | 26.360 | 23.155 | 1.00 | 40.68 | C  |
| ATOM   | 1267 | CD  | ARG | C | 727 | -0.906 | 26.565 | 24.377 | 1.00 | 43.72 | C  |
| ATOM   | 1268 | NE  | ARG | C | 727 | 0.384  | 27.073 | 23.976 | 1.00 | 42.55 | N  |
| ATOM   | 1269 | CZ  | ARG | C | 727 | 1.514  | 26.375 | 24.090 | 1.00 | 42.62 | C  |
| ATOM   | 1270 | NH1 | ARG | C | 727 | 2.643  | 26.918 | 23.684 | 1.00 | 41.95 | N  |
| ATOM   | 1271 | NH2 | ARG | C | 727 | 1.492  | 25.160 | 24.621 | 1.00 | 37.21 | N  |

TABLE 2a-continued

Data of atomic coordinates for accession code 2ZTT

| ATOM | 1272 | N | ILE | C | 728 | −4.210 | 29.661 | 21.420 | 1.00 | 40.67 | N |
|---|---|---|---|---|---|---|---|---|---|---|---|
| ATOM | 1273 | CA | ILE | C | 728 | −5.146 | 30.778 | 21.201 | 1.00 | 41.58 | C |
| ATOM | 1274 | C | ILE | C | 728 | −6.360 | 30.456 | 20.313 | 1.00 | 41.17 | C |
| ATOM | 1275 | O | ILE | C | 728 | −7.470 | 30.817 | 20.665 | 1.00 | 43.41 | O |
| ATOM | 1276 | CB | ILE | C | 728 | −4.481 | 32.076 | 20.649 | 1.00 | 42.06 | C |
| ATOM | 1277 | CG1 | ILE | C | 728 | −3.330 | 32.562 | 21.544 | 1.00 | 43.72 | C |
| ATOM | 1278 | CG2 | ILE | C | 728 | −5.507 | 33.191 | 20.671 | 1.00 | 44.48 | C |
| ATOM | 1279 | CD1 | ILE | C | 728 | −2.593 | 33.835 | 21.004 | 1.00 | 40.08 | C |
| ATOM | 1280 | N | ASP | C | 729 | −6.172 | 29.819 | 19.164 | 1.00 | 41.20 | N |
| ATOM | 1281 | CA | ASP | C | 729 | −7.319 | 29.490 | 18.257 | 1.00 | 39.44 | C |
| ATOM | 1282 | C | ASP | C | 729 | −8.241 | 28.421 | 18.815 | 1.00 | 39.63 | C |
| ATOM | 1283 | O | ASP | C | 729 | −9.434 | 28.343 | 18.407 | 1.00 | 39.75 | O |
| ATOM | 1284 | CB | ASP | C | 729 | −6.836 | 29.011 | 16.869 | 1.00 | 39.57 | C |
| ATOM | 1285 | CG | ASP | C | 729 | −6.048 | 30.078 | 16.074 | 1.00 | 41.01 | C |
| ATOM | 1286 | OD1 | ASP | C | 729 | −5.911 | 31.231 | 16.513 | 1.00 | 43.51 | O |
| ATOM | 1287 | OD2 | ASP | C | 729 | −5.476 | 29.719 | 15.008 | 1.00 | 44.06 | O |
| ATOM | 1288 | N | PHE | C | 730 | −7.708 | 27.546 | 19.664 | 1.00 | 36.80 | N |
| ATOM | 1289 | CA | PHE | C | 730 | −8.466 | 26.487 | 20.309 | 1.00 | 36.51 | C |
| ATOM | 1290 | C | PHE | C | 730 | −9.294 | 26.986 | 21.468 | 1.00 | 37.02 | C |
| ATOM | 1291 | O | PHE | C | 730 | −10.483 | 26.652 | 21.575 | 1.00 | 37.45 | O |
| ATOM | 1292 | CB | PHE | C | 730 | −7.555 | 25.317 | 20.798 | 1.00 | 34.36 | C |
| ATOM | 1293 | CG | PHE | C | 730 | −8.321 | 24.163 | 21.457 | 1.00 | 37.07 | C |
| ATOM | 1294 | CD1 | PHE | C | 730 | −9.543 | 23.654 | 20.867 | 1.00 | 31.11 | C |
| ATOM | 1295 | CD2 | PHE | C | 730 | −7.853 | 23.572 | 22.647 | 1.00 | 28.54 | C |
| ATOM | 1296 | CE2 | PHE | C | 730 | −10.238 | 22.601 | 21.440 | 1.00 | 28.97 | C |
| ATOM | 1297 | CE2 | PHE | C | 730 | −8.507 | 22.482 | 23.223 | 1.00 | 31.58 | C |
| ATOM | 1298 | CZ | PHE | C | 730 | −9.730 | 21.971 | 22.643 | 1.00 | 35.65 | C |
| ATOM | 1299 | N | GLU | C | 731 | −8.654 | 27.755 | 22.343 | 1.00 | 38.33 | N |
| ATOM | 1300 | CA | GLU | C | 731 | −9.294 | 28.552 | 23.410 | 1.00 | 39.99 | C |
| ATOM | 1301 | C | GLU | C | 731 | −10.398 | 29.518 | 22.913 | 1.00 | 41.16 | C |
| ATOM | 1302 | O | GLU | C | 731 | −11.336 | 29.858 | 23.639 | 1.00 | 40.73 | O |
| ATOM | 1303 | CB | GLU | C | 731 | −8.198 | 29.340 | 24.142 | 1.00 | 39.31 | C |
| ATOM | 1304 | CG | GLU | C | 731 | −7.241 | 28.395 | 24.914 | 1.00 | 41.09 | C |
| ATOM | 1305 | CD | GLU | C | 731 | −5.812 | 28.948 | 25.222 | 1.00 | 41.43 | C |
| ATOM | 1306 | OE1 | GLU | C | 731 | −4.934 | 28.125 | 25.572 | 1.00 | 42.41 | O |
| ATOM | 1307 | OE2 | GLU | C | 731 | −5.569 | 30.164 | 25.120 | 1.00 | 44.52 | O |
| ATOM | 1308 | N | SER | C | 732 | −10.287 | 29.945 | 21.670 | 1.00 | 42.51 | N |
| ATOM | 1309 | CA | SER | C | 732 | −11.203 | 30.910 | 21.075 | 1.00 | 43.57 | C |
| ATOM | 1310 | C | SER | C | 732 | −12.274 | 30.290 | 20.210 | 1.00 | 44.44 | C |
| ATOM | 1311 | O | SER | C | 732 | −13.109 | 31.011 | 19.644 | 1.00 | 45.76 | O |
| ATOM | 1312 | CB | SER | C | 732 | −10.386 | 31.847 | 20.231 | 1.00 | 42.66 | C |
| ATOM | 1313 | OG | SER | C | 732 | −9.695 | 32.709 | 21.114 | 1.00 | 47.96 | O |
| ATOM | 1314 | N | GLY | C | 733 | −12.216 | 28.970 | 20.060 | 1.00 | 45.56 | N |
| ATOM | 1315 | CA | GLY | C | 733 | −13.196 | 28.187 | 19.269 | 1.00 | 45.12 | C |
| ATOM | 1316 | C | GLY | C | 733 | −13.067 | 28.293 | 17.778 | 1.00 | 45.49 | C |
| ATOM | 1317 | O | GLY | C | 733 | −14.055 | 28.114 | 17.039 | 1.00 | 47.24 | O |
| ATOM | 1318 | N | ARG | C | 734 | −11.855 | 28.572 | 17.333 | 1.00 | 44.78 | N |
| ATOM | 1319 | CA | ARG | C | 734 | −11.492 | 28.897 | 15.972 | 1.00 | 45.41 | C |
| ATOM | 1320 | C | ARG | C | 734 | −11.072 | 27.650 | 15.209 | 1.00 | 45.98 | C |
| ATOM | 1321 | O | ARG | C | 734 | −11.126 | 27.633 | 13.974 | 1.00 | 47.34 | O |
| ATOM | 1322 | CB | ARG | C | 734 | −10.298 | 29.872 | 15.983 | 1.00 | 45.54 | C |
| ATOM | 1323 | CG | ARG | C | 734 | −10.674 | 31.269 | 15.740 | 1.00 | 48.78 | C |
| ATOM | 1324 | CD | ARG | C | 734 | −9.548 | 32.183 | 15.990 | 1.00 | 53.93 | C |
| ATOM | 1325 | NE | ARG | C | 734 | −10.123 | 33.455 | 16.404 | 1.00 | 59.71 | N |
| ATOM | 1326 | CZ | ARG | C | 734 | −9.550 | 34.285 | 17.275 | 1.00 | 62.10 | C |
| ATOM | 1327 | NH1 | ARG | C | 734 | −8.371 | 33.981 | 17.831 | 1.00 | 61.15 | N |
| ATOM | 1328 | NH2 | ARG | C | 734 | −10.162 | 35.413 | 17.595 | 1.00 | 61.37 | N |
| ATOM | 1329 | N | ILE | C | 735 | −10.570 | 26.656 | 15.962 | 1.00 | 45.56 | N |
| ATOM | 1330 | CA | ILE | C | 735 | −10.206 | 25.307 | 15.509 | 1.00 | 43.26 | C |
| ATOM | 1331 | C | ILE | C | 735 | −10.863 | 24.340 | 16.466 | 1.00 | 42.82 | C |
| ATOM | 1332 | O | ILE | C | 735 | −11.254 | 24.728 | 17.559 | 1.00 | 43.50 | O |
| ATOM | 1333 | CB | ILE | C | 735 | −8.646 | 25.079 | 15.415 | 1.00 | 42.11 | C |
| ATOM | 1334 | CG1 | ILE | C | 735 | −7.930 | 25.265 | 16.790 | 1.00 | 42.88 | C |
| ATOM | 1335 | CG2 | ILE | C | 735 | −8.098 | 26.013 | 14.410 | 1.00 | 42.74 | C |
| ATOM | 1336 | CD1 | ILE | C | 735 | −6.459 | 24.797 | 16.849 | 1.00 | 41.06 | C |
| ATOM | 1337 | N | LYS | C | 736 | −10.994 | 23.089 | 16.033 | 1.00 | 43.12 | N |
| ATOM | 1338 | CA | LYS | C | 736 | −11.555 | 22.018 | 16.812 | 1.00 | 43.05 | C |
| ATOM | 1339 | C | LYS | C | 736 | −10.408 | 21.210 | 17.471 | 1.00 | 43.05 | C |
| ATOM | 1340 | O | LYS | C | 736 | −9.2692 | 1.363 | 17.104 | 1.00 | 41.94 | O |
| ATOM | 1341 | CB | LYS | C | 736 | −12.386 | 21.114 | 15.912 | 1.00 | 44.08 | C |
| ATOM | 1342 | CG | LYS | C | 736 | −13.542 | 21.864 | 15.181 | 1.00 | 47.61 | C |
| ATOM | 1343 | CD | LYS | C | 736 | −14.891 | 21.099 | 15.327 | 1.00 | 52.42 | C |
| ATOM | 1344 | CE | LYS | C | 736 | −16.022 | 21.687 | 14.439 | 1.00 | 51.91 | C |
| ATOM | 1345 | NZ | LYS | C | 736 | −15.777 | 23.154 | 14.147 | 1.00 | 51.97 | N |
| ATOM | 1346 | N | LYS | C | 737 | −10.768 | 20.339 | 18.408 | 1.00 | 42.40 | N |
| ATOM | 1347 | CA | LYS | C | 737 | −9.844 | 19.608 | 19.279 | 1.00 | 43.79 | C |
| ATOM | 1348 | C | LYS | C | 737 | −8.951 | 18.623 | 18.521 | 1.00 | 43.36 | C |
| ATOM | 1349 | O | LYS | C | 737 | −7.816 | 18.409 | 18.919 | 1.00 | 43.68 | O |

TABLE 2a-continued

Data of atomic coordinates for accession code 2ZTT

| ATOM | 1350 | CB | LYS | C | 737 | −10.626 | 18.944 | 20.432 | 1.00 | 42.91 | C |
|---|---|---|---|---|---|---|---|---|---|---|---|
| ATOM | 1351 | CG | LYS | C | 737 | −11.333 | 17.682 | 20.077 | 1.00 | 47.49 | C |
| ATOM | 1352 | CD | LYS | C | 737 | −12.629 | 17.425 | 20.883 | 1.00 | 48.71 | C |
| ATOM | 1353 | CE | LYS | C | 737 | −13.168 | 15.994 | 20.591 | 1.00 | 48.68 | C |
| ATOM | 1354 | NZ | LYS | C | 737 | −14.338 | 15.605 | 21.431 | 1.00 | 50.38 | N |
| ATOM | 1355 | N | GLU | C | 738 | −9.461 | 18.049 | 17.420 | 1.00 | 43.01 | N |
| ATOM | 1356 | CA | GLU | C | 738 | −8.695 | 17.182 | 16.508 | 1.00 | 41.91 | C |
| ATOM | 1357 | C | GLU | C | 738 | −7.550 | 17.898 | 15.833 | 1.00 | 40.83 | C |
| ATOM | 1358 | O | GLU | C | 738 | −6.468 | 17.354 | 15.719 | 1.00 | 43.11 | O |
| ATOM | 1359 | CB | GLU | C | 738 | −9.593 | 16.484 | 15.467 | 1.00 | 42.64 | C |
| ATOM | 1360 | CG | GLU | C | 738 | −10.719 | 15.622 | 16.077 | 1.00 | 44.05 | C |
| ATOM | 1361 | CD | GLU | C | 738 | −11.991 | 16.421 | 16.475 | 1.00 | 48.17 | C |
| ATOM | 1362 | OE1 | GLU | C | 738 | −12.091 | 17.616 | 16.106 | 1.00 | 47.19 | O |
| ATOM | 1363 | OE2 | GLU | C | 738 | −12.885 | 15.844 | 17.176 | 1.00 | 50.56 | O |
| ATOM | 1364 | N | GLU | C | 739 | −7.755 | 19.133 | 15.430 | 1.00 | 40.51 | N |
| ATOM | 1365 | CA | GLU | C | 739 | −6.739 | 19.902 | 14.779 | 1.00 | 38.49 | C |
| ATOM | 1366 | C | GLU | C | 739 | −5.736 | 20.488 | 15.845 | 1.00 | 38.36 | C |
| ATOM | 1367 | O | GLU | C | 739 | −4.521 | 20.431 | 15.615 | 1.00 | 35.86 | O |
| ATOM | 1368 | CB | GLU | C | 739 | −7.375 | 21.023 | 13.978 | 1.00 | 39.37 | C |
| ATOM | 1369 | CG | GLU | C | 739 | −6.343 | 21.811 | 13.236 | 1.00 | 42.41 | C |
| ATOM | 1370 | CD | GLU | C | 739 | −6.937 | 22.900 | 12.425 | 1.00 | 50.80 | C |
| ATOM | 1371 | OE1 | GLU | C | 739 | −8.176 | 22.976 | 12.411 | 1.00 | 57.13 | O |
| ATOM | 1372 | OE2 | GLU | C | 739 | −6.183 | 23.682 | 11.798 | 1.00 | 53.98 | O |
| ATOM | 1373 | N | PHE | C | 740 | −6.254 | 21.066 | 16.949 | 1.00 | 36.39 | N |
| ATOM | 1374 | CA | PHE | C | 740 | −5.405 | 21.422 | 18.089 | 1.00 | 37.81 | C |
| ATOM | 1375 | C | PHE | C | 740 | −4.430 | 20.315 | 18.473 | 1.00 | 36.92 | C |
| ATOM | 1376 | O | PHE | C | 740 | −3.215 | 20.498 | 18.464 | 1.00 | 37.36 | O |
| ATOM | 1377 | CB | PHE | C | 740 | −6.216 | 21.878 | 19.316 | 1.00 | 38.07 | C |
| ATOM | 1378 | CG | PHE | C | 740 | −5.363 | 22.149 | 20.519 | 1.00 | 36.71 | C |
| ATOM | 1379 | CD1 | PHE | C | 740 | −4.571 | 23.276 | 20.583 | 1.00 | 37.06 | C |
| ATOM | 1380 | CD2 | PHE | C | 740 | −5.333 | 21.269 | 21.565 | 1.00 | 39.36 | C |
| ATOM | 1381 | CE1 | PHE | C | 740 | −3.716 | 23.481 | 21.713 | 1.00 | 36.38 | C |
| ATOM | 1382 | CE2 | PHE | C | 740 | −4.523 | 21.470 | 22.677 | 1.00 | 32.72 | C |
| ATOM | 1383 | CZ | PHE | C | 740 | −3.702 | 22.554 | 22.733 | 1.00 | 35.42 | C |
| ATOM | 1384 | N | THR | C | 741 | −4.949 | 19.144 | 18.783 | 1.00 | 36.96 | N |
| ATOM | 1385 | CA | THR | C | 741 | −4.089 | 18.106 | 19.271 | 1.00 | 36.72 | C |
| ATOM | 1386 | C | THR | C | 741 | −3.141 | 17.644 | 18.179 | 1.00 | 38.54 | C |
| ATOM | 1387 | O | THR | C | 741 | −1.936 | 17.512 | 18.433 | 1.00 | 38.78 | O |
| ATOM | 1388 | CB | THR | C | 741 | −4.841 | 16.970 | 20.062 | 1.00 | 37.38 | C |
| ATOM | 1389 | OG1 | THR | C | 741 | −5.436 | 16.019 | 19.177 | 1.00 | 37.67 | O |
| ATOM | 1390 | OG2 | THR | C | 741 | −5.876 | 17.526 | 20.978 | 1.00 | 34.37 | C |
| ATOM | 1391 | N | GLU | C | 742 | −3.612 | 17.487 | 16.934 | 1.00 | 38.36 | N |
| ATOM | 1392 | CA | GLU | C | 742 | −2.660 | 17.169 | 15.891 | 1.00 | 38.56 | C |
| ATOM | 1393 | C | GLU | C | 742 | −1.534 | 18.154 | 15.667 | 1.00 | 38.72 | C |
| ATOM | 1394 | O | GLU | C | 742 | −0.364 | 17.734 | 15.463 | 1.00 | 36.84 | O |
| ATOM | 1395 | CB | GLU | C | 742 | −3.284 | 16.906 | 14.606 | 1.00 | 39.60 | C |
| ATOM | 1396 | CG | GLU | C | 742 | −2.234 | 16.685 | 13.553 | 1.00 | 43.12 | C |
| ATOM | 1397 | CD | GLU | C | 742 | −2.711 | 15.730 | 12.469 | 1.00 | 46.62 | C |
| ATOM | 1398 | OE1 | GLU | C | 742 | −3.934 | 15.773 | 12.176 | 1.00 | 48.15 | O |
| ATOM | 1399 | OE2 | GLU | C | 742 | −1.871 | 14.936 | 11.937 | 1.00 | 50.84 | O |
| ATOM | 1400 | N | ILE | C | 743 | −1.874 | 19.444 | 15.671 | 1.00 | 38.39 | N |
| ATOM | 1401 | CA | ILE | C | 743 | −0.868 | 20.480 | 15.537 | 1.00 | 39.41 | C |
| ATOM | 1402 | C | ILE | C | 743 | 0.159 | 20.362 | 16.704 | 1.00 | 39.65 | C |
| ATOM | 1403 | O | ILE | C | 743 | 1.346 | 20.462 | 16.490 | 1.00 | 41.06 | O |
| ATOM | 1404 | CB | ILE | C | 743 | −1.507 | 21.895 | 15.498 | 1.00 | 39.35 | C |
| ATOM | 1405 | CG1 | ILE | C | 743 | −2.253 | 22.146 | 14.175 | 1.00 | 38.62 | C |
| ATOM | 1406 | CG2 | ILE | C | 743 | −0.490 | 22.953 | 15.631 | 1.00 | 36.77 | C |
| ATOM | 1407 | CD1 | ILE | C | 743 | −3.140 | 23.390 | 14.250 | 1.00 | 38.10 | C |
| HETATM | 1408 | N | MSE | C | 744 | −0.327 | 20.116 | 17.916 | 1.00 | 40.31 | N |
| HETATM | 1409 | CA | MSE | C | 744 | 0.526 | 20.057 | 19.094 | 1.00 | 40.07 | C |
| HETATM | 1410 | C | MSE | C | 744 | 1.398 | 18.821 | 18.984 | 1.00 | 38.84 | C |
| HETATM | 1411 | O | MSE | C | 744 | 2.586 | 18.863 | 19.355 | 1.00 | 35.82 | O |
| HETATM | 1412 | CB | MSE | C | 744 | −0.298 | 20.055 | 20.386 | 1.00 | 41.45 | C |
| HETATM | 1413 | CG | MSE | C | 744 | −0.923 | 21.409 | 20.780 | 1.00 | 40.05 | C |
| HETATM | 1414 | SE | MSE | C | 744 | 0.079 | 23.050 | 20.568 | 1.00 | 47.68 | SE |
| HETATM | 1415 | CE | MSE | C | 744 | −1.308 | 24.325 | 20.439 | 1.00 | 48.71 | C |
| ATOM | 1416 | N | LYS | C | 745 | 0.827 | 17.757 | 18.367 | 1.00 | 37.44 | N |
| ATOM | 1417 | CA | LYS | C | 745 | 1.563 | 16.506 | 18.169 | 1.00 | 36.57 | C |
| ATOM | 1418 | C | LYS | C | 745 | 2.704 | 16.711 | 17.234 | 1.00 | 36.20 | C |
| ATOM | 1419 | O | LYS | C | 745 | 3.827 | 16.237 | 17.472 | 1.00 | 35.88 | O |
| ATOM | 1420 | CB | LYS | C | 745 | 0.700 | 15.317 | 17.758 | 1.00 | 36.84 | C |
| ATOM | 1421 | CG | LYS | C | 745 | −0.583 | 15.128 | 18.593 | 1.00 | 41.47 | C |
| ATOM | 1422 | CD | LYS | C | 745 | −0.575 | 14.144 | 19.803 | 1.00 | 47.44 | C |
| ATOM | 1423 | CE | LYS | C | 745 | 0.723 | 14.210 | 20.535 | 1.00 | 47.05 | C |
| ATOM | 1424 | NZ | LYS | C | 745 | 1.773 | 13.620 | 19.664 | 1.00 | 42.95 | N |
| ATOM | 1425 | N | ILE | C | 746 | 2.460 | 17.508 | 16.200 | 1.00 | 34.99 | N |
| ATOM | 1426 | CA | ILE | C | 746 | 3.442 | 17.668 | 15.148 | 1.00 | 33.61 | C |
| ATOM | 1427 | C | ILE | C | 746 | 4.616 | 18.544 | 15.545 | 1.00 | 33.09 | C |

TABLE 2a-continued

Data of atomic coordinates for accession code 2ZTT

| ATOM | 1428 | O | ILE | C | 746 | 5.679 | 18.231 | 15.100 | 1.00 | 31.89 | O |
|---|---|---|---|---|---|---|---|---|---|---|---|
| ATOM | 1429 | CB | ILE | C | 746 | 2.884 | 18.264 | 13.826 | 1.00 | 32.44 | C |
| ATOM | 1430 | CG1 | ILE | C | 746 | 1.820 | 17.355 | 13.199 | 1.00 | 35.18 | C |
| ATOM | 1431 | CG2 | ILE | C | 746 | 4.024 | 18.427 | 12.807 | 1.00 | 29.77 | C |
| ATOM | 1432 | CD1 | ILE | C | 746 | 1.986 | 15.934 | 13.574 | 1.00 | 39.0 | C |
| ATOM | 1433 | N | CYS | C | 747 | 4.362 | 19.675 | 16.227 | 1.00 | 33.77 | N |
| ATOM | 1434 | CA | CYS | C | 747 | 5.376 | 20.529 | 16.865 | 1.00 | 36.59 | C |
| ATOM | 1435 | C | CYS | C | 747 | 6.280 | 19.695 | 17.735 | 1.00 | 38.13 | C |
| ATOM | 1436 | O | CYS | C | 747 | 7.458 | 19.782 | 17.621 | 1.00 | 41.19 | O |
| ATOM | 1437 | CB | CYS | C | 747 | 4.736 | 21.643 | 17.726 | 1.00 | 34.67 | C |
| ATOM | 1438 | SG | CYS | C | 747 | 3.701 | 22.796 | 16.784 | 1.00 | 42.32 | S |
| ATOM | 1439 | N | SER | C | 748 | 5.713 | 18.892 | 18.607 | 1.00 | 40.40 | N |
| ATOM | 1440 | CA | SER | C | 748 | 6.469 | 17.964 | 19.404 | 1.00 | 43.99 | C |
| ATOM | 1441 | C | SER | C | 748 | 7.392 | 17.059 | 18.580 | 1.00 | 44.67 | C |
| ATOM | 1442 | O | SER | C | 748 | 8.486 | 16.716 | 19.026 | 1.00 | 45.87 | O |
| ATOM | 1443 | CB | SER | C | 748 | 5.506 | 17.133 | 20.242 | 1.00 | 43.78 | C |
| ATOM | 1444 | OG | SER | C | 748 | 6.226 | 16.234 | 21.048 | 1.00 | 52.34 | O |
| ATOM | 1445 | N | THR | C | 749 | 6.969 | 16.667 | 17.373 | 1.00 | 45.57 | N |
| ATOM | 1446 | CA | THR | C | 749 | 7.829 | 15.819 | 16.536 | 1.00 | 43.45 | C |
| ATOM | 1447 | C | THR | C | 749 | 8.935 | 16.651 | 15.910 | 1.00 | 43.21 | C |
| ATOM | 1448 | O | THR | C | 749 | 10.120 | 16.254 | 15.930 | 1.00 | 42.33 | O |
| ATOM | 1449 | CB | THR | C | 749 | 7.007 | 15.114 | 15.468 | 1.00 | 42.47 | C |
| ATOM | 1450 | CG1 | THR | C | 749 | 6.152 | 14.187 | 16.122 | 1.00 | 41.27 | O |
| ATOM | 1451 | CG2 | THR | C | 749 | 7.893 | 14.333 | 14.501 | 1.00 | 43.39 | C |
| ATOM | 1452 | N | ILE | C | 750 | 8.550 | 17.800 | 15.340 | 1.00 | 42.83 | N |
| ATOM | 1453 | CA | ILE | C | 750 | 9.531 | 18.722 | 14.778 | 1.00 | 42.04 | C |
| ATOM | 1454 | C | ILE | C | 750 | 10.605 | 19.045 | 15.843 | 1.00 | 44.22 | C |
| ATOM | 1455 | O | ILE | C | 750 | 11.817 | 19.154 | 15.529 | 1.00 | 44.46 | O |
| ATOM | 1456 | CB | ILE | C | 750 | 8.886 | 20.023 | 14.230 | 1.00 | 41.11 | C |
| ATOM | 1457 | CG1 | ILE | C | 750 | 8.005 | 19.758 | 12.992 | 1.00 | 40.11 | C |
| ATOM | 1458 | CG2 | ILE | C | 750 | 9.979 | 20.888 | 13.715 | 1.00 | 40.69 | C |
| ATOM | 1459 | CD1 | ILE | C | 750 | 6.770 | 20.719 | 12.877 | 1.00 | 34.46 | C |
| ATOM | 1460 | N | GLU | C | 751 | 10.179 | 19.240 | 17.083 | 1.00 | 45.06 | N |
| ATOM | 1461 | CA | GLU | C | 751 | 11.159 | 19.465 | 18.169 | 1.00 | 48.35 | C |
| ATOM | 1462 | C | GLU | C | 751 | 12.034 | 18.241 | 18.516 | 1.00 | 50.23 | C |
| ATOM | 1463 | O | GLU | C | 751 | 13.187 | 18.412 | 18.930 | 1.00 | 50.55 | O |
| ATOM | 1464 | CB | GLU | C | 751 | 10.512 | 20.029 | 19.420 | 1.00 | 47.77 | C |
| ATOM | 1465 | CG | GLU | C | 751 | 9.886 | 21.322 | 19.205 | 1.00 | 50.64 | C |
| ATOM | 1466 | CD | GLU | C | 751 | 10.647 | 22.485 | 19.791 | 1.00 | 59.97 | C |
| ATOM | 1467 | OE1 | GLU | C | 751 | 10.694 | 22.562 | 21.046 | 1.00 | 64.10 | O |
| ATOM | 1468 | OE2 | GLU | C | 751 | 11.140 | 23.355 | 19.019 | 1.00 | 61.76 | O |
| ATOM | 1469 | N | GLU | C | 752 | 11.526 | 17.022 | 18.329 | 1.00 | 52.09 | N |
| ATOM | 1470 | CA | GLU | C | 752 | 12.399 | 15.858 | 18.483 | 1.00 | 54.05 | C |
| ATOM | 1471 | C | GLU | C | 752 | 13.530 | 15.903 | 17.457 | 1.00 | 54.51 | C |
| ATOM | 1472 | O | GLU | C | 752 | 14.683 | 15.729 | 17.819 | 1.00 | 54.77 | O |
| ATOM | 1473 | CB | GLU | C | 752 | 11.632 | 14.541 | 18.367 | 1.00 | 54.38 | C |
| ATOM | 1474 | CG | GLU | C | 752 | 10.633 | 14.343 | 19.499 | 1.00 | 57.98 | C |
| ATOM | 1475 | CD | GLU | C | 752 | 10.710 | 12.982 | 20.189 | 1.00 | 60.87 | C |
| ATOM | 1476 | OE1 | GLU | C | 752 | 10.963 | 11.942 | 19.513 | 1.00 | 65.12 | O |
| ATOM | 1477 | OE2 | GLU | C | 752 | 10.500 | 12.953 | 21.429 | 1.00 | 62.35 | O |
| ATOM | 1478 | N | LEU | C | 753 | 13.181 | 16.139 | 16.192 | 1.00 | 54.42 | N |
| ATOM | 1479 | CA | LEU | C | 753 | 14.121 | 16.249 | 15.077 | 1.00 | 55.54 | C |
| ATOM | 1480 | C | LEU | C | 753 | 15.111 | 17.433 | 15.181 | 1.00 | 57.07 | C |
| ATOM | 1481 | O | LEU | C | 753 | 16.085 | 17.526 | 14.408 | 1.00 | 56.19 | O |
| ATOM | 1482 | CB | LEU | C | 753 | 13.356 | 16.327 | 13.764 | 1.00 | 54.30 | C |
| ATOM | 1483 | CG | LEU | C | 753 | 12.423 | 15.153 | 13.436 | 1.00 | 52.59 | C |
| ATOM | 1484 | CD1 | LEU | C | 753 | 11.800 | 15.391 | 12.084 | 1.00 | 46.31 | C |
| ATOM | 1485 | CD2 | LEU | C | 753 | 13.183 | 13.811 | 13.473 | 1.00 | 46.95 | C |
| ATOM | 1486 | N | ARG | C | 754 | 14.817 | 18.320 | 16.132 | 1.00 | 59.27 | N |
| ATOM | 1487 | CA | ARG | C | 754 | 15.742 | 19.345 | 16.684 | 1.00 | 61.26 | C |
| ATOM | 1488 | C | ARG | C | 754 | 15.730 | 20.691 | 15.935 | 1.00 | 61.92 | C |
| ATOM | 1489 | O | ARG | C | 754 | 14.899 | 21.583 | 16.221 | 1.00 | 61.67 | O |
| ATOM | 1490 | CB | ARG | C | 754 | 17.160 | 18.781 | 16.889 | 1.00 | 61.79 | C |
| ATOM | 1491 | CG | ARG | C | 754 | 17.451 | 18.259 | 18.344 | 1.00 | 63.51 | C |
| ATOM | 1492 | CD | ARG | C | 754 | 17.387 | 16.724 | 18.542 | 1.00 | 65.75 | C |
| ATOM | 1493 | NE | ARG | C | 754 | 18.097 | 15.990 | 17.499 | 1.00 | 68.11 | N |
| ATOM | 1494 | CZ | ARG | C | 754 | 19.424 | 15.867 | 17.447 | 1.00 | 72.30 | C |
| ATOM | 1495 | NH1 | ARG | C | 754 | 20.186 | 16.415 | 18.399 | 1.00 | 72.65 | N |
| ATOM | 1496 | NH2 | ARG | C | 754 | 19.999 | 15.201 | 16.447 | 1.00 | 70.84 | N |
| TER | 1497 |  | ARG | C | 754 |  |  |  |  |  |  |
| ATOM | 1498 | N | GLY | D | −1 | −5.280 | 24.798 | 7.276 | 1.00 | 49.90 | N |
| ATOM | 1499 | CA | GLY | D | −1 | −4.617 | 26.147 | 7.074 | 1.00 | 49.78 | C |
| ATOM | 1500 | C | GLY | D | −1 | −3.396 | 26.277 | 7.985 | 1.00 | 49.82 | C |
| ATOM | 1501 | O | GLY | D | −1 | −2.254 | 26.391 | 7.538 | 1.00 | 48.43 | O |
| ATOM | 1502 | N | SER | D | 0 | −3.676 | 26.250 | 9.275 | 1.00 | 50.25 | N |
| ATOM | 1503 | CA | SER | D | 0 | −2.680 | 26.188 | 10.323 | 1.00 | 49.93 | C |
| ATOM | 1504 | C | SER | D | 0 | −2.169 | 24.755 | 10.450 | 1.00 | 49.62 | C |
| ATOM | 1505 | O | SER | D | 0 | −1.034 | 24.524 | 10.879 | 1.00 | 49.78 | O |

TABLE 2a-continued

Data of atomic coordinates for accession code 2ZTT

| ATOM | 1506 | CB | SER | D | 0 | −3.284 | 26.791 | 11.613 | 1.00 | 50.06 | C |
|---|---|---|---|---|---|---|---|---|---|---|---|
| ATOM | 1507 | OG | SER | D | 0 | −3.856 | 25.850 | 12.491 | 1.00 | 50.28 | O |
| HETATM | 1508 | N | MSE | D | 1 | −3.006 | 23.797 | 10.049 | 1.00 | 50.03 | N |
| HETATM | 1509 | CA | MSE | D | 1 | −2.579 | 22.434 | 9.751 | 1.00 | 50.09 | C |
| HETATM | 1510 | C | MSE | D | 1 | −1.598 | 22.330 | 8.603 | 1.00 | 49.21 | C |
| HETATM | 1511 | O | MSE | D | 1 | −0.490 | 21.759 | 8.764 | 1.00 | 48.78 | O |
| HETATM | 1512 | CB | MSE | D | 1 | −3.753 | 21.585 | 9.349 | 1.00 | 51.90 | C |
| HETATM | 1513 | CG | MSE | D | 1 | −4.286 | 20.771 | 10.445 | 1.00 | 55.14 | C |
| HETATM | 1514 | SE | MSE | D | 1 | −3.025 | 19.469 | 11.150 | 1.00 | 65.76 | SE |
| HETATM | 1515 | CE | MSE | D | 1 | −4.542 | 18.285 | 11.517 | 1.00 | 58.82 | C |
| ATOM | 1516 | N | GLU | D | 2 | −2.032 | 22.846 | 7.443 | 1.00 | 47.71 | N |
| ATOM | 1517 | CA | GLU | D | 2 | −1.277 | 22.844 | 6.194 | 1.00 | 47.34 | C |
| ATOM | 1518 | C | GLU | D | 2 | 0.146 | 23.241 | 6.503 | 1.00 | 43.96 | C |
| ATOM | 1519 | O | GLU | D | 2 | 1.067 | 22.503 | 6.208 | 1.00 | 44.29 | O |
| ATOM | 1520 | CB | GLU | D | 2 | −1.917 | 23.782 | 5.106 | 1.00 | 47.31 | C |
| ATOM | 1521 | CG | GLU | D | 2 | −3.187 | 23.229 | 4.366 | 1.00 | 50.74 | C |
| ATOM | 1522 | CD | GLU | D | 2 | −3.941 | 24.278 | 3.471 | 1.00 | 52.54 | C |
| ATOM | 1523 | OE1 | GLU | D | 2 | −5.039 | 23.963 | 2.934 | 1.00 | 61.33 | O |
| ATOM | 1524 | OE2 | GLU | D | 2 | −3.470 | 25.426 | 3.285 | 1.00 | 57.30 | O |
| ATOM | 1525 | N | ARG | D | 3 | 0.336 | 24.381 | 7.156 | 1.00 | 41.90 | N |
| ATOM | 1526 | CA | ARG | D | 3 | 1.688 | 24.916 | 7.344 | 1.00 | 38.16 | C |
| ATOM | 1527 | C | ARG | D | 3 | 2.580 | 24.127 | 8.299 | 1.00 | 38.15 | C |
| ATOM | 1528 | O | ARG | D | 3 | 3.820 | 24.187 | 8.199 | 1.00 | 35.54 | O |
| ATOM | 1529 | CB | ARG | D | 3 | 1.603 | 26.381 | 7.840 | 1.00 | 38.86 | C |
| ATOM | 1530 | CG | ARG | D | 3 | 1.739 | 26.565 | 9.417 | 1.00 | 38.69 | C |
| ATOM | 1531 | CD | ARG | D | 3 | 1.568 | 28.010 | 9.870 | 1.00 | 36.17 | C |
| ATOM | 1532 | NE | ARG | D | 3 | 1.012 | 28.087 | 11.237 | 1.00 | 33.74 | N |
| ATOM | 1533 | CZ | ARG | D | 3 | 0.651 | 29.239 | 11.804 | 1.00 | 34.46 | C |
| ATOM | 1534 | NH1 | ARG | D | 3 | 0.178 | 29.281 | 13.046 | 1.00 | 30.89 | N |
| ATOM | 1535 | NH2 | ARG | D | 3 | 0.806 | 30.375 | 11.129 | 1.00 | 35.90 | N |
| ATOM | 1536 | N | ILE | D | 4 | 1.991 | 23.465 | 9.285 | 1.00 | 37.77 | N |
| ATOM | 1537 | CA | ILE | D | 4 | 2.861 | 22.739 | 10.277 | 1.00 | 36.05 | C |
| ATOM | 1538 | C | ILE | D | 4 | 3.338 | 21.412 | 9.643 | 1.00 | 36.79 | C |
| ATOM | 1539 | O | ILE | D | 4 | 4.508 | 20.971 | 9.790 | 1.00 | 36.04 | O |
| ATOM | 1540 | CB | ILE | D | 4 | 2.186 | 22.579 | 11.707 | 1.00 | 35.78 | C |
| ATOM | 1541 | CG1 | ILE | D | 4 | 3.266 | 22.190 | 12.792 | 1.00 | 36.24 | C |
| ATOM | 1542 | CG2 | ILE | D | 4 | 1.117 | 21.497 | 11.764 | 1.00 | 31.65 | C |
| ATOM | 1543 | CD1 | ILE | D | 4 | 4.295 | 23.375 | 13.047 | 1.00 | 27.74 | C |
| ATOM | 1544 | N | LYS | D | 5 | 2.446 | 20.772 | 8.902 | 1.00 | 33.68 | N |
| ATOM | 1545 | CA | LYS | D | 5 | 2.816 | 19.610 | 8.081 | 1.00 | 35.52 | C |
| ATOM | 1546 | C | LYS | D | 5 | 3.871 | 19.928 | 7.076 | 1.00 | 37.28 | C |
| ATOM | 1547 | O | LYS | D | 5 | 4.885 | 19.183 | 6.958 | 1.00 | 39.06 | O |
| ATOM | 1548 | CB | LYS | D | 5 | 1.578 | 18.978 | 7.433 | 1.00 | 35.72 | C |
| ATOM | 1549 | CG | LYS | D | 5 | 0.561 | 18.70 | 8.499 | 1.00 | 36.0 | C |
| ATOM | 1550 | CD | LYS | D | 5 | −0.814 | 18.359 | 7.863 | 1.00 | 32.13 | C |
| ATOM | 1551 | CE | LYS | D | 5 | −0.801 | 16.977 | 7.569 | 1.00 | 26.89 | C |
| ATOM | 1552 | NZ | LYS | D | 5 | −1.484 | 16.365 | 8.687 | 1.00 | 26.20 | N |
| ATOM | 1553 | N | GLU | D | 6 | 3.757 | 21.052 | 6.377 | 1.00 | 38.21 | N |
| ATOM | 1554 | CA | GLU | D | 6 | 4.905 | 21.398 | 5.504 | 1.00 | 39.91 | C |
| ATOM | 1555 | C | GLU | D | 6 | 6.186 | 21.522 | 6.305 | 1.00 | 38.59 | C |
| ATOM | 1556 | O | GLU | D | 6 | 7.254 | 21.185 | 5.815 | 1.00 | 40.11 | O |
| ATOM | 1557 | CB | GLU | D | 6 | 4.698 | 22.685 | 4.689 | 1.00 | 39.21 | C |
| ATOM | 1558 | CG | GLU | D | 6 | 3.337 | 22.774 | 4.008 | 1.00 | 44.02 | C |
| ATOM | 1559 | CD | GLU | D | 6 | 3.049 | 24.114 | 3.300 | 1.00 | 45.09 | C |
| ATOM | 1560 | OE1 | GLU | D | 6 | 1.838 | 24.445 | 3.130 | 1.00 | 53.74 | O |
| ATOM | 1561 | OE2 | GLU | D | 6 | 3.987 | 24.821 | 2.880 | 1.00 | 50.39 | O |
| ATOM | 1562 | N | LEU | D | 7 | 6.108 | 22.054 | 7.505 | 1.00 | 37.55 | N |
| ATOM | 1563 | CA | LEU | D | 7 | 7.308 | 22.194 | 8.333 | 1.00 | 38.07 | C |
| ATOM | 1564 | C | LEU | D | 7 | 7.967 | 20.814 | 8.574 | 1.00 | 37.63 | C |
| ATOM | 1565 | O | LEU | D | 7 | 9.137 | 20.615 | 8.227 | 1.00 | 41.44 | O |
| ATOM | 1566 | CB | LEU | D | 7 | 6.982 | 22.968 | 9.631 | 1.00 | 36.07 | C |
| ATOM | 1567 | CG | LEU | D | 7 | 8.162 | 23.737 | 10.315 | 1.00 | 35.71 | C |
| ATOM | 1568 | CD1 | LEU | D | 7 | 7.648 | 24.606 | 11.426 | 1.00 | 26.41 | C |
| ATOM | 1569 | CD2 | LEU | D | 7 | 8.997 | 22.788 | 10.929 | 1.00 | 38.34 | C |
| ATOM | 1570 | N | ARG | D | 8 | 7.220 | 19.902 | 9.184 | 1.00 | 38.44 | N |
| ATOM | 1571 | CA | ARG | D | 8 | 7.546 | 18.500 | 9.457 | 1.00 | 37.43 | C |
| ATOM | 1572 | C | ARG | D | 8 | 8.050 | 17.799 | 8.180 | 1.00 | 38.19 | C |
| ATOM | 1573 | O | ARG | D | 8 | 9.004 | 17.020 | 8.223 | 1.00 | 34.64 | O |
| ATOM | 1574 | CB | ARG | D | 8 | 6.242 | 17.822 | 9.961 | 1.00 | 39.65 | C |
| ATOM | 1575 | CG | ARG | D | 8 | 6.137 | 16.244 | 10.026 | 1.00 | 40.36 | C |
| ATOM | 1576 | CD | ARG | D | 8 | 5.733 | 15.563 | 8.665 | 1.00 | 42.76 | C |
| ATOM | 1577 | NE | ARG | D | 8 | 4.322 | 15.703 | 8.221 | 1.00 | 43.36 | N |
| ATOM | 1578 | CZ | ARG | D | 8 | 3.287 | 15.237 | 8.900 | 1.00 | 45.90 | C |
| ATOM | 1579 | NH1 | ARG | D | 8 | 3.491 | 14.643 | 10.053 | 1.00 | 45.15 | N |
| ATOM | 1580 | NH2 | ARG | D | 8 | 2.027 | 15.358 | 8.440 | 1.00 | 48.75 | N |
| ATOM | 1581 | N | ASN | D | 9 | 7.367 | 18.040 | 7.057 | 1.00 | 35.34 | N |
| ATOM | 1582 | CA | ASN | D | 9 | 7.841 | 17.544 | 5.748 | 1.00 | 37.11 | C |
| ATOM | 1583 | C | ASN | D | 9 | 9.246 | 18.062 | 5.363 | 1.00 | 36.26 | C |

TABLE 2a-continued

Data of atomic coordinates for accession code 2ZTT

| ATOM | 1584 | O | ASN | D | 9 | 10.161 | 17.281 | 5.012 | 1.00 | 36.97 | O |
|---|---|---|---|---|---|---|---|---|---|---|---|
| ATOM | 1585 | CB | ASN | D | 9 | 6.852 | 17.930 | 4.601 | 1.00 | 37.93 | C |
| ATOM | 1586 | CG | ASN | D | 9 | 5.409 | 17.354 | 4.762 | 1.00 | 38.55 | C |
| ATOM | 1587 | OD1 | ASN | D | 9 | 5.073 | 16.601 | 5.687 | 1.00 | 38.01 | O |
| ATOM | 1588 | ND2 | ASN | D | 9 | 4.521 | 17.767 | 3.821 | 1.00 | 42.10 | N |
| ATOM | 1589 | N | LEU | D | 10 | 9.438 | 19.364 | 5.445 | 1.00 | 35.49 | N |
| ATOM | 1590 | CA | LEU | D | 10 | 10.752 | 19.956 | 5.204 | 1.00 | 37.0 | C |
| ATOM | 1591 | C | LEU | D | 10 | 11.861 | 19.512 | 6.208 | 1.00 | 37.09 | C |
| ATOM | 1592 | O | LEU | D | 10 | 13.026 | 19.481 | 5.850 | 1.00 | 36.40 | O |
| ATOM | 1593 | CB | LEU | D | 10 | 10.643 | 21.481 | 5.169 | 1.00 | 36.79 | C |
| ATOM | 1594 | CG | LEU | D | 10 | 10.622 | 22.184 | 3.800 | 1.00 | 39.02 | C |
| ATOM | 1595 | CD1 | LEU | D | 10 | 10.029 | 21.326 | 2.678 | 1.00 | 39.38 | C |
| ATOM | 1596 | CD2 | LEU | D | 10 | 9.972 | 23.556 | 3.890 | 1.00 | 37.69 | C |
| HETATM | 1597 | N | MSE | D | 11 | 11.463 | 19.145 | 7.423 | 1.00 | 39.14 | N |
| HETATM | 1598 | CA | MSE | D | 11 | 12.377 | 18.671 | 8.497 | 1.00 | 38.26 | C |
| HETATM | 1599 | C | MSE | D | 11 | 12.715 | 17.163 | 8.431 | 1.00 | 40.80 | C |
| HETATM | 160 | O | MSE | D | 11 | 13.608 | 16.681 | 9.182 | 1.00 | 39.31 | O |
| HETATM | 1601 | CB | MSE | D | 11 | 11.756 | 18.963 | 9.853 | 1.00 | 39.63 | C |
| HETATM | 1602 | CG | MSE | D | 11 | 11.828 | 20.387 | 10.323 | 1.00 | 37.84 | C |
| HETATM | 1603 | SE | MSE | D | 11 | 13.559 | 21.070 | 10.831 | 1.00 | 51.94 | SE |
| HETATM | 1604 | CE | MSE | D | 11 | 13.753 | 20.105 | 12.471 | 1.00 | 28.24 | C |
| ATOM | 1605 | N | SER | D | 12 | 12.025 | 16.421 | 7.532 | 1.00 | 41.21 | N |
| ATOM | 1606 | CA | SER | D | 12 | 12.334 | 15.007 | 7.262 | 1.00 | 41.58 | C |
| ATOM | 1607 | C | SER | D | 12 | 13.293 | 14.779 | 6.112 | 1.00 | 41.11 | C |
| ATOM | 1608 | O | SER | D | 12 | 13.489 | 13.645 | 5.692 | 1.00 | 40.53 | O |
| ATOM | 1609 | CB | SER | D | 12 | 11.052 | 14.260 | 6.956 | 1.00 | 40.95 | C |
| ATOM | 1610 | OG | SER | D | 12 | 10.615 | 14.658 | 5.662 | 1.00 | 47.73 | O |
| ATOM | 1611 | N | GLN | D | 13 | 13.848 | 15.874 | 5.589 | 1.00 | 42.15 | N |
| ATOM | 1612 | CA | GLN | D | 13 | 14.738 | 15.917 | 4.446 | 1.00 | 43.53 | C |
| ATOM | 1613 | C | GLN | D | 13 | 15.976 | 16.681 | 4.878 | 1.00 | 44.31 | C |
| ATOM | 1614 | O | GLN | D | 13 | 15.842 | 17.803 | 5.403 | 1.00 | 42.99 | O |
| ATOM | 1615 | CB | GLN | D | 13 | 14.101 | 16.742 | 3.331 | 1.00 | 43.58 | C |
| ATOM | 1616 | CG | GLN | D | 13 | 12.786 | 16.182 | 2.765 | 1.00 | 46.05 | C |
| ATOM | 1617 | CD | GLN | D | 13 | 12.955 | 14.818 | 2.200 | 1.00 | 44.82 | C |
| ATOM | 1618 | OE1 | GLN | D | 13 | 13.608 | 14.641 | 1.180 | 1.00 | 48.35 | O |
| ATOM | 1619 | NE2 | GLN | D | 13 | 12.383 | 13.823 | 2.878 | 1.00 | 46.91 | N |
| ATOM | 1620 | N | SER | D | 14 | 17.160 | 16.118 | 4.627 | 1.00 | 46.58 | N |
| ATOM | 1621 | CA | SER | D | 14 | 18.418 | 16.667 | 5.172 | 1.00 | 49.53 | C |
| ATOM | 1622 | C | SER | D | 14 | 18.812 | 18.062 | 4.696 | 1.00 | 50.58 | C |
| ATOM | 1623 | O | SER | D | 14 | 19.199 | 18.902 | 5.513 | 1.00 | 52.19 | O |
| ATOM | 1624 | CB | SER | D | 14 | 19.598 | 15.689 | 4.997 | 1.00 | 50.99 | C |
| ATOM | 1625 | OG | SER | D | 14 | 19.893 | 15.533 | 3.615 | 1.00 | 55.80 | O |
| ATOM | 1626 | N | ARG | D | 15 | 18.721 | 18.311 | 3.390 | 1.00 | 51.81 | N |
| ATOM | 1627 | CA | ARG | D | 15 | 19.040 | 19.608 | 2.765 | 1.00 | 52.06 | C |
| ATOM | 1628 | C | ARG | D | 15 | 18.371 | 20.797 | 3.505 | 1.00 | 51.30 | C |
| ATOM | 1629 | O | ARG | D | 15 | 19.043 | 21.717 | 3.939 | 1.00 | 51.42 | O |
| ATOM | 1630 | CB | ARG | D | 15 | 18.515 | 19.538 | 1.323 | 1.00 | 53.15 | C |
| ATOM | 1631 | CG | ARG | D | 15 | 19.255 | 20.346 | 0.259 | 1.00 | 56.76 | C |
| ATOM | 1632 | CD | ARG | D | 15 | 20.439 | 19.578 | −0.386 | 1.00 | 57.87 | C |
| ATOM | 1633 | NE | ARG | D | 15 | 21.210 | 20.403 | −1.329 | 1.00 | 60.71 | N |
| ATOM | 1634 | CZ | ARG | D | 15 | 22.472 | 20.168 | −1.719 | 1.00 | 60.47 | C |
| ATOM | 1635 | NH1 | ARG | D | 15 | 23.160 | 19.132 | −1.232 | 1.00 | 59.56 | N |
| ATOM | 1636 | NH2 | ARG | D | 15 | 23.056 | 20.988 | −2.600 | 1.00 | 62.15 | N |
| ATOM | 1637 | N | THR | D | 16 | 17.042 | 20.753 | 3.637 | 1.00 | 48.69 | N |
| ATOM | 1638 | CA | THR | D | 16 | 16.267 | 21.766 | 4.330 | 1.00 | 47.47 | C |
| ATOM | 1639 | C | THR | D | 16 | 16.256 | 21.617 | 5.868 | 1.00 | 47.63 | C |
| ATOM | 1640 | O | THR | D | 16 | 16.188 | 22.607 | 6.547 | 1.00 | 46.96 | O |
| ATOM | 1641 | CB | THR | D | 16 | 14.835 | 21.718 | 3.886 | 1.00 | 46.21 | C |
| ATOM | 1642 | OG1 | THR | D | 16 | 14.411 | 20.366 | 3.986 | 1.00 | 44.04 | O |
| ATOM | 1643 | CG2 | THR | D | 16 | 14.675 | 22.242 | 2.409 | 1.00 | 46.79 | C |
| ATOM | 1644 | N | ARG | D | 17 | 16.289 | 20.398 | 6.394 | 1.00 | 48.14 | N |
| ATOM | 1645 | CA | ARG | D | 17 | 16.394 | 20.214 | 7.834 | 1.00 | 50.83 | C |
| ATOM | 1646 | C | ARG | D | 17 | 17.510 | 21.145 | 8.297 | 1.00 | 51.11 | C |
| ATOM | 1647 | O | ARG | D | 17 | 17.350 | 21.839 | 9.261 | 1.00 | 51.92 | O |
| ATOM | 1648 | CB | ARG | D | 17 | 16.769 | 18.791 | 8.252 | 1.00 | 50.08 | C |
| ATOM | 1649 | CG | ARG | D | 17 | 16.448 | 18.538 | 9.752 | 1.00 | 52.45 | C |
| ATOM | 1650 | CD | ARG | D | 17 | 17.290 | 17.471 | 10.488 | 1.00 | 54.18 | C |
| ATOM | 1651 | NE | ARG | D | 17 | 16.816 | 16.069 | 10.372 | 1.00 | 61.05 | N |
| ATOM | 1652 | CZ | ARG | D | 17 | 16.845 | 15.147 | 11.362 | 1.00 | 61.25 | C |
| ATOM | 1653 | NH1 | ARG | D | 17 | 17.286 | 15.444 | 12.593 | 1.00 | 58.28 | N |
| ATOM | 1654 | NH2 | ARG | D | 17 | 16.404 | 13.903 | 11.129 | 1.00 | 61.74 | N |
| ATOM | 1655 | N | GLU | D | 18 | 18.616 | 21.153 | 7.553 | 1.00 | 51.13 | N |
| ATOM | 1656 | CA | GLU | D | 18 | 19.843 | 21.814 | 7.903 | 1.00 | 51.38 | C |
| ATOM | 1657 | C | GLU | D | 18 | 19.729 | 23.324 | 7.859 | 1.00 | 49.17 | C |
| ATOM | 1658 | O | GLU | D | 18 | 20.269 | 24.033 | 8.737 | 1.00 | 49.90 | O |
| ATOM | 1659 | CB | GLU | D | 18 | 20.942 | 21.310 | 6.947 | 1.00 | 52.71 | C |
| ATOM | 1660 | CG | GLU | D | 18 | 22.155 | 22.218 | 6.842 | 1.00 | 58.37 | C |
| ATOM | 1661 | CD | GLU | D | 18 | 23.353 | 21.682 | 7.592 | 1.00 | 65.83 | C |

TABLE 2a-continued

Data of atomic coordinates for accession code 2ZTT

| ATOM | 1662 | OE1 | GLU | D | 18 | 23.191 | 20.705 | 8.367 | 1.00 | 69.17 | O |
|---|---|---|---|---|---|---|---|---|---|---|---|
| ATOM | 1663 | OE2 | GLU | D | 18 | 24.460 | 22.250 | 7.413 | 1.00 | 68.21 | O |
| ATOM | 1664 | N | ILE | D | 19 | 19.031 | 23.823 | 6.845 | 1.00 | 46.48 | N |
| ATOM | 1665 | CA | ILE | D | 19 | 18.761 | 25.248 | 6.738 | 1.00 | 44.30 | C |
| ATOM | 1666 | C | ILE | D | 19 | 17.841 | 25.766 | 7.858 | 1.00 | 44.43 | C |
| ATOM | 1667 | O | ILE | D | 19 | 17.992 | 26.894 | 8.297 | 1.00 | 42.54 | O |
| ATOM | 1668 | CB | ILE | D | 19 | 18.132 | 25.627 | 5.377 | 1.00 | 43.97 | C |
| ATOM | 1669 | CG1 | ILE | D | 19 | 19.096 | 25.372 | 4.200 | 1.00 | 43.08 | C |
| ATOM | 1670 | CG2 | ILE | D | 19 | 17.754 | 27.047 | 5.360 | 1.00 | 40.79 | C |
| ATOM | 1671 | CD1 | ILE | D | 19 | 18.360 | 25.497 | 2.862 | 1.00 | 43.53 | C |
| ATOM | 1672 | N | LEU | D | 20 | 16.853 | 24.957 | 8.256 | 1.00 | 43.91 | N |
| ATOM | 1673 | CA | LEU | D | 20 | 15.883 | 25.335 | 9.275 | 1.00 | 43.22 | C |
| ATOM | 1674 | C | LEU | D | 20 | 16.474 | 25.337 | 10.701 | 1.00 | 43.45 | C |
| ATOM | 1675 | O | LEU | D | 20 | 16.086 | 26.150 | 11.540 | 1.00 | 43.63 | O |
| ATOM | 1676 | CB | LEU | D | 20 | 14.698 | 24.383 | 9.182 | 1.00 | 43.69 | C |
| ATOM | 1677 | CG | LEU | D | 20 | 13.404 | 24.812 | 8.464 | 1.00 | 44.45 | C |
| ATOM | 1678 | CD1 | LEU | D | 20 | 13.615 | 25.953 | 7.548 | 1.00 | 41.07 | C |
| ATOM | 1679 | CD2 | LEU | D | 20 | 12.638 | 23.646 | 7.742 | 1.00 | 44.20 | C |
| ATOM | 1680 | N | THR | D | 21 | 17.403 | 24.421 | 10.977 | 1.00 | 42.38 | N |
| ATOM | 1681 | CA | THR | D | 21 | 17.969 | 24.327 | 12.316 | 1.00 | 43.14 | C |
| ATOM | 1682 | C | THR | D | 21 | 19.195 | 25.226 | 12.522 | 1.00 | 42.48 | C |
| ATOM | 1683 | O | THR | D | 21 | 19.412 | 25.665 | 13.633 | 1.00 | 42.44 | O |
| ATOM | 1684 | CB | THR | D | 21 | 18.290 | 22.892 | 12.703 | 1.00 | 43.36 | C |
| ATOM | 1685 | OG1 | THR | D | 21 | 19.317 | 22.402 | 11.847 | 1.00 | 46.92 | O |
| ATOM | 1686 | CG2 | THR | D | 21 | 17.085 | 22.025 | 12.543 | 1.00 | 44.33 | C |
| ATOM | 1687 | N | LYS | D | 22 | 19.931 | 25.562 | 11.455 | 1.00 | 43.11 | N |
| ATOM | 1688 | CA | LYS | D | 22 | 21.103 | 26.430 | 11.563 | 1.00 | 43.78 | C |
| ATOM | 1689 | C | LYS | D | 22 | 20.929 | 27.862 | 11.087 | 1.00 | 43.91 | C |
| ATOM | 1690 | O | LYS | D | 22 | 21.770 | 28.679 | 11.395 | 1.00 | 43.40 | O |
| ATOM | 1691 | CB | LYS | D | 22 | 22.339 | 25.827 | 10.860 | 1.00 | 43.35 | C |
| ATOM | 1692 | CG | LYS | D | 22 | 22.675 | 24.394 | 11.174 | 1.00 | 47.10 | C |
| ATOM | 1693 | CD | LYS | D | 22 | 23.025 | 24.160 | 12.622 | 1.00 | 53.82 | C |
| ATOM | 1694 | CE | LYS | D | 22 | 24.517 | 24.558 | 12.930 | 1.00 | 57.10 | C |
| ATOM | 1695 | NZ | LYS | D | 22 | 24.954 | 25.946 | 12.456 | 1.00 | 55.72 | N |
| ATOM | 1696 | N | THR | D | 23 | 19.873 | 28.206 | 10.332 | 1.00 | 44.09 | N |
| ATOM | 1697 | CA | THR | D | 23 | 19.759 | 29.605 | 9.883 | 1.00 | 43.74 | C |
| ATOM | 1698 | C | THR | D | 23 | 18.942 | 30.316 | 10.939 | 1.00 | 44.42 | C |
| ATOM | 1699 | O | THR | D | 23 | 17.857 | 29.852 | 11.308 | 1.00 | 44.68 | O |
| ATOM | 1700 | CB | THR | D | 23 | 19.115 | 29.675 | 8.498 | 1.00 | 43.66 | C |
| ATOM | 1701 | OG1 | THR | D | 23 | 19.900 | 28.869 | 7.631 | 1.00 | 46.68 | O |
| ATOM | 1702 | CG2 | THR | D | 23 | 19.062 | 31.042 | 7.911 | 1.00 | 41.90 | C |
| ATOM | 1703 | N | THR | D | 24 | 19.443 | 31.441 | 11.452 | 1.00 | 44.36 | N |
| ATOM | 1704 | CA | THR | D | 24 | 18.682 | 32.134 | 12.468 | 1.00 | 42.86 | C |
| ATOM | 1705 | C | THR | D | 24 | 17.856 | 33.105 | 11.699 | 1.00 | 42.12 | C |
| ATOM | 1706 | O | THR | D | 24 | 18.243 | 33.482 | 10.586 | 1.00 | 40.98 | O |
| ATOM | 1707 | CB | THR | D | 24 | 19.544 | 32.927 | 13.442 | 1.00 | 42.92 | C |
| ATOM | 1708 | OG1 | THR | D | 24 | 20.205 | 33.950 | 12.727 | 1.00 | 40.02 | O |
| ATOM | 1709 | CG2 | THR | D | 24 | 20.585 | 32.006 | 14.201 | 1.00 | 45.16 | C |
| ATOM | 1710 | N | VAL | D | 25 | 16.757 | 33.557 | 12.315 | 1.00 | 43.28 | N |
| ATOM | 1711 | CA | VAL | D | 25 | 15.838 | 34.516 | 11.647 | 1.00 | 43.96 | C |
| ATOM | 1712 | C | VAL | D | 25 | 16.592 | 35.747 | 11.121 | 1.00 | 44.44 | C |
| ATOM | 1713 | O | VAL | D | 25 | 16.411 | 36.119 | 9.987 | 1.00 | 43.44 | O |
| ATOM | 1714 | CB | VAL | D | 25 | 14.644 | 34.913 | 12.551 | 1.00 | 43.84 | C |
| ATOM | 1715 | CG1 | VAL | D | 25 | 13.901 | 36.107 | 11.972 | 1.00 | 42.77 | C |
| ATOM | 1716 | CG2 | VAL | D | 25 | 13.704 | 33.770 | 12.715 | 1.00 | 44.10 | C |
| ATOM | 1717 | N | ASP | D | 26 | 17.449 | 36.357 | 11.948 | 1.00 | 46.21 | N |
| ATOM | 1718 | CA | ASP | D | 26 | 18.239 | 37.525 | 11.534 | 1.00 | 47.92 | C |
| ATOM | 1719 | C | ASP | D | 26 | 18.951 | 37.301 | 10.203 | 1.00 | 47.90 | C |
| ATOM | 1720 | O | ASP | D | 26 | 18.915 | 38.171 | 9.324 | 1.00 | 48.0 | O |
| ATOM | 1721 | CB | ASP | D | 26 | 19.303 | 37.881 | 12.611 | 1.00 | 50.36 | C |
| ATOM | 1722 | CG | ASP | D | 26 | 18.708 | 38.620 | 13.840 | 1.00 | 52.39 | C |
| ATOM | 1723 | OD1 | ASP | D | 26 | 17.839 | 39.527 | 13.661 | 1.00 | 54.37 | O |
| ATOM | 1724 | OD2 | ASP | D | 26 | 19.125 | 38.266 | 14.984 | 1.00 | 59.60 | O |
| ATOM | 1725 | N | HIS | D | 27 | 19.565 | 36.123 | 10.048 | 1.00 | 47.57 | N |
| ATOM | 1726 | CA | HIS | D | 27 | 20.450 | 35.840 | 8.905 | 1.00 | 47.18 | C |
| ATOM | 1727 | C | HIS | D | 27 | 19.689 | 35.405 | 7.710 | 1.00 | 48.10 | C |
| ATOM | 1728 | O | HIS | D | 27 | 20.165 | 35.559 | 6.611 | 1.00 | 48.23 | O |
| ATOM | 1729 | CB | HIS | D | 27 | 21.383 | 34.697 | 9.225 | 1.00 | 46.66 | C |
| ATOM | 1730 | CG | HIS | D | 27 | 22.446 | 35.047 | 10.203 | 1.00 | 44.72 | C |
| ATOM | 1731 | ND1 | HIS | D | 27 | 23.483 | 34.196 | 10.484 | 1.00 | 43.36 | N |
| ATOM | 1732 | CD2 | HIS | D | 27 | 22.667 | 36.174 | 10.917 | 1.00 | 43.50 | C |
| ATOM | 1733 | CE1 | HIS | D | 27 | 24.284 | 34.773 | 11.365 | 1.00 | 47.57 | C |
| ATOM | 1734 | NE2 | HIS | D | 27 | 23.823 | 35.983 | 11.621 | 1.00 | 44.42 | N |
| HETATM | 1735 | N | MSE | D | 28 | 18.527 | 34.813 | 7.903 | 1.00 | 49.70 | N |
| HETATM | 1736 | CA | MSE | D | 28 | 17.758 | 34.445 | 6.746 | 1.00 | 51.30 | C |
| HETATM | 1737 | C | MSE | D | 28 | 17.421 | 35.726 | 6.040 | 1.00 | 50.75 | C |
| HETATM | 1738 | O | MSE | D | 28 | 17.316 | 35.761 | 4.822 | 1.00 | 50.25 | O |
| HETATM | 1739 | CB | MSE | D | 28 | 16.467 | 33.722 | 7.123 | 1.00 | 53.91 | C |

TABLE 2a-continued

Data of atomic coordinates for accession code 2ZTT

| HETATM | 1740 | CG | MSE | D | 28 | 15.693 | 33.167 | 5.876 | 1.00 | 57.56 | C |
|---|---|---|---|---|---|---|---|---|---|---|---|
| HETATM | 1741 | SE | MSE | D | 28 | 16.770 | 31.976 | 4.660 | 1.00 | 76.18 | SE |
| HETATM | 1742 | CE | MSE | D | 28 | 17.129 | 33.058 | 3.086 | 1.00 | 63.68 | C |
| ATOM | 1743 | N | ALA | D | 29 | 17.271 | 36.800 | 6.808 | 1.00 | 50.53 | N |
| ATOM | 1744 | CA | ALA | D | 29 | 16.733 | 38.016 | 6.217 | 1.00 | 50.49 | C |
| ATOM | 1745 | C | ALA | D | 29 | 17.705 | 38.500 | 5.152 | 1.00 | 50.52 | C |
| ATOM | 1746 | O | ALA | D | 29 | 17.303 | 38.931 | 4.041 | 1.00 | 50.12 | O |
| ATOM | 1747 | CB | ALA | D | 29 | 16.444 | 39.063 | 7.262 | 1.00 | 49.78 | C |
| ATOM | 1748 | N | ILE | D | 30 | 18.981 | 38.310 | 5.466 | 1.00 | 48.96 | N |
| ATOM | 1749 | CA | ILE | D | 30 | 20.071 | 38.762 | 4.605 | 1.00 | 48.32 | C |
| ATOM | 1750 | C | ILE | D | 30 | 20.538 | 37.737 | 3.637 | 1.00 | 48.29 | C |
| ATOM | 1751 | O | ILE | D | 30 | 21.021 | 38.108 | 2.570 | 1.00 | 47.34 | O |
| ATOM | 1752 | CB | ILE | D | 30 | 21.294 | 39.246 | 5.405 | 1.00 | 47.24 | C |
| ATOM | 1753 | CG1 | ILE | D | 30 | 22.581 | 38.678 | 4.817 | 1.00 | 46.84 | C |
| ATOM | 1754 | CG2 | ILE | D | 30 | 21.210 | 38.774 | 6.817 | 1.00 | 49.71 | C |
| ATOM | 1755 | CD1 | ILE | D | 30 | 23.708 | 39.649 | 4.810 | 1.00 | 45.88 | C |
| ATOM | 1756 | N | ILE | D | 31 | 20.432 | 36.455 | 4.014 | 1.00 | 48.88 | N |
| ATOM | 1757 | CA | ILE | D | 31 | 20.891 | 35.381 | 3.148 | 1.00 | 49.52 | C |
| ATOM | 1758 | C | ILE | D | 31 | 20.082 | 35.360 | 1.867 | 1.00 | 50.81 | C |
| ATOM | 1759 | O | ILE | D | 31 | 20.644 | 35.049 | 0.849 | 1.00 | 50.93 | O |
| ATOM | 1760 | CB | ILE | D | 31 | 20.871 | 34.015 | 3.802 | 1.00 | 48.88 | C |
| ATOM | 1761 | CG1 | ILE | D | 31 | 22.100 | 33.816 | 4.685 | 1.00 | 47.41 | C |
| ATOM | 1762 | CG2 | ILE | D | 31 | 20.933 | 32.954 | 2.750 | 1.00 | 49.68 | C |
| ATOM | 1763 | CD1 | ILE | D | 31 | 22.042 | 32.505 | 5.476 | 1.00 | 46.04 | C |
| ATOM | 1764 | N | LYS | D | 32 | 18.797 | 35.744 | 1.941 | 1.00 | 53.05 | N |
| ATOM | 1765 | CA | LYS | D | 32 | 17.845 | 35.772 | 0.825 | 1.00 | 54.95 | C |
| ATOM | 1766 | C | LYS | D | 32 | 17.888 | 37.029 | −0.090 | 1.00 | 57.40 | C |
| ATOM | 1767 | O | LYS | D | 32 | 17.029 | 37.194 | −0.967 | 1.00 | 57.57 | O |
| ATOM | 1768 | CB | LYS | D | 32 | 16.418 | 35.664 | 1.389 | 1.00 | 54.43 | C |
| ATOM | 1769 | CG | LYS | D | 32 | 15.318 | 35.554 | 0.324 | 1.00 | 54.54 | C |
| ATOM | 1770 | CD | LYS | D | 32 | 13.890 | 35.652 | 0.888 | 1.00 | 54.83 | C |
| ATOM | 1771 | CE | LYS | D | 32 | 12.873 | 34.966 | −0.082 | 1.00 | 55.36 | C |
| ATOM | 1772 | NZ | LYS | D | 32 | 11.477 | 35.445 | 0.174 | 1.00 | 49.45 | N |
| ATOM | 1773 | N | LYS | D | 33 | 18.821 | 37.952 | 0.111 | 1.00 | 58.89 | N |
| ATOM | 1774 | CA | LYS | D | 33 | 18.988 | 38.994 | −0.904 | 1.00 | 60.34 | C |
| ATOM | 1775 | C | LYS | D | 33 | 19.722 | 38.403 | −2.092 | 1.00 | 61.21 | C |
| ATOM | 1776 | O | LYS | D | 33 | 19.633 | 38.916 | −3.204 | 1.00 | 61.74 | O |
| ATOM | 1777 | CB | LYS | D | 33 | 19.749 | 40.199 | −0.347 | 1.00 | 60.97 | C |
| ATOM | 1778 | CG | LYS | D | 33 | 18.839 | 41.373 | −0.064 | 1.00 | 61.78 | C |
| ATOM | 1779 | CD | LYS | D | 33 | 19.207 | 42.116 | 1.226 | 1.00 | 62.08 | C |
| ATOM | 1780 | CE | LYS | D | 33 | 17.943 | 42.358 | 2.054 | 1.00 | 60.94 | C |
| ATOM | 1781 | NZ | LYS | D | 33 | 18.131 | 43.264 | 3.241 | 1.00 | 61.70 | N |
| ATOM | 1782 | N | TYR | D | 34 | 20.437 | 37.309 | −1.841 | 1.00 | 62.16 | N |
| ATOM | 1783 | CA | TYR | D | 34 | 21.304 | 36.654 | −2.813 | 1.00 | 63.23 | C |
| ATOM | 1784 | C | TYR | D | 34 | 20.771 | 35.295 | −3.331 | 1.00 | 64.87 | C |
| ATOM | 1785 | O | TYR | D | 34 | 21.392 | 34.681 | −4.212 | 1.00 | 65.24 | O |
| ATOM | 1786 | CB | TYR | D | 34 | 22.719 | 36.496 | −2.210 | 1.00 | 63.18 | C |
| ATOM | 1787 | CG | TYR | D | 34 | 23.277 | 37.799 | −1.719 | 1.00 | 61.87 | C |
| ATOM | 1788 | CD1 | TYR | D | 34 | 23.184 | 38.151 | −0.374 | 1.00 | 62.46 | C |
| ATOM | 1789 | CD2 | TYR | D | 34 | 23.849 | 38.725 | −2.617 | 1.00 | 62.38 | C |
| ATOM | 1790 | CE2 | TYR | D | 34 | 23.672 | 39.386 | 0.096 | 1.00 | 60.26 | C |
| ATOM | 1791 | CE2 | TYR | D | 34 | 24.333 | 39.965 | −2.179 | 1.00 | 61.13 | C |
| ATOM | 1792 | CZ | TYR | D | 34 | 24.241 | 40.286 | −0.808 | 1.00 | 62.60 | C |
| ATOM | 1793 | OH | TYR | D | 34 | 24.715 | 41.497 | −0.339 | 1.00 | 63.25 | O |
| ATOM | 1794 | N | THR | D | 35 | 19.644 | 34.817 | −2.787 | 1.00 | 66.35 | N |
| ATOM | 1795 | CA | THR | D | 35 | 19.108 | 33.483 | −3.144 | 1.00 | 67.51 | C |
| ATOM | 1796 | C | THR | D | 35 | 17.581 | 33.476 | −3.140 | 1.00 | 68.0 | C |
| ATOM | 1797 | O | THR | D | 35 | 16.940 | 34.245 | −3.872 | 1.00 | 68.85 | O |
| ATOM | 1798 | CB | THR | D | 35 | 19.601 | 32.296 | −2.211 | 1.00 | 67.87 | C |
| ATOM | 1799 | OG1 | THR | D | 35 | 18.621 | 32.020 | −1.208 | 1.00 | 67.86 | O |
| ATOM | 180 | CG2 | THR | D | 35 | 20.994 | 32.544 | −1.538 | 1.00 | 69.01 | C |
| TER | 1801 | | THR | D | 35 | | | | | | |
| HETATM | 1802 | O | HOH | A | 3 | 16.498 | 5.473 | −12.133 | 1.00 | 36.22 | O |
| HETATM | 1803 | O | HOH | A | 5 | −4.064 | −7.047 | 13.062 | 1.00 | 33.32 | O |
| HETATM | 1804 | O | HOH | A | 8 | 10.367 | 2.124 | −0.913 | 1.00 | 40.10 | O |
| HETATM | 1805 | O | HOH | A | 10 | 16.032 | −0.931 | 8.260 | 1.00 | 43.76 | O |
| HETATM | 1806 | O | HOH | A | 12 | 10.102 | −7.592 | 8.132 | 1.00 | 39.91 | O |
| HETATM | 1807 | O | HOH | A | 14 | 17.132 | 5.807 | 4.823 | 1.00 | 40.85 | O |
| HETATM | 1808 | O | HOH | A | 15 | −4.005 | 4.240 | 5.893 | 1.00 | 39.35 | O |
| HETATM | 1809 | O | HOH | A | 16 | 10.310 | 2.279 | −4.243 | 1.00 | 40.90 | O |
| HETATM | 1810 | O | HOH | A | 17 | 17.759 | 8.005 | 11.404 | 1.00 | 41.03 | O |
| HETATM | 1811 | O | HOH | A | 19 | 10.643 | −2.268 | −10.491 | 1.00 | 44.78 | O |
| HETATM | 1812 | O | HOH | A | 20 | −4.436 | −7.798 | 10.392 | 1.00 | 44.87 | O |
| HETATM | 1813 | O | HOH | A | 25 | −6.887 | 4.204 | 6.182 | 1.00 | 49.43 | O |
| HETATM | 1814 | O | HOH | A | 26 | 18.833 | 8.898 | −11.699 | 1.00 | 47.35 | O |
| HETATM | 1815 | O | HOH | A | 29 | −4.254 | 13.085 | 9.442 | 1.00 | 49.90 | O |
| HETATM | 1816 | O | HOH | A | 30 | 8.624 | 16.385 | 0.018 | 1.00 | 49.78 | O |
| HETATM | 1817 | O | HOH | B | 38 | −13.593 | −10.490 | 20.432 | 1.00 | 37.75 | O |

TABLE 2a-continued

Data of atomic coordinates for accession code 2ZTT

| HETATM | 1818 | O | HOH | B | 39 | 8.022 | 3.239 | 0.116 | 1.00 | 44.66 | O |
|---|---|---|---|---|---|---|---|---|---|---|---|
| HETATM | 1819 | O | HOH | B | 40 | −2.677 | 13.408 | 16.571 | 1.00 | 50.37 | O |
| HETATM | 1820 | O | HOH | B | 41 | 3.896 | −12.786 | 19.848 | 1.00 | 52.74 | O |
| HETATM | 1821 | O | HOH | C | 1 | 3.714 | 20.707 | 21.195 | 1.00 | 30.49 | O |
| HETATM | 1822 | O | HOH | C | 2 | −0.668 | 27.236 | 14.955 | 1.00 | 33.79 | O |
| HETATM | 1823 | O | HOH | C | 7 | −13.566 | 20.957 | 19.701 | 1.00 | 38.70 | O |
| HETATM | 1824 | O | HOH | C | 11 | 9.942 | 17.208 | 21.571 | 1.00 | 38.59 | O |
| HETATM | 1825 | O | HOH | C | 18 | −3.754 | 27.614 | 14.714 | 1.00 | 43.33 | O |
| HETATM | 1826 | O | HOH | C | 21 | −2.560 | 31.676 | 13.436 | 1.00 | 42.88 | O |
| HETATM | 1827 | O | HOH | C | 23 | 8.321 | 26.509 | 21.572 | 1.00 | 45.47 | O |
| HETATM | 1828 | O | HOH | C | 27 | −10.525 | 22.799 | 12.811 | 1.00 | 48.41 | O |
| HETATM | 1829 | O | HOH | D | 38 | −3.438 | 16.803 | 7.371 | 1.00 | 35.07 | O |
| HETATM | 1830 | O | HOH | D | 39 | 22.642 | 31.998 | 10.794 | 1.00 | 38.47 | O |
| HETATM | 1831 | O | HOH | D | 40 | 0.638 | 25.728 | 12.605 | 1.00 | 41.61 | O |
| HETATM | 1832 | O | HOH | D | 41 | 23.861 | 32.080 | 8.864 | 1.00 | 43.83 | O |
| HETATM | 1833 | O | HOH | D | 42 | 2.508 | 15.035 | 3.098 | 1.00 | 49.15 | O |
| HETATM | 1834 | O | HOH | D | 43 | −2.725 | 27.847 | 3.029 | 1.00 | 58.80 | O |
| CONECT | 20 | 27 | | | | | | | | | |
| CONECT | 27 | 20 | 28 | | | | | | | | |
| CONECT | 28 | 27 | 29 | 31 | | | | | | | |
| CONECT | 29 | 28 | 30 | 35 | | | | | | | |
| CONECT | 30 | 29 | | | | | | | | | |
| CONECT | 31 | 28 | 32 | | | | | | | | |
| CONECT | 32 | 31 | 33 | | | | | | | | |
| CONECT | 33 | 32 | 34 | | | | | | | | |
| CONECT | 34 | 33 | | | | | | | | | |
| CONECT | 35 | 29 | | | | | | | | | |
| CONECT | 239 | 243 | | | | | | | | | |
| CONECT | 243 | 239 | 244 | | | | | | | | |
| CONECT | 244 | 243 | 245 | 247 | | | | | | | |
| CONECT | 245 | 244 | 246 | 251 | | | | | | | |
| CONECT | 246 | 245 | | | | | | | | | |
| CONECT | 247 | 244 | 248 | | | | | | | | |
| CONECT | 248 | 247 | 249 | | | | | | | | |
| CONECT | 249 | 248 | 250 | | | | | | | | |
| CONECT | 250 | 249 | | | | | | | | | |
| CONECT | 251 | 245 | | | | | | | | | |
| CONECT | 269 | 272 | | | | | | | | | |
| CONECT | 272 | 269 | 273 | | | | | | | | |
| CONECT | 273 | 272 | 274 | 276 | | | | | | | |
| CONECT | 274 | 273 | 275 | 28 | | | | | | | |
| CONECT | 275 | 274 | | | | | | | | | |
| CONECT | 276 | 273 | 277 | | | | | | | | |
| CONECT | 277 | 276 | 278 | | | | | | | | |
| CONECT | 278 | 277 | 279 | | | | | | | | |
| CONECT | 279 | 278 | | | | | | | | | |
| CONECT | 280 | 274 | | | | | | | | | |
| CONECT | 482 | 488 | | | | | | | | | |
| CONECT | 488 | 482 | 489 | | | | | | | | |
| CONECT | 489 | 488 | 490 | 492 | | | | | | | |
| CONECT | 490 | 489 | 491 | 496 | | | | | | | |
| CONECT | 491 | 490 | | | | | | | | | |
| CONECT | 492 | 489 | 493 | | | | | | | | |
| CONECT | 493 | 492 | 494 | | | | | | | | |
| CONECT | 494 | 493 | 495 | | | | | | | | |
| CONECT | 495 | 494 | | | | | | | | | |
| CONECT | 496 | 490 | | | | | | | | | |
| CONECT | 614 | 618 | | | | | | | | | |
| CONECT | 618 | 614 | 619 | | | | | | | | |
| CONECT | 619 | 618 | 620 | 622 | | | | | | | |
| CONECT | 620 | 619 | 621 | 626 | | | | | | | |
| CONECT | 621 | 620 | | | | | | | | | |
| CONECT | 622 | 619 | 623 | | | | | | | | |
| CONECT | 623 | 622 | 624 | | | | | | | | |
| CONECT | 624 | 623 | 625 | | | | | | | | |
| CONECT | 625 | 624 | | | | | | | | | |
| CONECT | 626 | 620 | | | | | | | | | |
| CONECT | 701 | 707 | | | | | | | | | |
| CONECT | 707 | 701 | 708 | | | | | | | | |
| CONECT | 708 | 707 | 709 | 711 | | | | | | | |
| CONECT | 709 | 708 | 710 | 715 | | | | | | | |
| CONECT | 710 | 709 | | | | | | | | | |
| CONECT | 711 | 708 | 712 | | | | | | | | |
| CONECT | 712 | 711 | 713 | | | | | | | | |
| CONECT | 713 | 712 | 714 | | | | | | | | |
| CONECT | 714 | 713 | | | | | | | | | |
| CONECT | 715 | 709 | | | | | | | | | |
| CONECT | 837 | 845 | | | | | | | | | |

TABLE 2a-continued

Data of atomic coordinates for accession code 2ZTT

| | | | | |
|---|---|---|---|---|
| CONECT | 845 | 837 | 846 | |
| CONECT | 846 | 845 | 847 | 849 |
| CONECT | 847 | 846 | 848 | 853 |
| CONECT | 848 | 847 | | |
| CONECT | 849 | 846 | 850 | |
| CONECT | 850 | 849 | 851 | |
| CONECT | 851 | 850 | 852 | |
| CONECT | 852 | 851 | | |
| CONECT | 853 | 847 | | |
| CONECT | 940 | 947 | | |
| CONECT | 947 | 940 | 948 | |
| CONECT | 948 | 947 | 949 | 951 |
| CONECT | 949 | 948 | 950 | 955 |
| CONECT | 950 | 949 | | |
| CONECT | 951 | 948 | 952 | |
| CONECT | 952 | 951 | 953 | |
| CONECT | 953 | 952 | 954 | |
| CONECT | 954 | 953 | | |
| CONECT | 955 | 949 | | |
| CONECT | 1159 | 1163 | | |
| CONECT | 1163 | 1159 | 1164 | |
| CONECT | 1164 | 1163 | 1165 | 1167 |
| CONECT | 1165 | 1164 | 1166 | 1171 |
| CONECT | 1166 | 1165 | | |
| CONECT | 1167 | 1164 | 1168 | |
| CONECT | 1168 | 1167 | 1169 | |
| CONECT | 1169 | 1168 | 1170 | |
| CONECT | 1170 | 1169 | | |
| CONECT | 1171 | 1165 | | |
| CONECT | 1189 | 1192 | | |
| CONECT | 1192 | 1189 | 1193 | |
| CONECT | 1193 | 1192 | 1194 | 1196 |
| CONECT | 1194 | 1193 | 1195 | 1200 |
| CONECT | 1195 | 1194 | | |
| CONECT | 1196 | 1193 | 1197 | |
| CONECT | 1197 | 1196 | 1198 | |
| CONECT | 1198 | 1197 | 1199 | |
| CONECT | 1199 | 1198 | | |
| CONECT | 1200 | 1194 | | |
| CONECT | 1402 | 1408 | | |
| CONECT | 1408 | 1402 | 1409 | |
| CONECT | 1409 | 1408 | 1410 | 1412 |
| CONECT | 1410 | 1409 | 1411 | 1416 |
| CONECT | 1411 | 1410 | | |
| CONECT | 1412 | 1409 | 1413 | |
| CONECT | 1413 | 1412 | 1414 | |
| CONECT | 1414 | 1413 | 1415 | |
| CONECT | 1415 | 1414 | | |
| CONECT | 1416 | 1410 | | |
| CONECT | 1504 | 1508 | | |
| CONECT | 1508 | 1504 | 1509 | |
| CONECT | 1509 | 1508 | 1510 | 1512 |
| CONECT | 1510 | 1509 | 1511 | 1516 |
| CONECT | 1511 | 1510 | | |
| CONECT | 1512 | 1509 | 1513 | |
| CONECT | 1513 | 1512 | 1514 | |
| CONECT | 1514 | 1513 | 1515 | |
| CONECT | 1515 | 1514 | | |
| CONECT | 1516 | 1510 | | |
| CONECT | 1591 | 1597 | | |
| CONECT | 1597 | 1591 | 1598 | |
| CONECT | 1598 | 1597 | 1599 | 1601 |
| CONECT | 1599 | 1598 | 1600 | 1605 |
| CONECT | 1600 | 1599 | | |
| CONECT | 1601 | 1598 | 1602 | |
| CONECT | 1602 | 1601 | 1603 | |
| CONECT | 1603 | 1602 | 1604 | |
| CONECT | 1604 | 1603 | | |
| CONECT | 1605 | 1599 | | |
| CONECT | 1727 | 1735 | | |
| CONECT | 1735 | 1727 | 1736 | |
| CONECT | 1736 | 1735 | 1737 | 1739 |
| CONECT | 1737 | 1736 | 1738 | 1743 |
| CONECT | 1738 | 1737 | | |
| CONECT | 1739 | 1736 | 1740 | |
| CONECT | 1740 | 1739 | 1741 | |
| CONECT | 1741 | 1740 | 1742 | |

TABLE 2a-continued

Data of atomic coordinates for accession code 2ZTT

| | | |
|---|---|---|
| CONECT | 1742 | 1741 |
| CONECT | 1743 | 1737 |
| MASTER 302 0 14 12 0 0 0 6 1830 4 140 22 | | |
| END | | |

TABLE 2b

Data of atomic coordinates for accession code 3A1G, which cites accession code 2ZTT The data of atomic coordinates registered in the Protein Data Bank under accession
code 3A1G, which cites accession code 2ZTT, as a related ID and starting model follow:

```
HEADER        TRANSFERASE                             02-APR-09   3A1G
TITLE         HIGH-RESOLUTION CRYSTAL STRUCTURE OF RNA POLYMERASE PB1-PB2
TITLE     2   SUBUNITS FROM INFLUENZA A VIRUS
COMPND        MOL_ID: 1;
COMPND    2   MOLECULE: RNA-DIRECTED RNA POLYMERASE CATALYTIC SUBUNIT;
COMPND    3   CHAIN: A, C;
COMPND    4   FRAGMENT: PB1 C-TERMINAL FRAGMENT, UNP RESIDUES 678-757;
COMPND    5   SYNONYM: POLYMERASE BASIC PROTEIN 1, PB1, RNA-DIRECTED RNA
COMPND    6   POLYMERASE SUBUNIT P1;
COMPND    7   EC: 2.7.7.48;
COMPND    8   ENGINEERED: YES;
COMPND    9   MOL_ID: 2;
COMPND   10   MOLECULE: POLYMERASE BASIC PROTEIN 2;
COMPND   11   CHAIN: B, D;
COMPND   12   FRAGMENT: PB2 N-TERMINAL RAGMENT, UNP RESIDUES 1-37;
COMPND   13   SYNONYM: RNA POLYMERASE PB2 SUBUNIT, RNA-DIRECTED RNA
COMPND   14   POLYMERASE SUBUNIT P3;
COMPND   15   ENGINEERED: YES
SOURCE        MOL_ID: 1;
SOURCE    2   ORGANISM_SCIENTIFIC: INFLUENZA A VIRUS (A/PUERTO
SOURCE    3   RICO/8/34(H1N1));
SOURCE    4   ORGANISM_TAXID: 211044;
SOURCE    5   STRAIN: STRAIN A/PUERTO RICO/8/1934 H1N1;
SOURCE    6   GENE: PB1;
SOURCE    7   EXPRESSION_SYSTEM: ESCHERICHIA COLI;
SOURCE    8   EXPRESSION_SYSTEM_TAXID: 562;
SOURCE    9   EXPRESSION_SYSTEM_STRAIN: BL21(DE3)RILCODONPLUS;
SOURCE   10   EXPRESSION_SYSTEM_VECTOR_TYPE: PLASMID;
SOURCE   11   EXPRESSION_SYSTEM_PLASMID: MODIFIED PET28;
SOURCE   12   MOL_ID: 2;
SOURCE   13   ORGANISM_SCIENTIFIC: INFLUENZA A VIRUS (A/PUERTO
SOURCE   14   RICO/8/34(H1N1));
SOURCE   15   ORGANISM_TAXID: 211044;
SOURCE   16   STRAIN: STRAIN A/PUERTO RICO/8/1934 H1N1;
SOURCE   17   GENE: PB2;
SOURCE   18   EXPRESSION_SYSTEM: ESCHERICHIA COLI;
SOURCE   19   EXPRESSION_SYSTEM_TAXID: 562;
SOURCE   20   EXPRESSION_SYSTEM_STRAIN: BL21(DE3)RILCODONPLUS;
SOURCE   21   EXPRESSION_SYSTEM_VECTOR_TYPE: PLASMID;
SOURCE   22   EXPRESSION_SYSTEM_PLASMID: MIDIFIED PET28
KEYWDS        INFLUENZA VIRUS, RNA POLYMERASE, CRYSTAL STRUCTURE,
KEYWDS    2   NUCLEOTIDE-BINDING, NUCLEOTIDYLTRANSFERASE, NUCLEUS, RNA
KEYWDS    3   REPLICATION, RNA-DIRECTED RNA POLYMERASE, TRANSFERASE,
KEYWDS    4   MITOCHONDRION, MRNA CAPPING, MRNA PROCESSING, VIRION
EXPDTA        X-RAY DIFFRACTION
AUTHOR        K.SUGIYAMA, S.-Y.PARK, E.OBAYASHI
REVDAT    2           07-JUL-09  3A1G     1        JRNL
REVDAT    1           09-JUN-09  3A1G     0
JRNL          AUTH          K. SUGIYAMA, E. OBAYASHI, A. KAWAGUCHI, Y. SUZUKI,
JRNL          AUTH    2     J. R. H. TAME, K. NAGATA, S.-Y. PARK
JRNL          TITL          STRUCTURAL INSIGHT INTO THE ESSENTIAL PB1-PB2
JRNL          TITL    2     SUBUNIT CONTACT OF THE INFLUENZA VIRUS RNA
JRNL          TITL    3     POLYMERASE
JRNL          REF           EMBO J.                       V. 28 1803 2009
JRNL          REFN                        ISSN 0261-4189
JRNL          PMID          19461581
JRNL          DOI           10.1038/EMBOJ.2009.138
REMARK   1
REMARK   2
REMARK   2           RESOLUTION.        1.70 ANGSTROMS.
REMARK   3
REMARK   3           REFINEMENT.
REMARK   3               PROGRAM        : REFMAC 5.1.24
REMARK   3               AUTHORS        : MURSHUDOV, VAGIN, DODSON
```

TABLE 2b-continued

Data of atomic coordinates for accession code 3AIG, which cites accession code 2ZTT

```
REMARK  3
REMARK  3            REFINEMENT TARGET : MAXIMUM LIKELIHOOD
REMARK  3
REMARK  3            DATA USED IN REFINEMENT.
REMARK  3   RESOLUTION RANGE HIGH       (ANGSTROMS):            1.70
REMARK  3   RESOLUTION RANGE LOW        (ANGSTROMS):           20.00
REMARK  3   DATA CUTOFF                 (SIGMA(F)):             0.000
REMARK  3   COMPLETENESS FOR RANGE      (%):                  100.0
REMARK  3   NUMBER OF REFLECTION:                            24512
REMARK  3
REMARK  3            FIT TO DATA USED IN REFINEMENT.
REMARK  3   CROSS-VALIDATION METHOD:                       THROUGHOUT
REMARK  3   FREE R VALUE TEST SET SELECTION:               RANDOM
REMARK  3   R VALUE            (WORKING + TEST SET):        0.240
REMARK  3   R VALUE            (WORKING SET):               0.238
REMARK  3   FREE R VALUE:                                   0.290
REMARK  3   FREE R VALUE TEST SET SIZE   (%):               5.100
REMARK  3   FREE R VALUE TEST SET COUNT:                    1315
REMARK  3
REMARK  3            FIT IN THE HIGHEST RESOLUTION BIN.
REMARK  3   TOTAL NUMBER OF BINS USED:                         20
REMARK  3   BIN RESOLUTION RANGE HIGH   (A):                    1.70
REMARK  3   BIN RESOLUTION RANGE LOW    (A):                    1.74
REMARK  3   REFLECTION IN BIN           (WORKING SET):       1399
REMARK  3   BIN COMPLETENESS            (WORKING + TEST) (%):  100.00
REMARK  3   BIN R VALUE                 (WORKING SET):          0.2350
REMARK  3   BIN FREE R VALUE SET COUNT:                        69
REMARK  3   BIN FREE R VALUE:                                   0.3100
REMARK  3
REMARK  3            NUMBER OF NON-HYDROGEN ATOMS USED IN REFINEMENT.
REMARK  3   PROTEIN ATOMS:                    1826
REMARK  3   NUCLEIC ACID ATOMS:                  0
REMARK  3   HETEROGEN ATOMS:                     0
REMARK  3   SOLVENT ATOMS:                      63
REMARK  3
REMARK  3            B VALUES.
REMARK  3   FROM WILSON PLOT            (A**2):            NULL
REMARK  3   MEAN B VALUE                (OVERALL, A**2):    36.54
REMARK  3   OVERALL ANISOTROPIC B VALUE.
REMARK  3       B11   (A**2):   4.34000
REMARK  3       B22   (A**2):  -2.46000
REMARK  3       B33   (A**2):  -1.69000
REMARK  3       B12   (A**2):   0.00000
REMARK  3       B13   (A**2):   0.70000
REMARK  3       B23   (A**2):   0.00000
REMARK  3
REMARK  3            ESTIMATED OVERALL COORDINATE ERROR.
REMARK  3   ESU BASED ON R VALUE                                  (A):      0.137
REMARK  3   ESU BASED ON FREE R VALUE                             (A):      0.139
REMARK  3   ESU BASED ON MAXIMUM LIKELIHOOD                       (A):      0.092
REMARK  3   ESU FOR B VALUES BASED ON MAXIMUM LIKELIHOOD          (A**2):   2.709
REMARK  3
REMARK  3   CORRELATION COEFFICIENTS.
REMARK  3       CORRELATION COEFFICIENT FO-FC:           0.931
REMARK  3       CORRELATION COEFFICIENT FO-FC FREE:      0.894
REMARK  3
REMARK  3            RMS DEVIATIONS FROM IDEAL VALUES              COUNT     RMS    WEIGHT
REMARK  3       BOND LENGTHS REFINED ATOMS        (A):           1844 ;    0.023 ;   0.022
REMARK  3       BOND LENGTHS OTHERS               (A):           NULL ;    NULL    NULL
REMARK  3       BOND ANGLES REFINED ATOMS         (DEGREES):     2448 ;    1.845 ;   1.975
REMARK  3       BOND ANGLES OTHERS                (DEGREES):     NULL ;    NULL    NULL
REMARK  3       TORSION ANGLES, PERIOD 1          (DEGREES):      218 ;    6.734 ;   5.000
REMARK  3       TORSION ANGLES, PERIOD 2          (DEGREES):       88 ;   37.835 ;  22.045
REMARK  3       TORSION ANGLES, PERIOD 3          (DEGREES):      400 ;   18.170 ;  15.000
REMARK  3       TORSION ANGLES, PERIOD 4          (DEGREES):       26 ;   18.653 ;  15.000
REMARK  3       CHIRAL-CENTER RESTRAINTS          (A**3):         268 ;    0.146 ;   0.200
REMARK  3       GENERAL PLANES REFINED ATOMS      (A):           1332 ;    0.006 ;   0.020
REMARK  3       GENERAL PLANES OTHERS             (A):           NULL ;    NULL    NULL
REMARK  3       NON-BONDED CONTACTS REFINED ATOMS (A):            948 ;    0.247 ;   0.200
REMARK  3       NON-BONDED CONTACTS OTHERS        (A):           NULL ;    NULL    NULL
REMARK  3       NON-BONDED TORSION REFINED ATOMS  (A):           1291 ;    0.308 ;   0.200
REMARK  3       NON-BONDED TORSION OTHERS         (A):           NULL ;    NULL    NULL
REMARK  3       H-BOND (X . . . Y) REFINED ATOMS  (A):             85 ;    0.158 ;   0.200
REMARK  3       H-BOND (X . . . Y) OTHERS         (A):           NULL ;    NULL    NULL
REMARK  3       POTENTIAL METAL-ION REFINED ATOMS (A):           NULL ;    NULL    NULL
REMARK  3       POTENTIAL METAL-ION OTHERS        (A):           NULL ;    NULL    NULL
REMARK  3       SYMMETRY VDW REFINED ATOMS        (A):             50 ;    0.226 ;   0.200
REMARK  3       SYMMETRY VDW OTHERS               (A):           NULL ;    NULL    NULL
```

TABLE 2b-continued

Data of atomic coordinates for accession code 3A1G, which cites accession code 2ZTT

| | | | | | |
|---|---|---|---|---|---|
| REMARK 3 | SYMMETRY H-BOND REFINED ATOMS | (A): | 6; | 0.264; | 0.200 |
| REMARK 3 | SYMMETRY H-BOND OTHERS | (A): | NULL; | NULL; | NULL |
| REMARK 3 | SYMMETRY METAL-ION REFINED ATOMS | (A): | NULL; | NULL; | NULL |
| REMARK 3 | SYMMETRY METAL-ION OTHERS | (A): | NULL; | NULL; | NULL |
| REMARK 3 | | | | | |
| REMARK 3 | ISOTROPIC THERMAL FACTOR RESTRAINTS. | | COUNT | RMS | WEIGHT |
| REMARK 3 | MAIN-CHAIN BOND REFINED ATOMS | (A**2): | 1152; | 1.503; | 1.500 |
| REMARK 3 | MAIN-CHAIN BOND OTHER ATOMS | (A**2): | NULL; | NULL; | NULL |
| REMARK 3 | MAIN-CHAIN ANGLE REFINED ATOMS | (A**2): | 1792; | 2.164; | 2.000 |
| REMARK 3 | SIDE-CHAIN BOND REFINED ATOMS | (A**2): | 777; | 3.729; | 3.000 |
| REMARK 3 | SIDE-CHAIN ANGLE REFINED ATOMS | (A**2): | 656; | 4.906; | 4.500 |
| REMARK 3 | | | | | |
| REMARK 3 | ANISOTROPIC THERMAL FACTOR RESTRAINTS. | | COUNT | RMS | WEIGHT |
| REMARK 3 | RIGID-BOND RESTRAINTS | (A**2): | NULL; | NULL; | NULL |
| REMARK 3 | SPHERICITY; FREE ATOMS | (A**2): | NULL; | NULL; | NULL |
| REMARK 3 | SPHERICITY; BONDED ATOMS | (A**2): | NULL; | NULL; | NULL |
| REMARK 3 | | | | | |
| REMARK 3 | NCS RESTRAINTS STATISTICS | | | | |
| REMARK 3 | NUMBER OF DIFFERENT NCS GROUPS: | | NULL | | |
| REMARK 3 | | | | | |
| REMARK 3 | TLS DETAILS | | | | |
| REMARK 3 | NUMBER OF TLS GROUPS: | NULL | | | |
| REMARK 3 | | | | | |
| REMARK 3 | BULK SOLVENT MODELLING. | | | | |
| REMARK 3 | METHOD USED : BABINET MODEL WITH MASK | | | | |
| REMARK 3 | PARAMETERS FOR MASK CALCULATION | | | | |
| REMARK 3 | VDW PROBE RADIUS: | 1.20 | | | |
| REMARK 3 | ION PROBE RADIUS: | 0.80 | | | |
| REMARK 3 | SHRINKAGE RADIUS: | 0.80 | | | |
| REMARK 3 | | | | | |
| REMARK 3 | OTHER REFINEMENT REMARKS: NULL | | | | |
| REMARK 4 | | | | | |
| REMARK 4 | 3A1G COMPLIES WITH FORMAT V. 3.20, 01-DEC-08 | | | | |
| REMARK 100 | | | | | |
| REMARK 100 | THIS ENTRY HAS BEEN PROCESSED BY PDBJ ON 06-APR-09. | | | | |
| REMARK 100 | THE RCSB ID CODE IS RCSB028691. | | | | |
| REMARK 200 | | | | | |
| REMARK 200 | EXPERIMENTAL DETAILS | | | | |
| REMARK 200 | EXPERIMENT TYPE: | | X-RAY DIFFRACTION | | |
| REMARK 200 | DATE OF DATA COLLECTION: | | 19-FEB-09 | | |
| REMARK 200 | TEMPERATURE | (KELVIN): | 100 | | |
| REMARK 200 | PH: | | NULL | | |
| REMARK 200 | NUMBER OF CRYSTALS USED: | | 1 | | |
| REMARK 200 | | | | | |
| REMARK 200 | SYNCHROTRON | (Y/N): | Y | | |
| REMARK 200 | RADIATION SOURCE: | | PHOTON FACTORY | | |
| REMARK 200 | BEAMLINE: | | BL-17A | | |
| REMARK 200 | X-RAY GENERATOR MODEL: | | NULL | | |
| REMARK 200 | MONOCHROMATIC OR LAUE | (M/L): | M | | |
| REMARK 200 | WAVELENGTH OR RANGE | (A): | 1.0 | | |
| REMARK 200 | MONOCHROMATOR: | | SAGITALLY FOCUSED SI(111) | | |
| REMARK 200 | OPTICS: | | NULL | | |
| REMARK 200 | | | | | |
| REMARK 200 | DETECTOR TYPE: | | CCD | | |
| REMARK 200 | DETECTOR MANUFACTURER: | | ADSC QUANTUM 270 | | |
| REMARK 200 | INTENSITY-INTEGRATION SOFTWARE: | | HKL-2000 | | |
| REMARK 200 | DATA SCALING SOFTWARE: | | HKL-2000 | | |
| REMARK 200 | | | | | |
| REMARK 200 | NUMBER OF UNIQUE REFLECTIONS: | | 25865 | | |
| REMARK 200 | RESOLUTION RANGE HIGH | (A): | 1.700 | | |
| REMARK 200 | RESOLUTION RANGE LOW | (A): | 50.000 | | |
| REMARK 200 | REJECTION CRITERIA(SIGMA(I)): | | 0.000 | | |
| REMARK 200 | | | | | |
| REMARK 200 | OVERALL. | | | | |
| REMARK 200 | COMPLETENESS FOR RANGE | (%): | 92.2 | | |
| REMARK 200 | DATA REDUNDANCY: | | 5.100 | | |
| REMARK 200 | R MERGE | (I): | 0.04400 | | |
| REMARK 200 | R SYM | (I): | NULL | | |
| REMARK 200 | <I/SIGMA(I)> FOR THE DATA SET: | | 0.0000 | | |
| REMARK 200 | | | | | |
| REMARK 200 | IN THE HIGHEST RESOLUTION SHELL. | | | | |
| REMARK 200 | HIGHEST RESOLUTION SHELL, RANGE HIGH | (A): | 1.70 | | |
| REMARK 200 | HIGHEST RESOLUTION SHELL, RANGE LOW | (A): | 1.76 | | |
| REMARK 200 | COMPLETENESS FOR SHELL | (%): | 73.0 | | |
| REMARK 200 | DATA REDUNDANCY IN SHELL: | | NULL | | |
| REMARK 200 | R MERGE FOR SHELL | (I): | 0.12400 | | |
| REMARK 200 | R SYM FOR SHELL | (I): | NULL | | |

TABLE 2b-continued

Data of atomic coordinates for accession code 3AIG, which cites accession code 2ZTT

| | | | | | | |
|---|---|---|---|---|---|---|
| REMARK 200 | <I/SIGMA(I)> FOR SHELL: | | | 25.000 | | |
| REMARK 200 | | | | | | |
| REMARK 200 | DIFFRACTION PROTOCOL: SINGLE WAVELENGTH | | | | | |
| REMARK 200 | METHOD USED TO DETERMINE THE STRUCTURE: MOLECULAR REPLACEMENT | | | | | |
| REMARK 200 | SOFTWARE USED: PHASER | | | | | |
| REMARK 200 | STARTING MODEL: PDB ENTRY 2ZTT | | | | | |
| REMARK 200 | | | | | | |
| REMARK 200 | REMARK: NULL | | | | | |
| REMARK 280 | | | | | | |
| REMARK 280 | CRYSTAL | | | | | |
| REMARK 280 | SOLVENT CONTENT, VS (%): 45.08 | | | | | |
| REMARK 280 | MATTHEWS COEFFICIENT, VM (ANGSTROMS**3/DA): 2.24 | | | | | |
| REMARK 280 | | | | | | |
| REMARK 280 | CRYSTALLIZATION CONDITIONS: 80 MM SODIUM CITRATE, 20% PEG 4000, | | | | | |
| REMARK 280 | VAPOR DIFFUSION, HANGING DROP, TEMPERATURE 298 K. | | | | | |
| REMARK 290 | | | | | | |
| REMARK 290 | CRYSTALLOGRAPHIC SYMMETRY | | | | | |
| REMARK 290 | SYMMETRY OPERATORS FOR SPACE GROUP: C 1 2 1 | | | | | |
| REMARK 290 | | | | | | |
| REMARK 290 | SYMOP SYMMETRY | | | | | |
| REMARK 290 | NNNMMM OPERATOR | | | | | |
| REMARK 290 | 1555 X, Y, Z | | | | | |
| REMARK 290 | 2555 −X, Y, −Z | | | | | |
| REMARK 290 | 3555 X + 1/2, Y + 1/2, Z | | | | | |
| REMARK 290 | 4555 −X + 1/2, Y + 1/2, −Z | | | | | |
| REMARK 290 | | | | | | |
| REMARK 290 | WHERE NNN -> OPERATOR NUMBER | | | | | |
| REMARK 290 | MMM -> TRANSLATION VECTOR | | | | | |
| REMARK 290 | | | | | | |
| REMARK 290 | CRYSTALLOGRAPHIC SYMMETRY TRANSFORMATIONS | | | | | |
| REMARK 290 | THE FOLLOWING TRANSFORMATIONS OPERATE ON THE ATOM/HETATM | | | | | |
| REMARK 290 | RECORDS IN THIS ENTRY TO PRODUCE CRYSTALLOGRAPHICALLY | | | | | |
| REMARK 290 | RELATED MOLECULES. | | | | | |
| REMARK 290 | SMTRY1 | 1 | 1.000000 | 0.000000 | 0.000000 | 0.00000 |
| REMARK 290 | SMTRY2 | 1 | 0.000000 | 1.000000 | 0.000000 | 0.00000 |
| REMARK 290 | SMTRY3 | 1 | 0.000000 | 0.000000 | 1.000000 | 0.00000 |
| REMARK 290 | SMTRY1 | 2 | −1.000000 | 0.000000 | 0.000000 | 0.00000 |
| REMARK 290 | SMTRY2 | 2 | 0.000000 | 1.000000 | 0.000000 | 0.00000 |
| REMARK 290 | SMTRY3 | 2 | 0.000000 | 0.000000 | −1.000000 | 0.00000 |
| REMARK 290 | SMTRY1 | 3 | 1.000000 | 0.000000 | 0.000000 | 30.35050 |
| REMARK 290 | SMTRY2 | 3 | 0.000000 | 1.000000 | 0.000000 | 34.99350 |
| REMARK 290 | SMTRY3 | 3 | 0.000000 | 0.000000 | 1.000000 | 0.00000 |
| REMARK 290 | SMTRY1 | 4 | −1.000000 | 0.000000 | 0.000000 | 30.35050 |
| REMARK 290 | SMTRY2 | 4 | 0.000000 | 1.000000 | 0.000000 | 34.99350 |
| REMARK 290 | SMTRY3 | 4 | 0.000000 | 0.000000 | −1.000000 | 0.00000 |
| REMARK 290 | | | | | | |
| REMARK 290 | REMARK: NULL | | | | | |
| REMARK 300 | | | | | | |
| REMARK 300 | BIOMOLECULE: 1, 2 | | | | | |
| REMARK 300 | SEE REMARK 350 FOR THE AUTHOR PROVIDED AND/OR PROGRAM | | | | | |
| REMARK 300 | GENERATED ASSEMBLY INFORMATION FOR THE STRUCTURE IN | | | | | |
| REMARK 300 | THIS ENTRY. THE REMARK MAY ALSO PROVIDE INFORMATION ON | | | | | |
| REMARK 300 | BURIED SURFACE AREA. | | | | | |
| REMARK 350 | | | | | | |
| REMARK 350 | COORDINATES FOR A COMPLETE MULTIMER REPRESENTING THE KNOWN | | | | | |
| REMARK 350 | BIOLOGICALLY SIGNIFICANT OLIGOMERIZATION STATE OF THE | | | | | |
| REMARK 350 | MOLECULE CAN BE GENERATED BY APPLYING BIOMT TRANSFORMATIONS | | | | | |
| REMARK 350 | GIVEN BELOW. BOTH NON-CRYSTALLOGRAPHIC AND | | | | | |
| REMARK 350 | CRYSTALLOGRAPHIC OPERATIONS ARE GIVEN. | | | | | |
| REMARK 350 | | | | | | |
| REMARK 350 | BIOMOLECULE: 1 | | | | | |
| REMARK 350 | AUTHOR DETERMINED BIOLOGICAL UNIT: DIMERIC | | | | | |
| REMARK 350 | SOFTWARE DETERMINED QUATERNARY STRUCTURE: DIMERIC | | | | | |
| REMARK 350 | SOFTWARE USED: PISA | | | | | |
| REMARK 350 | TOTAL BURIED SURFACE AREA: 3140 ANGSTROM**2 | | | | | |
| REMARK 350 | SURFACE AREA OF THE COMPLEX: 6930 ANGSTROM**2 | | | | | |
| REMARK 350 | CHANGE IN SOLVENT FREE ENERGY: −27.0 KCAL/MOL | | | | | |
| REMARK 350 | APPLY THE FOLLOWING TO CHAINS: A, B | | | | | |
| REMARK 350 | BIOMT1 | 1 | 1.000000 | 0.000000 | 0.000000 | 0.00000 |
| REMARK 350 | BIOMT2 | 1 | 0.000000 | 1.000000 | 0.000000 | 0.00000 |
| REMARK 350 | BIOMT3 | 1 | 0.000000 | 0.000000 | 1.000000 | 0.00000 |
| REMARK 350 | | | | | | |
| REMARK 350 | BIOMOLECULE: 2 | | | | | |
| REMARK 350 | AUTHOR DETERMINED BIOLOGICAL UNIT: DIMERIC | | | | | |
| REMARK 350 | SOFTWARE DETERMINED QUATERNARY STRUCTURE: DIMERIC | | | | | |
| REMARK 350 | SOFTWARE USED: PISA | | | | | |
| REMARK 350 | TOTAL BURIED SURFACE AREA: 2950 ANGSTROM**2 | | | | | |
| REMARK 350 | SURFACE AREA OF THE COMPLEX: 7000 ANGSTROM**2 | | | | | |

TABLE 2b-continued

Data of atomic coordinates for accession code 3AIG, which cites accession code 2ZTT

```
REMARK 350   CHANGE IN SOLVENT FREE ENERGY: −27.0 KCAL/MOL
REMARK 350   APPLY THE FOLLOWING TO CHAINS: C, D
REMARK 350     BIOMT1   1   1.000000   0.000000   0.000000   0.00000
REMARK 350     BIOMT2   1   0.000000   1.000000   0.000000   0.00000
REMARK 350     BIOMT3   1   0.000000   0.000000   1.000000   0.00000
REMARK 465
REMARK 465   MISSING RESIDUES
REMARK 465   THE FOLLOWING RESIDUES WERE NOT LOCATED IN THE
REMARK 465   EXPERIMENT. (M = MODEL NUMBER; RES = RESIDUE NAME; C = CHAIN
REMARK 465   IDENTIFIER; SSSEQ = SEQUENCE NUMBER; I = INSERTION CODE.)
REMARK 465
REMARK 465       M   RES   C   SSSEQI
REMARK 465           SER   A     678
REMARK 465           GLN   A     679
REMARK 465           ARG   A     680
REMARK 465           GLY   A     681
REMARK 465           VAL   A     682
REMARK 465           LEU   A     683
REMARK 465           GLU   A     684
REMARK 465           SER   B      36
REMARK 465           GLY   B      37
REMARK 465           SER   C     678
REMARK 465           GLN   C     679
REMARK 465           ARG   C     680
REMARK 465           GLY   C     681
REMARK 465           VAL   C     682
REMARK 465           LEU   C     683
REMARK 465           GLU   C     684
REMARK 465           SER   D      36
REMARK 465           GLY   D      37
REMARK 500
REMARK 500   GEOMETRY AND STEREOCHEMISTRY
REMARK 500   SUBTOPIC: COVALENT BOND LENGTHS
REMARK 500
REMARK 500   THE STEREOCHEMICAL PARAMETERS OF THE FOLLOWING RESIDUES
REMARK 500   HAVE VALUES WHICH DEVIATE FROM EXPECTED VALUES BY MORE
REMARK 500   THAN 6*RMSD (M = MODEL NUMBER; RES = RESIDUE NAME; C = CHAIN
REMARK 500   IDENTIFIER; SSEQ = SEQUENCE NUMBER; I = INSERTION CODE).
REMARK 500
REMARK 500   STANDARD TABLE:
REMARK 500   FORMAT: (10X, I3, 1X, 2(A3, 1X, A1, I4, A1, 1X, A4, 3X), 1X ,F6.3)
REMARK 500
REMARK 500   EXPECTED VALUES PROTEIN: ENGH AND HUBER, 1999
REMARK 500   EXPECTED VALUES NUCLEIC ACID: CLOWNEY ET AL 1996
REMARK 500
REMARK 500       M   RES   C   SSEQI   ATM1   RES   C   SSEQI   ATM2       DEVIATION
REMARK 500           CYS   A    693    CB     CYS   A    693    SG          −0.096
REMARK 500           GLU   B      2    CB     GLU   B      2    CG           0.122
REMARK 500           GLU   B      2    CG     GLU   B      2    CD           0.107
REMARK 500           CYS   C    693    CB     CYS   C    693    SG          −0.107
REMARK 500
REMARK 500   REMARK: NULL
REMARK 500
REMARK 500   GEOMETRY AND STEREOCHEMISTRY
REMARK 500   SUBTOPIC: COVALENT BOND ANGLES
REMARK 500
REMARK 500   THE STEREOCHEMICAL PARAMETERS OF THE FOLLOWING RESIDUES
REMARK 500   HAVE VALUES WHICH DEVIATE FROM EXPECTED VALUES BY MORE
REMARK 500   THAN 6*RMSD (M = MODEL NUMBER; RES = RESIDUE NAME; C = CHAIN
REMARK 500   IDENTIFIER; SSEQ = SEQUENCE NUMBER; I = INSERTION CODE).
REMARK 500
REMARK 500   STANDARD TABLE:
REMARK 500   FORMAT: (10X, I3, 1X, A3, 1X, A1, I4, A1, 3(1X, A4, 2X), 12X, F5.1)
REMARK 500
REMARK 500   EXPECTED VALUES PROTEIN: ENGH AND HUBER, 1999
REMARK 500   EXPECTED VALUES NUCLEIC ACID: CLOWNEY ET AL 1996
REMARK 500
REMARK 500       M   RES   C   SSEQI   ATM1   ATM2   ATM3
REMARK 500           LEU   B     10    CB  −  CG  −  CD1 ANGL. DEV. =  10.3 DEGREES
REMARK 500           ARG   C    723    NE  −  CZ  −  NH2 ANGL. DEV. =  −3.3 DEGREES
REMARK 500
REMARK 500   REMARK: NULL
REMARK 500
REMARK 500   GEOMETRY AND STEREOCHEMISTRY
REMARK 500   SUBTOPIC: TORSION ANGLES
REMARK 500
REMARK 500   TORSION ANGLES OUTSIDE THE EXPECTED RAMACHANDRAN REGIONS:.
REMARK 500   (M = MODEL NUMBER; RES = RESIDUE NAME; C = CHAIN IDENTIFIER;
```

TABLE 2b-continued

Data of atomic coordinates for accession code 3AIG, which cites accession code 2ZTT

| | | | | | | | | | | | | | |
|---|---|---|---|---|---|---|---|---|---|---|---|---|---|
| REMARK 500 | SSEQ = SEQUENCE NUMBER; I = INSERTION CODE). | | | | | | | | | | | | |
| REMARK 500 | | | | | | | | | | | | | |
| REMARK 500 | STANDARD TABLE: | | | | | | | | | | | | |
| REMARK 500 | FORMAT: (10X, I3, 1X, A3, 1X, A1, I4, A1, 4X, F7.2, 3X, F7.2) | | | | | | | | | | | | |
| REMARK 500 | | | | | | | | | | | | | |
| REMARK 500 | EXPECTED VALUES: GJ KLEYWEGT AND TA JONES (1996). PHI/PSI- | | | | | | | | | | | | |
| REMARK 500 | CHOLOGY: RAMACHANDRAN REVISITED. STRUCTURE 4, 1395–1400 | | | | | | | | | | | | |
| REMARK 500 | | | | | | | | | | | | | |
| REMARK 500 | | M | RES | C | SSEQI | PSI | | PHI | | | | | |
| REMARK 500 | | | SER | A | 703 | 57.07 | | −60.77 | | | | | |
| REMARK 500 | | | TYR | A | 705 | 57.49 | | −92.60 | | | | | |
| REMARK 500 | | | ARG | C | 706 | 98.07 | | −68.30 | | | | | |
| REMARK 500 | | | ILE | D | 30 | −70.06 | | −51.26 | | | | | |
| REMARK 500 | | | | | | | | | | | | | |
| REMARK 500 | REMARK: NULL | | | | | | | | | | | | |
| REMARK 500 | | | | | | | | | | | | | |
| REMARK 500 | GEOMETRY AND STEREOCHEMISTRY | | | | | | | | | | | | |
| REMARK 500 | SUBTOPIC: NON-CIS, NON-TRANS | | | | | | | | | | | | |
| REMARK 500 | | | | | | | | | | | | | |
| REMARK 500 | THE FOLLOWING PEPTIDE BONDS DEVIATE SIGNIFICANTLY FROM BOTH | | | | | | | | | | | | |
| REMARK 500 | CIS AND TRANS CONFORMATION. CIS BONDS, IF ANY, ARE LISTED | | | | | | | | | | | | |
| REMARK 500 | ON CISPEP RECORDS. TRANS IS DEFINED AS 180 +/− 30 AND | | | | | | | | | | | | |
| REMARK 500 | CIS IS DEFINED AS 0 +/− 30 DEGREES. | | | | | | | | | | | | |
| REMARK 500 | | | | | | | MODEL | OMEGA | | | | | |
| REMARK 500 | SER A | | 703 | | SER A | 704 | | | −147.02 | | | | |
| REMARK 500 | | | | | | | | | | | | | |
| REMARK 500 | REMARK: NULL | | | | | | | | | | | | |
| REMARK 500 | | | | | | | | | | | | | |
| REMARK 500 | GEOMETRY AND STEREOCHEMISTRY | | | | | | | | | | | | |
| REMARK 500 | SUBTOPIC: CHIRAL CENTERS | | | | | | | | | | | | |
| REMARK 500 | | | | | | | | | | | | | |
| REMARK 500 | UNEXPECTED CONFIGURATION OF THE FOLLOWING CHIRAL | | | | | | | | | | | | |
| REMARK 500 | CENTER(S) USING IMPROPER CA—C—CB—N CHIRALITY | | | | | | | | | | | | |
| REMARK 500 | M = MODEL NUMBER; RES = RESIDUE NAME; C = CHAIN | | | | | | | | | | | | |
| REMARK 500 | IDENTIFIER; SSEQ = SEQUENCE NUMBER; I = INSERTION CODE | | | | | | | | | | | | |
| REMARK 500 | | | | | | | | | | | | | |
| REMARK 500 | STANDARD TABLE: | | | | | | | | | | | | |
| REMARK 500 | FORMAT: (11X, I3, 1X, A3, 1X, A1, I4, A1, 6X, F5.1, 6X, A1, 10X, A1, 3X, A16) | | | | | | | | | | | | |
| REMARK 500 | | | | | | | | | | | | | |
| REMARK 500 | | M | RES | C | SSEQI | IMPROPER | EXPECTED | | FOUND | DETAILS | | | |
| REMARK 500 | | | GLU | A | 686 | 20.0 | L | | L | OUTSIDE RANGE | | | |
| REMARK 500 | | | | | | | | | | | | | |
| REMARK 500 | REMARK: NULL | | | | | | | | | | | | |
| REMARK 900 | | | | | | | | | | | | | |
| REMARK 900 | RELATED ENTRIES | | | | | | | | | | | | |
| REMARK 900 | RELATED ID: 2ZTT | | | RELATED DB: PDB | | | | | | | | | |
| DBREF | 3A1G | A | 678 | | 757 UNP | | P03431 | RDRP_I34A1 | | 678 | 757 | | |
| DBREF | 3A1G | B | 1 | | 37 UNP | | P03428 | PB2_I34A1 | | 1 | 37 | | |
| DBREF | 3A1G | C | 678 | | 757 UNP | | P03431 | RDRP_I34A1 | | 678 | 757 | | |
| DBREF | 3A1G | D | 1 | | 37 UNP | | P03428 | PB2_I34A1 | | 1 | 37 | | |
| SEQADV | 3A1G | GLY | | B | −2 UNP | P03428 | | | EXPRESSION TAG | | | | |
| SEQADV | 3A1G | GLY | | B | −1 UNP | P03428 | | | EXPRESSION TAG | | | | |
| SEQADV | 3A1G | SER | | B | 0 UNP | P03428 | | | EXPRESSION TAG | | | | |
| SEQADV | 3A1G | GLY | | D | −2 UNP | P03428 | | | EXPRESSION TAG | | | | |
| SEQADV | 3A1G | GLY | | D | −1 UNP | P03428 | | | EXPRESSION TAG | | | | |
| SEQADV | 3A1G | SER | | D | 0 UNP | P03428 | | | EXPRESSION TAG | | | | |
| SEQ ID NO: 2, wherein the methionine residues are selenomethionine residues | | | | | | | | | | | | | |
| SEQRES | 1 A | 80 | SER | GLN | ARG | GLY | VAL | LEU | GLU | ASP | GLU | GLN | MSE | TYR | GLN |
| SEQRES | 2 A | 80 | ARG | CYS | CYS | ASN | LEU | PHE | GLU | LYS | PHE | PHE | PRO | SER | SER |
| SEQRES | 3 A | 80 | SER | TYR | ARG | ARG | PRO | VAL | GLY | ILE | SER | SER | MSE | VAL | GLU |
| SEQRES | 4 A | 80 | ALA | MSE | VAL | SER | ARG | ALA | ARG | ILE | ASP | ALA | ARG | ILE | ASP |
| SEQRES | 5 A | 80 | PHE | GLU | SER | GLY | ARG | ILE | LYS | LYS | GLU | GLU | PHE | THR | GLU |
| SEQRES | 6 A | 80 | ILE | MSE | LYS | ILE | CYS | SER | THR | ILE | GLU | GLU | LEU | ARG | ARG |
| SEQRES | 7 A | 80 | GLN | LYS | | | | | | | | | | | |
| SEQ ID NO: 21 | | | | | | | | | | | | | | |
| SEQRES | 1 B | 40 | GLY | GLY | SER | MSE | GLU | ARG | ILE | LYS | GLU | LEU | ARG | ASN | LEU |
| SEQRES | 2 B | 40 | MSE | SER | GLN | SER | ARG | THR | ARG | GLU | ILE | LEU | THR | LYS | THR |
| SEQRES | 3 B | 40 | THR | VAL | ASP | HIS | MSE | ALA | ILE | ILE | LYS | LYS | TYR | THR | SER |
| SEQRES | 4 B | 40 | GLY | | | | | | | | | | | | |
| Residues 678-757 of SEQ ID NO: 16, wherein methionine residues are selenomethionine residues | | | | | | | | | | | | | | |
| SEQRES | 1 C | 80 | SER | GLN | ARG | GLY | VAL | LEU | GLU | ASP | GLU | GLN | MSE | TYR | GLN |
| SEQRES | 2 C | 80 | ARG | CYS | CYS | ASN | LEU | PHE | GLU | LYS | PHE | PHE | PRO | SER | SER |
| SEQRES | 3 C | 80 | SER | TYR | ARG | ARG | PRO | VAL | GLY | ILE | SER | SER | MSE | VAL | GLU |
| SEQRES | 4 C | 80 | ALA | MSE | VAL | SER | ARG | ALA | ARG | ILE | ASP | ALA | ARG | ILE | ASP |
| SEQRES | 5 C | 80 | PHE | GLU | SER | GLY | ARG | ILE | LYS | LYS | GLU | GLU | PHE | THR | GLU |
| SEQRES | 6 C | 80 | ILE | MSE | LYS | ILE | CYS | SER | THR | ILE | GLU | GLU | LEU | ARG | ARG |
| SEQRES | 7 C | 80 | GLN | LYS | | | | | | | | | | | |

TABLE 2b-continued

Data of atomic coordinates for accession code 3A1G, which cites accession code 2ZTT

| SEQ ID NO: 21 | | | | | | | | | | | | | | | |
|---|---|---|---|---|---|---|---|---|---|---|---|---|---|---|---|
| SEQRES | 1 | D | 40 | GLY | GLY | SER | MSE | GLU | ARG | ILE | LYS | GLU | LEU | ARG | ASN | LEU |
| SEQRES | 2 | D | 40 | MSE | SER | GLN | SER | ARG | THR | ARG | GLU | ILE | LEU | THR | LYS | THR |
| SEQRES | 3 | D | 40 | THR | VAL | ASP | HIS | MSE | ALA | ILE | ILE | LYS | LYS | TYR | THR | SER |
| SEQRES | 4 | D | 40 | GLY | | | | | | | | | | | | |
| MODRES | 3A1G | MSE | A | 688 | MET | SELENOMETHIONINE | | | | | | | | | | |
| MODRES | 3A1G | MSE | A | 714 | MET | SELENOMETHIONINE | | | | | | | | | | |
| MODRES | 3A1G | MSE | A | 718 | MET | SELENOMETHIONINE | | | | | | | | | | |
| MODRES | 3A1G | MSE | A | 744 | MET | SELENOMETHIONINE | | | | | | | | | | |
| MODRES | 3A1G | MSE | B | 1 | MET | SELENOMETHIONINE | | | | | | | | | | |
| MODRES | 3A1G | MSE | B | 11 | MET | SELENOMETHIONINE | | | | | | | | | | |
| MODRES | 3A1G | MSE | B | 28 | MET | SELENOMETHIONINE | | | | | | | | | | |
| MODRES | 3A1G | MSE | C | 688 | MET | SELENOMETHIONINE | | | | | | | | | | |
| MODRES | 3A1G | MSE | C | 714 | MET | SELENOMETHIONINE | | | | | | | | | | |
| MODRES | 3A1G | MSE | C | 718 | MET | SELENOMETHIONINE | | | | | | | | | | |
| MODRES | 3A1G | MSE | C | 744 | MET | SELENOMETHIONINE | | | | | | | | | | |
| MODRES | 3A1G | MSE | D | 1 | MET | SELENOMETHIONINE | | | | | | | | | | |
| MODRES | 3A1G | MSE | D | 11 | MET | SELENOMETHIONINE | | | | | | | | | | |
| MODRES | 3A1G | MSE | D | 28 | MET | SELENOMETHIONINE | | | | | | | | | | |
| HET | MSE | A | 688 | 8 | | | | | | | | | | | | |
| HET | MSE | A | 714 | 8 | | | | | | | | | | | | |
| HET | MSE | A | 718 | 8 | | | | | | | | | | | | |
| HET | MSE | A | 744 | 8 | | | | | | | | | | | | |
| HET | MSE | B | 1 | 8 | | | | | | | | | | | | |
| HET | MSE | B | 11 | 8 | | | | | | | | | | | | |
| HET | MSE | B | 28 | 8 | | | | | | | | | | | | |
| HET | MSE | C | 688 | 8 | | | | | | | | | | | | |
| HET | MSE | C | 714 | 8 | | | | | | | | | | | | |
| HET | MSE | C | 718 | 8 | | | | | | | | | | | | |
| HET | MSE | C | 744 | 8 | | | | | | | | | | | | |
| HET | MSE | D | 1 | 8 | | | | | | | | | | | | |
| HET | MSE | D | 11 | 8 | | | | | | | | | | | | |
| HET | MSE | D | 28 | 8 | | | | | | | | | | | | |
| HETNAM | MSE SELENOMETHIONINE | | | | | | | | | | | | | | | |
| FORMUL | 1 | MSE | 14 (C5 H11 N O2 SE) | | | | | | | | | | | | | |
| FORMUL | 5 | HOH | *63 (H2 O) | | | | | | | | | | | | | |
| HELIX | 1 | 1 | GLU | A | 686 | PHE | A | 700 | 1 | | | | | 15 | | |
| HELIX | 2 | 2 | SER | A | 713 | SER | A | 732 | 1 | | | | | 20 | | |
| HELIX | 3 | 3 | LYS | A | 736 | GLN | A | 756 | 1 | | | | | 21 | | |
| HELIX | 4 | 4 | GLY | B | −2 | MSE | B | 11 | 1 | | | | | 14 | | |
| HELIX | 5 | 5 | GLN | B | 13 | THR | B | 23 | 1 | | | | | 11 | | |
| HELIX | 6 | 6 | ASP | B | 26 | TYR | B | 34 | 1 | | | | | 9 | | |
| HELIX | 7 | 7 | ASP | C | 685 | PHE | C | 700 | 1 | | | | | 16 | | |
| HELIX | 8 | 8 | SER | C | 713 | SER | C | 732 | 1 | | | | | 20 | | |
| HELIX | 9 | 9 | LYS | C | 736 | GLN | C | 756 | 1 | | | | | 21 | | |
| HELIX | 10 | 10 | GLY | D | −2 | MSE | D | 11 | 1 | | | | | 14 | | |
| HELIX | 11 | 11 | GLN | D | 13 | THR | D | 23 | 1 | | | | | 11 | | |
| HELIX | 12 | 12 | ASP | D | 26 | TYR | D | 34 | 1 | | | | | 9 | | |
| LINK | | C | GLN | A | 687 | | | N | MSE | A | 688 | 1555 | 1555 | 1.34 | | |
| LINK | | C | MSE | A | 688 | | | N | TYR | A | 689 | 1555 | 1555 | 1.34 | | |
| LINK | | C | SER | A | 713 | | | N | MSE | A | 714 | 1555 | 1555 | 1.33 | | |
| LINK | | C | MSE | A | 714 | | | N | VAL | A | 715 | 1555 | 1555 | 1.33 | | |
| LINK | | C | ALA | A | 717 | | | N | MSE | A | 718 | 1555 | 1555 | 1.34 | | |
| LINK | | C | MSE | A | 718 | | | N | VAL | A | 719 | 1555 | 1555 | 1.33 | | |
| LINK | | C | ILE | A | 743 | | | N | MSE | A | 744 | 1555 | 1555 | 1.34 | | |
| LINK | | C | MSE | A | 744 | | | N | LYS | A | 745 | 1555 | 1555 | 1.33 | | |
| LINK | | C | SER | B | 0 | | | N | MSE | B | 1 | 1555 | 1555 | 1.34 | | |
| LINK | | C | MSE | B | 1 | | | N | GLU | B | 2 | 1555 | 1555 | 1.35 | | |
| LINK | | C | LEU | B | 10 | | | N | MSE | B | 11 | 1555 | 1555 | 1.31 | | |
| LINK | | C | MSE | B | 11 | | | N | SER | B | 12 | 1555 | 1555 | 1.33 | | |
| LINK | | C | HIS | B | 27 | | | N | MSE | B | 28 | 1555 | 1555 | 1.35 | | |
| LINK | | C | MSE | B | 28 | | | N | ALA | B | 29 | 1555 | 1555 | 1.33 | | |
| LINK | | C | GLN | C | 687 | | | N | MSE | C | 688 | 1555 | 1555 | 1.34 | | |
| LINK | | C | MSE | C | 688 | | | N | TYR | C | 689 | 1555 | 1555 | 1.33 | | |
| LINK | | C | SER | C | 713 | | | N | MSE | C | 714 | 1555 | 1555 | 1.33 | | |
| LINK | | C | MSE | C | 714 | | | N | VAL | C | 715 | 1555 | 1555 | 1.33 | | |
| LINK | | C | ALA | C | 717 | | | N | MSE | C | 718 | 1555 | 1555 | 1.32 | | |
| LINK | | C | MSE | C | 718 | | | N | VAL | C | 719 | 1555 | 1555 | 1.33 | | |
| LINK | | C | ILE | C | 743 | | | N | MSE | C | 744 | 1555 | 1555 | 1.35 | | |
| LINK | | C | MSE | C | 744 | | | N | LYS | C | 745 | 1555 | 1555 | 1.34 | | |
| LINK | | C | SER | D | 0 | | | N | MSE | D | 1 | 1555 | 1555 | 1.34 | | |
| LINK | | C | MSE | D | 1 | | | N | GLU | D | 2 | 1555 | 1555 | 1.33 | | |
| LINK | | C | LEU | D | 10 | | | N | MSE | D | 11 | 1555 | 1555 | 1.33 | | |
| LINK | | C | MSE | D | 11 | | | N | SER | D | 12 | 1555 | 1555 | 1.34 | | |
| LINK | | C | HIS | D | 27 | | | N | MSE | D | 28 | 1555 | 1555 | 1.35 | | |
| LINK | | C | MSE | D | 28 | | | N | ALA | D | 29 | 1555 | 1555 | 1.33 | | |
| CRYST1 | 60.701 | 69.987 | 61.348 | 90.00 | 97.94 | 90.00 | C 1 2 1 | 8 | | | | | | | | |
| ORIGX1 | 1.000000 | 0.000000 | 0.000000 | 0.00000 | | | | | | | | | | | | |

TABLE 2b-continued

Data of atomic coordinates for accession code 3AIG, which cites accession code 2ZTT

| | | | | | | | | | | |
|---|---|---|---|---|---|---|---|---|---|---|
| ORIGX2 | | 0.000000 | | 1.000000 | | 0.000000 | 0.00000 | | | |
| ORIGX3 | | 0.000000 | | 0.000000 | | 1.000000 | 0.00000 | | | |
| SCALE1 | | 0.016474 | | 0.000000 | | 0.002297 | 0.00000 | | | |
| SCALE2 | | 0.000000 | | 0.014288 | | 0.000000 | 0.00000 | | | |
| SCALES | | 0.000000 | | 0.000000 | | 0.016458 | 0.00000 | | | |
| ATOM | 1 | N | ASP | A | 685 | −23.210 | −22.248 | −1.613 | 1.00 | 52.78 | N |
| ATOM | 2 | CA | ASP | A | 685 | −21.768 | −21.877 | −1.646 | 1.00 | 52.86 | C |
| ATOM | 3 | C | ASP | A | 685 | −21.419 | −21.064 | −0.383 | 1.00 | 52.05 | C |
| ATOM | 4 | O | ASP | A | 685 | −21.296 | −21.661 | 0.694 | 1.00 | 52.38 | O |
| ATOM | 5 | CB | ASP | A | 685 | −21.407 | −21.208 | −2.977 | 1.00 | 52.96 | C |
| ATOM | 6 | CG | ASP | A | 685 | −21.186 | −22.234 | −4.097 | 1.00 | 54.83 | C |
| ATOM | 7 | OD1 | ASP | A | 685 | −21.158 | −21.842 | −5.287 | 1.00 | 57.14 | O |
| ATOM | 8 | OD2 | ASP | A | 685 | −21.053 | −23.452 | −3.798 | 1.00 | 57.14 | O |
| ATOM | 9 | N | GLU | A | 686 | −21.270 | −19.744 | −0.478 | 1.00 | 51.01 | N |
| ATOM | 10 | CA | GLU | A | 686 | −21.410 | −18.932 | 0.744 | 1.00 | 49.09 | C |
| ATOM | 11 | C | GLU | A | 686 | −22.145 | −17.615 | 0.674 | 1.00 | 48.25 | C |
| ATOM | 12 | O | GLU | A | 686 | −21.882 | −16.703 | −0.128 | 1.00 | 47.10 | O |
| ATOM | 13 | CB | GLU | A | 686 | −20.205 | −18.908 | 1.703 | 1.00 | 49.37 | C |
| ATOM | 14 | CG | GLU | A | 686 | −20.397 | −19.725 | 3.034 | 1.00 | 49.70 | C |
| ATOM | 15 | CD | GLU | A | 686 | −21.598 | −19.302 | 3.913 | 1.00 | 52.67 | C |
| ATOM | 16 | OE1 | GLU | A | 686 | −22.734 | −19.804 | 3.710 | 1.00 | 54.77 | O |
| ATOM | 17 | OE2 | GLU | A | 686 | −21.404 | −18.496 | 4.843 | 1.00 | 51.65 | O |
| ATOM | 18 | N | GLN | A | 687 | −23.118 | −17.553 | 1.562 | 1.00 | 47.04 | N |
| ATOM | 19 | CA | GLN | A | 687 | −23.976 | −16.400 | 1.684 | 1.00 | 46.82 | C |
| ATOM | 20 | C | GLN | A | 687 | −23.201 | −15.273 | 2.355 | 1.00 | 45.38 | C |
| ATOM | 21 | O | GLN | A | 687 | −23.554 | −14.123 | 2.159 | 1.00 | 44.69 | O |
| ATOM | 22 | CB | GLN | A | 687 | −25.227 | −16.753 | 2.496 | 1.00 | 47.21 | C |
| ATOM | 23 | CG | GLN | A | 687 | −26.121 | −17.799 | 1.842 | 1.00 | 47.92 | C |
| ATOM | 24 | CD | GLN | A | 687 | −27.219 | −18.326 | 2.770 | 1.00 | 49.03 | C |
| ATOM | 25 | OE1 | GLN | A | 687 | −28.138 | −19.004 | 2.361 | 1.00 | 52.38 | O |
| ATOM | 26 | NE2 | GLN | A | 687 | −27.130 | −18.006 | 4.072 | 1.00 | 50.81 | N |
| HETATM | 27 | N | MSE | A | 688 | −22.166 | −15.606 | 3.134 | 1.00 | 44.36 | N |
| HETATM | 28 | CA | MSE | A | 688 | −21.271 | −14.584 | 3.724 | 1.00 | 45.91 | C |
| HETATM | 29 | C | MSE | A | 688 | −20.522 | −13.814 | 2.641 | 1.00 | 42.77 | C |
| HETATM | 30 | O | MSE | A | 688 | −20.504 | −12.593 | 2.662 | 1.00 | 42.07 | O |
| HETATM | 31 | CB | MSE | A | 688 | −20.212 | −15.171 | 4.630 | 1.00 | 44.99 | C |
| HETATM | 32 | CG | MSE | A | 688 | −20.645 | −16.197 | 5.602 | 1.00 | 48.41 | C |
| HETATM | 33 | SE | MSE | A | 688 | −19.861 | −15.648 | 7.237 | 1.00 | 56.79 | SE |
| HETATM | 34 | CE | MSE | A | 688 | −21.339 | −14.432 | 7.632 | 1.00 | 46.39 | C |
| ATOM | 35 | N | TYR | A | 689 | −19.887 | −14.534 | 1.713 | 1.00 | 41.05 | N |
| ATOM | 36 | CA | TYR | A | 689 | −19.286 | −13.887 | 0.534 | 1.00 | 38.70 | C |
| ATOM | 37 | C | TYR | A | 689 | −20.356 | −13.103 | −0.249 | 1.00 | 37.24 | C |
| ATOM | 38 | O | TYR | A | 689 | −20.083 | −12.004 | −0.730 | 1.00 | 34.74 | O |
| ATOM | 39 | CB | TYR | A | 689 | −18.527 | −14.902 | −0.367 | 1.00 | 39.73 | C |
| ATOM | 40 | CG | TYR | A | 689 | −17.303 | −15.611 | 0.262 | 1.00 | 40.98 | C |
| ATOM | 41 | CD1 | TYR | A | 689 | −16.019 | −15.074 | 0.171 | 1.00 | 41.86 | C |
| ATOM | 42 | CD2 | TYR | A | 689 | −17.442 | −16.837 | 0.897 | 1.00 | 43.78 | C |
| ATOM | 43 | CE1 | TYR | A | 689 | −14.898 | −15.743 | 0.720 | 1.00 | 44.40 | C |
| ATOM | 44 | CE2 | TYR | A | 689 | −16.343 | −17.516 | 1.454 | 1.00 | 44.16 | C |
| ATOM | 45 | CZ | TYR | A | 689 | −15.080 | −16.964 | 1.370 | 1.00 | 43.87 | C |
| ATOM | 46 | OH | TYR | A | 689 | −14.017 | −17.654 | 1.932 | 1.00 | 44.94 | O |
| ATOM | 47 | N | GLN | A | 690 | −21.580 | −13.638 | −0.355 | 1.00 | 36.78 | N |
| ATOM | 48 | CA | GLN | A | 690 | −22.662 | −12.939 | −1.048 | 1.00 | 36.56 | C |
| ATOM | 49 | C | GLN | A | 690 | −23.071 | −11.670 | −0.293 | 1.00 | 35.17 | C |
| ATOM | 50 | O | GLN | A | 690 | −23.352 | −10.650 | −0.911 | 1.00 | 34.27 | O |
| ATOM | 51 | CB | GLN | A | 690 | −23.925 | −13.824 | −1.276 | 1.00 | 38.14 | C |
| ATOM | 52 | CG | GLN | A | 690 | −24.908 | −13.280 | −2.343 | 1.00 | 42.65 | C |
| ATOM | 53 | CD | GLN | A | 690 | −24.300 | −13.214 | −3.758 | 1.00 | 48.96 | C |
| ATOM | 54 | OE1 | GLN | A | 690 | −24.429 | −12.204 | −4.468 | 1.00 | 50.33 | O |
| ATOM | 55 | NE2 | GLN | A | 690 | −23.616 | −14.288 | −4.157 | 1.00 | 50.10 | N |
| ATOM | 56 | N | ARG | A | 691 | −23.093 | −11.744 | 1.032 | 1.00 | 33.77 | N |
| ATOM | 57 | CA | ARG | A | 691 | −23.377 | −10.545 | 1.829 | 1.00 | 33.27 | C |
| ATOM | 58 | C | ARG | A | 691 | −22.321 | −9.444 | 1.589 | 1.00 | 31.63 | C |
| ATOM | 59 | O | ARG | A | 691 | −22.654 | −8.247 | 1.522 | 1.00 | 31.84 | O |
| ATOM | 60 | CB | ARG | A | 691 | −23.401 | −10.852 | 3.306 | 1.00 | 33.58 | C |
| ATOM | 61 | CG | ARG | A | 691 | −23.988 | −9.690 | 4.101 | 1.00 | 37.22 | C |
| ATOM | 62 | CD | ARG | A | 691 | −24.604 | −10.120 | 5.408 | 1.00 | 42.44 | C |
| ATOM | 63 | NE | ARG | A | 691 | −25.491 | −9.067 | 5.906 | 1.00 | 47.39 | N |
| ATOM | 64 | CZ | ARG | A | 691 | −26.335 | −9.213 | 6.925 | 1.00 | 50.29 | C |
| ATOM | 65 | NH1 | ARG | A | 691 | −26.411 | −10.364 | 7.584 | 1.00 | 51.18 | N |
| ATOM | 66 | NH2 | ARG | A | 691 | −27.106 | −8.201 | 7.292 | 1.00 | 53.64 | N |
| ATOM | 67 | N | CYS | A | 692 | −21.064 | −9.852 | 1.559 | 1.00 | 30.31 | N |
| ATOM | 68 | CA | CYS | A | 692 | −20.007 | −8.855 | 1.308 | 1.00 | 28.91 | C |
| ATOM | 69 | C | CYS | A | 692 | −20.159 | −8.307 | −0.099 | 1.00 | 28.68 | C |
| ATOM | 70 | O | CYS | A | 692 | −20.064 | −7.098 | −0.315 | 1.00 | 28.25 | O |
| ATOM | 71 | CB | CYS | A | 692 | −18.632 | −9.462 | 1.542 | 1.00 | 27.82 | C |
| ATOM | 72 | SG | CYS | A | 692 | −18.374 | −9.983 | 3.244 | 1.00 | 30.05 | S |
| ATOM | 73 | N | CYS | A | 693 | −20.450 | −9.181 | −1.062 | 1.00 | 29.22 | N |

TABLE 2b-continued

Data of atomic coordinates for accession code 3AIG, which cites accession code 2ZTT

| ATOM | 74 | CA | CYS | A | 693 | −20.504 | −8.741 | −2.471 | 1.00 | 31.29 | C |
|---|---|---|---|---|---|---|---|---|---|---|---|
| ATOM | 75 | C | CYS | A | 693 | −21.658 | −7.825 | −2.705 | 1.00 | 30.09 | C |
| ATOM | 76 | O | CYS | A | 693 | −21.547 | −6.804 | −3.406 | 1.00 | 31.32 | O |
| ATOM | 77 | CB | CYS | A | 693 | −20.574 | −9.944 | −3.435 | 1.00 | 31.28 | C |
| ATOM | 78 | SG | CYS | A | 693 | −19.006 | −10.571 | −3.738 | 1.00 | 42.70 | S |
| ATOM | 79 | N | ASN | A | 694 | −22.782 | −8.163 | −2.075 | 1.00 | 31.32 | N |
| ATOM | 80 | CA | ASN | A | 694 | −23.970 | −7.360 | −2.132 | 1.00 | 31.02 | C |
| ATOM | 81 | C | ASN | A | 694 | −23.768 | −5.964 | −1.580 | 1.00 | 30.36 | C |
| ATOM | 82 | O | ASN | A | 694 | −24.311 | −4.991 | −2.122 | 1.00 | 31.27 | O |
| ATOM | 83 | CB | ASN | A | 694 | −25.113 | −8.022 | −1.354 | 1.00 | 33.01 | C |
| ATOM | 84 | CG | ASN | A | 694 | −25.684 | −9.242 | −2.091 | 1.00 | 36.49 | C |
| ATOM | 85 | OD1 | ASN | A | 694 | −25.440 | −9.423 | −3.281 | 1.00 | 40.87 | O |
| ATOM | 86 | ND2 | ASN | A | 694 | −26.424 | −10.062 | −1.385 | 1.00 | 38.87 | N |
| ATOM | 87 | N | LEU | A | 695 | −23.042 | −5.892 | −0.463 | 1.00 | 29.56 | N |
| ATOM | 88 | CA | LEU | A | 695 | −22.712 | −4.579 | 0.144 | 1.00 | 27.96 | C |
| ATOM | 89 | C | LEU | A | 695 | −21.805 | −3.752 | −0.755 | 1.00 | 27.53 | C |
| ATOM | 90 | O | LEU | A | 695 | −21.980 | −2.529 | −0.893 | 1.00 | 26.91 | O |
| ATOM | 91 | CB | LEU | A | 695 | −22.109 | −4.743 | 1.527 | 1.00 | 28.06 | C |
| ATOM | 92 | CG | LEU | A | 695 | −21.795 | −3.414 | 2.238 | 1.00 | 29.00 | C |
| ATOM | 93 | CD1 | LEU | A | 695 | −23.145 | −2.687 | 2.415 | 1.00 | 30.25 | C |
| ATOM | 94 | CD2 | LEU | A | 695 | −21.195 | −3.684 | 3.560 | 1.00 | 31.18 | C |
| ATOM | 95 | N | PHE | A | 696 | −20.788 | −4.395 | −1.306 | 1.00 | 27.90 | N |
| ATOM | 96 | CA | PHE | A | 696 | −19.906 | −3.727 | −2.246 | 1.00 | 28.04 | C |
| ATOM | 97 | C | PHE | A | 696 | −20.625 | −2.989 | −3.380 | 1.00 | 29.35 | C |
| ATOM | 98 | O | PHE | A | 696 | −20.298 | −1.845 | −3.704 | 1.00 | 28.33 | O |
| ATOM | 99 | CB | PHE | A | 696 | −18.856 | −4.725 | −2.753 | 1.00 | 26.70 | C |
| ATOM | 100 | CG | PHE | A | 696 | −17.731 | −4.075 | −3.477 | 1.00 | 26.96 | C |
| ATOM | 101 | CD1 | PHE | A | 696 | −16.593 | −3.673 | −2.763 | 1.00 | 25.19 | C |
| ATOM | 102 | CD2 | PHE | A | 696 | −17.789 | −3.898 | −4.862 | 1.00 | 29.28 | C |
| ATOM | 103 | CE1 | PHE | A | 696 | −15.522 | −3.062 | −3.424 | 1.00 | 28.78 | C |
| ATOM | 104 | CE2 | PHE | A | 696 | −16.715 | −3.276 | −5.546 | 1.00 | 25.79 | C |
| ATOM | 105 | CZ | PHE | A | 696 | −15.562 | −2.876 | −4.777 | 1.00 | 26.81 | C |
| ATOM | 106 | N | GLU | A | 697 | −21.658 | −3.625 | −3.941 | 1.00 | 29.66 | N |
| ATOM | 107 | CA | GLU | A | 697 | −22.491 | −3.042 | −4.969 | 1.00 | 32.15 | C |
| ATOM | 108 | C | GLU | A | 697 | −23.270 | −1.787 | −4.547 | 1.00 | 31.09 | C |
| ATOM | 109 | O | GLU | A | 697 | −23.672 | −1.010 | −5.402 | 1.00 | 32.00 | O |
| ATOM | 110 | CB | GLU | A | 697 | −23.399 | −4.142 | −5.529 | 1.00 | 32.09 | C |
| ATOM | 111 | CG | GLU | A | 697 | −22.717 | −5.103 | −6.555 | 1.00 | 39.03 | C |
| ATOM | 112 | CD | GLU | A | 697 | −21.193 | −5.258 | −6.421 | 1.00 | 44.99 | C |
| ATOM | 113 | OE1 | GLU | A | 697 | −20.453 | −4.381 | −6.958 | 1.00 | 48.10 | O |
| ATOM | 114 | OE2 | GLU | A | 697 | −20.725 | −6.270 | −5.811 | 1.00 | 48.61 | O |
| ATOM | 115 | N | LYS | A | 698 | −23.458 | −1.571 | −3.236 | 1.00 | 29.27 | N |
| ATOM | 116 | CA | LYS | A | 698 | −24.016 | −0.335 | −2.705 | 1.00 | 28.82 | C |
| ATOM | 117 | C | LYS | A | 698 | −23.031 | 0.818 | −2.767 | 1.00 | 26.73 | C |
| ATOM | 118 | O | LYS | A | 698 | −23.451 | 1.964 | −2.769 | 1.00 | 26.15 | O |
| ATOM | 119 | CB | LYS | A | 698 | −24.492 | −0.481 | −1.266 | 1.00 | 28.37 | C |
| ATOM | 120 | CG | LYS | A | 698 | −25.378 | −1.709 | −0.951 | 1.00 | 33.64 | C |
| ATOM | 121 | CD | LYS | A | 698 | −25.854 | −1.561 | 0.488 | 1.00 | 36.84 | C |
| ATOM | 122 | CE | LYS | A | 698 | −26.964 | −2.518 | 0.925 | 1.00 | 42.83 | C |
| ATOM | 123 | NZ | LYS | A | 698 | −27.227 | −2.291 | 2.431 | 1.00 | 43.76 | N |
| ATOM | 124 | N | PHE | A | 699 | −21.728 | 0.513 | −2.803 | 1.00 | 25.92 | N |
| ATOM | 125 | CA | PHE | A | 699 | −20.707 | 1.566 | −2.998 | 1.00 | 27.12 | C |
| ATOM | 126 | C | PHE | A | 699 | −20.274 | 1.730 | −4.442 | 1.00 | 28.46 | C |
| ATOM | 127 | O | PHE | A | 699 | −19.876 | 2.818 | −4.853 | 1.00 | 27.91 | O |
| ATOM | 128 | CB | PHE | A | 699 | −19.478 | 1.225 | −2.178 | 1.00 | 25.00 | C |
| ATOM | 129 | CG | PHE | A | 699 | −19.729 | 1.234 | −0.712 | 1.00 | 25.91 | C |
| ATOM | 130 | CD1 | PHE | A | 699 | −19.532 | 2.403 | 0.007 | 1.00 | 25.11 | C |
| ATOM | 131 | CD2 | PHE | A | 699 | −20.218 | 0.093 | −0.063 | 1.00 | 24.97 | C |
| ATOM | 132 | CE1 | PHE | A | 699 | −19.788 | 2.473 | 1.370 | 1.00 | 22.78 | C |
| ATOM | 133 | CE2 | PHE | A | 699 | −20.477 | 0.134 | 1.310 | 1.00 | 25.04 | C |
| ATOM | 134 | CZ | PHE | A | 699 | −20.229 | 1.313 | 2.023 | 1.00 | 24.18 | C |
| ATOM | 135 | N | PHE | A | 700 | −20.333 | 0.627 | −5.199 | 1.00 | 30.34 | N |
| ATOM | 136 | CA | PHE | A | 700 | −19.933 | 0.635 | −6.587 | 1.00 | 33.99 | C |
| ATOM | 137 | C | PHE | A | 700 | −21.027 | −0.007 | −7.475 | 1.00 | 36.82 | C |
| ATOM | 138 | O | PHE | A | 700 | −20.874 | −1.145 | −7.908 | 1.00 | 37.84 | O |
| ATOM | 139 | CB | PHE | A | 700 | −18.562 | −0.050 | −6.746 | 1.00 | 32.80 | C |
| ATOM | 140 | CG | PHE | A | 700 | −17.431 | 0.643 | −6.004 | 1.00 | 33.68 | C |
| ATOM | 141 | CD1 | PHE | A | 700 | −16.752 | 1.713 | −6.578 | 1.00 | 33.84 | C |
| ATOM | 142 | CD2 | PHE | A | 700 | −17.027 | 0.206 | −4.724 | 1.00 | 32.98 | C |
| ATOM | 143 | CE1 | PHE | A | 700 | −15.718 | 2.375 | −5.899 | 1.00 | 33.18 | C |
| ATOM | 144 | CE2 | PHE | A | 700 | −16.003 | 0.854 | −4.049 | 1.00 | 30.68 | C |
| ATOM | 145 | CZ | PHE | A | 700 | −15.342 | 1.927 | −4.633 | 1.00 | 31.29 | C |
| ATOM | 146 | N | PRO | A | 701 | −22.147 | 0.712 | −7.694 | 1.00 | 40.25 | N |
| ATOM | 147 | CA | PRO | A | 701 | −23.334 | 0.209 | −8.395 | 1.00 | 43.45 | C |
| ATOM | 148 | C | PRO | A | 701 | −23.098 | −0.427 | −9.748 | 1.00 | 46.54 | C |
| ATOM | 149 | O | PRO | A | 701 | −22.030 | −0.281 | −10.350 | 1.00 | 47.25 | O |
| ATOM | 150 | CB | PRO | A | 701 | −24.201 | 1.458 | −8.561 | 1.00 | 42.93 | C |
| ATOM | 151 | CG | PRO | A | 701 | −23.885 | 2.279 | −7.416 | 1.00 | 41.74 | C |

TABLE 2b-continued

Data of atomic coordinates for accession code 3AIG, which cites accession code 2ZTT

| ATOM | 152 | CD | PRO | A | 701 | −22.373 | 2.089 | −7.224 | 1.00 | 40.15 | C |
|---|---|---|---|---|---|---|---|---|---|---|---|
| ATOM | 153 | N | SER | A | 702 | −24.119 | −1.159 | −10.177 | 1.00 | 49.95 | N |
| ATOM | 154 | CA | SER | A | 702 | −24.216 | −1.760 | −11.501 | 1.00 | 53.18 | C |
| ATOM | 155 | C | SER | A | 702 | −24.471 | −0.705 | −12.595 | 1.00 | 54.38 | C |
| ATOM | 156 | O | SER | A | 702 | −24.337 | −1.002 | −13.787 | 1.00 | 55.20 | O |
| ATOM | 157 | CB | SER | A | 702 | −25.303 | −2.844 | −11.501 | 1.00 | 53.18 | C |
| ATOM | 158 | OG | SER | A | 702 | −25.046 | −3.811 | −10.484 | 1.00 | 55.62 | O |
| ATOM | 159 | N | SER | A | 703 | −24.840 | 0.514 | −12.187 | 1.00 | 56.27 | N |
| ATOM | 160 | CA | SER | A | 703 | −24.587 | 1.714 | −12.990 | 1.00 | 57.91 | C |
| ATOM | 161 | C | SER | A | 703 | −23.056 | 1.764 | −13.120 | 1.00 | 58.84 | C |
| ATOM | 162 | O | SER | A | 703 | −22.388 | 2.762 | −12.810 | 1.00 | 59.06 | O |
| ATOM | 163 | CB | SER | A | 703 | −25.153 | 2.953 | −12.286 | 1.00 | 58.10 | C |
| ATOM | 164 | OG | SER | A | 703 | −24.628 | 4.158 | −12.824 | 1.00 | 58.42 | O |
| ATOM | 165 | N | SER | A | 704 | −22.547 | 0.657 | −13.662 | 1.00 | 60.05 | N |
| ATOM | 166 | CA | SER | A | 704 | −21.243 | 0.059 | −13.348 | 1.00 | 60.74 | C |
| ATOM | 167 | C | SER | A | 704 | −19.955 | 0.884 | −13.331 | 1.00 | 61.19 | C |
| ATOM | 168 | O | SER | A | 704 | −19.129 | 0.685 | −12.425 | 1.00 | 61.62 | O |
| ATOM | 169 | CB | SER | A | 704 | −21.029 | −1.178 | −14.221 | 1.00 | 60.70 | C |
| ATOM | 170 | OG | SER | A | 704 | −19.652 | −1.505 | −14.286 | 1.00 | 61.11 | O |
| ATOM | 171 | N | TYR | A | 705 | −19.779 | 1.777 | −14.308 | 1.00 | 61.27 | N |
| ATOM | 172 | CA | TYR | A | 705 | −18.439 | 2.300 | −14.636 | 1.00 | 61.56 | C |
| ATOM | 173 | C | TYR | A | 705 | −17.985 | 3.605 | −13.946 | 1.00 | 60.95 | C |
| ATOM | 174 | O | TYR | A | 705 | −17.644 | 4.589 | −14.600 | 1.00 | 61.64 | O |
| ATOM | 175 | CB | TYR | A | 705 | −18.237 | 2.368 | −16.161 | 1.00 | 62.03 | C |
| ATOM | 176 | CG | TYR | A | 705 | −16.946 | 1.711 | −16.641 | 1.00 | 62.80 | C |
| ATOM | 177 | CD1 | TYR | A | 705 | −15.942 | 2.462 | −17.263 | 1.00 | 63.09 | C |
| ATOM | 178 | CD2 | TYR | A | 705 | −16.737 | 0.331 | −16.478 | 1.00 | 63.10 | C |
| ATOM | 179 | CE1 | TYR | A | 705 | −14.758 | 1.861 | −17.701 | 1.00 | 62.96 | C |
| ATOM | 180 | CE2 | TYR | A | 705 | −15.557 | −0.283 | −16.914 | 1.00 | 62.81 | C |
| ATOM | 181 | CZ | TYR | A | 705 | −14.573 | 0.487 | −17.523 | 1.00 | 63.18 | C |
| ATOM | 182 | OH | TYR | A | 705 | −13.406 | −0.114 | −17.958 | 1.00 | 63.67 | O |
| ATOM | 183 | N | ARG | A | 706 | −17.977 | 3.596 | −12.620 | 1.00 | 60.04 | N |
| ATOM | 184 | CA | ARG | A | 706 | −17.201 | 4.571 | −11.852 | 1.00 | 58.80 | C |
| ATOM | 185 | C | ARG | A | 706 | −16.285 | 3.716 | −10.966 | 1.00 | 57.23 | C |
| ATOM | 186 | O | ARG | A | 706 | −16.178 | 3.914 | −9.755 | 1.00 | 57.15 | O |
| ATOM | 187 | CB | ARG | A | 706 | −18.108 | 5.524 | −11.048 | 1.00 | 59.20 | C |
| ATOM | 188 | CG | ARG | A | 706 | −18.507 | 5.043 | −9.652 | 1.00 | 60.76 | C |
| ATOM | 189 | CD | ARG | A | 706 | −19.752 | 4.176 | −9.671 | 1.00 | 62.26 | C |
| ATOM | 190 | NE | ARG | A | 706 | −20.942 | 4.956 | −9.344 | 1.00 | 64.47 | N |
| ATOM | 191 | CZ | ARG | A | 706 | −22.174 | 4.649 | −9.732 | 1.00 | 65.71 | C |
| ATOM | 192 | NH1 | ARG | A | 706 | −22.383 | 3.577 | −10.486 | 1.00 | 66.72 | N |
| ATOM | 193 | NH2 | ARG | A | 706 | −23.197 | 5.419 | −9.376 | 1.00 | 65.75 | N |
| ATOM | 194 | N | ARG | A | 707 | −15.621 | 2.773 | −11.631 | 1.00 | 54.84 | N |
| ATOM | 195 | CA | ARG | A | 707 | −14.962 | 1.605 | −11.036 | 1.00 | 52.78 | C |
| ATOM | 196 | C | ARG | A | 707 | −14.016 | 1.800 | −9.836 | 1.00 | 50.90 | C |
| ATOM | 197 | O | ARG | A | 707 | −13.333 | 2.820 | −9.721 | 1.00 | 50.71 | O |
| ATOM | 198 | CB | ARG | A | 707 | −14.229 | 0.835 | −12.146 | 1.00 | 53.30 | C |
| ATOM | 199 | CG | ARG | A | 707 | −15.080 | 0.588 | −13.392 | 1.00 | 54.59 | C |
| ATOM | 200 | CD | ARG | A | 707 | −16.133 | −0.507 | −13.186 | 1.00 | 57.02 | C |
| ATOM | 201 | NE | ARG | A | 707 | −15.574 | −1.851 | −13.306 | 1.00 | 58.65 | N |
| ATOM | 202 | CZ | ARG | A | 707 | −16.278 | −2.980 | −13.233 | 1.00 | 59.14 | C |
| ATOM | 203 | NH1 | ARG | A | 707 | −17.591 | −2.954 | −13.038 | 1.00 | 60.23 | N |
| ATOM | 204 | NH2 | ARG | A | 707 | −15.662 | −4.148 | −13.359 | 1.00 | 59.60 | N |
| ATOM | 205 | N | PRO | A | 708 | −13.970 | 0.798 | −8.936 | 1.00 | 48.46 | N |
| ATOM | 206 | CA | PRO | A | 708 | −13.003 | 0.773 | −7.852 | 1.00 | 46.66 | C |
| ATOM | 207 | C | PRO | A | 708 | −11.642 | 0.312 | −8.354 | 1.00 | 45.31 | C |
| ATOM | 208 | O | PRO | A | 708 | −11.568 | −0.329 | −9.404 | 1.00 | 45.04 | O |
| ATOM | 209 | CB | PRO | A | 708 | −13.572 | −0.296 | −6.914 | 1.00 | 46.66 | C |
| ATOM | 210 | CG | PRO | A | 708 | −14.342 | −1.195 | −7.799 | 1.00 | 47.16 | C |
| ATOM | 211 | CD | PRO | A | 708 | −14.865 | −0.373 | −8.915 | 1.00 | 48.63 | C |
| ATOM | 212 | N | VAL | A | 709 | −10.583 | 0.587 | −7.597 | 1.00 | 43.44 | N |
| ATOM | 213 | CA | VAL | A | 709 | −9.269 | 0.031 | −7.943 | 1.00 | 42.32 | C |
| ATOM | 214 | C | VAL | A | 709 | −9.152 | −1.488 | −7.654 | 1.00 | 41.01 | C |
| ATOM | 215 | O | VAL | A | 709 | −9.321 | −1.962 | −6.513 | 1.00 | 40.36 | O |
| ATOM | 216 | CB | VAL | A | 709 | −8.012 | 0.936 | −7.490 | 1.00 | 43.03 | C |
| ATOM | 217 | CG1 | VAL | A | 709 | −8.410 | 2.134 | −6.630 | 1.00 | 44.12 | C |
| ATOM | 218 | CG2 | VAL | A | 709 | −6.878 | 0.128 | −6.860 | 1.00 | 41.19 | C |
| ATOM | 219 | N | GLY | A | 710 | −8.882 | −2.237 | −8.723 | 1.00 | 39.19 | N |
| ATOM | 220 | CA | GLY | A | 710 | −8.806 | −3.690 | −8.668 | 1.00 | 36.97 | C |
| ATOM | 221 | C | GLY | A | 710 | −7.882 | −4.230 | −7.592 | 1.00 | 35.16 | C |
| ATOM | 222 | O | GLY | A | 710 | −8.181 | −5.238 | −6.962 | 1.00 | 34.76 | O |
| ATOM | 223 | N | ILE | A | 711 | −6.769 | −3.566 | −7.346 | 1.00 | 34.30 | N |
| ATOM | 224 | CA | ILE | A | 711 | −5.828 | −4.100 | −6.380 | 1.00 | 34.81 | C |
| ATOM | 225 | C | ILE | A | 711 | −6.086 | −3.721 | −4.903 | 1.00 | 33.52 | C |
| ATOM | 226 | O | ILE | A | 711 | −5.393 | −4.200 | −4.011 | 1.00 | 33.75 | O |
| ATOM | 227 | CB | ILE | A | 711 | −4.334 | −3.873 | −6.829 | 1.00 | 36.03 | C |
| ATOM | 228 | CG1 | ILE | A | 711 | −3.915 | −2.420 | −6.625 | 1.00 | 39.00 | C |
| ATOM | 229 | CG2 | ILE | A | 711 | −4.154 | −4.361 | −8.289 | 1.00 | 37.52 | C |

TABLE 2b-continued

Data of atomic coordinates for accession code 3AIG, which cites accession code 2ZTT

| ATOM | 230 | CD1 | ILE | A | 711 | −2.401 | −2.252 | −6.436 | 1.00 | 40.34 | C |
|---|---|---|---|---|---|---|---|---|---|---|---|
| ATOM | 231 | N | SER | A | 712 | −7.074 | −2.858 | −4.659 | 1.00 | 31.69 | N |
| ATOM | 232 | CA | SER | A | 712 | −7.497 | −2.513 | −3.304 | 1.00 | 30.89 | C |
| ATOM | 233 | C | SER | A | 712 | −8.286 | −3.656 | −2.688 | 1.00 | 27.79 | C |
| ATOM | 234 | O | SER | A | 712 | −8.983 | −4.356 | −3.407 | 1.00 | 26.57 | O |
| ATOM | 235 | CB | SER | A | 712 | −8.407 | −1.274 | −3.285 | 1.00 | 30.86 | C |
| ATOM | 236 | OG | SER | A | 712 | −7.671 | −0.096 | −3.584 | 1.00 | 37.69 | O |
| ATOM | 237 | N | SER | A | 713 | −8.147 | −3.828 | −1.378 | 1.00 | 26.91 | N |
| ATOM | 238 | CA | SER | A | 713 | −9.075 | −4.660 | −0.609 | 1.00 | 26.06 | C |
| ATOM | 239 | C | SER | A | 713 | −10.491 | −4.079 | −0.757 | 1.00 | 26.02 | C |
| ATOM | 240 | O | SER | A | 713 | −10.690 | −2.872 | −1.025 | 1.00 | 25.47 | O |
| ATOM | 241 | CB | SER | A | 713 | −8.638 | −4.791 | 0.873 | 1.00 | 26.17 | C |
| ATOM | 242 | OG | SER | A | 713 | −8.769 | −3.537 | 1.598 | 1.00 | 28.34 | O |
| HETATM | 243 | N | MSE | A | 714 | −11.490 | −4.932 | −0.562 | 1.00 | 23.64 | N |
| HETATM | 244 | CA | MSE | A | 714 | −12.902 | −4.529 | −0.648 | 1.00 | 24.33 | C |
| HETATM | 245 | C | MSE | A | 714 | −13.179 | −3.399 | 0.323 | 1.00 | 22.84 | C |
| HETATM | 246 | O | MSE | A | 714 | −13.696 | −2.394 | −0.101 | 1.00 | 22.23 | O |
| HETATM | 247 | CB | MSE | A | 714 | −13.783 | −5.748 | −0.380 | 1.00 | 23.61 | C |
| HETATM | 248 | CG | MSE | A | 714 | −13.661 | −6.770 | −1.493 | 1.00 | 20.65 | C |
| HETATM | 249 | SE | MSE | A | 714 | −14.853 | −8.274 | −0.970 | 1.00 | 31.68 | SE |
| HETATM | 250 | CE | MSE | A | 714 | −16.547 | −7.437 | −1.247 | 1.00 | 27.25 | C |
| ATOM | 251 | N | VAL | A | 715 | −12.757 | −3.537 | 1.580 | 1.00 | 21.91 | N |
| ATOM | 252 | CA | VAL | A | 715 | −13.044 | −2.539 | 2.622 | 1.00 | 22.50 | C |
| ATOM | 253 | C | VAL | A | 715 | −12.289 | −1.218 | 2.292 | 1.00 | 23.31 | C |
| ATOM | 254 | O | VAL | A | 715 | −12.834 | −0.115 | 2.466 | 1.00 | 23.19 | O |
| ATOM | 255 | CB | VAL | A | 715 | −12.704 | −3.042 | 4.043 | 1.00 | 22.70 | C |
| ATOM | 256 | CG1 | VAL | A | 715 | −11.223 | −3.325 | 4.200 | 1.00 | 23.42 | C |
| ATOM | 257 | CG2 | VAL | A | 715 | −13.176 | −2.056 | 5.107 | 1.00 | 24.03 | C |
| ATOM | 258 | N | GLU | A | 716 | −11.050 | −1.308 | 1.815 | 1.00 | 23.32 | N |
| ATOM | 259 | CA | GLU | A | 716 | −10.413 | −0.055 | 1.454 | 1.00 | 26.13 | C |
| ATOM | 260 | C | GLU | A | 716 | −11.099 | 0.748 | 0.350 | 1.00 | 24.41 | C |
| ATOM | 261 | O | GLU | A | 716 | −11.239 | 1.969 | 0.491 | 1.00 | 24.20 | O |
| ATOM | 262 | CB | GLU | A | 716 | −8.887 | −0.182 | 1.261 | 1.00 | 25.92 | C |
| ATOM | 263 | CG | GLU | A | 716 | −8.320 | −0.986 | 0.150 | 1.00 | 31.26 | C |
| ATOM | 264 | CD | GLU | A | 716 | −6.788 | −1.065 | 0.297 | 1.00 | 32.93 | C |
| ATOM | 265 | OE1 | GLU | A | 716 | −6.269 | −2.209 | 0.436 | 1.00 | 40.96 | O |
| ATOM | 266 | OE2 | GLU | A | 716 | −6.152 | 0.025 | 0.331 | 1.00 | 39.74 | O |
| ATOM | 267 | N | ALA | A | 717 | −11.595 | 0.057 | −0.693 | 1.00 | 23.98 | N |
| ATOM | 268 | CA | ALA | A | 717 | −12.382 | 0.654 | −1.748 | 1.00 | 23.52 | C |
| ATOM | 269 | C | ALA | A | 717 | −13.654 | 1.281 | −1.242 | 1.00 | 22.65 | C |
| ATOM | 270 | O | ALA | A | 717 | −13.969 | 2.414 | −1.617 | 1.00 | 22.90 | O |
| ATOM | 271 | CB | ALA | A | 717 | −12.731 | 0.388 | −2.817 | 1.00 | 23.87 | C |
| HETATM | 272 | N | MSE | A | 718 | −14.375 | 0.533 | −0.401 | 1.00 | 21.84 | N |
| HETATM | 273 | CA | MSE | A | 718 | −15.621 | 1.023 | 0.104 | 1.00 | 22.16 | C |
| HETATM | 274 | C | MSE | A | 718 | −15.464 | 2.210 | 0.999 | 1.00 | 20.50 | C |
| HETATM | 275 | O | MSE | A | 718 | −16.176 | 3.181 | 0.844 | 1.00 | 19.98 | O |
| HETATM | 276 | CB | MSE | A | 718 | −16.381 | −0.112 | 0.790 | 1.00 | 21.26 | C |
| HETATM | 277 | CG | MSE | A | 718 | −16.536 | −1.347 | −0.156 | 1.00 | 20.20 | C |
| HETATM | 278 | SE | MSE | A | 718 | −16.771 | −3.010 | 0.940 | 1.00 | 34.67 | SE |
| HETATM | 279 | CE | MSE | A | 718 | −18.308 | −2.429 | 0.921 | 1.00 | 10.24 | C |
| ATOM | 280 | N | VAL | A | 719 | −14.448 | 2.200 | 1.857 | 1.00 | 20.51 | N |
| ATOM | 281 | CA | VAL | A | 719 | −14.255 | 3.346 | 2.735 | 1.00 | 21.38 | C |
| ATOM | 282 | C | VAL | A | 719 | −13.832 | 4.586 | 1.933 | 1.00 | 21.54 | C |
| ATOM | 283 | O | VAL | A | 719 | −14.269 | 5.703 | 2.228 | 1.00 | 21.39 | O |
| ATOM | 284 | CB | VAL | A | 719 | −13.222 | 3.032 | 3.796 | 1.00 | 20.50 | C |
| ATOM | 285 | CG1 | VAL | A | 719 | −12.779 | 4.343 | 4.544 | 1.00 | 25.34 | C |
| ATOM | 286 | CG2 | VAL | A | 719 | −13.820 | 1.996 | 4.807 | 1.00 | 21.95 | C |
| ATOM | 287 | N | SER | A | 720 | −12.934 | 4.407 | 0.966 | 1.00 | 22.70 | N |
| ATOM | 288 | CA | SER | A | 720 | −12.546 | 5.517 | 0.103 | 1.00 | 22.72 | C |
| ATOM | 289 | C | SER | A | 720 | −13.742 | 6.134 | −0.604 | 1.00 | 22.24 | C |
| ATOM | 290 | O | SER | A | 720 | −13.939 | 7.354 | −0.553 | 1.00 | 23.03 | O |
| ATOM | 291 | CB | SER | A | 720 | −11.498 | 5.069 | −0.912 | 1.00 | 23.51 | C |
| ATOM | 292 | OG | SER | A | 720 | −11.214 | 6.189 | −1.730 | 1.00 | 30.24 | O |
| ATOM | 293 | N | ARG | A | 721 | −14.547 | 5.293 | −1.228 | 1.00 | 22.43 | N |
| ATOM | 294 | CA | ARG | A | 721 | −15.793 | 5.755 | −1.874 | 1.00 | 21.30 | C |
| ATOM | 295 | C | ARG | A | 721 | −16.806 | 6.461 | −0.921 | 1.00 | 20.74 | C |
| ATOM | 296 | O | ARG | A | 721 | −17.351 | 7.524 | −1.234 | 1.00 | 18.82 | O |
| ATOM | 297 | CB | ARG | A | 721 | −16.416 | 4.599 | −2.642 | 1.00 | 23.57 | C |
| ATOM | 298 | CG | ARG | A | 721 | −17.709 | 4.968 | −3.385 | 1.00 | 24.39 | C |
| ATOM | 299 | CD | ARG | A | 721 | −17.340 | 6.074 | −4.418 | 1.00 | 31.42 | C |
| ATOM | 300 | NE | ARG | A | 721 | −18.439 | 6.597 | −5.222 | 1.00 | 37.09 | N |
| ATOM | 301 | CZ | ARG | A | 721 | −18.934 | 6.025 | −6.321 | 1.00 | 39.97 | C |
| ATOM | 302 | NH1 | ARG | A | 721 | −18.448 | 4.863 | −6.756 | 1.00 | 40.51 | N |
| ATOM | 303 | NH2 | ARG | A | 721 | −19.924 | 6.614 | −6.984 | 1.00 | 39.39 | N |
| ATOM | 304 | N | ALA | A | 722 | −16.983 | 5.893 | 0.288 | 1.00 | 20.38 | N |
| ATOM | 305 | CA | ALA | A | 722 | −17.867 | 6.447 | 1.298 | 1.00 | 20.28 | C |
| ATOM | 306 | C | ALA | A | 722 | −17.467 | 7.867 | 1.630 | 1.00 | 20.32 | C |
| ATOM | 307 | O | ALA | A | 722 | −18.297 | 8.765 | 1.697 | 1.00 | 17.94 | O |

TABLE 2b-continued

Data of atomic coordinates for accession code 3AIG, which cites accession code 2ZTT

| ATOM | 308 | CB | ALA | A | 722 | −17.826 | 5.619 | 2.522 | 1.00 | 18.82 | C |
|---|---|---|---|---|---|---|---|---|---|---|---|
| ATOM | 309 | N | ARG | A | 723 | −16.162 | 8.082 | 1.788 | 1.00 | 20.65 | N |
| ATOM | 310 | CA | ARG | A | 723 | −15.653 | 9.428 | 2.134 | 1.00 | 21.75 | C |
| ATOM | 311 | C | ARG | A | 723 | −15.872 | 10.434 | 1.004 | 1.00 | 20.94 | C |
| ATOM | 312 | O | ARG | A | 723 | −16.333 | 11.549 | 1.271 | 1.00 | 20.38 | O |
| ATOM | 313 | CB | ARG | A | 723 | −14.155 | 9.362 | 2.478 | 1.00 | 21.00 | C |
| ATOM | 314 | CG | ARG | A | 723 | −13.959 | 8.709 | 3.842 | 1.00 | 20.39 | C |
| ATOM | 315 | CD | ARG | A | 723 | −12.483 | 8.467 | 4.136 | 1.00 | 25.26 | C |
| ATOM | 316 | NE | ARG | A | 723 | −12.309 | 8.234 | 5.558 | 1.00 | 23.68 | N |
| ATOM | 317 | CZ | ARG | A | 723 | −11.272 | 7.597 | 6.090 | 1.00 | 23.86 | C |
| ATOM | 318 | NH1 | ARG | A | 723 | −10.325 | 7.067 | 5.312 | 1.00 | 25.41 | N |
| ATOM | 319 | NH2 | ARG | A | 723 | −11.191 | 7.469 | 7.410 | 1.00 | 28.97 | N |
| ATOM | 320 | N | ILE | A | 724 | −15.526 | 10.048 | −0.221 | 1.00 | 22.43 | N |
| ATOM | 321 | CA | ILE | A | 724 | −15.694 | 10.950 | −1.377 | 1.00 | 21.10 | C |
| ATOM | 322 | C | ILE | A | 724 | −17.196 | 11.308 | −1.520 | 1.00 | 21.72 | C |
| ATOM | 323 | O | ILE | A | 724 | −17.544 | 12.489 | −1.659 | 1.00 | 21.00 | O |
| ATOM | 324 | CB | ILE | A | 724 | −15.248 | 10.306 | −2.651 | 1.00 | 23.56 | C |
| ATOM | 325 | CG1 | ILE | A | 724 | −13.743 | 10.048 | −2.600 | 1.00 | 23.06 | C |
| ATOM | 326 | CG2 | ILE | A | 724 | −15.627 | 11.168 | −3.879 | 1.00 | 23.53 | C |
| ATOM | 327 | CD1 | ILE | A | 724 | −13.315 | 9.069 | −3.688 | 1.00 | 27.02 | C |
| ATOM | 328 | N | ASP | A | 725 | −18.068 | 10.314 | −1.423 | 1.00 | 22.24 | N |
| ATOM | 329 | CA | ASP | A | 725 | −19.507 | 10.550 | −1.585 | 1.00 | 23.02 | C |
| ATOM | 330 | C | ASP | A | 725 | −20.062 | 11.406 | −0.450 | 1.00 | 22.47 | C |
| ATOM | 331 | O | ASP | A | 725 | −20.832 | 12.308 | −0.671 | 1.00 | 21.55 | O |
| ATOM | 332 | CB | ASP | A | 725 | −20.350 | 9.263 | −1.687 | 1.00 | 23.79 | C |
| ATOM | 333 | CG | ASP | A | 725 | −20.072 | 8.455 | −2.949 | 1.00 | 25.20 | C |
| ATOM | 334 | OD1 | ASP | A | 725 | −19.536 | 8.981 | −3.989 | 1.00 | 28.04 | O |
| ATOM | 335 | OD2 | ASP | A | 725 | −20.394 | 7.261 | −2.915 | 1.00 | 26.34 | O |
| ATOM | 336 | N | ALA | A | 726 | −19.632 | 11.168 | 0.775 | 1.00 | 22.64 | N |
| ATOM | 337 | CA | ALA | A | 726 | −20.143 | 11.936 | 1.893 | 1.00 | 20.79 | C |
| ATOM | 338 | C | ALA | A | 726 | −19.779 | 13.429 | 1.767 | 1.00 | 21.18 | C |
| ATOM | 339 | O | ALA | A | 726 | −20.605 | 14.302 | 2.014 | 1.00 | 19.45 | O |
| ATOM | 340 | CB | ALA | A | 726 | −19.680 | 11.349 | 3.175 | 1.00 | 22.80 | C |
| ATOM | 341 | N | ARG | A | 727 | −18.555 | 13.756 | 1.336 | 1.00 | 21.44 | N |
| ATOM | 342 | CA | ARG | A | 727 | −18.229 | 15.176 | 1.177 | 1.00 | 23.97 | C |
| ATOM | 343 | C | ARG | A | 727 | −19.084 | 15.845 | 0.094 | 1.00 | 23.36 | C |
| ATOM | 344 | O | ARG | A | 727 | −19.595 | 16.969 | 0.294 | 1.00 | 24.32 | O |
| ATOM | 345 | CB | ARG | A | 727 | −16.732 | 15.311 | 0.855 | 1.00 | 24.69 | C |
| ATOM | 346 | CG | ARG | A | 727 | −15.853 | 14.915 | 2.058 | 1.00 | 29.13 | C |
| ATOM | 347 | CD | ARG | A | 727 | −14.407 | 15.202 | 1.776 | 1.00 | 37.73 | C |
| ATOM | 348 | NE | ARG | A | 727 | −13.996 | 14.384 | 0.673 | 1.00 | 44.29 | N |
| ATOM | 349 | CZ | ARG | A | 727 | −12.875 | 14.540 | −0.002 | 1.00 | 48.41 | C |
| ATOM | 350 | NH1 | ARG | A | 727 | −12.025 | 15.498 | 0.348 | 1.00 | 49.88 | N |
| ATOM | 351 | NH2 | ARG | A | 727 | −12.611 | 13.719 | −1.012 | 1.00 | 47.37 | N |
| ATOM | 352 | N | ILE | A | 728 | −19.260 | 15.154 | −1.020 | 1.00 | 22.87 | N |
| ATOM | 353 | CA | ILE | A | 728 | −19.982 | 15.714 | −2.203 | 1.00 | 23.51 | C |
| ATOM | 354 | C | ILE | A | 728 | −21.445 | 15.823 | −1.789 | 1.00 | 23.39 | C |
| ATOM | 355 | O | ILE | A | 728 | −22.104 | 16.821 | −2.076 | 1.00 | 24.46 | O |
| ATOM | 356 | CB | ILE | A | 728 | −19.863 | 14.836 | −3.462 | 1.00 | 24.73 | C |
| ATOM | 357 | CG1 | ILE | A | 728 | −18.448 | 14.933 | −4.036 | 1.00 | 29.01 | C |
| ATOM | 358 | CG2 | ILE | A | 728 | −20.945 | 15.237 | −4.544 | 1.00 | 25.66 | C |
| ATOM | 359 | CD1 | ILE | A | 728 | −18.053 | 13.753 | −4.969 | 1.00 | 33.60 | C |
| ATOM | 360 | N | ASP | A | 729 | −21.933 | 14.798 | −1.113 | 1.00 | 22.79 | N |
| ATOM | 361 | CA | ASP | A | 729 | −23.355 | 14.772 | −0.757 | 1.00 | 22.94 | C |
| ATOM | 362 | C | ASP | A | 729 | −23.719 | 15.778 | 0.313 | 1.00 | 24.19 | C |
| ATOM | 363 | O | ASP | A | 729 | −24.831 | 16.360 | 0.288 | 1.00 | 23.82 | O |
| ATOM | 364 | CB | ASP | A | 729 | −23.776 | 13.359 | −0.337 | 1.00 | 23.03 | C |
| ATOM | 365 | CG | ASP | A | 729 | −23.835 | 12.382 | −1.509 | 1.00 | 24.77 | C |
| ATOM | 366 | OD1 | ASP | A | 729 | −23.811 | 12.808 | −2.684 | 1.00 | 28.52 | O |
| ATOM | 367 | OD2 | ASP | A | 729 | −23.820 | 11.163 | −1.274 | 1.00 | 26.69 | O |
| ATOM | 368 | N | PHE | A | 730 | −22.788 | 16.042 | 1.241 | 1.00 | 21.91 | N |
| ATOM | 369 | CA | PHE | A | 730 | −22.959 | 17.039 | 2.265 | 1.00 | 22.76 | C |
| ATOM | 370 | C | PHE | A | 730 | −22.936 | 18.441 | 1.615 | 1.00 | 24.60 | C |
| ATOM | 371 | O | PHE | A | 730 | −23.833 | 19.287 | 1.857 | 1.00 | 24.92 | O |
| ATOM | 372 | CB | PHE | A | 730 | −21.880 | 16.857 | 3.350 | 1.00 | 23.81 | C |
| ATOM | 373 | CG | PHE | A | 730 | −21.980 | 17.846 | 4.456 | 1.00 | 24.89 | C |
| ATOM | 374 | CD1 | PHE | A | 730 | −23.223 | 18.143 | 5.022 | 1.00 | 25.70 | C |
| ATOM | 375 | CD2 | PHE | A | 730 | −20.874 | 18.451 | 4.947 | 1.00 | 21.78 | C |
| ATOM | 376 | CE1 | PHE | A | 730 | −23.317 | 19.064 | 6.056 | 1.00 | 26.83 | C |
| ATOM | 377 | CE2 | PHE | A | 730 | −20.947 | 19.379 | 5.982 | 1.00 | 23.52 | C |
| ATOM | 378 | CZ | PHE | A | 730 | −22.178 | 19.666 | 6.547 | 1.00 | 23.08 | C |
| ATOM | 379 | N | GLU | A | 731 | −21.930 | 18.660 | 0.761 | 1.00 | 26.80 | N |
| ATOM | 380 | CA | GLU | A | 731 | −21.860 | 19.879 | −0.066 | 1.00 | 28.38 | C |
| ATOM | 381 | C | GLU | A | 731 | −23.189 | 20.148 | −0.823 | 1.00 | 27.69 | C |
| ATOM | 382 | O | GLU | A | 731 | −23.629 | 21.309 | −0.938 | 1.00 | 27.78 | O |
| ATOM | 383 | CB | GLU | A | 731 | −20.690 | 19.718 | −1.049 | 1.00 | 28.41 | C |
| ATOM | 384 | CG | GLU | A | 731 | −20.493 | 20.798 | −2.099 | 1.00 | 30.41 | C |
| ATOM | 385 | CD | GLU | A | 731 | −19.470 | 20.331 | −3.117 | 1.00 | 29.51 | C |

TABLE 2b-continued

Data of atomic coordinates for accession code 3AIG, which cites accession code 2ZTT

| ATOM | 386 | OE1 | GLU | A | 731 | −19.718 | 20.418 | −4.323 | 1.00 | 37.03 | O |
|---|---|---|---|---|---|---|---|---|---|---|---|
| ATOM | 387 | OE2 | GLU | A | 731 | −18.438 | 19.804 | −2.699 | 1.00 | 36.49 | O |
| ATOM | 388 | N | SER | A | 732 | −23.805 | 19.095 | −1.340 | 1.00 | 29.13 | N |
| ATOM | 389 | CA | SER | A | 732 | −24.957 | 19.219 | −2.263 | 1.00 | 31.76 | C |
| ATOM | 390 | C | SER | A | 732 | −26.302 | 19.302 | −1.536 | 1.00 | 32.84 | C |
| ATOM | 391 | O | SER | A | 732 | −27.335 | 19.590 | −2.156 | 1.00 | 34.22 | O |
| ATOM | 392 | CB | SER | A | 732 | −24.958 | 18.081 | −3.270 | 1.00 | 32.21 | C |
| ATOM | 393 | OG | SER | A | 732 | −25.458 | 16.905 | −2.694 | 1.00 | 36.69 | O |
| ATOM | 394 | N | GLY | A | 733 | −26.271 | 19.046 | −0.235 | 1.00 | 32.86 | N |
| ATOM | 395 | CA | GLY | A | 733 | −27.461 | 19.110 | 0.619 | 1.00 | 33.28 | C |
| ATOM | 396 | C | GLY | A | 733 | −28.221 | 17.807 | 0.766 | 1.00 | 33.39 | C |
| ATOM | 397 | O | GLY | A | 733 | −29.206 | 17.781 | 1.490 | 1.00 | 35.17 | O |
| ATOM | 398 | N | ARG | A | 734 | −27.762 | 16.744 | 0.113 | 1.00 | 32.05 | N |
| ATOM | 399 | CA | ARG | A | 734 | −28.400 | 15.409 | 0.145 | 1.00 | 32.16 | C |
| ATOM | 400 | C | ARG | A | 734 | −28.313 | 14.738 | 1.530 | 1.00 | 32.01 | C |
| ATOM | 401 | O | ARG | A | 734 | −29.157 | 13.889 | 1.891 | 1.00 | 31.33 | O |
| ATOM | 402 | CB | ARG | A | 734 | −27.768 | 14.468 | −0.873 | 1.00 | 31.86 | C |
| ATOM | 403 | CG | ARG | A | 734 | −27.962 | 14.800 | −2.345 | 1.00 | 35.21 | C |
| ATOM | 404 | CD | ARG | A | 734 | −27.596 | 13.619 | −3.229 | 1.00 | 34.21 | C |
| ATOM | 405 | NE | ARG | A | 734 | −28.763 | 12.962 | −3.864 | 1.00 | 46.87 | N |
| ATOM | 406 | CZ | ARG | A | 734 | −29.249 | 11.780 | −3.511 | 1.00 | 46.08 | C |
| ATOM | 407 | NH1 | ARG | A | 734 | −28.680 | 11.092 | −2.533 | 1.00 | 49.87 | N |
| ATOM | 408 | NH2 | ARG | A | 734 | −30.288 | 11.271 | −4.145 | 1.00 | 45.68 | N |
| ATOM | 409 | N | ILE | A | 735 | −27.259 | 15.064 | 2.273 | 1.00 | 30.34 | N |
| ATOM | 410 | CA | ILE | A | 735 | −27.155 | 14.615 | 3.668 | 1.00 | 28.39 | C |
| ATOM | 411 | C | ILE | A | 735 | −26.910 | 15.791 | 4.573 | 1.00 | 28.92 | C |
| ATOM | 412 | O | ILE | A | 735 | −26.430 | 16.832 | 4.130 | 1.00 | 28.26 | O |
| ATOM | 413 | CB | ILE | A | 735 | −26.127 | 13.481 | 3.849 | 1.00 | 28.64 | C |
| ATOM | 414 | CG1 | ILE | A | 735 | −24.706 | 13.999 | 3.564 | 1.00 | 26.52 | C |
| ATOM | 415 | CG2 | ILE | A | 735 | −26.482 | 12.299 | 2.946 | 1.00 | 27.75 | C |
| ATOM | 416 | CD1 | ILE | A | 735 | −23.528 | 13.022 | 3.990 | 1.00 | 26.92 | C |
| ATOM | 417 | N | LYS | A | 736 | −27.255 | 15.666 | 5.846 | 1.00 | 29.00 | N |
| ATOM | 418 | CA | LYS | A | 736 | −27.169 | 16.767 | 6.756 | 1.00 | 30.55 | C |
| ATOM | 419 | C | LYS | A | 736 | −25.866 | 16.614 | 7.521 | 1.00 | 29.64 | C |
| ATOM | 420 | O | LYS | A | 736 | −25.261 | 15.545 | 7.435 | 1.00 | 28.49 | O |
| ATOM | 421 | CB | LYS | A | 736 | −28.360 | 16.747 | 7.731 | 1.00 | 32.31 | C |
| ATOM | 422 | CG | LYS | A | 736 | −29.159 | 18.059 | 7.722 | 1.00 | 35.90 | C |
| ATOM | 423 | CD | LYS | A | 736 | −29.502 | 18.558 | 6.308 | 1.00 | 40.21 | C |
| ATOM | 424 | CE | LYS | A | 736 | −29.601 | 20.085 | 6.268 | 1.00 | 42.37 | C |
| ATOM | 425 | NZ | LYS | A | 736 | −29.623 | 20.608 | 4.880 | 1.00 | 46.03 | N |
| ATOM | 426 | N | LYS | A | 737 | −25.476 | 17.658 | 8.253 | 1.00 | 29.56 | N |
| ATOM | 427 | CA | LYS | A | 737 | −24.181 | 17.692 | 8.988 | 1.00 | 31.28 | C |
| ATOM | 428 | C | LYS | A | 737 | −24.066 | 16.513 | 9.951 | 1.00 | 31.49 | C |
| ATOM | 429 | O | LYS | A | 737 | −23.012 | 15.926 | 10.074 | 1.00 | 29.46 | O |
| ATOM | 430 | CB | LYS | A | 737 | −23.930 | 19.047 | 9.678 | 1.00 | 31.43 | C |
| ATOM | 431 | CG | LYS | A | 737 | −24.651 | 19.334 | 11.017 | 1.00 | 38.43 | C |
| ATOM | 432 | CD | LYS | A | 737 | −23.934 | 18.708 | 12.283 | 1.00 | 43.30 | C |
| ATOM | 433 | CE | LYS | A | 737 | −22.401 | 18.663 | 12.169 | 1.00 | 46.80 | C |
| ATOM | 434 | NZ | LYS | A | 737 | −21.684 | 19.722 | 12.940 | 1.00 | 46.77 | N |
| ATOM | 435 | N | GLU | A | 738 | −25.170 | 16.158 | 10.625 | 1.00 | 31.73 | N |
| ATOM | 436 | CA | GLU | A | 738 | −25.150 | 15.025 | 11.562 | 1.00 | 32.69 | C |
| ATOM | 437 | C | GLU | A | 738 | −24.869 | 13.689 | 10.885 | 1.00 | 31.00 | C |
| ATOM | 438 | O | GLU | A | 738 | −24.186 | 12.832 | 11.440 | 1.00 | 30.63 | O |
| ATOM | 439 | CB | GLU | A | 738 | −26.481 | 14.954 | 12.362 | 1.00 | 32.59 | C |
| ATOM | 440 | CG | GLU | A | 738 | −26.830 | 16.224 | 13.144 | 1.00 | 36.34 | C |
| ATOM | 441 | CD | GLU | A | 738 | −27.382 | 17.402 | 12.308 | 1.00 | 38.97 | C |
| ATOM | 442 | OE1 | GLU | A | 738 | −27.734 | 17.249 | 11.112 | 1.00 | 37.53 | O |
| ATOM | 443 | OE2 | GLU | A | 738 | −27.498 | 18.504 | 12.887 | 1.00 | 44.90 | O |
| ATOM | 444 | N | GLU | A | 739 | −25.424 | 13.508 | 9.689 | 1.00 | 29.80 | N |
| ATOM | 445 | CA | GLU | A | 739 | −25.204 | 12.327 | 8.884 | 1.00 | 27.97 | C |
| ATOM | 446 | C | GLU | A | 739 | −23.763 | 12.303 | 8.375 | 1.00 | 25.53 | C |
| ATOM | 447 | O | GLU | A | 739 | −23.116 | 11.279 | 8.404 | 1.00 | 23.97 | O |
| ATOM | 448 | CB | GLU | A | 739 | −26.161 | 12.312 | 7.696 | 1.00 | 29.17 | C |
| ATOM | 449 | CG | GLU | A | 739 | −27.506 | 11.618 | 7.890 | 1.00 | 29.12 | C |
| ATOM | 450 | CD | GLU | A | 739 | −28.393 | 11.808 | 6.646 | 1.00 | 29.80 | C |
| ATOM | 451 | OE1 | GLU | A | 739 | −28.687 | 12.962 | 6.298 | 1.00 | 30.57 | O |
| ATOM | 452 | OE2 | GLU | A | 739 | −28.715 | 10.804 | 5.991 | 1.00 | 37.99 | O |
| ATOM | 453 | N | PHE | A | 740 | −23.287 | 13.440 | 7.856 | 1.00 | 23.52 | N |
| ATOM | 454 | CA | PHE | A | 740 | −21.900 | 13.542 | 7.369 | 1.00 | 22.10 | C |
| ATOM | 455 | C | PHE | A | 740 | −20.907 | 13.181 | 8.507 | 1.00 | 21.61 | C |
| ATOM | 456 | O | PHE | A | 740 | −19.985 | 12.376 | 8.353 | 1.00 | 20.70 | O |
| ATOM | 457 | CB | PHE | A | 740 | −21.637 | 14.979 | 6.885 | 1.00 | 21.57 | C |
| ATOM | 458 | CG | PHE | A | 740 | −20.193 | 15.239 | 6.542 | 1.00 | 22.86 | C |
| ATOM | 459 | CD1 | PHE | A | 740 | −19.666 | 14.791 | 5.325 | 1.00 | 24.40 | C |
| ATOM | 460 | CD2 | PHE | A | 740 | −19.381 | 15.943 | 7.432 | 1.00 | 22.01 | C |
| ATOM | 461 | CE1 | PHE | A | 740 | −18.319 | 15.019 | 4.989 | 1.00 | 22.69 | C |
| ATOM | 462 | CE2 | PHE | A | 740 | −17.996 | 16.183 | 7.087 | 1.00 | 20.45 | C |
| ATOM | 463 | CZ | PHE | A | 740 | −17.511 | 15.718 | 5.876 | 1.00 | 22.56 | C |

TABLE 2b-continued

Data of atomic coordinates for accession code 3AIG, which cites accession code 2ZTT

| | | | | | | | | | | |
|---|---|---|---|---|---|---|---|---|---|---|
| ATOM | 464 | N | THR | A | 741 | −21.030 | 13.860 | 9.640 | 1.00 | 22.80 | N |
| ATOM | 465 | CA | THR | A | 741 | −20.119 | 13.545 | 10.759 | 1.00 | 24.65 | C |
| ATOM | 466 | C | THR | A | 741 | −20.143 | 12.052 | 11.160 | 1.00 | 25.06 | C |
| ATOM | 467 | O | THR | A | 741 | −19.088 | 11.424 | 11.344 | 1.00 | 23.14 | O |
| ATOM | 468 | CB | THR | A | 741 | −20.333 | 14.476 | 11.993 | 1.00 | 24.83 | C |
| ATOM | 469 | OG1 | THR | A | 741 | −21.668 | 14.316 | 12.476 | 1.00 | 28.76 | O |
| ATOM | 470 | CG2 | THR | A | 741 | −20.169 | 15.912 | 11.597 | 1.00 | 24.93 | C |
| ATOM | 471 | N | GLU | A | 742 | −21.330 | 11.469 | 11.254 | 1.00 | 23.26 | N |
| ATOM | 472 | CA | GLU | A | 742 | −21.423 | 10.070 | 11.664 | 1.00 | 25.04 | C |
| ATOM | 473 | C | GLU | A | 742 | −20.809 | 9.105 | 10.625 | 1.00 | 24.32 | C |
| ATOM | 474 | O | GLU | A | 742 | −20.036 | 8.195 | 10.972 | 1.00 | 22.53 | O |
| ATOM | 475 | CB | GLU | A | 742 | −22.845 | 9.725 | 12.086 | 1.00 | 26.90 | C |
| ATOM | 476 | CG | GLU | A | 742 | −22.976 | 8.336 | 12.640 | 1.00 | 31.81 | C |
| ATOM | 477 | CD | GLU | A | 742 | −24.373 | 8.024 | 13.173 | 1.00 | 37.01 | C |
| ATOM | 478 | OE1 | GLU | A | 742 | −25.285 | 8.885 | 13.145 | 1.00 | 42.95 | O |
| ATOM | 479 | OE2 | GLU | A | 742 | −24.530 | 6.885 | 13.615 | 1.00 | 41.83 | O |
| ATOM | 480 | N | ILE | A | 743 | −21.017 | 9.396 | 9.332 | 1.00 | 20.85 | N |
| ATOM | 481 | CA | ILE | A | 743 | −20.389 | 8.650 | 8.284 | 1.00 | 20.79 | C |
| ATOM | 482 | C | ILE | A | 743 | −18.838 | 8.706 | 8.362 | 1.00 | 20.07 | C |
| ATOM | 483 | O | ILE | A | 743 | −18.199 | 7.676 | 8.274 | 1.00 | 20.94 | O |
| ATOM | 484 | CB | ILE | A | 743 | −20.861 | 9.105 | 6.860 | 1.00 | 23.05 | C |
| ATOM | 485 | CG1 | ILE | A | 743 | −22.301 | 8.753 | 6.717 | 1.00 | 22.72 | C |
| ATOM | 486 | CG2 | ILE | A | 743 | −20.060 | 8.363 | 5.828 | 1.00 | 21.68 | C |
| ATOM | 487 | CD1 | ILE | A | 743 | −23.014 | 9.440 | 5.555 | 1.00 | 22.99 | C |
| HETATM | 488 | N | MSE | A | 744 | −18.274 | 9.895 | 8.611 | 1.00 | 20.59 | N |
| HETATM | 489 | CA | MSE | A | 744 | −16.835 | 10.073 | 8.558 | 1.00 | 21.81 | C |
| HETATM | 490 | C | MSE | A | 744 | −16.226 | 9.346 | 9.773 | 1.00 | 21.73 | C |
| HETATM | 491 | O | MSE | A | 744 | −15.097 | 8.756 | 9.677 | 1.00 | 21.60 | O |
| HETATM | 492 | CB | MSE | A | 744 | −16.463 | 11.571 | 8.527 | 1.00 | 22.45 | C |
| HETATM | 493 | CG | MSE | A | 744 | −16.921 | 12.340 | 7.258 | 1.00 | 21.51 | C |
| HETATM | 494 | SE | MSE | A | 744 | −16.341 | 11.437 | 5.615 | 1.00 | 28.77 | SE |
| HETATM | 495 | CE | MSE | A | 744 | −14.498 | 11.789 | 5.944 | 1.00 | 27.99 | C |
| ATOM | 496 | N | LYS | A | 745 | −16.947 | 9.421 | 10.892 | 1.00 | 24.54 | N |
| ATOM | 497 | CA | LYS | A | 745 | −16.495 | 8.789 | 12.163 | 1.00 | 23.33 | C |
| ATOM | 498 | C | LYS | A | 745 | −16.540 | 7.258 | 11.995 | 1.00 | 24.55 | C |
| ATOM | 499 | O | LYS | A | 745 | −15.586 | 6.569 | 12.402 | 1.00 | 24.12 | O |
| ATOM | 500 | CB | LYS | A | 745 | −17.362 | 9.222 | 13.349 | 1.00 | 24.75 | C |
| ATOM | 501 | CG | LYS | A | 745 | −17.391 | 10.719 | 13.514 | 1.00 | 25.72 | C |
| ATOM | 502 | CD | LYS | A | 745 | −16.968 | 11.327 | 14.818 | 1.00 | 34.83 | C |
| ATOM | 503 | CE | LYS | A | 745 | −15.524 | 11.220 | 14.878 | 1.00 | 32.96 | C |
| ATOM | 504 | NZ | LYS | A | 745 | −15.367 | 9.748 | 15.214 | 1.00 | 27.64 | N |
| ATOM | 505 | N | ILE | A | 746 | −17.636 | 6.753 | 11.400 | 1.00 | 23.33 | N |
| ATOM | 506 | CA | ILE | A | 746 | −17.739 | 5.286 | 11.131 | 1.00 | 23.00 | C |
| ATOM | 507 | C | ILE | A | 746 | −16.580 | 4.845 | 10.192 | 1.00 | 22.74 | C |
| ATOM | 508 | O | ILE | A | 746 | −15.868 | 3.872 | 10.438 | 1.00 | 22.60 | O |
| ATOM | 509 | CB | ILE | A | 746 | −19.151 | 4.828 | 10.693 | 1.00 | 23.38 | C |
| ATOM | 510 | CG1 | ILE | A | 746 | −20.189 | 5.082 | 11.812 | 1.00 | 24.96 | C |
| ATOM | 511 | CG2 | ILE | A | 746 | −19.152 | 3.355 | 10.239 | 1.00 | 22.33 | C |
| ATOM | 512 | CD1 | ILE | A | 746 | −21.617 | 4.911 | 11.254 | 1.00 | 26.14 | C |
| ATOM | 513 | N | CYS | A | 747 | −16.330 | 5.603 | 9.126 | 1.00 | 23.46 | N |
| ATOM | 514 | CA | CYS | A | 747 | −15.189 | 5.292 | 8.260 | 1.00 | 22.84 | C |
| ATOM | 515 | C | CYS | A | 747 | −13.876 | 5.223 | 8.995 | 1.00 | 24.42 | C |
| ATOM | 516 | O | CYS | A | 747 | −13.072 | 4.330 | 8.761 | 1.00 | 25.38 | O |
| ATOM | 517 | CB | CYS | A | 747 | −15.094 | 6.340 | 7.139 | 1.00 | 23.87 | C |
| ATOM | 518 | SG | CYS | A | 747 | −16.400 | 6.257 | 5.873 | 1.00 | 25.32 | S |
| ATOM | 519 | N | SER | A | 748 | −13.650 | 6.167 | 9.898 | 1.00 | 24.29 | N |
| ATOM | 520 | CA | SER | A | 748 | −12.374 | 6.157 | 10.599 | 1.00 | 26.22 | C |
| ATOM | 521 | C | SER | A | 748 | −12.369 | 4.933 | 11.525 | 1.00 | 25.42 | C |
| ATOM | 522 | O | SER | A | 748 | −11.340 | 4.331 | 11.700 | 1.00 | 27.73 | O |
| ATOM | 523 | CB | SER | A | 748 | −12.153 | 7.465 | 11.370 | 1.00 | 26.71 | C |
| ATOM | 524 | OG | SER | A | 748 | −13.077 | 7.519 | 12.411 | 1.00 | 35.80 | O |
| ATOM | 525 | N | THR | A | 749 | −13.518 | 4.528 | 12.047 | 1.00 | 25.69 | N |
| ATOM | 526 | CA | THR | A | 749 | −13.569 | 3.329 | 12.924 | 1.00 | 26.66 | C |
| ATOM | 527 | C | THR | A | 749 | −13.231 | 2.090 | 12.102 | 1.00 | 27.71 | C |
| ATOM | 528 | O | THR | A | 749 | −12.466 | 1.225 | 12.534 | 1.00 | 28.31 | O |
| ATOM | 529 | CB | THR | A | 749 | −14.926 | 3.207 | 13.579 | 1.00 | 26.15 | C |
| ATOM | 530 | OG1 | THR | A | 749 | −15.087 | 4.323 | 14.472 | 1.00 | 29.05 | O |
| ATOM | 531 | CG2 | THR | A | 749 | −15.064 | 1.938 | 14.365 | 1.00 | 28.30 | C |
| ATOM | 532 | N | ILE | A | 750 | −13.834 | 2.005 | 10.934 | 1.00 | 26.54 | N |
| ATOM | 533 | CA | ILE | A | 750 | −13.662 | 0.888 | 10.037 | 1.00 | 27.07 | C |
| ATOM | 534 | C | ILE | A | 750 | −12.184 | 0.794 | 9.650 | 1.00 | 28.29 | C |
| ATOM | 535 | O | ILE | A | 750 | −11.628 | −0.302 | 9.584 | 1.00 | 28.06 | O |
| ATOM | 536 | CB | ILE | A | 750 | −14.569 | 1.030 | 8.779 | 1.00 | 28.24 | C |
| ATOM | 537 | CG1 | ILE | A | 750 | −16.068 | 0.860 | 9.151 | 1.00 | 26.65 | C |
| ATOM | 538 | CG2 | ILE | A | 750 | −14.095 | 0.037 | 7.677 | 1.00 | 24.59 | C |
| ATOM | 539 | CD1 | ILE | A | 750 | −17.053 | 1.270 | 8.007 | 1.00 | 25.86 | C |
| ATOM | 540 | N | GLU | A | 751 | −11.569 | 1.946 | 9.360 | 1.00 | 30.06 | N |
| ATOM | 541 | CA | GLU | A | 751 | −10.146 | 2.029 | 9.024 | 1.00 | 32.40 | C |

TABLE 2b-continued

Data of atomic coordinates for accession code 3AIG, which cites accession code 2ZTT

| ATOM | 542 | C | GLU | A | 751 | −9.260 | 1.542 | 10.159 | 1.00 | 34.03 | C |
|---|---|---|---|---|---|---|---|---|---|---|---|
| ATOM | 543 | O | GLU | A | 751 | −8.246 | 0.899 | 9.908 | 1.00 | 33.92 | O |
| ATOM | 544 | CB | GLU | A | 751 | −9.716 | 3.438 | 8.636 | 1.00 | 32.25 | C |
| ATOM | 545 | CG | GLU | A | 751 | −10.247 | 3.923 | 7.306 | 1.00 | 37.02 | C |
| ATOM | 546 | CD | GLU | A | 751 | −9.348 | 3.638 | 6.128 | 1.00 | 44.36 | C |
| ATOM | 547 | OE1 | GLU | A | 751 | −8.324 | 4.366 | 6.004 | 1.00 | 46.44 | O |
| ATOM | 548 | OE2 | GLU | A | 751 | −9.698 | 2.735 | 5.307 | 1.00 | 43.64 | O |
| ATOM | 549 | N | GLU | A | 752 | −9.639 | 1.868 | 11.387 | 1.00 | 34.90 | N |
| ATOM | 550 | CA | GLU | A | 752 | −8.996 | 1.298 | 12.572 | 1.00 | 37.77 | C |
| ATOM | 551 | C | GLU | A | 752 | −9.106 | −0.242 | 12.604 | 1.00 | 37.47 | C |
| ATOM | 552 | O | GLU | A | 752 | −8.113 | −0.928 | 12.862 | 1.00 | 38.83 | O |
| ATOM | 553 | CB | GLU | A | 752 | −9.610 | 1.904 | 13.834 | 1.00 | 37.72 | C |
| ATOM | 554 | CG | GLU | A | 752 | −8.620 | 2.095 | 14.936 | 1.00 | 41.77 | C |
| ATOM | 555 | CD | GLU | A | 752 | −9.182 | 2.836 | 16.141 | 1.00 | 45.88 | C |
| ATOM | 556 | OE1 | GLU | A | 752 | −10.080 | 3.697 | 15.970 | 1.00 | 44.09 | O |
| ATOM | 557 | OE2 | GLU | A | 752 | −8.687 | 2.558 | 17.266 | 1.00 | 47.43 | O |
| ATOM | 558 | N | LEU | A | 753 | −10.303 | −0.779 | 12.352 | 1.00 | 39.77 | N |
| ATOM | 559 | CA | LEU | A | 753 | −10.514 | −2.242 | 12.307 | 1.00 | 39.90 | C |
| ATOM | 560 | C | LEU | A | 753 | −9.848 | −2.949 | 11.108 | 1.00 | 42.60 | C |
| ATOM | 561 | O | LEU | A | 753 | −9.720 | −4.169 | 11.127 | 1.00 | 43.18 | O |
| ATOM | 562 | CB | LEU | A | 753 | −12.016 | −2.587 | 12.347 | 1.00 | 39.01 | C |
| ATOM | 563 | CG | LEU | A | 753 | −12.859 | −2.194 | 13.570 | 1.00 | 37.73 | C |
| ATOM | 564 | CD1 | LEU | A | 753 | −14.349 | −2.383 | 13.343 | 1.00 | 35.97 | C |
| ATOM | 565 | CD2 | LEU | A | 753 | −12.418 | −2.946 | 14.824 | 1.00 | 39.76 | C |
| ATOM | 566 | N | ARG | A | 754 | −9.409 | −2.212 | 10.087 | 1.00 | 45.07 | N |
| ATOM | 567 | CA | ARG | A | 754 | −8.692 | −2.826 | 8.943 | 1.00 | 48.40 | C |
| ATOM | 568 | C | ARG | A | 754 | −7.243 | −3.075 | 9.311 | 1.00 | 50.89 | C |
| ATOM | 569 | O | ARG | A | 754 | −6.704 | −4.167 | 9.101 | 1.00 | 51.66 | O |
| ATOM | 570 | CB | ARG | A | 754 | −8.648 | −1.907 | 7.724 | 1.00 | 48.12 | C |
| ATOM | 571 | CG | ARG | A | 754 | −9.941 | −1.434 | 7.115 | 1.00 | 49.04 | C |
| ATOM | 572 | CD | ARG | A | 754 | −9.584 | −0.411 | 6.038 | 1.00 | 49.85 | C |
| ATOM | 573 | NE | ARG | A | 754 | −8.488 | −0.921 | 5.217 | 1.00 | 48.78 | N |
| ATOM | 574 | CZ | ARG | A | 754 | −7.556 | −0.197 | 4.591 | 1.00 | 49.73 | C |
| ATOM | 575 | NH1 | ARG | A | 754 | −7.529 | 1.126 | 4.650 | 1.00 | 49.45 | N |
| ATOM | 576 | NH2 | ARG | A | 754 | −6.615 | −0.821 | 3.894 | 1.00 | 46.70 | N |
| ATOM | 577 | N | ARG | A | 755 | −6.625 | −2.031 | 9.852 | 1.00 | 53.73 | N |
| ATOM | 578 | CA | ARG | A | 755 | −5.204 | −2.008 | 10.170 | 1.00 | 56.44 | C |
| ATOM | 579 | C | ARG | A | 755 | −4.808 | −3.097 | 11.168 | 1.00 | 57.63 | C |
| ATOM | 580 | O | ARG | A | 755 | −3.645 | −3.504 | 11.203 | 1.00 | 58.23 | O |
| ATOM | 581 | CB | ARG | A | 755 | −4.797 | −0.623 | 10.669 | 1.00 | 56.50 | C |
| ATOM | 582 | CG | ARG | A | 755 | −4.478 | 0.360 | 9.556 | 1.00 | 58.53 | C |
| ATOM | 583 | CD | ARG | A | 755 | −5.709 | 1.096 | 9.006 | 1.00 | 59.55 | C |
| ATOM | 584 | NE | ARG | A | 755 | −5.463 | 1.644 | 7.667 | 1.00 | 60.84 | N |
| ATOM | 585 | CZ | ARG | A | 755 | −4.948 | 2.851 | 7.409 | 1.00 | 61.25 | C |
| ATOM | 586 | NH1 | ARG | A | 755 | −4.620 | 3.682 | 8.395 | 1.00 | 60.48 | N |
| ATOM | 587 | NH2 | ARG | A | 755 | −4.755 | 3.231 | 6.148 | 1.00 | 60.98 | N |
| ATOM | 588 | N | GLN | A | 756 | −5.776 | −3.574 | 11.951 | 1.00 | 59.15 | N |
| ATOM | 589 | CA | GLN | A | 756 | −5.566 | −4.731 | 12.828 | 1.00 | 61.13 | C |
| ATOM | 590 | C | GLN | A | 756 | −6.403 | −5.952 | 12.404 | 1.00 | 61.52 | C |
| ATOM | 591 | O | GLN | A | 756 | −6.983 | −6.648 | 13.247 | 1.00 | 62.26 | O |
| ATOM | 592 | CB | GLN | A | 756 | −5.787 | −4.368 | 14.306 | 1.00 | 60.85 | C |
| ATOM | 593 | CG | GLN | A | 756 | −4.841 | −5.118 | 15.260 | 1.00 | 62.62 | C |
| ATOM | 594 | CD | GLN | A | 756 | −4.920 | −4.643 | 16.710 | 1.00 | 62.19 | C |
| ATOM | 595 | OE1 | GLN | A | 756 | −5.838 | −5.012 | 17.452 | 1.00 | 63.80 | O |
| ATOM | 596 | NE2 | GLN | A | 756 | −3.944 | −3.838 | 17.124 | 1.00 | 62.31 | N |
| ATOM | 597 | N | LYS | A | 757 | −6.450 | −6.193 | 11.090 | 1.00 | 62.09 | N |
| ATOM | 598 | CA | LYS | A | 757 | −6.988 | −7.424 | 10.474 | 1.00 | 62.57 | C |
| ATOM | 599 | C | LYS | A | 757 | −8.488 | −7.381 | 10.193 | 1.00 | 62.78 | C |
| ATOM | 600 | O | LYS | A | 757 | −9.058 | −6.388 | 9.730 | 1.00 | 62.47 | O |
| ATOM | 601 | CB | LYS | A | 757 | −6.640 | −8.689 | 11.288 | 1.00 | 62.71 | C |
| ATOM | 602 | CG | LYS | A | 757 | −5.141 | −8.964 | 11.503 | 1.00 | 62.98 | C |
| ATOM | 603 | CD | LYS | A | 757 | −4.929 | −10.018 | 12.605 | 1.00 | 62.80 | C |
| ATOM | 604 | CE | LYS | A | 757 | −4.881 | −11.448 | 12.060 | 1.00 | 63.41 | C |
| ATOM | 605 | NZ | LYS | A | 757 | −6.112 | −11.874 | 11.319 | 1.00 | 63.61 | N |
| ATOM | 606 | OXT | LYS | A | 757 | −9.172 | −8.385 | 10.418 | 1.00 | 63.34 | O |
| TER | 607 | | LYS | A | 757 | | | | | | |
| ATOM | 608 | N | GLY | B | −2 | −30.787 | 7.360 | 5.493 | 1.00 | 31.01 | N |
| ATOM | 609 | CA | GLY | B | −2 | −30.828 | 7.059 | 4.039 | 1.00 | 27.98 | C |
| ATOM | 610 | C | GLY | B | −2 | −29.791 | 6.037 | 3.619 | 1.00 | 27.09 | C |
| ATOM | 611 | O | GLY | B | −2 | −29.272 | 5.269 | 4.463 | 1.00 | 27.24 | O |
| ATOM | 612 | N | GLY | B | −1 | −29.553 | 5.965 | 2.321 | 1.00 | 26.54 | N |
| ATOM | 613 | CA | GLY | B | −1 | −28.650 | 4.946 | 1.771 | 1.00 | 24.15 | C |
| ATOM | 614 | C | GLY | B | −1 | −27.195 | 5.064 | 2.235 | 1.00 | 24.83 | C |
| ATOM | 615 | O | GLY | B | −1 | −26.504 | 4.038 | 2.377 | 1.00 | 22.20 | O |
| ATOM | 616 | N | SER | B | 0 | −26.717 | 6.288 | 2.374 | 1.00 | 24.79 | N |
| ATOM | 617 | CA | SER | B | 0 | −25.318 | 6.525 | 2.787 | 1.00 | 24.36 | C |
| ATOM | 618 | C | SER | B | 0 | −25.123 | 5.988 | 4.204 | 1.00 | 24.59 | C |
| ATOM | 619 | O | SER | B | 0 | −24.142 | 5.341 | 4.491 | 1.00 | 23.90 | O |

TABLE 2b-continued

Data of atomic coordinates for accession code 3AIG, which cites accession code 2ZTT

| ATOM | 620 | CB | SER | B | 0 | −25.028 | 8.010 | 2.743 | 1.00 | 25.61 | C |
|---|---|---|---|---|---|---|---|---|---|---|---|
| ATOM | 621 | OG | SER | B | 0 | −25.111 | 8.497 | 1.420 | 1.00 | 26.56 | O |
| HETATM | 622 | N | MSE | B | 1 | −26.097 | 6.258 | 5.081 | 1.00 | 23.64 | N |
| HETATM | 623 | CA | MSE | B | 1 | −26.102 | 5.684 | 6.404 | 1.00 | 25.00 | C |
| HETATM | 624 | C | MSE | B | 1 | −26.271 | 4.209 | 6.430 | 1.00 | 24.94 | C |
| HETATM | 625 | O | MSE | B | 1 | −25.551 | 3.574 | 7.182 | 1.00 | 24.68 | O |
| HETATM | 626 | CB | MSE | B | 1 | −27.158 | 6.319 | 7.317 | 1.00 | 26.27 | C |
| HETATM | 627 | CG | MSE | B | 1 | −26.902 | 7.678 | 7.718 | 1.00 | 28.36 | C |
| HETATM | 628 | SE | MSE | B | 1 | −25.262 | 7.987 | 8.836 | 1.00 | 46.18 | SE |
| HETATM | 629 | CE | MSE | B | 1 | −25.043 | 6.724 | 9.658 | 1.00 | 13.56 | C |
| ATOM | 630 | N | GLU | B | 2 | −27.246 | 3.648 | 5.692 | 1.00 | 24.23 | N |
| ATOM | 631 | CA | GLU | B | 2 | −27.484 | 2.197 | 5.673 | 1.00 | 27.38 | C |
| ATOM | 632 | C | GLU | B | 2 | −26.204 | 1.466 | 5.329 | 1.00 | 24.84 | C |
| ATOM | 633 | O | GLU | B | 2 | −25.841 | 0.489 | 5.977 | 1.00 | 25.38 | O |
| ATOM | 634 | CB | GLU | B | 2 | −28.527 | 1.767 | 4.564 | 1.00 | 27.51 | C |
| ATOM | 635 | CG | GLU | B | 2 | −28.291 | 2.325 | 3.041 | 1.00 | 33.29 | C |
| ATOM | 636 | CD | GLU | B | 2 | −27.773 | 1.369 | 1.837 | 1.00 | 33.80 | C |
| ATOM | 637 | OE1 | GLU | B | 2 | −27.158 | 1.907 | 0.823 | 1.00 | 33.56 | O |
| ATOM | 638 | OE2 | GLU | B | 2 | −27.994 | 0.101 | 1.847 | 1.00 | 40.17 | O |
| ATOM | 639 | N | ARG | B | 3 | −25.576 | 1.906 | 4.254 | 1.00 | 21.85 | N |
| ATOM | 640 | CA | ARG | B | 3 | −24.463 | 1.137 | 3.714 | 1.00 | 21.13 | C |
| ATOM | 641 | C | ARG | B | 3 | −23.220 | 1.208 | 4.627 | 1.00 | 20.07 | C |
| ATOM | 642 | O | ARG | B | 3 | −22.487 | 0.225 | 4.772 | 1.00 | 23.72 | O |
| ATOM | 643 | CB | ARG | B | 3 | −24.129 | 1.582 | 2.285 | 1.00 | 20.91 | C |
| ATOM | 644 | CG | ARG | B | 3 | −23.387 | 2.900 | 2.222 | 1.00 | 20.27 | C |
| ATOM | 645 | CD | ARG | B | 3 | −23.334 | 3.295 | 0.769 | 1.00 | 23.41 | C |
| ATOM | 646 | NE | ARG | B | 3 | −22.609 | 4.525 | 0.637 | 1.00 | 23.46 | N |
| ATOM | 647 | CZ | ARG | B | 3 | −22.189 | 5.042 | −0.525 | 1.00 | 24.53 | C |
| ATOM | 648 | NH1 | ARG | B | 3 | −21.476 | 6.174 | −0.500 | 1.00 | 21.67 | N |
| ATOM | 649 | NH2 | ARG | B | 3 | −22.436 | 4.429 | −1.689 | 1.00 | 24.84 | N |
| ATOM | 650 | N | ILE | B | 4 | −22.993 | 2.360 | 5.263 | 1.00 | 20.36 | N |
| ATOM | 651 | CA | ILE | B | 4 | −21.820 | 2.462 | 6.158 | 1.00 | 20.25 | C |
| ATOM | 652 | C | ILE | B | 4 | −22.030 | 1.677 | 7.434 | 1.00 | 21.88 | C |
| ATOM | 653 | O | ILE | B | 4 | −21.095 | 1.060 | 7.954 | 1.00 | 20.56 | O |
| ATOM | 654 | CB | ILE | B | 4 | −21.366 | 3.943 | 6.345 | 1.00 | 19.46 | C |
| ATOM | 655 | CG1 | ILE | B | 4 | −19.852 | 4.003 | 6.654 | 1.00 | 22.09 | C |
| ATOM | 656 | CG2 | ILE | B | 4 | −22.215 | 4.653 | 7.423 | 1.00 | 20.45 | C |
| ATOM | 657 | CD1 | ILE | B | 4 | −18.888 | 3.546 | 5.595 | 1.00 | 24.34 | C |
| ATOM | 658 | N | LYS | B | 5 | −23.267 | 1.715 | 7.942 | 1.00 | 21.78 | N |
| ATOM | 659 | CA | LYS | B | 5 | −23.637 | 0.901 | 9.138 | 1.00 | 23.53 | C |
| ATOM | 660 | C | LYS | B | 5 | −23.492 | −0.601 | 8.845 | 1.00 | 22.86 | C |
| ATOM | 661 | O | LYS | B | 5 | −22.962 | −1.380 | 9.701 | 1.00 | 22.97 | O |
| ATOM | 662 | CB | LYS | B | 5 | −25.056 | 1.293 | 9.613 | 1.00 | 24.26 | C |
| ATOM | 663 | CG | LYS | B | 5 | −25.125 | 2.670 | 10.278 | 1.00 | 24.47 | C |
| ATOM | 664 | CD | LYS | B | 5 | −26.418 | 3.019 | 10.985 | 1.00 | 28.71 | C |
| ATOM | 665 | CE | LYS | B | 5 | −26.188 | 4.306 | 11.755 | 1.00 | 33.37 | C |
| ATOM | 666 | NZ | LYS | B | 5 | −27.322 | 4.682 | 12.660 | 1.00 | 40.32 | N |
| ATOM | 667 | N | GLU | B | 6 | −23.942 | −1.042 | 7.681 | 1.00 | 22.28 | N |
| ATOM | 668 | CA | GLU | B | 6 | −23.784 | −2.442 | 7.271 | 1.00 | 22.98 | C |
| ATOM | 669 | C | GLU | B | 6 | −22.264 | −2.846 | 7.197 | 1.00 | 21.39 | C |
| ATOM | 670 | O | GLU | B | 6 | −21.876 | −3.891 | 7.656 | 1.00 | 21.77 | O |
| ATOM | 671 | CB | GLU | B | 6 | −24.503 | −2.762 | 5.963 | 1.00 | 26.13 | C |
| ATOM | 672 | CG | GLU | B | 6 | −24.255 | −4.260 | 5.591 | 1.00 | 30.11 | C |
| ATOM | 673 | CD | GLU | B | 6 | −25.312 | −4.913 | 4.705 | 1.00 | 39.40 | C |
| ATOM | 674 | OE1 | GLU | B | 6 | −26.084 | −4.192 | 4.025 | 1.00 | 41.61 | O |
| ATOM | 675 | OE2 | GLU | B | 6 | −25.343 | −6.178 | 4.673 | 1.00 | 40.60 | O |
| ATOM | 676 | N | LEU | B | 7 | −21.436 | −2.005 | 6.573 | 1.00 | 20.54 | N |
| ATOM | 677 | CA | LEU | B | 7 | −20.002 | −2.245 | 6.515 | 1.00 | 20.39 | C |
| ATOM | 678 | C | LEU | B | 7 | −19.442 | −2.307 | 7.927 | 1.00 | 21.69 | C |
| ATOM | 679 | O | LEU | B | 7 | −18.711 | −3.237 | 8.270 | 1.00 | 21.20 | O |
| ATOM | 680 | CB | LEU | B | 7 | −19.328 | −1.162 | 5.700 | 1.00 | 19.81 | C |
| ATOM | 681 | CG | LEU | B | 7 | −17.776 | −1.355 | 5.619 | 1.00 | 18.81 | C |
| ATOM | 682 | CD1 | LEU | B | 7 | −17.385 | −2.688 | 5.189 | 1.00 | 22.58 | C |
| ATOM | 683 | CD2 | LEU | B | 7 | −17.335 | −0.372 | 4.487 | 1.00 | 19.36 | C |
| ATOM | 684 | N | ARG | B | 8 | −19.829 | −1.357 | 8.784 | 1.00 | 22.12 | N |
| ATOM | 685 | CA | ARG | B | 8 | −19.360 | −1.416 | 10.172 | 1.00 | 23.82 | C |
| ATOM | 686 | C | ARG | B | 8 | −19.787 | −2.726 | 10.844 | 1.00 | 23.49 | C |
| ATOM | 687 | O | ARG | B | 8 | −18.990 | −3.379 | 11.530 | 1.00 | 24.77 | O |
| ATOM | 688 | CB | ARG | B | 8 | −19.923 | −0.218 | 10.927 | 1.00 | 23.90 | C |
| ATOM | 689 | CG | ARG | B | 8 | −19.171 | 0.006 | 12.275 | 1.00 | 25.50 | C |
| ATOM | 690 | CD | ARG | B | 8 | −19.825 | −0.767 | 13.344 | 1.00 | 28.31 | C |
| ATOM | 691 | NE | ARG | B | 8 | −21.260 | −0.714 | 13.088 | 1.00 | 32.20 | N |
| ATOM | 692 | CZ | ARG | B | 8 | −22.006 | 0.377 | 13.275 | 1.00 | 23.96 | C |
| ATOM | 693 | NH1 | ARG | B | 8 | −21.470 | 1.466 | 13.778 | 1.00 | 32.11 | N |
| ATOM | 694 | NH2 | ARG | B | 8 | −23.314 | 0.353 | 13.008 | 1.00 | 30.38 | N |
| ATOM | 695 | N | ASN | B | 9 | −21.008 | −3.151 | 10.573 | 1.00 | 23.93 | N |
| ATOM | 696 | CA | ASN | B | 9 | −21.486 | −4.404 | 11.167 | 1.00 | 24.81 | C |
| ATOM | 697 | C | ASN | B | 9 | −20.746 | −5.636 | 10.667 | 1.00 | 23.64 | C |

TABLE 2b-continued

Data of atomic coordinates for accession code 3AIG, which cites accession code 2ZTT

| ATOM | 698 | O | ASN | B | 9 | −20.490 | −6.523 | 11.429 | 1.00 | 23.96 | O |
|---|---|---|---|---|---|---|---|---|---|---|---|
| ATOM | 699 | CB | ASN | B | 9 | −22.953 | −4.592 | 10.956 | 1.00 | 25.70 | C |
| ATOM | 700 | CG | ASN | B | 9 | −23.772 | −3.426 | 11.484 | 1.00 | 31.22 | C |
| ATOM | 701 | OD1 | ASN | B | 9 | −23.310 | −2.622 | 12.333 | 1.00 | 34.73 | O |
| ATOM | 702 | ND2 | ASN | B | 9 | −24.963 | −3.289 | 10.947 | 1.00 | 34.64 | N |
| ATOM | 703 | N | LEU | B | 10 | −20.445 | −5.670 | 9.376 | 1.00 | 23.53 | N |
| ATOM | 704 | CA | LEU | B | 10 | −19.622 | −6.751 | 8.802 | 1.00 | 24.42 | C |
| ATOM | 705 | C | LEU | B | 10 | −18.182 | −6.776 | 9.311 | 1.00 | 23.58 | C |
| ATOM | 706 | O | LEU | B | 10 | −17.586 | −7.838 | 9.448 | 1.00 | 24.45 | O |
| ATOM | 707 | CB | LEU | B | 10 | −19.664 | −6.616 | 7.291 | 1.00 | 25.45 | C |
| ATOM | 708 | CG | LEU | B | 10 | −20.665 | −7.467 | 6.509 | 1.00 | 30.00 | C |
| ATOM | 709 | CD1 | LEU | B | 10 | −21.734 | −8.367 | 7.250 | 1.00 | 28.04 | C |
| ATOM | 710 | CD2 | LEU | B | 10 | −21.154 | −6.889 | 5.195 | 1.00 | 26.74 | C |
| HETATM | 711 | N | MSE | B | 11 | −17.625 | −5.622 | 9.597 | 1.00 | 20.63 | N |
| HETATM | 712 | CA | MSE | B | 11 | −16.283 | −5.574 | 10.173 | 1.00 | 23.07 | C |
| HETATM | 713 | C | MSE | B | 11 | −16.250 | −5.936 | 11.657 | 1.00 | 23.28 | C |
| HETATM | 714 | O | MSE | B | 11 | −15.164 | −6.023 | 12.254 | 1.00 | 22.58 | O |
| HETATM | 715 | CB | MSE | B | 11 | −15.686 | −4.204 | 9.976 | 1.00 | 21.87 | C |
| HETATM | 716 | CG | MSE | B | 11 | −15.511 | −3.808 | 8.525 | 1.00 | 23.59 | C |
| HETATM | 717 | SE | MSE | B | 11 | −14.003 | −4.783 | 7.723 | 1.00 | 26.44 | SE |
| HETATM | 718 | CE | MSE | B | 11 | −12.674 | −3.981 | 8.833 | 1.00 | 24.76 | C |
| ATOM | 719 | N | SER | B | 12 | −17.414 | −6.103 | 12.277 | 1.00 | 23.40 | N |
| ATOM | 720 | CA | SER | B | 12 | −17.520 | −6.469 | 13.695 | 1.00 | 24.55 | C |
| ATOM | 721 | C | SER | B | 12 | −17.520 | −7.957 | 13.955 | 1.00 | 26.44 | C |
| ATOM | 722 | O | SER | B | 12 | −17.454 | −8.343 | 15.126 | 1.00 | 27.53 | O |
| ATOM | 723 | CB | SER | B | 12 | −18.816 | −5.909 | 14.340 | 1.00 | 24.41 | C |
| ATOM | 724 | OG | SER | B | 12 | −18.857 | −4.525 | 14.140 | 1.00 | 25.82 | O |
| ATOM | 725 | N | GLN | B | 13 | −17.586 | −8.780 | 12.900 | 1.00 | 26.53 | N |
| ATOM | 726 | CA | GLN | B | 13 | −17.500 | −10.235 | 13.063 | 1.00 | 28.28 | C |
| ATOM | 727 | C | GLN | B | 13 | −16.299 | −10.776 | 12.288 | 1.00 | 28.55 | C |
| ATOM | 728 | O | GLN | B | 13 | −16.073 | −10.407 | 11.137 | 1.00 | 27.04 | O |
| ATOM | 729 | CB | GLN | B | 13 | −18.741 | −10.900 | 12.512 | 1.00 | 29.59 | C |
| ATOM | 730 | CG | GLN | B | 13 | −20.072 | −10.382 | 13.129 | 1.00 | 33.27 | C |
| ATOM | 731 | CD | GLN | B | 13 | −21.093 | −11.504 | 13.432 | 1.00 | 40.29 | C |
| ATOM | 732 | OE1 | GLN | B | 13 | −22.177 | −11.522 | 12.853 | 1.00 | 43.53 | O |
| ATOM | 733 | NE2 | GLN | B | 13 | −20.747 | −12.429 | 14.324 | 1.00 | 36.09 | N |
| ATOM | 734 | N | SER | B | 14 | −15.559 | −11.683 | 12.903 | 1.00 | 29.32 | N |
| ATOM | 735 | CA | SER | B | 14 | −14.258 | −12.072 | 12.340 | 1.00 | 30.71 | C |
| ATOM | 736 | C | SER | B | 14 | −14.324 | −12.593 | 10.890 | 1.00 | 28.59 | C |
| ATOM | 737 | O | SER | B | 14 | −13.467 | −12.216 | 10.107 | 1.00 | 30.91 | O |
| ATOM | 738 | CB | SER | B | 14 | −13.553 | −13.089 | 13.247 | 1.00 | 32.06 | C |
| ATOM | 739 | OG | SER | B | 14 | −14.280 | −14.292 | 13.232 | 1.00 | 36.59 | O |
| ATOM | 740 | N | ARG | B | 15 | −15.269 | −13.463 | 10.545 | 1.00 | 29.33 | N |
| ATOM | 741 | CA | ARG | B | 15 | −15.265 | −14.110 | 9.192 | 1.00 | 28.62 | C |
| ATOM | 742 | C | ARG | B | 15 | −15.458 | −13.055 | 8.109 | 1.00 | 28.17 | C |
| ATOM | 743 | O | ARG | B | 15 | −14.721 | −13.010 | 7.123 | 1.00 | 28.15 | O |
| ATOM | 744 | CB | ARG | B | 15 | −16.330 | −15.221 | 9.053 | 1.00 | 29.63 | C |
| ATOM | 745 | CG | ARG | B | 15 | −16.353 | −15.971 | 7.671 | 1.00 | 32.12 | C |
| ATOM | 746 | CD | ARG | B | 15 | −15.200 | −16.994 | 7.394 | 1.00 | 38.40 | C |
| ATOM | 747 | NE | ARG | B | 15 | −13.915 | −16.349 | 7.206 | 1.00 | 41.74 | N |
| ATOM | 748 | CZ | ARG | B | 15 | −13.295 | −16.164 | 6.029 | 1.00 | 39.12 | C |
| ATOM | 749 | NH1 | ARG | B | 15 | −13.802 | −16.593 | 4.874 | 1.00 | 39.59 | N |
| ATOM | 750 | NH2 | ARG | B | 15 | −12.148 | −15.530 | 6.033 | 1.00 | 39.22 | N |
| ATOM | 751 | N | THR | B | 16 | −16.479 | −12.212 | 8.272 | 1.00 | 26.58 | N |
| ATOM | 752 | CA | THR | B | 16 | −16.700 | −11.131 | 7.287 | 1.00 | 24.44 | C |
| ATOM | 753 | C | THR | B | 16 | −15.577 | −10.074 | 7.283 | 1.00 | 24.53 | C |
| ATOM | 754 | O | THR | B | 16 | −15.263 | −9.523 | 6.211 | 1.00 | 23.71 | O |
| ATOM | 755 | CB | THR | B | 16 | −18.078 | −10.489 | 7.388 | 1.00 | 26.91 | C |
| ATOM | 756 | OG1 | THR | B | 16 | −18.458 | −10.271 | 8.756 | 1.00 | 22.76 | O |
| ATOM | 757 | CG2 | THR | B | 16 | −19.095 | −11.400 | 6.710 | 1.00 | 26.70 | C |
| ATOM | 758 | N | ARG | B | 17 | −15.036 | −9.745 | 8.453 | 1.00 | 23.49 | N |
| ATOM | 759 | CA | ARG | B | 17 | −13.919 | −.812 | 8.517 | 1.00 | 24.67 | C |
| ATOM | 760 | C | ARG | B | 17 | −12.748 | −9.361 | 7.679 | 1.00 | 26.13 | C |
| ATOM | 761 | O | ARG | B | 17 | −12.147 | −8.620 | 6.890 | 1.00 | 24.21 | O |
| ATOM | 762 | CB | ARG | B | 17 | −13.517 | −8.546 | 9.950 | 1.00 | 24.38 | C |
| ATOM | 763 | CG | ARG | B | 17 | −12.306 | −7.674 | 10.111 | 1.00 | 26.71 | C |
| ATOM | 764 | CD | ARG | B | 17 | −12.120 | −7.414 | 11.569 | 1.00 | 30.98 | C |
| ATOM | 765 | NE | ARG | B | 17 | −10.904 | −6.653 | 11.835 | 1.00 | 33.93 | N |
| ATOM | 766 | CZ | ARG | B | 17 | −10.518 | −6.318 | 13.068 | 1.00 | 36.29 | C |
| ATOM | 767 | NH1 | ARG | B | 17 | −11.281 | −6.622 | 14.104 | 1.00 | 37.54 | N |
| ATOM | 768 | NH2 | ARG | B | 17 | −9.406 | −5.636 | 13.260 | 1.00 | 39.02 | N |
| ATOM | 769 | N | GLU | B | 18 | −12.453 | −10.646 | 7.851 | 1.00 | 26.07 | N |
| ATOM | 770 | CA | GLU | B | 18 | −11.407 | −11.308 | 7.068 | 1.00 | 27.15 | C |
| ATOM | 771 | C | GLU | B | 18 | −11.641 | −11.207 | 5.568 | 1.00 | 27.17 | C |
| ATOM | 772 | O | GLU | B | 18 | −10.720 | −10.793 | 4.823 | 1.00 | 28.19 | O |
| ATOM | 773 | CB | GLU | B | 18 | −11.372 | −12.761 | 7.455 | 1.00 | 28.66 | C |
| ATOM | 774 | CG | GLU | B | 18 | −10.635 | −13.096 | 8.657 | 1.00 | 35.19 | C |
| ATOM | 775 | CD | GLU | B | 18 | −10.449 | −14.600 | 8.701 | 1.00 | 42.34 | C |

TABLE 2b-continued

Data of atomic coordinates for accession code 3AIG, which cites accession code 2ZTT

| ATOM | 776 | OE1 | GLU | B | 18 | −11.465 | −15.324 | 8.732 | 1.00 | 40.67 | O |
|---|---|---|---|---|---|---|---|---|---|---|---|
| ATOM | 777 | OE2 | GLU | B | 18 | −9.290 | −15.050 | 8.618 | 1.00 | 48.56 | O |
| ATOM | 778 | N | ILE | B | 19 | −12.849 | −11.559 | 5.115 | 1.00 | 25.32 | N |
| ATOM | 779 | CA | ILE | B | 19 | −13.201 | −11.520 | 3.714 | 1.00 | 24.40 | C |
| ATOM | 780 | C | ILE | B | 19 | −12.934 | −10.100 | 3.203 | 1.00 | 23.78 | C |
| ATOM | 781 | O | ILE | B | 19 | −12.266 | −9.904 | 2.192 | 1.00 | 23.81 | O |
| ATOM | 782 | CB | ILE | B | 19 | −14.673 | −11.922 | 3.456 | 1.00 | 23.74 | C |
| ATOM | 783 | CG1 | ILE | B | 19 | −14.932 | −13.390 | 3.804 | 1.00 | 24.74 | C |
| ATOM | 784 | CG2 | ILE | B | 19 | −15.056 | −11.646 | 1.995 | 1.00 | 24.41 | C |
| ATOM | 785 | CD1 | ILE | B | 19 | −16.461 | −13.775 | 3.646 | 1.00 | 24.40 | C |
| ATOM | 786 | N | LEU | B | 20 | −13.417 | −9.087 | 3.936 | 1.00 | 22.51 | N |
| ATOM | 787 | CA | LEU | B | 20 | −13.387 | −7.734 | 3.420 | 1.00 | 22.90 | C |
| ATOM | 788 | C | LEU | B | 20 | −12.003 | −7.089 | 3.412 | 1.00 | 23.65 | C |
| ATOM | 789 | O | LEU | B | 20 | −11.720 | −6.266 | 2.557 | 1.00 | 23.55 | O |
| ATOM | 790 | CB | LEU | B | 20 | −14.444 | −6.811 | 4.165 | 1.00 | 22.60 | C |
| ATOM | 791 | CG | LEU | B | 20 | −15.901 | −7.189 | 3.990 | 1.00 | 24.25 | C |
| ATOM | 792 | CD1 | LEU | B | 20 | −16.712 | −6.548 | 5.144 | 1.00 | 22.83 | C |
| ATOM | 793 | CD2 | LEU | B | 20 | −16.410 | −6.687 | 2.693 | 1.00 | 24.70 | C |
| ATOM | 794 | N | THR | B | 21 | −11.153 | −7.476 | 4.363 | 1.00 | 23.03 | N |
| ATOM | 795 | CA | THR | B | 21 | −9.812 | −6.910 | 4.49 | 1.00 | 25.47 | C |
| ATOM | 796 | C | THR | B | 21 | −8.803 | −7.583 | 3.582 | 1.00 | 25.80 | C |
| ATOM | 797 | O | THR | B | 21 | −7.882 | −6.919 | 3.130 | 1.00 | 25.81 | O |
| ATOM | 798 | CB | THR | B | 21 | −9.351 | −7.025 | 5.944 | 1.00 | 26.09 | C |
| ATOM | 799 | OG1 | THR | B | 21 | −9.436 | −8.396 | 6.337 | 1.00 | 33.16 | O |
| ATOM | 800 | CG2 | THR | B | 21 | −10.344 | −6.250 | 6.862 | 1.00 | 25.26 | C |
| ATOM | 801 | N | LYS | B | 22 | −9.014 | −8.867 | 3.333 | 1.00 | 26.15 | N |
| ATOM | 802 | CA | LYS | B | 22 | −8.045 | −9.700 | 2.603 | 1.00 | 27.81 | C |
| ATOM | 803 | C | LYS | B | 22 | −8.301 | −9.782 | 1.112 | 1.00 | 27.91 | C |
| ATOM | 804 | O | LYS | B | 22 | −7.372 | −9.913 | 0.290 | 1.00 | 28.92 | O |
| ATOM | 805 | CB | LYS | B | 22 | −8.033 | −11.100 | 3.217 | 1.00 | 27.54 | C |
| ATOM | 806 | CG | LYS | B | 22 | −7.519 | −11.141 | 4.646 | 1.00 | 30.10 | C |
| ATOM | 807 | CD | LYS | B | 22 | −7.171 | −12.595 | 5.030 | 1.00 | 34.21 | C |
| ATOM | 808 | CE | LYS | B | 22 | −7.450 | −12.841 | 6.480 | 1.00 | 37.73 | C |
| ATOM | 809 | NZ | LYS | B | 22 | −6.305 | −12.300 | 7.239 | 1.00 | 41.56 | N |
| ATOM | 810 | N | THR | B | 23 | −9.562 | −9.755 | 0.730 | 1.00 | 27.07 | N |
| ATOM | 811 | CA | THR | B | 23 | −9.956 | −9.977 | −0.652 | 1.00 | 28.14 | C |
| ATOM | 812 | C | THR | B | 23 | −9.833 | −8.691 | −1.498 | 1.00 | 28.04 | C |
| ATOM | 813 | O | THR | B | 23 | −10.333 | −7.639 | −1.137 | 1.00 | 27.02 | O |
| ATOM | 814 | CB | THR | B | 23 | −11.355 | −10.472 | −0.709 | 1.00 | 27.36 | C |
| ATOM | 815 | OG1 | THR | B | 23 | −11.523 | −11.560 | 0.252 | 1.00 | 29.07 | O |
| ATOM | 816 | CG2 | THR | B | 23 | −11.769 | −10.883 | −2.170 | 1.00 | 30.98 | C |
| ATOM | 817 | N | THR | B | 24 | −9.131 | −8.789 | −2.618 | 1.00 | 27.52 | N |
| ATOM | 818 | CA | THR | B | 24 | −8.979 | −7.632 | −3.463 | 1.00 | 27.25 | C |
| ATOM | 819 | C | THR | B | 24 | −10.183 | −7.524 | −4.347 | 1.00 | 26.49 | C |
| ATOM | 820 | O | THR | B | 24 | −10.870 | −8.518 | −4.603 | 1.00 | 27.79 | O |
| ATOM | 821 | CB | THR | B | 24 | −7.691 | −7.695 | −4.309 | 1.00 | 28.59 | C |
| ATOM | 822 | OG1 | THR | B | 24 | −7.796 | −8.740 | −5.272 | 1.00 | 30.02 | O |
| ATOM | 823 | CG2 | THR | B | 24 | −6.518 | −8.010 | −3.397 | 1.00 | 28.37 | C |
| ATOM | 824 | N | VAL | B | 25 | −10.428 | −6.306 | −4.827 | 1.00 | 26.53 | N |
| ATOM | 825 | CA | VAL | B | 25 | −11.541 | −6.016 | −5.711 | 1.00 | 26.64 | C |
| ATOM | 826 | C | VAL | B | 25 | −11.468 | −6.883 | −6.956 | 1.00 | 29.87 | C |
| ATOM | 827 | O | VAL | B | 25 | −12.494 | −7.446 | −7.423 | 1.00 | 30.46 | O |
| ATOM | 828 | CB | VAL | B | 25 | −11.526 | −4.509 | −6.047 | 1.00 | 27.57 | C |
| ATOM | 829 | CG1 | VAL | B | 25 | −12.291 | −4.199 | −7.249 | 1.00 | 27.21 | C |
| ATOM | 830 | CG2 | VAL | B | 25 | −12.150 | −3.746 | −4.869 | 1.00 | 26.52 | C |
| ATOM | 831 | N | ASP | B | 26 | −10.261 | −6.991 | −7.505 | 1.00 | 31.22 | N |
| ATOM | 832 | CA | ASP | B | 26 | −10.023 | −7.809 | −8.713 | 1.00 | 34.84 | C |
| ATOM | 833 | C | ASP | B | 26 | −10.441 | −9.233 | −8.577 | 1.00 | 36.17 | C |
| ATOM | 834 | O | ASP | B | 26 | −10.874 | −9.831 | −9.546 | 1.00 | 39.36 | O |
| ATOM | 835 | CB | ASP | B | 26 | −8.542 | −7.840 | −9.051 | 1.00 | 34.75 | C |
| ATOM | 836 | CG | ASP | B | 26 | −8.151 | −6.740 | −9.954 | 1.00 | 38.48 | C |
| ATOM | 837 | OD1 | ASP | B | 26 | −9.056 | −6.136 | −10.528 | 1.00 | 41.60 | O |
| ATOM | 838 | OD2 | ASP | B | 26 | −6.942 | −6.464 | −10.074 | 1.00 | 39.27 | O |
| ATOM | 839 | N | HIS | B | 27 | −10.229 | −9.805 | −7.403 | 1.00 | 36.95 | N |
| ATOM | 840 | CA | HIS | B | 27 | −10.519 | −11.202 | −7.204 | 1.00 | 38.06 | C |
| ATOM | 841 | C | HIS | B | 27 | −12.050 | −11.455 | −7.064 | 1.00 | 38.73 | C |
| ATOM | 842 | O | HIS | B | 27 | −12.460 | −12.617 | −6.902 | 1.00 | 38.29 | O |
| ATOM | 843 | CB | HIS | B | 27 | −9.716 | −11.753 | −6.027 | 1.00 | 37.82 | C |
| ATOM | 844 | CG | HIS | B | 27 | −8.229 | −11.871 | −6.277 | 1.00 | 37.95 | C |
| ATOM | 845 | ND1 | HIS | B | 27 | −7.679 | −11.854 | −7.541 | 1.00 | 39.67 | N |
| ATOM | 846 | CD2 | HIS | B | 27 | −7.193 | −12.031 | −5.425 | 1.00 | 37.37 | C |
| ATOM | 847 | CE1 | HIS | B | 27 | −6.366 | −11.970 | −7.455 | 1.00 | 35.14 | C |
| ATOM | 848 | NE2 | HIS | B | 27 | −6.042 | −12.080 | −6.182 | 1.00 | 39.22 | N |
| HETATM | 849 | N | MSE | B | 28 | −12.877 | −10.391 | −7.158 | 1.00 | 39.01 | N |
| HETATM | 850 | CA | MSE | B | 28 | −14.303 | −10.474 | −6.790 | 1.00 | 39.29 | C |
| HETATM | 851 | C | MSE | B | 28 | −15.145 | −11.141 | −7.806 | 1.00 | 39.56 | C |
| HETATM | 852 | O | MSE | B | 28 | −16.001 | −11.943 | −7.449 | 1.00 | 39.66 | O |
| HETATM | 853 | CB | MSE | B | 28 | −14.941 | −9.094 | −6.546 | 1.00 | 40.92 | C |

TABLE 2b-continued

Data of atomic coordinates for accession code 3AIG, which cites accession code 2ZTT

| | | | | | | | | | | |
|---|---|---|---|---|---|---|---|---|---|---|
| HETATM | 854 | CG | MSE | B | 28 | −14.775 | −8.517 | −5.174 | 1.00 | 41.88 | C |
| HETATM | 855 | SE | MSE | B | 28 | −15.876 | −6.859 | −5.114 | 1.00 | 41.25 | SE |
| HETATM | 856 | CE | MSE | B | 28 | −15.706 | −6.453 | −7.022 | 1.00 | 44.41 | C |
| ATOM | 857 | N | ALA | B | 29 | −14.947 | −10.761 | −9.060 | 1.00 | 38.45 | N |
| ATOM | 858 | CA | ALA | B | 29 | −15.594 | −11.455 | −10.152 | 1.00 | 39.47 | C |
| ATOM | 859 | C | ALA | B | 29 | −15.147 | −12.889 | −10.051 | 1.00 | 38.00 | C |
| ATOM | 860 | O | ALA | B | 29 | −15.966 | −13.762 | −10.210 | 1.00 | 39.32 | O |
| ATOM | 861 | CB | ALA | B | 29 | −15.211 | −10.855 | −11.495 | 1.00 | 38.67 | C |
| ATOM | 862 | N | ILE | B | 30 | −13.854 | −13.113 | −9.742 | 1.00 | 37.63 | N |
| ATOM | 863 | CA | ILE | B | 30 | −13.278 | −14.473 | −9.725 | 1.00 | 35.75 | C |
| ATOM | 864 | C | ILE | B | 30 | −14.036 | −15.380 | −8.730 | 1.00 | 35.07 | C |
| ATOM | 865 | O | ILE | B | 30 | −14.597 | −16.428 | −9.107 | 1.00 | 34.85 | O |
| ATOM | 866 | CB | ILE | B | 30 | −11.707 | −14.474 | −9.430 | 1.00 | 34.61 | C |
| ATOM | 867 | CG1 | ILE | B | 30 | −10.922 | −13.614 | −10.454 | 1.00 | 36.03 | C |
| ATOM | 868 | CG2 | ILE | B | 30 | −11.120 | −15.869 | −9.457 | 1.00 | 34.84 | C |
| ATOM | 869 | CD1 | ILE | B | 30 | −9.391 | −13.469 | −10.126 | 1.00 | 36.23 | C |
| ATOM | 870 | N | ILE | B | 31 | −14.037 | −14.972 | −7.468 | 1.00 | 34.96 | N |
| ATOM | 871 | CA | ILE | B | 31 | −14.787 | −15.681 | −6.419 | 1.00 | 34.73 | C |
| ATOM | 872 | C | ILE | B | 31 | −16.276 | −15.744 | −6.749 | 1.00 | 34.68 | C |
| ATOM | 873 | O | ILE | B | 31 | −16.885 | −16.797 | −6.626 | 1.00 | 33.51 | O |
| ATOM | 874 | CB | ILE | B | 31 | −14.598 | −15.011 | −5.062 | 1.00 | 34.45 | C |
| ATOM | 875 | CG1 | ILE | B | 31 | −13.168 | −15.184 | −4.582 | 1.00 | 35.76 | C |
| ATOM | 876 | CG2 | ILE | B | 31 | −15.632 | −15.537 | −4.045 | 1.00 | 35.41 | C |
| ATOM | 877 | CD1 | ILE | B | 31 | −12.581 | −13.856 | −3.965 | 1.00 | 34.84 | C |
| ATOM | 878 | N | LYS | B | 32 | −16.859 | −14.603 | −7.138 | 1.00 | 35.82 | N |
| ATOM | 879 | CA | LYS | B | 32 | −18.270 | −14.560 | −7.515 | 1.00 | 38.27 | C |
| ATOM | 880 | C | LYS | B | 32 | −18.641 | −15.547 | −8.630 | 1.00 | 38.07 | C |
| ATOM | 881 | O | LYS | B | 32 | −19.709 | −16.160 | −8.577 | 1.00 | 37.19 | O |
| ATOM | 882 | CB | LYS | B | 32 | −18.715 | −13.133 | −7.912 | 1.00 | 38.71 | C |
| ATOM | 883 | CG | LYS | B | 32 | −19.315 | −12.280 | −6.799 | 1.00 | 41.46 | C |
| ATOM | 884 | CD | LYS | B | 32 | −20.181 | −11.103 | −7.362 | 1.00 | 40.98 | C |
| ATOM | 885 | CE | LYS | B | 32 | −19.292 | −9.883 | −7.759 | 1.00 | 45.08 | C |
| ATOM | 886 | NZ | LYS | B | 32 | −20.013 | −8.595 | −8.084 | 1.00 | 44.88 | N |
| ATOM | 887 | N | LYS | B | 33 | −17.758 | −15.735 | −9.620 | 1.00 | 37.71 | N |
| ATOM | 888 | CA | LYS | B | 33 | −18.054 | −16.660 | −10.713 | 1.00 | 38.85 | C |
| ATOM | 889 | C | LYS | B | 33 | −18.347 | −18.066 | −10.202 | 1.00 | 38.35 | C |
| ATOM | 890 | O | LYS | B | 33 | −19.237 | −18.751 | −10.722 | 1.00 | 38.41 | O |
| ATOM | 891 | CB | LYS | B | 33 | −16.920 | −16.681 | −11.746 | 1.00 | 39.25 | C |
| ATOM | 892 | CG | LYS | B | 33 | −17.159 | −17.577 | −12.948 | 1.00 | 41.33 | C |
| ATOM | 893 | CD | LYS | B | 33 | −15.967 | −17.478 | −13.920 | 1.00 | 40.47 | C |
| ATOM | 894 | CE | LYS | B | 33 | −16.162 | −18.252 | −15.238 | 1.00 | 40.98 | C |
| ATOM | 895 | NZ | LYS | B | 33 | −14.878 | −18.326 | −16.028 | 1.00 | 45.24 | N |
| ATOM | 896 | N | TYR | B | 34 | −17.624 | −18.478 | −9.153 | 1.00 | 36.25 | N |
| ATOM | 897 | CA | TYR | B | 34 | −17.761 | −19.813 | −8.596 | 1.00 | 36.50 | C |
| ATOM | 898 | C | TYR | B | 34 | −18.536 | −19.827 | −7.293 | 1.00 | 37.95 | C |
| ATOM | 899 | O | TYR | B | 34 | −18.436 | −20.747 | −6.492 | 1.00 | 37.18 | O |
| ATOM | 900 | CB | TYR | B | 34 | −16.378 | −20.466 | −8.447 | 1.00 | 35.03 | C |
| ATOM | 901 | CG | TYR | B | 34 | −15.689 | −20.607 | −9.783 | 1.00 | 31.97 | C |
| ATOM | 902 | CD1 | TYR | B | 34 | −14.821 | −19.627 | −10.234 | 1.00 | 31.15 | C |
| ATOM | 903 | CD2 | TYR | B | 34 | −15.939 | −21.688 | −10.610 | 1.00 | 30.16 | C |
| ATOM | 904 | CE1 | TYR | B | 34 | −14.197 | −19.742 | −11.476 | 1.00 | 30.81 | C |
| ATOM | 905 | CE2 | TYR | B | 34 | −15.309 | −21.805 | −11.869 | 1.00 | 29.32 | C |
| ATOM | 906 | CZ | TYR | B | 34 | −14.448 | −20.832 | −12.277 | 1.00 | 29.23 | C |
| ATOM | 907 | OH | TYR | B | 34 | −13.792 | −20.870 | −13.484 | 1.00 | 30.92 | O |
| ATOM | 908 | N | THR | B | 35 | −19.314 | −18.772 | −7.100 | 1.00 | 40.23 | N |
| ATOM | 909 | CA | THR | B | 35 | −20.356 | −18.749 | −6.089 | 1.00 | 43.06 | C |
| ATOM | 910 | C | THR | B | 35 | −21.715 | −18.867 | −6.750 | 1.00 | 43.69 | C |
| ATOM | 911 | O | THR | B | 35 | −22.395 | −19.883 | −6.582 | 1.00 | 46.10 | O |
| ATOM | 912 | CB | THR | B | 35 | −20.324 | −17.455 | −5.330 | 1.00 | 43.39 | C |
| ATOM | 913 | OG1 | THR | B | 35 | −19.166 | −17.458 | −4.484 | 1.00 | 43.20 | O |
| ATOM | 914 | CG2 | THR | B | 35 | −21.619 | −17.287 | −4.495 | 1.00 | 44.15 | C |
| TER | 915 | | THR | B | 35 | | | | 1.00 | | |
| ATOM | 916 | N | ASP | C | 685 | −24.829 | 18.659 | 25.170 | 1.00 | 60.50 | N |
| ATOM | 917 | CA | ASP | C | 685 | −23.912 | 17.466 | 25.082 | 1.00 | 60.40 | C |
| ATOM | 918 | C | ASP | C | 685 | −23.619 | 16.800 | 26.439 | 1.00 | 60.09 | C |
| ATOM | 919 | O | ASP | C | 685 | −22.664 | 16.024 | 26.599 | 1.00 | 60.32 | O |
| ATOM | 920 | CB | ASP | C | 685 | −22.645 | 17.783 | 24.283 | 1.00 | 60.57 | C |
| ATOM | 921 | CG | ASP | C | 685 | −22.867 | 17.648 | 22.781 | 1.00 | 61.54 | C |
| ATOM | 922 | OD1 | ASP | C | 685 | −22.264 | 16.737 | 22.169 | 1.00 | 62.77 | O |
| ATOM | 923 | OD2 | ASP | C | 685 | −23.666 | 18.432 | 22.216 | 1.00 | 61.79 | O |
| ATOM | 924 | N | GLU | C | 686 | −24.479 | 17.137 | 27.395 | 1.00 | 59.25 | N |
| ATOM | 925 | CA | GLU | C | 686 | −24.849 | 16.294 | 28.512 | 1.00 | 58.54 | C |
| ATOM | 926 | C | GLU | C | 686 | −25.606 | 15.095 | 27.939 | 1.00 | 58.06 | C |
| ATOM | 927 | O | GLU | C | 686 | −25.783 | 14.075 | 28.604 | 1.00 | 57.93 | O |
| ATOM | 928 | CB | GLU | C | 686 | −25.796 | 17.069 | 29.437 | 1.00 | 58.64 | C |
| ATOM | 929 | CG | GLU | C | 686 | −25.290 | 18.428 | 29.915 | 1.00 | 60.36 | C |
| ATOM | 930 | CD | GLU | C | 686 | −25.289 | 19.510 | 28.826 | 1.00 | 62.88 | C |
| ATOM | 931 | OE1 | GLU | C | 686 | −26.171 | 20.399 | 28.867 | 1.00 | 62.43 | O |

TABLE 2b-continued

Data of atomic coordinates for accession code 3AIG, which cites accession code 2ZTT

| ATOM | 932 | OE2 | GLU | C | 686 | −24.403 | 19.479 | 27.938 | 1.00 | 63.09 | O |
|---|---|---|---|---|---|---|---|---|---|---|---|
| ATOM | 933 | N | GLN | C | 687 | −26.078 | 15.253 | 26.701 | 1.00 | 57.20 | N |
| ATOM | 934 | CA | GLN | C | 687 | −26.857 | 14.231 | 26.012 | 1.00 | 56.62 | C |
| ATOM | 935 | C | GLN | C | 687 | −25.996 | 13.100 | 25.429 | 1.00 | 55.48 | C |
| ATOM | 936 | O | GLN | C | 687 | −26.475 | 11.977 | 25.349 | 1.00 | 55.29 | O |
| ATOM | 937 | CB | GLN | C | 687 | −27.788 | 14.856 | 24.956 | 1.00 | 56.66 | C |
| ATOM | 938 | CG | GLN | C | 687 | −29.211 | 15.163 | 25.485 | 1.00 | 57.61 | C |
| ATOM | 939 | CD | GLN | C | 687 | −30.163 | 15.697 | 24.407 | 1.00 | 57.92 | C |
| ATOM | 940 | OE1 | GLN | C | 687 | −30.610 | 14.950 | 23.532 | 1.00 | 59.13 | O |
| ATOM | 941 | NE2 | GLN | C | 687 | −30.486 | 16.990 | 24.481 | 1.00 | 58.11 | N |
| HETATM | 942 | N | MSE | C | 688 | −24.750 | 13.391 | 25.033 | 1.00 | 54.65 | N |
| HETATM | 943 | CA | MSE | C | 688 | −23.766 | 12.344 | 24.692 | 1.00 | 54.25 | C |
| HETATM | 944 | C | MSE | C | 688 | −23.492 | 11.508 | 25.937 | 1.00 | 53.29 | C |
| HETATM | 945 | O | MSE | C | 688 | −23.545 | 10.285 | 25.894 | 1.00 | 53.15 | O |
| HETATM | 946 | CB | MSE | C | 688 | −22.436 | 12.923 | 24.188 | 1.00 | 55.21 | C |
| HETATM | 947 | CG | MSE | C | 688 | −22.449 | 13.586 | 22.805 | 1.00 | 57.33 | C |
| HETATM | 948S | E | MSE | C | 688 | −22.809 | 12.397 | 21.299 | 1.00 | 66.73 | SE |
| HETATM | 949 | CE | MSE | C | 688 | −23.569 | 13.685 | 20.024 | 1.00 | 60.28 | C |
| ATOM | 950 | N | TYR | C | 689 | −23.220 | 12.185 | 27.052 | 1.00 | 52.07 | N |
| ATOM | 951 | CA | TYR | C | 689 | −23.041 | 11.526 | 28.350 | 1.00 | 50.90 | C |
| ATOM | 952 | C | TYR | C | 689 | −24.296 | 10.759 | 28.753 | 1.00 | 49.90 | C |
| ATOM | 953 | O | TYR | C | 689 | −24.215 | 9.646 | 29.257 | 1.00 | 49.51 | O |
| ATOM | 954 | CB | TYR | C | 689 | −22.672 | 12.556 | 29.437 | 1.00 | 51.40 | C |
| ATOM | 955 | CG | TYR | C | 689 | −21.184 | 12.799 | 29.637 | 1.00 | 52.31 | C |
| ATOM | 956 | CD1 | TYR | C | 689 | −20.399 | 11.879 | 30.329 | 1.00 | 53.26 | C |
| ATOM | 957 | CD2 | TYR | C | 689 | −20.570 | 13.962 | 29.168 | 1.00 | 53.53 | C |
| ATOM | 958 | CE1 | TYR | C | 689 | −19.044 | 12.091 | 30.529 | 1.00 | 54.06 | C |
| ATOM | 959 | CE2 | TYR | C | 689 | −19.208 | 14.193 | 29.366 | 1.00 | 54.16 | C |
| ATOM | 960 | CZ | TYR | C | 689 | −18.455 | 13.247 | 30.048 | 1.00 | 54.40 | C |
| ATOM | 961 | OH | TYR | C | 689 | −17.117 | 13.448 | 30.261 | 1.00 | 53.97 | O |
| ATOM | 962 | N | GLN | C | 690 | −25.462 | 11.359 | 28.514 | 1.00 | 48.86 | N |
| ATOM | 963 | CA | GLN | C | 690 | −26.744 | 10.780 | 28.898 | 1.00 | 47.73 | C |
| ATOM | 964 | C | GLN | C | 690 | −27.019 | 9.490 | 28.137 | 1.00 | 46.50 | C |
| ATOM | 965 | O | GLN | C | 690 | −27.539 | 8.549 | 28.706 | 1.00 | 45.52 | O |
| ATOM | 966 | CB | GLN | C | 690 | −27.872 | 11.806 | 28.701 | 1.00 | 48.46 | C |
| ATOM | 967 | CG | GLN | C | 690 | −29.290 | 11.294 | 28.915 | 1.00 | 51.36 | C |
| ATOM | 968 | CD | GLN | C | 690 | −29.592 | 10.842 | 30.335 | 1.00 | 54.81 | C |
| ATOM | 969 | OE1 | GLN | C | 690 | −30.447 | 9.974 | 30.535 | 1.00 | 56.99 | O |
| ATOM | 970 | NE2 | GLN | C | 690 | −28.923 | 11.438 | 31.330 | 1.00 | 55.14 | N |
| ATOM | 971 | N | ARG | C | 691 | −26.615 | 9.470 | 26.865 | 1.00 | 44.85 | N |
| ATOM | 972 | CA | ARG | C | 691 | −26.709 | 8.309 | 25.979 | 1.00 | 44.27 | C |
| ATOM | 973 | C | ARG | C | 691 | −25.934 | 7.109 | 26.537 | 1.00 | 42.63 | C |
| ATOM | 974 | O | ARG | C | 691 | −26.422 | 5.961 | 26.525 | 1.00 | 41.80 | O |
| ATOM | 975 | CB | ARG | C | 691 | −26.112 | 8.694 | 24.633 | 1.00 | 44.83 | C |
| ATOM | 976 | CG | ARG | C | 691 | −26.702 | 7.999 | 23.439 | 1.00 | 47.98 | C |
| ATOM | 977 | CD | ARG | C | 691 | −26.236 | 8.697 | 22.179 | 1.00 | 52.95 | C |
| ATOM | 978 | NE | ARG | C | 691 | −26.658 | 8.004 | 20.966 | 1.00 | 56.20 | N |
| ATOM | 979 | CZ | ARG | C | 691 | −26.242 | 8.324 | 19.743 | 1.00 | 57.95 | C |
| ATOM | 980 | NH1 | ARG | C | 691 | −25.388 | 9.329 | 19.572 | 1.00 | 57.68 | N |
| ATOM | 981 | NH2 | ARG | C | 691 | −26.675 | 7.631 | 18.690 | 1.00 | 58.58 | N |
| ATOM | 982 | N | CYS | C | 692 | −24.722 | 7.404 | 26.994 | 1.00 | 40.36 | N |
| ATOM | 983 | CA | CYS | C | 692 | −23.832 | 6.417 | 27.601 | 1.00 | 38.69 | C |
| ATOM | 984 | C | CYS | C | 692 | −24.430 | 5.838 | 28.883 | 1.00 | 38.18 | C |
| ATOM | 985 | O | CYS | C | 692 | −24.414 | 4.627 | 29.068 | 1.00 | 35.68 | O |
| ATOM | 986 | CB | CYS | C | 692 | −22.445 | 7.005 | 27.812 | 1.00 | 38.76 | C |
| ATOM | 987 | SG | CYS | C | 692 | −21.649 | 7.470 | 26.253 | 1.00 | 37.64 | S |
| ATOM | 988 | N | CYS | C | 693 | −24.992 | 6.696 | 29.743 | 1.00 | 38.42 | N |
| ATOM | 989 | CA | CYS | C | 693 | −25.659 | 6.241 | 30.977 | 1.00 | 39.62 | C |
| ATOM | 990 | C | CYS | C | 693 | −26.856 | 5.338 | 30.785 | 1.00 | 38.72 | C |
| ATOM | 991 | O | CYS | C | 693 | −26.966 | 4.311 | 31.468 | 1.00 | 39.25 | O |
| ATOM | 992 | CB | CYS | C | 693 | −26.160 | 7.437 | 31.775 | 1.00 | 40.79 | C |
| ATOM | 993 | SG | CYS | C | 693 | −24.875 | 8.143 | 32.646 | 1.00 | 47.90 | S |
| ATOM | 994 | N | ASN | C | 694 | −27.762 | 5.742 | 29.895 | 1.00 | 37.97 | N |
| ATOM | 995 | CA | ASN | C | 694 | −28.911 | 4.944 | 29.535 | 1.00 | 38.06 | C |
| ATOM | 996 | C | ASN | C | 694 | −28.464 | 3.580 | 29.036 | 1.00 | 36.68 | C |
| ATOM | 997 | O | ASN | C | 694 | −29.112 | 2.583 | 29.314 | 1.00 | 37.99 | O |
| ATOM | 998 | CB | ASN | C | 694 | −29.755 | 5.612 | 28.434 | 1.00 | 38.04 | C |
| ATOM | 999 | CG | ASN | C | 694 | −30.491 | 6.862 | 28.915 | 1.00 | 40.69 | C |
| ATOM | 1000 | OD1 | ASN | C | 694 | −30.448 | 7.227 | 30.090 | 1.00 | 42.41 | O |
| ATOM | 1001 | ND2 | ASN | C | 694 | −31.160 | 7.523 | 27.993 | 1.00 | 40.50 | N |
| ATOM | 1002 | N | LEU | C | 695 | −27.366 | 3.540 | 28.285 | 1.00 | 36.40 | N |
| ATOM | 1003 | CA | LEU | C | 695 | −26.917 | 2.249 | 27.728 | 1.00 | 33.46 | C |
| ATOM | 1004 | C | LEU | C | 695 | −26.315 | 1.399 | 28.845 | 1.00 | 33.41 | C |
| ATOM | 1005 | 0 | LEU | C | 695 | −26.588 | 0.202 | 28.982 | 1.00 | 31.53 | O |
| ATOM | 1006 | CB | LEU | C | 695 | −25.937 | 2.430 | 26.551 | 1.00 | 33.81 | C |
| ATOM | 1007 | CG | LEU | C | 695 | −25.557 | 1.070 | 25.934 | 1.00 | 31.93 | C |
| ATOM | 1008 | CD1 | LEU | C | 695 | −26.786 | 0.244 | 25.533 | 1.00 | 31.26 | C |
| ATOM | 1009 | CD2 | LEU | C | 695 | −24.649 | 1.269 | 24.756 | 1.00 | 34.72 | C |

TABLE 2b-continued

Data of atomic coordinates for accession code 3AIG, which cites accession code 2ZTT

| ATOM | 1010 | N   | PHE | C | 696 | −25.497 | 2.032  | 29.656 | 1.00 | 32.67 | N |
|------|------|-----|-----|---|-----|---------|--------|--------|------|-------|---|
| ATOM | 1011 | CA  | PHE | C | 696 | −24.980 | 1.367  | 30.858 | 1.00 | 34.42 | C |
| ATOM | 1012 | C   | PHE | C | 696 | −26.060 | 0.689  | 31.693 | 1.00 | 35.53 | C |
| ATOM | 1013 | O   | PHE | C | 696 | −25.864 | −0.435 | 32.179 | 1.00 | 34.13 | O |
| ATOM | 1014 | CB  | PHE | C | 696 | −24.217 | 2.358  | 31.723 | 1.00 | 33.47 | C |
| ATOM | 1015 | CG  | PHE | C | 696 | −23.421 | 1.693  | 32.820 | 1.00 | 34.85 | C |
| ATOM | 1016 | CD1 | PHE | C | 696 | −22.113 | 1.300  | 32.590 | 1.00 | 31.68 | C |
| ATOM | 1017 | CD2 | PHE | C | 696 | −23.990 | 1.465  | 34.082 | 1.00 | 34.58 | C |
| ATOM | 1018 | CE1 | PHE | C | 696 | −21.356 | 0.684  | 33.600 | 1.00 | 33.56 | C |
| ATOM | 1019 | CE2 | PHE | C | 696 | −23.246 | 0.857  | 35.088 | 1.00 | 33.71 | C |
| ATOM | 1020 | CZ  | PHE | C | 696 | −21.933 | 0.469  | 34.850 | 1.00 | 31.72 | C |
| ATOM | 1021 | N   | GLU | C | 697 | −27.207 | 1.352  | 31.867 | 1.00 | 37.84 | N |
| ATOM | 1022 | CA  | GLU | C | 697 | −28.308 | 0.769  | 32.643 | 1.00 | 39.18 | C |
| ATOM | 1023 | C   | GLU | C | 697 | −28.912 | −0.471 | 32.017 | 1.00 | 39.41 | C |
| ATOM | 1024 | O   | GLU | C | 697 | −29.586 | −1.254 | 32.707 | 1.00 | 40.08 | O |
| ATOM | 1025 | CB  | GLU | C | 697 | −29.414 | 1.792  | 32.885 | 1.00 | 39.80 | C |
| ATOM | 1026 | CG  | GLU | C | 697 | −28.894 | 3.166  | 33.266 | 1.00 | 45.29 | C |
| ATOM | 1027 | CD  | GLU | C | 697 | −29.071 | 3.485  | 34.722 | 1.00 | 50.19 | C |
| ATOM | 1028 | OE1 | GLU | C | 697 | −29.879 | 4.396  | 35.019 | 1.00 | 49.63 | O |
| ATOM | 1029 | OE2 | GLU | C | 697 | −28.410 | 2.827  | 35.560 | 1.00 | 52.56 | O |
| ATOM | 1030 | N   | LYS | C | 698 | −28.692 | −0.672 | 30.716 | 1.00 | 37.81 | N |
| ATOM | 1031 | CA  | LYS | C | 698 | −29.100 | −1.913 | 30.091 | 1.00 | 36.37 | C |
| ATOM | 1032 | C   | LYS | C | 698 | −28.159 | −3.057 | 30.465 | 1.00 | 34.34 | C |
| ATOM | 1033 | O   | LYS | C | 698 | −28.572 | −4.210 | 30.422 | 1.00 | 34.26 | O |
| ATOM | 1034 | CB  | LYS | C | 698 | −29.182 | −1.757 | 28.571 | 1.00 | 36.10 | C |
| ATOM | 1035 | CG  | LYS | C | 698 | −30.186 | −0.695 | 28.142 | 1.00 | 40.02 | C |
| ATOM | 1036 | CD  | LYS | C | 698 | −30.382 | −0.665 | 26.642 | 1.00 | 45.85 | C |
| ATOM | 1037 | CE  | LYS | C | 698 | −31.590 | 0.193  | 26.257 | 1.00 | 50.97 | C |
| ATOM | 1038 | NZ  | LYS | C | 698 | −31.696 | 0.432  | 24.762 | 1.00 | 55.37 | N |
| ATOM | 1039 | N   | PHE | C | 699 | −26.926 | −2.731 | 30.850 | 1.00 | 33.53 | N |
| ATOM | 1040 | CA  | PHE | C | 699 | −25.959 | −3.729 | 31.357 | 1.00 | 33.62 | C |
| ATOM | 1041 | C   | PHE | C | 699 | −26.036 | −3.913 | 32.854 | 1.00 | 34.35 | C |
| ATOM | 1042 | O   | PHE | C | 699 | −25.743 | −4.998 | 33.351 | 1.00 | 34.91 | O |
| ATOM | 1043 | CB  | PHE | C | 699 | −24.520 | −3.402 | 30.951 | 1.00 | 31.44 | C |
| ATOM | 1044 | CG  | PHE | C | 699 | −24.320 | −3.433 | 29.477 | 1.00 | 29.81 | C |
| ATOM | 1045 | CD1 | PHE | C | 699 | −23.938 | −4.615 | 28.861 | 1.00 | 28.58 | C |
| ATOM | 1046 | CD2 | PHE | C | 699 | −24.601 | −2.312 | 28.702 | 1.00 | 27.61 | C |
| ATOM | 1047 | CE1 | PHE | C | 699 | −23.803 | −4.696 | 27.502 | 1.00 | 29.53 | C |
| ATOM | 1048 | CE2 | PHE | C | 699 | −24.456 | −2.375 | 27.350 | 1.00 | 27.39 | C |
| ATOM | 1049 | CZ  | PHE | C | 699 | −24.074 | −3.551 | 26.742 | 1.00 | 27.74 | C |
| ATOM | 1050 | N   | PHE | C | 700 | −26.444 | −2.853 | 33.560 | 1.00 | 36.12 | N |
| ATOM | 1051 | CA  | PHE | C | 700 | −26.498 | −2.905 | 35.027 | 1.00 | 37.84 | C |
| ATOM | 1052 | C   | PHE | C | 700 | −27.787 | −2.255 | 35.513 | 1.00 | 39.36 | C |
| ATOM | 1053 | O   | PHE | C | 700 | −27.771 | −1.136 | 36.026 | 1.00 | 38.17 | O |
| ATOM | 1054 | CB  | PHE | C | 700 | −25.252 | −2.246 | 35.629 | 1.00 | 37.21 | C |
| ATOM | 1055 | CG  | PHE | C | 700 | −23.946 | −2.915 | 35.229 | 1.00 | 37.88 | C |
| ATOM | 1056 | CD1 | PHE | C | 700 | −23.451 | −4.008 | 35.945 | 1.00 | 37.13 | C |
| ATOM | 1057 | CD2 | PHE | C | 700 | −23.222 | −2.456 | 34.127 | 1.00 | 37.39 | C |
| ATOM | 1058 | CE1 | PHE | C | 700 | −22.238 | −4.625 | 35.564 | 1.00 | 38.05 | C |
| ATOM | 1059 | CE2 | PHE | C | 700 | −22.013 | −3.060 | 33.738 | 1.00 | 35.97 | C |
| ATOM | 1060 | CZ  | PHE | C | 700 | −21.527 | −4.146 | 34.465 | 1.00 | 37.01 | C |
| ATOM | 1061 | N   | PRO | C | 701 | −28.922 | −2.955 | 35.308 | 1.00 | 40.99 | N |
| ATOM | 1062 | CA  | PRO | C | 701 | −30.218 | −2.409 | 35.678 | 1.00 | 43.02 | C |
| ATOM | 1063 | C   | PRO | C | 701 | −30.394 | −2.435 | 37.185 | 1.00 | 44.72 | C |
| ATOM | 1064 | O   | PRO | C | 701 | −29.678 | −3.153 | 37.881 | 1.00 | 45.01 | O |
| ATOM | 1065 | CB  | PRO | C | 701 | −31.203 | −3.363 | 34.997 | 1.00 | 42.62 | C |
| ATOM | 1066 | CG  | PRO | C | 701 | −30.499 | −4.655 | 34.963 | 1.00 | 41.90 | C |
| ATOM | 1067 | CD  | PRO | C | 701 | −29.047 | −4.297 | 34.710 | 1.00 | 40.96 | C |
| ATOM | 1068 | N   | SER | C | 702 | −31.343 | −1.647 | 37.682 | 1.00 | 46.97 | N |
| ATOM | 1069 | CA  | SER | C | 702 | −31.626 | −1.605 | 39.118 | 1.00 | 48.66 | C |
| ATOM | 1070 | C   | SER | C | 702 | −32.167 | −2.947 | 39.589 | 1.00 | 49.64 | C |
| ATOM | 1071 | O   | SER | C | 702 | −32.009 | −3.318 | 40.759 | 1.00 | 50.51 | O |
| ATOM | 1072 | CB  | SER | C | 702 | −32.636 | −0.505 | 39.419 | 1.00 | 48.83 | C |
| ATOM | 1073 | OG  | SER | C | 702 | −33.719 | −0.581 | 38.509 | 1.00 | 50.43 | O |
| ATOM | 1074 | N   | SER | C | 703 | −32.793 | −3.675 | 38.669 | 1.00 | 50.19 | N |
| ATOM | 1075 | CA  | SER | C | 703 | −33.345 | −5.004 | 38.954 | 1.00 | 51.34 | C |
| ATOM | 1076 | C   | SER | C | 703 | −32.273 | −6.094 | 39.152 | 1.00 | 52.21 | C |
| ATOM | 1077 | O   | SER | C | 703 | −32.598 | −7.273 | 39.401 | 1.00 | 52.66 | O |
| ATOM | 1078 | CB  | SER | C | 703 | −34.296 | −5.412 | 37.836 | 1.00 | 51.29 | C |
| ATOM | 1079 | OG  | SER | C | 703 | −33.618 | −5.479 | 36.594 | 1.00 | 49.82 | O |
| ATOM | 1080 | N   | SER | C | 704 | −31.005 | −5.702 | 39.038 | 1.00 | 53.28 | N |
| ATOM | 1081 | CA  | SER | C | 704 | −29.889 | −6.646 | 39.185 | 1.00 | 54.02 | C |
| ATOM | 1082 | C   | SER | C | 704 | −29.034 | −6.357 | 40.417 | 1.00 | 54.26 | C |
| ATOM | 1083 | O   | SER | C | 704 | −28.819 | −5.201 | 40.776 | 1.00 | 54.19 | O |
| ATOM | 1084 | CB  | SER | C | 704 | −29.022 | −6.658 | 37.918 | 1.00 | 53.70 | C |
| ATOM | 1085 | OG  | SER | C | 704 | −27.846 | −7.428 | 38.113 | 1.00 | 54.92 | O |
| ATOM | 1086 | N   | TYR | C | 705 | −28.572 | −7.426 | 41.064 | 1.00 | 54.94 | N |
| ATOM | 1087 | CA  | TYR | C | 705 | −27.663 | −7.337 | 42.207 | 1.00 | 55.53 | C |

TABLE 2b-continued

Data of atomic coordinates for accession code 3AIG, which cites accession code 2ZTT

| ATOM | 1088 | C | TYR | C | 705 | −26.223 | −7.496 | 41.738 | 1.00 | 55.47 | C |
|---|---|---|---|---|---|---|---|---|---|---|---|
| ATOM | 1089 | O | TYR | C | 705 | −25.284 | −7.202 | 42.480 | 1.00 | 55.55 | O |
| ATOM | 1090 | CB | TYR | C | 705 | −27.981 | −8.417 | 43.247 | 1.00 | 56.51 | C |
| ATOM | 1091 | CG | TYR | C | 705 | −27.746 | −9.829 | 42.749 | 1.00 | 56.88 | C |
| ATOM | 1092 | CD1 | TYR | C | 705 | −26.501 | −10.441 | 42.890 | 1.00 | 57.91 | C |
| ATOM | 1093 | CD2 | TYR | C | 705 | −28.778 | −10.558 | 42.142 | 1.00 | 59.23 | C |
| ATOM | 1094 | CE1 | TYR | C | 705 | −26.278 | −11.739 | 42.426 | 1.00 | 58.56 | C |
| ATOM | 1095 | CE2 | TYR | C | 705 | −28.567 | −11.868 | 41.682 | 1.00 | 58.61 | C |
| ATOM | 1096 | CZ | TYR | C | 705 | −27.315 | −12.445 | 41.829 | 1.00 | 58.10 | C |
| ATOM | 1097 | OH | TYR | C | 705 | −27.102 | −13.725 | 41.374 | 1.00 | 57.63 | O |
| ATOM | 1098 | N | ARG | C | 706 | −26.049 | −7.994 | 40.516 | 1.00 | 55.33 | N |
| ATOM | 1099 | CA | ARG | C | 706 | −24.733 | −7.980 | 39.868 | 1.00 | 54.64 | C |
| ATOM | 1100 | C | ARG | C | 706 | −24.369 | −6.528 | 39.558 | 1.00 | 53.90 | C |
| ATOM | 1101 | O | ARG | C | 706 | −24.847 | −5.955 | 38.568 | 1.00 | 54.18 | O |
| ATOM | 1102 | CB | ARG | C | 706 | −24.756 | −8.818 | 38.589 | 1.00 | 55.24 | C |
| ATOM | 1103 | CG | ARG | C | 706 | −24.550 | −10.301 | 38.813 | 1.00 | 56.49 | C |
| ATOM | 1104 | CD | ARG | C | 706 | −25.405 | −11.141 | 37.857 | 1.00 | 59.21 | C |
| ATOM | 1105 | NE | ARG | C | 706 | −26.820 | −11.137 | 38.234 | 1.00 | 60.45 | N |
| ATOM | 1106 | CZ | ARG | C | 706 | −27.632 | −12.197 | 38.169 | 1.00 | 61.92 | C |
| ATOM | 1107 | NH1 | ARG | C | 706 | −27.180 | −13.382 | 37.761 | 1.00 | 62.51 | N |
| ATOM | 1108 | NH2 | ARG | C | 706 | −28.907 | −12.075 | 38.528 | 1.00 | 62.04 | N |
| ATOM | 1109 | N | ARG | C | 707 | −23.564 | −5.927 | 40.431 | 1.00 | 52.52 | N |
| ATOM | 1110 | CA | ARG | C | 707 | −23.148 | −4.542 | 40.259 | 1.00 | 51.37 | C |
| ATOM | 1111 | C | ARG | C | 707 | −21.746 | −4.416 | 39.642 | 1.00 | 49.71 | C |
| ATOM | 1112 | O | ARG | C | 707 | −20.896 | −5.282 | 39.851 | 1.00 | 49.60 | O |
| ATOM | 1113 | CB | ARG | C | 707 | −23.244 | −3.769 | 41.585 | 1.00 | 52.22 | C |
| ATOM | 1114 | CG | ARG | C | 707 | −24.643 | −3.739 | 42.231 | 1.00 | 52.76 | C |
| ATOM | 1115 | CD | ARG | C | 707 | −25.785 | −3.405 | 41.237 | 1.00 | 55.82 | C |
| ATOM | 1116 | NE | ARG | C | 707 | −26.123 | −1.983 | 41.168 | 1.00 | 57.65 | N |
| ATOM | 1117 | CZ | ARG | C | 707 | −27.260 | −1.453 | 41.621 | 1.00 | 59.78 | C |
| ATOM | 1118 | NH1 | ARG | C | 707 | −28.193 | −2.226 | 42.174 | 1.00 | 61.65 | N |
| ATOM | 1119 | NH2 | ARG | C | 707 | −27.476 | −0.146 | 41.522 | 1.00 | 59.25 | N |
| ATOM | 1120 | N | PRO | C | 708 | −21.510 | −3.326 | 38.881 | 1.00 | 48.10 | N |
| ATOM | 1121 | CA | PRO | C | 708 | −20.257 | −3.068 | 38.152 | 1.00 | 46.63 | C |
| ATOM | 1122 | C | PRO | C | 708 | −19.089 | −2.762 | 39.073 | 1.00 | 45.51 | C |
| ATOM | 1123 | O | PRO | C | 708 | −19.304 | −2.202 | 40.144 | 1.00 | 45.85 | O |
| ATOM | 1124 | CB | PRO | C | 708 | −20.588 | −1.818 | 37.327 | 1.00 | 46.93 | C |
| ATOM | 1125 | CG | PRO | C | 708 | −21.722 | −1.154 | 38.084 | 1.00 | 47.63 | C |
| ATOM | 1126 | CD | PRO | C | 708 | −22.509 | −2.255 | 38.679 | 1.00 | 47.74 | C |
| ATOM | 1127 | N | VAL | C | 709 | −17.860 | −3.094 | 38.678 | 1.00 | 44.10 | N |
| ATOM | 1128 | CA | VAL | C | 709 | −16.735 | −2.686 | 39.525 | 1.00 | 42.61 | C |
| ATOM | 1129 | C | VAL | C | 709 | −16.441 | −1.216 | 39.294 | 1.00 | 41.97 | C |
| ATOM | 1130 | O | VAL | C | 709 | −16.391 | −0.731 | 38.142 | 1.00 | 41.65 | O |
| ATOM | 1131 | CB | VAL | C | 709 | −15.447 | −3.624 | 39.504 | 1.00 | 42.94 | C |
| ATOM | 1132 | CG1 | VAL | C | 709 | −15.798 | −5.092 | 39.245 | 1.00 | 41.33 | C |
| ATOM | 1133 | CG2 | VAL | C | 709 | −14.352 | −3.121 | 38.609 | 1.00 | 44.64 | C |
| ATOM | 1134 | N | GLY | C | 710 | −16.315 | −0.500 | 40.410 | 1.00 | 40.45 | N |
| ATOM | 1135 | CA | GLY | C | 710 | −16.114 | 0.940 | 40.413 | 1.00 | 40.01 | C |
| ATOM | 1136 | C | GLY | C | 710 | −14.888 | 1.471 | 39.664 | 1.00 | 39.22 | C |
| ATOM | 1137 | O | GLY | C | 710 | −14.959 | 2.519 | 39.042 | 1.00 | 39.50 | O |
| ATOM | 1138 | N | ILE | C | 711 | −13.770 | 0.766 | 39.707 | 1.00 | 39.28 | N |
| ATOM | 1139 | CA | ILE | C | 711 | −12.563 | 1.280 | 39.060 | 1.00 | 39.40 | C |
| ATOM | 1140 | C | ILE | C | 711 | −12.490 | 0.982 | 37.554 | 1.00 | 38.66 | C |
| ATOM | 1141 | O | ILE | C | 711 | −11.630 | 1.497 | 36.857 | 1.00 | 39.56 | O |
| ATOM | 1142 | CB | ILE | C | 711 | −11.276 | 0.771 | 39.736 | 1.00 | 40.69 | C |
| ATOM | 1143 | CG1 | ILE | C | 711 | −11.382 | −0.741 | 40.017 | 1.00 | 41.45 | C |
| ATOM | 1144 | CG2 | ILE | C | 711 | −11.000 | 1.606 | 40.986 | 1.00 | 41.28 | C |
| ATOM | 1145 | CD1 | ILE | C | 711 | −10.042 | −1.447 | 40.183 | 1.00 | 45.72 | C |
| ATOM | 1146 | N | SER | C | 712 | −13.372 | 0.120 | 37.088 | 1.00 | 38.01 | N |
| ATOM | 1147 | CA | SER | C | 712 | −13.483 | −0.244 | 35.683 | 1.00 | 36.94 | C |
| ATOM | 1148 | C | SER | C | 712 | −14.016 | 0.933 | 34.853 | 1.00 | 34.67 | C |
| ATOM | 1149 | O | SER | C | 712 | −14.923 | 1.656 | 35.302 | 1.00 | 34.15 | O |
| ATOM | 1150 | CB | SER | C | 712 | −14.433 | −1.446 | 35.567 | 1.00 | 37.28 | C |
| ATOM | 1151 | OG | SER | C | 712 | −14.646 | −1.804 | 34.222 | 1.00 | 42.70 | O |
| ATOM | 1152 | N | SER | C | 713 | −13.473 | 1.108 | 33.653 | 1.00 | 32.86 | N |
| ATOM | 1153 | CA | SER | C | 713 | −14.099 | 1.991 | 32.658 | 1.00 | 31.17 | C |
| ATOM | 1154 | C | SER | C | 713 | −15.481 | 1.479 | 32.344 | 1.00 | 31.13 | C |
| ATOM | 1155 | O | SER | C | 713 | −15.753 | 0.277 | 32.451 | 1.00 | 30.44 | O |
| ATOM | 1156 | CB | SER | C | 713 | −13.277 | 2.086 | 31.372 | 1.00 | 31.88 | C |
| ATOM | 1157 | OG | SER | C | 713 | −13.359 | 0.855 | 30.660 | 1.00 | 30.37 | O |
| HETATM | 1158 | N | MSE | C | 714 | −16.366 | 2.391 | 31.943 | 1.00 | 29.96 | N |
| HETATM | 1159 | CA | MSE | C | 714 | −17.719 | 2.032 | 31.573 | 1.00 | 29.72 | C |
| HETATM | 1160 | C | MSE | C | 714 | −17.706 | 0.887 | 30.560 | 1.00 | 28.02 | C |
| HETATM | 1161 | O | MSE | C | 714 | −18.450 | −0.093 | 30.719 | 1.00 | 27.08 | O |
| HETATM | 1162 | CB | MSE | C | 714 | −18.435 | 3.254 | 31.009 | 1.00 | 30.47 | C |
| HETATM | 1163 | CG | MSE | C | 714 | −18.818 | 4.248 | 32.128 | 1.00 | 28.56 | C |
| HETATM | 1164 | SE | MSE | C | 714 | −19.605 | 5.814 | 31.260 | 1.00 | 36.31 | SE |
| HETATM | 1165 | CE | MSE | C | 714 | −21.308 | 5.089 | 31.093 | 1.00 | 31.73 | C |

TABLE 2b-continued

Data of atomic coordinates for accession code 3AIG, which cites accession code 2ZTT

| ATOM | 1166 | N | VAL | C | 715 | −16.892 | 1.057 | 29.524 | 1.00 | 26.74 | N |
|---|---|---|---|---|---|---|---|---|---|---|---|
| ATOM | 1167 | CA | VAL | C | 715 | −16.816 | 0.044 | 28.449 | 1.00 | 26.95 | C |
| ATOM | 1168 | C | VAL | C | 715 | −16.340 | −1.303 | 28.966 | 1.00 | 27.46 | C |
| ATOM | 1169 | O | VAL | C | 715 | −16.939 | −2.336 | 28.645 | 1.00 | 26.72 | O |
| ATOM | 1170 | CB | VAL | C | 715 | −16.098 | 0.481 | 27.133 | 1.00 | 26.64 | C |
| ATOM | 1171 | CG1 | VAL | C | 715 | −14.607 | 0.788 | 27.333 | 1.00 | 28.13 | C |
| ATOM | 1172 | CG2 | VAL | C | 715 | −16.369 | −0.600 | 26.028 | 1.00 | 25.52 | C |
| ATOM | 1173 | N | GLU | C | 716 | −15.270 | −1.318 | 29.752 | 1.00 | 27.42 | N |
| ATOM | 1174 | CA | GLU | C | 716 | −14.794 | −2.622 | 30.249 | 1.00 | 29.45 | C |
| ATOM | 1175 | C | GLU | C | 716 | −15.855 | −3.337 | 31.106 | 1.00 | 28.99 | C |
| ATOM | 1176 | O | GLU | C | 716 | −16.094 | −4.530 | 30.929 | 1.00 | 29.31 | O |
| ATOM | 1177 | CB | GLU | C | 716 | −13.405 | −2.535 | 30.876 | 1.00 | 30.02 | C |
| ATOM | 1178 | CG | GLU | C | 716 | −13.316 | −1.936 | 32.196 | 1.00 | 36.61 | C |
| ATOM | 1179 | CD | GLU | C | 716 | −11.885 | −1.841 | 32.651 | 1.00 | 41.43 | C |
| ATOM | 1180 | OE1 | GLU | C | 716 | −11.416 | −0.684 | 32.753 | 1.00 | 44.23 | O |
| ATOM | 1181 | OE2 | GLU | C | 716 | −11.247 | −2.920 | 32.848 | 1.00 | 41.94 | O |
| ATOM | 1182 | N | ALA | C | 717 | −16.555 | −2.592 | 31.969 | 1.00 | 28.58 | N |
| ATOM | 1183 | CA | ALA | C | 717 | −17.679 | −3.140 | 32.741 | 1.00 | 28.58 | C |
| ATOM | 1184 | C | ALA | C | 717 | −18.777 | −3.756 | 31.893 | 1.00 | 27.70 | C |
| ATOM | 1185 | O | ALA | C | 717 | −19.242 | −4.871 | 32.155 | 1.00 | 28.27 | O |
| ATOM | 1186 | CB | ALA | C | 717 | −18.290 | −2.039 | 33.682 | 1.00 | 29.45 | C |
| HETATM | 1187 | N | MSE | C | 718 | −19.190 | −3.037 | 30.870 | 1.00 | 27.45 | N |
| HETATM | 1188 | CA | MSE | C | 718 | −20.271 | −3.456 | 30.051 | 1.00 | 27.45 | C |
| HETATM | 1189 | C | MSE | C | 718 | −19.881 | −4.667 | 29.246 | 1.00 | 24.40 | C |
| HETATM | 1190 | O | MSE | C | 718 | −20.644 | −5.607 | 29.149 | 1.00 | 24.70 | O |
| HETATM | 1191 | CB | MSE | C | 718 | −20.672 | −2.314 | 29.132 | 1.00 | 26.78 | C |
| HETATM | 1192 | CG | MSE | C | 718 | −20.912 | −1.019 | 29.981 | 1.00 | 27.71 | C |
| HETATM | 1193 | SE | MSE | C | 718 | −20.925 | 0.615 | 28.869 | 1.00 | 39.21 | SE |
| HETATM | 1194 | CE | MSE | C | 718 | −22.516 | 0.136 | 28.376 | 1.00 | 15.88 | C |
| ATOM | 1195 | N | VAL | C | 719 | −18.688 | −4.656 | 28.651 | 1.00 | 24.18 | N |
| ATOM | 1196 | CA | VAL | C | 719 | −18.273 | −5.844 | 27.874 | 1.00 | 24.56 | C |
| ATOM | 1197 | C | VAL | C | 719 | −18.150 | −7.073 | 28.807 | 1.00 | 25.24 | C |
| ATOM | 1198 | O | VAL | C | 719 | −18.588 | −8.187 | 28.460 | 1.00 | 24.64 | O |
| ATOM | 1199 | CB | VAL | C | 719 | −16.957 | −5.632 | 27.139 | 1.00 | 21.96 | C |
| ATOM | 1200 | CG1 | VAL | C | 719 | −16.480 | −6.942 | 26.473 | 1.00 | 25.20 | C |
| ATOM | 1201 | CG2 | VAL | C | 719 | −17.137 | −4.533 | 26.053 | 1.00 | 24.24 | C |
| ATOM | 1202 | N | SER | C | 720 | −17.557 | −6.878 | 29.983 | 1.00 | 27.05 | N |
| ATOM | 1203 | CA | SER | C | 720 | −17.401 | −7.990 | 30.935 | 1.00 | 28.14 | C |
| ATOM | 1204 | C | SER | C | 720 | −18.762 | −8.599 | 31.288 | 1.00 | 28.68 | C |
| ATOM | 1205 | O | SER | C | 720 | −18.956 | −9.819 | 31.201 | 1.00 | 27.48 | O |
| ATOM | 1206 | CB | SER | C | 720 | −16.593 | −7.552 | 32.173 | 1.00 | 29.29 | C |
| ATOM | 1207 | OG | SER | C | 720 | −16.519 | −8.610 | 33.123 | 1.00 | 34.06 | O |
| ATOM | 1208 | N | ARG | C | 721 | −19.727 | −7.739 | 31.627 | 1.00 | 28.19 | N |
| ATOM | 1209 | CA | ARG | C | 721 | −21.123 | −8.135 | 31.852 | 1.00 | 28.83 | C |
| ATOM | 1210 | C | ARG | C | 721 | −21.773 | −8.806 | 30.639 | 1.00 | 28.55 | C |
| ATOM | 1211 | O | ARG | C | 721 | −22.389 | −9.846 | 30.784 | 1.00 | 27.73 | O |
| ATOM | 1212 | CB | ARG | C | 721 | −21.968 | −6.953 | 32.372 | 1.00 | 28.83 | C |
| ATOM | 1213 | CG | ARG | C | 721 | −23.489 | −7.299 | 32.673 | 1.00 | 30.82 | C |
| ATOM | 1214 | CD | ARG | C | 721 | −23.537 | −8.361 | 33.814 | 1.00 | 35.43 | C |
| ATOM | 1215 | NE | ARG | C | 721 | −24.865 | −8.888 | 34.145 | 1.00 | 39.85 | N |
| ATOM | 1216 | CZ | ARG | C | 721 | −25.731 | −8.345 | 35.006 | 1.00 | 42.31 | C |
| ATOM | 1217 | NH1 | ARG | C | 721 | −25.461 | −7.202 | 35.626 | 1.00 | 40.62 | N |
| ATOM | 1218 | NH2 | ARG | C | 721 | −26.897 | −8.955 | 35.241 | 1.00 | 45.29 | N |
| ATOM | 1219 | N | ALA | C | 722 | −21.608 | −8.270 | 29.428 | 1.00 | 27.03 | N |
| ATOM | 1220 | CA | ALA | C | 722 | −22.276 | −8.897 | 28.269 | 1.00 | 26.75 | C |
| ATOM | 1221 | C | ALA | C | 722 | −21.739 | −10.314 | 28.048 | 1.00 | 26.26 | C |
| ATOM | 1222 | O | ALA | C | 722 | −22.478 | −11.204 | 27.697 | 1.00 | 25.94 | O |
| ATOM | 1223 | CB | ALA | C | 722 | −22.014 | −8.076 | 27.002 | 1.00 | 27.45 | C |
| ATOM | 1224 | N | ARG | C | 723 | −20.436 | −10.495 | 28.232 | 1.00 | 25.83 | N |
| ATOM | 1225 | CA | ARG | C | 723 | −19.814 | −11.840 | 28.076 | 1.00 | 26.52 | C |
| ATOM | 1226 | C | ARG | C | 723 | −20.304 | −12.839 | 29.122 | 1.00 | 27.77 | C |
| ATOM | 1227 | O | ARG | C | 723 | −20.669 | −13.947 | 28.777 | 1.00 | 27.88 | O |
| ATOM | 1228 | CB | ARG | C | 723 | −18.292 | −11.762 | 28.168 | 1.00 | 26.78 | C |
| ATOM | 1229 | CG | ARG | C | 723 | −17.597 | −11.283 | 26.872 | 1.00 | 27.15 | C |
| ATOM | 1230 | CD | ARG | C | 723 | −16.133 | −10.988 | 27.113 | 1.00 | 31.51 | C |
| ATOM | 1231 | NE | ARG | C | 723 | −15.483 | −10.749 | 25.823 | 1.00 | 27.30 | N |
| ATOM | 1232 | CZ | ARG | C | 723 | −14.358 | −10.079 | 25.620 | 1.00 | 31.54 | C |
| ATOM | 1233 | NH1 | ARG | C | 723 | −13.677 | −9.502 | 26.630 | 1.00 | 26.98 | N |
| ATOM | 1234 | NH2 | ARG | C | 723 | −13.926 | −9.996 | 24.372 | 1.00 | 30.25 | N |
| ATOM | 1235 | N | ILE | C | 724 | −20.309 | −12.433 | 30.387 | 1.00 | 29.63 | N |
| ATOM | 1236 | CA | ILE | C | 724 | −20.897 | −13.274 | 31.470 | 1.00 | 30.96 | C |
| ATOM | 1237 | C | ILE | C | 724 | −22.351 | −13.670 | 31.144 | 1.00 | 30.26 | C |
| ATOM | 1238 | O | ILE | C | 724 | −22.724 | −14.826 | 31.200 | 1.00 | 29.77 | O |
| ATOM | 1239 | CB | ILE | C | 724 | −20.843 | −12.560 | 32.898 | 1.00 | 32.14 | C |
| ATOM | 1240 | CG1 | ILE | C | 724 | −19.413 | −12.200 | 33.330 | 1.00 | 34.48 | C |
| ATOM | 1241 | CG2 | ILE | C | 724 | −21.398 | −13.471 | 33.979 | 1.00 | 31.69 | C |
| ATOM | 1242 | CD1 | ILE | C | 724 | −18.392 | −13.199 | 32.975 | 1.00 | 39.35 | C |
| ATOM | 1243 | N | ASP | C | 725 | −23.163 | −12.682 | 30.807 | 1.00 | 30.20 | N |

TABLE 2b-continued

Data of atomic coordinates for accession code 3AIG, which cites accession code 2ZTT

| ATOM | 1244 | CA | ASP | C | 725 | −24.563 | −12.887 | 30.445 | 1.00 | 29.69 | C |
| --- | --- | --- | --- | --- | --- | --- | --- | --- | --- | --- | --- |
| ATOM | 1245 | C | ASP | C | 725 | −24.733 | −13.774 | 29.220 | 1.00 | 28.95 | C |
| ATOM | 1246 | O | ASP | C | 725 | −25.634 | −14.618 | 29.180 | 1.00 | 30.02 | O |
| ATOM | 1247 | CB | ASP | C | 725 | −25.278 | −11.550 | 30.225 | 1.00 | 30.21 | C |
| ATOM | 1248 | CG | ASP | C | 725 | −25.653 | −10.817 | 31.540 | 1.00 | 32.39 | C |
| ATOM | 1249 | OD1 | ASP | C | 725 | −25.417 | −11.330 | 32.665 | 1.00 | 33.37 | O |
| ATOM | 1250 | OD2 | ASP | C | 725 | −26.213 | −9.698 | 31.437 | 1.00 | 33.12 | O |
| ATOM | 1251 | N | ALA | C | 726 | −23.917 | −13.570 | 28.186 | 1.00 | 28.66 | N |
| ATOM | 1252 | CA | ALA | C | 726 | −24.056 | −14.356 | 26.966 | 1.00 | 27.48 | C |
| ATOM | 1253 | C | ALA | C | 726 | −23.820 | −15.829 | 27.247 | 1.00 | 28.40 | C |
| ATOM | 1254 | O | ALA | C | 726 | −24.558 | −16.674 | 26.772 | 1.00 | 27.48 | O |
| ATOM | 1255 | CB | ALA | C | 726 | −23.104 | −13.872 | 25.914 | 1.00 | 28.55 | C |
| ATOM | 1256 | N | ARG | C | 727 | −22.774 | −16.119 | 28.026 | 1.00 | 28.15 | N |
| ATOM | 1257 | CA | ARG | C | 727 | −22.449 | −17.493 | 28.410 | 1.00 | 31.40 | C |
| ATOM | 1258 | C | ARG | C | 727 | −23.602 | −18.155 | 29.149 | 1.00 | 31.28 | C |
| ATOM | 1259 | O | ARG | C | 727 | −23.967 | −19.303 | 28.853 | 1.00 | 31.64 | O |
| ATOM | 1260 | CB | ARG | C | 727 | −21.224 | −17.527 | 29.304 | 1.00 | 31.66 | C |
| ATOM | 1261 | CG | ARG | C | 727 | −19.981 | −18.045 | 28.627 | 1.00 | 37.03 | C |
| ATOM | 1262 | CD | ARG | C | 727 | −19.076 | −16.951 | 28.150 | 1.00 | 42.40 | C |
| ATOM | 1263 | NE | ARG | C | 727 | −18.177 | −16.472 | 29.200 | 1.00 | 46.49 | N |
| ATOM | 1264 | CZ | ARG | C | 727 | −16.961 | −15.966 | 28.991 | 1.00 | 47.82 | C |
| ATOM | 1265 | NH1 | ARG | C | 727 | −16.439 | −15.898 | 27.770 | 1.00 | 48.88 | N |
| ATOM | 1266 | NH2 | ARG | C | 727 | −16.242 | −15.536 | 30.021 | 1.00 | 50.30 | N |
| ATOM | 1267 | N | ILE | C | 728 | −24.171 | −17.443 | 30.103 | 1.00 | 31.83 | N |
| ATOM | 1268 | CA | ILE | C | 728 | −25.221 | −18.028 | 30.935 | 1.00 | 33.15 | C |
| ATOM | 1269 | C | ILE | C | 728 | −26.474 | −18.226 | 30.087 | 1.00 | 33.11 | C |
| ATOM | 1270 | O | ILE | C | 728 | −27.145 | −19.257 | 30.205 | 1.00 | 33.87 | O |
| ATOM | 1271 | CB | ILE | C | 728 | −25.483 | −17.173 | 32.183 | 1.00 | 33.39 | C |
| ATOM | 1272 | CG | ILE | C | 728 | −24.255 | −17.192 | 33.095 | 1.00 | 34.67 | C |
| ATOM | 1273 | CG2 | ILE | C | 728 | −26.732 | −17.627 | 32.915 | 1.00 | 36.27 | C |
| ATOM | 1274 | CD1 | ILE | C | 728 | −23.729 | −18.551 | 33.495 | 1.00 | 39.21 | C |
| ATOM | 1275 | N | ASP | C | 729 | −26.764 | −17.272 | 29.202 | 1.00 | 33.33 | N |
| ATOM | 1276 | CA | ASP | C | 729 | −27.985 | −17.326 | 28.400 | 1.00 | 34.13 | C |
| ATOM | 1277 | C | ASP | C | 729 | −27.876 | −18.437 | 27.347 | 1.00 | 33.85 | C |
| ATOM | 1278 | O | ASP | C | 729 | −28.884 | −19.049 | 26.966 | 1.00 | 35.06 | O |
| ATOM | 1279 | CB | ASP | C | 729 | −28.337 | −15.956 | 27.746 | 1.00 | 33.56 | C |
| ATOM | 1280 | CG | ASP | C | 729 | −28.740 | −14.894 | 28.760 | 1.00 | 37.25 | C |
| ATOM | 1281 | OD1 | ASP | C | 729 | −29.179 | −15.248 | 29.881 | 1.00 | 41.79 | O |
| ATOM | 1282 | OD2 | ASP | C | 729 | −28.628 | −13.675 | 28.459 | 1.00 | 35.90 | O |
| ATOM | 1283 | N | PHE | C | 730 | −26.664 | −18.684 | 26.859 | 1.00 | 31.79 | N |
| ATOM | 1284 | CA | PHE | C | 730 | −26.441 | −19.755 | 25.892 | 1.00 | 32.38 | C |
| ATOM | 1285 | C | PHE | C | 730 | −26.622 | −21.094 | 26.608 | 1.00 | 32.96 | C |
| ATOM | 1286 | O | PHE | C | 730 | −27.282 | −22.002 | 26.118 | 1.00 | 32.78 | O |
| ATOM | 1287 | CB | PHE | C | 730 | −25.027 | −19.625 | 25.301 | 1.00 | 30.28 | C |
| ATOM | 1288 | CG | PHE | C | 730 | −24.707 | −20.625 | 24.203 | 1.00 | 32.06 | C |
| ATOM | 1289 | CD1 | PHE | C | 730 | −25.699 | −21.124 | 23.366 | 1.00 | 30.57 | C |
| ATOM | 1290 | CD2 | PHE | C | 730 | −23.420 | −21.024 | 23.991 | 1.00 | 28.30 | C |
| ATOM | 1291 | CE1 | PHE | C | 730 | −25.401 | −22.016 | 22.357 | 1.00 | 29.27 | C |
| ATOM | 1292 | CE2 | PHE | C | 730 | −23.110 | −21.926 | 22.995 | 1.00 | 28.67 | C |
| ATOM | 1293 | CZ | PHE | C | 730 | −24.099 | −22.426 | 22.177 | 1.00 | 29.77 | C |
| ATOM | 1294 | N | GLU | C | 731 | −26.042 | −21.180 | 27.793 | 1.00 | 35.38 | N |
| ATOM | 1295 | CA | GLU | C | 731 | −26.093 | −22.397 | 28.606 | 1.00 | 37.50 | C |
| ATOM | 1296 | C | GLU | C | 731 | −27.545 | −22.728 | 28.944 | 1.00 | 38.56 | C |
| ATOM | 1297 | O | GLU | C | 731 | −27.931 | −23.897 | 28.952 | 1.00 | 39.50 | O |
| ATOM | 1298 | CB | GLU | C | 731 | −25.280 | −22.152 | 29.877 | 1.00 | 37.14 | C |
| ATOM | 1299 | CG | GLU | C | 731 | −25.124 | −23.332 | 30.852 | 1.00 | 39.18 | C |
| ATOM | 1300 | CD | GLU | C | 731 | −24.600 | −22.853 | 32.193 | 1.00 | 38.95 | C |
| ATOM | 1301 | OE1 | GLU | C | 731 | −25.308 | −23.016 | 33.205 | 1.00 | 44.10 | O |
| ATOM | 1302 | OE2 | GLU | C | 731 | −23.486 | −22.288 | 32.238 | 1.00 | 40.82 | O |
| ATOM | 1303 | N | SER | C | 732 | −28.353 | −21.706 | 29.206 | 1.00 | 40.24 | N |
| ATOM | 1304 | CA | SER | C | 732 | −29.736 | −21.926 | 29.605 | 1.00 | 41.51 | C |
| ATOM | 1305 | C | SER | C | 732 | −30.648 | −22.206 | 28.423 | 1.00 | 42.41 | C |
| ATOM | 1306 | O | SER | C | 732 | −31.715 | −22.775 | 28.592 | 1.00 | 43.72 | O |
| ATOM | 1307 | CB | SER | C | 732 | −30.276 | −20.736 | 30.399 | 1.00 | 42.45 | C |
| ATOM | 1308 | OG | SER | C | 732 | −30.833 | −19.755 | 29.531 | 1.00 | 44.40 | O |
| ATOM | 1309 | N | GLY | C | 733 | −30.232 | −21.810 | 27.232 | 1.00 | 42.05 | N |
| ATOM | 1310 | CA | GLY | C | 733 | −31.095 | −21.920 | 26.065 | 1.00 | 42.95 | C |
| ATOM | 1311 | C | GLY | C | 733 | −31.843 | −20.635 | 25.776 | 1.00 | 43.14 | C |
| ATOM | 1312 | O | GLY | C | 733 | −32.625 | −20.567 | 24.824 | 1.00 | 44.09 | O |
| ATOM | 1313 | N | ARG | C | 734 | −31.608 | −19.604 | 26.586 | 1.00 | 42.77 | N |
| ATOM | 1314 | CA | ARG | C | 734 | −32.238 | −18.300 | 26.376 | 1.00 | 42.63 | C |
| ATOM | 1315 | C | ARG | C | 734 | −31.802 | −17.648 | 25.058 | 1.00 | 42.06 | C |
| ATOM | 1316 | O | ARG | C | 734 | −32.583 | −16.911 | 24.432 | 1.00 | 42.85 | O |
| ATOM | 1317 | CB | ARG | C | 734 | −31.962 | −17.373 | 27.555 | 1.00 | 43.07 | C |
| ATOM | 1318 | CG | ARG | C | 734 | −32.770 | −16.085 | 27.525 | 1.00 | 45.24 | C |
| ATOM | 1319 | CD | ARG | C | 734 | −32.531 | −15.253 | 28.782 | 1.00 | 51.41 | C |
| ATOM | 1320 | NE | ARG | C | 734 | −32.934 | −13.859 | 28.602 | 1.00 | 54.43 | N |
| ATOM | 1321 | CZ | ARG | C | 734 | −34.181 | −13.411 | 28.704 | 1.00 | 57.25 | C |

TABLE 2b-continued

Data of atomic coordinates for accession code 3AIG, which cites accession code 2ZTT

| ATOM | 1322 | NH1 | ARG | C | 734 | −35.180 | −14.242 | 29.004 | 1.00 | 57.63 | N |
|---|---|---|---|---|---|---|---|---|---|---|---|
| ATOM | 1323 | NH2 | ARG | C | 734 | −34.427 | −12.120 | 28.516 | 1.00 | 59.19 | N |
| ATOM | 1324 | N | ILE | C | 735 | −30.561 | −17.923 | 24.644 | 1.00 | 40.85 | N |
| ATOM | 1325 | CA | ILE | C | 735 | −30.082 | −17.496 | 23.339 | 1.00 | 38.99 | C |
| ATOM | 1326 | C | ILE | C | 735 | −29.537 | −18.682 | 22.541 | 1.00 | 38.98 | C |
| ATOM | 1327 | O | ILE | C | 735 | −29.093 | −19.693 | 23.109 | 1.00 | 38.83 | O |
| ATOM | 1328 | CB | ILE | C | 735 | −29.037 | −16.306 | 23.399 | 1.00 | 38.33 | C |
| ATOM | 1329 | CG1 | ILE | C | 735 | −27.659 | −16.757 | 23.924 | 1.00 | 37.30 | C |
| ATOM | 1330 | CG2 | ILE | C | 735 | −29.615 | −15.071 | 24.134 | 1.00 | 38.70 | C |
| ATOM | 1331 | CD1 | ILE | C | 735 | −26.619 | −15.638 | 23.924 | 1.00 | 37.01 | C |
| ATOM | 1332 | N | LYS | C | 736 | −29.590 | −18.544 | 21.218 | 1.00 | 38.95 | N |
| ATOM | 1333 | CA | LYS | C | 736 | −29.214 | −19.586 | 20.284 | 1.00 | 39.02 | C |
| ATOM | 1334 | C | LYS | C | 736 | −27.692 | −19.474 | 19.952 | 1.00 | 38.33 | C |
| ATOM | 1335 | O | LYS | C | 736 | −27.081 | −18.441 | 20.243 | 1.00 | 37.32 | O |
| ATOM | 1336 | CB | LYS | C | 736 | −30.093 | −19.452 | 19.032 | 1.00 | 40.66 | C |
| ATOM | 1337 | CG | LYS | C | 736 | −31.382 | −20.301 | 19.011 | 1.00 | 42.74 | C |
| ATOM | 1338 | CD | LYS | C | 736 | −32.268 | −20.163 | 20.263 | 1.00 | 47.29 | C |
| ATOM | 1339 | CE | LYS | C | 736 | −32.177 | −21.399 | 21.187 | 1.00 | 48.80 | C |
| ATOM | 1340 | NZ | LYS | C | 736 | −33.239 | −21.440 | 22.261 | 1.00 | 48.52 | N |
| ATOM | 1341 | N | LYS | C | 737 | −27.089 | −20.512 | 19.373 | 1.00 | 37.90 | N |
| ATOM | 1342 | CA | LYS | C | 737 | −25.630 | −20.514 | 19.124 | 1.00 | 38.42 | C |
| ATOM | 1343 | C | LYS | C | 737 | −25.206 | −19.347 | 18.232 | 1.00 | 37.74 | C |
| ATOM | 1344 | O | LYS | C | 737 | −24.203 | −18.707 | 18.498 | 1.00 | 36.56 | O |
| ATOM | 1345 | CB | LYS | C | 737 | −25.092 | −21.872 | 18.598 | 1.00 | 39.28 | C |
| ATOM | 1346 | CG | LYS | C | 737 | −25.183 | −22.152 | 17.081 | 1.00 | 43.56 | C |
| ATOM | 1347 | CD | LYS | C | 737 | −24.230 | −21.266 | 16.191 | 1.00 | 46.86 | C |
| ATOM | 1348 | CE | LYS | C | 737 | −22.722 | −21.510 | 16.358 | 1.00 | 48.10 | C |
| ATOM | 1349 | NZ | LYS | C | 737 | −22.199 | −22.642 | 15.562 | 1.00 | 50.22 | N |
| ATOM | 1350 | N | GLU | C | 738 | −26.002 | −19.068 | 17.194 | 1.00 | 37.11 | N |
| ATOM | 1351 | CA | GLU | C | 738 | −25.691 | −17.979 | 16.273 | 1.00 | 37.38 | C |
| ATOM | 1352 | C | GLU | C | 738 | −25.699 | −16.639 | 16.993 | 1.00 | 36.06 | C |
| ATOM | 1353 | O | GLU | C | 738 | −24.863 | −15.793 | 16.718 | 1.00 | 34.77 | O |
| ATOM | 1354 | CB | GLU | C | 738 | −26.667 | −17.943 | 15.082 | 1.00 | 37.85 | C |
| ATOM | 1355 | CG | GLU | C | 738 | −26.752 | −19.264 | 14.275 | 1.00 | 41.82 | C |
| ATOM | 1356 | CD | GLU | C | 738 | −27.422 | −20.431 | 15.024 | 1.00 | 45.16 | C |
| ATOM | 1357 | OE1 | GLU | C | 738 | −28.130 | −20.207 | 16.035 | 1.00 | 46.24 | O |
| ATOM | 1358 | OE2 | GLU | C | 738 | −27.233 | −21.592 | 14.592 | 1.00 | 49.00 | O |
| ATOM | 1359 | N | GLU | C | 739 | −26.666 | −16.442 | 17.892 | 1.00 | 35.36 | N |
| ATOM | 1360 | CA | GLU | C | 739 | −26.729 | −15.226 | 18.721 | 1.00 | 33.88 | C |
| ATOM | 1361 | C | GLU | C | 739 | −25.541 | −15.084 | 19.686 | 1.00 | 31.64 | C |
| ATOM | 1362 | O | GLU | C | 739 | −24.946 | −14.015 | 19.784 | 1.00 | 30.00 | O |
| ATOM | 1363 | CB | GLU | C | 739 | −28.066 | −15.168 | 19.473 | 1.00 | 34.73 | C |
| ATOM | 1364 | CG | GLU | C | 739 | −28.241 | −13.964 | 20.404 | 1.00 | 36.20 | C |
| ATOM | 1365 | CD | GLU | C | 739 | −29.733 | −13.728 | 20.796 | 1.00 | 38.00 | C |
| ATOM | 1366 | OE1 | GLU | C | 739 | −30.538 | −14.697 | 20.739 | 1.00 | 42.45 | O |
| ATOM | 1367 | OE2 | GLU | C | 739 | −30.077 | −12.570 | 21.167 | 1.00 | 43.72 | O |
| ATOM | 1368 | N | PHE | C | 740 | −25.220 | −16.165 | 20.404 | 1.00 | 28.86 | N |
| ATOM | 1369 | CA | PHE | C | 740 | −24.048 | −16.245 | 21.254 | 1.00 | 27.29 | C |
| ATOM | 1370 | C | PHE | C | 740 | −22.819 | −15.815 | 20.479 | 1.00 | 25.60 | C |
| ATOM | 1371 | O | PHE | C | 740 | −22.111 | −14.944 | 20.920 | 1.00 | 25.74 | O |
| ATOM | 1372 | CB | PHE | C | 740 | −23.876 | −17.678 | 21.787 | 1.00 | 26.25 | C |
| ATOM | 1373 | CG | PHE | C | 740 | −22.656 | −17.868 | 22.598 | 1.00 | 27.50 | C |
| ATOM | 1374 | CD1 | PHE | C | 740 | −22.562 | −17.309 | 23.872 | 1.00 | 29.82 | C |
| ATOM | 1375 | CD2 | PHE | C | 740 | −21.581 | −18.562 | 22.076 | 1.00 | 28.40 | C |
| ATOM | 1376 | CE1 | PHE | C | 740 | −21.401 | −17.460 | 24.628 | 1.00 | 26.48 | C |
| ATOM | 1377 | CE2 | PHE | C | 740 | −20.402 | −18.709 | 22.788 | 1.00 | 27.35 | C |
| ATOM | 1378 | CZ | PHE | C | 740 | −20.321 | −18.166 | 24.085 | 1.00 | 28.14 | C |
| ATOM | 1379 | N | THR | C | 741 | −22.565 | −16.465 | 19.343 | 1.00 | 24.86 | N |
| ATOM | 1380 | CA | THR | C | 741 | −21.371 | −16.145 | 18.532 | 1.00 | 26.81 | C |
| ATOM | 1381 | C | THR | C | 741 | −21.325 | −14.674 | 18.112 | 1.00 | 25.69 | C |
| ATOM | 1382 | O | THR | C | 741 | −20.289 | −14.041 | 18.201 | 1.00 | 26.39 | O |
| ATOM | 1383 | CB | THR | C | 741 | −21.277 | −17.057 | 17.281 | 1.00 | 26.55 | C |
| ATOM | 1384 | OG1 | THR | C | 741 | −22.436 | −16.833 | 16.470 | 1.00 | 32.37 | O |
| ATOM | 1385 | CG2 | THR | C | 741 | −21.228 | −18.507 | 17.720 | 1.00 | 26.88 | C |
| ATOM | 1386 | N | GLU | C | 742 | −22.469 | −14.109 | 17.714 | 1.00 | 25.53 | N |
| ATOM | 1387 | CA | GLU | C | 742 | −22.528 | −12.724 | 17.278 | 1.00 | 26.50 | C |
| ATOM | 1388 | C | GLU | C | 742 | −22.232 | −11.785 | 18.433 | 1.00 | 25.74 | C |
| ATOM | 1389 | O | GLU | C | 742 | −21.440 | −10.837 | 18.289 | 1.00 | 22.47 | O |
| ATOM | 1390 | CB | GLU | C | 742 | −23.895 | −12.424 | 16.659 | 1.00 | 27.21 | C |
| ATOM | 1391 | CG | GLU | C | 742 | −23.948 | −11.139 | 15.855 | 1.00 | 30.36 | C |
| ATOM | 1392 | CD | GLU | C | 742 | −25.222 | −10.960 | 15.043 | 1.00 | 31.74 | C |
| ATOM | 1393 | OE1 | GLU | C | 742 | −26.042 | −11.900 | 14.874 | 1.00 | 39.86 | O |
| ATOM | 1394 | OE2 | GLU | C | 742 | −25.394 | −9.823 | 14.595 | 1.00 | 36.02 | O |
| ATOM | 1395 | N | ILE | C | 743 | −22.828 | −12.057 | 19.598 | 1.00 | 23.48 | N |
| ATOM | 1396 | CA | ILE | C | 743 | −22.527 | −11.252 | 20.788 | 1.00 | 22.33 | C |
| ATOM | 1397 | C | ILE | C | 743 | −21.022 | −11.306 | 21.152 | 1.00 | 22.37 | C |
| ATOM | 1398 | O | ILE | C | 743 | −20.446 | −10.253 | 21.366 | 1.00 | 22.93 | O |
| ATOM | 1399 | CB | ILE | C | 743 | −23.355 | −11.642 | 22.026 | 1.00 | 22.44 | C |

TABLE 2b-continued

Data of atomic coordinates for accession code 3AIG, which cites accession code 2ZTT

| ATOM | 1400 | CG1 | ILE | C | 743 | −24.842 | −11.370 | 21.747 | 1.00 | 23.32 | C |
|---|---|---|---|---|---|---|---|---|---|---|---|
| ATOM | 1401 | CG2 | ILE | C | 743 | −22.853 | −10.875 | 23.253 | 1.00 | 22.57 | C |
| ATOM | 1402 | CD1 | ILE | C | 743 | −25.780 | −12.058 | 22.728 | 1.00 | 27.90 | C |
| HETATM | 1403 | N | MSE | C | 744 | −20.398 | −12.503 | 21.124 | 1.00 | 22.46 | N |
| HETATM | 1404 | CA | MSE | C | 744 | −19.005 | −12.640 | 21.532 | 1.00 | 24.34 | C |
| HETATM | 1405 | C | MSE | C | 744 | −18.080 | −11.934 | 20.534 | 1.00 | 23.21 | C |
| HETATM | 1406 | O | MSE | C | 744 | −17.157 | −11.283 | 20.947 | 1.00 | 24.43 | O |
| HETATM | 1407 | CB | MSE | C | 744 | −18.598 | −14.105 | 21.772 | 1.00 | 24.47 | C |
| HETATM | 1408 | CG | MSE | C | 744 | −19.480 | −14.827 | 22.814 | 1.00 | 26.26 | C |
| HETATM | 1409 | SE | MSE | C | 744 | −19.343 | −13.913 | 24.564 | 1.00 | 33.88 | SE |
| HETATM | 1410 | CE | MSE | C | 744 | −17.655 | −14.614 | 25.144 | 1.00 | 34.61 | C |
| ATOM | 1411 | N | LYS | C | 745 | −18.397 | −12.021 | 19.240 | 1.00 | 24.72 | N |
| ATOM | 1412 | CA | LYS | C | 745 | −17.603 | −11.332 | 18.189 | 1.00 | 24.91 | C |
| ATOM | 1413 | C | LYS | C | 745 | −17.706 | −9.820 | 18.343 | 1.00 | 24.82 | C |
| ATOM | 1414 | O | LYS | C | 745 | −16.710 | −9.127 | 18.207 | 1.00 | 22.88 | O |
| ATOM | 1415 | CB | LYS | C | 745 | −18.124 | −11.685 | 16.791 | 1.00 | 26.57 | C |
| ATOM | 1416 | CG | LYS | C | 745 | −18.183 | −13.196 | 16.502 | 1.00 | 29.04 | C |
| ATOM | 1417 | CD | LYS | C | 745 | −17.001 | −13.963 | 16.950 | 1.00 | 39.22 | C |
| ATOM | 1418 | CE | LYS | C | 745 | −15.949 | −14.029 | 15.889 | 1.00 | 37.70 | C |
| ATOM | 1419 | NZ | LYS | C | 745 | −15.706 | −12.586 | 15.516 | 1.00 | 37.52 | N |
| ATOM | 1420 | N | ILE | C | 746 | −18.920 | −9.312 | 18.620 | 1.00 | 23.85 | N |
| ATOM | 1421 | CA | ILE | C | 746 | −19.063 | −7.872 | 18.841 | 1.00 | 23.76 | C |
| ATOM | 1422 | C | ILE | C | 746 | −18.250 | −7.433 | 20.094 | 1.00 | 22.87 | C |
| ATOM | 1423 | O | ILE | C | 746 | −17.636 | −6.418 | 20.067 | 1.00 | 21.48 | O |
| ATOM | 1424 | CB | ILE | C | 746 | −20.582 | −7.381 | 18.853 | 1.00 | 22.12 | C |
| ATOM | 1425 | CG1 | ILE | C | 746 | −21.280 | −7.725 | 17.514 | 1.00 | 25.30 | C |
| ATOM | 1426 | CG2 | ILE | C | 746 | −20.663 | −5.910 | 19.255 | 1.00 | 22.74 | C |
| ATOM | 1427 | CD1 | ILE | C | 746 | −22.765 | −7.607 | 17.577 | 1.00 | 25.59 | C |
| ATOM | 1428 | N | CYS | C | 747 | −18.238 | −8.227 | 21.173 | 1.00 | 22.02 | N |
| ATOM | 1429 | CA | CYS | C | 747 | −17.521 | −7.855 | 22.388 | 1.00 | 22.41 | C |
| ATOM | 1430 | C | CYS | C | 747 | −16.063 | −7.778 | 22.044 | 1.00 | 22.55 | C |
| ATOM | 1431 | O | CYS | C | 747 | −15.327 | −6.885 | 22.500 | 1.00 | 25.24 | O |
| ATOM | 1432 | CB | CYS | C | 747 | −17.724 | −8.942 | 23.440 | 1.00 | 22.30 | C |
| ATOM | 1433 | SG | CYS | C | 747 | −19.344 | −8.820 | 24.179 | 1.00 | 27.30 | S |
| ATOM | 1434 | N | SER | C | 748 | −15.636 | −8.750 | 21.236 | 1.00 | 22.58 | N |
| ATOM | 1435 | CA | SER | C | 748 | −14.225 | −8.805 | 20.821 | 1.00 | 23.42 | C |
| ATOM | 1436 | C | SER | C | 748 | −13.862 | −7.549 | 20.020 | 1.00 | 24.60 | C |
| ATOM | 1437 | O | SER | C | 748 | −12.825 | −6.955 | 20.196 | 1.00 | 24.94 | O |
| ATOM | 1438 | CB | SER | C | 748 | −13.918 | −10.088 | 20.035 | 1.00 | 23.85 | C |
| ATOM | 1439 | OG | SER | C | 748 | −13.795 | −11.177 | 20.954 | 1.00 | 30.58 | O |
| ATOM | 1440 | N | THR | C | 749 | −14.769 | −7.108 | 19.177 | 1.00 | 22.93 | N |
| ATOM | 1441 | CA | THR | C | 749 | −14.507 | −5.886 | 18.383 | 1.00 | 23.53 | C |
| ATOM | 1442 | C | THR | C | 749 | −14.461 | −4.656 | 19.278 | 1.00 | 23.37 | C |
| ATOM | 1443 | O | THR | C | 749 | −13.673 | −3.771 | 19.075 | 1.00 | 23.09 | O |
| ATOM | 1444 | CB | THR | C | 749 | −15.629 | −5.785 | 17.312 | 1.00 | 24.24 | C |
| ATOM | 1445 | OG1 | THR | C | 749 | −15.495 | −6.903 | 16.416 | 1.00 | 24.59 | O |
| ATOM | 1446 | CG2 | THR | C | 749 | −15.564 | −4.473 | 16.535 | 1.00 | 26.14 | C |
| ATOM | 1447 | N | ILE | C | 750 | −15.351 | −4.585 | 20.257 | 1.00 | 24.39 | N |
| ATOM | 1448 | CA | ILE | C | 750 | −15.383 | −3.447 | 21.126 | 1.00 | 25.09 | C |
| ATOM | 1449 | C | ILE | C | 750 | −14.120 | −3.410 | 21.972 | 1.00 | 26.72 | C |
| ATOM | 1450 | O | ILE | C | 750 | −13.575 | −2.339 | 22.239 | 1.00 | 25.30 | O |
| ATOM | 1451 | CB | ILE | C | 750 | −16.669 | −3.495 | 22.030 | 1.00 | 26.73 | C |
| ATOM | 1452 | CG1 | ILE | C | 750 | −17.937 | −3.307 | 21.177 | 1.00 | 26.16 | C |
| ATOM | 1453 | CG2 | ILE | C | 750 | −16.599 | −2.447 | 23.172 | 1.00 | 27.26 | C |
| ATOM | 1454 | CD1 | ILE | C | 750 | −19.253 | −3.808 | 21.862 | 1.00 | 23.34 | C |
| ATOM | 1455 | N | GLU | C | 751 | −13.664 | −4.584 | 22.395 | 1.00 | 27.35 | N |
| ATOM | 1456 | CA | GLU | C | 751 | −12.413 | −4.641 | 23.152 | 1.00 | 30.83 | C |
| ATOM | 1457 | C | GLU | C | 751 | −11.254 | −4.125 | 22.341 | 1.00 | 31.68 | C |
| ATOM | 1458 | O | GLU | C | 751 | −10.432 | −3.401 | 22.877 | 1.00 | 32.64 | O |
| ATOM | 1459 | CB | GLU | C | 751 | −12.142 | −6.035 | 23.703 | 1.00 | 31.73 | C |
| ATOM | 1460 | CG | GLU | C | 751 | −13.110 | −6.386 | 24.808 | 1.00 | 37.38 | C |
| ATOM | 1461 | CD | GLU | C | 751 | −12.449 | −6.518 | 26.162 | 1.00 | 43.79 | C |
| ATOM | 1462 | OE1 | GLU | C | 751 | −11.672 | −7.500 | 26.342 | 1.00 | 44.50 | O |
| ATOM | 1463 | OE2 | GLU | C | 751 | −12.749 | −5.671 | 27.049 | 1.00 | 46.07 | O |
| ATOM | 1464 | N | GLU | C | 752 | −11.192 | −4.473 | 21.052 | 1.00 | 32.32 | N |
| ATOM | 1465 | CA | GLU | C | 752 | −10.161 | −3.965 | 20.151 | 1.00 | 34.44 | C |
| ATOM | 1466 | C | GLU | C | 752 | −10.242 | −2.434 | 20.004 | 1.00 | 35.42 | C |
| ATOM | 1467 | O | GLU | C | 752 | −9.213 | −1.745 | 19.940 | 1.00 | 35.01 | O |
| ATOM | 1468 | CB | GLU | C | 752 | −10.304 | −4.657 | 18.790 | 1.00 | 34.16 | C |
| ATOM | 1469 | CG | GLU | C | 752 | −9.163 | −4.443 | 17.836 | 1.00 | 37.19 | C |
| ATOM | 1470 | CD | GLU | C | 752 | −9.296 | −5.270 | 16.571 | 1.00 | 37.83 | C |
| ATOM | 1471 | OE1 | GLU | C | 752 | −10.120 | −6.214 | 16.519 | 1.00 | 42.83 | O |
| ATOM | 1472 | OE2 | GLU | C | 752 | −8.566 | −4.952 | 15.614 | 1.00 | 43.93 | O |
| ATOM | 1473 | N | LEU | C | 753 | −11.467 | −1.914 | 19.942 | 1.00 | 35.55 | N |
| ATOM | 1474 | CA | LEU | C | 753 | −11.700 | −0.456 | 19.848 | 1.00 | 37.47 | C |
| ATOM | 1475 | C | LEU | C | 753 | −11.267 | 0.301 | 21.094 | 1.00 | 39.72 | C |
| ATOM | 1476 | O | LEU | C | 753 | −10.867 | 1.449 | 20.986 | 1.00 | 40.62 | O |
| ATOM | 1477 | CB | LEU | C | 753 | −13.164 | −0.127 | 19.493 | 1.00 | 36.45 | C |

TABLE 2b-continued

Data of atomic coordinates for accession code 3AIG, which cites accession code 2ZTT

| ATOM | 1478 | CG | LEU | C | 753 | −13.650 | −0.499 | 18.079 | 1.00 | 34.61 | C |
|---|---|---|---|---|---|---|---|---|---|---|---|
| ATOM | 1479 | CD1 | LEU | C | 753 | −15.171 | −0.299 | 17.917 | 1.00 | 34.47 | C |
| ATOM | 1480 | CD2 | LEU | C | 753 | −12.836 | 0.297 | 17.008 | 1.00 | 36.38 | C |
| ATOM | 1481 | N | ARG | C | 754 | −11.342 | −0.331 | 22.263 | 1.00 | 42.72 | N |
| ATOM | 1482 | CA | ARG | C | 754 | −10.920 | 0.292 | 23.524 | 1.00 | 46.81 | C |
| ATOM | 1483 | C | ARG | C | 754 | −9.446 | 0.635 | 23.513 | 1.00 | 49.37 | C |
| ATOM | 1484 | O | ARG | C | 754 | −9.057 | 1.806 | 23.634 | 1.00 | 49.81 | O |
| ATOM | 1485 | CB | ARG | C | 754 | −11.089 | −0.674 | 24.685 | 1.00 | 46.92 | C |
| ATOM | 1486 | CG | ARG | C | 754 | −12.463 | −0.917 | 25.177 | 1.00 | 48.50 | C |
| ATOM | 1487 | CD | ARG | C | 754 | −12.473 | −2.194 | 26.008 | 1.00 | 52.21 | C |
| ATOM | 1488 | NE | ARG | C | 754 | −11.982 | −2.003 | 27.374 | 1.00 | 54.41 | N |
| ATOM | 1489 | CZ | ARG | C | 754 | −10.791 | −2.390 | 27.832 | 1.00 | 57.00 | C |
| ATOM | 1490 | NH1 | ARG | C | 754 | −9.916 | −2.998 | 27.045 | 1.00 | 56.72 | N |
| ATOM | 1491 | NH2 | ARG | C | 754 | −10.470 | −2.159 | 29.098 | 1.00 | 57.17 | N |
| ATOM | 1492 | N | ARG | C | 755 | −8.651 | −0.424 | 23.357 | 1.00 | 52.47 | N |
| ATOM | 1493 | CA | ARG | C | 755 | −7.217 | −0.460 | 23.674 | 1.00 | 55.25 | C |
| ATOM | 1494 | C | ARG | C | 755 | −6.355 | 0.233 | 22.636 | 1.00 | 56.82 | C |
| ATOM | 1495 | O | ARG | C | 755 | −5.186 | 0.535 | 22.888 | 1.00 | 57.28 | O |
| ATOM | 1496 | CB | ARG | C | 755 | −6.767 | −1.919 | 23.789 | 1.00 | 55.52 | C |
| ATOM | 1497 | CG | ARG | C | 755 | −7.375 | −2.676 | 24.957 | 1.00 | 57.13 | C |
| ATOM | 1498 | CD | ARG | C | 755 | −7.909 | −4.016 | 24.508 | 1.00 | 59.24 | C |
| ATOM | 1499 | NE | ARG | C | 755 | −7.704 | −5.039 | 25.530 | 1.00 | 61.56 | N |
| ATOM | 1500 | CZ | ARG | C | 755 | −7.590 | −6.341 | 25.284 | 1.00 | 61.43 | C |
| ATOM | 1501 | NH1 | ARG | C | 755 | −7.664 | −6.804 | 24.037 | 1.00 | 61.77 | N |
| ATOM | 1502 | NH2 | ARG | C | 755 | −7.392 | −7.178 | 26.292 | 1.00 | 61.55 | N |
| ATOM | 1503 | N | GLN | C | 756 | −6.950 | 0.477 | 21.472 | 1.00 | 58.63 | N |
| ATOM | 1504 | CA | GLN | C | 756 | −6.243 | 0.967 | 20.307 | 1.00 | 60.47 | C |
| ATOM | 1505 | C | GLN | C | 756 | −6.045 | 2.476 | 20.396 | 1.00 | 60.88 | C |
| ATOM | 1506 | O | GLN | C | 756 | −6.720 | 3.149 | 21.183 | 1.00 | 61.53 | O |
| ATOM | 1507 | CB | GLN | C | 756 | −7.032 | 0.599 | 19.056 | 1.00 | 60.89 | C |
| ATOM | 1508 | CG | GLN | C | 756 | −6.197 | 0.142 | 17.873 | 1.00 | 62.80 | C |
| ATOM | 1509 | CD | GLN | C | 756 | −7.049 | −0.577 | 16.828 | 1.00 | 64.96 | C |
| ATOM | 1510 | OE1 | GLN | C | 756 | −8.285 | −0.576 | 16.908 | 1.00 | 65.81 | O |
| ATOM | 1511 | NE2 | GLN | C | 756 | −6.392 | −1.199 | 15.849 | 1.00 | 64.69 | N |
| ATOM | 1512 | N | LYS | C | 757 | −5.120 | 2.981 | 19.578 | 1.00 | 61.52 | N |
| ATOM | 1513 | CA | LYS | C | 757 | −4.625 | 4.374 | 19.599 | 1.00 | 61.73 | C |
| ATOM | 1514 | C | LYS | C | 757 | −3.527 | 4.594 | 20.648 | 1.00 | 61.97 | C |
| ATOM | 1515 | O | LYS | C | 757 | −2.421 | 4.996 | 20.293 | 1.00 | 61.96 | O |
| ATOM | 1516 | CB | LYS | C | 757 | −5.754 | 5.397 | 19.775 | 1.00 | 61.72 | C |
| ATOM | 1517 | CG | LYS | C | 757 | −5.413 | 6.792 | 19.281 | 1.00 | 60.95 | C |
| ATOM | 1518 | CD | LYS | C | 757 | −6.113 | 7.856 | 20.112 | 1.00 | 61.31 | C |
| ATOM | 1519 | CE | LYS | C | 757 | −7.631 | 7.637 | 20.211 | 1.00 | 60.93 | C |
| ATOM | 1520 | NZ | LYS | C | 757 | −8.345 | 7.706 | 18.893 | 1.00 | 60.60 | N |
| ATOM | 1521 | OXT | LYS | C | 757 | −3.708 | 4.389 | 21.856 | 1.00 | 62.23 | O |
| TER | 1522 | | LYS | C | 757 | | | | | 1.00 | |
| ATOM | 1523 | N | GLY | D | −2 | −33.787 | −9.024 | 20.452 | 1.00 | 43.97 | N |
| ATOM | 1524 | CA | GLY | D | −2 | −33.508 | −9.499 | 21.837 | 1.00 | 42.91 | C |
| ATOM | 1525 | C | GLY | D | −2 | −32.726 | −8.434 | 22.561 | 1.00 | 42.48 | C |
| ATOM | 1526 | O | GLY | D | −2 | −31.939 | −7.714 | 21.942 | 1.00 | 42.97 | O |
| ATOM | 1527 | N | GLY | D | −1 | −32.935 | −8.327 | 23.872 | 1.00 | 41.81 | N |
| ATOM | 1528 | CA | GLY | D | −1 | −32.286 | −7.281 | 24.661 | 1.00 | 39.76 | C |
| ATOM | 1529 | C | GLY | D | −1 | −30.766 | −7.376 | 24.681 | 1.00 | 38.48 | C |
| ATOM | 1530 | O | GLY | D | −1 | −30.097 | −6.357 | 24.696 | 1.00 | 37.41 | O |
| ATOM | 1531 | N | SER | D | 0 | −30.253 | −8.606 | 24.679 | 1.00 | 37.78 | N |
| ATOM | 1532 | CA | SER | D | 0 | −28.809 | −8.898 | 24.743 | 1.00 | 37.64 | C |
| ATOM | 1533 | C | SER | D | 0 | −28.109 | −8.385 | 23.498 | 1.00 | 36.26 | C |
| ATOM | 1534 | O | SER | D | 0 | −27.041 | −7.745 | 23.568 | 1.00 | 35.77 | O |
| ATOM | 1535 | CB | SER | D | 0 | −28.596 | −10.422 | 24.820 | 1.00 | 37.96 | C |
| ATOM | 1536 | OG | SER | D | 0 | −29.035 | −10.931 | 26.063 | 1.00 | 41.99 | O |
| HETATM | 1537 | N | MSE | D | 1 | −28.728 | −8.686 | 22.354 | 1.00 | 35.61 | N |
| HETATM | 1538 | CA | MSE | D | 1 | −28.250 | −8.230 | 21.055 | 1.00 | 35.61 | C |
| HETATM | 1539 | C | MSE | D | 1 | −28.392 | −6.745 | 20.896 | 1.00 | 34.20 | C |
| HETATM | 1540 | O | MSE | D | 1 | −27.464 | −6.087 | 20.439 | 1.00 | 33.62 | O |
| HETATM | 1541 | CB | MSE | D | 1 | −28.987 | −8.933 | 19.901 | 1.00 | 36.57 | C |
| HETATM | 1542 | CG | MSE | D | 1 | −28.329 | −8.741 | 18.549 | 1.00 | 37.97 | C |
| HETATM | 1543 | SE | MSE | D | 1 | −26.569 | −9.655 | 18.513 | 1.00 | 46.73 | SE |
| HETATM | 1544 | CE | MSE | D | 1 | −27.197 | −11.415 | 18.154 | 1.00 | 41.93 | C |
| ATOM | 1545 | N | GLU | D | 2 | −29.541 | −6.192 | 21.269 | 1.00 | 33.79 | N |
| ATOM | 1546 | CA | GLU | D | 2 | −29.735 | −4.765 | 21.046 | 1.00 | 34.38 | C |
| ATOM | 1547 | C | GLU | D | 2 | −28.723 | −3.907 | 21.828 | 1.00 | 32.74 | C |
| ATOM | 1548 | O | GLU | D | 2 | −28.173 | −2.934 | 21.297 | 1.00 | 32.38 | O |
| ATOM | 1549 | CB | GLU | D | 2 | −31.211 | −4.346 | 21.261 | 1.00 | 35.18 | C |
| ATOM | 1550 | CG | GLU | D | 2 | −31.664 | −4.172 | 22.705 | 1.00 | 42.59 | C |
| ATOM | 1551 | CD | GLU | D | 2 | −31.975 | −2.711 | 23.092 | 1.00 | 49.06 | C |
| ATOM | 1552 | OE1 | GLU | D | 2 | −31.399 | −2.223 | 24.102 | 1.00 | 51.63 | O |
| ATOM | 1553 | OE2 | GLU | D | 2 | −32.800 | −2.060 | 22.401 | 1.00 | 51.88 | O |
| ATOM | 1554 | N | ARG | D | 3 | −28.476 | −4.262 | 23.084 | 1.00 | 29.91 | N |
| ATOM | 1555 | CA | ARG | D | 3 | −27.547 | −3.481 | 23.883 | 1.00 | 29.68 | C |

TABLE 2b-continued

Data of atomic coordinates for accession code 3AIG, which cites accession code 2ZTT

| ATOM | 1556 | C | ARG | D | 3 | −26.119 | −3.582 | 23.361 | 1.00 | 27.65 | C |
|---|---|---|---|---|---|---|---|---|---|---|---|
| ATOM | 1557 | O | ARG | D | 3 | −25.397 | −2.596 | 23.373 | 1.00 | 28.11 | O |
| ATOM | 1558 | CB | ARG | D | 3 | −27.627 | −3.863 | 25.372 | 1.00 | 28.42 | C |
| ATOM | 1559 | CG | ARG | D | 3 | −27.112 | −5.248 | 25.721 | 1.00 | 30.94 | C |
| ATOM | 1560 | CD | ARG | D | 3 | −27.465 | −5.627 | 27.150 | 1.00 | 31.21 | C |
| ATOM | 1561 | NE | ARG | D | 3 | −26.833 | −6.895 | 27.481 | 1.00 | 31.39 | N |
| ATOM | 1562 | CZ | ARG | D | 3 | −26.739 | −7.439 | 28.694 | 1.00 | 34.65 | C |
| ATOM | 1563 | NH1 | ARG | D | 3 | −26.116 | −8.606 | 28.842 | 1.00 | 33.35 | N |
| ATOM | 1564 | NH2 | ARG | D | 3 | −27.264 | −6.832 | 29.756 | 1.00 | 33.72 | N |
| ATOM | 1565 | N | ILE | D | 4 | −25.696 | −4.778 | 22.941 | 1.00 | 27.66 | N |
| ATOM | 1566 | CA | ILE | D | 4 | −24.281 | −4.928 | 22.471 | 1.00 | 25.99 | C |
| ATOM | 1567 | C | ILE | D | 4 | −24.053 | −4.187 | 21.152 | 1.00 | 25.90 | C |
| ATOM | 1568 | O | ILE | D | 4 | −23.051 | −3.541 | 20.947 | 1.00 | 23.71 | O |
| ATOM | 1569 | CB | ILE | D | 4 | −23.795 | −6.393 | 22.460 | 1.00 | 26.70 | C |
| ATOM | 1570 | CG1 | ILE | D | 4 | −22.263 | −6.458 | 22.521 | 1.00 | 27.51 | C |
| ATOM | 1571 | CG2 | ILE | D | 4 | −24.294 | −7.177 | 21.204 | 1.00 | 26.33 | C |
| ATOM | 1572 | CD1 | ILE | D | 4 | −21.575 | −5.891 | 23.756 | 1.00 | 27.68 | C |
| ATOM | 1573 | N | LYS | D | 5 | −25.059 | −4.226 | 20.292 | 1.00 | 26.50 | N |
| ATOM | 1574 | CA | LYS | D | 5 | −24.982 | −3.452 | 19.041 | 1.00 | 27.99 | C |
| ATOM | 1575 | C | LYS | D | 5 | −25.046 | −1.942 | 19.253 | 1.00 | 28.77 | C |
| ATOM | 1576 | O | LYS | D | 5 | −24.379 | −1.166 | 18.548 | 1.00 | 30.34 | O |
| ATOM | 1577 | CB | LYS | D | 5 | −26.076 | −3.891 | 18.101 | 1.00 | 28.69 | C |
| ATOM | 1578 | CG | LYS | D | 5 | −25.870 | −5.238 | 17.461 | 1.00 | 30.26 | C |
| ATOM | 1579 | CD | LYS | D | 5 | −27.060 | −5.551 | 16.506 | 1.00 | 32.51 | C |
| ATOM | 1580 | CE | LYS | D | 5 | −26.828 | −6.831 | 15.760 | 1.00 | 37.39 | C |
| ATOM | 1581 | NZ | LYS | D | 5 | −27.980 | −7.221 | 14.896 | 1.00 | 39.91 | N |
| ATOM | 1582 | N | GLU | D | 6 | −25.868 | −1.507 | 20.195 | 1.00 | 28.57 | N |
| ATOM | 1583 | CA | GLU | D | 6 | −25.838 | −0.124 | 20.648 | 1.00 | 29.57 | C |
| ATOM | 1584 | C | GLU | D | 6 | −24.432 | 0.267 | 21.203 | 1.00 | 27.39 | C |
| ATOM | 1585 | O | GLU | D | 6 | −23.928 | 1.354 | 20.891 | 1.00 | 28.89 | O |
| ATOM | 1586 | CB | GLU | D | 6 | −26.876 | 0.076 | 21.745 | 1.00 | 29.59 | C |
| ATOM | 1587 | CG | GLU | D | 6 | −28.350 | 0.234 | 21.319 | 1.00 | 35.46 | C |
| ATOM | 1588 | CD | GLU | D | 6 | −29.223 | 0.640 | 22.497 | 1.00 | 35.04 | C |
| ATOM | 1589 | OE1 | GLU | D | 6 | −29.337 | 1.861 | 22.748 | 1.00 | 44.14 | O |
| ATOM | 1590 | OE2 | GLU | D | 6 | −29.769 | −0.244 | 23.208 | 1.00 | 44.16 | O |
| ATOM | 1591 | N | LEU | D | 7 | −23.803 | −0.586 | 22.046 | 1.00 | 27.06 | N |
| ATOM | 1592 | CA | LEU | D | 7 | −22.441 | −0.299 | 22.482 | 1.00 | 24.98 | C |
| ATOM | 1593 | C | LEU | D | 7 | −21.504 | −0.229 | 21.285 | 1.00 | 25.91 | C |
| ATOM | 1594 | O | LEU | D | 7 | −20.638 | 0.656 | 21.237 | 1.00 | 22.86 | O |
| ATOM | 1595 | CB | LEU | D | 7 | −21.869 | −1.329 | 23.520 | 1.00 | 24.15 | C |
| ATOM | 1596 | CG | LEU | D | 7 | −20.477 | −1.020 | 24.149 | 1.00 | 24.72 | C |
| ATOM | 1597 | CD1 | LEU | D | 7 | −20.375 | 0.408 | 24.719 | 1.00 | 25.87 | C |
| ATOM | 1598 | CD2 | LEU | D | 7 | −20.158 | −2.078 | 25.267 | 1.00 | 26.76 | C |
| ATOM | 1599 | N | ARG | D | 8 | −21.656 | −1.154 | 20.334 | 1.00 | 26.69 | N |
| ATOM | 1600 | CA | ARG | D | 8 | −20.766 | −1.136 | 19.142 | 1.00 | 29.65 | C |
| ATOM | 1601 | C | ARG | D | 8 | −20.950 | 0.200 | 18.441 | 1.00 | 28.43 | C |
| ATOM | 1602 | O | ARG | D | 8 | −19.961 | 0.811 | 18.046 | 1.00 | 31.04 | O |
| ATOM | 1603 | CB | ARG | D | 8 | −21.106 | −2.284 | 18.167 | 1.00 | 28.54 | C |
| ATOM | 1604 | CG | ARG | D | 8 | −20.559 | −2.131 | 16.683 | 1.00 | 30.92 | C |
| ATOM | 1605 | CD | ARG | D | 8 | −21.023 | −3.283 | 15.756 | 1.00 | 33.24 | C |
| ATOM | 1606 | NE | ARG | D | 8 | −22.442 | −3.317 | 15.443 | 1.00 | 33.24 | N |
| ATOM | 1607 | CZ | ARG | D | 8 | −23.054 | −4.396 | 14.940 | 1.00 | 37.93 | C |
| ATOM | 1608 | NH1 | ARG | D | 8 | −22.389 | −5.532 | 14.702 | 1.00 | 37.49 | N |
| ATOM | 1609 | NH2 | ARG | D | 8 | −24.342 | −4.359 | 14.672 | 1.00 | 38.56 | N |
| ATOM | 1610 | N | ASN | D | 9 | −22.198 | 0.640 | 18.297 | 1.00 | 29.96 | N |
| ATOM | 1611 | CA | ASN | D | 9 | −22.505 | 1.942 | 17.641 | 1.00 | 30.06 | C |
| ATOM | 1612 | C | ASN | D | 9 | −21.879 | 3.120 | 18.392 | 1.00 | 29.58 | C |
| ATOM | 1613 | O | ASN | D | 9 | −21.289 | 4.001 | 17.779 | 1.00 | 29.71 | O |
| ATOM | 1614 | CB | ASN | D | 9 | −24.000 | 2.145 | 17.431 | 1.00 | 32.61 | C |
| ATOM | 1615 | CG | ASN | D | 9 | −24.324 | 3.316 | 16.455 | 1.00 | 35.47 | C |
| ATOM | 1616 | OD1 | ASN | D | 9 | −23.898 | 3.320 | 15.286 | 1.00 | 42.12 | O |
| ATOM | 1617 | ND2 | ASN | D | 9 | −25.094 | 4.290 | 16.940 | 1.00 | 39.42 | N |
| ATOM | 1618 | N | LEU | D | 10 | −21.953 | 3.109 | 19.712 | 1.00 | 28.72 | N |
| ATOM | 1619 | CA | LEU | D | 10 | −21.295 | 4.153 | 20.504 | 1.00 | 27.74 | C |
| ATOM | 1620 | C | LEU | D | 10 | −19.768 | 4.190 | 20.417 | 1.00 | 26.89 | C |
| ATOM | 1621 | O | LEU | D | 10 | −19.180 | 5.252 | 20.422 | 1.00 | 26.83 | O |
| ATOM | 1622 | CB | LEU | D | 10 | −21.769 | 4.095 | 21.961 | 1.00 | 28.51 | C |
| ATOM | 1623 | CG | LEU | D | 10 | −23.106 | 4.779 | 22.196 | 1.00 | 31.04 | C |
| ATOM | 1624 | CD1 | LEU | D | 10 | −24.210 | 4.294 | 21.317 | 1.00 | 36.46 | C |
| ATOM | 1625 | CD2 | LEU | D | 10 | −23.477 | 4.750 | 23.637 | 1.00 | 28.86 | C |
| HETATM | 1626 | N | MSE | D | 11 | −19.125 | 3.028 | 20.311 | 1.00 | 26.42 | N |
| HETATM | 1627 | CA | MSE | D | 11 | −17.704 | 2.959 | 20.201 | 1.00 | 27.47 | C |
| HETATM | 1628 | C | MSE | D | 11 | −17.203 | 3.315 | 18.801 | 1.00 | 27.30 | C |
| HETATM | 1629 | O | MSE | D | 11 | −16.002 | 3.361 | 18.614 | 1.00 | 28.31 | O |
| HETATM | 1630 | CB | MSE | D | 11 | −17.143 | 1.576 | 20.598 | 1.00 | 26.43 | C |
| HETATM | 1631 | CG | MSE | D | 11 | −17.316 | 1.133 | 22.073 | 1.00 | 26.01 | C |
| HETATM | 1632 | SE | MSE | D | 11 | −16.342 | 2.213 | 23.268 | 1.00 | 30.59 | SE |
| HETATM | 1633 | CE | MSE | D | 11 | −14.619 | 1.646 | 22.711 | 1.00 | 30.42 | C |

TABLE 2b-continued

Data of atomic coordinates for accession code 3AIG, which cites accession code 2ZTT

| ATOM | 1634 | N | SER | D | 12 | −18.128 | 3.551 | 17.859 | 1.00 | 28.54 | N |
|---|---|---|---|---|---|---|---|---|---|---|---|
| ATOM | 1635 | CA | SER | D | 12 | −17.819 | 3.878 | 16.457 | 1.00 | 29.51 | C |
| ATOM | 1636 | C | SER | D | 12 | −17.683 | 5.363 | 16.213 | 1.00 | 30.95 | C |
| ATOM | 1637 | O | SER | D | 12 | −17.245 | 5.756 | 15.130 | 1.00 | 31.76 | O |
| ATOM | 1638 | CB | SER | D | 12 | −18.913 | 3.329 | 15.510 | 1.00 | 28.96 | C |
| ATOM | 1639 | OG | SER | D | 12 | −19.008 | 1.928 | 15.659 | 1.00 | 31.48 | O |
| ATOM | 1640 | N | GLN | D | 13 | −18.044 | 6.172 | 17.209 | 1.00 | 32.94 | N |
| ATOM | 1641 | CA | GLN | D | 13 | −18.065 | 7.640 | 17.132 | 1.00 | 34.40 | C |
| ATOM | 1642 | C | GLN | D | 13 | −17.113 | 8.127 | 18.230 | 1.00 | 35.47 | C |
| ATOM | 1643 | O | GLN | D | 13 | −17.263 | 7.725 | 19.375 | 1.00 | 34.23 | O |
| ATOM | 1644 | CB | GLN | D | 13 | −19.482 | 8.142 | 17.399 | 1.00 | 35.53 | C |
| ATOM | 1645 | CG | GLN | D | 13 | −20.488 | 7.526 | 16.426 | 1.00 | 39.13 | C |
| ATOM | 1646 | CD | GLN | D | 13 | −21.934 | 7.579 | 16.880 | 1.00 | 44.08 | C |
| ATOM | 1647 | OE1 | GLN | D | 13 | −22.413 | 6.710 | 17.618 | 1.00 | 46.34 | O |
| ATOM | 1648 | NE2 | GLN | D | 13 | −22.649 | 8.577 | 16.407 | 1.00 | 45.53 | N |
| ATOM | 1649 | N | SER | D | 14 | −16.138 | 8.972 | 17.877 | 1.00 | 35.61 | N |
| ATOM | 1650 | CA | SER | D | 14 | −14.989 | 9.231 | 18.736 | 1.00 | 36.29 | C |
| ATOM | 1651 | C | SER | D | 14 | −15.353 | 9.840 | 20.104 | 1.00 | 36.16 | C |
| ATOM | 1652 | O | SER | D | 14 | −14.687 | 9.528 | 21.089 | 1.00 | 34.81 | O |
| ATOM | 1653 | CB | SER | D | 14 | −13.947 | 10.094 | 18.026 | 1.00 | 36.98 | C |
| ATOM | 1654 | OG | SER | D | 14 | −14.495 | 11.361 | 17.725 | 1.00 | 39.62 | O |
| ATOM | 1655 | N | ARG | D | 15 | −16.391 | 10.677 | 20.160 | 1.00 | 35.82 | N |
| ATOM | 1656 | CA | ARG | D | 15 | −16.730 | 11.378 | 21.403 | 1.00 | 36.99 | C |
| ATOM | 1657 | C | ARG | D | 15 | −17.221 | 10.377 | 22.409 | 1.00 | 36.35 | C |
| ATOM | 1658 | O | ARG | D | 15 | −16.693 | 10.296 | 23.526 | 1.00 | 37.00 | O |
| ATOM | 1659 | CB | ARG | D | 15 | −17.816 | 12.454 | 21.221 | 1.00 | 37.17 | C |
| ATOM | 1660 | CG | ARG | D | 15 | −18.188 | 13.171 | 22.536 | 1.00 | 41.10 | C |
| ATOM | 1661 | CD | ARG | D | 15 | −17.020 | 14.010 | 23.131 | 1.00 | 44.42 | C |
| ATOM | 1662 | NE | ARG | D | 15 | −17.202 | 14.288 | 24.558 | 1.00 | 47.04 | N |
| ATOM | 1663 | CZ | ARG | D | 15 | −16.469 | 13.758 | 25.541 | 1.00 | 49.46 | C |
| ATOM | 1664 | NH1 | ARG | D | 15 | −16.736 | 14.071 | 26.809 | 1.00 | 50.64 | N |
| ATOM | 1665 | NH2 | ARG | D | 15 | −15.466 | 12.923 | 25.273 | 1.00 | 48.08 | N |
| ATOM | 1666 | N | THR | D | 16 | −18.223 | 9.598 | 22.015 | 1.00 | 35.06 | N |
| ATOM | 1667 | CA | THR | D | 16 | −18.840 | 8.650 | 22.942 | 1.00 | 34.24 | C |
| ATOM | 1668 | C | THR | D | 16 | −17.894 | 7.511 | 23.260 | 1.00 | 33.17 | C |
| ATOM | 1669 | O | THR | D | 16 | −17.936 | 6.970 | 24.388 | 1.00 | 32.35 | O |
| ATOM | 1670 | CB | THR | D | 16 | −20.158 | 8.114 | 22.417 | 1.00 | 33.98 | C |
| ATOM | 1671 | OG1 | THR | D | 16 | −20.000 | 7.701 | 21.049 | 1.00 | 31.71 | O |
| ATOM | 1672 | CG2 | THR | D | 16 | −21.271 | 9.160 | 22.499 | 1.00 | 34.65 | C |
| ATOM | 1673 | N | ARG | D | 17 | −17.033 | 7.151 | 22.300 | 1.00 | 32.76 | N |
| ATOM | 1674 | CA | ARG | D | 17 | −15.936 | 6.215 | 22.559 | 1.00 | 32.48 | C |
| ATOM | 1675 | C | ARG | D | 17 | −14.968 | 6.751 | 23.646 | 1.00 | 31.64 | C |
| ATOM | 1676 | O | ARG | D | 17 | −14.650 | 6.049 | 24.587 | 1.00 | 30.55 | O |
| ATOM | 1677 | CB | ARG | D | 17 | −15.206 | 5.854 | 21.277 | 1.00 | 32.00 | C |
| ATOM | 1678 | CG | ARG | D | 17 | −13.892 | 5.159 | 21.455 | 1.00 | 32.49 | C |
| ATOM | 1679 | CD | ARG | D | 17 | −13.406 | 4.641 | 20.122 | 1.00 | 33.02 | C |
| ATOM | 1680 | NE | ARG | D | 17 | −12.149 | 3.943 | 20.214 | 1.00 | 34.40 | N |
| ATOM | 1681 | CZ | ARG | D | 17 | −11.322 | 3.783 | 19.186 | 1.00 | 37.09 | C |
| ATOM | 1682 | NH1 | ARG | D | 17 | −11.647 | 4.288 | 17.999 | 1.00 | 43.14 | N |
| ATOM | 1683 | NH2 | ARG | D | 17 | −10.196 | 3.116 | 19.334 | 1.00 | 38.70 | N |
| ATOM | 1684 | N | GLU | D | 18 | −14.558 | 8.006 | 23.517 | 1.00 | 31.47 | N |
| ATOM | 1685 | CA | GLU | D | 18 | −13.764 | 8.697 | 24.533 | 1.00 | 34.17 | C |
| ATOM | 1686 | C | GLU | D | 18 | −14.447 | 8.607 | 25.897 | 1.00 | 31.85 | C |
| ATOM | 1687 | O | GLU | D | 18 | −13.828 | 8.137 | 26.849 | 1.00 | 32.47 | O |
| ATOM | 1688 | CB | GLU | D | 18 | −13.546 | 10.149 | 24.080 | 1.00 | 34.07 | C |
| ATOM | 1689 | CG | GLU | D | 18 | −12.432 | 10.904 | 24.764 | 1.00 | 39.59 | C |
| ATOM | 1690 | CD | GLU | D | 18 | −12.479 | 12.395 | 24.423 | 1.00 | 39.20 | C |
| ATOM | 1691 | OE1 | GLU | D | 18 | −12.872 | 12.735 | 23.278 | 1.00 | 44.67 | O |
| ATOM | 1692 | OE2 | GLU | D | 18 | −12.150 | 13.218 | 25.308 | 1.00 | 47.85 | O |
| ATOM | 1693 | N | ILE | D | 19 | −15.718 | 9.003 | 26.005 | 1.00 | 30.07 | N |
| ATOM | 1694 | CA | ILE | D | 19 | −16.484 | 8.896 | 27.275 | 1.00 | 29.70 | C |
| ATOM | 1695 | C | ILE | D | 19 | −16.449 | 7.484 | 27.847 | 1.00 | 30.22 | C |
| ATOM | 1696 | O | ILE | D | 19 | −16.040 | 7.262 | 29.012 | 1.00 | 30.72 | O |
| ATOM | 1697 | CB | ILE | D | 19 | −17.953 | 9.335 | 27.090 | 1.00 | 28.97 | C |
| ATOM | 1698 | CG1 | ILE | D | 19 | −17.945 | 10.822 | 26.744 | 1.00 | 29.76 | C |
| ATOM | 1699 | CG2 | ILE | D | 19 | −18.821 | 8.999 | 28.344 | 1.00 | 28.70 | C |
| ATOM | 1700 | CD1 | ILE | D | 19 | −19.211 | 11.378 | 26.341 | 1.00 | 25.75 | C |
| ATOM | 1701 | N | LEU | D | 20 | −16.861 | 6.504 | 27.021 | 1.00 | 28.49 | N |
| ATOM | 1702 | CA | LEU | D | 20 | −17.025 | 5.138 | 27.498 | 1.00 | 29.83 | C |
| ATOM | 1703 | C | LEU | D | 20 | −15.699 | 4.506 | 27.921 | 1.00 | 30.62 | C |
| ATOM | 1704 | O | LEU | D | 20 | −15.678 | 3.653 | 28.825 | 1.00 | 29.58 | O |
| ATOM | 1705 | CB | LEU | D | 20 | −17.636 | 4.277 | 26.362 | 1.00 | 30.06 | C |
| ATOM | 1706 | CG | LEU | D | 20 | −19.099 | 3.862 | 26.290 | 1.00 | 33.21 | C |
| ATOM | 1707 | CD1 | LEU | D | 20 | −20.076 | 4.387 | 27.320 | 1.00 | 31.98 | C |
| ATOM | 1708 | CD2 | LEU | D | 20 | −19.630 | 3.971 | 24.869 | 1.00 | 31.67 | C |
| ATOM | 1709 | N | THR | D | 21 | −14.611 | 4.889 | 27.261 | 1.00 | 30.79 | N |
| ATOM | 1710 | CA | THR | D | 21 | −13.322 | 4.286 | 27.538 | 1.00 | 32.68 | C |
| ATOM | 1711 | C | THR | D | 21 | −12.621 | 4.937 | 28.712 | 1.00 | 33.70 | C |

TABLE 2b-continued

Data of atomic coordinates for accession code 3AIG, which cites accession code 2ZTT

| ATOM | 1712 | O | THR | D | 21 | −11.913 | 4.260 | 29.457 | 1.00 | 34.14 | O |
|---|---|---|---|---|---|---|---|---|---|---|---|
| ATOM | 1713 | CB | THR | D | 21 | −12.367 | 4.343 | 26.343 | 1.00 | 33.24 | C |
| ATOM | 1714 | OG1 | THR | D | 21 | −12.213 | 5.702 | 25.934 | 1.00 | 36.04 | O |
| ATOM | 1715 | CG2 | THR | D | 21 | −12.912 | 3.471 | 25.191 | 1.00 | 30.71 | C |
| ATOM | 1716 | N | LYS | D | 22 | −12.823 | 6.233 | 28.888 | 1.00 | 34.82 | N |
| ATOM | 1717 | CA | LYS | D | 22 | −12.060 | 6.946 | 29.930 | 1.00 | 35.75 | C |
| ATOM | 1718 | C | LYS | D | 22 | −12.769 | 7.123 | 31.252 | 1.00 | 35.76 | C |
| ATOM | 1719 | O | LYS | D | 22 | −12.102 | 7.301 | 32.294 | 1.00 | 37.30 | O |
| ATOM | 1720 | CB | LYS | D | 22 | −11.598 | 8.308 | 29.440 | 1.00 | 36.04 | C |
| ATOM | 1721 | CG | LYS | D | 22 | −10.540 | 8.274 | 28.367 | 1.00 | 37.28 | C |
| ATOM | 1722 | CD | LYS | D | 22 | −10.276 | 9.685 | 27.926 | 1.00 | 41.85 | C |
| ATOM | 1723 | CE | LYS | D | 22 | −9.413 | 9.739 | 26.684 | 1.00 | 43.25 | C |
| ATOM | 1724 | NZ | LYS | D | 22 | −9.375 | 11.166 | 26.269 | 1.00 | 47.58 | N |
| ATOM | 1725 | N | THR | D | 23 | −14.096 | 7.088 | 31.232 | 1.00 | 35.35 | N |
| ATOM | 1726 | CA | THR | D | 23 | −14.894 | 7.330 | 32.421 | 1.00 | 33.96 | C |
| ATOM | 1727 | C | THR | D | 23 | −15.059 | 6.077 | 33.252 | 1.00 | 33.48 | C |
| ATOM | 1728 | O | THR | D | 23 | −15.505 | 5.054 | 32.758 | 1.00 | 32.05 | O |
| ATOM | 1729 | CB | THR | D | 23 | −16.240 | 7.923 | 32.068 | 1.00 | 34.24 | C |
| ATOM | 1730 | OG1 | THR | D | 23 | −16.013 | 9.017 | 31.164 | 1.00 | 33.20 | O |
| ATOM | 1731 | CG2 | THR | D | 23 | −16.949 | 8.440 | 33.332 | 1.00 | 34.18 | C |
| ATOM | 1732 | N | THR | D | 24 | −14.674 | 6.139 | 34.526 | 1.00 | 32.53 | N |
| ATOM | 1733 | CA | THR | D | 24 | −14.815 | 4.961 | 35.361 | 1.00 | 32.14 | C |
| ATOM | 1734 | C | THR | D | 24 | −16.229 | 4.872 | 35.888 | 1.00 | 32.63 | C |
| ATOM | 1735 | O | THR | D | 24 | −16.932 | 5.891 | 35.977 | 1.00 | 32.72 | O |
| ATOM | 1736 | CB | THR | D | 24 | −13.835 | 4.982 | 36.553 | 1.00 | 33.23 | C |
| ATOM | 1737 | OG1 | THR | D | 24 | −14.115 | 6.120 | 37.368 | 1.00 | 32.33 | O |
| ATOM | 1738 | CG2 | THR | D | 24 | −12.398 | 5.008 | 36.078 | 1.00 | 33.20 | C |
| ATOM | 1739 | N | VAL | D | 25 | −16.661 | 3.678 | 36.287 | 1.00 | 31.48 | N |
| ATOM | 1740 | CA | VAL | D | 25 | −18.007 | 3.522 | 36.796 | 1.00 | 32.68 | C |
| ATOM | 1741 | C | VAL | D | 25 | −18.188 | 4.423 | 38.019 | 1.00 | 34.78 | C |
| ATOM | 1742 | O | VAL | D | 25 | −19.200 | 5.074 | 38.145 | 1.00 | 35.56 | O |
| ATOM | 1743 | CB | VAL | D | 25 | −18.341 | 2.063 | 37.147 | 1.00 | 32.61 | C |
| ATOM | 1744 | CG1 | VAL | D | 25 | −19.604 | 1.975 | 37.881 | 1.00 | 33.19 | C |
| ATOM | 1745 | CG2 | VAL | D | 25 | −18.499 | 1.258 | 35.847 | 1.00 | 30.60 | C |
| ATOM | 1746 | N | ASP | D | 26 | −17.193 | 4.468 | 38.895 | 1.00 | 37.00 | N |
| ATOM | 1747 | CA | ASP | D | 26 | −17.290 | 5.338 | 40.075 | 1.00 | 40.52 | C |
| ATOM | 1748 | C | ASP | D | 26 | −17.598 | 6.779 | 39.740 | 1.00 | 41.59 | C |
| ATOM | 1749 | O | ASP | D | 26 | −18.359 | 7.441 | 40.445 | 1.00 | 44.05 | O |
| ATOM | 1750 | CB | ASP | D | 26 | −15.999 | 5.279 | 40.876 | 1.00 | 40.71 | C |
| ATOM | 1751 | CG | ASP | D | 26 | −15.986 | 4.134 | 41.860 | 1.00 | 42.83 | C |
| ATOM | 1752 | OD1 | ASP | D | 26 | −17.078 | 3.766 | 42.361 | 1.00 | 48.66 | O |
| ATOM | 1753 | OD2 | ASP | D | 26 | −14.886 | 3.611 | 42.145 | 1.00 | 45.91 | O |
| ATOM | 1754 | N | HIS | D | 27 | −16.991 | 7.288 | 38.688 | 1.00 | 42.54 | N |
| ATOM | 1755 | CA | HIS | D | 27 | −17.153 | 8.686 | 38.380 | 1.00 | 43.24 | C |
| ATOM | 1756 | C | HIS | D | 27 | −18.541 | 9.012 | 37.782 | 1.00 | 44.37 | C |
| ATOM | 1757 | O | HIS | D | 27 | −18.802 | 10.175 | 37.493 | 1.00 | 43.66 | O |
| ATOM | 1758 | CB | HIS | D | 27 | −15.990 | 9.178 | 37.509 | 1.00 | 42.95 | C |
| ATOM | 1759 | CG | HIS | D | 27 | −14.669 | 9.225 | 38.224 | 1.00 | 41.88 | C |
| ATOM | 1760 | ND1 | HIS | D | 27 | −13.459 | 9.254 | 37.560 | 1.00 | 39.62 | N |
| ATOM | 1761 | CD2 | HIS | D | 27 | −14.373 | 9.183 | 39.541 | 1.00 | 40.19 | C |
| ATOM | 1762 | CE1 | HIS | D | 27 | −12.477 | 9.269 | 38.444 | 1.00 | 40.64 | C |
| ATOM | 1763 | NE2 | HIS | D | 27 | −13.002 | 9.214 | 39.654 | 1.00 | 42.27 | N |
| HETATM | 1764 | N | MSE | D | 28 | −19.421 | 7.994 | 37.659 | 1.00 | 45.21 | N |
| HETATM | 1765 | CA | MSE | D | 28 | −20.726 | 8.103 | 36.982 | 1.00 | 46.59 | C |
| HETATM | 1766 | C | MSE | D | 28 | −21.777 | 8.763 | 37.837 | 1.00 | 46.84 | C |
| HETATM | 1767 | O | MSE | D | 28 | −22.548 | 9.565 | 37.333 | 1.00 | 46.75 | O |
| HETATM | 1768 | CB | MSE | D | 28 | −21.295 | 6.730 | 36.570 | 1.00 | 47.13 | C |
| HETATM | 1769 | CG | MSE | D | 28 | −20.652 | 6.056 | 35.374 | 1.00 | 47.31 | C |
| HETATM | 1770 | SE | MSE | D | 28 | −21.669 | 4.396 | 35.020 | 1.00 | 49.34 | SE |
| HETATM | 1771 | CE | MSE | D | 28 | −22.373 | 4.049 | 36.820 | 1.00 | 52.02 | C |
| ATOM | 1772 | N | ALA | D | 29 | −21.846 | 8.370 | 39.108 | 1.00 | 46.46 | N |
| ATOM | 1773 | CA | ALA | D | 29 | −22.701 | 9.048 | 40.073 | 1.00 | 46.81 | C |
| ATOM | 1774 | C | ALA | D | 29 | −22.301 | 10.508 | 40.008 | 1.00 | 46.20 | C |
| ATOM | 1775 | O | ALA | D | 29 | −23.145 | 11.375 | 39.802 | 1.00 | 47.02 | O |
| ATOM | 1776 | CB | ALA | D | 29 | −22.458 | 8.499 | 41.479 | 1.00 | 47.10 | C |
| ATOM | 1777 | N | ILE | D | 30 | −20.995 | 10.735 | 40.167 | 1.00 | 45.06 | N |
| ATOM | 1778 | CA | ILE | D | 30 | −20.373 | 12.062 | 40.194 | 1.00 | 44.44 | C |
| ATOM | 1779 | C | ILE | D | 30 | −20.781 | 12.924 | 38.988 | 1.00 | 42.90 | C |
| ATOM | 1780 | O | ILE | D | 30 | −21.525 | 13.896 | 39.158 | 1.00 | 42.91 | O |
| ATOM | 1781 | CB | ILE | D | 30 | −18.811 | 11.954 | 40.332 | 1.00 | 43.88 | C |
| ATOM | 1782 | CG1 | ILE | D | 30 | −18.443 | 11.062 | 41.534 | 1.00 | 45.22 | C |
| ATOM | 1783 | CG2 | ILE | D | 30 | −18.173 | 13.321 | 40.465 | 1.00 | 45.05 | C |
| ATOM | 1784 | CD1 | ILE | D | 30 | −16.928 | 10.901 | 41.793 | 1.00 | 44.79 | C |
| ATOM | 1785 | N | ILE | D | 31 | −20.310 | 12.578 | 37.787 | 1.00 | 41.59 | N |
| ATOM | 1786 | CA | ILE | D | 31 | −20.638 | 13.384 | 36.600 | 1.00 | 40.89 | C |
| ATOM | 1787 | C | ILE | D | 31 | −22.149 | 13.501 | 36.433 | 1.00 | 41.33 | C |
| ATOM | 1788 | O | ILE | D | 31 | −22.675 | 14.577 | 36.111 | 1.00 | 40.31 | O |
| ATOM | 1789 | CB | ILE | D | 31 | −19.999 | 12.820 | 35.292 | 1.00 | 41.19 | C |

TABLE 2b-continued

Data of atomic coordinates for accession code 3AIG, which cites accession code 2ZTT

| ATOM | 1790 | CG1 | ILE | D | 31 | −18.492 | 13.055 | 35.289 | 1.00 | 41.02 | C |
|---|---|---|---|---|---|---|---|---|---|---|---|
| ATOM | 1791 | CG2 | ILE | D | 31 | −20.662 | 13.446 | 34.047 | 1.00 | 40.83 | C |
| ATOM | 1792 | CD1 | ILE | D | 31 | −17.677 | 12.171 | 34.334 | 1.00 | 40.79 | C |
| ATOM | 1793 | N | LYS | D | 32 | −22.850 | 12.396 | 36.670 | 1.00 | 41.68 | N |
| ATOM | 1794 | CA | LYS | D | 32 | −24.292 | 12.361 | 36.454 | 1.00 | 43.30 | C |
| ATOM | 1795 | C | LYS | D | 32 | −25.063 | 13.251 | 37.467 | 1.00 | 44.15 | C |
| ATOM | 1796 | O | LYS | D | 32 | −26.134 | 13.764 | 37.146 | 1.00 | 43.94 | O |
| ATOM | 1797 | CB | LYS | D | 32 | −24.808 | 10.896 | 36.386 | 1.00 | 43.66 | C |
| ATOM | 1798 | CG | LYS | D | 32 | −24.479 | 10.109 | 35.057 | 1.00 | 43.62 | C |
| ATOM | 1799 | CD | LYS | D | 32 | −23.101 | 10.451 | 34.344 | 1.00 | 44.16 | C |
| ATOM | 1800 | CE | LYS | D | 32 | −22.438 | 9.219 | 33.633 | 1.00 | 42.93 | C |
| ATOM | 1801 | NZ | LYS | D | 32 | −21.214 | 9.375 | 32.662 | 1.00 | 34.69 | N |
| ATOM | 1802 | N | LYS | D | 33 | −24.506 | 13.498 | 38.659 | 1.00 | 45.80 | N |
| ATOM | 1803 | CA | LYS | D | 33 | −25.128 | 14.480 | 39.584 | 1.00 | 46.89 | C |
| ATOM | 1804 | C | LYS | D | 33 | −25.220 | 15.902 | 39.002 | 1.00 | 47.78 | C |
| ATOM | 1805 | O | LYS | D | 33 | −26.218 | 16.604 | 39.215 | 1.00 | 47.34 | O |
| ATOM | 1806 | CB | LYS | D | 33 | −24.445 | 14.518 | 40.962 | 1.00 | 47.31 | C |
| ATOM | 1807 | CG | LYS | D | 33 | −25.076 | 15.557 | 41.932 | 1.00 | 46.71 | C |
| ATOM | 1808 | CD | LYS | D | 33 | −24.409 | 15.567 | 43.295 | 1.00 | 47.75 | C |
| ATOM | 1809 | CE | LYS | D | 33 | −24.969 | 16.668 | 44.189 | 1.00 | 49.61 | C |
| ATOM | 1810 | NZ | LYS | D | 33 | −24.607 | 16.432 | 45.620 | 1.00 | 51.01 | N |
| ATOM | 1811 | N | TYR | D | 34 | −24.200 | 16.317 | 38.251 | 1.00 | 48.58 | N |
| ATOM | 1812 | CA | TYR | D | 34 | −24.151 | 17.684 | 37.721 | 1.00 | 50.25 | C |
| ATOM | 1813 | C | TYR | D | 34 | −24.439 | 17.717 | 36.223 | 1.00 | 51.48 | C |
| ATOM | 1814 | O | TYR | D | 34 | −23.957 | 18.593 | 35.484 | 1.00 | 51.34 | O |
| ATOM | 1815 | CB | TYR | D | 34 | −22.814 | 18.363 | 38.075 | 1.00 | 50.76 | C |
| ATOM | 1816 | CG | TYR | D | 34 | −22.327 | 18.014 | 39.463 | 1.00 | 50.43 | C |
| ATOM | 1817 | CD1 | TYR | D | 34 | −21.508 | 16.917 | 39.648 | 1.00 | 51.93 | C |
| ATOM | 1818 | CD2 | TYR | D | 34 | −22.699 | 18.764 | 40.584 | 1.00 | 50.70 | C |
| ATOM | 1819 | CE1 | TYR | D | 34 | −21.062 | 16.552 | 40.893 | 1.00 | 53.15 | C |
| ATOM | 1820 | CE2 | TYR | D | 34 | −22.244 | 18.410 | 41.868 | 1.00 | 51.76 | C |
| ATOM | 1821 | CZ | TYR | D | 34 | −21.420 | 17.290 | 41.996 | 1.00 | 52.99 | C |
| ATOM | 1822 | OH | TYR | D | 34 | −20.937 | 16.861 | 43.210 | 1.00 | 53.89 | O |
| ATOM | 1823 | N | THR | D | 35 | −25.236 | 16.739 | 35.792 | 1.00 | 52.83 | N |
| ATOM | 1824 | CA | THR | D | 35 | −25.768 | 16.670 | 34.434 | 1.00 | 53.89 | C |
| ATOM | 1825 | C | THR | D | 35 | −27.171 | 17.258 | 34.442 | 1.00 | 54.19 | C |
| ATOM | 1826 | O | THR | D | 35 | −27.337 | 18.456 | 34.659 | 1.00 | 54.59 | O |
| ATOM | 1827 | CB | THR | D | 35 | −25.817 | 15.213 | 33.922 | 1.00 | 54.03 | C |
| ATOM | 1828 | OG1 | THR | D | 35 | −24.627 | 14.927 | 33.166 | 1.00 | 54.37 | O |
| ATOM | 1829 | CG2 | THR | D | 35 | −27.026 | 14.996 | 33.031 | 1.00 | 54.94 | C |
| TER | 1830 | | THR | D | 35 | | | | 1.00 | | |
| HETATM | 1831 | O | HOH | A | 2 | −20.909 | 8.034 | 1.761 | 1.00 | 21.65 | O |
| HETATM | 1832 | O | HOH | A | 3 | −22.767 | 10.044 | 1.057 | 1.00 | 22.31 | O |
| HETATM | 1833 | O | HOH | A | 5 | −13.148 | 9.509 | 7.972 | 1.00 | 27.54 | O |
| HETATM | 1834 | O | HOH | A | 6 | −21.348 | 5.128 | −4.302 | 1.00 | 28.68 | O |
| HETATM | 1835 | O | HOH | A | 10 | −14.780 | −20.624 | 2.484 | 1.00 | 31.86 | O |
| HETATM | 1836 | O | HOH | A | 11 | −9.930 | 6.381 | 2.375 | 1.00 | 31.04 | O |
| HETATM | 1837 | O | HOH | A | 12 | −26.437 | 10.886 | −1.487 | 1.00 | 33.02 | O |
| HETATM | 1838 | O | HOH | A | 13 | −28.144 | 8.609 | 4.735 | 1.00 | 34.59 | O |
| HETATM | 1839 | O | HOH | A | 17 | −9.826 | 3.633 | 2.311 | 1.00 | 34.34 | O |
| HETATM | 1840 | O | HOH | A | 20 | −7.681 | −4.084 | 4.085 | 1.00 | 35.38 | O |
| HETATM | 1841 | O | HOH | A | 21 | −11.297 | 8.863 | 0.091 | 1.00 | 36.63 | O |
| HETATM | 1842 | O | HOH | A | 25 | −14.083 | 7.298 | 14.695 | 1.00 | 37.54 | O |
| HETATM | 1843 | O | HOH | A | 26 | −14.210 | 4.617 | 16.978 | 1.00 | 38.00 | O |
| HETATM | 1844 | O | HOH | A | 37 | −24.076 | 8.736 | −2.926 | 1.00 | 39.45 | O |
| HETATM | 1845 | O | HOH | A | 40 | −16.653 | −19.181 | 6.153 | 1.00 | 42.43 | O |
| HETATM | 1846 | O | HOH | A | 42 | −26.442 | −4.936 | −3.531 | 1.00 | 42.21 | O |
| HETATM | 1847 | O | HOH | A | 43 | −29.419 | 8.959 | −1.253 | 1.00 | 43.06 | O |
| HETATM | 1848 | O | HOH | A | 44 | −9.342 | 1.856 | −3.061 | 1.00 | 42.93 | O |
| HETATM | 1849 | O | HOH | A | 46 | −24.402 | 14.571 | −4.725 | 1.00 | 41.29 | O |
| HETATM | 1850 | O | HOH | A | 48 | −27.254 | 20.964 | −4.515 | 1.00 | 45.57 | O |
| HETATM | 1851 | O | HOH | A | 52 | −27.038 | 20.045 | 8.103 | 1.00 | 44.03 | O |
| HETATM | 1852 | O | HOH | A | 57 | −25.759 | 19.978 | 3.485 | 1.00 | 46.21 | O |
| HETATM | 1853 | O | HOH | A | 58 | −19.070 | −22.018 | 2.897 | 1.00 | 48.74 | O |
| HETATM | 1854 | O | HOH | A | 62 | −17.487 | 9.038 | −5.590 | 1.00 | 47.58 | O |
| HETATM | 1855 | O | HOH | A | 63 | −17.270 | −20.099 | 3.511 | 1.00 | 48.85 | O |
| HETATM | 1856 | O | HOH | B | 38 | −30.257 | 8.955 | 7.785 | 1.00 | 40.82 | O |
| HETATM | 1857 | O | HOH | B | 39 | −21.793 | 5.718 | 3.000 | 1.00 | 20.64 | O |
| HETATM | 1858 | O | HOH | B | 40 | −28.451 | 8.916 | 1.868 | 1.00 | 34.18 | O |
| HETATM | 1859 | O | HOH | B | 41 | −21.008 | −10.987 | 9.540 | 1.00 | 33.58 | O |
| HETATM | 1860 | O | HOH | B | 42 | −27.430 | −0.794 | 7.796 | 1.00 | 36.80 | O |
| HETATM | 1861 | O | HOH | B | 43 | −17.883 | −14.676 | 11.932 | 1.00 | 36.89 | O |
| HETATM | 1862 | O | HOH | B | 44 | −25.141 | −7.059 | 2.399 | 1.00 | 37.52 | O |
| HETATM | 1863 | O | HOH | B | 45 | −5.480 | −8.935 | −6.615 | 1.00 | 38.89 | O |
| HETATM | 1864 | O | HOH | B | 46 | −5.205 | −8.070 | −9.415 | 1.00 | 41.71 | O |
| HETATM | 1865 | O | HOH | B | 47 | −11.252 | −11.011 | 11.363 | 1.00 | 41.86 | O |
| HETATM | 1866 | O | HOH | B | 49 | −29.336 | 5.084 | 10.634 | 1.00 | 43.80 | O |
| HETATM | 1867 | O | HOH | B | 56 | −30.837 | 5.253 | 7.381 | 1.00 | 45.71 | O |

TABLE 2b-continued

Data of atomic coordinates for accession code 3AIG, which cites accession code 2ZTT

| HETATM | 1868 | O | HOH | B | 61 | −6.704 | −11.489 | −1.667 | 1.00 | 49.44 | O |
| --- | --- | --- | --- | --- | --- | --- | --- | --- | --- | --- | --- |
| HETATM | 1869 | O | HOH | C | 7 | −25.032 | −10.540 | 26.863 | 1.00 | 30.39 | O |
| HETATM | 1870 | O | HOH | C | 8 | −15.715 | −11.990 | 23.216 | 1.00 | 30.11 | O |
| HETATM | 1871 | O | HOH | C | 15 | −13.870 | −7.221 | 14.386 | 1.00 | 33.82 | O |
| HETATM | 1872 | O | HOH | C | 27 | −10.521 | −8.248 | 21.205 | 1.00 | 37.89 | O |
| HETATM | 1873 | O | HOH | C | 28 | −14.222 | −8.728 | 29.383 | 1.00 | 39.86 | O |
| HETATM | 1874 | O | HOH | C | 29 | −21.080 | −16.616 | 32.588 | 1.00 | 39.47 | O |
| HETATM | 1875 | O | HOH | C | 30 | −14.020 | −6.064 | 29.724 | 1.00 | 39.70 | O |
| HETATM | 1876 | O | HOH | C | 36 | −14.783 | −9.918 | 16.252 | 1.00 | 40.03 | O |
| HETATM | 1877 | O | HOH | C | 41 | −15.353 | −4.434 | 35.000 | 1.00 | 41.37 | O |
| HETATM | 1878 | O | HOH | C | 50 | −17.591 | −4.625 | 36.358 | 1.00 | 45.99 | O |
| HETATM | 1879 | O | HOH | C | 53 | −21.738 | −15.559 | 14.512 | 1.00 | 46.38 | O |
| HETATM | 1880 | O | HOH | C | 54 | −30.446 | −17.211 | 31.038 | 1.00 | 48.59 | O |
| HETATM | 1881 | O | HOH | C | 55 | −30.677 | −4.840 | 29.519 | 1.00 | 45.57 | O |
| HETATM | 1882 | O | HOH | C | 60 | −23.772 | −8.134 | 13.352 | 1.00 | 48.36 | O |
| HETATM | 1883 | O | HOH | D | 38 | −25.291 | −8.113 | 25.446 | 1.00 | 26.96 | O |
| HETATM | 1884 | O | HOH | D | 39 | −22.835 | 8.457 | 19.560 | 1.00 | 41.80 | O |
| HETATM | 1885 | O | HOH | D | 40 | −27.006 | −12.610 | 26.573 | 1.00 | 31.89 | O |
| HETATM | 1886 | O | HOH | D | 41 | −23.483 | 0.168 | 15.918 | 1.00 | 35.74 | O |
| HETATM | 1887 | O | HOH | D | 42 | −27.703 | −7.529 | 32.355 | 1.00 | 37.42 | O |
| HETATM | 1888 | O | HOH | D | 43 | −20.438 | 9.837 | 14.960 | 1.00 | 38.38 | O |
| HETATM | 1889 | O | HOH | D | 44 | −12.021 | 9.629 | 42.391 | 1.00 | 42.51 | O |
| HETATM | 1890 | O | HOH | D | 45 | −18.098 | 12.039 | 17.977 | 1.00 | 42.89 | O |
| HETATM | 1891 | O | HOH | D | 47 | −29.509 | 2.676 | 25.275 | 1.00 | 42.28 | O |
| HETATM | 1892 | O | HOH | D | 51 | −12.088 | 8.083 | 34.711 | 1.00 | 44.85 | O |
| HETATM | 1893 | O | HOH | D | 59 | −12.946 | 5.147 | 42.098 | 1.00 | 47.44 | O |
| CONECT | 20 | 27 | | | | | | | | | |
| CONECT | 27 | 20 | 28 | | | | | | | | |
| CONECT | 28 | 27 | 29 | 31 | | | | | | | |
| CONECT | 29 | 28 | 30 | 35 | | | | | | | |
| CONECT | 30 | 29 | | | | | | | | | |
| CONECT | 31 | 28 | 32 | | | | | | | | |
| CONECT | 32 | 31 | 33 | | | | | | | | |
| CONECT | 33 | 32 | 34 | | | | | | | | |
| CONECT | 34 | 33 | | | | | | | | | |
| CONECT | 35 | 29 | | | | | | | | | |
| CONECT | 239 | 243 | | | | | | | | | |
| CONECT | 243 | 239 | 244 | | | | | | | | |
| CONECT | 244 | 243 | 245 | 247 | | | | | | | |
| CONECT | 245 | 244 | 246 | 251 | | | | | | | |
| CONECT | 246 | 245 | | | | | | | | | |
| CONECT | 247 | 244 | 248 | | | | | | | | |
| CONECT | 248 | 247 | 249 | | | | | | | | |
| CONECT | 249 | 248 | 250 | | | | | | | | |
| CONECT | 250 | 249 | | | | | | | | | |
| CONECT | 251 | 245 | | | | | | | | | |
| CONECT | 269 | 272 | | | | | | | | | |
| CONECT | 272 | 269 | 273 | | | | | | | | |
| CONECT | 273 | 272 | 274 | 276 | | | | | | | |
| CONECT | 274 | 273 | 275 | 280 | | | | | | | |
| CONECT | 275 | 274 | | | | | | | | | |
| CONECT | 276 | 273 | 277 | | | | | | | | |
| CONECT | 277 | 276 | 278 | | | | | | | | |
| CONECT | 278 | 277 | 279 | | | | | | | | |
| CONECT | 279 | 278 | | | | | | | | | |
| CONECT | 280 | 274 | | | | | | | | | |
| CONECT | 482 | 488 | | | | | | | | | |
| CONECT | 488 | 482 | 489 | | | | | | | | |
| CONECT | 489 | 488 | 490 | 492 | | | | | | | |
| CONECT | 490 | 489 | 491 | 496 | | | | | | | |
| CONECT | 491 | 490 | | | | | | | | | |
| CONECT | 492 | 489 | 493 | | | | | | | | |
| CONECT | 493 | 492 | 494 | | | | | | | | |
| CONECT | 494 | 493 | 495 | | | | | | | | |
| CONECT | 495 | 494 | | | | | | | | | |
| CONECT | 496 | 490 | | | | | | | | | |
| CONECT | 618 | 622 | | | | | | | | | |
| CONECT | 622 | 618 | 623 | | | | | | | | |
| CONECT | 623 | 622 | 624 | 626 | | | | | | | |
| CONECT | 624 | 623 | 625 | 630 | | | | | | | |
| CONECT | 625 | 624 | | | | | | | | | |
| CONECT | 626 | 623 | 627 | | | | | | | | |
| CONECT | 627 | 626 | 628 | | | | | | | | |
| CONECT | 628 | 627 | 629 | | | | | | | | |
| CONECT | 629 | 628 | | | | | | | | | |
| CONECT | 630 | 624 | | | | | | | | | |
| CONECT | 705 | 711 | | | | | | | | | |
| CONECT | 711 | 705 | 712 | | | | | | | | |

TABLE 2b-continued

Data of atomic coordinates for accession code 3AIG, which cites accession code 2ZTT

| | | | | |
|---|---|---|---|---|
| CONECT | 712 | 711 | 713 | 715 |
| CONECT | 713 | 712 | 714 | 719 |
| CONECT | 714 | 713 | | |
| CONECT | 715 | 712 | 716 | |
| CONECT | 716 | 715 | 717 | |
| CONECT | 717 | 716 | 718 | |
| CONECT | 718 | 717 | | |
| CONECT | 719 | 713 | | |
| CONECT | 841 | 849 | | |
| CONECT | 849 | 841 | 850 | |
| CONECT | 850 | 849 | 851 | 853 |
| CONECT | 851 | 850 | 852 | 857 |
| CONECT | 852 | 851 | | |
| CONECT | 853 | 850 | 854 | |
| CONECT | 854 | 853 | 855 | |
| CONECT | 855 | 854 | 856 | |
| CONECT | 856 | 855 | | |
| CONECT | 857 | 851 | | |
| CONECT | 935 | 942 | | |
| CONECT | 942 | 935 | 943 | |
| CONECT | 943 | 942 | 944 | 946 |
| CONECT | 944 | 943 | 945 | 950 |
| CONECT | 945 | 944 | | |
| CONECT | 946 | 943 | 947 | |
| CONECT | 947 | 946 | 948 | |
| CONECT | 948 | 947 | 949 | |
| CONECT | 949 | 948 | | |
| CONECT | 950 | 944 | | |
| CONECT | 1154 | 1158 | | |
| CONECT | 1158 | 1154 | 1159 | |
| CONECT | 1159 | 1158 | 1160 | 1162 |
| CONECT | 1160 | 1159 | 1161 | 1166 |
| CONECT | 1161 | 1160 | | |
| CONECT | 1162 | 1159 | 1163 | |
| CONECT | 1163 | 1162 | 1164 | |
| CONECT | 1164 | 1163 | 1165 | |
| CONECT | 1165 | 1164 | | |
| CONECT | 1166 | 1160 | | |
| CONECT | 1184 | 1187 | | |
| CONECT | 1187 | 1184 | 1188 | |
| CONECT | 1188 | 1187 | 1189 | 1191 |
| CONECT | 1189 | 1188 | 1190 | 1195 |
| CONECT | 1190 | 1189 | | |
| CONECT | 1191 | 1188 | 1192 | |
| CONECT | 1192 | 1191 | 1193 | |
| CONECT | 1193 | 1192 | 1194 | |
| CONECT | 1194 | 1193 | | |
| CONECT | 1195 | 1189 | | |
| CONECT | 1397 | 1403 | | |
| CONECT | 1403 | 1397 | 1404 | |
| CONECT | 1404 | 1403 | 1405 | 1407 |
| CONECT | 1405 | 1404 | 1406 | 1411 |
| CONECT | 1406 | 1405 | | |
| CONECT | 1407 | 1404 | 1408 | |
| CONECT | 1408 | 1407 | 1409 | |
| CONECT | 1409 | 1408 | 1410 | |
| CONECT | 1410 | 1409 | | |
| CONECT | 1411 | 1405 | | |
| CONECT | 1533 | 1537 | | |
| CONECT | 1537 | 1533 | 1538 | |
| CONECT | 1538 | 1537 | 1539 | 1541 |
| CONECT | 1539 | 1538 | 1540 | 1545 |
| CONECT | 1540 | 1539 | | |
| CONECT | 1541 | 1538 | 1542 | |
| CONECT | 1542 | 1541 | 1543 | |
| CONECT | 1543 | 1542 | 1544 | |
| CONECT | 1544 | 1543 | | |
| CONECT | 1545 | 1539 | | |
| CONECT | 1620 | 1626 | | |
| CONECT | 1626 | 1620 | 1627 | |
| CONECT | 1627 | 1626 | 1628 | 1630 |
| CONECT | 1628 | 1627 | 1629 | 1634 |
| CONECT | 1629 | 1628 | | |
| CONECT | 1630 | 1627 | 1631 | |
| CONECT | 1631 | 1630 | 1632 | |
| CONECT | 1632 | 1631 | 1633 | |
| CONECT | 1633 | 1632 | | |
| CONECT | 1634 | 1628 | | |

TABLE 2b-continued

Data of atomic coordinates for accession code 3AIG, which cites accession code 2ZTT

| CONECT | 1756 | 1764 | | | | | | | | | |
|---|---|---|---|---|---|---|---|---|---|---|---|
| CONECT | 1764 | 1756 | 1765 | | | | | | | | |
| CONECT | 1765 | 1764 | 1766 | 1768 | | | | | | | |
| CONECT | 1766 | 1765 | 1767 | 1772 | | | | | | | |
| CONECT | 1767 | 1766 | | | | | | | | | |
| CONECT | 1768 | 1765 | 1769 | | | | | | | | |
| CONECT | 1769 | 1768 | 1770 | | | | | | | | |
| CONECT | 1770 | 1769 | 1771 | | | | | | | | |
| CONECT | 1771 | 1770 | | | | | | | | | |
| CONECT | 1772 | 1766 | | | | | | | | | |
| MASTER | | 364 | 0 | 14 | 12 | 0 | 0 | 0 | 6 1889 | 4 | 140 | 22 |
| END | | | | | | | | | | | | |

REFERENCES

1. D. Elton, P. Digard, L. Tiley, J. Ortin, in Current Topics in Influenza Virology Y. Kawaoka, Ed. (Horizon Scientific Press, Norfolk, 2005) pp. 1-92.
2. F. Tarendeau et al., Nat Struct Mol Biol 14, 229 (2007).
3. D. Guilligay et al., Nat Struct Mol Biol 15, 500 (2008).
4. X. He et al., Nature 454, 1123 (2008).
5. E. Obayashi et al., Nature 454, 1127 (2008).
6. F. Tarendeau et al., PLoS Pathog 4, e1000136 (2008).
7. A. Portela, P. Digard, J Gen Virol 83, 723 (2002).
8. G. R. Whittaker, P. Digard, in Current Topics in Influenza Virology Y. Kawaoka, Ed. (Horizon Scientific Press, Norfolk, 2005) pp. 37-64.
9. S. J. Plotch, M. Bouloy, I. Ulmanen, R. M. Krug, Cell 23, 847 (1981).
10. L. L. Poon, D. C. Pritlove, E. Fodor, G. G. Brownlee, J Virol 73, 3473 (1999).
11. H. Zheng, H. A. Lee, P. Palese, A. Garcia-Sastre, J Virol 73, 5240 (1999).
12. C. Cianci, L. Tiley, M. Krystal, J Virol 69, 3995 (1995).
13. M. L. Li, B. C. Ramirez, R. M. Krug, Embo J 17, 5844 (1998).
14. E. Fodor, L. J. Mingay, M. Crow, T. Deng, G. G. Brownlee, J Virol 77, 5017 (2003).
15. P. Gastaminza, B. Perales, A. M. Falcon, J. Ortin, J Virol 77, 5098 (2003).
16. K. Nagata, Kawaguchi, A. and Naito, T., Rev. Med. Virol. 18, 247 (2008).
17. C. St Angelo, G. E. Smith, M. D. Summers, R. M. Krug, J Virol 61, 361 (1987).
18. P. Digard, V. C. Blok, S. C. Inglis, Virology 171, 162 (1989).
19. S. K. Biswas, D. P. Nayak, J Virol 70, 6716 (1996).
20. S. Gonzalez, T. Zurcher, J. Ortin, Nucleic Acids Res 24, 4456 (1996).
21. E. L. Poole, L. Medcalf, D. Elton, P. Digard, FEBS Lett 581, 5300 (2007).
22. T. Toyoda, D. M. Adyshev, M. Kobayashi, A. Iwata, A. Ishihama, J Gen Virol 77 (Pt 9), 2149 (1996).
23. Y. Ohtsu, Y. Honda, Y. Sakata, H. Kato, T. Toyoda, Microbiol Immunol 46, 167 (2002).
24. E. Poole, D. Elton, L. Medcalf, P. Digard, Virology 321, 120 (2004).
25. B. Perales, S. de la Luna, I. Palacios, J. Ortin, J Virol 70, 1678 (1996).
26. M. Ochoa et al., Virus Res 37, 305 (1995).
27. J. Barcena et al., J Virol 68, 6900 (1994).
28. E. Krissinel, K. Henrick, J Mol Biol 372, 774 (2007).
29. L. Potterton et al., Acta Crystallogr D Biol Crystallogr 60, 2288 (2004).
30. A. C. Wallace, R. A. Laskowski, J. M. Thornton, Protein Eng 8, 127 (1995).
S1. E. Obayashi et al., Nature 454, 1127 (2008).
S2. A. Kawaguchi, K. Nagata, Embo J 26, 4566 (2007).
S3. Z. Otwinowski, W. Minor, Methods Enzymol. 276, 307 (1997).
S4. T. R. Schneider, G. M. Sheldrick, Acta Crystallogr D Biol Crystallogr 58, 1772 (2002).
S5. T. C. Terwilliger, J. Berendzen, J. Acta Crystallogr D Biol Crystallogr 55, 849 (1999).
S6. T. C. Terwilliger, Methods Enzymol. 374, 22 (2003).
S7. P. Emsley, K. Cowtan, Acta Crystallogr D Biol Crystallogr 60, 2126 (2004).
S8. G. N. Murshudov, A. A. Vagin, E. J. Dodson, Acta Crystallogr D Biol Crystallogr 53, 240 (1997).
S9. R. A. Laskowski, D. S. Moss, J. M. Thornton, J Mol Biol 231, 1049 (1993).
S10. Vreede, F. T., Jung, T. E. and Brownlee, G. G., J Virol, 78, 9568-9572 (2004).
S11. Fodor, E., Crow, M., Mingay, L. J., Deng, T., Sharps, J., Fechter, P. and Brownlee, G. G., Virol, Vol. 76, pp. 8989-9001 (2002).
S12. Treanor, J., Perkins, M., Battaglia, R. and Murphy, B. R. J Virol, 68, 7684-7688 (1994).
S13. Yin, Y. W. and Steitz, T. A. Science, 298, 1387-1395 (2002).
S14. Hara, K., Schmidt, F. I., Crow, M. and Brownlee, G. G. J Virol, 80, 7789-7798 (2006).
S15. Neumann, G., Watanabe, T., Ito, H., Watanabe, S., Goto, H., Gao, P., Hughes, M., Perez, D. R., Donis, R., Hoffmann, E., Hobom, G. and Kawaoka, Y., Proc Natl Acad Sci USA, 96, 9345-9350 (1999).
S16. Sheldrick, G. M. SHELXS86-Program for crystal structure solution. University of Gottingen, Germany (1986).

INDUSTRIAL APPLICABILITY

The present invention enables the expression of RNA polymerase proteins derived from influenza virus and the provision of a crystallization method for obtaining information on the three-dimensional structure of the proteins to thereby develop anti-influenza virus drugs.

Sequence Listing Free Text

<SEQ ID NO: 1>

SEQ ID NO: 1 shows the nucleotide sequence of DNA encoding residues 678-757 of the RNA polymerase PB1 subunit in influenza A/Puerto Rico/8/34 H1N1.

<SEQ ID NO: 2>

SEQ ID NO: 2 shows the amino acid sequence at positions 678-757 of the RNA polymerase PB1 subunit in influenza A/Puerto Rico/8/34 H1N1.

<SEQ ID NO: 3>

SEQ ID NO: 3 shows the nucleotide sequence of DNA encoding residues 1-37 of the RNA polymerase PB2 subunit in influenza A/Puerto Rico/8/34 H1N1.

<SEQ ID NO: 4>

SEQ ID NO: 4 shows the amino acid sequence at positions 1-37 of the RNA polymerase PB2 subunit in influenza A/Puerto Rico/8/34 H1N1.

<SEQ ID NO: 5>

SEQ ID NO: 5 shows the nucleotide sequence of DNA encoding residues 678-751 of the RNA polymerase PB1 subunit in influenza A virus (A/Duck/Hong Kong/2986.1/2000 (H5N1)).

<SEQ ID NO: 6>

SEQ ID NO: 6 shows the amino acid sequence at positions 678-751 of the RNA polymerase PB1 subunit in influenza A virus (A/Duck/Hong Kong/2986.1/2000 (H5N1)).

<SEQ ID NO: 7>

SEQ ID NO: 7 shows the nucleotide sequence of DNA encoding residues 1-37 of the RNA polymerase PB2 subunit in influenza A virus (A/Duck/Hong Kong/2986.1/2000 (H5N1)).

<SEQ ID NO: 8>

SEQ ID NO: 8 shows the amino acid sequence at positions 1-37 of the RNA polymerase PB2 subunit in influenza A virus (A/Duck/Hong Kong/2986.1/2000 (H5N1)).

<SEQ ID NO: 9>

SEQ ID NO: 9 shows the nucleotide sequence of DNA encoding residues 678-757 of the RNA polymerase PB1 subunit in influenza A virus (A/Equine/London/1416/1973 (H7N7)).

<SEQ ID NO: 10>

SEQ ID NO: 10 shows the amino acid sequence at positions 678-757 of the RNA polymerase PB1 subunit in influenza A virus (A/Equine/London/1416/1973 (H7N7)).

<SEQ ID NO: 11>

SEQ ID NO: 11 shows the nucleotide sequence of DNA encoding residues 1-37 of the RNA polymerase PB2 subunit in influenza A virus (A/Equine/London/1416/1973 (H7N7)).

<SEQ ID NO: 12>

SEQ ID NO: 12 shows the amino acid sequence at positions 1-37 of the RNA polymerase PB2 subunit in influenza A virus (A/Equine/London/1416/1973 (H7N7)).

<SEQ ID NO: 13>

SEQ ID NO: 13 shows the nucleotide sequence of a specific primer corresponding to the luciferase coding region at nucleotide sequence positions 351-380.

<SEQ ID NO: 14>

SEQ ID NO: 14 shows the nucleotide sequence of a specific primer complementary to the luciferase coding region at nucleotide sequence positions 681-700.

<SEQ ID NO: 15>

SEQ ID NO: 15 shows the nucleotide sequence of DNA encoding the full-length RNA polymerase PB1 subunit in influenza A/Puerto Rico/8/34 H1N1.

<SEQ ID NO: 16>

SEQ ID NO: 16 shows the amino acid sequence of the full-length RNA polymerase PB1 subunit in influenza A/Puerto Rico/8/34 H1N1.

<SEQ ID NO: 17>

SEQ ID NO: 17 shows the nucleotide sequence of DNA encoding the full-length RNA polymerase PB2 subunit in influenza A/Puerto Rico/8/34 H1N1.

<SEQ ID NO: 18>

SEQ ID NO: 18 shows the amino acid sequence of the full-length RNA polymerase PB2 subunit in influenza A/Puerto Rico/8/34 H1N1.

<SEQ ID NO: 19>

SEQ ID NO: 19 shows the nucleotide sequence of DNA encoding residues 1-86 of the RNA polymerase PB2 subunit in influenza A/Puerto Rico/8/34 H1N1.

<SEQ ID NO: 20>

SEQ ID NO: 20 shows the amino acid sequence at positions 1-86 of the RNA polymerase PB2 subunit in influenza A/Puerto Rico/8/34 H1N1.

The invention claimed is:

1. A complex comprising a polypeptide shown in (a1) or (a2) below and a polypeptide shown in (b1) or (b2) below:
   (a1) a PB1 polypeptide which consists of the amino acid sequence of SEQ ID NO: 2; or
   (a2) a PB1 polypeptide which consists of an amino acid sequence with at least 90% identity to the amino acid sequence of SEQ ID NO: 2 and which has binding activity to a fragment of influenza virus RNA polymerase PB2 subunit; and
   (b1) a PB2 polypeptide which consists of the amino acid sequence of SEQ ID NO: 4; or
   (b2) a PB2 polypeptide which consists of an amino acid sequence with at least 90% identity to the amino acid sequence of SEQ ID NO: 4 and which has binding activity to a fragment of influenza virus RNA polymerase PB1 subunit.

2. The complex of claim 1, wherein the polypeptides are (a1) and (b1).

3. A method for producing the complex according to claim 1, which comprises culturing a cell transformed with a DNA encoding the polypeptide shown in (a1) or (a2) and a DNA encoding the polypeptide shown in (b1) or (b2), and collecting the complex according to claim 1 from the cultured product.

4. A recombinant vector comprising a DNA encoding the polypeptide shown in (a1) or (a2) and a DNA encoding the polypeptide of (b1) or (b2) below:
   (a1) a PB1 polypeptide which consists of the amino acid sequence of SEQ ID NO: 2; or
   (a2) a PB1 polypeptide which consists of an amino acid sequence with at least 90% identity to the amino acid sequence of SEQ ID NO: 2 and which has binding activity to a fragment of influenza virus RNA polymerase PB2 subunit; and
   (b1) a PB2 polypeptide which consists of the amino acid sequence of SEQ ID NO: 4; or
   (b2) a PB2 polypeptide which consists of an amino acid sequence with at least 90% identity to the amino acid sequence of SEQ ID NO: 4 and which has binding activity to a fragment of influenza virus RNA polymerase PB1 subunit.

5. The recombinant vector of claim 4, wherein the polypeptides are (a1) and (b1).

6. A cell transformed with a DNA encoding the polypeptide shown in (a1) or (a2) and a DNA encoding the polypeptide shown in (b1) or (b2) below:
   (a1) a PB1 polypeptide which consists of the amino acid sequence of SEQ ID NO: 2; or
   (a2) a PB1 polypeptide which consists of an amino acid sequence with at least 90% identity to the amino acid sequence of SEQ ID NO: 2 and which has binding activity to a fragment of influenza virus RNA polymerase PB2 subunit; and
   (b1) a PB2 polypeptide which consists of the amino acid sequence of SEQ ID NO: 4; or
   (b2) a PB2 polypeptide which consists of an amino acid sequence with at least 90% identity to the amino acid sequence of SEQ ID NO: 4 and which has binding activity to a fragment of influenza virus RNA polymerase PB1 subunit.

7. The transformed cell of claim 6, wherein the polypeptides are (a1) and (b1).

8. A monoclinic crystal having a space group of $P2_1$ of a complex consisting of a complex of SEQ ID NO: 2 and SEQ ID NO: 21, wherein the crystal has a unit lattice of a=44.27 Å, b=61.48 Å and c=45.47 Å with an angle of β=103.4° and all methionine residues in the amino acid sequences are selenomethionine.

9. A method for producing the crystal of the complex of claim 8, which comprises contacting a solution of the complex with a precipitant.

10. The method according to claim 9, wherein the precipitant comprises potassium phosphate and PEG 4000.

11. A method for screening a compound capable of serving as an active ingredient in anti-influenza drugs, which comprises the steps of:
  allowing a fragment of PB1 subunit and a fragment of PB2 subunit to contact each other in vitro in the presence of a candidate compound; and
  selecting a compound which inhibits the interaction between the fragment of PB1 subunit and the fragment of PB2 subunit, wherein the fragment of PB1 subunit consists of a polypeptide shown in (a1) or (a2) below, and the fragment of PB2 subunit consists of a polypeptide shown in (b1) or (b2) below:
  (a1) a PB1 polypeptide which consists of the amino acid sequence of SEQ ID NO: 2; or
  (a2) a PB1 polypeptide which consists of an amino acid sequence with at least 90% identity to the amino acid sequence of SEQ ID NO: 2 and which has binding activity to a fragment of influenza virus RNA polymerase PB2 subunit; and
  (b1) a PB2 polypeptide which consists of the amino acid sequence of SEQ ID NO: 4 or 20; or
  (b2) a PB2 polypeptide which consists of an amino acid sequence with at least 90% identity to the amino acid sequence of SEQ ID NO: 4 or 20 and which has binding activity to a fragment of influenza virus RNA polymerase PB1 subunit.

12. The method of claim 11, wherein the polypeptides are (a1) and (b1).

13. A method of identifying compounds for modulating the activity of a complex of a viral influenza RNA polymerase, said method comprising:
  (a) obtaining the crystal of claim 8;
  (b) determining the three-dimensional structure of the complex using the crystal of (a) using the X-ray diffraction method to obtain atomic coordinates of the structure;
  (c) constructing a three dimensional model and
  (d) designing or screening for a candidate compound that interacts with an interaction site between a fragment of PB1 subunit and a fragment of PB2 subunit, wherein the interaction site of the fragment of PB1 subunit comprises amino acid residues Leu 695, Lys 698, Phe 699, Val 715, Asp 725, Ile746 and Ile 750 in the amino acid sequence of SEQ ID NO: 16 or the corresponding residues of SEQ ID NO: 2.

14. The method according to claim 13, wherein amino acid residues in the interaction site of the fragment of PB2 subunit comprise at least one amino acid residue selected from the group consisting of amino acid residues Glu 2, Arg 3, Ile 4, Lys 5, Glu 6, Leu 7, Arg 8, Asn 9 and Leu 10 in the amino acid sequence of SEQ ID NO: 4, 18 or 20.

15. The method according to claim 13, wherein amino acid residues in the interaction site of the fragment of PB2 subunit comprise at least one amino acid residue selected from the group consisting of Glu 2, Arg 3, Ile 4, Glu 6, Leu 7 and Leu 10 in the amino acid sequence of SEQ ID NO: 4, 18 or 20.

16. The method as in one of claims 11, 13, 14 and 15, in which the candidate substance is at least one selected from the group consisting of a peptide, an antibody, and a nucleic acid or a salt thereof.

17. The method according to claim 13, wherein amino acid residues in the interaction site of the fragment of PB1 subunit are Leu 695, Lys 698, Phe 699, Val 715, Asp 725, Ile746 and Ile 750 in the amino acid sequence of SEQ ID NO: 16 or the corresponding residues in the amino acid sequence of SEQ ID NO: 2.

18. The method according to claim 13, wherein an amino acid residue in the interaction site of the fragment of PB1 subunit is Val 715 in the amino acid sequence of SEQ ID NO: 16 or the corresponding residues in the amino acid sequence of SEQ ID NO: 2.

19. The method according to claim 13, wherein amino acid residues in the interaction site of the fragment of PB2 subunit are Glu 2, Arg 3, Ile 4, Glu 6, Leu 7 and Leu 10 in the amino acid sequence of SEQ ID NO: 4, 18 or 20.

20. The method according to claim 11 wherein
  (b1) is a polypeptide which consists of the amino acid sequence of SEQ ID NO: 4; or
  (b2) is a polypeptide which consists of an amino acid sequence with at least 90% identity to the amino acid sequence of SEQ ID NO: 4 which has binding activity to a fragment of influenza virus RNA polymerase PB1 subunit.

* * * * *

SEQUENCE LISTING

```
<160> NUMBER OF SEQ ID NOS: 21

<210> SEQ ID NO 1
<211> LENGTH: 240
<212> TYPE: DNA
<213> ORGANISM: Influenza A virus
<220> FEATURE:
<221> NAME/KEY: CDS
<222> LOCATION: (1)..(240)

<400> SEQUENCE: 1 agt caa aga gga gta ctt gag gat gaa caa atg tac caa agg tgc tgc      48
Ser Gln Arg Gly Val Leu Glu Asp Glu Gln Met Tyr Gln Arg Cys Cys
1               5                   10                  15 aat tta ttt gaa aaa ttc ttc ccc agc agt tca tac aga aga cca gtc      96
Asn Leu Phe Glu Lys Phe Phe Pro Ser Ser Ser Tyr Arg Arg Pro Val
            20                  25                  30 ggg ata tcc agt atg gtg gag gct atg gtt tcc aga gcc cga att gat     144
Gly Ile Ser Ser Met Val Glu Ala Met Val Ser Arg Ala Arg Ile Asp
        35                  40                  45 gca cgg att gat ttc gaa tct gga agg ata aag aaa gaa gag ttc act     192
Ala Arg Ile Asp Phe Glu Ser Gly Arg Ile Lys Lys Glu Glu Phe Thr
    50                  55                  60
```

```
gag atc atg aag atc tgt tcc acc att gaa gag ctc aga cgg caa aaa    240
Glu Ile Met Lys Ile Cys Ser Thr Ile Glu Glu Leu Arg Arg Gln Lys
 65                  70                  75                  80

<210> SEQ ID NO 2
<211> LENGTH: 80
<212> TYPE: PRT
<213> ORGANISM: Influenza A virus

<400> SEQUENCE: 2

Ser Gln Arg Gly Val Leu Glu Asp Glu Gln Met Tyr Gln Arg Cys Cys
  1               5                  10                  15

Asn Leu Phe Glu Lys Phe Phe Pro Ser Ser Ser Tyr Arg Arg Pro Val
             20                  25                  30

Gly Ile Ser Ser Met Val Glu Ala Met Val Ser Arg Ala Arg Ile Asp
         35                  40                  45

Ala Arg Ile Asp Phe Glu Ser Gly Arg Ile Lys Lys Glu Glu Phe Thr
     50                  55                  60

Glu Ile Met Lys Ile Cys Ser Thr Ile Glu Glu Leu Arg Arg Gln Lys
 65                  70                  75                  80

<210> SEQ ID NO 3
<211> LENGTH: 111
<212> TYPE: DNA
<213> ORGANISM: Influenza A virus
<220> FEATURE:
<221> NAME/KEY: CDS
<222> LOCATION: (1)..(111)

<400> SEQUENCE: 3 atg gaa aga ata aaa gaa cta aga aat cta atg tcg cag tct cgc acc    48
Met Glu Arg Ile Lys Glu Leu Arg Asn Leu Met Ser Gln Ser Arg Thr
  1               5                  10                  15 cgc gag ata ctc aca aaa acc acc gtg gac cat atg gcc ata atc aag    96
Arg Glu Ile Leu Thr Lys Thr Thr Val Asp His Met Ala Ile Ile Lys
             20                  25                  30 aag tac aca tca gga                                                111
Lys Tyr Thr Ser Gly
         35

<210> SEQ ID NO 4
<211> LENGTH: 37
<212> TYPE: PRT
<213> ORGANISM: Influenza A virus

<400> SEQUENCE: 4

Met Glu Arg Ile Lys Glu Leu Arg Asn Leu Met Ser Gln Ser Arg Thr
  1               5                  10                  15

Arg Glu Ile Leu Thr Lys Thr Thr Val Asp His Met Ala Ile Ile Lys
             20                  25                  30

Lys Tyr Thr Ser Gly
         35

<210> SEQ ID NO 5
<211> LENGTH: 222
<212> TYPE: DNA
<213> ORGANISM: Influenza A virus
<220> FEATURE:
<221> NAME/KEY: CDS
<222> LOCATION: (1)..(222)

<400> SEQUENCE: 5 agc caa agg gga att ctt gag gat gaa cag atg tat cag aag tgc tgc    48
Ser Gln Arg Gly Ile Leu Glu Asp Glu Gln Met Tyr Gln Lys Cys Cys
```

```
                1               5                   10                  15
aat cta ttc gag aaa ttc ttc cct agc agt tca tat cgg agg cca gtt              96
Asn Leu Phe Glu Lys Phe Phe Pro Ser Ser Ser Tyr Arg Arg Pro Val
                20                  25                  30 gga att tcc agc atg gtg gag gcc atg gtg tct agg gcc cga att gat             144
Gly Ile Ser Ser Met Val Glu Ala Met Val Ser Arg Ala Arg Ile Asp
            35                  40                  45 gca cga att gac ttc gaa tct gga agg att aag aaa gaa gag ttt gct             192
Ala Arg Ile Asp Phe Glu Ser Gly Arg Ile Lys Lys Glu Glu Phe Ala
        50                  55                  60 gag atc atg aag atc tgt tcc acc att gaa                                     222
Glu Ile Met Lys Ile Cys Ser Thr Ile Glu
65                  70

<210> SEQ ID NO 6
<211> LENGTH: 74
<212> TYPE: PRT
<213> ORGANISM: Influenza A virus

<400> SEQUENCE: 6

Ser Gln Arg Gly Ile Leu Glu Asp Glu Gln Met Tyr Gln Lys Cys Cys
1               5                   10                  15

Asn Leu Phe Glu Lys Phe Phe Pro Ser Ser Ser Tyr Arg Arg Pro Val
                20                  25                  30

Gly Ile Ser Ser Met Val Glu Ala Met Val Ser Arg Ala Arg Ile Asp
            35                  40                  45

Ala Arg Ile Asp Phe Glu Ser Gly Arg Ile Lys Lys Glu Glu Phe Ala
        50                  55                  60

Glu Ile Met Lys Ile Cys Ser Thr Ile Glu
65                  70

<210> SEQ ID NO 7
<211> LENGTH: 111
<212> TYPE: DNA
<213> ORGANISM: Influenza A virus
<220> FEATURE:
<221> NAME/KEY: CDS
<222> LOCATION: (1)..(111)

<400> SEQUENCE: 7 atg gag aga ata aaa gaa tta aga gat cta atg tcg cag tcc cgc act              48
Met Glu Arg Ile Lys Glu Leu Arg Asp Leu Met Ser Gln Ser Arg Thr
1               5                   10                  15 cgc gag ata cta aca aaa acc act gtg gac cat atg gcc ata atc aag              96
Arg Glu Ile Leu Thr Lys Thr Thr Val Asp His Met Ala Ile Ile Lys
                20                  25                  30 aaa tac aca tca gga                                                          111
Lys Tyr Thr Ser Gly
            35

<210> SEQ ID NO 8
<211> LENGTH: 37
<212> TYPE: PRT
<213> ORGANISM: Influenza A virus

<400> SEQUENCE: 8

Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
                20                  25                  30

Lys Tyr Thr Ser Gly
            35
```

```
<210> SEQ ID NO 9
<211> LENGTH: 243
<212> TYPE: DNA
<213> ORGANISM: Influenza A virus
<220> FEATURE:
<221> NAME/KEY: CDS
<222> LOCATION: (1)..(243)

<400> SEQUENCE: 9 agc caa agg gga gta ctc gaa gat gag cag atg tac cag aaa tgt tgc        48
Ser Gln Arg Gly Val Leu Glu Asp Glu Gln Met Tyr Gln Lys Cys Cys
1               5                   10                  15 aac ctg ttt gaa aaa ttc ttc ccc agc agc tca tac aga aga cca gtc        96
Asn Leu Phe Glu Lys Phe Phe Pro Ser Ser Ser Tyr Arg Arg Pro Val
            20                  25                  30 gga att tct agt atg gtt gag gcc atg gtg tcc agg gcc cgc att gac       144
Gly Ile Ser Ser Met Val Glu Ala Met Val Ser Arg Ala Arg Ile Asp
        35                  40                  45 gca cgg att gac ttc gaa tct gga cgg ata aag aag gag gag ttc gct       192
Ala Arg Ile Asp Phe Glu Ser Gly Arg Ile Lys Lys Glu Glu Phe Ala
    50                  55                  60 gag atc atg aaa atc tgt tcc acc att gaa gag ctc aga cgg caa aaa       240
Glu Ile Met Lys Ile Cys Ser Thr Ile Glu Glu Leu Arg Arg Gln Lys
65                  70                  75                  80 tag                                                                   243

<210> SEQ ID NO 10
<211> LENGTH: 80
<212> TYPE: PRT
<213> ORGANISM: Influenza A virus

<400> SEQUENCE: 10

Ser Gln Arg Gly Val Leu Glu Asp Glu Gln Met Tyr Gln Lys Cys Cys
1               5                   10                  15

Asn Leu Phe Glu Lys Phe Phe Pro Ser Ser Ser Tyr Arg Arg Pro Val
            20                  25                  30

Gly Ile Ser Ser Met Val Glu Ala Met Val Ser Arg Ala Arg Ile Asp
        35                  40                  45

Ala Arg Ile Asp Phe Glu Ser Gly Arg Ile Lys Lys Glu Glu Phe Ala
    50                  55                  60

Glu Ile Met Lys Ile Cys Ser Thr Ile Glu Glu Leu Arg Arg Gln Lys
65                  70                  75                  80

<210> SEQ ID NO 11
<211> LENGTH: 111
<212> TYPE: DNA
<213> ORGANISM: Influenza A virus
<220> FEATURE:
<221> NAME/KEY: CDS
<222> LOCATION: (1)..(111)

<400> SEQUENCE: 11 atg gag aga ata aaa gaa ctg aga gat cta atg tca cag tcc cgc acc        48
Met Glu Arg Ile Lys Glu Leu Arg Asp Leu Met Ser Gln Ser Arg Thr
1               5                   10                  15 cgc gag ata ctc aca aaa acc act gtg gac cat atg gcc ata atc aag        96
Arg Glu Ile Leu Thr Lys Thr Thr Val Asp His Met Ala Ile Ile Lys
            20                  25                  30 aaa tac aca tca gga                                                   111
Lys Tyr Thr Ser Gly
        35
```

-continued

<210> SEQ ID NO 12
<211> LENGTH: 37
<212> TYPE: PRT
<213> ORGANISM: Influenza A virus

<400> SEQUENCE: 12

```
Met Glu Arg Ile Lys Glu Leu Arg Asp Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly
        35
```

<210> SEQ ID NO 13
<211> LENGTH: 30
<212> TYPE: DNA
<213> ORGANISM: Artificial
<220> FEATURE:
<223> OTHER INFORMATION: Primer

<400> SEQUENCE: 13
tatgaacatt tcgcagccta ccgtagtgtt               30

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
ccggaatgat ttgattgcca                          20

<210> SEQ ID NO 15
<211> LENGTH: 2274
<212> TYPE: DNA
<213> ORGANISM: Influenza A virus
<220> FEATURE:
<221> NAME/KEY: CDS
<222> LOCATION: (1)..(2274)

<400> SEQUENCE: 15

```
atg gat gtc aat ccg acc tta ctt ttc tta aaa gtg cca gca caa aat     48
Met Asp Val Asn Pro Thr Leu Leu Phe Leu Lys Val Pro Ala Gln Asn
1               5                   10                  15 gct ata agc aca act ttc cct tat acc gga gac cct cct tac agc cat    96
Ala Ile Ser Thr Thr Phe Pro Tyr Thr Gly Asp Pro Pro Tyr Ser His
            20                  25                  30 ggg aca gga aca gga tac acc atg gat act gtc aac agg aca cat cag   144
Gly Thr Gly Thr Gly Tyr Thr Met Asp Thr Val Asn Arg Thr His Gln
        35                  40                  45 tac tca gaa aag gca aga tgg aca aca aac acc gaa act gga gca ccg   192
Tyr Ser Glu Lys Ala Arg Trp Thr Thr Asn Thr Glu Thr Gly Ala Pro
    50                  55                  60 caa ctc aac ccg att gat ggg cca ctg cca gaa gac aat gaa cca agt   240
Gln Leu Asn Pro Ile Asp Gly Pro Leu Pro Glu Asp Asn Glu Pro Ser
65                  70                  75                  80 ggt tat gcc caa aca gat tgt gta ttg gaa gca atg gct ttc ctt gag   288
Gly Tyr Ala Gln Thr Asp Cys Val Leu Glu Ala Met Ala Phe Leu Glu
                85                  90                  95 gaa tcc cat cct ggt att ttt gaa aac tcg tgt att gaa acg atg gag   336
Glu Ser His Pro Gly Ile Phe Glu Asn Ser Cys Ile Glu Thr Met Glu
            100                 105                 110
```

```
gtt gtt cag caa aca cga gta gac aag ctg aca caa ggc cga cag acc        384
Val Val Gln Gln Thr Arg Val Asp Lys Leu Thr Gln Gly Arg Gln Thr
            115                 120                 125 tat gac tgg act tta aat aga aac cag cct gct gca aca gca ttg gcc        432
Tyr Asp Trp Thr Leu Asn Arg Asn Gln Pro Ala Ala Thr Ala Leu Ala
    130                 135                 140 aac aca ata gaa gtg ttc aga tca aat ggc ctc acg gcc aat gag tct        480
Asn Thr Ile Glu Val Phe Arg Ser Asn Gly Leu Thr Ala Asn Glu Ser
145                 150                 155                 160 gga agg ctc ata gac ttc ctt aag gat gta atg gag tca atg aaa aaa        528
Gly Arg Leu Ile Asp Phe Leu Lys Asp Val Met Glu Ser Met Lys Lys
                165                 170                 175 gaa gaa atg ggg atc aca act cat ttt cag aga aag aga cgg gtg aga        576
Glu Glu Met Gly Ile Thr Thr His Phe Gln Arg Lys Arg Arg Val Arg
            180                 185                 190 gac aat atg act aag aaa atg ata aca cag aga aca ata ggt aaa agg        624
Asp Asn Met Thr Lys Lys Met Ile Thr Gln Arg Thr Ile Gly Lys Arg
        195                 200                 205 aaa cag aga ttg aac aaa agg agt tat cta att aga gca ttg acc ctg        672
Lys Gln Arg Leu Asn Lys Arg Ser Tyr Leu Ile Arg Ala Leu Thr Leu
    210                 215                 220 aac aca atg acc aaa gat gct gag aga ggg aag cta aaa cgg aga gca        720
Asn Thr Met Thr Lys Asp Ala Glu Arg Gly Lys Leu Lys Arg Arg Ala
225                 230                 235                 240 att gca acc cca ggg atg caa ata agg ggg ttt gta tac ttt gtt gag        768
Ile Ala Thr Pro Gly Met Gln Ile Arg Gly Phe Val Tyr Phe Val Glu
                245                 250                 255 aca ctg gca agg agt ata tgt gag aaa ctt gaa caa tca ggg ttg cca        816
Thr Leu Ala Arg Ser Ile Cys Glu Lys Leu Glu Gln Ser Gly Leu Pro
            260                 265                 270 gtt gga ggc aat gag aag aaa gca aag ttg gca aat gtt gta agg aag        864
Val Gly Gly Asn Glu Lys Lys Ala Lys Leu Ala Asn Val Val Arg Lys
        275                 280                 285 atg atg acc aat tct cag gac acc gaa ctt tct ttg acc atc act gga        912
Met Met Thr Asn Ser Gln Asp Thr Glu Leu Ser Leu Thr Ile Thr Gly
    290                 295                 300 gat aac acc aaa tgg aac gaa aat cag aat cct cgg atg ttt ttg gcc        960
Asp Asn Thr Lys Trp Asn Glu Asn Gln Asn Pro Arg Met Phe Leu Ala
305                 310                 315                 320 atg atc aca tat atg acc aga aat cag ccc gaa tgg ttc aga aat gtt       1008
Met Ile Thr Tyr Met Thr Arg Asn Gln Pro Glu Trp Phe Arg Asn Val
                325                 330                 335 cta agt att gct cca ata atg ttc tca aac aaa atg gcg aga ctg gga       1056
Leu Ser Ile Ala Pro Ile Met Phe Ser Asn Lys Met Ala Arg Leu Gly
            340                 345                 350 aaa ggg tat atg ttt gag agc aag agt atg aaa ctt aga act caa ata       1104
Lys Gly Tyr Met Phe Glu Ser Lys Ser Met Lys Leu Arg Thr Gln Ile
        355                 360                 365 cct gca gaa atg cta gca agc att gat ttg aaa tat ttc aat gat tca       1152
Pro Ala Glu Met Leu Ala Ser Ile Asp Leu Lys Tyr Phe Asn Asp Ser
    370                 375                 380 aca aga aag aag att gaa aaa atc cga ccg ctc tta ata gag ggg act       1200
Thr Arg Lys Lys Ile Glu Lys Ile Arg Pro Leu Leu Ile Glu Gly Thr
385                 390                 395                 400 gca tca ttg agc cct gga atg atg atg ggc atg ttc aat atg tta agc       1248
Ala Ser Leu Ser Pro Gly Met Met Met Gly Met Phe Asn Met Leu Ser
                405                 410                 415 act gta tta ggc gtc tcc atc ctg aat ctt gga caa aag aga tac acc       1296
Thr Val Leu Gly Val Ser Ile Leu Asn Leu Gly Gln Lys Arg Tyr Thr
            420                 425                 430
```

```
aag act act tac tgg tgg gat ggt ctt caa tcc tct gac gat ttt gct    1344
Lys Thr Thr Tyr Trp Trp Asp Gly Leu Gln Ser Ser Asp Asp Phe Ala
        435                 440                 445 ctg att gtg aat gca ccc aat cat gaa ggg att caa gcc gga gtc gac    1392
Leu Ile Val Asn Ala Pro Asn His Glu Gly Ile Gln Ala Gly Val Asp
    450                 455                 460 agg ttt tat cga acc tgt aag cta cat gga atc aat atg agc aag aaa    1440
Arg Phe Tyr Arg Thr Cys Lys Leu His Gly Ile Asn Met Ser Lys Lys
465                 470                 475                 480 aag tct tac ata aac aga aca ggt aca ttt gaa ttc aca agt ttt ttc    1488
Lys Ser Tyr Ile Asn Arg Thr Gly Thr Phe Glu Phe Thr Ser Phe Phe
                485                 490                 495 tat cgt tat ggg ttt gtt gcc aat ttc agc atg gag ctt ccc agt ttt    1536
Tyr Arg Tyr Gly Phe Val Ala Asn Phe Ser Met Glu Leu Pro Ser Phe
            500                 505                 510 ggt gtg tct ggg agc aac gag tca gcg gac atg agt att gga gtt act    1584
Gly Val Ser Gly Ser Asn Glu Ser Ala Asp Met Ser Ile Gly Val Thr
        515                 520                 525 gtc atc aaa aac aat atg ata aac aat gat ctt ggt cca gca aca gct    1632
Val Ile Lys Asn Asn Met Ile Asn Asn Asp Leu Gly Pro Ala Thr Ala
    530                 535                 540 caa atg gcc ctt cag ttg ttc atc aaa gat tac agg tac acg tac cga    1680
Gln Met Ala Leu Gln Leu Phe Ile Lys Asp Tyr Arg Tyr Thr Tyr Arg
545                 550                 555                 560 tgc cat aga ggt gac aca caa ata caa acc cga aga tca ttt gaa ata    1728
Cys His Arg Gly Asp Thr Gln Ile Gln Thr Arg Arg Ser Phe Glu Ile
                565                 570                 575 aag aaa ctg tgg gag caa acc cgt tcc aaa gct gga ctg ctg gtc tcc    1776
Lys Lys Leu Trp Glu Gln Thr Arg Ser Lys Ala Gly Leu Leu Val Ser
            580                 585                 590 gac gga ggc cca aat tta tac aac att aga aat ctc cac att cct gaa    1824
Asp Gly Gly Pro Asn Leu Tyr Asn Ile Arg Asn Leu His Ile Pro Glu
        595                 600                 605 gtc tgc cta aaa tgg gaa ttg atg gat gag gat tac cag ggg cgt tta    1872
Val Cys Leu Lys Trp Glu Leu Met Asp Glu Asp Tyr Gln Gly Arg Leu
    610                 615                 620 tgc aac cca ctg aac cca ttt gtc agc cat aaa gaa att gaa tca atg    1920
Cys Asn Pro Leu Asn Pro Phe Val Ser His Lys Glu Ile Glu Ser Met
625                 630                 635                 640 aac aat gca gtg atg atg cca gca cat ggt cca gcc aaa aac atg gag    1968
Asn Asn Ala Val Met Met Pro Ala His Gly Pro Ala Lys Asn Met Glu
                645                 650                 655 tat gat gct gtt gca aca aca cac tcc tgg atc ccc aaa aga aat cga    2016
Tyr Asp Ala Val Ala Thr Thr His Ser Trp Ile Pro Lys Arg Asn Arg
            660                 665                 670 tcc atc ttg aat aca agt caa aga gga gta ctt gaa gat gaa caa atg    2064
Ser Ile Leu Asn Thr Ser Gln Arg Gly Val Leu Glu Asp Glu Gln Met
        675                 680                 685 tac caa agg tgc tgc aat tta ttt gaa aaa ttc ttc ccc agc agt tca    2112
Tyr Gln Arg Cys Cys Asn Leu Phe Glu Lys Phe Phe Pro Ser Ser Ser
    690                 695                 700 tac aga aga cca gtc ggg ata tcc agt atg gtg gag gct atg gtt tcc    2160
Tyr Arg Arg Pro Val Gly Ile Ser Ser Met Val Glu Ala Met Val Ser
705                 710                 715                 720 aga gcc cga att gat gca cgg att gat ttc gaa tct gga agg ata aag    2208
Arg Ala Arg Ile Asp Ala Arg Ile Asp Phe Glu Ser Gly Arg Ile Lys
                725                 730                 735 aaa gaa gag ttc act gag atc atg aag atc tgt tcc acc att gaa gag    2256
Lys Glu Glu Phe Thr Glu Ile Met Lys Ile Cys Ser Thr Ile Glu Glu
            740                 745                 750
```

-continued

```
ctc aga cgg caa aaa tag                                              2274
Leu Arg Arg Gln Lys
        755

<210> SEQ ID NO 16
<211> LENGTH: 757
<212> TYPE: PRT
<213> ORGANISM: Influenza A virus

<400> SEQUENCE: 16

Met Asp Val Asn Pro Thr Leu Leu Phe Leu Lys Val Pro Ala Gln Asn
1               5                   10                  15

Ala Ile Ser Thr Thr Phe Pro Tyr Thr Gly Asp Pro Pro Tyr Ser His
                20                  25                  30

Gly Thr Gly Thr Gly Tyr Thr Met Asp Thr Val Asn Arg Thr His Gln
            35                  40                  45

Tyr Ser Glu Lys Ala Arg Trp Thr Thr Asn Thr Glu Thr Gly Ala Pro
        50                  55                  60

Gln Leu Asn Pro Ile Asp Gly Pro Leu Pro Glu Asp Asn Glu Pro Ser
65                  70                  75                  80

Gly Tyr Ala Gln Thr Asp Cys Val Leu Glu Ala Met Ala Phe Leu Glu
                85                  90                  95

Glu Ser His Pro Gly Ile Phe Glu Asn Ser Cys Ile Glu Thr Met Glu
            100                 105                 110

Val Val Gln Gln Thr Arg Val Asp Lys Leu Thr Gln Gly Arg Gln Thr
        115                 120                 125

Tyr Asp Trp Thr Leu Asn Arg Asn Gln Pro Ala Ala Thr Ala Leu Ala
130                 135                 140

Asn Thr Ile Glu Val Phe Arg Ser Asn Gly Leu Thr Ala Asn Glu Ser
145                 150                 155                 160

Gly Arg Leu Ile Asp Phe Leu Lys Asp Val Met Glu Ser Met Lys Lys
                165                 170                 175

Glu Glu Met Gly Ile Thr Thr His Phe Gln Arg Lys Arg Arg Val Arg
            180                 185                 190

Asp Asn Met Thr Lys Lys Met Ile Thr Gln Arg Thr Ile Gly Lys Arg
        195                 200                 205

Lys Gln Arg Leu Asn Lys Arg Ser Tyr Leu Ile Arg Ala Leu Thr Leu
    210                 215                 220

Asn Thr Met Thr Lys Asp Ala Glu Arg Gly Lys Leu Lys Arg Arg Ala
225                 230                 235                 240

Ile Ala Thr Pro Gly Met Gln Ile Arg Gly Phe Val Tyr Phe Val Glu
                245                 250                 255

Thr Leu Ala Arg Ser Ile Cys Glu Lys Leu Glu Gln Ser Gly Leu Pro
            260                 265                 270

Val Gly Gly Asn Glu Lys Lys Ala Lys Leu Ala Asn Val Val Arg Lys
        275                 280                 285

Met Met Thr Asn Ser Gln Asp Thr Glu Leu Ser Leu Thr Ile Thr Gly
    290                 295                 300

Asp Asn Thr Lys Trp Asn Glu Asn Gln Asn Pro Arg Met Phe Leu Ala
305                 310                 315                 320

Met Ile Thr Tyr Met Thr Arg Asn Gln Pro Glu Trp Phe Arg Asn Val
                325                 330                 335

Leu Ser Ile Ala Pro Ile Met Phe Ser Asn Lys Met Ala Arg Leu Gly
            340                 345                 350

Lys Gly Tyr Met Phe Glu Ser Lys Ser Met Lys Leu Arg Thr Gln Ile
        355                 360                 365
```

```
Pro Ala Glu Met Leu Ala Ser Ile Asp Leu Lys Tyr Phe Asn Asp Ser
    370                 375                 380

Thr Arg Lys Lys Ile Glu Lys Ile Arg Pro Leu Leu Ile Glu Gly Thr
385                 390                 395                 400

Ala Ser Leu Ser Pro Gly Met Met Met Gly Met Phe Asn Met Leu Ser
                405                 410                 415

Thr Val Leu Gly Val Ser Ile Leu Asn Leu Gly Gln Lys Arg Tyr Thr
                420                 425                 430

Lys Thr Thr Tyr Trp Trp Asp Gly Leu Gln Ser Ser Asp Asp Phe Ala
            435                 440                 445

Leu Ile Val Asn Ala Pro Asn His Glu Gly Ile Gln Ala Gly Val Asp
            450                 455                 460

Arg Phe Tyr Arg Thr Cys Lys Leu His Gly Ile Asn Met Ser Lys Lys
465                 470                 475                 480

Lys Ser Tyr Ile Asn Arg Thr Gly Thr Phe Glu Phe Thr Ser Phe Phe
                485                 490                 495

Tyr Arg Tyr Gly Phe Val Ala Asn Phe Ser Met Glu Leu Pro Ser Phe
                500                 505                 510

Gly Val Ser Gly Ser Asn Glu Ser Ala Asp Met Ser Ile Gly Val Thr
            515                 520                 525

Val Ile Lys Asn Asn Met Ile Asn Asn Asp Leu Gly Pro Ala Thr Ala
530                 535                 540

Gln Met Ala Leu Gln Leu Phe Ile Lys Asp Tyr Arg Tyr Thr Tyr Arg
545                 550                 555                 560

Cys His Arg Gly Asp Thr Gln Ile Gln Thr Arg Arg Ser Phe Glu Ile
                565                 570                 575

Lys Lys Leu Trp Glu Gln Thr Arg Ser Lys Ala Gly Leu Leu Val Ser
            580                 585                 590

Asp Gly Gly Pro Asn Leu Tyr Asn Ile Arg Asn Leu His Ile Pro Glu
            595                 600                 605

Val Cys Leu Lys Trp Glu Leu Met Asp Glu Asp Tyr Gln Gly Arg Leu
            610                 615                 620

Cys Asn Pro Leu Asn Pro Phe Val Ser His Lys Glu Ile Glu Ser Met
625                 630                 635                 640

Asn Asn Ala Val Met Met Pro Ala His Gly Pro Ala Lys Asn Met Glu
                645                 650                 655

Tyr Asp Ala Val Ala Thr Thr His Ser Trp Ile Pro Lys Arg Asn Arg
                660                 665                 670

Ser Ile Leu Asn Thr Ser Gln Arg Gly Val Leu Glu Asp Glu Gln Met
            675                 680                 685

Tyr Gln Arg Cys Cys Asn Leu Phe Glu Lys Phe Phe Pro Ser Ser Ser
            690                 695                 700

Tyr Arg Arg Pro Val Gly Ile Ser Ser Met Val Glu Ala Met Val Ser
705                 710                 715                 720

Arg Ala Arg Ile Asp Ala Arg Ile Asp Phe Glu Ser Gly Arg Ile Lys
                725                 730                 735

Lys Glu Glu Phe Thr Glu Ile Met Lys Ile Cys Ser Thr Ile Glu Glu
                740                 745                 750

Leu Arg Arg Gln Lys
            755

<210> SEQ ID NO 17
<211> LENGTH: 2280
<212> TYPE: DNA
```

```
<213> ORGANISM: Influenza A virus
<220> FEATURE:
<221> NAME/KEY: CDS
<222> LOCATION: (1)..(2280)

<400> SEQUENCE: 17
```

| | | | | | | | | | | | | | | | | |
|---|---|---|---|---|---|---|---|---|---|---|---|---|---|---|---|---|
| atg | gaa | aga | ata | aaa | gaa | cta | aga | aat | cta | atg | tcg | cag | tct | cgc | acc | 48 |
| Met | Glu | Arg | Ile | Lys | Glu | Leu | Arg | Asn | Leu | Met | Ser | Gln | Ser | Arg | Thr | |
| 1 | | | | 5 | | | | | 10 | | | | | 15 | | |
| cgc | gag | ata | ctc | aca | aaa | acc | acc | gtg | gac | cat | atg | gcc | ata | atc | aag | 96 |
| Arg | Glu | Ile | Leu | Thr | Lys | Thr | Thr | Val | Asp | His | Met | Ala | Ile | Ile | Lys | |
| | | | 20 | | | | | 25 | | | | | 30 | | | |
| aag | tac | aca | tca | gga | aga | cag | gag | aag | aac | cca | gca | ctt | agg | atg | aaa | 144 |
| Lys | Tyr | Thr | Ser | Gly | Arg | Gln | Glu | Lys | Asn | Pro | Ala | Leu | Arg | Met | Lys | |
| | | 35 | | | | | 40 | | | | | 45 | | | | |
| tgg | atg | atg | gca | atg | aaa | tat | cca | att | aca | gca | gac | aag | agg | ata | acg | 192 |
| Trp | Met | Met | Ala | Met | Lys | Tyr | Pro | Ile | Thr | Ala | Asp | Lys | Arg | Ile | Thr | |
| | 50 | | | | | 55 | | | | | 60 | | | | | |
| gaa | atg | att | cct | gag | aga | aat | gag | caa | gga | caa | act | tta | tgg | agt | aaa | 240 |
| Glu | Met | Ile | Pro | Glu | Arg | Asn | Glu | Gln | Gly | Gln | Thr | Leu | Trp | Ser | Lys | |
| 65 | | | | | 70 | | | | | 75 | | | | | 80 | |
| atg | aat | gat | gcc | gga | tca | gac | cga | gtg | atg | gta | tca | cct | ctg | gct | gtg | 288 |
| Met | Asn | Asp | Ala | Gly | Ser | Asp | Arg | Val | Met | Val | Ser | Pro | Leu | Ala | Val | |
| | | | | 85 | | | | | 90 | | | | | 95 | | |
| aca | tgg | tgg | aat | agg | aat | gga | cca | atg | aca | aat | aca | gtt | cat | tat | cca | 336 |
| Thr | Trp | Trp | Asn | Arg | Asn | Gly | Pro | Met | Thr | Asn | Thr | Val | His | Tyr | Pro | |
| | | | 100 | | | | | 105 | | | | | 110 | | | |
| aaa | atc | tac | aaa | act | tat | ttt | gaa | aga | gtc | gaa | agg | cta | aag | cat | gga | 384 |
| Lys | Ile | Tyr | Lys | Thr | Tyr | Phe | Glu | Arg | Val | Glu | Arg | Leu | Lys | His | Gly | |
| | | 115 | | | | | 120 | | | | | 125 | | | | |
| acc | ttt | ggc | cct | gtc | cat | ttt | aga | aac | caa | gtc | aaa | ata | cgt | cgg | aga | 432 |
| Thr | Phe | Gly | Pro | Val | His | Phe | Arg | Asn | Gln | Val | Lys | Ile | Arg | Arg | Arg | |
| | 130 | | | | | 135 | | | | | 140 | | | | | |
| gtt | gac | ata | aat | cct | ggt | cat | gca | gat | ctc | agt | gcc | aag | gag | gca | cag | 480 |
| Val | Asp | Ile | Asn | Pro | Gly | His | Ala | Asp | Leu | Ser | Ala | Lys | Glu | Ala | Gln | |
| 145 | | | | | 150 | | | | | 155 | | | | | 160 | |
| gat | gta | atc | atg | gaa | gtt | gtt | ttc | cct | aac | gaa | gtg | gga | gcc | agg | ata | 528 |
| Asp | Val | Ile | Met | Glu | Val | Val | Phe | Pro | Asn | Glu | Val | Gly | Ala | Arg | Ile | |
| | | | | 165 | | | | | 170 | | | | | 175 | | |
| cta | aca | tcg | gaa | tcg | caa | cta | acg | ata | acc | aaa | gag | aag | aaa | gaa | gaa | 576 |
| Leu | Thr | Ser | Glu | Ser | Gln | Leu | Thr | Ile | Thr | Lys | Glu | Lys | Lys | Glu | Glu | |
| | | | 180 | | | | | 185 | | | | | 190 | | | |
| ctc | cag | gat | tgc | aaa | att | tct | cct | ttg | atg | gtt | gca | tac | atg | ttg | gag | 624 |
| Leu | Gln | Asp | Cys | Lys | Ile | Ser | Pro | Leu | Met | Val | Ala | Tyr | Met | Leu | Glu | |
| | | 195 | | | | | 200 | | | | | 205 | | | | |
| aga | gaa | ctg | gtc | cgc | aaa | acg | aga | ttc | ctc | cca | gtg | gct | ggt | gga | aca | 672 |
| Arg | Glu | Leu | Val | Arg | Lys | Thr | Arg | Phe | Leu | Pro | Val | Ala | Gly | Gly | Thr | |
| | 210 | | | | | 215 | | | | | 220 | | | | | |
| agc | agt | gtg | tac | att | gaa | gtg | ttg | cat | ttg | act | caa | gga | aca | tgc | tgg | 720 |
| Ser | Ser | Val | Tyr | Ile | Glu | Val | Leu | His | Leu | Thr | Gln | Gly | Thr | Cys | Trp | |
| 225 | | | | | 230 | | | | | 235 | | | | | 240 | |
| gaa | cag | atg | tat | act | cca | gga | ggg | gaa | gtg | aag | aat | gat | gat | gtt | gat | 768 |
| Glu | Gln | Met | Tyr | Thr | Pro | Gly | Gly | Glu | Val | Lys | Asn | Asp | Asp | Val | Asp | |
| | | | | 245 | | | | | 250 | | | | | 255 | | |
| caa | agc | ttg | att | att | gct | gct | agg | aac | ata | gtg | aga | aga | gct | gca | gta | 816 |
| Gln | Ser | Leu | Ile | Ile | Ala | Ala | Arg | Asn | Ile | Val | Arg | Arg | Ala | Ala | Val | |
| | | | 260 | | | | | 265 | | | | | 270 | | | |
| tca | gca | gac | cca | cta | gca | tct | tta | ttg | gag | atg | tgc | cac | agc | aca | cag | 864 |
| Ser | Ala | Asp | Pro | Leu | Ala | Ser | Leu | Leu | Glu | Met | Cys | His | Ser | Thr | Gln | |
| | | 275 | | | | | 280 | | | | | 285 | | | | |
| att | ggt | gga | att | agg | atg | gta | gac | atc | ctt | aag | cag | aac | cca | aca | gaa | 912 |

-continued

| | | |
|---|---|---|
| Ile Gly Gly Ile Arg Met Val Asp Ile Leu Lys Gln Asn Pro Thr Glu<br>290                295                  300 | | |
| gag caa gcc gtg ggt ata tgc aag gct gca atg gga ctg aga att agc<br>Glu Gln Ala Val Gly Ile Cys Lys Ala Ala Met Gly Leu Arg Ile Ser<br>305               310              315            320 | 960 | |
| tca tcc ttc agt ttt ggt gga ttc aca ttt aag aga aca agc gga tca<br>Ser Ser Phe Ser Phe Gly Gly Phe Thr Phe Lys Arg Thr Ser Gly Ser<br>                   325              330              335 | 1008 | |
| tca gtc aag aga gag gaa gag gtg ctt acg ggc aat ctt caa aca ttg<br>Ser Val Lys Arg Glu Glu Glu Val Leu Thr Gly Asn Leu Gln Thr Leu<br>               340              345              350 | 1056 | |
| aag ata aga gtg cat gag gga tat gaa gag ttc aca atg gtt ggg aga<br>Lys Ile Arg Val His Glu Gly Tyr Glu Glu Phe Thr Met Val Gly Arg<br>           355              360              365 | 1104 | |
| aga gca aca gcc ata ctc aga aaa gca acc agg aga ttg att cag ctg<br>Arg Ala Thr Ala Ile Leu Arg Lys Ala Thr Arg Arg Leu Ile Gln Leu<br>370               375              380 | 1152 | |
| ata gtg agt ggg aga gac gaa cag tcg att gcc gaa gca ata att gtg<br>Ile Val Ser Gly Arg Asp Glu Gln Ser Ile Ala Glu Ala Ile Ile Val<br>385               390              395            400 | 1200 | |
| gcc atg gta ttt tca caa gag gat tgt atg ata aaa gca gtt aga ggt<br>Ala Met Val Phe Ser Gln Glu Asp Cys Met Ile Lys Ala Val Arg Gly<br>                   405              410              415 | 1248 | |
| gat ctg aat ttc gtc aat agg gcg aat cag cga ctg aat cct atg cat<br>Asp Leu Asn Phe Val Asn Arg Ala Asn Gln Arg Leu Asn Pro Met His<br>               420              425              430 | 1296 | |
| caa ctt tta aga cat ttt cag aag gat gcg aaa gtg ctt ttt caa aat<br>Gln Leu Leu Arg His Phe Gln Lys Asp Ala Lys Val Leu Phe Gln Asn<br>           435              440              445 | 1344 | |
| tgg gga gtt gaa cct atc gac aat gtg atg gga atg att ggg ata ttg<br>Trp Gly Val Glu Pro Ile Asp Asn Val Met Gly Met Ile Gly Ile Leu<br>450               455              460 | 1392 | |
| ccc gac atg act cca agc atc gag atg tca atg aga gga gtg aga atc<br>Pro Asp Met Thr Pro Ser Ile Glu Met Ser Met Arg Gly Val Arg Ile<br>465               470              475            480 | 1440 | |
| agc aaa atg ggt gta gat gag tac tcc agc acg gag agg gta gtg gtg<br>Ser Lys Met Gly Val Asp Glu Tyr Ser Ser Thr Glu Arg Val Val Val<br>                   485              490              495 | 1488 | |
| agc att gac cgg ttc ttg aga gtc cgg gac caa cga gga aat gta cta<br>Ser Ile Asp Arg Phe Leu Arg Val Arg Asp Gln Arg Gly Asn Val Leu<br>           500              505              510 | 1536 | |
| ctg tct ccc gag gag gtc agt gaa aca cag gga aca gag aaa ctg aca<br>Leu Ser Pro Glu Glu Val Ser Glu Thr Gln Gly Thr Glu Lys Leu Thr<br>           515              520              525 | 1584 | |
| ata act tac tca tcg tca atg atg tgg gag att aat ggt cct gaa tca<br>Ile Thr Tyr Ser Ser Ser Met Met Trp Glu Ile Asn Gly Pro Glu Ser<br>530               535              540 | 1632 | |
| gtg ttg gtc aat acc tat caa tgg atc atc aga aac tgg gaa act gtt<br>Val Leu Val Asn Thr Tyr Gln Trp Ile Ile Arg Asn Trp Glu Thr Val<br>545               550              555            560 | 1680 | |
| aaa att cag tgg tcc cag aac cct aca atg cta tac aat aaa atg gaa<br>Lys Ile Gln Trp Ser Gln Asn Pro Thr Met Leu Tyr Asn Lys Met Glu<br>                   565              570              575 | 1728 | |
| ttt gaa cca ttt cag tct tta gta cct aag gcc att aga ggc caa tac<br>Phe Glu Pro Phe Gln Ser Leu Val Pro Lys Ala Ile Arg Gly Gln Tyr<br>           580              585              590 | 1776 | |
| agt ggg ttt gtg aga act ctg ttc caa caa atg agg gat gtg ctt ggg<br>Ser Gly Phe Val Arg Thr Leu Phe Gln Gln Met Arg Asp Val Leu Gly<br>           595              600              605 | 1824 | |
| aca ttt gat acc gca cag ata ata aaa ctt ctt ccc ttc gca gcc gct | 1872 | |

-continued

```
Thr Phe Asp Thr Ala Gln Ile Ile Lys Leu Leu Pro Phe Ala Ala Ala
    610                 615                 620 cca cca aag caa agt aga atg cag ttc tcc tca ttt act gtg aat gtg       1920
Pro Pro Lys Gln Ser Arg Met Gln Phe Ser Ser Phe Thr Val Asn Val
625                 630                 635                 640 agg gga tca gga atg aga ata ctt gta agg ggc aat tct cct gta ttc       1968
Arg Gly Ser Gly Met Arg Ile Leu Val Arg Gly Asn Ser Pro Val Phe
            645                 650                 655 aac tac aac aag gcc acg aag aga ctc aca gtt ctc gga aag gat gct       2016
Asn Tyr Asn Lys Ala Thr Lys Arg Leu Thr Val Leu Gly Lys Asp Ala
        660                 665                 670 ggc act tta acc gaa gac cca gat gaa ggc aca gct gga gtg gag tcc       2064
Gly Thr Leu Thr Glu Asp Pro Asp Glu Gly Thr Ala Gly Val Glu Ser
    675                 680                 685 gct gtt ctg agg gga ttc ctc att ctg ggc aaa gaa gac agg aga tat       2112
Ala Val Leu Arg Gly Phe Leu Ile Leu Gly Lys Glu Asp Arg Arg Tyr
690                 695                 700 ggg cca gca tta agc atc aat gaa ctg agc aac ctt gcg aaa gga gag       2160
Gly Pro Ala Leu Ser Ile Asn Glu Leu Ser Asn Leu Ala Lys Gly Glu
705                 710                 715                 720 aag gct aat gtg cta att ggg caa gga gac gtg gtg ttg gta atg aaa       2208
Lys Ala Asn Val Leu Ile Gly Gln Gly Asp Val Val Leu Val Met Lys
            725                 730                 735 cga aaa cgg gac tct agc ata ctt act gac agc cag aca gcg acc aaa       2256
Arg Lys Arg Asp Ser Ser Ile Leu Thr Asp Ser Gln Thr Ala Thr Lys
        740                 745                 750 aga att cgg atg gcc atc aat tag                                       2280
Arg Ile Arg Met Ala Ile Asn
    755

<210> SEQ ID NO 18
<211> LENGTH: 759
<212> TYPE: PRT
<213> ORGANISM: Influenza A virus

<400> SEQUENCE: 18

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30

Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
    50                  55                  60

Glu Met Ile Pro Glu Arg Asn Glu Gln Gly Gln Thr Leu Trp Ser Lys
65                  70                  75                  80

Met Asn Asp Ala Gly Ser Asp Arg Val Met Val Ser Pro Leu Ala Val
                85                  90                  95

Thr Trp Trp Asn Arg Asn Gly Pro Met Thr Asn Thr Val His Tyr Pro
            100                 105                 110

Lys Ile Tyr Lys Thr Tyr Phe Glu Arg Val Glu Arg Leu Lys His Gly
        115                 120                 125

Thr Phe Gly Pro Val His Phe Arg Asn Gln Val Lys Ile Arg Arg Arg
    130                 135                 140

Val Asp Ile Asn Pro Gly His Ala Asp Leu Ser Ala Lys Glu Ala Gln
145                 150                 155                 160

Asp Val Ile Met Glu Val Val Phe Pro Asn Glu Val Gly Ala Arg Ile
                165                 170                 175
```

```
Leu Thr Ser Glu Ser Gln Leu Thr Ile Thr Lys Glu Lys Lys Glu Glu
            180                 185                 190

Leu Gln Asp Cys Lys Ile Ser Pro Leu Met Val Ala Tyr Met Leu Glu
        195                 200                 205

Arg Glu Leu Val Arg Lys Thr Arg Phe Leu Pro Val Ala Gly Gly Thr
    210                 215                 220

Ser Ser Val Tyr Ile Glu Val Leu His Leu Thr Gln Gly Thr Cys Trp
225                 230                 235                 240

Glu Gln Met Tyr Thr Pro Gly Gly Glu Val Lys Asn Asp Asp Val Asp
                245                 250                 255

Gln Ser Leu Ile Ile Ala Ala Arg Asn Ile Val Arg Arg Ala Ala Val
            260                 265                 270

Ser Ala Asp Pro Leu Ala Ser Leu Leu Glu Met Cys His Ser Thr Gln
        275                 280                 285

Ile Gly Gly Ile Arg Met Val Asp Ile Leu Lys Gln Asn Pro Thr Glu
    290                 295                 300

Glu Gln Ala Val Gly Ile Cys Lys Ala Ala Met Gly Leu Arg Ile Ser
305                 310                 315                 320

Ser Ser Phe Ser Phe Gly Gly Phe Thr Phe Lys Arg Thr Ser Gly Ser
                325                 330                 335

Ser Val Lys Arg Glu Glu Glu Val Leu Thr Gly Asn Leu Gln Thr Leu
            340                 345                 350

Lys Ile Arg Val His Glu Gly Tyr Glu Glu Phe Thr Met Val Gly Arg
        355                 360                 365

Arg Ala Thr Ala Ile Leu Arg Lys Ala Thr Arg Arg Leu Ile Gln Leu
    370                 375                 380

Ile Val Ser Gly Arg Asp Glu Gln Ser Ile Ala Glu Ala Ile Ile Val
385                 390                 395                 400

Ala Met Val Phe Ser Gln Glu Asp Cys Met Ile Lys Ala Val Arg Gly
                405                 410                 415

Asp Leu Asn Phe Val Asn Arg Ala Asn Gln Arg Leu Asn Pro Met His
            420                 425                 430

Gln Leu Leu Arg His Phe Gln Lys Asp Ala Lys Val Leu Phe Gln Asn
        435                 440                 445

Trp Gly Val Glu Pro Ile Asp Asn Val Met Gly Met Ile Gly Ile Leu
    450                 455                 460

Pro Asp Met Thr Pro Ser Ile Glu Met Ser Met Arg Gly Val Arg Ile
465                 470                 475                 480

Ser Lys Met Gly Val Asp Glu Tyr Ser Ser Thr Glu Arg Val Val Val
                485                 490                 495

Ser Ile Asp Arg Phe Leu Arg Val Arg Asp Gln Arg Gly Asn Val Leu
            500                 505                 510

Leu Ser Pro Glu Glu Val Ser Glu Thr Gln Gly Thr Glu Lys Leu Thr
        515                 520                 525

Ile Thr Tyr Ser Ser Ser Met Met Trp Glu Ile Asn Gly Pro Glu Ser
    530                 535                 540

Val Leu Val Asn Thr Tyr Gln Trp Ile Arg Asn Trp Glu Thr Val
545                 550                 555                 560

Lys Ile Gln Trp Ser Gln Asn Pro Thr Met Leu Tyr Asn Lys Met Glu
                565                 570                 575

Phe Glu Pro Phe Gln Ser Leu Val Pro Lys Ala Ile Arg Gly Gln Tyr
            580                 585                 590

Ser Gly Phe Val Arg Thr Leu Phe Gln Gln Met Arg Asp Val Leu Gly
        595                 600                 605
```

```
Thr Phe Asp Thr Ala Gln Ile Ile Lys Leu Leu Pro Phe Ala Ala Ala
    610                 615                 620

Pro Pro Lys Gln Ser Arg Met Gln Phe Ser Ser Phe Thr Val Asn Val
625                 630                 635                 640

Arg Gly Ser Gly Met Arg Ile Leu Val Arg Gly Asn Ser Pro Val Phe
                645                 650                 655

Asn Tyr Asn Lys Ala Thr Lys Arg Leu Thr Val Leu Gly Lys Asp Ala
            660                 665                 670

Gly Thr Leu Thr Glu Asp Pro Asp Glu Gly Thr Ala Gly Val Glu Ser
        675                 680                 685

Ala Val Leu Arg Gly Phe Leu Ile Leu Gly Lys Glu Asp Arg Arg Tyr
    690                 695                 700

Gly Pro Ala Leu Ser Ile Asn Glu Leu Ser Asn Leu Ala Lys Gly Glu
705                 710                 715                 720

Lys Ala Asn Val Leu Ile Gly Gln Gly Asp Val Val Leu Val Met Lys
                725                 730                 735

Arg Lys Arg Asp Ser Ser Ile Leu Thr Asp Ser Gln Thr Ala Thr Lys
            740                 745                 750

Arg Ile Arg Met Ala Ile Asn
        755

<210> SEQ ID NO 19
<211> LENGTH: 258
<212> TYPE: DNA
<213> ORGANISM: Influenza A virus
<220> FEATURE:
<221> NAME/KEY: CDS
<222> LOCATION: (1)..(258)

<400> SEQUENCE: 19 atg gaa aga ata aaa gaa cta aga aat cta atg tcg cag tct cgc acc     48
Met Glu Arg Ile Lys Glu Leu Arg Asn Leu Met Ser Gln Ser Arg Thr
1               5                   10                  15 cgc gag ata ctc aca aaa acc acc gtg gac cat atg gcc ata atc aag     96
Arg Glu Ile Leu Thr Lys Thr Thr Val Asp His Met Ala Ile Ile Lys
            20                  25                  30 aag tac aca tca gga aga cag gag aag aac cca gca ctt agg atg aaa    144
Lys Tyr Thr Ser Gly Arg Gln Glu Lys Asn Pro Ala Leu Arg Met Lys
        35                  40                  45 tgg atg atg gca atg aaa tat cca att aca gca gac aag agg ata acg    192
Trp Met Met Ala Met Lys Tyr Pro Ile Thr Ala Asp Lys Arg Ile Thr
    50                  55                  60 gaa atg att cct gag aga aat gag caa gga caa act tta tgg agt aaa    240
Glu Met Ile Pro Glu Arg Asn Glu Gln Gly Gln Thr Leu Trp Ser Lys
65                  70                  75                  80 atg aat gat gcc gga tca                                            258
Met Asn Asp Ala Gly Ser
                85

<210> SEQ ID NO 20
<211> LENGTH: 86
<212> TYPE: PRT
<213> ORGANISM: Influenza A virus

<400> SEQUENCE: 20

Met Glu Arg Ile Lys Glu Leu Arg Asn Leu Met Ser Gln Ser Arg Thr
1               5                   10                  15

Arg Glu Ile Leu Thr Lys Thr Thr Val Asp His Met Ala Ile Ile Lys
            20                  25                  30
```

```
Lys Tyr Thr Ser Gly Arg Gln Glu Lys Asn Pro Ala Leu Arg Met Lys
        35                  40                  45

Trp Met Met Ala Met Lys Tyr Pro Ile Thr Ala Asp Lys Arg Ile Thr
 50                  55                  60

Glu Met Ile Pro Glu Arg Asn Glu Gln Gly Gln Thr Leu Trp Ser Lys
 65                  70                  75                  80

Met Asn Asp Ala Gly Ser
                 85

<210> SEQ ID NO 21
<211> LENGTH: 40
<212> TYPE: PRT
<213> ORGANISM: Influenza A virus
<220> FEATURE:
<221> NAME/KEY: misc_feature
<222> LOCATION: (1)..(40)
<223> OTHER INFORMATION: Any Xaa is Selenomethionine

<400> SEQUENCE: 21

Gly Gly Ser Xaa Glu Arg Ile Lys Glu Leu Arg Asn Leu Xaa Ser Gln
 1               5                  10                  15

Ser Arg Thr Arg Glu Ile Leu Thr Lys Thr Thr Val Asp His Xaa Ala
         20                  25                  30

Ile Ile Lys Lys Tyr Thr Ser Gly
             35                  40
```